(12) United States Patent
Chiosis et al.

(10) Patent No.: US 10,421,758 B2
(45) Date of Patent: Sep. 24, 2019

(54) SELECTIVE GRP94 INHIBITORS AND USES THEREOF

(71) Applicant: Memorial Sloan-Kettering Cancer Center, New York, NY (US)

(72) Inventors: Gabriela Chiosis, New York, NY (US); Pengrong Yan, New York, NY (US); Pallav Patel, Fresh Meadows, NY (US); Hardik J. Patel, Kew Gardens, NY (US); Tony Taldone, Forest Hills, NY (US); Chenghua Yang, New York, NY (US); Weilin Sun, Princeton, NJ (US); Stefan O. Ochiana, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 14/912,082

(22) PCT Filed: Aug. 15, 2014

(86) PCT No.: PCT/US2014/051332
§ 371 (c)(1),
(2) Date: Feb. 12, 2016

(87) PCT Pub. No.: WO2015/023976
PCT Pub. Date: Feb. 19, 2015

(65) Prior Publication Data
US 2016/0194328 A1 Jul. 7, 2016

Related U.S. Application Data

(60) Provisional application No. 61/866,932, filed on Aug. 16, 2013.

(51) Int. Cl.
C40B 30/02 (2006.01)
G01N 33/50 (2006.01)
(Continued)

(52) U.S. Cl.
CPC ......... *C07D 473/34* (2013.01); *C07D 519/00* (2013.01); *G01N 33/5011* (2013.01); *G16B 35/00* (2019.02); *G16C 20/60* (2019.02)

(58) Field of Classification Search
CPC .... C07D 473/34; C07D 519/00; C40B 30/02; G01N 33/5011
(Continued)

(56) References Cited

U.S. PATENT DOCUMENTS 7,241,890 B2   7/2007   Kasibhatla et al.
7,439,359 B2   10/2008  Chiosis et al.
(Continued)

FOREIGN PATENT DOCUMENTS

CN    1501928 A     6/2004
CN    101490052 A   7/2009
(Continued)

OTHER PUBLICATIONS

Chiosis et al. (AN 2011:1656071, DN 156:92369, ZCAPLUS, abstract of U.S. Pat. No. 9,403,828).*
(Continued)

*Primary Examiner* — Sabiha N Qazi
(74) *Attorney, Agent, or Firm* — Choate, Hall & Stewart LLP; John P. Rearick

(57) ABSTRACT

The disclosure relates to novel selective Grp94 inhibitors, compositions comprising an effective amount of such compounds, and methods to treat or prevent a condition, such as cancer, comprising administering to an animal in need thereof an effective amount of such compounds.

32 Claims, 49 Drawing Sheets

Specification includes a Sequence Listing.

(51) Int. Cl.
    *C07D 473/34*     (2006.01)
    *C07D 519/00*     (2006.01)
    *G16B 35/00*     (2019.01)
    *G16C 20/60*     (2019.01)

(58) Field of Classification Search
    USPC .......................... 514/210.21; 544/118, 278
    See application file for complete search history.

(56) References Cited

U.S. PATENT DOCUMENTS

| | | | |
|---|---|---|---|
| 7,834,181 B2 * | 11/2010 | Chiosis | C07D 473/34 |
| | | | 544/276 |
| 8,703,942 B2 * | 4/2014 | Chiosis | C07D 473/34 |
| | | | 435/375 |
| 9,328,114 B2 | 5/2016 | Chiosis et al. | |
| 9,346,808 B2 | 5/2016 | Sun et al. | |
| 9,403,828 B2 * | 8/2016 | Chiosis | C07D 519/00 |
| 9,546,170 B2 | 1/2017 | Taldone et al. | |
| 9,701,678 B2 | 7/2017 | Chiosis et al. | |
| 9,926,321 B2 | 3/2018 | Sun et al. | |
| 10,000,494 B2 | 6/2018 | Chiosis | |
| 10,167,285 B2 | 1/2019 | Chiosis et al. | |
| 10,172,863 B2 | 1/2019 | Chiosis et al. | |
| 2004/0102458 A1 | 5/2004 | Chiosis et al. | |
| 2005/0049263 A1 | 3/2005 | Kasibhatla et al. | |
| 2005/0107343 A1 | 5/2005 | Kasibhatla et al. | |
| 2005/0113339 A1 | 5/2005 | Kasibhatla et al. | |
| 2005/0113340 A1 | 5/2005 | Kasibhatla et al. | |
| 2005/0256183 A1 | 11/2005 | Kasibhatla et al. | |
| 2008/0253965 A1 | 10/2008 | Chiosis et al. | |
| 2009/0298857 A1 | 12/2009 | Chiosis et al. | |
| 2010/0015128 A1 | 1/2010 | Lee et al. | |
| 2010/0016586 A1 | 1/2010 | Bajji et al. | |
| 2011/0104054 A1 | 5/2011 | Chiosis et al. | |
| 2011/0312980 A1 | 12/2011 | Chiosis | |
| 2012/0022070 A1 | 1/2012 | Min et al. | |
| 2013/0109684 A1 | 5/2013 | Blagg et al. | |
| 2014/0088121 A1 | 3/2014 | Sun et al. | |
| 2014/0227183 A1 | 8/2014 | Chiosis et al. | |
| 2014/0378452 A1 | 12/2014 | Chiosis | |
| 2016/0264577 A1 | 9/2016 | Sun et al. | |
| 2016/0310497 A1 | 10/2016 | Chiosis et al. | |
| 2016/0333014 A1 | 11/2016 | Chiosis | |
| 2017/0151247 A1 | 6/2017 | Taldone et al. | |
| 2017/0342073 A1 | 11/2017 | Chiosis et al. | |
| 2019/0023708 A1 | 1/2019 | Chiosis | |

FOREIGN PATENT DOCUMENTS

| | | |
|---|---|---|
| JP | 2009-521446 A | 6/2009 |
| WO | WO-95/02597 A1 | 1/1995 |
| WO | WO-03/037860 A2 | 5/2003 |
| WO | WO-2006/084030 A2 | 8/2006 |
| WO | WO-2007/075572 A2 | 7/2007 |
| WO | WO-2007/134298 A2 | 11/2007 |
| WO | WO-2008/005937 A2 | 1/2008 |
| WO | WO-2008/115719 A1 | 9/2008 |
| WO | WO-2011/044394 A1 | 4/2011 |
| WO | WO-2012/138894 A1 | 10/2012 |
| WO | WO-2012/138896 A1 | 10/2012 |
| WO | WO-2013/009655 A2 | 1/2013 |
| WO | WO-2013/009657 A1 | 1/2013 |

OTHER PUBLICATIONS

Ali, M. M. et al. Crystal structure of an Hsp90-nucleotide-p23/Sba1 closed chaperone complex, Nature 440, 1013-1017 (2006).
Andrews, D. et al., Results of a pilot study involving the use of an antisense oligodeoxynucleotide directed against the insulin-like growth factor type I receptor in malignant astrocytomas, J. Clin. Oncol., 19(8):2189-200 (2001).
Arteaga, C. et al., Growth inhibition of human breast cancer cells in vitro with an antibody against the type I somatomedin receptor, Cancer Res., 49(22):6237-41 (1989).
Bartlett et al, Transforming growth factor-beta mRNA expression and growth control of human ovarian carcinoma cells, Brit. J. Cancer, 65(5):655-60 (1992).
Baserga, R., et al., The IGF-1 receptor in cancer biology, Int. J. Cancer; 107:873-7 (2003).
Buck, E. et al, Inactivation of Akt by the epidermal growth factor receptor inhibitor erlotinib is mediated by HER-3 in pancreatic and colorectal tumor cell lines and contributes to erlotinib sensitivity, Mol Cancer Ther, 5:2051-2059 (2006).
Caldas-Lopes, E. et al., Hsp90 inhibitor PU-H71, a multimodal inhibitor of malignancy, induces complete responses in triple-negative breast cancer models, Proc. Natl. Acad. Sci. USA, 106: 8368-73 (2009).
Chavany, C. et al., pl85erbB2 binds to GRP94 in vivo Dissociation of the pI85erbB2/GRP94 heterocomplex by benzoquinone ansamycins precedes depletion of pI85erbB2, J. Biol. Chem, 271: 4974-4977 (1996).
Chen, B. et al., The HSP90 family of genes in the human genome: Insights into their divergence and evolution, Genomics, 86: 627-637 (2005).
Chene, P. et al, ATPases as drug targets: learning from their structure, Nat. Rev. Drug Discov., 1: 665-673 (2002).
Cheng, J-C, et al, TGF-Beta Induces Serous Borderline Ovarian Tumor Cell Invasion by Activating EMT butTriggers Apoptosis in Low-Grade Serous Ovarian Carcinoma Cells, PLoS ONE, 7(8): e42436. doi: 10.1371 (2012).
D'Ambrosio, C. et al., A soluble insulin-like growth factor I receptor that induces apoptosis of tumor cells in vivo and inhibits tumorigenesis, Cancer Res, 56(17): 4013-20 (1996).
Dollins, D. E., et al, Structure of unliganded GRP94, the endoplasmic reticulum Hsp90. Basis for nucleotide-induced conformational change, J. Biol. Chem., 280:30438-30447 (2005).
Dollins, D.E., et al, Structures of GRP94-nucleotide complexes reveal mechanistic differences between the hsp90 chaperones, Mol. Cell, 28:41-56 (2007).
Duerfeldt, A.S., et al, Development of a Grp94 inhibitor, J.Am. Chem. Soc., 134:9796-9804 (2012).
Ferraro, D. et al., Inhibition of triple-negative breast cancer models by combinations of antibodies to EGFR, Proc. Natl. Acad. Sci. USA., 110(5): 1815-20 (2013).
Frey, S. et al, The ATPase cycle of the endoplasmic chaperone Grp94, J. Biol. Chem, 282:35612-35620 (2007).
Friesner, R.A. et al, Extra precision glide: Docking and scoring incorporating a model of hydrophobic enclosure for protein-ligand complexes, J. Med. Chem, 49:6177-6196 (2006).
Friesner, R.A. et al., Glide: a new approach for rapid, accurate docking and scoring. 1. Method and assessment of docking accuracy, J. Med. Chem, 47:1739-49 (2004).
Garcia-Echeverria, C. et al., In vivo antitumor activity of NVP-AEW541—A novel, potent, and selective inhibitor of the IGF-IR kinase, Cancer Cell, 5(3):231-9 (2004).
Halgren, T. et al, New method for fast and accurate binding-site identification and analysis, Chemical Biology & Drug Design, 69:146-148 (2007).
Halgren, T.A. et al, Glide: a new approach for rapid, accurate docking and scoring. 2. Enrichment factors in database screening, J. Med. Chem., 47:1750-1759 (2004).
Halgren, T.A. et al,. Identifying and Characterizing Binding Sites and Assessing Druggability, J. Chem. Information and Modeling, 49:377-389 (2009).
He, H. et al. Identification of potent water soluble purine-scaffold inhibitors of the heat shock protein 90, J. Med.Chem, 49:381-90 (2006).
Immormino, R. M. et al, Different poses for ligand and chaperone in inhibitor-bound Hsp90 and GRP94: implications for paralog-specific drug design, J. Mal. Biol., 388:1033-1042 (2009).
Immormino, R. M. et al, Structural and quantum chemical studies of 8-aryl-sulfanyl adenine class Hsp90 inhibitors, J. Med. Chem, 49:4953-4960 (2006).

(56) References Cited

OTHER PUBLICATIONS

Jhaveri, K., et al, Advances in the clinical development of heat shock protein 90(Hsp90) inhibitors in cancers, Biochim. Biophys. Acta., 1823:742-755 (2012).
Johnson, J. L. et al, Evolution and function of diverse Hsp90 homologs and cochaperone proteins, Biochim. Biophys. Acta., 1823:607-613 (2012).
Kim, T.E. & Murren, J.R., Lapatinib Ditosylate GlaxoSmithKline, IDrugs 6, 886-893 (2003).
Leroith, D. et al., The insulin-like growth factor system and cancer, Cancer Lett., 195(2): 127-37 (2003).
Leskovar, A., et al, The ATPase cycle of the mitochondrial Hsp90 analog Trapl, J. Biol. Chem, 283: 11677-11688 (2008).
Long, L., et al., Loss of the metastatic phenotype in murine carcinoma cells expressing an antisense RNA to the insulin-like growth factor receptor, Cancer Res, 55(5): 1006-9 (1995).
Marzec, M. et al, GRP94: An HSP90-like protein specialized for protein folding and quality control in the endoplasmic reticulum, Biochim. Biophys. Acta., 1823:774-787 (2012).
McLaughlin, S. H.et al, Independent ATPase activity of Hsp90 subunits creates a flexible assembly platform, J. Mal. Biol, 344:813-826 (2004).
Moulick, K. et al. Affinity-based proteomics reveal cancer-specific networks coordinated by Hsp90, Nat. Chem. Biol., 7:818-26 (2011).
Mueller et al., Fibroblast-secreted hepatocyte growth factor mediates epidermal growth factor receptor tyrosine kinase inhibitor resistance in triple-negative breast cancers through paracrine activation of Met, Breast Cancer Res., 14( 4):R104 (2012).
Ostrovsky, O. et al, The chaperone activity of GRP94 toward insulinlike growth factor II is necessary for the stress response to serum deprivation, Mal. Biol. Cell, 20:1855-1864 (2009).
Pearl, L. H.et al, The Hsp90 molecular chaperone: an open and shut case for treatment, Biochem. J., 410:439-453 (2008).
Pietrzkowski, Z. et al., Inhibition of growth of prostatic cancer cell lines by peptide analogues of insulin-like growth factor 1, Cancer Res., 53(5):1102-6 (1993).
Richter, K. et al, Conserved conformational changes in the ATPase cycle of human hsp90, J. Biol. Chem., 283:17757-17765 (2008).
Rodina, A. et al., Selective compounds define Hsp90 as a major inhibitor of apoptosis in small-cell lung cancer, Nat. Chem. Biol., 3:498-507 (2007).
Schulte, T.W. et al., Interaction of radicicol with members of the heat shock protein 90 family of molecular chaperones, Mol. Endo., 13:1435-1448 (1999).
Siwak, D. et al, Targeting the Epidermal Growth Factor Receptor in Epithelial Ovarian Cancer: Current Knowledge and Future Challenges, Journal of Oncology, 2010; doi:l0.1155/2010/568938).
Sokolowska, I. et al. Proteomic analysis of plasma membranes isolated from undifferentiated and differentiated HepaRG cells, Proteome Sci., 10, 4 7 (2012).
Soldano, K. L. et al, Structure of the N-terminal domain of GRP94: Basis for ligand specificity and regulation, J. Biol. Chem, 279:48330-48338 (2003).
Sreedhar, A. S. et al, Hsp90 isoforms: functions, expression and clinical importance, FEBS letters, 562:11-15 (2004).
Wanderling, S. et al., GRP94 is essential for mesoderm induction and muscle development because it regulates insulin-like growth factor secretion, Mol. Biol. Cell, 18:3764-75 (2007).
Wittman, M., et al., Discovery of a 1H-Benzoimidazol-2-yl)-1H-pyridin-2-one (BMS-536924) Inhibitor of Insulin-like Growth Factor I Receptor Kinase with in Vivo Antitumor Activity, J. Med. Chem., 48(18):5639-43 (2005).
Workman, P.et al, Drugging the cancer chaperone Hsp90: combinatorial therapeutic exploitation of oncogene addiction and tumor stress, Ann. NY. Acad. Sci., 1113: 202-216 (2007).
Xu, W. et al, Hsp90, not Grp94, regulates the intracellular trafficking and stability of nascent ErbB2, Cell Stress Chaperones, 7:91-96 (2002).
Yang, Y. et al. Heat shock protein gp96 is a master chaperone for toll-like receptors and is important in the innate function of macrophages, Immunity 26, 215-26 (2007).
Yarden, Y. & Sliwkowski, M. X., Untangling the ErbB signaling network, Nat. Rev. Mal. Cell Biol., 2:127-137 (2001).
Yun, T. J et al, EC144, a Synthetic Inhibitor of Heat Shock Protein 90, Blocks Innate and Adaptive Immune Responses in Models of Inflammation and Autoimmunity, The Journal of Immunology, 186: 563-575 (2011).
Zhang, L.et al, EGFR and ErbB2 differentially regulate Raf-1 translocation and activation, Lab. Invest., 82:71-78 (2002).
Dymock, B. W., et al., Inhibitors of HSP90 and other chaperones for the treatment of cancer, Expert Opinion, Ther. Patents, 14(6): 837-0847 (2004).
Immormino, R.M. et al., Ligand-induced conformational shift in the N-terminal domain of GRP94, an Hsp90 chaperone, J. Biol. Chem., 279(44):46162-71 (2004).
International Search Report for PCT/US2014/051332, 7 pages (dated Feb. 18, 2015).
Llaugher, L. et al., Evaluation of 8-Arylsulfanyl, 8-Arylsulfonyl Adenine Derivatives as Inhibitors of the Heat Shock Protein 90, J. Med. Chem., 48: 2892-2905 (2005).
Lucas, B. et al., Facile Synthesis of a Library of 9-Alkyl-8-benzyl-9H-purin-6-ylamine Derivatives, J. Comb. Chem., 3: 518-520 (2001).
Written Opinion for PCT/US2014/051332, 8 pages (dated Feb. 18, 2015).
Author Unknown, 1H-benzimidazole-1-acetamide, 4-amino-2-(phenylmethyl)-, CAS RN 1216054-06-6, STN Entry Date Apr. 4, 2010.
Author Unknown, 1H-benzimidazole-1-acetamide, 4-amino-2-[(4-fluorophenyl)methyl]-, CAS RN 1216006-29-9, STN Entry Date Apr. 4, 2010.
Author Unknown, 1H-benzimidazole-1-acetic acid hydrazide, 4-amino-2-(phenylmethyl)-, CAS RN 1216116-95-8, STN Entry Date Apr. 4, 2010.
Author Unknown, 1H-benzimidazole-1-propanamine, 4-amino-N,N-dimethyl-2-(phenylmethyl)-, CAS RN 1216041-15-4, STN Entry Date Apr. 4, 2010.
Author Unknown,1H-benzimidazole-1-acetamide,4-amino-N-methyl-2-(phenylmethyl)-, CAS RN 1216259-68-5, STN Entry Date Apr. 4, 2010.
Author Unknown,1H-benzimidazole-1-ethanamine, 4-amino-N,N-dimethyl-2-(phenylmethyl)-, CAS RN 1216217-64-9, STN Entry Date Apr. 4, 2010.
Biamonte, M.A. et al., Preparation of 8-(Arylsulfanyl) adenines with Diazonium Salts under Mild, Aerobic Conditions, Journal of Organic Chemistry, 70(2):717-720 (2005).
Dickey, C.A. et al., Development of a high throughput drug screening assay for the detection of changes in tau levels—proof of concept with HSP90 inhibitors, Curr. Alzheimer Res., 2(2):231-8 (2005).
Kang, J. et al., Inhibition of neuroblastoma xenograft growth by HSP90 inhibitors, Anticancer Res., 26(3A):1903-8 (2006).
Zhang, H. et al, Identification of new biomarkers for clinical trials of HSP90 inhibitors, Molecular Cancer Therapeutics, 5(5): 1256-1264 (2006).
Patel, P. D. et al, Paralog-selective Hsp90 inhibitors define tumor-specific regulation of HER2, Nature Chemical Biology, 9: 677-684 (2013).

* cited by examiner

| Compd | Grp94:Hsp90α selectivity | Grp94:Trap-1 selectivity |
|---|---|---|
| PU-H3 | >100 | 10 |
| PU-H54 | >25 | 5 |
| PU-H39 | >100 | >100 |
| PU-H38 | >100 | 4 |
| PU-H4 | >100 | 15 |
| PU-H40 | >100 | >100 |
| PU-H27 | >100 | >100 |
| PU-H42 | >100 | 10 |
| PU-WS13 | 140 | 35 |
| PU-H51 | >100 | >100 |
| PU-H52 | 50 | 10 |
| PU-H36 | >100 | 35 |
| PU-27 | >10 | >10 |
| PU-34 | >10 | 3 |

FIG. 1c

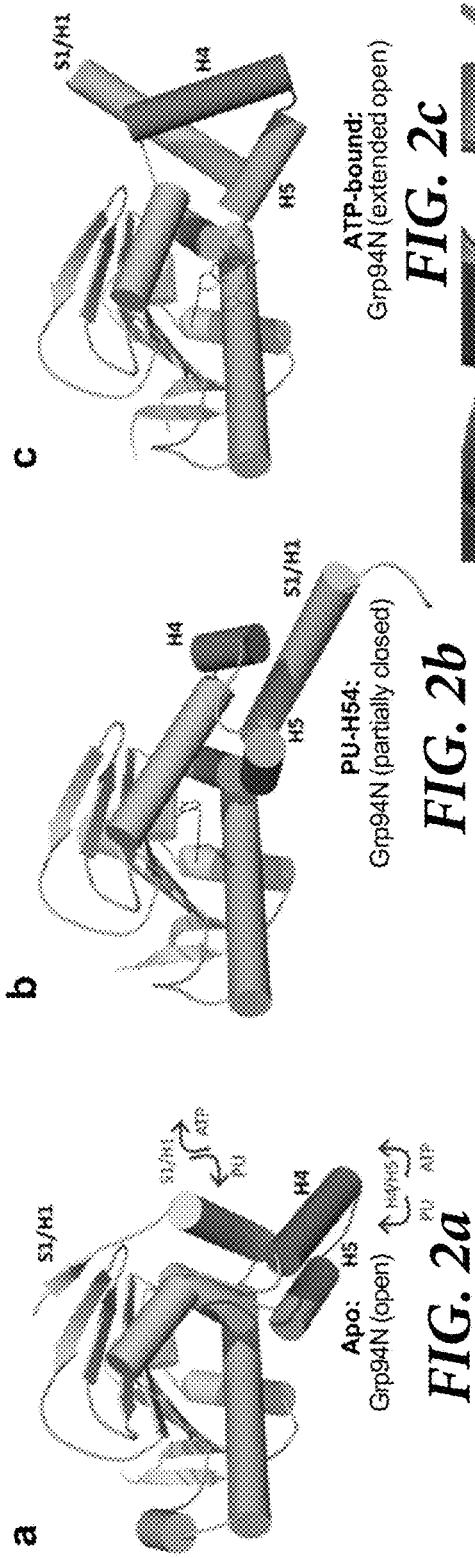
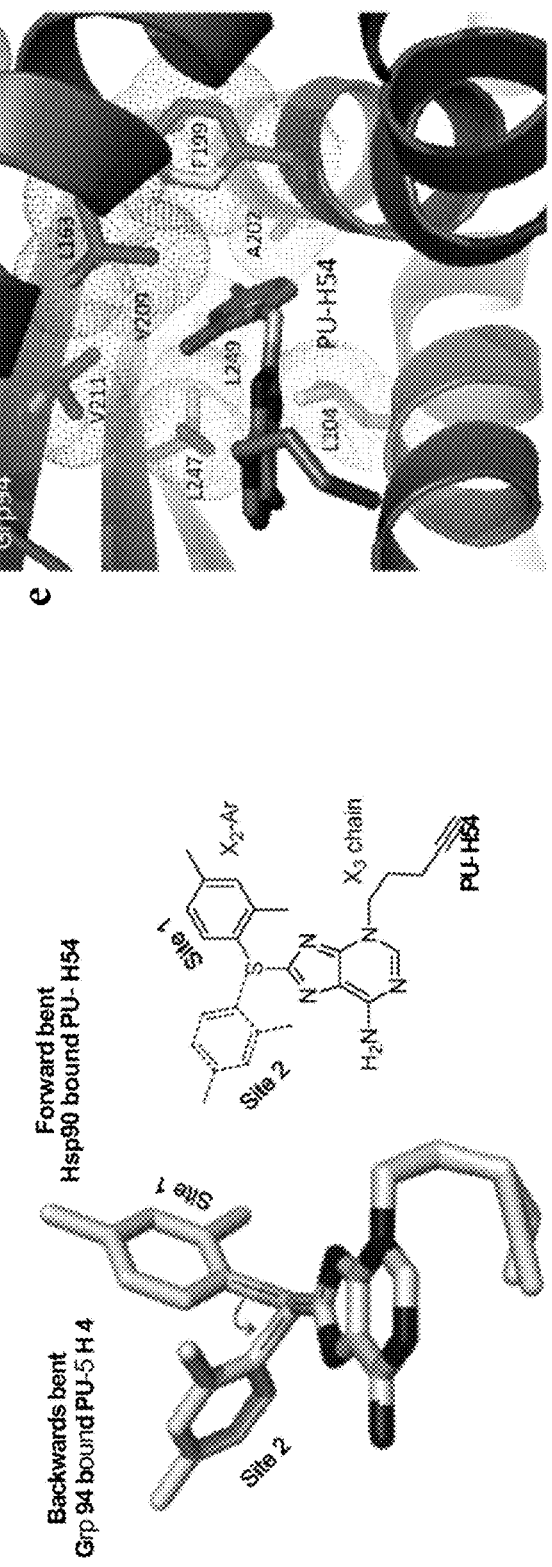
FIG. 2a FIG. 2b FIG. 2c FIG. 2d FIG. 2e

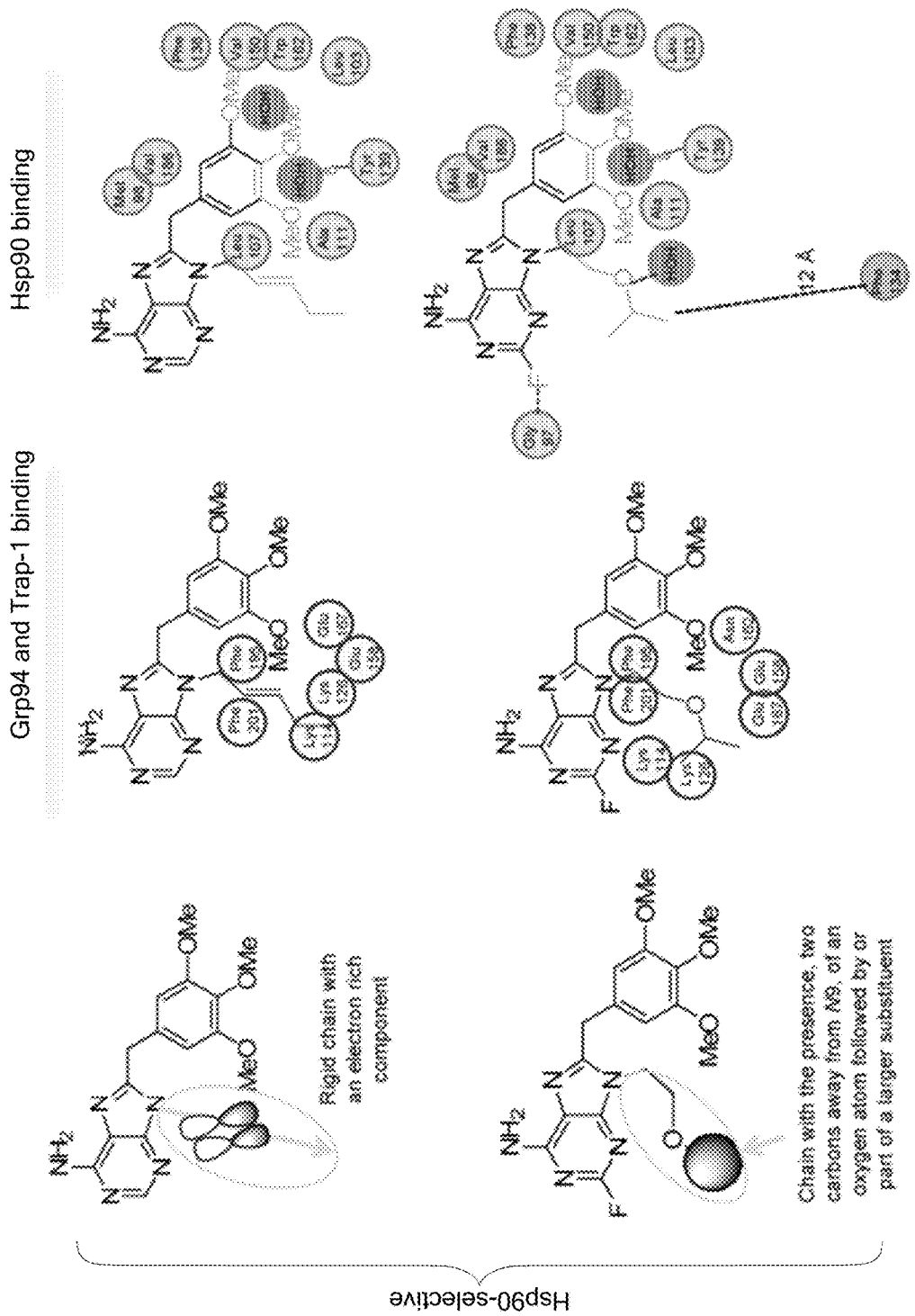

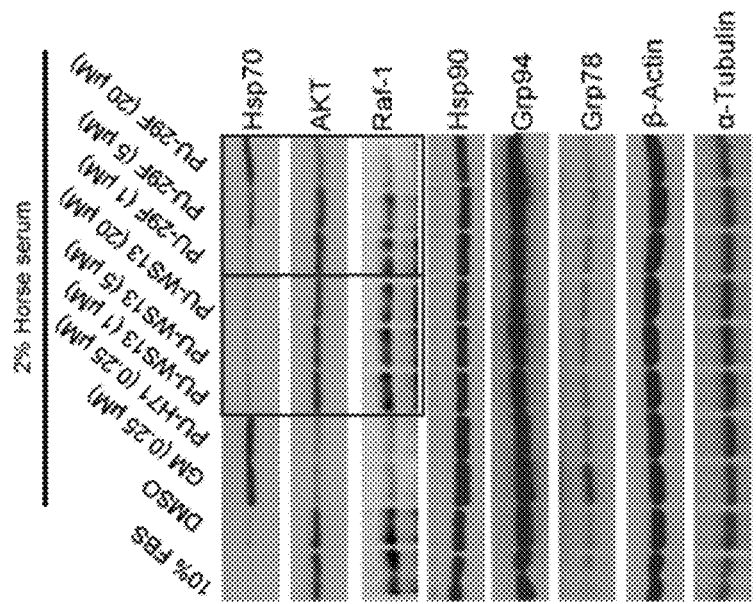
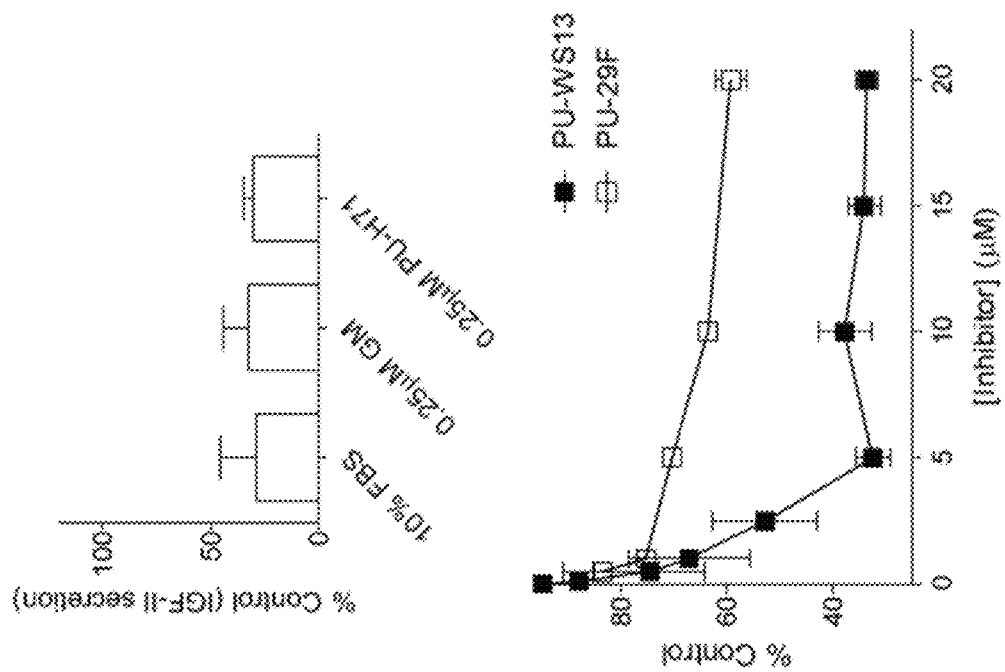
FIG. 5b
FIG. 5a

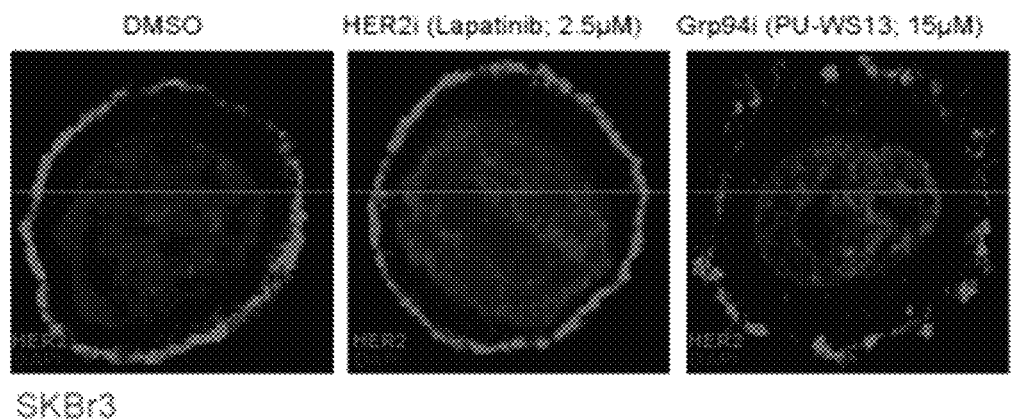
FIG. 8f
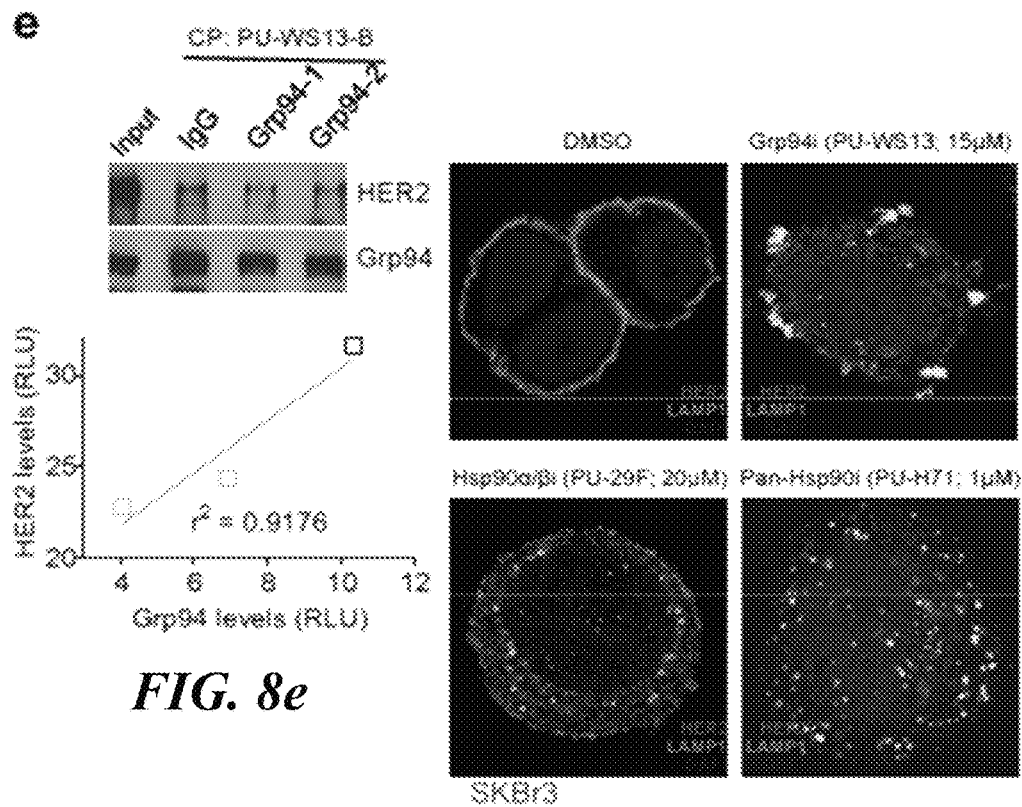
FIG. 8e
FIG. 8g

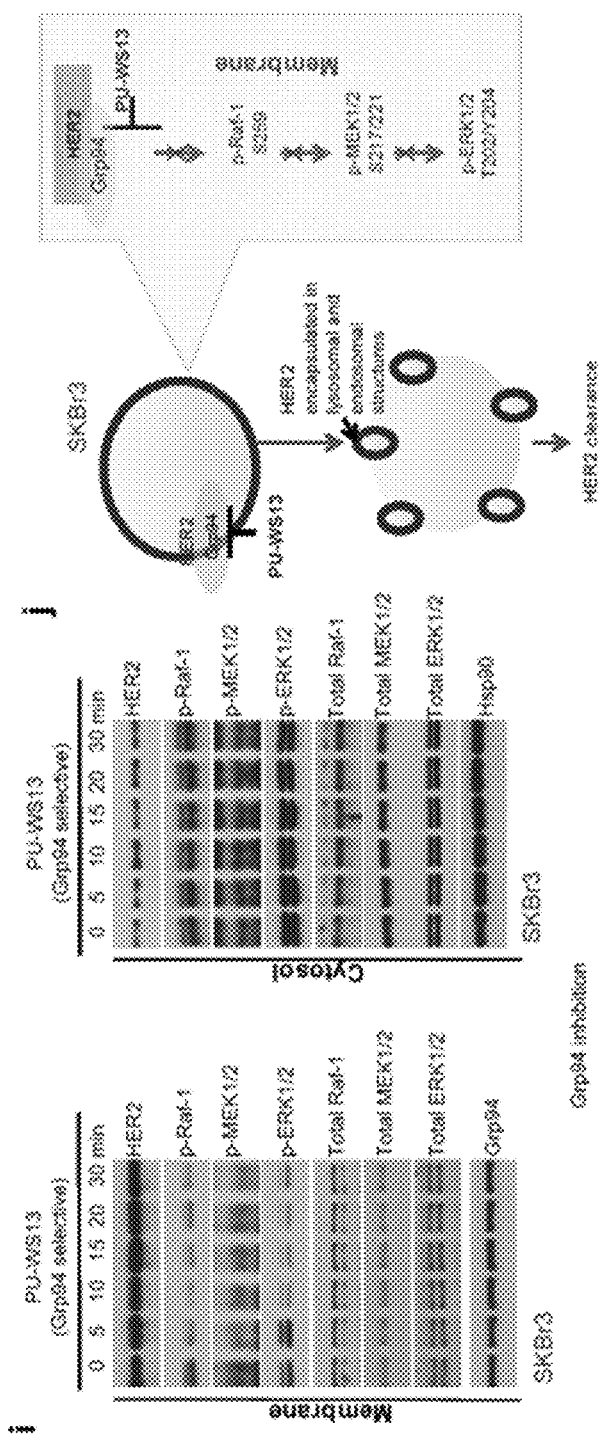
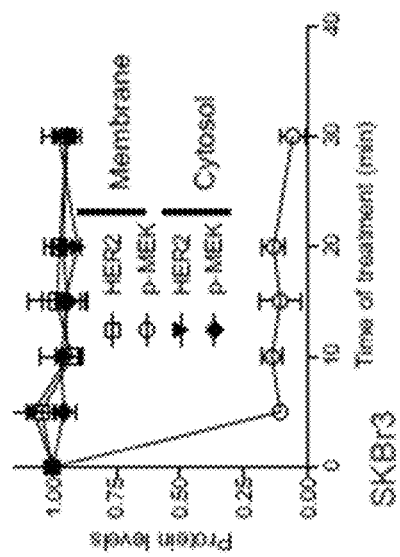
FIG. 8i
FIG. 8j

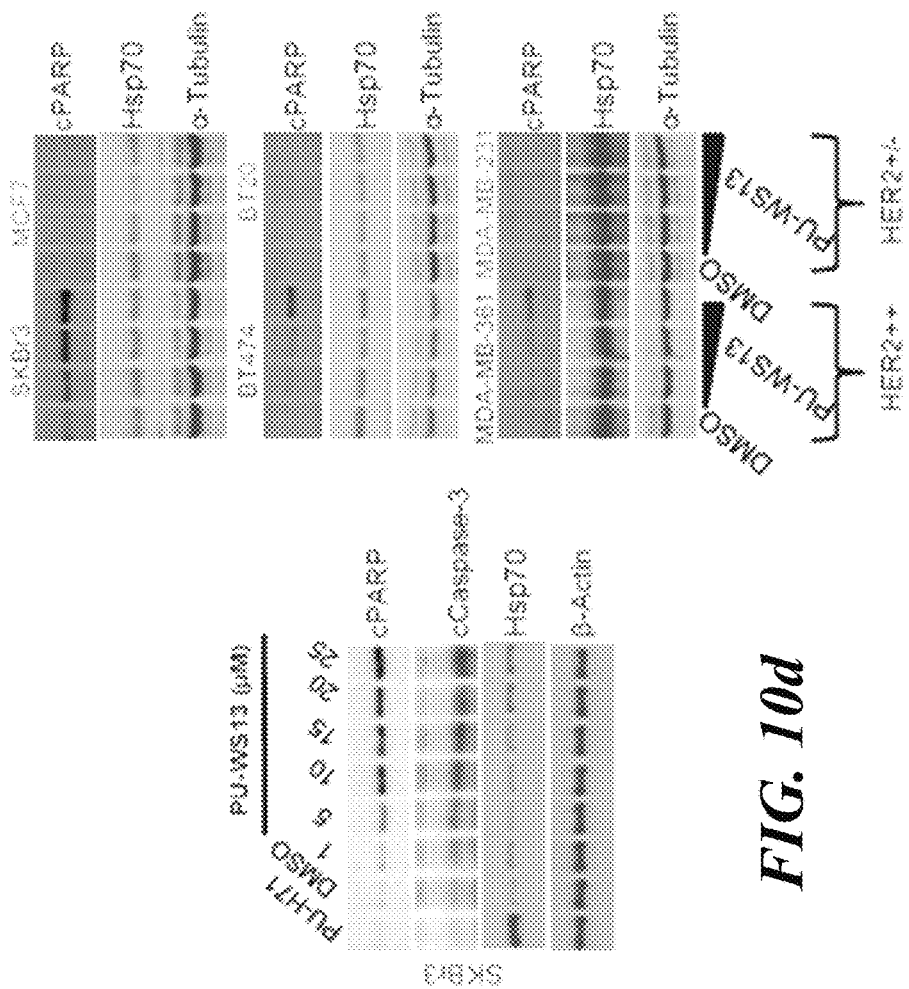
FIG. 10e
FIG. 10d
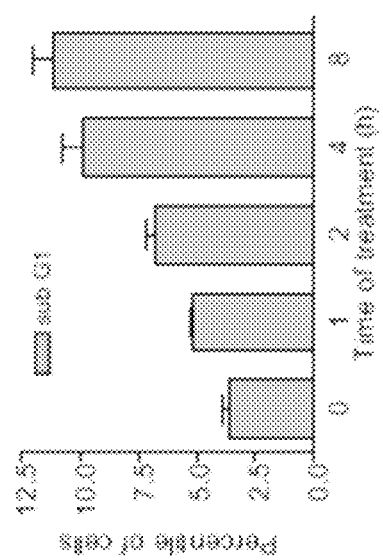
FIG. 10c

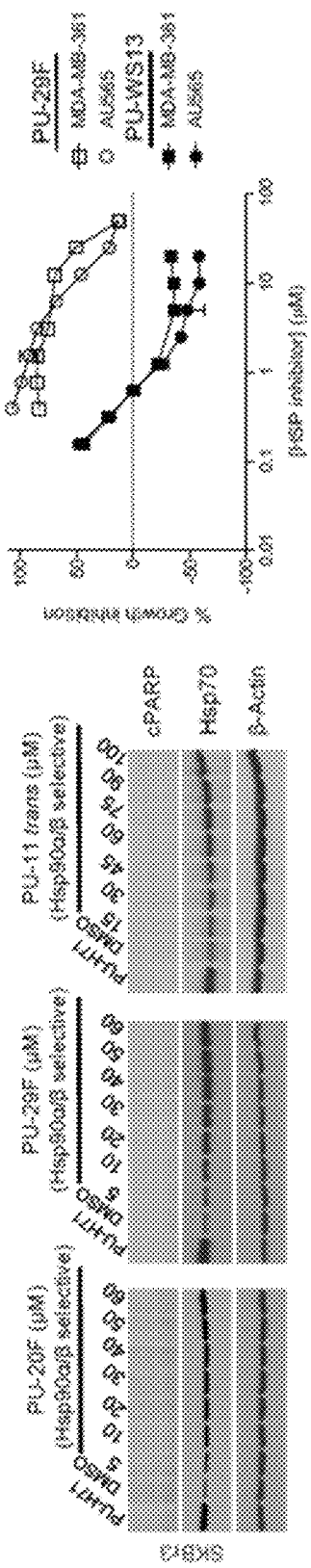
FIG. 11c
FIG. 11b
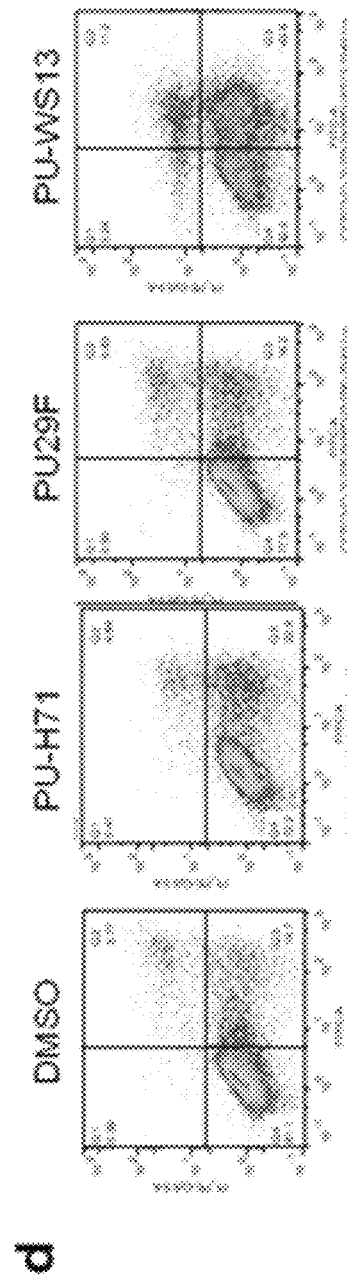
FIG. 11d
Treatment of HER2-overexpressing SKBr3 breast cancer cells with the Grp94 inhibitor PU-WS13 is more potent at killing these cells through apoptosis than is inhibition of Hsp90 alone by PU-29F or pan-Hsp90 inhibition by PU-H71.

Treatment of EGFR-overexpressing PANC-1 cells with the Grp94 inhibitor PU-WS13 is more potent at killing these cells through apoptosis than is inhibition of Hsp90 alone by PU-29F or pan-Hsp90 inhibition by PU-H71.

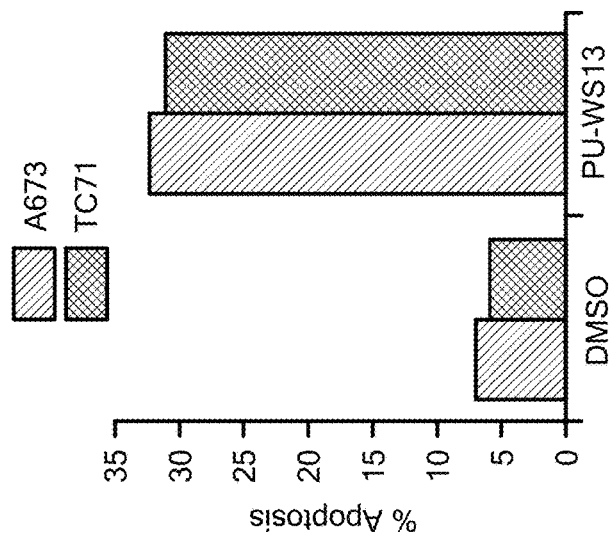
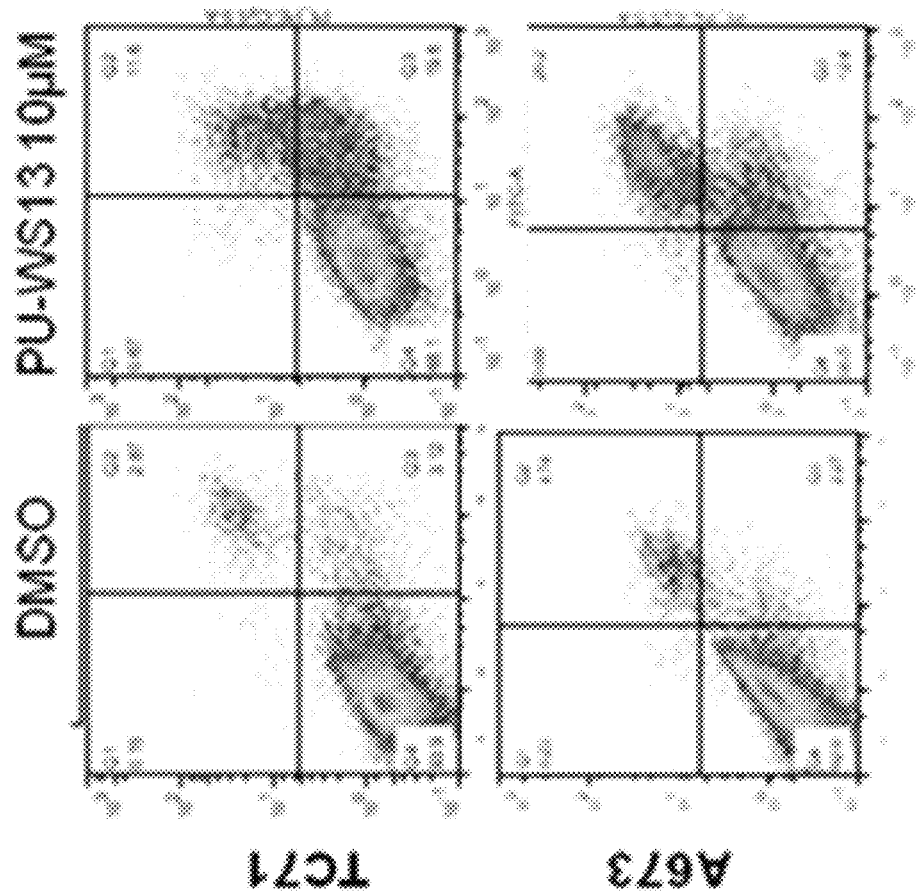
FIG. 16a
FIG. 16b

COMPOUND 40

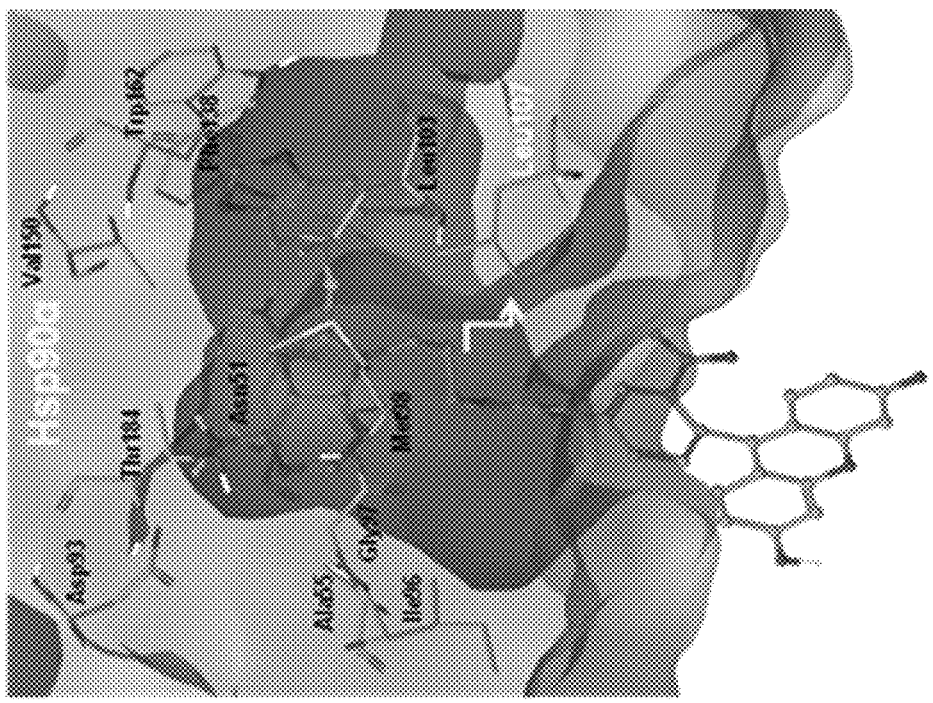
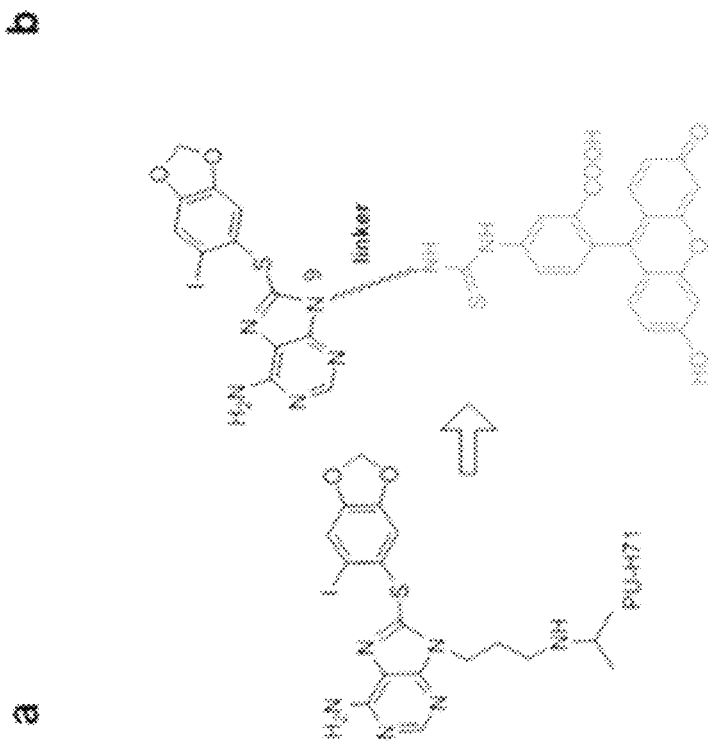
FIG. 21b
FIG. 21a

SELECTIVE GRP94 INHIBITORS AND USES THEREOF

CROSS REFERENCE TO RELATED APPLICATIONS

The present application is the national phase of International Patent Application No. PCT/US2014/051332, filed Aug. 15, 2014, which claims priority to U.S. provisional patent application No. 61/866,932, filed Aug. 16, 2013, the entire contents of which are hereby incorporated by reference.

GOVERNMENT SUPPORT

This invention was made, with government support under AI090501 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 12, 2014, is named 2003080-0708_SL.txt and is 17,757 bytes in size.

FIELD

The disclosure relates to selective Grp94 inhibitors, compositions comprising an effective amount of such compounds, and methods to treat or prevent a condition, such as cancer, comprising administering to an animal in need thereof an effective amount of such compounds.

BACKGROUND

The Hsp90s are a family of molecular chaperones that play important roles in regulating and maintaining the functionality of cells under proteotoxic stress and pathogenic pressure (Workman, P., Burrows, F., Neckers, L. & Rosen, N. Drugging the cancer chaperone Hsp90: combinatorial therapeutic exploitation of oncogene addiction and tumor stress. *Ann. N.Y. Acad. Sci.* 1113, 202-216 (2007)). In humans, cytoplasmic heat shock protein 90 alpha and beta (Hsp90α and β), endoplasmic reticulum (ER) glucose-regulated protein 94 (Grp94) and the mitochondrial tumor necrosis factor receptor-associated protein 1 (Trap-1) are the four known Hsp90 paralogs (Sreedhar, A. S., Kalmar, E., Csermely, P. & Shen, Y. F. Hsp90 isoforms: functions, expression and clinical importance. *FEBS letters*. 562, 11-15 (2004); Johnson, J. L. Evolution and function of diverse Hsp90 homologs and cochaperone proteins. Biochim. Biophys. Acta. 1823, 607-613 (2012)). These proteins are ATP dependent and belong to the GHKL (Gyrase B, Hsp90, Histidine Kinases, MutL) ATPase superfamily, which is characterized by a distinct ATP binding "Bergerat fold" located in the N-terminal domain (NTD) (Chene, P. ATPases as drug targets: learning from their structure. *Nat. Rev. Drug Discov.* 1, 665-673 (2002)). Binding and release of the nucleotide drives the catalytic cycle of the Hsp90s and thereby assists in the refolding of client proteins through a series of association-dissociation catalytic cycles. Occupancy of this regulatory pocket by small molecule inhibitors inactivates Hsp90 chaperone function, and several pan-Hsp90 inhibitors have demonstrated potent reversal of the disease phenotype when tested in models of cancer, neurodegeneration, infection, and inflammatory disease. Due to these therapeutic activities, a select number of these compounds have also moved to the clinic for the treatment of cancers (Jhaveri, K., Taldone, T., Modi, S. & Chiosis, G. Advances in the clinical development of heat shock protein 90 (Hsp90) inhibitors in cancers. *Biochim. Biophys. Acta.* 1823, 742-755 (2012))

Despite considerable interest in the use of pharmacologic Hsp90 inhibitors for the treatment of disease, little is known about the contribution of each paralog to the observed therapeutic benefit. To date, all published studies have used pan-Hsp90 inhibitors to inactivate Hsp90s and the processes that depend on them, making it impossible to correlate the role of individual paralogs with the biological effects. This is particularly unsatisfying, considering that the chaperoning roles of these Hsp90s do not overlap. Thus, for example, while there is a considerable literature on the response of cytosolic Hsp90 to inhibitors, no study satisfactorily differentiates the role of the α and β paralogs. Furthermore, although both Grp94 and Trap-1 are abundant in the cancer cell, little is known about their contribution to the malignant phenotype (Sreedhar, A. S., Kalmar, E., Csermely, P. & Shen, Y. F. Hsp90 isoforms: functions, expression and clinical importance. *FEBS letters*. 562, 11-15 (2004); Johnson, J. L. Evolution and function of diverse Hsp90 homologs and cochaperone proteins. Biochim. Biophys. Acta. 1823, 607-613 (2012); Marzec, M., Eletto, D. & Argon, Y. GRP94: An HSP90-like protein specialized for protein folding and quality control in the endoplasmic reticulum. Biochim. Biophys. Acta. 1823, 774-787 (2012); Chen, B. The HSP90 family of genes in the human genome: Insights into their divergence and evolution. *Genomics* 86, 627-637 (2005)).

In large part the predicament of being unable to study individual paralogs in cancer cells, despite their divergent roles, stems from a lack of suitable tools. While pan-Hsp90 inhibitors, genetic manipulations in yeast and human cells, mutant cell lines, and gene deficient mice have shed light on several Hsp90-dependent cancer mechanisms, many challenges still remain. In particular, strategies that address the biology of Hsp90s and their individual paralogs in an endogenous cellular environment where the chaperones are limiting but not absent (i.e. in un-engineered cancer cell lines and in primary samples) are needed. Ideally, this gap can be filled by chemical tools that probe and manipulate a protein's function in a controlled manner. Such tools would complement traditional biochemical and biological approaches by aiding the molecular characterization of biomolecules both in vitro and within their natural biological contexts.

While useful both as therapeutics and as tools to dissect the cell-specific effects and mechanisms associated with Hsp90 paralogs in select phenotypes, the discovery of paralog specific Hsp90 inhibitors is particularly challenging because of a high degree of conservation in their ATP regulatory ligand binding cavities, the pocket to which the known synthetic ligands bind. Indeed, we and others found that most reported Hsp90 inhibitors bind equally well to the majority of these paralogs (Marzec, M., Eletto, D. & Argon, Y. GRP94: An HSP90-like protein specialized for protein folding and quality control in the endoplasmic reticulum. Biochim. Biophys. Acta. 1823, 774-787 (2012); Schulte, T. W. et al. Interaction of radicicol with members of the heat shock protein 90 family of molecular chaperones. Mol. Endo. 13, 1435-1448 (1999). Crystal structures of the cytoplasmic Hsp90 (α and β) N-terminal domain, either in the apo form or in complex with regulatory nucleotides or small molecules, are essentially superimposable (Immormino, R.

M., Kang, Y., Chiosis, G. & Gewirth, D. T. Structural and quantum chemical studies of 8-aryl-sulfanyl adenine class Hsp90 inhibitors. J. Med. Chem. 49, 4953-4960 (2006); Soldano, K. L., Jivan, A., Nicchitta, C. V. & Gewirth, D. T. Structure of the N-terminal domain of GRP94: Basis for ligand specificity and regulation. J. Biol. Chem. 279, 48330-48338 (2003)). In addition, while slightly different docking orientations were observed for some small molecule ligands when bound to Hsp90 and Grp94, these have, as of yet, failed to translate into appreciable selectivity and specific cellular activity through individual paralog inhibition (Marzec, M., Eletto, D. & Argon, Y. GRP94: An HSP90-like protein specialized for protein folding and quality control in the endoplasmic reticulum. Biochim. Biophys. Acta. 1823, 774-787 (2012); Immormino, R. M. et al. Different poses for ligand and chaperone in inhibitor-bound Hsp90 and GRP94: implications for paralog-specific drug design. J. Mol. Biol. 388, 10331042 (2009); (Duerfeldt, A. S., et al. Development of a Grp94 inhibitor. J. Am. Chem. Soc. 134, 9796-9804 (2012)).

Paradoxically, despite the high degree of sequence conservation in their ATP binding pockets, crystallographic and biochemical studies have shown that when bound to nucleotides, Hsp90α/β, Grp94 and Trap-1 adopt distinctly different conformations and hydrolyze ATP with notably different rates. Specifically, when bound to adenyl imidodiphosphate (AMP-PNP) a non-hydrolyzable ATP analog, the "lids" of the two N-terminal domains (NTD) of the yeast Hsp90α dimer move from the "open" to the "closed" conformation, trapping the bound nucleotide within the ATP binding cavity. The two closed NTDs then meet to form a second dimer interface that supplements the obligatory dimeric interactions contributed by the two C-terminal domains and importantly, aligns the catalytic residues for ATP hydrolysis. In contrast, the NTD "lids" of Grp94 do not close upon nucleotide binding but instead adopt a unique "extended open" conformation that does not cover the ATP binding pocket and does not allow for strong dimeric interactions between NTDs. As a result, nucleotide-bound Grp94 adopts a twisted "V" shape with their NTDs not symmetrically opposed, but, rather, oriented in opposite directions (Ali, M. M. et al. Crystal structure of an Hsp90-nucleotide-p23/Sba1 closed chaperone complex. Nature 440, 1013-1017 (2006); Dollins, D. E., Immormino, R. M. & Gewirth, D. T. Structure of unliganded GRP94, the endoplasmic reticulum Hsp90. Basis for nucleotide-induced conformational change. J. Biol. Chem. 280, 30438-30447 (2005)). In Trap-1, ATP binding leads to a predominantly closed conformation, albeit with kinetics slower than in the cytosolic Hsp90 (Leskovar, A., Wegele, H., Werbeck, N. D., Buchner, J. & Reinstein, J. The ATPase cycle of the mitochondrial Hsp90 analog Trapl. J. Biol. Chem. 283, 11677-11688 (2008)). Nonetheless this is insufficient to commit Trap-1 to nucleotide hydrolysis and is instead followed by re-opening of the chaperone conformation. Together, the biochemical evidence suggests that the overall structure and conformational flexibility of the proteins plays an important role in configuring the ATP-binding sites of these chaperones.

In the present disclosure, we take advantage of the conformational distinctions between the paralogs and use the chemical diversity imprinted into the purine-scaffold class to demonstrate that the identification of Hsp90 paralog-specific ligands is possible. We explain the source of paralog binding specificity using structural and modeling analyses. We then use several of the identified paralog specific inhibitors to provide novel insights into the tumor-specific chaperoning of a client protein by individual Hsp90s.

SUMMARY OF INVENTION

The present disclosure relates to the discovery that paralogs of Hsp90, although very similar, interact with structurally related inhibitors in a very different manner. An understanding of the structural attributes of these inhibitors and their binding to the target proteins has led to the development of inhibitors that are selective for particular paralogs of Hsp90, as described herein. In particular, new compounds that show high specificity for Grp94 have been developed. In some embodiments, Grp94 selective compounds are capable of inhibiting Grp94 without inhibiting the other Hsp90 paralogs, including Hsp90α, Hsp90β and Trap-1. As a result, the selective Grp94 inhibitors of the disclosure can be used in the treatment of various types of cancer. Moreover, the therapeutic benefits can be obtained without a feed-back up-regulation of anti-apoptotic and resistance-mediating heat shock proteins, such as Hsp70.

The disclosure provides evidence that Grp94 has an allosteric binding site that partially overlaps with the ATP/ADP binding site and contains a hydrophobic pocket that is not fully exposed in the other Hsp90 paralogs. Grp94 inhibitors of the disclosure contain chemical moieties that can occupy the allosteric binding site and thus prevent binding of ATP/ADP.

The full length amino acid sequence of human Grp94 (SEQ ID NO:1) is shown in Table 1. As discussed herein, selective Grp94 inhibitors of the disclosure interact with specific amino acids comprising the N-terminal domain (NTD) of Grp94. In particular, Grp94 inhibitors of the disclosure can interact (e.g., make steric and electrostatic contacts) with two specific binding sites of SEQ ID NO:1, referred to herein as "binding site 1" and "binding site 2". Binding site 1 is comprised of at least five amino acids which include Ile247, Val211, Phe199, Met154 and Leu163. Binding site 1 can also include the amino acids Leu159, Tyr 200, and Trp223. Interaction of ligands (e.g., ATP or small molecule inhibitors) with the amino acids comprising binding site 1 are conserved in all four paralogs-Grp94, Hsp90α, Hsp90β, and Trap-1. Binding site 2 is comprised of at least seven amino acids of SEQ ID NO:1, which includes Phe195, Gly198, Val209, Ala202, Leu104, Leu249 and Phe203. Binding site 2 (also referred to herein as the "Grp94 specific binding site"), which is specific for the Grp94 paralog, is located in the cleft region adjoining the ATP/ADP binding site. Notably, access to binding site 2 is blocked by Phe138 in Hsp90α and Hsp90β, and Phe205 in Trap-1. Hence, Grp94 inhibitors of the disclosure are capable of interacting with specific amino acids occupying binding site 2 of the Grp94 NTD, which allows for selective binding to the Grp94 paralog. In some embodiments, Grp94 inhibitors of the disclosure exhibit weaker binding to the other Hsp90 paralogs than Grp94.

Accordingly, in one aspect, the disclosure provides new compounds that exhibit affinity for Grp94 and thus, are capable of inhibiting the biological activity of Grp94. In some embodiments, the Grp94 inhibitors interact with six or more of the amino acids comprising binding site 1 and binding site 2 of the Grp94 NTD. In particular embodiments, the Grp94 inhibitors of the disclosure can interact with six, seven, eight, nine, ten, eleven or twelve of the amino acids comprising binding site 1 and binding site 2 of the Grp94 NTD. In other embodiments, the Grp94 inhibitors of the disclosure interact with six or more amino acids selected from Phe195, Gly198, Val209, Ala202, Ile247, Leu249, Phe203, Leu104, Val211, Phe199, Met154 and Leu163 of SEQ ID NO:1. For instance, the Grp94 inhibitors of the disclosure can interact with six, seven, eight, nine, ten, eleven or twelve of the amino acids selected from Phe195, Gly198, Val209, Ala202, Ile247, Leu249, Phe203, Leu104, Val211, Phe199, Met154 and Leu163 of SEQ ID NO. 1.

In particular embodiments, the Grp94 inhibitors of the disclosure are capable of interacting with three or more of the amino acids in binding site 2 (i.e., the Grp94 selective binding site) of the Grp94 NTD. For instance, the Grp94 inhibitors can interact with three, four, five, six or seven of the amino acids of binding site 2 of the Grp94 NTD. In some such embodiments, the Grp94 inhibitors of the disclosure are capable of interacting with three or more amino acids selected from Phe195, Gly198, Val209, Ala202, Leu104, Leu249 and Phe203 of SEQ ID NO:1. For instance, the Grp94 inhibitors of the disclosure can interact with three, four, five, six or seven amino acids selected from Phe195, Gly198, Val209, Ala202, Leu104, Leu249 and Phe203 of SEQ ID NO:1.

In particular embodiments, the Grp94 selective inhibitors of the disclosure are capable of interacting with the amino acids Ala202, Leu104 and Leu249 of SEQ ID NO:1. In other embodiments, the Grp94 selective inhibitors of the disclosure are capable of interacting with the amino acids Gly198, Val209, Ala202, Leu249 and Phe203 of SEQ ID NO:1. In other embodiments, the Grp94 selective inhibitors of the disclosure are capable of interacting with the amino acids Phe195, Val209, Ala202 of SEQ ID NO:1. In other embodiments, the Grp94 selective inhibitors of the disclosure are capable of interacting with the amino acids Leu104, Val209, Ala202 of SEQ ID NO:1. In still other embodiments, the Grp94 selective inhibitors of the disclosure are capable of interacting with the amino acids Phe195, Leu249 and Leu104 of SEQ ID NO:1. In still other embodiments, the Grp94 selective inhibitors of the disclosure are capable of interacting with the amino acids Phe195, Gly198 and Val209 of SEQ ID NO:1. In still other embodiments, the Grp94 selective inhibitors of the disclosure are capable of interacting with the amino acids Leu104, Leu249 and Phe203 of SEQ ID NO:1.

The Grp94 inhibitors of the disclosure can be purine-scaffold compounds or can be based on scaffolds related to purine (e.g., fused amino pyridine compounds). All Grp94 inhibitors that contain a purine scaffold or a scaffold related to purine will be referred to hereinafter as a purine-scaffold inhibitor or a purine-scaffold compound. In some embodiments, the Grp94 inhibitors are adenine scaffold inhibitors. In some embodiments, the Grp94 inhibitors are adenine scaffold compounds.

In particular embodiments, the purine-scaffold (e.g., adenine-scaffold) inhibitors can be substituted at the 8-position with a linker group bonded to an aryl or heteroaryl group. For instance, the substituent bonded to the 8-position of the purine ring can be an arylsulfanyl group, an arylsulfoxyl group, an arylsulfonyl group, a benzyl group, an arylcarbonyl group, an aniline group or a phenoxy group. In some such embodiments, the aryl or heteroaryl group at the 8-position of the purine ring interacts with amino acids comprising binding site 1 and binding site 2 of SEQ ID NO:1. For instance, the aryl or heteroaryl group at the 8-position of the purine ring can interact with six, seven, eight, nine, ten, eleven or twelve of the amino acids selected from Phe195, Gly198, Val209, Ala202, Ile247, Leu249, Phe203, Leu104, Val211, Phe199, Met154 and Leu163 of SEQ ID NO. 1. In other embodiments, the aryl or heteroaryl group at the 8-position of the purine ring can interact with three, four, five, six or seven amino acids selected from Phe195, Gly198, Val209, Ala202, Leu104, Leu249 and Phe203 of SEQ ID NO:1. The purine portion of the purine-scaffold Grp94 inhibitors of the disclosure generally interacts with amino acids that are conserved in all Hsp90 paralogs. For instance, the purine portion can form favorable interactions with Asp149, Thr245, Ala111, Gly153, Lys114, Asp110, Ala108 and Asn107 of SEQ ID NO:1.

In some embodiments, the Grp94 inhibitors of the disclosure are water soluble. As used herein, water soluble is defined as having a solubility of above 0.5 mg/mL in distilled water at ambient temperatures. In some embodiments, the water solubility of the purine-scaffold inhibitors of the disclosure can be greater than 3 mg/mL, greater than 4 mg/mL, greater than 5 mg/mL, greater than 10 mg/mL, greater than 20 mg/mL, or greater than 40 mg/mL in distilled water at ambient temperatures. As will be discussed herein, the purine-scaffold inhibitors of the disclosure can be formulated as salts to increase their water solubility.

In one embodiment, the Grp94 inhibitor of the disclosure is a compound of Formula (I). In another embodiment, the Grp94 inhibitor of the disclosure is a compound of Formula (II). In another embodiment, the Grp94 inhibitor of the disclosure is a compound of Formula (III). In another embodiment, the Grp94 inhibitor of the disclosure is a compound of Formula (IV). In another embodiment, the Grp94 inhibitor of the disclosure is a compound of Formula (V).

Grp94 inhibitors of the disclosure are highly selective for Grp94 relative to the other Hsp90 paralogs. In some embodiments, the Grp94 inhibitors exhibit a greater than 10-fold preference for Grp94 over Hsp90α, Hsp90β and/or Trap-1. In other embodiments, the Grp94 inhibitors exhibit a greater than 20-fold preference for Grp94 over Hsp90α, Hsp90β and/or Trap-1. In yet other embodiments, the Grp94 inhibitors exhibit a greater than 50-fold preference for Grp94 over Hsp90α, Hsp90β and/or Trap-1. In yet other embodiments, the Grp94 inhibitors exhibit a greater than 100-fold preference for Grp94 over Hsp90α, Hsp90β and/or Trap-1. In yet other embodiments, the Grp94 inhibitors exhibit a greater than 500-fold preference for Grp94 over Hsp90α, Hsp90β and/or Trap-1. In some embodiments, the selectivity of the Grp94 inhibitors for binding to Grp94 over the other Hsp90 paralogs is measured using a fluorescence polarization assay. For example, the selectivity may be measured in a fluorescence polarization assay as described herein.

Grp94 inhibitors can be used to treat a variety of Hsp90 cancers including but not limited to colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, leukemias, myelomas (e.g., multiple myeloma), myeloproliferative neoplasms and gynecologic cancers including ovarian, cervical, and endometrial cancers. In some embodiments, the Grp94 inhibitor can be used in combination with radiation therapy. In other embodiments, the Grp94 inhibitor can be used in combination with a fluoropyrimidine-based or platinum-based chemotherapy.

In particular embodiments, the Grp94 inhibitors of the disclosure can be used to treat human epidermal growth factor receptor 2 (HER2) dependent cancers such as breast cancer, ovarian cancer, gastric cancer, esophageal cancer and non-small-cell lung cancers. In some such embodiments, the Grp94 inhibitors of the disclosure can be used in combination with a therapeutic reagent that interferes with the HER2 receptor (e.g., trastuzumab (herceptin)).

In some embodiments, the Grp94 inhibitors of the disclosure can be used to treat epidermal growth factor receptor (EGFR) dependent cancers such as pancreatic cancer, neck cancer, breast cancer, ovarian cancer, cervical cancer, bladder and esophageal cancers. In some such embodiments, the Grp94 inhibitors of the disclosure can be used to treat endocrine-resistant breast and ovarian cancers (e.g., tumors resistant to tamoxifen). The Grp94 inhibitors of the disclosure may be used in combination with an antiestrogen such as a selective estrogen receptor modulator (e.g., tamoxifen) or an aromatase inhibitor (e.g., exemestone or anastrozole).

In some embodiments, the Grp94 inhibitors of the disclosure can be used to treat EGFR dependent cancers that are resistant to therapy with EGFR inhibitors. In one such embodiment, the cancer is pancreatic cancer that is resistant to therapy with EGFR inhibitors. The Grp94 inhibitor can be used in combination with an EGFR inhibitor. In particular embodiments, a Grp94 inhibitor is used in combination with the EGFR inhibitor erlotinib in the treatment of pancreatic cancer.

In other embodiments, the Grp94 inhibitors of the disclosure can be used to treat Insulin growth factor 1 receptor (IGF1R) dependent tumors. In particular, the Grp94 inhibitors of the disclosure can be used in treating cancers with altered expression of the IGFIR where the receptor is necessary for pathogenesis and tumor progression. In a particular embodiment, the IGFIR dependent cancer is Ewing's sarcoma. In another particular embodiment, the IGFIR dependent tumor is ovarian cancer.

The Grp94 inhibitors of the present disclosure can also be used to treat autoimmune diseases, inflammatory and neurodegenerative diseases, rheumatoid arthritis and diabetes. In some such embodiments, the Grp94 inhibitors of the disclosure have an anti-angiogenic effect in type 1 diabetes. In particular, the Grp94 inhibitors of the disclosure can display an anti-angiogenic effect on human endothelial cells.

The Grp94 inhibitors of the disclosure are capable of modulating inflammatory responses through the inhibition of the Grp94 chaperoning of Toll-like receptors (TLRs), particularly TLR9. In particular embodiments, the Grp94 inhibitors of the disclosure can be used in the treatment of inflammatory diseases such as lupus erythematosus, rheumatoid arthritis, ischemia reperfusion injury, atherosclerotic lesions, antibiotic associated colitis, and septic shock.

As described herein, the Grp94 inhibitors of the disclosure, when provided at a low enough dose, can be administered to cancer patients without a feed-back up-regulation of anti-apoptotic and resistance-mediating heat shock proteins, such as Hsp70. As such, the Grp94 inhibitors of the disclosure can be administered to patients without concomitant administration of an Hsp70 inhibitor. Hence, in accordance with one aspect of the disclosure, methods of treating cancer by treating a human patient suffering from cancer without up-regulation of Hsp70 are provided. Such methods involve administration of a Grp94 inhibitor of the disclosure in an amount sufficient to inhibit Grp94 without inhibiting other Hsp90 paralogs (i.e., Hsp90α, Hsp90β and/or Trap-1). In one embodiment, a Grp94 inhibitor of the disclosure can be administered to a cancer patient in an amount sufficient to inhibit Grp94 without inhibiting Hsp90α. In one embodiment, a Grp94 inhibitor of the disclosure can be administered to a cancer patient in an amount sufficient to inhibit Grp94 without inhibiting Hsp90β. In another embodiment, a Grp94 inhibitor of the disclosure can be administered to a cancer patient in an amount sufficient to inhibit Grp94 without inhibiting TRAP-1. In another embodiment, a Grp94 inhibitor of the disclosure can be administered to a cancer patient in an amount sufficient to inhibit Grp94 without up-regulation of Hsp70.

Furthermore, the Grp94 inhibitors of the disclosure are particularly effective in inducing apoptosis in cancer cells that overexpress tyrosine kinase receptors, particularly HER2 and EGFR. The ability of the Grp94 inhibitors to induce apoptosis stems in part from the inventors' discoveries that Grp94 has a role in maintaining high density HER2 and EGFR species at the plasma membrane. The associated aberrant signaling of these overexpressed proteins also requires Grp94. The present invention encompasses the recognition that Grp94 inhibition of HER2 and EGFR overexpressing tumors are highly sensitive to Grp94 inhibition and readily undergo apoptosis upon administration of a selective Grp94 inhibitor. Accordingly, in one aspect, methods of inducing apoptosis of HER2 and EGFR overexpressing tumors are provided by administration of a Grp94 inhibitor of the disclosure.

In another aspect the disclosure provides a versatile experimental assay that can test rapidly and accurately the binding affinity of all major Hsp90 paralogs and has a testing range that spans low nanomolar to millimolar binding affinities. The assay relies on using novel fluorescently labeled probes in fluorescence polarization (FP) assays. The fluorescently labeled probes, referred to herein as FP probes or FP tracers, are capable of binding to the four Hsp90 paralogs, Grp94, Hsp90α, Hsp90β and Trap-1, and therefore, can be used to determine the affinity and selectivity of Hsp90 inhibitors to the four Hsp90 paralogs. Exemplary new FP probes are described herein.

BRIEF DESCRIPTION OF THE FIGURES

FIG. 1a shows structures of select Grp94 selective compounds and their subtype classification. FIG. 1b shows binding affinity of Grp94 selective compound for the four Hsp90 paralogs. Data are presented as mean±s.d. (n=3). Values for PU-H71, a pan-Hsp90 inhibitor are presented for comparison. FIG. 1c shows Selectivity profile analysis for the select ligands.

FIG. 2a shows that Grp94 Apo adopts an "open" conformation similar to that observed in all Hsp90 N structures. FIG. 2b shows the "partially closed" conformation seen in the Grp94N:PU-H54 complex, which is characterized by the incorporation of strand 1 into a longer helix 1 and the downward rotation of helix 1 away from the core of the N-domain. Helices 4 and 5 reorient to straddle the repositioned helix 1. FIG. 2c shows the "extended open" lid configuration seen in all nucleotide-bound structures of Grp94N. Steric and electrostatic clashes contributed by the phosphate moieties of the nucleotide cause the Helices 1, 4, and 5 open up to fully expose ATP binding pocket. FIG. 2d shows the overlay of Hsp90- and Grp94-bound PU-H54 reveals an 80° torsional rotation about the sulfanyl linker (highlighted in red) when inserted into the Grp94-specific channel. FIG. 2e shows the interactions of PU-H54 bound to Grp94 showing the increased hydrophobic stabilization of the 8-aryl group when bound into Site 2.

FIG. 4 shows functionalities that confer Grp94- and Hsp90α/β selectivity: FIG. 4a and FIG. 4d show the general scheme portraying the two Grp94- and the two Hsp90α/β-selective ligand subtypes. FIG. 4b and FIG. 4c show interactions of the two Grp94-selective ligand subtypes with the paralogs that confer selectivity and affinity for Grp94 and lessen binding to Hsp90α, Hsp90β and Trap-1. FIG. 4e and FIG. 4f show interactions of the two Hsp90α/β-selective ligand subtypes with the paralogs that lessen binding to Grp94 and Trap-1 and confer selectivity and affinity for Hsp90α/β.

FIG. 5 shows Grp94 and Hsp90α/β selective compounds exhibit selective paralog inhibition of IGF-II secretion by differentiated C2C12 cells. FIG. 5a shows differentiated C2C12 cells were treated for 24 hrs with the indicated compounds. IGF-II secretion in the media from each experimental condition was measured and quantified against vehicle only treated cells (DMSO). Data are presented as mean±SEM (n=4). FIG. 5b shows representative Western blot of cells as in FIG. 5a. Only pan-Hsp90 inhibitors (geldanamycin (GM) and PU-H71) and the Hsp90 inhibitor (PU-29F) induce Hsp70 and degrade AKT, while the Grp94 inhibitor (PU-WS13) has no effect on these Hsp90-mediated functions. FIG. 5d (left) shows representative confocal microscopy image of HEK293 cells transfected with Empty vector or HA-TLR9 and stained as indicated. FIG. 5d (right) shows representative western blot confirming HA-TLR9 transfection of cells as indicated in the left panel. FIG. 5f shows representative image of HEK293 cells transfected with HA-TLR9 (green) and treated for 24 h with the indicated concentrations of PU-WS13 or PU-29F. Only the pan-Hsp90 inhibitors (GM, PU-H71) both inhibit TLR9 trafficking and induce Hsp70. The Hsp90 inhibitor (PU-29F) fails to inhibit TLR9 trafficking while it induces Hsp70. The Grp94 inhibitor (PU-WS13) inhibits TLR9 trafficking but fails to induce Hsp70.

FIG. 6 shows that HER2 is sensitive to Hsp90 paralog inhibition in a tumor-specific manner. FIGS. 6a-c data are presented as mean±s.d. (n=3).

FIG. 7 shows that HER2 is regulated by the Hsp90 paralogs in a cellular compartment and a cell-specific manner. FIG. 7a-1 shows representative western blot of SKBr3 and MCF7 cells treated for 24 h with the pan-Hsp90 inhibitor PU-H71 (1 µM), vehicle (DMSO), PU-WS13 (15 µM) or the indicated concentrations of the Grp94-selective inhibitors PU-WS13 and PU-H39. FIG. 7a-2 shows representative western blot of SKBr3 and MCF7 cells treated for 24 h with the pan-Hsp90 inhibitor PU-H71 (1 µM), vehicle (DMSO) or the indicated concentrations of the Hsp90α/β selective inhibitor PU-29F, PU-20F and PU-11. FIG. 7b (top) shows representative western blot of SKBr3 and MCF7 cells in which Grp94 was knocked-down by means of three distinct siRNAs generated against Grp94 or by a control siRNA (scramble). For comparison cell were also treated for 24 h with the pan-Hsp90 inhibitor PU-H71 (1 µM), vehicle (DMSO) and the Grp94 inhibitors PU-WS13 (15 µM) and PU-H39 (40 µM). FIG. 7b (bottom) shows representative western blot of SKBr3 and MCF7 cells in which Hsp90 was knocked-down by means of eight distinct siRNAs generated against the indicated Hsp90 paralogs or by a control siRNA (scramble). For comparison cell were also treated for 24 h with the pan-Hsp90 inhibitor PU-H71 (1 µM), vehicle (DMSO) and the Hsp90 inhibitors PU-29F (25 µM) and PU-20F (30 µM).

FIG. 8 shows Grp94 and Hsp90 regulate distinct HER2 functions in HER2-overexpressing cancer cells. FIG. 8e shows representative affinity purification blot and the correlative analysis between Grp94 and HER2 levels in complexes isolated from extracts in which Grp94 levels were first reduced by IP with the indicated antibodies. FIG. 8f and FIG. 8g show fluorescence microscopy images of SKBr3 cells treated for 4 h with vehicle or inhibitors and then stained with the indicated markers upon fixation and permeabilization. FIG. 8h and FIG. 8i show representative WB of SKBr3 cells treated for the indicated times with 20 µM of PU-WS13 or PU-29F. Proteins in membrane and cytosolic fractions were plotted against the time of treatment. Data are presented as mean±SEM (n=3). FIG. 8j shows schematic representation of changes in both HER2 structure and function that occur at the plasma membrane of SKBr3 cells upon Grp94 inhibition.

FIG. 10 shows Grp94 inhibition alone is sufficient to induce apoptosis in and reduce the viability of HER2 overexpressing breast cancer cells. FIG. 10c shows cell killing (subG1 population) was determined in SKBr3 cells treated for the indicated times with PU-WS13 (15 µM). FIGS. 10d and 10e show representative WB of cancer cells treated for 24 h with PU-WS13 or vehicle.

FIG. 11 shows Grp94 but not Hsp90 inhibition alone is sufficient to induce death of HER2-overexpressing cells. FIGS. 11a and 11b show representative western blots of HER2-overexpresssing cells treated for 24 h with the pan-Hsp90 inhibitor PU-H71 (1 µM), vehicle (DMSO) or the indicated concentrations of the Grp94 selective inhibitor PU-WS13 or Hsp90α/β selective inhibitors PU-29F, PU-20F and PU-11. Cleaved PARP (cPARP) and cleaved caspase-3 (cCaspase-3) levels were monitored to demonstrate induction of apoptosis or the lack of it. β-actin, loading control. Hsp70, specificity control. Hsp70 induction for Hsp90 inhibitors indicates inhibition of the cytosolic Hsp90 at the tested concentrations. Lack or minimal Hsp70 induction for Grp94 inhibitors indicates no inhibition of the cytosolic Hsp90 at the tested concentrations. FIG. 11c shows HER2++ breast cancer cells were treated for 72 h with the Hsp90α/β selective inhibitor PU-29F or the Grp94 selective inhibitor PU-WS13 and cell viability was assessed using a viability assay that quantifies ATP levels. Y-axis values below zero indicate killing of the initial cell population. FIG. 11d shows double staining with Annexin V and 7AAD indicates induction of apoptosis following treatment of the SKBr3 HER2-overexpressing cells for 48 h with PU-WS13 (10 µM).

FIG. 14 shows that EGFR overexpressing cancer cells are sensitive to the Grp94 selective inhibitor PU-WS13.

FIG. 16 shows that the Grp94 selective inhibitor PU-WS13 induces apoptosis in IGF1R overexpressing Ewing sarcoma cell lines (FIG. 16a). Double staining with Annexin V and 7AAD indicates induction of apoptosis (FIG. 16b).

FIG. 21a shows the strategy for designing FP probes based on the Hsp90 inhibitor PU-H71. FIG. 21b shows probe 43a docked into the HSP90α ATP binding pocket (PDB ID: 2FWZ) as generated by Glide (version 5.0). Modeling shows potential steric clach between the probe and Leu107 for linkers containing less than 3 carbons.

DETAILED DESCRIPTION OF THE INVENTION

Figure 2F:
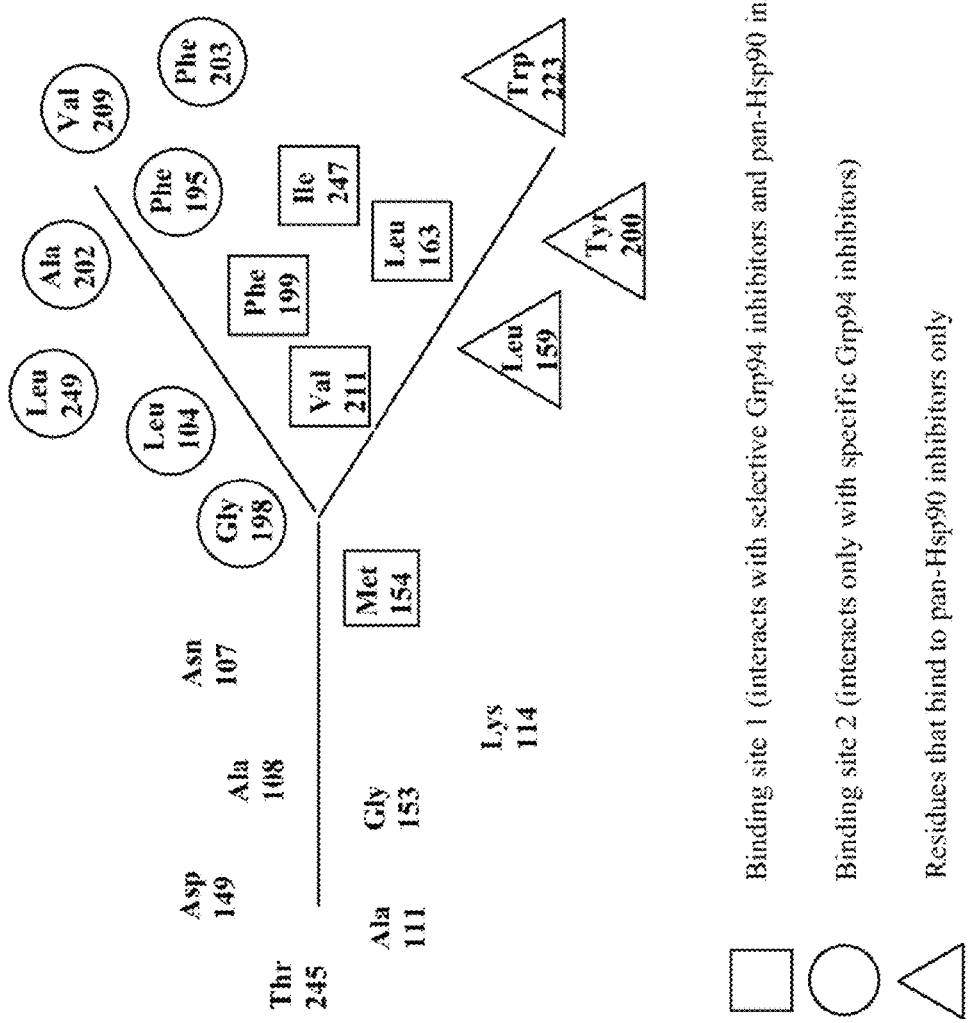
FIG. 2f shows a simple two-dimensional schematic showing approximate locations of the amino acids of binding site 1 and binding site 2 of Grp94.

The present disclosure provides, among other things, Grp94 selective inhibitors. These Grp94 selective inhibitors are capable of inhibiting Grp94 without inhibiting the other Hsp90 paralogs, including Hsp90α, HSP90β and Trap-1. Accordingly, the Grp94 inhibitors of the disclosure can antagonize the chaperone function of Grp94 without inhibiting the chaperone function of the other Hsp90 paralogs, including Hsp90α, HSP90β and Trap-1. The compounds of the disclosure can be used in therapeutic methods by administering a therapeutically effective amount of a compound of the disclosure to an individual, including a human, in need of treatment for cancer, a neurodegenerative disease, an autoimmune disease, an inflammatory disease or other condition for which Grp94 inhibition is relevant. In particular embodiments, the Grp94 inhibitors of the disclosure can be administered at a dosage that inhibits Grp94 without inhibiting the biological activity (e.g., chaperone function) of Hsp90α, HSP90β and/or Trap-1.

As used in this application, the term "treatment" refers to delaying the onset of symptoms, reducing the severity or delaying the symptomatic progression of cancer, neurodegenerative disease or other condition in the individual. A cure of the disease is not required to fall within the scope of treatment. Further, it will be appreciated that the specific results of these treatment goals will vary from individual to individual, and that some individuals may obtain greater or lesser benefits than the statistical average for a representative population. Thus, treatment refers to administration of composition to an individual in need, with the expectation that they will obtain a therapeutic benefit.

The term "administering" refers to the act of introducing into the individual the therapeutic compound. In general, any route of administration can be used. Thus, administration by oral, intrathecal, intravenous, intramuscular or parenteral injection is appropriate depending on the nature of the condition to be treated. Administration may also be done to the brain by inhalation because there is a compartment at the upper side of the nose that connects with the brain without having the blood brain barrier capillaries. Compounds that do not cross the blood brain barrier are preferred for this mode of administration, although this characteristic is not strictly required.

The term "therapeutically effective amount" encompasses both the amount of the compound administered and the schedule of administration that on a statistical basis obtains the result of preventing, reducing the severity or delaying the progression of the disease in the individual. As will be appreciated, preferred amounts will vary from compound to compound in order to balance toxicity/tolerance with therapeutic efficacy and the mode of administration.

5.1 Identification of Grp94 Selective Binding Site

To identify paralog specific Hsp90 inhibitors, an in-house generated library of over 130 purine-scaffold (PU)-compounds in a fluorescence polarization (FP) based assay to test for binding to recombinant Hsp90α and Grp94. FP methods described herein make use of fluorescently labeled probes (tracers) that bind to the different Hsp90 paralogs. Thus, one aspect of the present invention is the provision of fluorescently labelled Grp94 inhibitors, wherein any compound described herein is derivatized with a fluorescent label. Methods of making such labelled compounds are described herein and in International Patent Publication No. WO/2013/009657, the entire contents of which is hereby incorporated by reference. The present invention also encompasses radiolabelled analogs of provided compounds. Methods of making such radiolabelled compounds are known in the art, for example in International Patent Publication No. WO/2013/009655, the entire contents of which is hereby incorporated by reference.

Potential inhibitors of the respective paralogs are determined by measuring the ability of the inhibitor to disrupt binding of the fluorescently labeled probe to the specific Hsp90 paralog. The present invention provides a series of new fluorescently labeled probes are described that can bind to all four Hsp90 paralogs. Accordingly, competition assays can be conducted using a single fluorescently labeled probe for each of the different Hsp90 paralogs being analyzed. Alternatively, more than one labeled probe can be used in the binding assays. For instance, the probe Cy3B-GM was used in determining the binding of small molecule inhibitors to Hsp90α, Hsp90β and Grp94 while the fluorescently labeled probe PU-FITC3 was used in determining the binding of small molecule inhibitors to Trap-1. The structures of Cy3B-GM and PU-FITC3 are shown below:

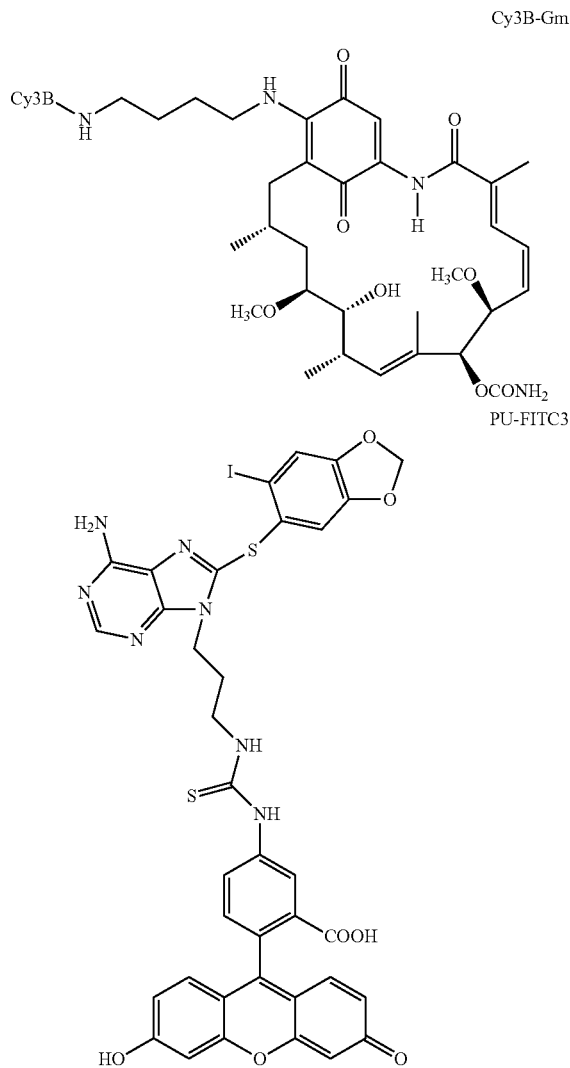

Figures 1A, 1B:
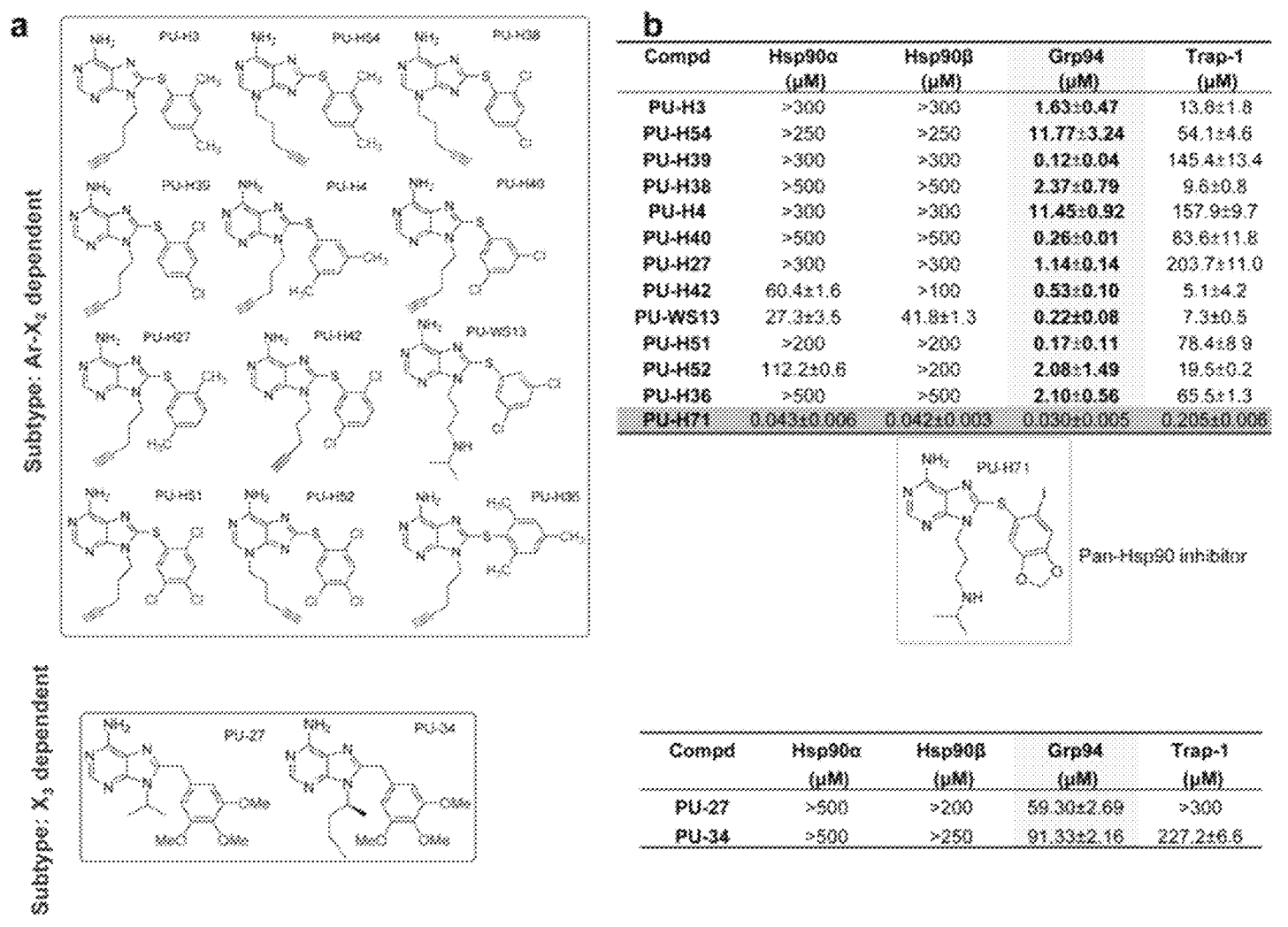
Figures 1, 7A:
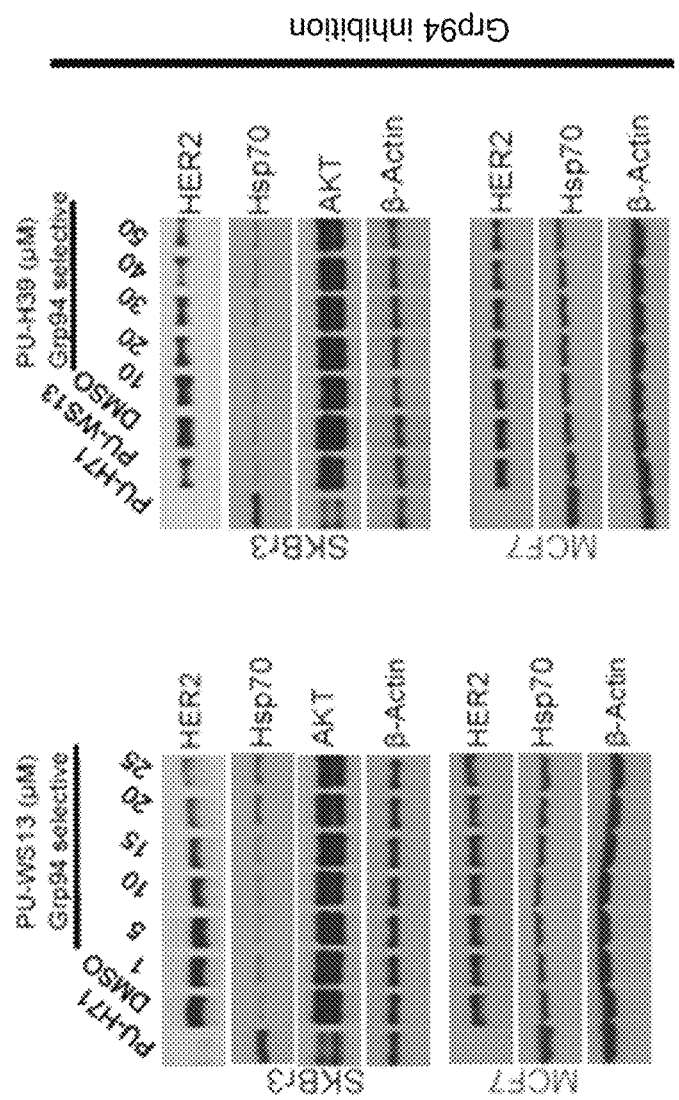

Select derivatives were also analyzed for binding to Hsp90β and Trap-1. The purine-scaffold library was designed with bias for binding to the Hsp90 Bergerat-type pockets. As expected from the high analogy in the Hsp90 ATP-binding pockets, a majority of the tested compounds exhibited similar affinities for the two paralogs and comprised chemical spaces of little or no selectivity. Nonetheless, a chemical space with selectivity for Grp94 was identified. The structures of these compounds as well as their binding affinity to the different paralogs of HSP90 are shown in FIG. 1. Importantly, select compounds of the Grp94 selective chemical space exhibited greater than 100-fold preference for Grp94 over Hsp90α/β and a 10- to 100-fold preference over Trap-1.

Figure 3B:
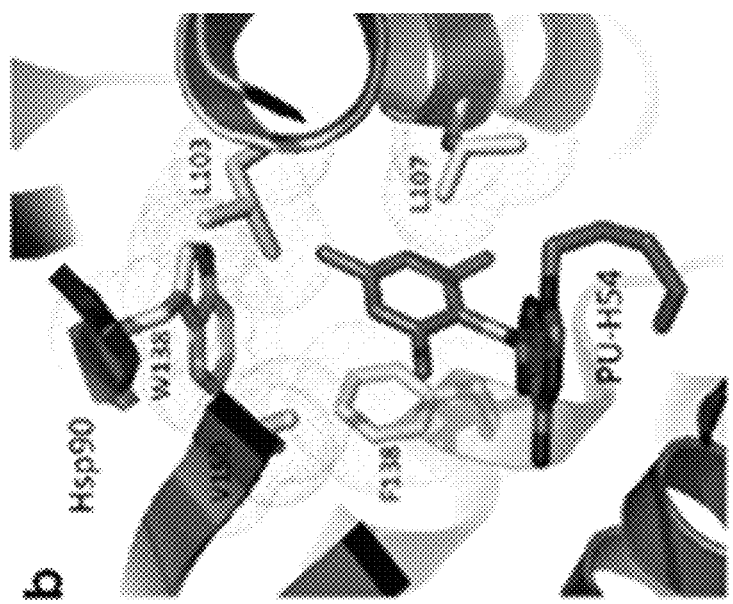
FIGS. 3a and 3b show PU-H54 bound to Site 1 of Hsp90α NTD. The purine scaffold maintains all previously observed purine-protein contacts, and the 8-aryl group extends upwards into a hydrophobic channel between helix 3 and the beta sheet core where it is sandwiched into Site 1, which is formed by the non-polar side chains of Leu107 on one side and Phe138 on the other. The pent-4-ynyl tail at the N3 position packs beneath the purine ring, as has been observed previously for this substituent. The asymmetric 8-aryl group of PU-H54 adopts both the s-trans (25%) and s-cis (75%) configurations in the crystal structure, giving rise to a pseudosymmetric 8-aryl ring in the binding pocket.
Figure 3A:
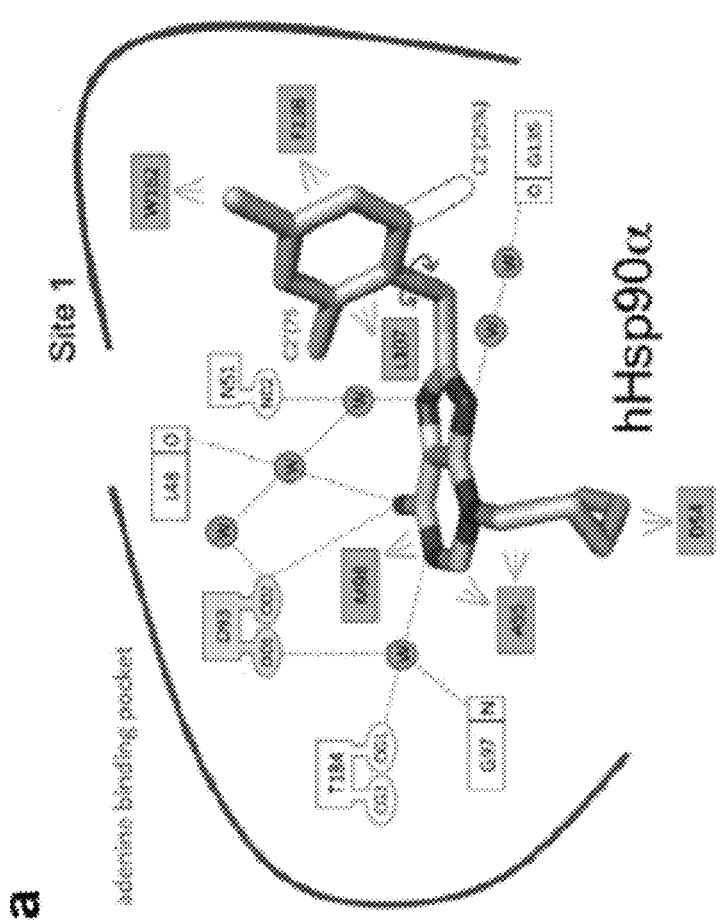
Figure 3C:
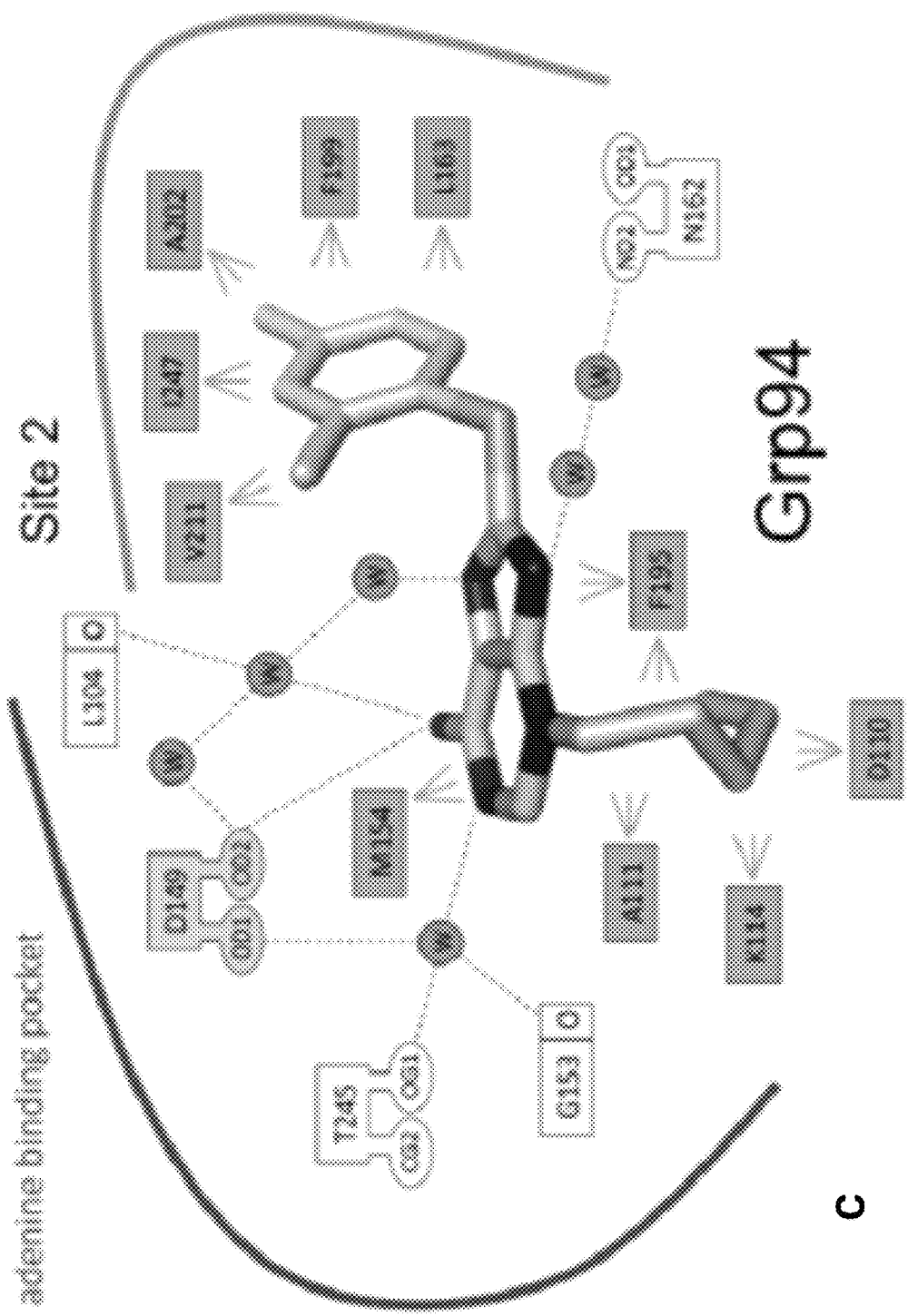
FIG. 3c shows PU-H54 bound to Grp94. The structure of PU-H54 bound to Grp94 shows that while the purine moiety of the ligand maintains contacts with conserved residues in the ATP pocket, the 8-aryl group adopts a strikingly different conformation compared to that of the Hsp90-bound PU-H54, specifically a "backwards" orientation. Concurrent with this backwards pose of the ligand, Phe199 of Grp94 swings away from the binding pocket by 4 Å to expose a deep, almost completely hydrophobic cleft. The hydrophobic cleft is lined by binding site 2 amino acids Phe195, Gly198, Val209, Ala202, Leu104, Leu249, and Phe203 as well as part of binding site 1 amino acids Phe199, Ile247, Val211, Met154 and Leu163.
Figures 2, 7A:
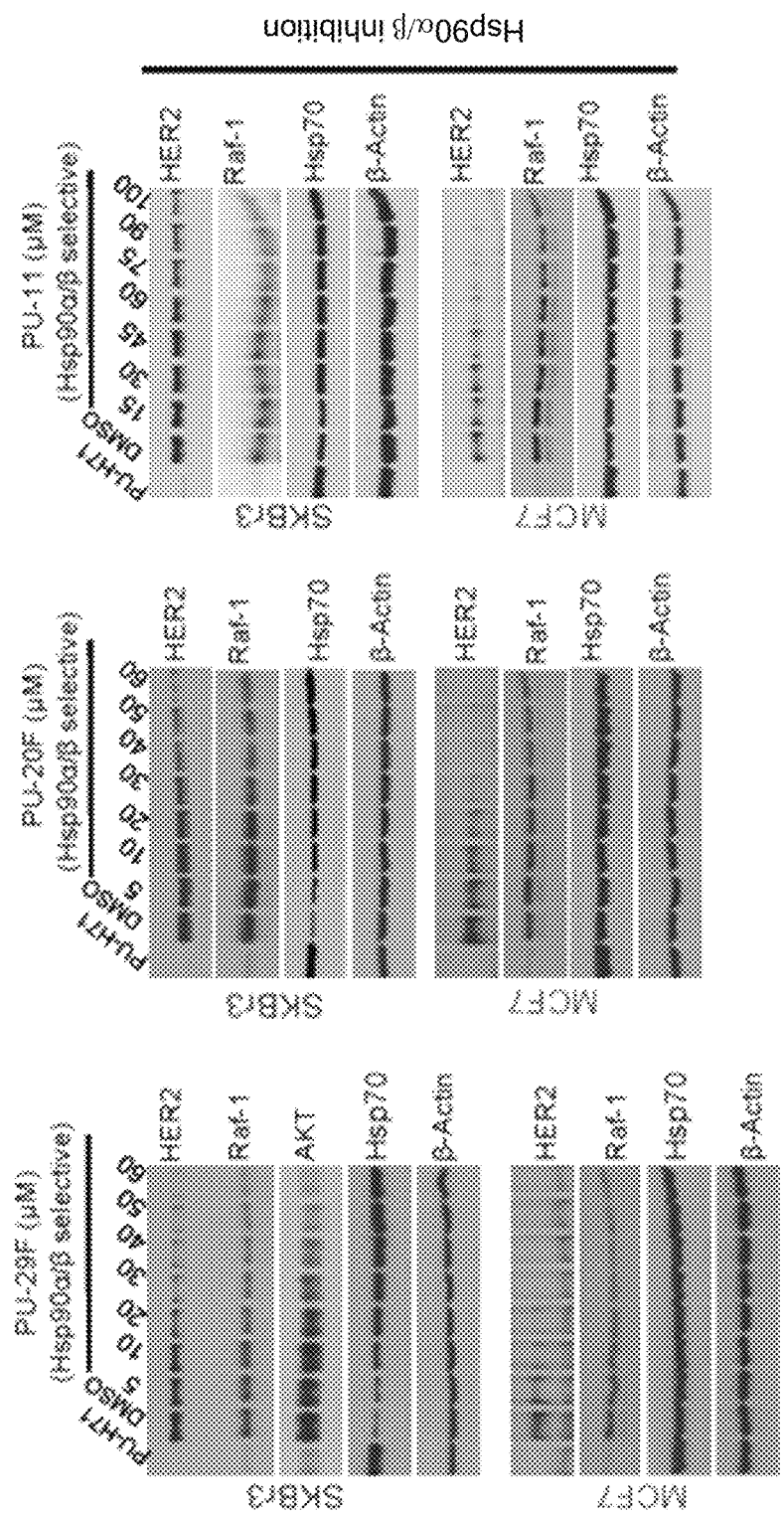
FIG. 2 shows that PU-H54 unveils a novel drugable pocket in Grp94.
FIG. 7a shows that Grp94 inhibition leads to reduced steady-state levels of HER2 in SKBr3 but not in MCF7 cells, whereas Hsp90 inhibition downregulates HER2 in both SKBr3 and MCF7 cells.

Despite the strong Grp94 selectivity uncovered in the screening experiments, modeling of these compounds into the ATP binding pockets of existing structures of Grp94 and Hsp90 did not reveal significant differences that could account for the observed binding selectivity. Therefore, the structure of the Grp94-specific ligand PU-H54 in complex with the NTD fragment of both Grp94 and human Hsp90α (Grp94N and Hsp90 NTD, respectively) was determined (FIGS. 2 and 3). In agreement with previous crystal structures, the tertiary structure of Hsp90 in complex with PU-H54 was essentially identical to that of all other hHsp90N-ligand complexes (Immormino, R. M., Kang, Y., Chiosis, G. & Gewirth, D. T. Structural and quantum chemical studies of 8-aryl-sulfanyl adenine class Hsp90 inhibitors. *J. Med. Chem.* 49, 4953-4960 (2006)) (FIG. 2a, b). While inserted into this pocket, PU-H54 lacks X2-Ar substituents that would confer it strong binding, providing an explanation for the low affinity of this ligand for Hsp90 (FIG. 1b).

In the structure of the Grp94:PU-H54 complex, on the other hand, the helix 1,4,5 "lid" region in Grp94 adopted a novel "partially closed" conformation, whereby strand 1 and helix 1 were pulled away from the core of the N domain, and helices 4 and 5 shifted upwards to straddle the top of helix 1 (FIG. 2a-c). These rearrangements also repositioned helix 3 of Grp94, resulting in a slightly larger ATP binding pocket. The structure of PU-H54 bound to Grp94 showed that while the purine moiety of the ligand maintained contacts with conserved residues in the ATP pocket (FIG. 2c), the 8-aryl group adopted a strikingly different conformation compared to that of the Hsp90-bound PU-H54 (FIG. 2d). Overlaying the Hsp90- and Grp94-bound PU-H54 ligands revealed an ~80° torsional rotation of the 8-aryl group about the sulfanyl linker, where the Hsp90-bound ligand adopted the "forward" rotation, and the Grp94-bound ligand adopted a novel "backwards" rotation (FIG. 2d). Concurrent with this backwards pose of the ligand, Phe199 of Grp94 swings away from the binding pocket by 4 Å to expose a deep, almost completely hydrophobic cleft (FIG. 2e—Not all amino acid residues of the binding site are depicted).

For convenience of description, we have divided the hydrophobic cleft into two distinct binding sites referred to as "binding site 1" and "binding site 2" of the NTD of Grp94. The full length sequence of human Grp94 is shown as SEQ ID NO:1 in Table 1, below. See also U.S. Pat. Nos. 7,991,601 and 7,589,174. The sequence of the N-terminal Domain of human Hsp90α (amino acids 1-236) is shown as SEQ ID NO:2 in Table 1. The sequence of the N-terminal Domain of human Hsp90 β (amino acids 1-233) is shown as SEQ ID NO:3 in Table 1. The full length sequence of human TRAP-1 is shown as SEQ ID NO:4 in Table 1. A simple two-dimensional schematic showing approximate locations of the amino acids of binding site 1 and binding site 2 is shown in FIG. 2f Binding site 1 is lined by at least the amino acids Ile247, Val211, Phe199, Met154 and Leu163 of SEQ ID NO:1. Binding site 1 can also include the amino acids Leu159, Trp223, and Tyr200 of SEQ ID NO:1 (not shown). Notably, interaction of ligands (e.g., ATP or small molecule inhibitors) with the amino acids comprising binding site 1 are conserved in Hsp90α, Hsp90β, and Trap-1. Binding site 2 is lined by the amino acids Phe195, Gly198, Val209, Ala202, Phe203, Leu104, and Leu249 of SEQ ID NO:1. A similar cavity composed of the equivalent, conserved, residues of binding site 2 is also present in the other Grp94 paralogs but access to binding site 2 is blocked by Phe138 in Hsp90α and Hsp90β, and Phe205 in Trap-1. Accordingly, binding site 2 of SEQ ID NO:1 is a Grp94 specific binding site. The hydrophobic X2-Ar of Grp94-bound PU-H54 is inserted into this newly-revealed non-polar binding site 2 and makes stabilizing contacts with at least 5 of its residues. In FIG. 2f, the residues Leu159, Tyr200, and Trp223

(marked in triangles) do not interact with the Grp94 selective inhibitors of the disclosure. However, these residues are capable of interacting with pan-Hsp90 inhibitors (e.g., PU-H71). Notably, residues Asp149, Asn107, Thr245, Ala111, Gly153, Ala108, and Lys 114 (FIG. 2f) are conserved in all Hsp90 paralogs. Accordingly, the purine portion of pan-Hsp90 inhibitors and selective Grp94 inhibitors of the disclosure interact with these residues.

TABLE 1

Sequence of Human Hsp90 paralogs

| SEQ ID NO. | Description | Sequence |
|---|---|---|
| 1 | Grp94 Sequence (Human) | MRALWVLGLCCVLLTFGSVRADDEVDVDGTV EEDLGKSREGSRTDDEVVQREEEAIQLDGLN ASQIRELREKSEKFAFQAEVNRMMKLIINSL YKNKEIFLRELISNASDALDKIRLISLTDEN ALSGNEELTVKIKCDKEKNLLHVTDTGVGMT REELVKNLGTIAKSGTSEFLNKMTEAQEDGQ STSELIGQFGVGFYSAFLVADKVIVTSKHNN DTQHIWESDSNEFSVIADPRGNTLGRGTTIT LVLKEEASDYLELDTIKNLVKKYSQFINFPI YVWSSKTETVEEPMEEEEAAKEEKEESDDEA AVEEEEEEKKPKTKKVEKTVWDWELMNDIKP IWQRPSKEVEEDEYKAFYKSFSKESDDPMAY IHFTAEGEVTFKSILFVPTSAPRGLFDEYGS KKSDYIKLYVRRVFITDDFHDMMPKYLNFVK GVVDSDDLPLNVSRETLQQHKLLKVIRKKLV RKTLDMIKKIADDKYNDTFWKEFGTNIKLGV IEDHSNRTRLAKLLRFQSSHHPTDITSLDQY VERMKEKQDKIYFMAGSSRKEAESSPFVERL LKKGYEVIYLTEPVDEYCIQALPEFDGKRFQ NAKEGVKFDESEKTKESREAVEKEFEPLLNW MKDKALKDKIEKAVVSQRLTESPCALVASQY GWSGNMERIMKAQAYQTGKDISTNYYASQKK TFEINPRHPLIRDMLRRIKEDEDDKTVLDLA VVLFETATLRSGYLLPDTKAYGDRIERMLRL SLNIDPAKVEEEPEEEPEETAEDTTEDTEQD EDEEMDVGTDEEEETAKESTAEKDEL |
| 2 | Hsp90α | MGSSHHHHHHSSGLVPRGSHMPEETQTQDQP MEEEEVETFAFQAEIAQLMSLIINTFYSNKE IFLRELISNSSDALDKIRYESLTDPSKLDSG KELHINLIPNKQDRTLTIVDTGIGMTKADLI NNLGTIAKSGTKAFMEALQAGADISMIGQFG VGFYSAYLVAEKVTVITKHNDDEQYAWESSA GGSFTVRTDTGEPMGRGTVILHLKEDQTEYL EERRIKEIVKKHSQFIGYPITLFVEKERDKE VSDDEAE |
| 3 | Hsp90β | DPTLMPEEVHHGEEEVETFAFQAEIAQLMSL IINTFYSNKEIFLRELISNASDALDKIRYES LTDPSKLDSGKELKIDIIPNPQERTLTLVDT GIGMTKADLINNLGTIAKSGTKAFMEALQAG ADISMIGQFGVGFYSAYLVAEKVVVITKHND DEQYAWESSAGGSFTVRADHGEPIGRGTKVI LHLKEDQTEYLEERRVKEVVKKHSQFIGYPI TLYLEKEREKGEFNSKLGCFGG |
| 4 | TRAP-1 | MARELRALLLWGRRLRPLLRAPALAAVPGGK PILCPRRTTAQLGPRRNPAWSLQAGRLFSTQ TAEDKEEPLHSIISSTESVQGSTSKHEFQAE TKKLLDIVARSLYSEKEVFIRELISNASDAL EKLRHKLVSDGQALPEMEIHLQTNAEKGTIT IQDTGIGMTQEELVSNLGTIARSGSKAFLDA LQNQAEASSKIIGQFGVGFYSAFMVADRVEV YSRSAAPGSLGYQWLSDGSGVFEIAEASGVR TGTKIIIHLKSDCKEFSSEARVRDVVTKYSN FVSFPLYLNGRRMNTLQAIWMMDPKDVREWQ HEEFYRYVAQAHDKPRYTLHYKTDAPLNIRS IFYVPDMKPSMFDVSRELGSSVALYSRKVLI QTKATDILPKWLRFIRGVVDSEDIPLNLSRE LLQESALIRKLRDVLQQRLIKFFIDQSKKDA EKYAKFFEDYGLFMREGIVTATEQEVKEDIA KLLRYESSALPSGQLTSLSEYASRMRAGTRN IYYLCAPNRHLAEHSPYYEAMKKKDTEVLFC FEQFDELTLLHLREFDKKKLISVETDIVVDH |

TABLE 1-continued

Sequence of Human Hsp90 paralogs

| SEQ ID NO. | Description | Sequence |
|---|---|---|
| | | YKEEKFEDRSPAAECLSEKETEELMAWMRNV LGSRVTNVKVTLRLDTHPAMVTVLEMGAARH FLRMQQLAKTQEERAQLLQPTLEINPRHALI KKLNQLRASEPGLAQLLVDQIYENAMIAAGL VDDPRAMVGRLNELLVKALERH |

5.2 Ligand Characteristics that Confer Grp94 Selectivity

Figures 4A, 4B, 4C:
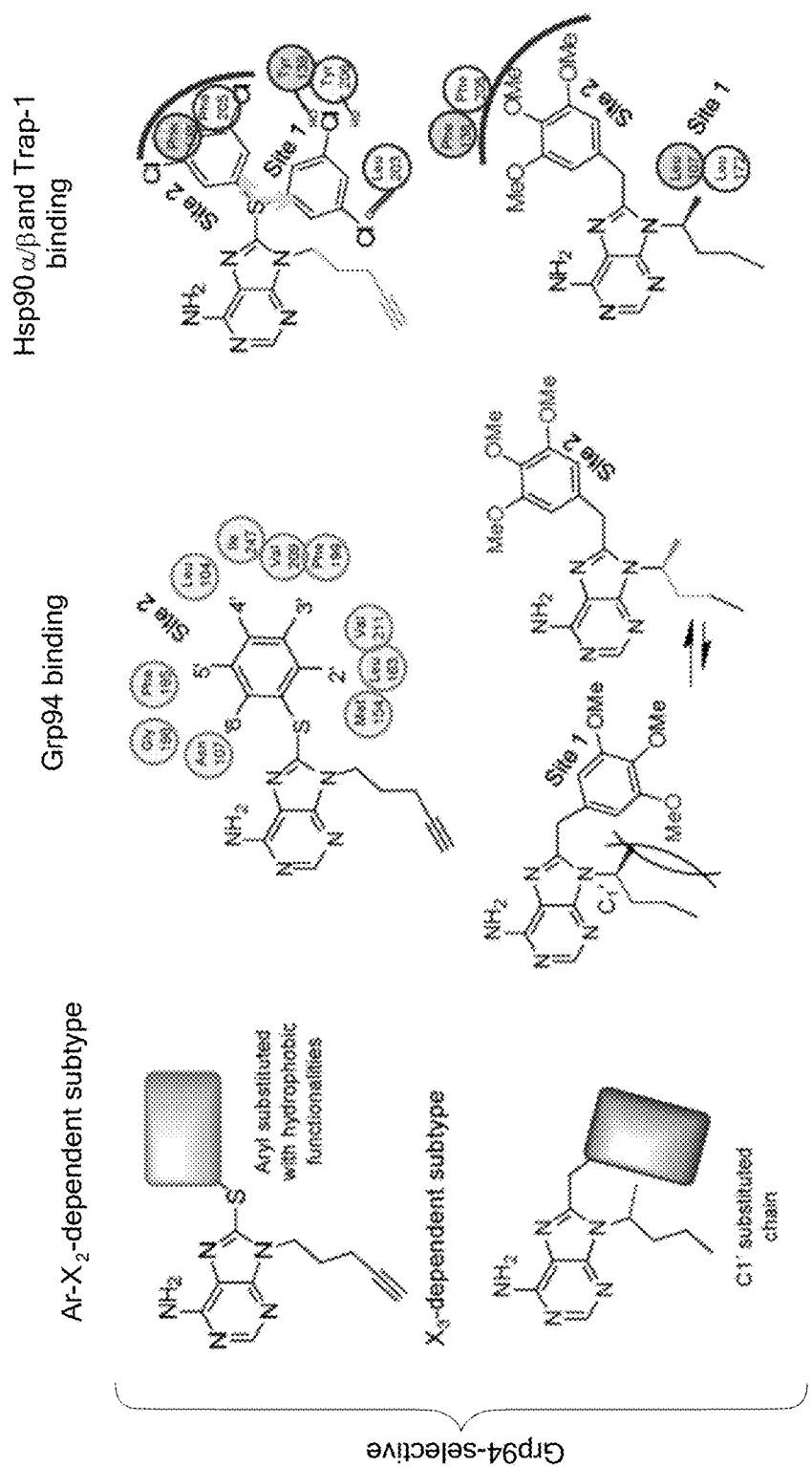
Figure 5C:
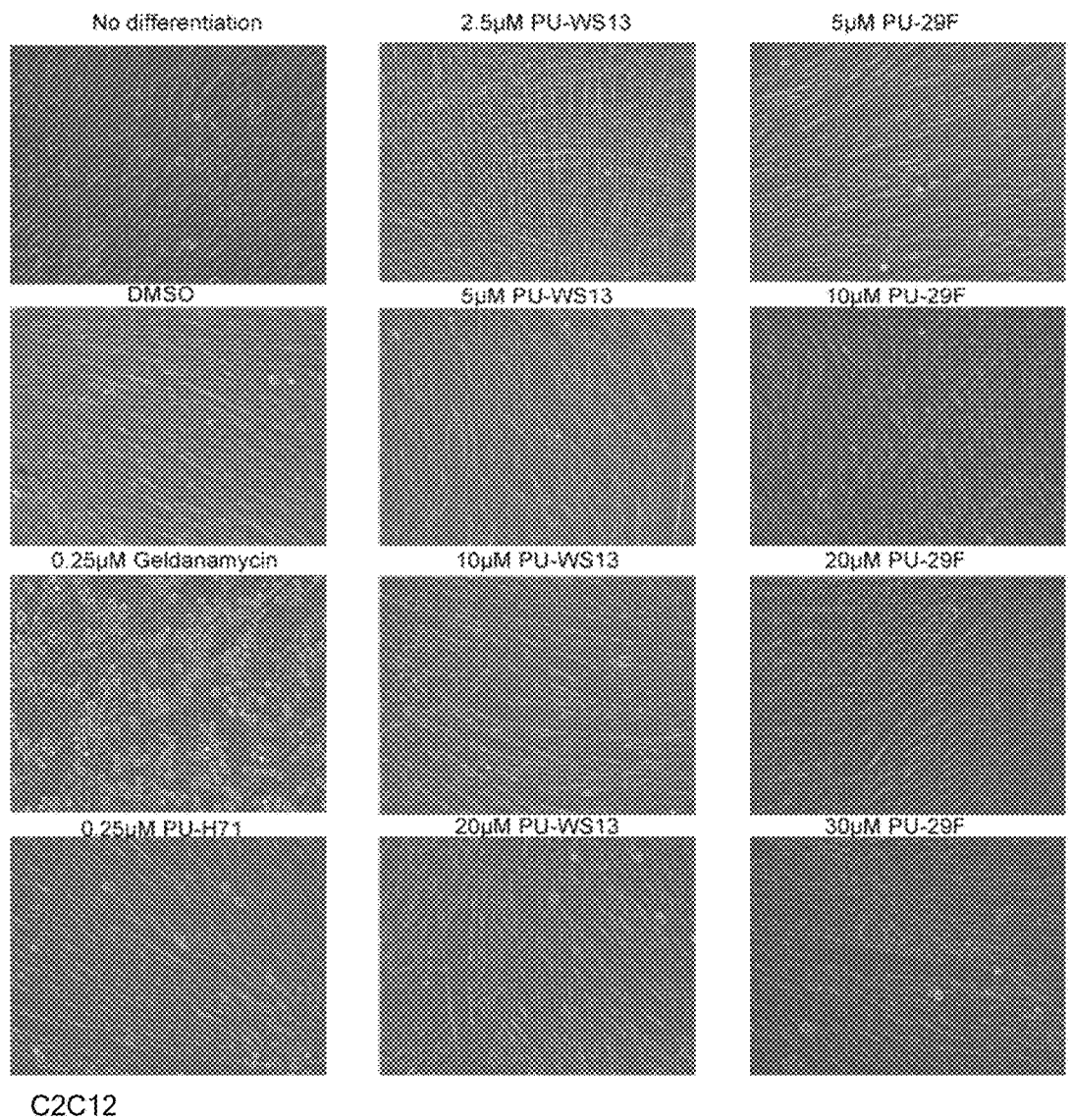
FIG. 5c viability of C2C12 cells was visualized by light microscopy. Cells were first treated with or without the differentiation agent (2% horse serum) then added vehicle (DMSO) or the indicated concentrations of inhibitors for 24 h. The appearance of rounded, floating cells in the GM treated conditions is indicative of cell killing. Representative images are shown.
Figure 5D:
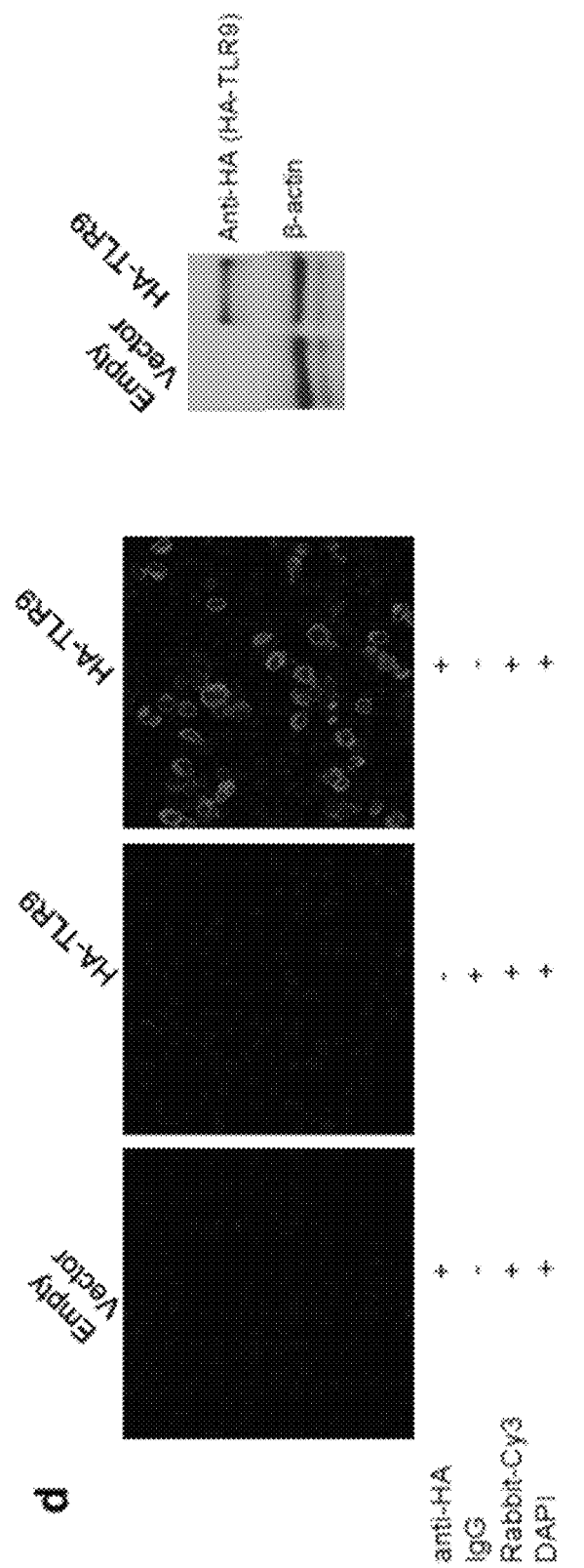
FIGS. 5d and 5f show trafficking of Toll-like receptor 9 (TLR9) to the cell surface.
Figure 5E:
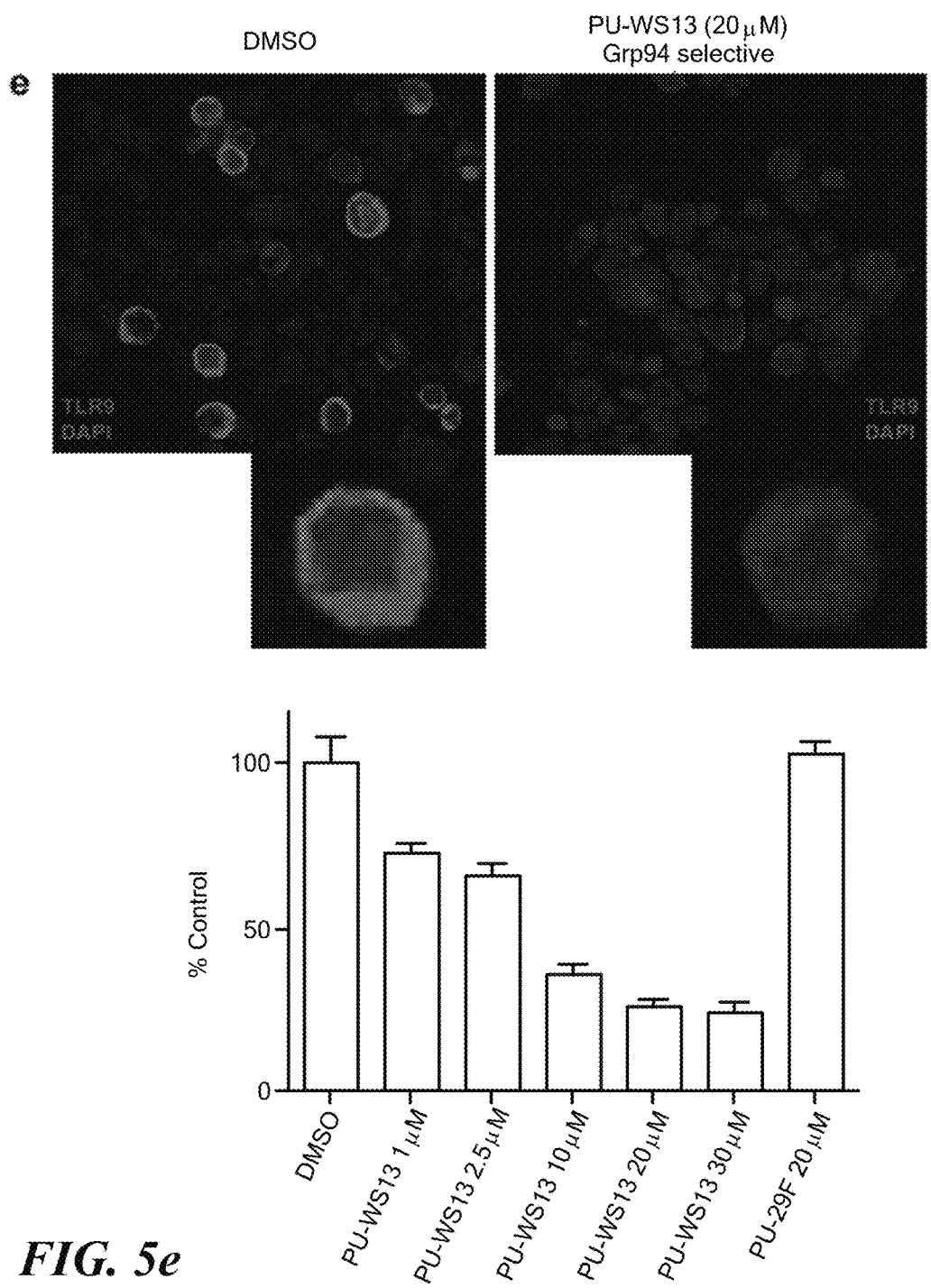
FIG. 5e shows representative image and quantification of quadruplicate experimental conditions of HEK293 cells transfected with HA-TLR9 (red) and treated for 24 h with the indicated concentrations of PU-WS13 or PU-29F. Blue=DAPI.
Figure 5F:
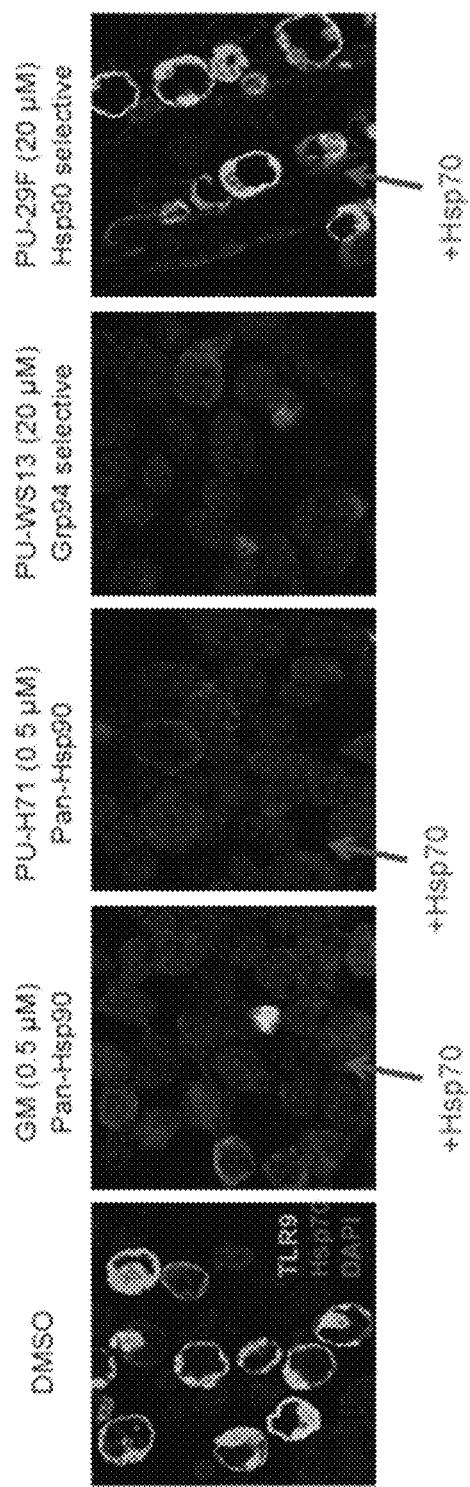
Figure 5G:
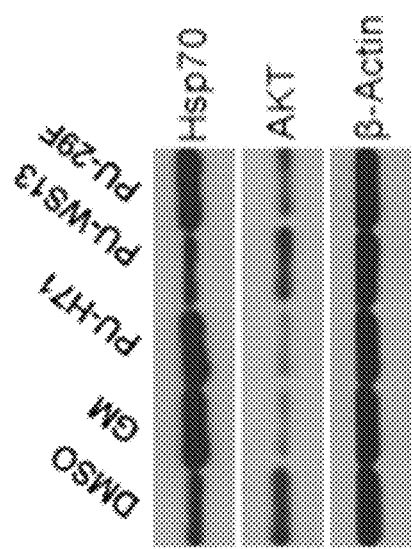
FIG. 5g shows representative Western blot of cells as in FIG. 5f.

We next analyzed the functionalities that, when attached onto the purine-scaffold, confer Grp94-specific binding. On close inspection, the Grp94 selective inhibitors could be classified into two structural subtypes: Ar-X2- and X3-dependent (FIG. 1a and FIG. 4a). In the Ar-X2-dependent subtype, we identified compounds of high binding affinity for Grp94 (FIG. 1b) and also remarkable selectivity (greater than 100-fold) for Grp94 over Hsp90α/β and Trap-1. Energy minimizations indicated that a subset of these compounds preferred the backwards bent conformation even in the unbound state. In addition, the preferential presence of hydrophobic substituents in the Grp94 selective binding site was observed. These allow for favorable proximity to the side chains of binding site 2 and binding site 1 (see FIG. 2f) of Grp94. These matched hydrophobic interactions provide a rationale for the preferential presence of these groups on the Grp94 selective ligands. Notably, the Hsp90α/β and Trap-1 paralogs were unable to accommodate these derivatives due to unfavorable interactions with several pocket residues (FIG. 4c, top).

In the X3-dependent subtype, the presence of a methyl group at the C1'-position of the N9 alkyl chain also yielded compounds with more than 10-fold selectivity for Grp94 over Hsp90α/β and Trap-1. Molecular modeling indicated that the C1' methyl group favored the placement of the 8-aryl ring into the backwards bent conformation, resulting in binding into Site 2 of Grp94 (FIG. 4b, bottom). In contrast to the Ar-X2-dependent subtype described above, the affinity of these compounds for Grp94 was modest (60-90 μM), reflecting the less hydrophobic character of the X2-substituents (i.e. trimethoxy). Hsp90α/β and Trap-1 could not accommodate these inhibitors, potentially due to unfavorable interactions between the C1' methyl and substituents on the 8-aryl ring and between the ligand and several pocket residues (FIG. 4c, bottom).

Accordingly, in the purine-scaffold series, a two-log selectivity for Grp94 over other Hsp90 paralogs and a favorable affinity is limited to those compounds that favor or may accommodate the "backwards" conformation and feature an aryl ring with hydrophobic substituents on the 2', 3', 4' and/or 5' positions in the configuration described above. Both characteristics portend favorable interactions of the ligand with Site 2 of Grp94.

Based on the foregoing, novel Grp94 inhibitors with scaffolds based on purine were identified based on their ability to accommodate the "backwards" conformation and to make favorable hydrophobic contacts with the amino acids lining binding site 1 and binding site 2 of Grp94. Accordingly, in one aspect, the disclosure provides new compounds that exhibit affinity for Grp94 and thus, are capable of inhibiting the biological activity of Grp94. In some embodiments, the Grp94 inhibitors interact with six or more of the amino acids comprising binding site 1 and binding site 2 of the Grp94 NTD. In particular embodiments, the Grp94 inhibitors of the disclosure can interact with six, seven, eight, nine, ten, eleven or twelve of the amino acids comprising binding site 1 and binding site 2 of the Grp94 NTD. In other embodiments, the Grp94 inhibitors of the disclosure interact with six or more amino acids selected from Phe195, Gly198, Val209, Ala202, Ile247, Leu249, Phe203, Leu104, Val211, Phe199, Met154 and Leu163 of SEQ ID NO:1. For instance, the Grp94 inhibitors of the disclosure can interact with six, seven, eight, nine, ten, eleven or twelve of the amino acids selected from Phe195, Gly198, Val209, Ala202, Ile247, Leu249, Phe203, Leu104, Val211, Phe199, Met154 and Leu163 of SEQ ID NO. 1.

In particular embodiments, the Grp94 inhibitors of the disclosure are capable of interacting with three or more of the amino acids in binding site 2 (i.e., the Grp94 selective binding site) of the Grp94 NTD. For instance, the Grp94 inhibitors can interact with three, four, five, six or seven of the amino acids of binding site 2 of the Grp94 NTD. In some such embodiments, the Grp94 inhibitors of the disclosure are capable of interacting with three or more amino acids selected from Phe195, Gly198, Val209, Ala202, Leu104, Leu249 and Phe203 of SEQ ID NO:1. For instance, the Grp94 inhibitors of the disclosure can interact with three, four, five, six or seven amino acids selected from Phe195, Gly198, Val209, Ala202, Leu104, Leu249 and Phe203 of SEQ ID NO:1.

In some embodiments, the Grp94 selective inhibitors of the disclosure are capable of interacting with the amino acids Ala202, Leu104 and Leu249 of SEQ ID NO:1. In other embodiments, the Grp94 selective inhibitors of the disclosure are capable of interacting with the amino acids Gly198, Val209, Ala202, Leu249 and Phe203 of SEQ ID NO:1. In other embodiments, the Grp94 selective inhibitors of the disclosure are capable of interacting with the amino acids Phe195, Val209, Ala202 of SEQ ID NO:1. In other embodiments, the Grp94 selective inhibitors of the disclosure are capable of interacting with the amino acids Leu104, Val209, Ala202 of SEQ ID NO:1. In still other embodiments, the Grp94 selective inhibitors of the disclosure are capable of interacting with the amino acids Phe195, Leu249 and Leu104 of SEQ ID NO:1. In still other embodiments, the Grp94 selective inhibitors of the disclosure are capable of interacting with the amino acids Phe195, Gly198 and Val209 of SEQ ID NO:1. In still other embodiments, the Grp94 selective inhibitors of the disclosure are capable of interacting with the amino acids Leu104, Leu249 and Phe203 of SEQ ID NO:1.

5.3 Grp94 Inhibitors with Scaffolds Based on Purine

In one aspect, the disclosure provides selective Grp94 inhibitors with scaffolds related to purine (e.g., fused amino pyridine compounds). In some embodiments, the Grp94 inhibitors are adenine scaffold inhibitors. In some embodiments, the Grp94 inhibitors are adenine scaffold inhibitors.

In particular embodiments, the purine-scaffold (e.g., adenine-scaffold) inhibitors can be substituted at 8-position with a linker group bonded to an aryl or heteroaryl group. For instance, the substituent bonded to the 8-position of the purine ring can be an arylsulfanyl group, an arylsulfoxyl group, an arylsulfonyl group, a benzyl group, an aniline group, an arylcarbonyl group, or a phenoxy group. In some such embodiments, the aryl or heteroaryl group at the 8-position of the purine ring interact with amino acids comprising binding site 1 and binding site 2 of SEQ ID NO:1. For instance, the aryl or heteroaryl group at the 8-position of the purine ring can interact with six, seven, eight, nine, ten, eleven or twelve of the amino acids selected from Phe195, Gly198, Val209, Ala202, Ile247, Leu249, Phe203, Leu104, Val211, Phe199, Met154 and Leu163 of SEQ ID NO. 1. In other embodiments, the aryl or heteroaryl group at the 8-position of the purine ring can interact with three, four, five, six or seven amino acids selected from Phe195, Gly198, Val209, Ala202, Ile247, Leu249 and Phe203 of SEQ ID NO:1. The purine portion of the purine-scaffold Grp94 inhibitors of the disclosure generally interacts with amino acids that are conserved in all Hsp90 paralogs. For instance, the purine portion can form favorable interactions with Asp149, Thr245, Ala111, Gly153, Lys114, Ala108 and Asn107 of SEQ ID NO:1.

Owing to the hydrophobic nature of the intermolecular interactions responsible for binding of ligands to the Grp94 receptor, developing water soluble inhibitors that have a desired level of cell permeability posed a challenge. Surprisingly, we have discovered that by specification modifications of the functionality at the N-9 or N-3 position of the purine scaffold, water soluble inhibitors that retain their high selectivity for Grp94 over the other Hsp90 paralogs can be developed. Hence, in particular embodiments, the purine-scaffold Grp94 inhibitors of the disclosure are water soluble. For instance, the water solubility of the purine-scaffold inhibitors of the disclosure can be greater than 0.5 mg/mL at neutral pH and ambient temperatures. For instance, the water solubility of the purine-scaffold inhibitors of the disclosure can be greater than 0.5 mg/mL, greater than 1 mg/mL, greater than 2 mg/mL, greater than 1 mg/mL, 2 mg/mL, 3 mg/mL, greater than 4 mg/mL, greater than 5 mg/mL, greater than 6 mg/mL, greater than 10 mg/mL, greater than 15 mg/mL, greater than 20 mg/mL, greater than 25 mg/mL, greater than 30 mg/mL, greater than 40 mg/mL or greater than 50 mg/mL in distilled water at ambient temperatures.

In embodiments where Grp94 inhibitors of the disclosure are only slightly soluble or insoluble, the inhibitors can be formulated in a vehicle that increases their solubility. For instance, the Grp94 inhibitors of the disclosure can be delivered in a vesicle, in particular a liposome.

In all of the compounds of the present disclosure, the compound may be as depicted, or as a pharmaceutically acceptable salt thereof. In one embodiment, the pharmaceutically acceptable salt is a hydrochloride-salt, a phosphate salt, a sulfate-salt, a citrate salt, an oxalate salt, a benzene sulfonic acid-salt, a para-toluenesulfonic acid-salt, a mesylate salt, a tartrate salt, a lactobionate salt, a succinate salt or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a phosphate-salt.

In naming options for $X^1$, $X^2$, $X^3$, $X^4$, $X^5$, $X^6$, Y, Q, $Z^1$, $Z^2$, $Z^3$, $Z^4$, $Z^5$, $Z^6$, $Z^6$, $Z^7$, $Z^8$ $R^1$, $R^2$, $R^3$, $R^4$, $R^7$, and $R^8$ the name refers to the type of group that is directly attached to the central structure, which group may include additional functionality. Thus, "alkyl" group refers to a linear, cyclic or branched saturated hydrocarbon, for example a hydrocarbon having from 1 to 10 carbon atoms, in which the atom directly attached to the central structure is a carbon atom. Such an alkyl group may include substituents other than hydrogen, for example an oxygen-containing group including without limitation hydroxyl and alkoxy; a halogen group; a nitrogen-containing group including without limitation amino, amido and alkylamino; an aryl group; a sulfur-containing group including without limitation thioalkyl; and/or a non-aromatic cyclic group including heterocycles and carbocycles.

Carbon atoms in these substituents may increase the total number of carbon atoms in the alkyl group to above 10 without departing from the invention. All references to alkyl groups in the specification and claims hereof encompass both substituted and unsubstituted alkyl groups unless the context is clearly to the contrary.

"Aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

"Alkenyl" group refers to a linear, cyclic or branched hydrocarbon, for example a hydrocarbon having from 1 to 10 carbon atoms, and at least one double bond, in which the atom directly attached to the central structure is a carbon atom. The alkenyl group may include any of the substituents mentioned above for an alkyl group. All references to alkenyl groups in the specification and claims hereof encompass both substituted and unsubstituted alkenyl groups unless the context is clearly to the contrary.

"Alkynyl" group refers to a linear, cyclic or branched hydrocarbon, for example a hydrocarbon having from 1 to 10 carbon atoms, and at least one triple bond, in which the atom directly attached to the central structure is a carbon atom. The alkynyl group may include any of the substituents mentioned above for an alkyl group. All references to alkynyl groups in the specification and claims hereof encompass both substituted and unsubstituted alkynyl groups unless the context is clearly to the contrary.

"Aryl" group refers to any group derived from a simple aromatic ring. Aryl group includes heteroaryl. An aryloxy substituent is an aryl group connected to the central structure through an oxygen atom. The aryl group may include any of the substituents mentioned above for an alkyl group, and in addition an aryl group may include an alkyl, alkenyl or alkynyl group. All references to aryl groups in the specification and claims hereof encompass both substituted and unsubstituted aryl groups unless the context is clearly to the contrary.

"Arylalkyl" refers to alkyl groups in which a hydrogen atom has been replaced with an aryl group. Such groups include, without limitation, benzyl, cinnamyl, and dihyrocinnamyl.

"Amino" group refers to any group which consists of a nitrogen attached by single bonds to carbon or hydrogen atoms. In certain instances, the nitrogen of the amino group is directly bound to the central structure. In other instances, an amino group may be a substituent on or within a group, with the nitrogen of the amino group being attached to the central structure through one or more intervening atoms. Examples of amino groups include $NH_2$, alkylamino, alkenylamino groups and N-containing non-aromatic heterocyclic moiety (i.e., cyclic amines). Amino groups may be substituted or unsubstituted. All references to amino groups in the specification and claims hereof encompass substituted and unsubstituted amino groups unless the context is clearly to the contrary.

"Halogen" group refers to fluorine, chlorine, bromine or iodine.

"Heterocyclic" group refers to a moiety containing at least one atom of carbon, and at least one atom of an element other than carbon, such as sulfur, oxygen or nitrogen within a ring structure. These heterocyclic groups may be either aromatic rings or saturated and unsaturated non-aromatic rings. Heterocyclic groups may be substituted or unsubstituted. All references to heterocyclic groups in the specification and claims encompass substituted and unsubstituted heterocyclic groups unless the context is clearly to the contrary.

"—($C_3$-$C_8$)cycloalkyl" refers to a saturated monocyclic hydrocarbon having 3, 4, 5, 6, 7, or 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

"—($C_3$-$C_8$)heterocycloalkyl" refers to a saturated monocyclic hydrocarbon having 3, 4, 5, 6, 7, carbon atoms and one heteroatom independently selected from nitrogen, oxygen, and sulfur.

"-(5- or 6-membered)heteroaryl" refers to a monocyclic aromatic heterocycle ring of 5 or 6 members, i.e., a monocyclic aromatic ring comprising at least one heteroatom independently selected from nitrogen, oxygen, and sulfur. In one embodiment, the -(5- or 6-membered)heteroaryl ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or $^{131}I$), mass-tags including, but not limited to, stable isotopes (e.g., $^{13}C$, $^{2}H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels are signal generating reporter groups which can be detected without further modifications. Detectable moities may be analyzed by methods including, but not limited to fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FLASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

In the compounds of the invention, all of the atoms have sufficient hydrogen or non-hydrogen substituents to satisfy valence, or the compound includes a pharmaceutically acceptable counterion, for example in the case of a quaternary amine.

5.3.1 Grp94 Inhibitors of Formula (I)

In one aspect, the disclosure encompasses purine-scaffold compounds that are substituted at the 8-position with a linker group bonded to an aryl or heteroaryl group and are further substituted at the N-9 position. Such compounds are represented schematically in Formula (I):

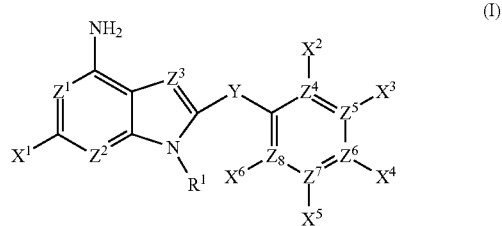

or a pharmaceutically acceptable salt thereof, wherein:

(a) Y is —C(R$^Y$)$_2$—, —S—, —NR—, —O—,

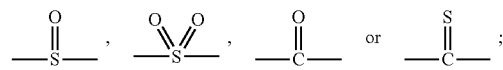

(b) each of $Z^1$ and $Z^3$ are independently —CH— or —N—;

(c) $Z^2$ is —N— or —CR$^{10}$—, wherein R$^{10}$ is H or unsubstituted or substituted —(C$_1$-C$_6$)aliphatic;

(d) each of $Z^4$, $Z^5$, $Z^6$, $Z^7$ and $Z^8$ are independently —C— or —N—, with the provisos that at least one of $Z^4$, $Z^6$ and $Z^7$ is —C— and no three consecutive $Z^4$ through $Z^8$ are N;

(e) $X^1$ is —H, -halo, —N(R)$_2$, —OR, —CN, or unsubstituted or substituted —(C$_1$-C$_6$)aliphatic;

(f) each of $X^2$, $X^3$, $X^4$, $X^5$, and $X^6$ are independently —H, -halo, —SR, —N(R)$_2$, —OR, —CN, —NO$_2$, —CN, —C(O)

R, —C(O)₂R, —S(O)R, —S(O)₂R, —C(O)N(R)₂, —SO₂N(R)₂, —OC(O)R, —N(R)C(O)R, —N(R)SO₂R, —OC(O)N(R)₂, unsubstituted or substituted —(C₁-C₆)aliphatic, or an unsubstituted or substituted group selected from (5- or 6-membered)aryl, (5- or 6-membered)arylalkyl, and (5- or 6-membered)heterocyclic aromatic or heterocyclic non-aromatic group; with the provisos that at least one of $X^2$, $X^4$ and $X^5$ is —H and that $X^2$ is absent when $Z^4$ is —N—, $X^3$ is absent when $Z^5$ is —N—, $X^4$ is absent when $Z^6$ is —N— and $X^5$ is absent when $Z^7$ is —N—;

(g) $R^1$ is —(C₁-C₆)aliphatic-N⁺—(R²)(R³)(R⁴), —(C₁-C₆)aliphatic-N—R³R⁴, —(C₁-C₆)aliphatic-C(=O)N—R³R⁴, —(C₁-C₆)aliphatic-R³R⁴, —(C₁-C₆)aliphatic-R²R³R⁴, —(C₁-C₆)aliphatic-N—CR²R³R⁴, —(C₁-C₆)aliphatic-C(halo)₃, —(C₁-C₆)aliphatic-alkenyl, —(C₁-C₆)aliphatic-alkynyl, —(C₁-C₆)aliphatic-(C₃-C₈)cycloalkyl, —(C₁-C₆)aliphatic-(C₃-C₈)heterocyclo, —(C₁-C₆)aliphatic-phenyl, —(C₁-C₆)aliphatic-(5 or 6-membered)heteroaryl, —(C₁-C₆)aliphatic-cyano, where the cyloalkyl, heterocyclo, heteroaryl, or phenyl is unsubstituted or substituted, with the proviso that when all of $R^2$-$R^4$ are present the compound further comprises a pharmaceutically acceptable counter ion;

(h) $R^2$ and $R^3$ are independently hydrogen, —N(R)₂, —CH₂CH(OH)R⁴, —CH(OH)CH₂R⁴, —CH₂SO₂NHR⁴, —CH₂NHSO₂R⁴, or unsubstituted or substituted —(C₁-C₆)aliphatic, or $R^3$ and $R^4$ form an unsubstituted or substituted 3- to 7-membered heterocyclic ring when taken together with the nitrogen to which they are attached;

(i) $R^4$ is hydrogen, halogen, or unsubstituted or substituted —(C₁-C₆)aliphatic;

(j) each $R^Y$ is independently R, —OR, or halo;

(k) $Z^3$ can be cyclized with $X^2$ to form a cyclic aryl, heteroaryl, alkyl or heteroalkyl ring; and (l) each R is independently hydrogen, unsubstituted $C_{1-6}$ aliphatic, or $C_{1-6}$ aliphatic substituted with halo, —OH, —CN, or —NH₂;

wherein each substituted group is substituted with one or more groups selected from halo, —N(R)₂, —OR, —CN, oxo, unsubstituted $C_{1-6}$ aliphatic, or $C_{1-6}$ aliphatic substituted with halo, —OH, —CN, or —NH₂.

In some embodiments, a compound of formula (I) or pharmaceutically acceptable salt thereof is defined wherein:

(a) Y is —CH₂—, —S—, —NH—, —O—,

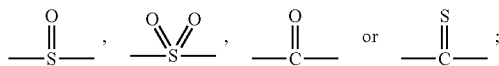

(b) each of $Z^1$ and $Z^3$ are independently —CH— or —N—;

(c) $Z^2$ is —CH—, —N—, or —CR¹⁰—, wherein $R^{10}$ is —(C₁-C₆)alkyl;

(d) each of $Z^4$, $Z^5$, $Z^6$, $Z^7$ and $Z^8$ are independently —C— or —N—, with the provisos that at least one of $Z^4$, $Z^6$ and $Z^7$ is —C— and no three consecutive $Z^4$ through $Z^8$ are N;

(e) $X^1$ is —H, -halo, —NH₂, —CN, —(C₁-C₆)alkyl, —O(C₁-C₆)alkyl, —CH₂OH, —C(halo)₃, —CH(halo)₂, —CH₂(halo), —OC(halo)₃, —OCH(halo)₂, or —OCH₂(halo);

(f) each of $X^2$, $X^3$, $X^4$, and $X^5$ are independently —H, -halo, —NH₂, —CN, —(C₁-C₆)alkyl, —O(C₁-C₆)alkyl, —CH₂OH, —C(halo)₃, —CH(halo)₂, —CH₂(halo), —OC(halo)₃, —OCH(halo)₂, —OCH₂(halo), or an unsubstituted or substituted (5- or 6-membered)aryl, heterocyclic aromatic or non-aromatic group selected from pyridyl, furyl, thiophenyl, pyrrolyl, oxazolyl, imidazolyl, phenyl, benzyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl, with the provisos that at least one of $X^2$, $X^4$ and $X^5$ is —H and that $X^2$ is absent when $Z^4$ is —N—, $X^3$ is absent when $Z^5$ is —N—, $X^4$ is absent when $Z^6$ is —N— and $X^5$ is absent when $Z^7$ is —N—;

(g) $X^6$ is —H when $Z^8$ is —C— or absent when $Z^8$ is —N—;

(h) $R^1$ is —(CH₂)$_m$—N⁺—(R²)(R³)(R⁴), —(CH₂)$_m$—N—R³R⁴, —(CH₂)$_m$—C(=O)N—R³R⁴, —(CH₂)$_m$—R³R⁴, —(CH₂)$_m$—C(halo)₃, —(CH₂)$_m$-alkenyl, —(CH₂)$_m$-alkenyl-CH₃, —(CH₂)$_m$-alkynyl, —(CH₂)$_m$-alkynyl-CH₃, —(CH₂)$_m$—(C₃-C₈)cycloalkyl, —(CH₂)$_m$—(C₃-C₈)heterocycloalkyl, —(CH₂)$_m$-phenyl, —(CH₂)$_m$-(5 or 6-membered)heteroaryl, —(CH₂)$_m$-cyano, where m is 1, 2, 3, 4 or 5 and where the cyloalkyl, heterocycle or phenyl is unsubstituted or substituted with one or more $X^1$ groups, with the proviso that when all of $R^2$-$R^4$ are present the compound further comprises a pharmaceutically acceptable counter ion;

(i) $R^2$ and $R^3$ are independently hydrogen, methyl, ethyl, ethenyl, ethynyl, propyl, butyl, pentyl, hexyl, isopropyl, c-propyl, t-butyl, isobutyl, —C(halo)₃, —CH(halo)₂, —CH₂(halo), —CH₂C(halo)₃, —CH₂CH(halo)₂, —CH₂CH₂(halo), —NHCH₂C(halo)₃, —CH₂CH(halo)₂, —CH₂CH₂(halo), —CH₂OH, —CH₂CH₂OH, —CH₂C(CH₃)₂OH, —CH₂CH(CH₃)OH, —C(CH₃)₂CH₂OH, —CH₂CH(OH)R⁴, —CH₂SO₂NHR⁴, —CH₂SO₂NHR⁴ or $R^2$ and $R^3$ form an unsubstituted or substituted aziridine, azetidine, pyrrolidine, piperazine, or piperidine ring when taken together with the nitrogen to which they are attached;

(j) $R^4$ is hydrogen, methyl, ethyl, isopropyl, t-butyl, isobutyl, or —C(halo)₃; and (k) $Z^3$ can be cyclized with $X^2$ to form a cyclic aryl, heteroaryl, alkyl or heteroalkyl ring.

In one embodiment, $Z^1$, $Z^2$ and $Z^3$ are —N—. In another embodiment, $Z^1$ and $Z^3$ are —N— and $Z^2$ is —CH—. In another embodiment, $Z^1$ is —CH— and $Z^2$ and $Z^3$ are —N—.

In another embodiment, $Z^4$, $Z^5$, $Z^6$, $Z^7$ and $Z^8$ are —C—. In another embodiment, $Z^4$ is —N— and $Z^5$, $Z^6$, $Z^7$ and $Z^8$ are —C—. In another embodiment, $Z^5$ is —N— and $Z^4$, $Z^6$, $Z^7$ and $Z^8$ are —C—. In another embodiment, $Z^6$ is —N— and $Z^4$, $Z^5$, $Z^7$ and $Z^8$ are —C—. In another embodiment, $Z^7$ is —N— and $Z^4$, $Z^5$, $Z^6$ and $Z^8$ are —C—. In another embodiment, $Z^8$ is —N— and $Z^4$, $Z^5$, $Z^6$ and $Z^7$ are —C—. In another embodiment, $Z^7$ and $Z^4$ are —N— and $Z^5$, $Z^6$ and $Z^8$ are —C—. In another embodiment, $Z^5$ and $Z^8$ are —N— and $Z^4$, $Z^6$ and $Z^7$ are —C—.

In another embodiment, Y is —S—, —CH₂—, or

In another embodiment, Y is S or

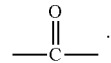

In another embodiment, Y is —S— or —CH$_2$—. In another embodiment, Y is —S— or —O—. In another embodiment, Y is —S—. In another embodiment, Y is —CH$_2$—. In another embodiment, Y is

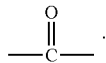

In some embodiments, Y is —C(R$^Y$)$_2$—, wherein each R$^Y$ is independently hydrogen, —OH, or halo.

In certain embodiments, R$^1$ is —(CH$_2$)$_m$—N—(R$^3$)(R$^4$). In one such embodiment, R$^1$ is —(CH$_2$)$_2$—N—(R$^3$)(R$^4$). In another such embodiment, R$^1$ is —(CH$_2$)$_3$—N—(R$^3$)(R$^4$). In another such embodiment, R$^1$ is —(CH$_2$)$_2$—N—(R$^3$)(R$^4$), R$^3$ is —H and R$^4$ is isopropyl or isobutyl. In another such embodiment, R$^1$ is —(CH$_2$)$_3$—N—(R$^3$)(R$^4$), R$^3$ is —H and R$^4$ is isopropyl or isobutyl. In another such embodiment, R$^1$ is —(CH$_2$)$_3$—N—(R$^3$)(R$^4$), R$^3$ is —H and R$^4$ is isobutyl. In another such embodiment, R$^1$ is —(CH$_2$)$_3$—N—(R$^3$)(R$^4$), R$^3$ is —H and R$^4$ is isopropyl. It will be understood, that in these embodiments, the amine functionality may exist as a free base or as an acid addition salt. Acid addition salts can be prepared by addition of a suitable acid, as is well understood in the art. In particular embodiments, the acid addition salt may be a hydrochloride salt, a phosphate salt, a sulfate salt, a lactate salt, a citrate salt, a succinate salt, a benzene sulfonic acid salt, a para-toluenesulfonic acid salt, or a fumaric acid-salt. In another embodiment, the acid addition salt is a hydrochloride salt or a sulfate salt. In another embodiment, the acid addition salt is a hydrochloride salt. In another embodiment, the acid addition salt is a sulfate salt. In another embodiment, the acid addition salt is a phosphate salt. When prepared as an acid addition salt, the purine-scaffold inhibitors are rendered water soluble. Solubility may be increased even further by production of higher order salts, particularly di-salts. For instance, in embodiments where Z$^1$ is —N—, the nitrogen is ionizable and can be converted to an acid addition salt under strongly acidic conditions (e.g., pH of less than 3). Accordingly, Grp94 inhibitors of the disclosure in which Z$^1$ is —N— and the R$^1$ group contains an amine functionality can be converted into di-salts. In certain embodiments, the Grp94 inhibitors of the disclosure can be in the form of a di-HCl salt.

In some embodiments, R$^2$ and R$^3$ are independently hydrogen, methyl, ethyl, ethenyl, ethynyl, propyl, butyl, pentyl, hexyl, isopropyl, c-propyl, t-butyl, isobutyl, —C(halo)$_3$, —CH(halo)$_2$, —CH$_2$(halo), —CH$_2$C(halo)$_3$, —CH$_2$CH(halo)$_2$, —CH$_2$CH$_2$(halo), —NHCH$_2$C(halo)$_3$, —CH$_2$CH(halo)$_2$, —CH$_2$CH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)$_2$CH$_2$OH, —CH(CH$_3$)CH(OH)R$^4$, —CH$_2$CH(OH)R$^4$, —CH$_2$SO$_2$NHR$^4$, —CH$_2$NHSO$_2$R$^4$ or R$^2$ and R$^3$ form an unsubstituted or substituted aziridine, azetidine, pyrrolidine, piperazine, or piperidine ring when taken together with the nitrogen to which they are attached.

In some embodiments, R$^3$ and R$^4$ form an unsubstituted or substituted 3- to 7-membered heterocyclic ring when taken together with the nitrogen to which they are attached. In some embodiments, R$^2$ and R$^3$ form an unsubstituted or substituted 3- to 7-membered heterocyclic ring when taken together with the nitrogen to which they are attached.

In certain embodiments, R$^1$ is —(CH$_2$)$_m$—CF$_3$. In one such embodiment, R$^1$ is —(CH$_2$)$_3$—CF$_3$. In another such embodiment, R$^1$ is —(CH$_2$)$_4$—CF$_3$.

In some embodiments, R$^1$ is —(C$_1$-C$_6$)aliphatic-alkynyl. In some embodiments, R$^1$ is —(CH$_2$)$_3$CCH.
In some embodiments, R$^1$ is —(C$_1$-C$_6$)aliphatic-R$^3$R$^4$.
In some embodiments, R$^1$ is —(C$_1$-C$_6$)aliphatic-phenyl.
In some embodiments, R$^1$ is —(C$_1$-C$_6$)aliphatic-heteroaryl.
In some embodiments, R$^1$ is —(C$_1$-C$_6$)aliphatic-heterocyclo.
In some embodiments, R$^1$ is —(CH$_2$)$_m$—NHR$^2$.

In certain embodiments, R$^1$ is —(CH$_2$)$_m$—C(=O)N—(R$^3$)(R$^4$). In one such embodiment, R$^1$ is —(CH$_2$)$_3$—C(=O)NH$_2$. In another such embodiment, R$^1$ is (CH$_2$)$_4$—C(=O)NH$_2$. In another such embodiment, R$^1$ is (CH$_2$)$_5$—C(=O)NH$_2$.

In another embodiment, X$^1$ is —H. In another embodiment, X$^1$ is a halogen atom. In another embodiment, X$^1$ is —F. In another embodiment, X$^1$ is —Cl.

In another embodiment, X$^2$ is a halogen atom, —OCH$_3$, or —OCF$_3$ and X$^3$, X$^4$, X$^5$ and X$^6$ are —H. In another embodiment X$^2$ is —Cl and X$^3$, X$^4$, X$^5$ and X$^6$ are —H. In another embodiment X$^2$ is —OCH$_3$ and X$^3$, X$^4$, X$^5$ and X$^6$ are —H. In another embodiment X$^2$ is —OCF$_3$ and X$^3$, X$^4$, X$^5$ and X$^6$ are —H.

In another embodiment, X$^4$ is a halogen atom and X$^2$, X$^3$, X$^5$ and X$^6$ are —H. In another embodiment X$^4$ is —Cl and X$^2$, X$^3$, X$^5$ and X$^6$ are —H. In another embodiment X$^4$ is —OCH$_3$ and X$^2$, X$^3$, X$^5$ and X$^6$ are —H. In another embodiment X$^4$ is —OCF$_3$ and X$^2$, X$^3$, X$^5$ and X$^6$ are —H.

In some embodiments X$^2$, X$^3$, and X$^5$ are halogen and X$^4$ and X$^6$ are hydrogen. In some embodiments X$^2$, X$^3$, and X$^4$ are halogen and X$^5$ and X$^6$ are hydrogen. In some embodiments X$^2$, X$^3$, and X$^5$ are halogen and X$^4$ and X$^6$ are hydrogen. In some embodiments X$^3$, X$^4$, and X$^5$ are halogen and X$^2$ and X$^6$ are hydrogen.

In some embodiments, X$^2$, X$^4$, and X$^6$ are methyl and X$^3$ and X$^5$ are hydrogen.

In certain embodiments, Z$^4$ and Z$^6$ are —C—, X$^2$ and X$^4$ are independently selected from —H, -halo, —(C$_1$-C$_3$)alkyl and —O(C$_1$-C$_3$)alkyl and Z$^5$, Z$^7$ and Z$^8$ are either an unsubstituted carbon or a nitrogen atom. In one such embodiment, at least one of X$^2$ and X$^4$ are -halo. In another such embodiment, both X$^2$ and X$^4$ are —Cl. In another such embodiment, at least one of X$^2$ and X$^4$ are alkyl groups. In another such embodiment, both X$^2$ and X$^4$ are —CH$_3$. In another such embodiment, at least one of X$^2$ and X$^4$ are —OCH$_3$. In another such embodiment, at least one of X$^2$ and X$^4$ are —CF$_3$.

In certain embodiments, Z$^4$ and Z$^7$ are —C—, X$^2$ and X$^5$ are independently selected from —H, -halo, —(C$_1$-C$_3$)alkyl and —O(C$_1$-C$_3$)alkyl and Z$^5$, Z$^6$ and Z$^8$ are either an unsubstituted carbon or a nitrogen atom. In one such embodiment, at least one of X$^2$ and X$^5$ are halogen atoms. In another such embodiment, both X$^2$ and X$^5$ are —Cl. In another such embodiment, at least one of X$^2$ and X$^4$ are alkyl groups. In another such embodiment, both X$^2$ and X$^5$ are —CH$_3$. In another such embodiment, at least one of X$^2$ and X$^4$ are —CF$_3$.

In certain embodiments, Z$^5$ and Z$^7$ are —C—, X$^3$ and X$^5$ are independently selected from —H, -halo, —(C$_1$-C$_3$)alkyl, —O(C$_1$-C$_3$)alkyl, unsubstituted or substituted —(C$_1$-C$_6$) aliphatic, or unsubstituted or substituted phenyl, and Z$^4$, Z$^6$ and Z$^8$ are either an unsubstituted carbon or a nitrogen atom. In one such embodiment, at least one of X$^3$ and X$^5$ are halogen atoms. In another such embodiment, both X$^3$ and X$^5$ are —Cl. In another such embodiment, at least one of X$^3$ and X$^5$ are alkyl groups. In another such embodiment, both X$^3$ and X$^5$ are —CH$_3$. In another such embodiment, at least one of X$^3$ and X$^5$ are —CF$_3$.

In some embodiments, the Grp94 inhibitors of Formula (I) are of Formula (Ia):

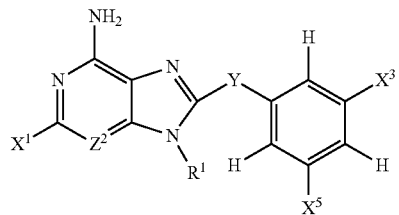

Ia or a pharmaceutically acceptable salt thereof, wherein each of $X^1$, $Z^2$, $R^1$, Y, $X^3$, and $X^5$ is as defined above and described in classes and subclasses herein, both singly and in combination.

In some embodiments, the Grp94 inhibitors of Formula (I) are of Formula (Ib):

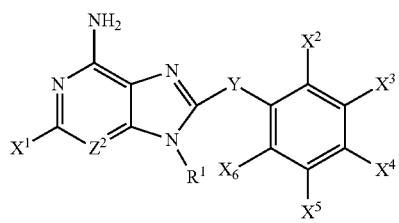

Ib or a pharmaceutically acceptable salt thereof, wherein $R^1$ is as defined above where i) the —($C_1$-$C_6$)aliphatic group attached to the ring nitrogen is —$(CH_2)_3$— or ii) m is 3; and each of $X^1$, $Z^2$, Y, $X^2$, $X^3$, $X^4$, $X^5$ and $X^6$ is as defined above and described in classes and subclasses herein, both singly and in combination.

In some embodiments, the Grp94 inhibitors of Formula (I) have one of the Formula of Table 2, wherein each substituent is as defined above and described in classes and subclasses herein, both singly and in combination.

TABLE 2

| Formula | Compound |
|---|---|
| IA | 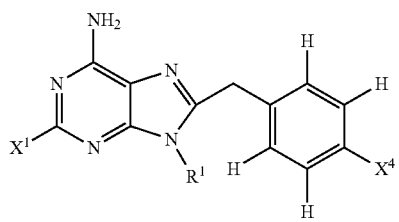 |
| IB | 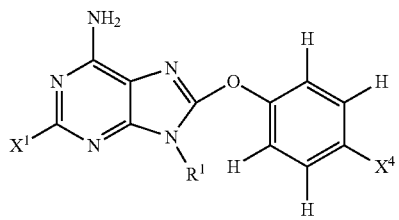 |

TABLE 2-continued

| Formula | Compound |
|---|---|
| IC | 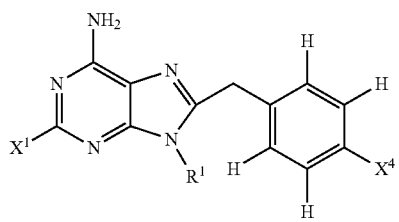 |
| ID | 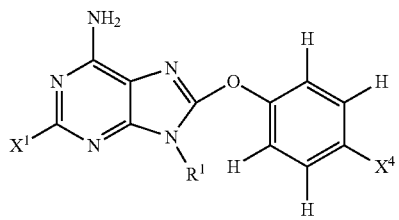 |
| IE | 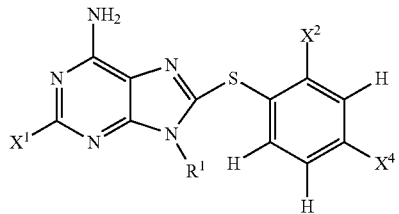 |
| IF | 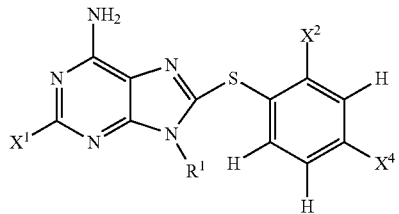 |
| IG | 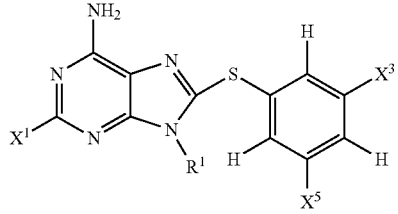 |
| IH | 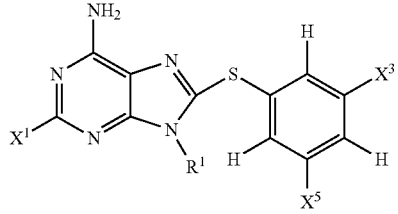 |
| II | 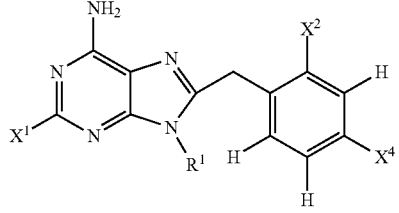 |

TABLE 2-continued
| Formula | Compound |
|---|---|
| IJ | 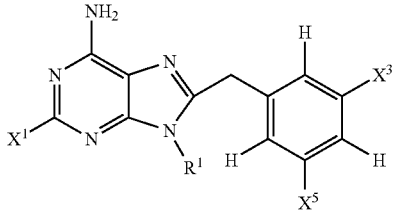 |
| IK | 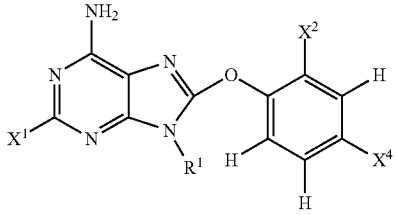 |
| IL | 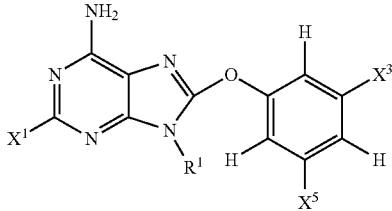 |
| IM | 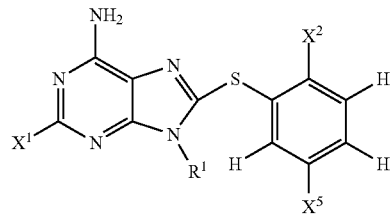 |
| IN | 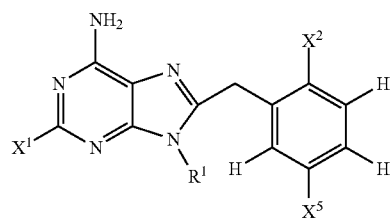 |
| IO | 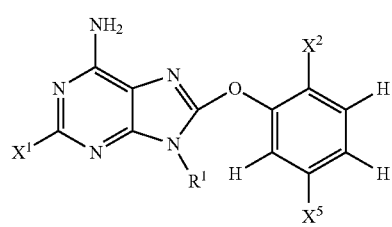 |
| IP | 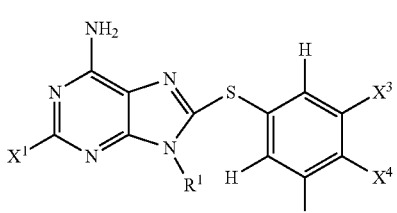 |
| IQ | 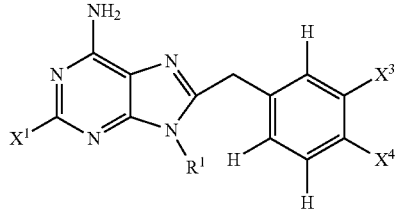 |
| IR | 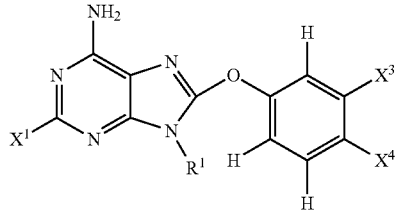 |
| IS | 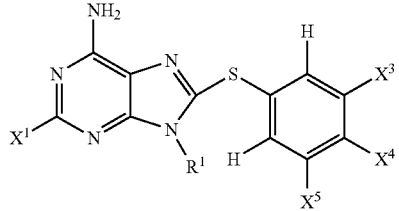 |
| IT | 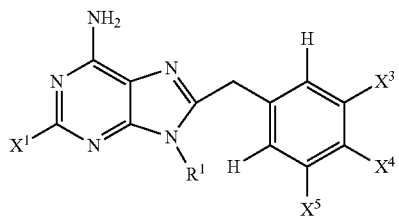 |
| IU | 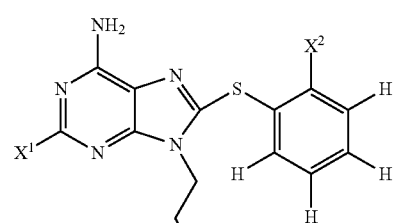 |
| IV | 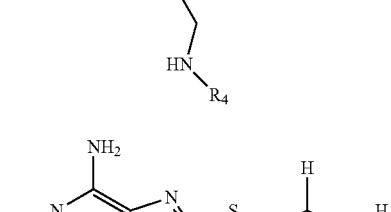 |

TABLE 2-continued
| Formula | Compound |
|---|---|
| IW | 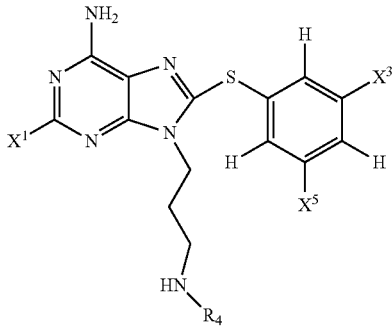 |
| IX | 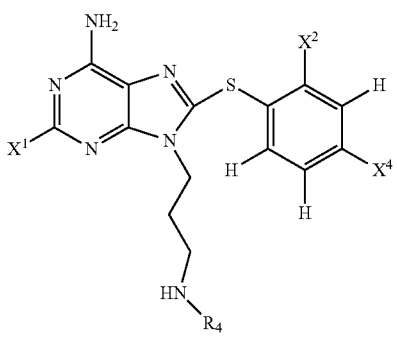 |
| IY | 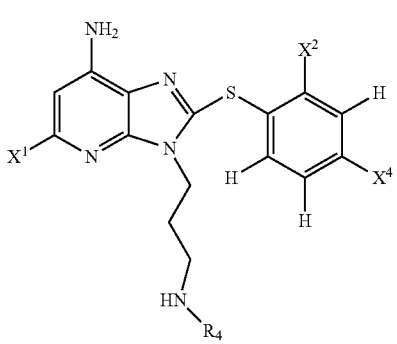 |
| IZ | 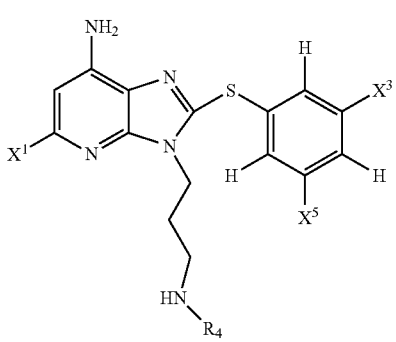 |
| IAA | 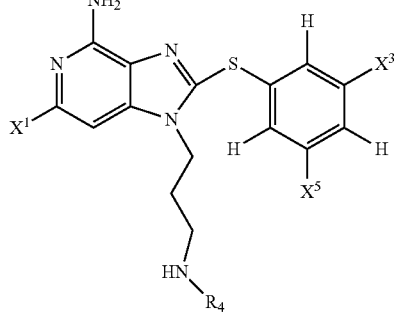 |
| IAB | 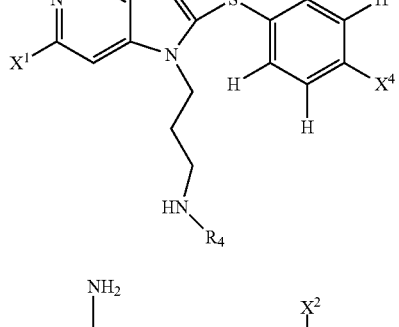 |
| IAC | 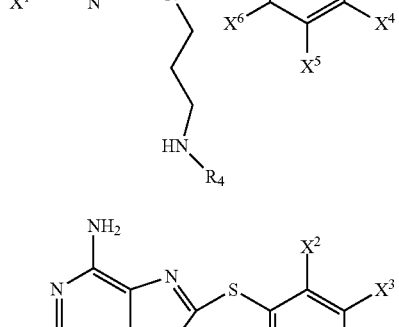 |
| IAD | 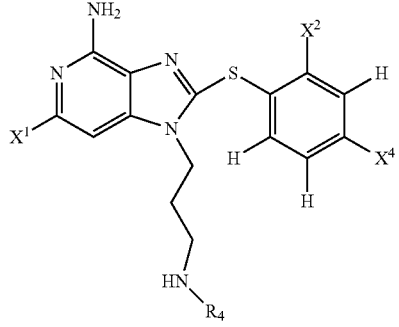 |
| IAE | 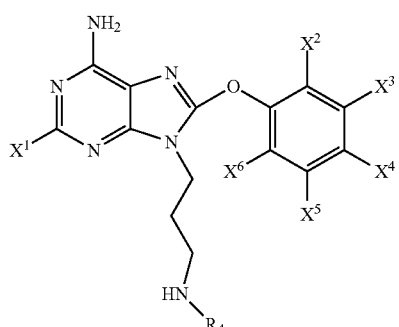 |

TABLE 2-continued
| Formula | Compound |
|---|---|
| IAF | 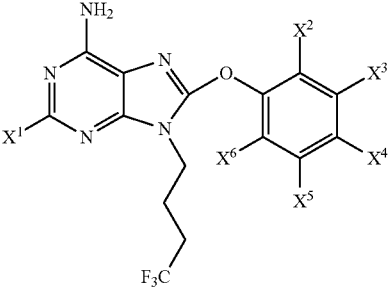 |
| IAG | 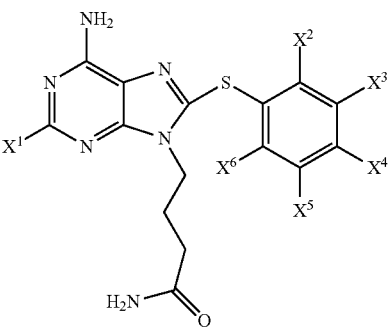 |
| IAH | 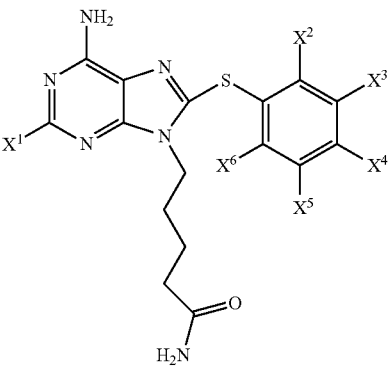 |
| IAI | 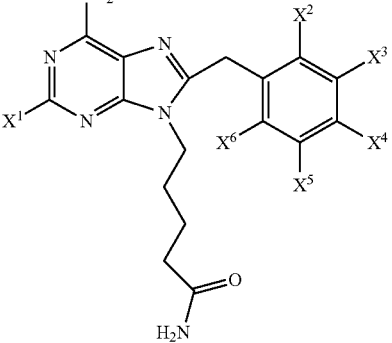 |
| IAJ | 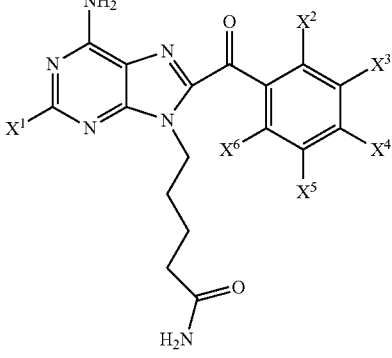 |
| IAK | 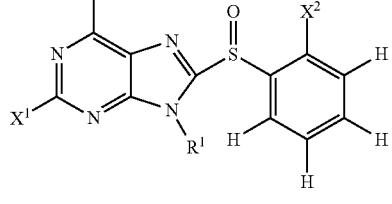 |
| IAL | 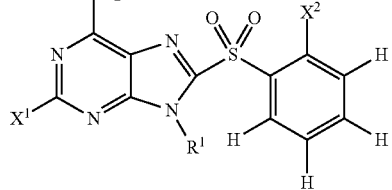 |
| IAM | 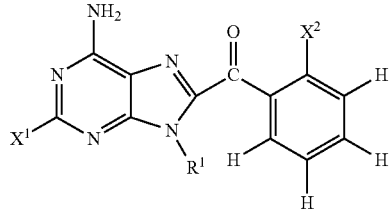 |
| IAN | 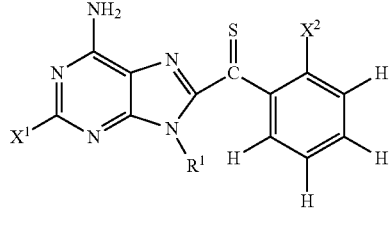 |
| IAO | 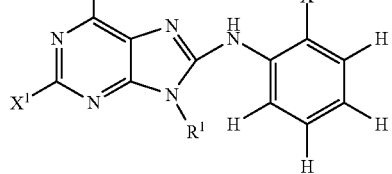 |

TABLE 2-continued

| Formula | Compound |
|---|---|
| IAP | (structure) |
| IAQ | (structure) |
| IAR | (structure) |
| IAS | (structure) |
| IAT | (structure) |
| IAU | (structure) |
| IAV | (structure) |
| IAW | (structure) |
| IAX | (structure) |
| IAY | (structure) |
| IAZ | (structure) |
| IBA | (structure) |
| IBB | (structure) |
| IBC | (structure) |

TABLE 2-continued

| Formula | Compound |
|---|---|
| IBD | (structure with OH, X², X⁴) |
| IBE | (structure with F, X², X⁴) |
| IBF | (structure with S=O, X², X⁵) |
| IBG | (structure with SO₂, X², X⁵) |
| IBH | (structure with C=O, X², X⁵) |
| IBI | (structure with C=S, X², X⁵) |
| IBJ | (structure with NH, X², X⁵) |
| IBK | (structure with OH, X², X⁵) |
| IBL | (structure with F, X², X⁵) |
| IBM | (structure with S=O, X³, X⁵) |
| IBN | (structure with SO₂, X³, X⁵) |
| IBO | (structure with C=O, X³, X⁵) |
| IBP | (structure with C=S, X³, X⁵) |
| IBQ | (structure with NH, X³, X⁵) |

TABLE 2-continued

| Formula | Compound |
|---|---|
| IBR | (structure) |
| IBS | (structure) |
| IBT | (structure) |
| IBU | (structure) |
| IBV | (structure) |
| IBW | (structure) |
| IBX | (structure) |
| IBY | (structure) |
| IBZ | (structure) |
| ICA | (structure) |
| ICB | (structure) |
| ICC | (structure) |
| ICD | (structure) |
| ICE | (structure) |

TABLE 2-continued
| Formula | Compound |
|---|---|
| ICF | 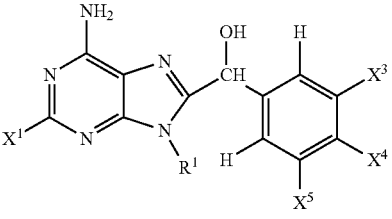 |
| ICC | 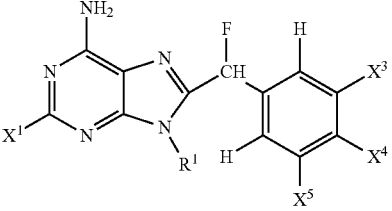 |
| ICD | 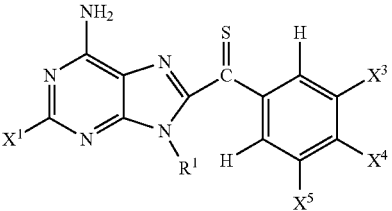 |
| ICE | 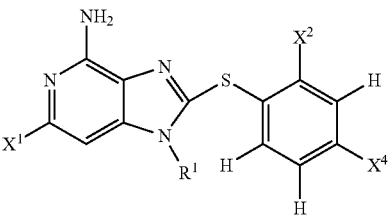 |
| ICF | 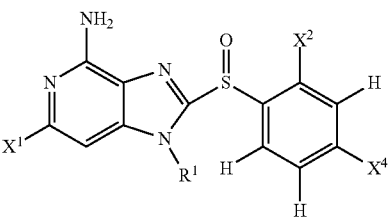 |
| ICG | 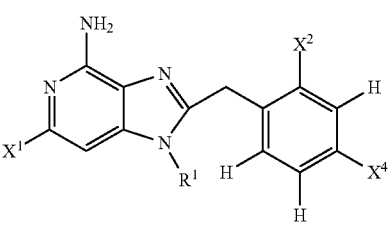 |
| ICH | 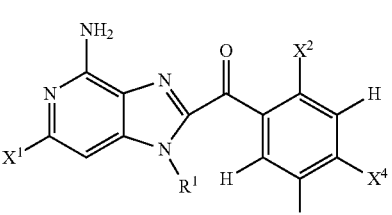 |
| ICI | 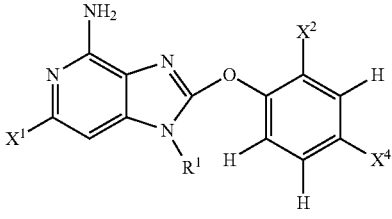 |
| ICJ | 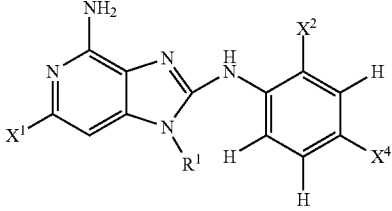 |
| ICK | 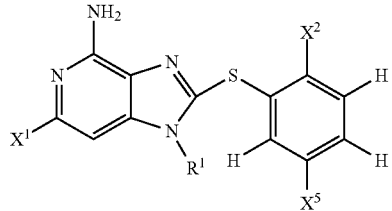 |
| ICL | 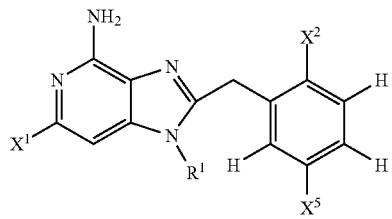 |
| ICM | 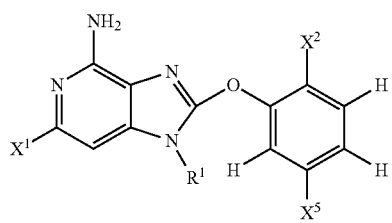 |
| ICN | 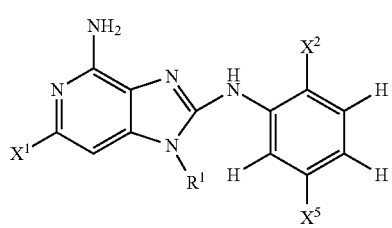 |
| ICO | 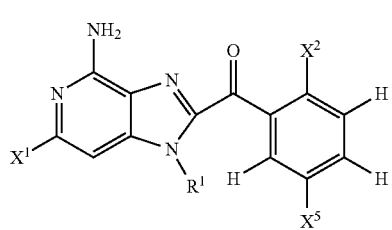 |

TABLE 2-continued

| Formula | Compound |
|---|---|
| ICP | (structure) |
| ICQ | (structure) |
| ICR | (structure) |
| ICS | (structure) |
| ICT | (structure) |
| ICU | (structure) |
| ICV | (structure) |
| ICW | (structure) |
| ICX | (structure) |
| ICY | (structure) |
| ICZ | (structure) |
| IDA | (structure) |
| IDB | (structure) |
| IDC | (structure) |

TABLE 2-continued

| Formula | Compound |
|---|---|
| IDD | (structure) |
| IDE | (structure) |
| IDF | (structure) |
| IDG | (structure) |
| IDH | (structure) |

Illustrative compounds of Formula (I) are listed below in Tables 2A, 2B, 2C, 2D and 3.

TABLE 2A

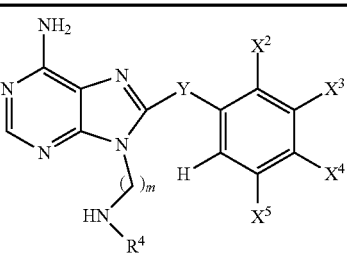

and pharmaceutically acceptable salts thereof, where:

| m | $R^4$ | Y | $X^2$ | $X^3$ | $X^4$ | $X^5$ |
|---|---|---|---|---|---|---|
| 2 | $CH(CH_3)_2$ | S | H | Cl | H | H |
| 2 | $CH_2CH_2OH$ | S | H | H | H | Cl |
| 2 | $CH_2CH(CH_3)OH$ | S | H | H | Cl | H |
| 2 | $CH(CH_3)CH_2OH$ | S | Cl | H | H | H |
| 2 | $CH(CH_3)CH(CH_3)OH$ | S | H | Br | H | H |
| 2 | $C(CH_3)_2CH_2OH$ | S | H | H | H | Br |
| 2 | $CH_2C(CH_3)_2OH$ | S | H | H | Br | H |
| 2 | $CH_2CHF_2$ | S | Br | H | H | H |
| 2 | $CH_2CF_3$ | S | H | I | H | H |
| 2 | $CH_2CH(CH_3)_2$ | S | H | H | H | I |
| 2 | $CH_2C(CH_3)_3$ | S | H | H | I | H |
| 2 | $H_2C-C\equiv N$ | S | I | H | H | H |
| 3 | $H_2C-C\equiv CH$ | S | H | $CH_3$ | H | H |
| 3 | $CH(CH_3)_2$ | S | H | H | H | $CH_3$ |
| 3 | $CH_2CH_2OH$ | S | H | H | $CH_3$ | H |
| 3 | $CH_2CH(CH_3)OH$ | S | $CH_3$ | H | H | H |
| 3 | $CH(CH_3)CH_2OH$ | S | H | $C_2H_5$ | H | H |
| 3 | $CH(CH_3)CH(CH_3)OH$ | S | H | H | H | $C_2H_5$ |
| 3 | $C(CH_3)_2CH_2OH$ | S | H | H | $C_2H_5$ | H |
| 3 | $CH_2C(CH_3)_2OH$ | S | $C_2H_5$ | H | H | H |
| 3 | $CH_2CHF_2$ | S | H | i-$C_3H_7$ | H | H |
| 3 | $CH_2CF_3$ | S | H | H | H | i-$C_3H_7$ |
| 3 | $CH_2CH(CH_3)_2$ | S | H | H | i-$C_3H_7$ | H |
| 3 | $CH_2C(CH_3)_3$ | S | i-$C_3H_7$ | H | H | H |
| 3 | $H_2C-C\equiv N$ | O | H | Cl | H | H |
| 3 | $H_2C-C\equiv CH$ | O | H | H | H | Cl |
| 2 | $CH(CH_3)_2$ | O | H | H | Cl | H |
| 2 | $CH_2CH_2OH$ | O | Cl | H | H | H |
| 2 | $CH_2CH(CH_3)OH$ | O | H | Br | H | H |
| 2 | $CH(CH_3)CH_2OH$ | O | H | H | H | Br |
| 2 | $CH(CH_3)CH(CH_3)OH$ | O | H | H | Br | H |
| 2 | $C(CH_3)_2CH_2OH$ | O | Br | H | H | H |
| 2 | $CH_2C(CH_3)_2OH$ | O | H | I | H | H |
| 2 | $CH_2CHF_2$ | O | H | H | H | I |
| 2 | $CH_2CF_3$ | O | H | H | I | H |
| 2 | $CH_2CH(CH_3)_2$ | O | I | H | H | H |
| 3 | $CH_2C(CH_3)_3$ | O | H | $CH_3$ | H | H |
| 3 | $H_2C-C\equiv N$ | O | H | H | H | $CH_3$ |
| 3 | $H_2C-C\equiv CH$ | O | H | H | $CH_3$ | H |
| 3 | $CH(CH_3)_2$ | O | $CH_3$ | H | H | H |
| 3 | $CH_2CH_2OH$ | O | H | $C_2H_5$ | H | H |
| 3 | $CH_2CH(CH_3)OH$ | O | H | H | H | $C_2H_5$ |
| 3 | $CH(CH_3)CH_2OH$ | O | H | H | $C_2H_5$ | H |
| 3 | $CH(CH_3)CH(CH_3)OH$ | O | $C_2H_5$ | H | H | H |
| 3 | $C(CH_3)_2CH_2OH$ | O | H | i-$C_3H_7$ | H | H |
| 3 | $CH_2C(CH_3)_2OH$ | O | H | H | H | i-$C_3H_7$ |
| 3 | $CH_2CHF_2$ | O | H | H | i-$C_3H_7$ | H |
| 3 | $CH_2CF_3$ | O | i-$C_3H_7$ | H | H | H |
| 2 | $CH_2CH(CH_3)_2$ | S=O | H | Cl | H | H |
| 2 | $CH_2C(CH_3)_3$ | S=O | H | H | H | Cl |
| 2 | $H_2C-C\equiv N$ | S=O | H | H | Cl | H |
| 2 | $H_2C-C\equiv CH$ | S=O | Cl | H | H | H |
| 2 | $CH(CH_3)_2$ | S=O | H | Br | H | H |
| 2 | $CH_2CH_2OH$ | S=O | H | H | H | Br |
| 2 | $CH_2CH(CH_3)OH$ | S=O | H | H | Br | H |
| 2 | $CH(CH_3)CH_2OH$ | S=O | Br | H | H | H |
| 2 | $CH(CH_3)CH(CH_3)OH$ | S=O | H | I | H | H |
| 2 | $C(CH_3)_2CH_2OH$ | S=O | H | H | H | I |
| 2 | $CH_2C(CH_3)_2OH$ | S=O | H | H | I | H |
| 2 | $CH_2CHF_2$ | S=O | I | H | H | H |
| 3 | $CH_2CF_3$ | S=O | H | $CH_3$ | H | H |

TABLE 2A-continued

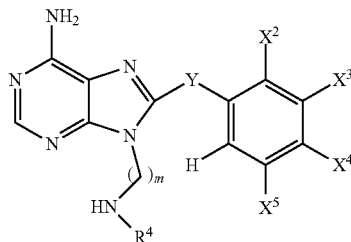

and pharmaceutically acceptable salts thereof, where:

| m | R⁴ | Y | X² | X³ | X⁴ | X⁵ |
|---|---|---|---|---|---|---|
| 3 | CH₂CH(CH₃)₂ | S=O | H | H | H | CH₃ |
| 3 | CH₂C(CH₃)₃ | S=O | H | H | CH₃ | H |
| 3 | H₂C—C≡N | S=O | CH₃ | H | H | H |
| 3 | H₂C—C≡CH | S=O | H | C₂H₅ | H | H |
| 3 | CH(CH₃)₂ | S=O | H | H | H | C₂H₅ |
| 3 | CH₂CH₂OH | S=O | H | H | C₂H₅ | H |
| 3 | CH₂CH(CH₃)OH | S=O | C₂H₅ | H | H | H |
| 3 | CH(CH₃)CH₂OH | S=O | H | i-C₃H₇ | H | H |
| 3 | CH(CH₃)₂ | S=O | H | H | H | i-C₃H₇ |
| 3 | CH₂CH₂OH | S=O | H | H | i-C₃H₇ | H |
| 3 | CH₂CH(CH₃)OH | S=O | i-C₃H₇ | H | H | H |
| 2 | CH(CH₃)CH₂OH | O=S=O | H | Cl | H | H |
| 2 | CH(CH₃)CH(CH₃)OH | O=S=O | H | H | H | Cl |
| 2 | C(CH₃)₂CH₂OH | O=S=O | H | H | Cl | H |
| 2 | CH₂C(CH₃)₂OH | O=S=O | Cl | H | H | H |
| 2 | CH₂CHF₂ | O=S=O | H | Br | H | H |
| 2 | CH₂CF₃ | O=S=O | H | H | H | Br |
| 2 | CH₂CH(CH₃)₂ | O=S=O | H | H | Br | H |
| 2 | CH₂C(CH₃)₃ | O=S=O | Br | H | H | H |
| 2 | H₂C—C≡N | O=S=O | H | I | H | H |
| 2 | H₂C—C≡CH | O=S=O | H | H | H | I |
| 2 | CH(CH₃)₂ | O=S=O | H | H | I | H |
| 2 | CH₂CH₂OH | O=S=O | I | H | H | H |
| 3 | CH₂CH(CH₃)OH | O=S=O | H | CH₃ | H | H |
| 3 | CH(CH₃)CH₂OH | O=S=O | H | H | H | CH₃ |
| 3 | CH₂CH(CH₃)OH | O=S=O | H | H | CH₃ | H |
| 3 | C(CH₃)₂CH₂OH | O=S=O | CH₃ | H | H | H |
| 3 | CH₂C(CH₃)₂OH | O=S=O | H | C₂H₅ | H | H |
| 3 | CH₂CHF₂ | O=S=O | H | H | H | C₂H₅ |
| 3 | CH₂CF₃ | O=S=O | H | H | C₂H₅ | H |
| 3 | CH₂CH(CH₃)₂ | O=S=O | C₂H₅ | H | H | H |
| 3 | CH₂C(CH₃)₃ | O=S=O | H | i-C₃H₇ | H | H |
| 3 | H₂C—C≡N | O=S=O | H | H | H | i-C₃H₇ |
| 3 | H₂C—C≡CH | O=S=O | H | H | i-C₃H₇ | H |
| 3 | CH(CH₃)₂ | O=S=O | i-C₃H₇ | H | H | H |
| 2 | CH₂CH₂OH | NH | H | Cl | H | H |
| 2 | CH₂CH(CH₃)OH | NH | H | H | H | Cl |
| 2 | CH(CH₃)CH₂OH | NH | H | H | Cl | H |
| 2 | CH(CH₃)CH(CH₃)OH | NH | Cl | H | H | H |
| 2 | C(CH₃)₂CH₂OH | NH | H | Br | H | H |
| 2 | CH₂C(CH₃)₂OH | NH | H | H | H | Br |
| 2 | CH₂CHF₂ | NH | H | H | Br | H |
| 2 | CH₂CF₃ | NH | Br | H | H | H |
| 2 | CH₂CH(CH₃)₂ | NH | H | I | H | H |
| 2 | CH₂C(CH₃)₃ | NH | H | H | H | I |
| 2 | H₂C—C≡N | NH | H | H | I | H |
| 2 | H₂C—C≡CH | NH | I | H | H | H |
| 3 | CH(CH₃)₂ | NH | H | CH₃ | H | H |
| 3 | CH₂CH₂OH | NH | H | H | H | CH₃ |
| 3 | CH₂CH(CH₃)OH | NH | H | H | CH₃ | H |
| 3 | CH(CH₃)CH₂OH | NH | CH₃ | H | H | H |
| 3 | CH(CH₃)CH(CH₃)OH | NH | H | C₂H₅ | H | H |
| 3 | C(CH₃)₂CH₂OH | NH | H | H | H | C₂H₅ |
| 3 | CH₂C(CH₃)₂OH | NH | H | H | C₂H₅ | H |
| 3 | CH₂CHF₂ | NH | C₂H₅ | H | H | H |
| 3 | CH₂CF₃ | NH | H | i-C₃H₇ | H | H |
| 3 | CH₂CH(CH₃)₂ | NH | H | H | H | i-C₃H₇ |
| 3 | CH₂C(CH₃)₃ | NH | H | H | i-C₃H₇ | H |
| 3 | H₂C—C≡N | NH | i-C₃H₇ | H | H | H |
| 2 | H₂C—C≡CH | C=O | H | Cl | H | H |
| 2 | CH(CH₃)₂ | C=O | H | H | H | Cl |
| 2 | CH₂CH₂OH | C=O | H | H | Cl | H |
| 2 | CH₂CH(CH₃)OH | C=O | Cl | H | H | H |
| 2 | CH(CH₃)CH₂OH | C=O | H | Br | H | H |
| 2 | CH(CH₃)CH(CH₃)OH | C=O | H | H | H | Br |
| 2 | C(CH₃)₂CH₂OH | C=O | H | H | Br | H |
| 2 | CH₂C(CH₃)₂OH | C=O | Br | H | H | H |
| 2 | CH₂CHF₂ | C=O | H | I | H | H |
| 2 | CH₂CF₃ | C=O | H | H | H | I |
| 2 | CH₂CH(CH₃)₂ | C=O | H | H | I | H |
| 2 | CH₂C(CH₃)₃ | C=O | I | H | H | H |
| 3 | H₂C—C≡N | C=O | H | CH₃ | H | H |
| 3 | H₂C—C≡CH | C=O | H | H | H | CH₃ |
| 3 | CH(CH₃)₂ | C=O | H | H | CH₃ | H |
| 3 | CH₂CH₂OH | C=O | CH₃ | H | H | H |
| 3 | CH₂CH(CH₃)OH | C=O | H | C₂H₅ | H | H |
| 3 | CH(CH₃)CH₂OH | C=O | H | H | H | C₂H₅ |
| 3 | CH(CH₃)CH(CH₃)OH | C=O | H | H | C₂H₅ | H |
| 3 | C(CH₃)₂CH₂OH | C=O | C₂H₅ | H | H | H |
| 3 | CH₂C(CH₃)₂OH | C=O | H | i-C₃H₇ | H | H |
| 3 | CH₂CHF₂ | C=O | H | H | H | i-C₃H₇ |
| 3 | CH₂CF₃ | C=O | H | H | i-C₃H₇ | H |
| 3 | CH₂CH(CH₃)₂ | C=O | i-C₃H₇ | H | H | H |
| 2 | CH₂C(CH₃)₃ | C=S | H | Cl | H | H |
| 2 | H₂C—C≡N | C=S | H | H | H | Cl |
| 2 | H₂C—C≡CH | C=S | H | H | Cl | H |
| 2 | CH(CH₃)₂ | C=S | Cl | H | H | H |
| 2 | CH₂CH₂OH | C=S | H | Br | H | H |
| 2 | CH₂CH(CH₃)OH | C=S | H | H | H | Br |
| 2 | CH(CH₃)CH₂OH | C=S | H | H | Br | H |
| 2 | CH(CH₃)CH(CH₃)OH | C=S | Br | H | H | H |
| 2 | C(CH₃)₂CH₂OH | C=S | H | I | H | H |
| 2 | CH₂C(CH₃)₂OH | C=S | H | H | H | I |
| 2 | CH₂CHF₂ | C=S | H | H | I | H |
| 2 | CH₂CF₃ | C=S | I | H | H | H |
| 3 | CH₂CH(CH₃)₂ | C=S | H | CH₃ | H | H |
| 3 | CH₂C(CH₃)₃ | C=S | H | H | H | CH₃ |
| 3 | H₂C—C≡N | C=S | H | H | CH₃ | H |
| 3 | H₂C—C≡CH | C=S | CH₃ | H | H | H |
| 3 | CH(CH₃)₂ | C=S | H | C₂H₅ | H | H |
| 3 | CH₂CH₂OH | C=S | H | H | H | C₂H₅ |
| 3 | CH₂CH(CH₃)OH | C=S | H | H | C₂H₅ | H |
| 3 | CH(CH₃)CH₂OH | C=S | C₂H₅ | H | H | H |
| 3 | CH(CH₃)CH(CH₃)OH | C=S | H | i-C₃H₇ | H | H |
| 3 | C(CH₃)₂CH₂OH | C=S | H | H | H | i-C₃H₇ |
| 3 | CH₂C(CH₃)₂OH | C=S | H | H | i-C₃H₇ | H |
| 3 | CH₂CHF₂ | C=S | i-C₃H₇ | H | H | H |
| 2 | CH₂CF₃ | CH₂ | H | Cl | H | H |
| 2 | CH₂CH(CH₃)₂ | CH₂ | H | H | H | Cl |
| 2 | CH₂C(CH₃)₃ | CH₂ | H | H | Cl | H |
| 2 | H₂C—C≡N | CH₂ | Cl | H | H | H |
| 2 | H₂C—C≡CH | CH₂ | H | Br | H | H |
| 2 | CH(CH₃)₂ | CH₂ | H | H | H | Br |
| 2 | CH₂CH₂OH | CH₂ | H | H | Br | H |
| 2 | CH₂CH(CH₃)OH | CH₂ | Br | H | H | H |
| 2 | CH(CH₃)CH(CH₃)OH | CH₂ | H | H | H | I |
| 2 | C(CH₃)₂CH₂OH | CH₂ | H | H | I | H |
| 2 | CH₂C(CH₃)₂OH | CH₂ | I | H | H | H |
| 3 | CH₂CHF₂ | CH₂ | H | CH₃ | H | H |
| 3 | CH₂CF₃ | CH₂ | H | H | H | CH₃ |

TABLE 2A-continued

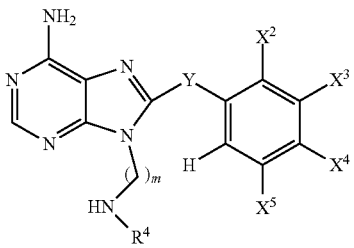

and pharmaceutically acceptable salts thereof, where:

| m | R⁴ | Y | X² | X³ | X⁴ | X⁵ |
|---|---|---|---|---|---|---|
| 3 | CH₂CH(CH₃)₂ | CH₂ | H | H | CH₃ | H |
| 3 | CH₂C(CH₃)₃ | CH₂ | CH₃ | H | H | H |
| 3 | H₂C—C≡N | CH₂ | H | C₂H₅ | H | H |
| 3 | H₂C—C≡CH | CH₂ | H | H | H | C₂H₅ |
| 3 | CH(CH₃)₂ | CH₂ | H | H | C₂H₅ | H |
| 3 | CH₂CH₂OH | CH₂ | C₂H₅ | H | H | H |
| 3 | CH₂CH(CH₃)OH | CH₂ | H | i-C₃H₇ | H | H |
| 3 | CH(CH₃)CH₂OH | CH₂ | H | H | H | i-C₃H₇ |
| 3 | CH(CH₃)CH(CH₃)OH | CH₂ | H | H | i-C₃H₇ | H |
| 3 | C(CH₃)₂CH₂OH | CH₂ | i-C₃H₇ | H | H | H |
| 2 | CH₂C(CH₃)₂OH | CH—OH | H | Cl | H | H |
| 2 | CH₂CHF₂ | CH—OH | H | H | H | Cl |
| 2 | CH₂CF₃ | CH—OH | H | H | Cl | H |
| 2 | CH₂CH(CH₃)₂ | CH—OH | Cl | H | H | H |
| 2 | CH₂C(CH₃)₃ | CH—OH | H | Br | H | H |
| 2 | H₂C—C≡N | CH—OH | H | H | H | Br |
| 2 | H₂C—C≡CH | CH—OH | H | H | Br | H |
| 2 | CH(CH₃)₂ | CH—OH | Br | H | H | H |
| 2 | CH₂CH₂OH | CH—OH | H | I | H | H |
| 2 | CH₂CH(CH₃)OH | CH—OH | H | H | H | I |
| 2 | CH(CH₃)CH₂OH | CH—OH | H | H | I | H |
| 2 | CH(CH₃)CH(CH₃)OH | CH—OH | I | H | H | H |
| 3 | C(CH₃)₂CH₂OH | CH—OH | H | CH₃ | H | H |
| 3 | CH₂C(CH₃)₂OH | CH—OH | H | H | H | CH₃ |
| 3 | CH₂CHF₂ | CH—OH | H | H | CH₃ | H |
| 3 | CH₂CF₃ | CH—OH | CH₃ | H | H | H |
| 3 | CH₂CH(CH₃)₂ | CH—OH | H | C₂H₅ | H | H |
| 3 | CH₂C(CH₃)₃ | CH—OH | H | H | H | C₂H₅ |
| 3 | H₂C—C≡N | CH—OH | H | H | C₂H₅ | H |
| 3 | H₂C—C≡CH | CH—OH | C₂H₅ | H | H | H |
| 3 | CH(CH₃)₂ | CH—OH | H | i-C₃H₇ | H | H |
| 3 | CH₂CH₂OH | CH—OH | H | H | H | i-C₃H₇ |
| 3 | CH₂CH(CH₃)OH | CH—OH | H | H | i-C₃H₇ | H |
| 3 | CH(CH₃)CH₂OH | CH—OH | i-C₃H₇ | H | H | H |
| 2 | CH(CH₃)CH(CH₃)OH | CH—F | H | Cl | H | H |
| 2 | C(CH₃)₂CH₂OH | CH—F | H | H | H | Cl |
| 2 | CH₂C(CH₃)₂OH | CH—F | H | H | Cl | H |
| 2 | CH₂CHF₂ | CH—F | Cl | H | H | H |
| 2 | CH₂CF₃ | CH—F | H | Br | H | H |
| 2 | CH₂CH(CH₃)₂ | CH—F | H | H | H | Br |
| 2 | CH₂C(CH₃)₃ | CH—F | H | H | Br | H |
| 2 | H₂C—C≡N | CH—F | Br | H | H | H |
| 2 | H₂C—C≡CH | CH—F | H | I | H | H |
| 2 | CH(CH₃)₂ | CH—F | H | H | H | I |
| 2 | CH₂CH₂OH | CH—F | H | H | I | H |
| 2 | CH₂CH(CH₃)OH | CH—F | I | H | H | H |
| 3 | CH(CH₃)CH₂OH | CH—F | H | CH₃ | H | H |
| 3 | CH(CH₃)CH(CH₃)OH | CH—F | H | H | H | CH₃ |
| 3 | C(CH₃)₂CH₂OH | CH—F | H | H | CH₃ | H |
| 3 | CH₂C(CH₃)₂OH | CH—F | CH₃ | H | H | H |
| 3 | CH₂CHF₂ | CH—F | H | C₂H₅ | H | H |
| 3 | CH₂CF₃ | CH—F | H | H | H | C₂H₅ |
| 3 | CH₂CH(CH₃)₂ | CH—F | H | H | C₂H₅ | H |
| 3 | CH₂C(CH₃)₃ | CH—F | C₂H₅ | H | H | H |
| 3 | H₂C—C≡N | CH—F | H | i-C₃H₇ | H | H |
| 3 | H₂C—C≡CH | CH—F | H | H | H | i-C₃H₇ |
| 3 | CH(CH₃)₂ | CH—F | H | H | i-C₃H₇ | H |
| 3 | CH₂CH₂OH | CH—F | i-C₃H₇ | H | H | H |
| 2 | CH₂CH(CH₃)OH | S | H | Cl | H | Cl |
| 2 | CH(CH₃)CH₂OH | S | Cl | H | Cl | H |
| 2 | CH(CH₃)CH(CH₃)OH | S | Cl | H | H | Cl |
| 2 | C(CH₃)₂CH₂OH | S | H | Br | H | Br |
| 2 | CH₂C(CH₃)₂OH | S | Br | H | Br | H |
| 2 | CH₂CHF₂ | S | Br | H | H | Br |
| 2 | CH₂CF₃ | S | H | I | H | I |
| 2 | CH₂CH(CH₃)₂ | S | I | H | I | H |
| 2 | CH₂C(CH₃)₃ | S | I | H | H | I |
| 2 | H₂C—C≡N | S | H | CH₃ | H | CH₃ |
| 2 | H₂C—C≡CH | S | CH₃ | H | CH₃ | H |
| 2 | CH(CH₃)₂ | S | CH₃ | H | H | CH₃ |
| 3 | CH₂CH₂OH | S | H | C₂H₅ | H | C₂H₅ |
| 3 | CH₂CH(CH₃)OH | S | C₂H₅ | H | C₂H₅ | H |
| 3 | CH(CH₃)CH₂OH | S | C₂H₅ | H | H | C₂H₅ |
| 3 | CH(CH₃)CH(CH₃)OH | S | H | i-C₃H₇ | H | i-C₃H₇ |
| 3 | C(CH₃)₂CH₂OH | S | i-C₃H₇ | H | i-C₃H₇ | H |
| 3 | CH₂C(CH₃)₂OH | S | i-C₃H₇ | H | H | i-C₃H₇ |
| 3 | CH₂CHF₂ | O | H | Cl | H | Cl |
| 3 | CH₂CF₃ | O | Cl | H | Cl | H |
| 3 | CH₂CH(CH₃)₂ | O | Cl | H | H | Cl |
| 3 | CH₂C(CH₃)₃ | O | H | Br | H | Br |
| 3 | H₂C—C≡N | O | Br | H | Br | H |
| 3 | H₂C—C≡CH | O | Br | H | H | Br |
| 2 | CH(CH₃)₂ | O | H | I | H | I |
| 2 | CH₂CH₂OH | O | I | H | I | H |
| 2 | CH₂CH(CH₃)OH | O | I | H | H | I |
| 2 | CH(CH₃)CH₂OH | O | H | CH₃ | H | CH₃ |
| 2 | CH(CH₃)CH(CH₃)OH | O | CH₃ | H | CH₃ | H |
| 2 | C(CH₃)₂CH₂OH | O | CH₃ | H | H | CH₃ |
| 2 | CH₂C(CH₃)₂OH | O | H | C₂H₅ | H | C₂H₅ |
| 2 | CH₂CHF₂ | O | C₂H₅ | H | C₂H₅ | H |
| 2 | CH₂CF₃ | O | C₂H₅ | H | H | C₂H₅ |
| 2 | CH₂CH(CH₃)₂ | O | H | i-C₃H₇ | H | i-C₃H₇ |
| 2 | CH₂C(CH₃)₃ | O | i-C₃H₇ | H | i-C₃H₇ | H |
| 2 | H₂C—C≡N | O | i-C₃H₇ | H | H | i-C₃H₇ |
| 3 | H₂C—C≡CH | S=O | H | Cl | H | Cl |
| 3 | CH(CH₃)₂ | S=O | Cl | H | Cl | H |
| 3 | CH₂CH₂OH | S=O | Cl | H | H | Cl |
| 3 | CH₂CH(CH₃)OH | S=O | H | Br | H | Br |
| 3 | CH(CH₃)CH₂OH | S=O | Br | H | Br | H |
| 3 | CH(CH₃)CH(CH₃)OH | S=O | Br | H | H | Br |
| 3 | C(CH₃)₂CH₂OH | S=O | H | I | H | I |
| 3 | CH₂C(CH₃)₂OH | S=O | I | H | I | H |
| 3 | CH₂CHF₂ | S=O | I | H | H | I |
| 3 | CH₂CF₃ | S=O | H | CH₃ | H | CH₃ |
| 3 | CH₂CH(CH₃)₂ | S=O | CH₃ | H | CH₃ | H |
| 3 | CH₂C(CH₃)₃ | S=O | CH₃ | H | H | CH₃ |
| 2 | H₂C—C≡N | S=O | H | C₂H₅ | H | C₂H₅ |
| 2 | H₂C—C≡CH | S=O | C₂H₅ | H | C₂H₅ | H |
| 2 | CH(CH₃)₂ | S=O | C₂H₅ | H | H | C₂H₅ |
| 2 | CH₂CH₂OH | S=O | H | i-C₃H₇ | H | i-C₃H₇ |
| 2 | CH₂CH(CH₃)OH | S=O | i-C₃H₇ | H | i-C₃H₇ | H |
| 2 | CH(CH₃)CH₂OH | S=O | i-C₃H₇ | H | H | i-C₃H₇ |
| 2 | CH(CH₃)CH(CH₃)OH | O=S=O | H | Cl | H | Cl |
| 2 | C(CH₃)₂CH₂OH | O=S=O | Cl | H | Cl | H |
| 2 | CH₂C(CH₃)₂OH | O=S=O | Cl | H | H | Cl |
| 2 | CH₂CHF₂ | O=S=O | H | Br | H | Br |
| 2 | CH₂CF₃ | O=S=O | Br | H | Br | H |

TABLE 2A-continued

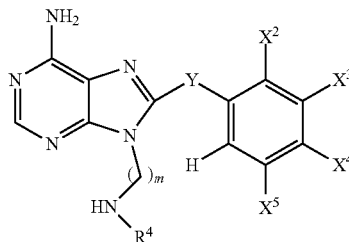

and pharmaceutically acceptable salts thereof, where:

| m | R⁴ | Y | X² | X³ | X⁴ | X⁵ |
|---|---|---|---|---|---|---|
| 2 | CH₂CH(CH₃)₂ | O=S=O | Br | H | H | Br |
| 3 | CH₂C(CH₃)₃ | O=S=O | H | I | H | I |
| 3 | H₂C—C≡N | O=S=O | I | H | I | H |
| 3 | H₂C—C≡CH | O=S=O | I | H | H | I |
| 3 | CH(CH₃)₂ | O=S=O | H | CH₃ | H | CH₃ |
| 3 | CH₂CH₂OH | O=S=O | CH₃ | H | CH₃ | H |
| 3 | CH₂CH(CH₃)OH | O=S=O | CH₃ | H | H | CH₃ |
| 3 | CH(CH₃)CH₂OH | O=S=O | H | C₂H₅ | H | C₂H₅ |
| 3 | CH(CH₃)CH(CH₃)OH | O=S=O | C₂H₅ | H | C₂H₅ | H |
| 3 | C(CH₃)₂CH₂OH | O=S=O | C₂H₅ | H | H | C₂H₅ |
| 3 | CH₂C(CH₃)₂OH | O=S=O | H | i-C₃H₇ | H | i-C₃H₇ |
| 3 | CH₂CHF₂ | O=S=O | i-C₃H₇ | H | i-C₃H₇ | H |
| 3 | CH₂CF₃ | O=S=O | i-C₃H₇ | H | H | i-C₃H₇ |
| 2 | CH₂CH(CH₃)₂ | NH | H | Cl | H | Cl |
| 2 | CH₂C(CH₃)₃ | NH | Cl | H | Cl | H |
| 2 | H₂C—C≡N | NH | Cl | H | H | Cl |
| 2 | H₂C—C≡CH | NH | H | Br | H | Br |
| 2 | CH(CH₃)₂ | NH | Br | H | Br | H |
| 2 | CH₂CH₂OH | NH | Br | H | H | Br |
| 2 | CH₂CH(CH₃)OH | NH | H | I | H | I |
| 2 | CH(CH₃)CH₂OH | NH | I | H | I | H |
| 2 | CH(CH₃)CH(CH₃)OH | NH | I | H | H | I |
| 2 | C(CH₃)₂CH₂OH | NH | H | CH₃ | H | CH₃ |
| 2 | CH₂C(CH₃)₂OH | NH | CH₃ | H | CH₃ | H |
| 2 | CH₂CHF₂ | NH | CH₃ | H | H | CH₃ |
| 3 | CH₂CF₃ | NH | H | C₂H₅ | H | C₂H₅ |
| 3 | CH₂CH(CH₃)₂ | NH | C₂H₅ | H | C₂H₅ | H |
| 3 | CH₂C(CH₃)₃ | NH | C₂H₅ | H | H | C₂H₅ |
| 3 | H₂C—C≡N | NH | H | i-C₃H₇ | H | i-C₃H₇ |
| 3 | H₂C—C≡CH | NH | i-C₃H₇ | H | i-C₃H₇ | H |
| 3 | CH(CH₃)₂ | NH | i-C₃H₇ | H | H | i-C₃H₇ |
| 3 | CH₂CH₂OH | C=O | H | Cl | H | Cl |
| 3 | CH₂CH(CH₃)OH | C=O | Cl | H | Cl | H |
| 3 | CH(CH₃)CH₂OH | C=O | Cl | H | H | Cl |
| 3 | CH(CH₃)CH(CH₃)OH | C=O | H | Br | H | Br |
| 3 | C(CH₃)₂CH₂OH | C=O | Br | H | Br | H |
| 3 | CH₂C(CH₃)₂OH | C=O | Br | H | H | Br |
| 3 | CH₂CHF₂ | C=O | H | I | H | I |
| 2 | CH₂CF₃ | C=O | I | H | I | H |
| 2 | CH₂CH(CH₃)₂ | C=O | I | H | H | I |
| 2 | CH₂C(CH₃)₃ | C=O | H | CH₃ | H | CH₃ |
| 2 | H₂C—C≡N | C=O | CH₃ | H | CH₃ | H |
| 2 | H₂C—C≡CH | C=O | CH₃ | H | H | CH₃ |
| 2 | CH(CH₃)₂ | C=O | H | C₂H₅ | H | C₂H₅ |
| 2 | CH₂CH₂OH | C=O | C₂H₅ | H | C₂H₅ | H |
| 2 | CH₂CH(CH₃)OH | C=O | C₂H₅ | H | H | C₂H₅ |
| 2 | CH(CH₃)CH₂OH | C=O | H | i-C₃H₇ | H | i-C₃H₇ |
| 2 | CH(CH₃)CH(CH₃)OH | C=O | i-C₃H₇ | H | i-C₃H₇ | H |
| 2 | C(CH₃)₂CH₂OH | C=O | i-C₃H₇ | H | H | i-C₃H₇ |
| 3 | CH₂C(CH₃)₂OH | C=S | H | Cl | H | Cl |
| 3 | CH₂CHF₂ | C=S | Cl | H | Cl | H |
| 3 | CH₂CF₃ | C=S | Cl | H | H | Cl |
| 3 | CH₂CH(CH₃)₂ | C=S | H | Br | H | Br |
| 3 | CH₂C(CH₃)₃ | C=S | Br | H | Br | H |
| 3 | H₂C—C≡N | C=S | Br | H | H | Br |
| 3 | H₂C—C≡CH | C=S | H | I | H | I |
| 3 | CH(CH₃)₂ | C=S | I | H | I | H |
| 3 | CH₂CH₂OH | C=S | I | H | H | I |
| 3 | CH₂CH(CH₃)OH | C=S | H | CH₃ | H | CH₃ |
| 2 | CH(CH₃)CH₂OH | C=S | CH₃ | H | CH₃ | H |
| 2 | CH(CH₃)CH(CH₃)OH | C=S | CH₃ | H | H | CH₃ |
| 2 | C(CH₃)₂CH₂OH | C=S | H | C₂H₅ | H | C₂H₅ |
| 2 | CH₂C(CH₃)₂OH | C=S | C₂H₅ | H | C₂H₅ | H |
| 2 | CH₂CHF₂ | C=S | C₂H₅ | H | H | C₂H₅ |
| 2 | CH₂CF₃ | C=S | H | i-C₃H₇ | H | i-C₃H₇ |
| 2 | CH₂CH(CH₃)₂ | C=S | i-C₃H₇ | H | i-C₃H₇ | H |
| 2 | CH₂C(CH₃)₃ | C=S | i-C₃H₇ | H | H | i-C₃H₇ |
| 3 | H₂C—C≡N | CH₂ | H | Cl | H | Cl |
| 3 | H₂C—C≡CH | CH₂ | Cl | H | Cl | H |
| 3 | CH(CH₃)₂ | CH₂ | Cl | H | H | Cl |
| 3 | CH₂CH₂OH | CH₂ | H | Br | H | Br |
| 3 | CH₂CH(CH₃)OH | CH₂ | Br | H | Br | H |
| 3 | CH(CH₃)CH₂OH | CH₂ | Br | H | H | Br |
| 3 | CH(CH₃)CH(CH₃)OH | CH₂ | H | I | H | I |
| 2 | C(CH₃)₂CH₂OH | CH₂ | I | H | I | H |
| 2 | CH₂C(CH₃)₂OH | CH₂ | I | H | H | I |
| 2 | CH₂CHF₂ | CH₂ | H | CH₃ | H | CH₃ |
| 2 | CH₂CF₃ | CH₂ | CH₃ | H | CH₃ | H |
| 2 | CH₂CH(CH₃)₂ | CH₂ | CH₃ | H | H | CH₃ |
| 3 | CH₂C(CH₃)₃ | CH₂ | H | C₂H₅ | H | C₂H₅ |
| 3 | H₂C—C≡N | CH₂ | C₂H₅ | H | C₂H₅ | H |
| 3 | H₂C—C≡CH | CH₂ | C₂H₅ | H | H | C₂H₅ |
| 3 | CH(CH₃)₂ | CH₂ | H | i-C₃H₇ | H | i-C₃H₇ |
| 3 | CH₂CH₂OH | CH₂ | i-C₃H₇ | H | i-C₃H₇ | H |
| 3 | CH₂CH(CH₃)OH | CH₂ | i-C₃H₇ | H | H | i-C₃H₇ |
| 2 | CH(CH₃)CH₂OH | CH—OH | H | Cl | H | Cl |
| 2 | CH(CH₃)CH(CH₃)OH | CH—OH | Cl | H | Cl | H |
| 2 | C(CH₃)₂CH₂OH | CH—OH | Cl | H | H | Cl |
| 2 | CH₂C(CH₃)₂OH | CH—OH | H | Br | H | Br |
| 2 | CH₂CHF₂ | CH—OH | Br | H | Br | H |
| 2 | CH₂CF₃ | CH—OH | Br | H | H | Br |
| 3 | CH₂CH(CH₃)₂ | CH—OH | H | I | H | I |
| 3 | CH₂C(CH₃)₃ | CH—OH | I | H | I | H |
| 3 | H₂C—C≡N | CH—OH | I | H | H | I |
| 3 | H₂C—C≡CH | CH—OH | H | CH₃ | H | CH₃ |
| 3 | CH(CH₃)₂ | CH—OH | CH₃ | H | CH₃ | H |
| 3 | CH₂CH₂OH | CH—OH | CH₃ | H | H | CH₃ |
| 2 | CH₂CH(CH₃)OH | CH—OH | H | C₂H₅ | H | C₂H₅ |
| 2 | CH(CH₃)CH₂OH | CH—OH | C₂H₅ | H | C₂H₅ | H |
| 2 | CH(CH₃)CH(CH₃)OH | CH—OH | C₂H₅ | H | H | C₂H₅ |
| 2 | C(CH₃)₂CH₂OH | CH—OH | H | i-C₃H₇ | H | i-C₃H₇ |
| 2 | CH₂C(CH₃)₂OH | CH—OH | i-C₃H₇ | H | i-C₃H₇ | H |
| 2 | CH₂CHF₂ | CH—OH | i-C₃H₇ | H | H | i-C₃H₇ |
| 3 | CH₂CF₃ | CH—F | H | Cl | H | Cl |
| 3 | CH₂CH(CH₃)₂ | CH—F | Cl | H | Cl | H |
| 3 | CH₂C(CH₃)₃ | CH—F | Cl | H | H | Cl |
| 3 | H₂C—C≡N | CH—F | H | Br | H | Br |
| 3 | H₂C—C≡CH | CH—F | Br | H | Br | H |
| 3 | CH(CH₃)₂ | CH—F | Br | H | H | Br |
| 2 | CH₂CH₂OH | CH—F | H | I | H | I |
| 2 | CH₂CH(CH₃)OH | CH—F | I | H | I | H |
| 2 | CH(CH₃)CH₂OH | CH—F | I | H | H | I |
| 2 | CH(CH₃)CH(CH₃)OH | CH—F | H | CH₃ | H | CH₃ |
| 2 | C(CH₃)₂CH₂OH | CH—F | CH₃ | H | CH₃ | H |

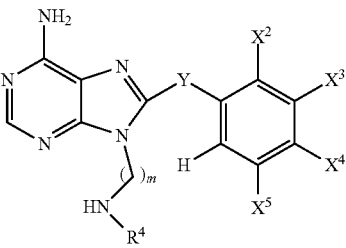

TABLE 2A-continued

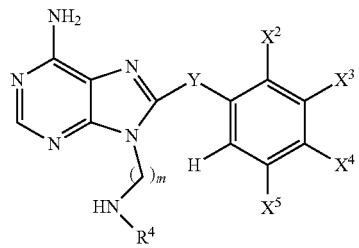

and pharmaceutically acceptable salts thereof, where:

| m | R$^4$ | Y | X$^2$ | X$^3$ | X$^4$ | X$^5$ |
|---|---|---|---|---|---|---|
| 2 | CH$_2$C(CH$_3$)$_2$OH | CH—F | CH$_3$ | H | H | CH$_3$ |
| 3 | CH$_2$CHF$_2$ | CH—F | H | C$_2$H$_5$ | H | C$_2$H$_5$ |
| 3 | CH$_2$CF$_3$ | CH—F | C$_2$H$_5$ | H | C$_2$H$_5$ | H |
| 3 | CH$_2$CH(CH$_3$)$_2$ | CH—F | C$_2$H$_5$ | H | H | C$_2$H$_5$ |
| 3 | CH$_2$C(CH$_3$)$_3$ | CH—F | H | i-C$_3$H$_7$ | H | i-C$_3$H$_7$ |
| 3 | H$_2$C—C≡N | CH—F | i-C$_3$H$_7$ | H | i-C$_3$H$_7$ | H |
| 3 | H$_2$C—C≡CH | CH—F | i-C$_3$H$_7$ | H | H | i-C$_3$H$_7$ |
| 2 | CH(CH$_3$)$_2$ | S | H | Cl | Cl | Cl |
| 2 | CH$_2$CH$_2$OH | S | Cl | Cl | H | Cl |
| 2 | CH$_2$CH(CH$_3$)OH | S | H | Br | Br | Br |
| 2 | CH(CH$_3$)CH$_2$OH | S | Br | Br | H | Br |
| 2 | CH(CH$_3$)CH(CH$_3$)OH | S | H | I | I | I |
| 2 | C(CH$_3$)$_2$CH$_2$OH | S | I | I | H | I |
| 3 | CH$_2$C(CH$_3$)$_2$OH | S | H | CH$_3$ | CH$_3$ | CH$_3$ |
| 3 | CH$_2$CHF$_2$ | S | CH$_3$ | CH$_3$ | H | CH$_3$ |
| 3 | CH$_2$CF$_3$ | S | H | C$_2$H$_5$ | C$_2$H$_5$ | C$_2$H$_5$ |
| 3 | CH$_2$CH(CH$_3$)$_2$ | S | C$_2$H$_5$ | C$_2$H$_5$ | H | C$_2$H$_5$ |
| 3 | CH$_2$C(CH$_3$)$_3$ | S | H | i-C$_3$H$_7$ | i-C$_3$H$_7$ | i-C$_3$H$_7$ |
| 3 | H$_2$C—C≡N | S | i-C$_3$H$_7$ | i-C$_3$H$_7$ | H | i-C$_3$H$_7$ |
| 2 | H$_2$C—C≡CH | O | H | Cl | Cl | Cl |
| 2 | CH(CH$_3$)$_2$ | O | Cl | Cl | H | Cl |
| 2 | CH$_2$CH$_2$OH | O | H | Br | Br | Br |
| 2 | CH$_2$CH(CH$_3$)OH | O | Br | Br | H | Br |
| 2 | CH(CH$_3$)CH$_2$OH | O | H | I | I | I |
| 2 | CH(CH$_3$)CH(CH$_3$)OH | O | I | I | H | I |
| 3 | C(CH$_3$)$_2$CH$_2$OH | O | H | CH$_3$ | CH$_3$ | CH$_3$ |
| 3 | CH$_2$C(CH$_3$)$_2$OH | O | CH$_3$ | CH$_3$ | H | CH$_3$ |
| 3 | CH$_2$CHF$_2$ | O | H | C$_2$H$_5$ | C$_2$H$_5$ | C$_2$H$_5$ |
| 3 | CH$_2$CF$_3$ | O | C$_2$H$_5$ | C$_2$H$_5$ | H | C$_2$H$_5$ |
| 3 | CH$_2$CH(CH$_3$)$_2$ | O | H | i-C$_3$H$_7$ | i-C$_3$H$_7$ | i-C$_3$H$_7$ |
| 3 | CH$_2$C(CH$_3$)$_3$ | O | i-C$_3$H$_7$ | i-C$_3$H$_7$ | H | i-C$_3$H$_7$ |
| 2 | H$_2$C—C≡N | S=O | H | Cl | Cl | Cl |
| 2 | H$_2$C—C≡CH | S=O | Cl | Cl | H | Cl |
| 2 | CH(CH$_3$)$_2$ | S=O | H | Br | Br | Br |
| 2 | CH$_2$CH$_2$OH | S=O | Br | Br | H | Br |
| 2 | CH$_2$CH(CH$_3$)OH | S=O | H | I | I | I |
| 2 | CH(CH$_3$)CH$_2$OH | S=O | I | I | H | I |
| 3 | CH(CH$_3$)CH(CH$_3$)OH | S=O | H | CH$_3$ | CH$_3$ | CH$_3$ |
| 3 | C(CH$_3$)$_2$CH$_2$OH | S=O | CH$_3$ | CH$_3$ | H | CH$_3$ |
| 3 | CH$_2$C(CH$_3$)$_2$OH | S=O | H | C$_2$H$_5$ | C$_2$H$_5$ | C$_2$H$_5$ |
| 3 | CH$_2$CHF$_2$ | S=O | C$_2$H$_5$ | C$_2$H$_5$ | H | C$_2$H$_5$ |
| 3 | CH$_2$CF$_3$ | S=O | H | i-C$_3$H$_7$ | i-C$_3$H$_7$ | i-C$_3$H$_7$ |
| 3 | CH$_2$CH(CH$_3$)$_2$ | S=O | i-C$_3$H$_7$ | i-C$_3$H$_7$ | H | i-C$_3$H$_7$ |
| 2 | CH$_2$C(CH$_3$)$_3$ | O=S=O | H | Cl | Cl | Cl |
| 2 | H$_2$C—C≡N | O=S=O | Cl | Cl | H | Cl |
| 2 | H$_2$C—C≡CH | O=S=O | H | Br | Br | Br |
| 2 | CH(CH$_3$)$_2$ | O=S=O | Br | Br | H | Br |
| 2 | CH$_2$CH$_2$OH | O=S=O | H | I | I | I |
| 2 | CH$_2$CH(CH$_3$)OH | O=S=O | I | I | H | I |
| 3 | CH(CH$_3$)CH$_2$OH | O=S=O | H | CH$_3$ | CH$_3$ | CH$_3$ |
| 3 | CH(CH$_3$)CH(CH$_3$)OH | O=S=O | CH$_3$ | CH$_3$ | H | CH$_3$ |
| 3 | C(CH$_3$)$_2$CH$_2$OH | O=S=O | H | C$_2$H$_5$ | C$_2$H$_5$ | C$_2$H$_5$ |
| 3 | CH$_2$C(CH$_3$)$_2$OH | O=S=O | C$_2$H$_5$ | C$_2$H$_5$ | H | C$_2$H$_5$ |
| 3 | CH$_2$CHF$_2$ | O=S=O | H | i-C$_3$H$_7$ | i-C$_3$H$_7$ | i-C$_3$H$_7$ |
| 3 | CH$_2$CF$_3$ | O=S=O | i-C$_3$H$_7$ | i-C$_3$H$_7$ | H | i-C$_3$H$_7$ |
| 2 | CH$_2$CH(CH$_3$)$_2$ | NH | H | Cl | Cl | Cl |
| 2 | CH$_2$C(CH$_3$)$_3$ | NH | Cl | Cl | H | Cl |
| 2 | H$_2$C—C≡N | NH | H | Br | Br | Br |
| 2 | H$_2$C—C≡CH | NH | Br | Br | H | Br |
| 2 | CH(CH$_3$)$_2$ | NH | H | I | I | I |
| 2 | CH$_2$CH$_2$OH | NH | I | I | H | I |
| 3 | CH$_2$CH(CH$_3$)OH | NH | H | CH$_3$ | CH$_3$ | CH$_3$ |
| 3 | CH(CH$_3$)CH$_2$OH | NH | CH$_3$ | CH$_3$ | H | CH$_3$ |
| 3 | CH(CH$_3$)CH(CH$_3$)OH | NH | H | C$_2$H$_5$ | C$_2$H$_5$ | C$_2$H$_5$ |
| 3 | C(CH$_3$)$_2$CH$_2$OH | NH | C$_2$H$_5$ | C$_2$H$_5$ | H | C$_2$H$_5$ |
| 3 | CH$_2$C(CH$_3$)$_2$OH | NH | H | i-C$_3$H$_7$ | i-C$_3$H$_7$ | i-C$_3$H$_7$ |
| 3 | CH$_2$CHF$_2$ | NH | i-C$_3$H$_7$ | i-C$_3$H$_7$ | H | i-C$_3$H$_7$ |
| 2 | CH$_2$CF$_3$ | C=O | H | Cl | Cl | Cl |
| 2 | CH$_2$CH(CH$_3$)$_2$ | C=O | Cl | Cl | H | Cl |
| 2 | CH$_2$C(CH$_3$)$_3$ | C=O | H | Br | Br | Br |
| 2 | H$_2$C—C≡N | C=O | Br | Br | H | Br |
| 2 | H$_2$C—C≡CH | C=O | H | I | I | I |
| 3 | CH(CH$_3$)$_2$ | C=O | I | I | H | I |
| 3 | CH$_2$CH$_2$OH | C=O | H | CH$_3$ | CH$_3$ | CH$_3$ |
| 3 | CH$_2$CH(CH$_3$)OH | C=O | CH$_3$ | CH$_3$ | H | CH$_3$ |
| 3 | CH(CH$_3$)CH$_2$OH | C=O | H | C$_2$H$_5$ | C$_2$H$_5$ | C$_2$H$_5$ |
| 3 | CH(CH$_3$)CH(CH$_3$)OH | C=O | C$_2$H$_5$ | C$_2$H$_5$ | H | C$_2$H$_5$ |
| 3 | C(CH$_3$)$_2$CH$_2$OH | C=O | H | i-C$_3$H$_7$ | i-C$_3$H$_7$ | i-C$_3$H$_7$ |
| 3 | CH$_2$C(CH$_3$)$_2$OH | C=O | i-C$_3$H$_7$ | i-C$_3$H$_7$ | H | i-C$_3$H$_7$ |
| 2 | CH$_2$CHF$_2$ | C=S | H | Cl | Cl | Cl |
| 2 | CH$_2$CF$_3$ | C=S | Cl | Cl | H | Cl |
| 2 | CH$_2$CH(CH$_3$)$_2$ | C=S | H | Br | Br | Br |
| 2 | CH$_2$C(CH$_3$)$_3$ | C=S | Br | Br | H | Br |
| 2 | H$_2$C—C≡N | C=S | H | I | I | I |
| 2 | H$_2$C—C≡CH | C=S | I | I | H | I |
| 3 | CH(CH$_3$)$_2$ | C=S | H | CH$_3$ | CH$_3$ | CH$_3$ |
| 3 | CH$_2$CH$_2$OH | C=S | CH$_3$ | CH$_3$ | H | CH$_3$ |
| 3 | CH$_2$CH(CH$_3$)OH | C=S | H | C$_2$H$_5$ | C$_2$H$_5$ | C$_2$H$_5$ |
| 3 | CH(CH$_3$)CH$_2$OH | C=S | C$_2$H$_5$ | C$_2$H$_5$ | H | C$_2$H$_5$ |
| 3 | CH(CH$_3$)CH(CH$_3$)OH | C=S | H | i-C$_3$H$_7$ | i-C$_3$H$_7$ | i-C$_3$H$_7$ |
| 3 | C(CH$_3$)$_2$CH$_2$OH | C=S | i-C$_3$H$_7$ | i-C$_3$H$_7$ | H | i-C$_3$H$_7$ |
| 2 | CH$_2$C(CH$_3$)$_2$OH | CH$_2$ | H | Cl | Cl | Cl |
| 2 | CH$_2$CHF$_2$ | CH$_2$ | Cl | Cl | H | Cl |
| 2 | CH$_2$CF$_3$ | CH$_2$ | H | Br | Br | Br |
| 2 | CH$_2$CH(CH$_3$)$_2$ | CH$_2$ | Br | Br | H | Br |
| 2 | CH$_2$C(CH$_3$)$_3$ | CH$_2$ | H | I | I | I |
| 2 | H$_2$C—C≡N | CH$_2$ | I | I | H | I |
| 3 | H$_2$C—C≡CH | CH$_2$ | H | CH$_3$ | CH$_3$ | CH$_3$ |
| 3 | CH(CH$_3$)$_2$ | CH$_2$ | CH$_3$ | CH$_3$ | H | CH$_3$ |
| 3 | CH$_2$CH$_2$OH | CH$_2$ | H | C$_2$H$_5$ | C$_2$H$_5$ | C$_2$H$_5$ |
| 3 | CH$_2$CH(CH$_3$)OH | CH$_2$ | C$_2$H$_5$ | C$_2$H$_5$ | H | C$_2$H$_5$ |
| 3 | CH(CH$_3$)CH$_2$OH | CH$_2$ | H | i-C$_3$H$_7$ | i-C$_3$H$_7$ | i-C$_3$H$_7$ |
| 3 | CH(CH$_3$)CH(CH$_3$)OH | CH$_2$ | i-C$_3$H$_7$ | i-C$_3$H$_7$ | H | i-C$_3$H$_7$ |
| 2 | C(CH$_3$)$_2$CH$_2$OH | CH—OH | H | Cl | Cl | Cl |
| 2 | CH$_2$C(CH$_3$)$_2$OH | CH—OH | Cl | Cl | H | Cl |
| 2 | CH$_2$CHF$_2$ | CH—OH | H | Br | Br | Br |
| 2 | CH$_2$CF$_3$ | CH—OH | Br | Br | H | Br |
| 2 | CH$_2$CH(CH$_3$)$_2$ | CH—OH | H | I | I | I |

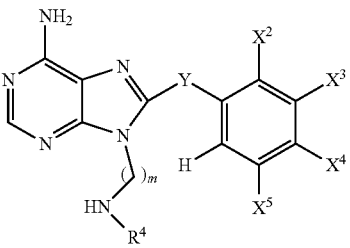

TABLE 2A-continued

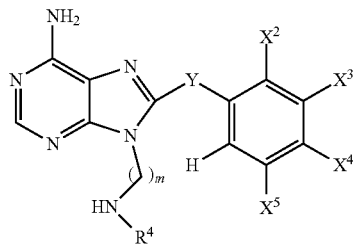

and pharmaceutically acceptable salts thereof, where:

| m | R⁴ | Y | X² | X³ | X⁴ | X⁵ |
|---|---|---|---|---|---|---|
| 2 | CH₂C(CH₃)₃ | CH—OH | I | I | H | I |
| 3 | H₂C—C≡N | CH—OH | H | CH₃ | CH₃ | CH₃ |
| 3 | H₂C—C≡CH | CH—OH | CH₃ | CH₃ | H | CH₃ |
| 3 | CH(CH₃)₂ | CH—OH | H | C₂H₅ | C₂H₅ | C₂H₅ |
| 3 | CH₂CH₂OH | CH—OH | C₂H₅ | C₂H₅ | H | C₂H₅ |
| 3 | CH₂CH(CH₃)OH | CH—OH | H | i-C₃H₇ | i-C₃H₇ | i-C₃H₇ |
| 3 | CH(CH₃)CH₂OH | CH—OH | i-C₃H₇ | i-C₃H₇ | H | i-C₃H₇ |
| 2 | CH(CH₃)CH(CH₃)OH | CH—F | H | Cl | Cl | Cl |
| 2 | C(CH₃)₂CH₂OH | CH—F | Cl | Cl | H | Cl |
| 2 | CH₂C(CH₃)₂OH | CH—F | H | Br | Br | Br |
| 2 | CH₂CHF₂ | CH—F | Br | Br | H | Br |
| 2 | CH₂CF₃ | CH—F | H | I | I | I |
| 2 | CH₂CH(CH₃)₂ | CH—F | I | I | H | I |
| 3 | CH₂C(CH₃)₃ | CH—F | H | CH₃ | CH₃ | CH₃ |
| 3 | H₂C—C≡N | CH—F | CH₃ | CH₃ | H | CH₃ |
| 3 | H₂C—C≡CH | CH—F | H | C₂H₅ | C₂H₅ | C₂H₅ |
| 3 | CH(CH₃)₂ | CH—F | C₂H₅ | C₂H₅ | H | C₂H₅ |
| 3 | CH₂CH₂OH | CH—F | H | i-C₃H₇ | i-C₃H₇ | i-C₃H₇ |
| 3 | CH₂CH(CH₃)OH | CH—F | i-C₃H₇ | i-C₃H₇ | H | i-C₃H₇ |
| 2 | CH(CH₃)CH₂OH | S | I | H | Cl | H |
| 2 | CH(CH₃)CH(CH₃)OH | S=O | I | H | H | Cl |
| 2 | C(CH₃)₂CH₂OH | O=S=O | Br | H | Cl | H |
| 2 | CH₂C(CH₃)₂OH | CH₂ | Br | H | H | Cl |
| 2 | CH₂CHF₂ | C=O | Br | H | I | H |
| 2 | CH₂CF₃ | C=S | Br | H | H | I |
| 3 | CH₂CH(CH₃)₂ | CH—OH | I | H | Br | H |
| 3 | CH₂C(CH₃)₃ | CH—F | I | H | H | Br |
| 3 | H₂C—C≡N | O | I | Cl | H | Cl |
| 3 | H₂C—C≡CH | NH | Br | Cl | H | Cl |

TABLE 2B

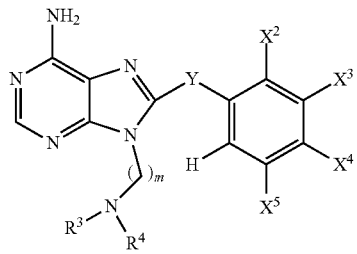

and pharmaceutically acceptable salts thereof, where:

| m | R³, R⁴ | Y | X² | X³ | X⁴ | X⁵ |
|---|---|---|---|---|---|---|
| 2 | aziridine | S | H | Cl | H | Cl |
| 2 | azetidine | S | Cl | H | Cl | H |
| 2 | pyrrolidine | S | Cl | H | H | Cl |
| 2 | piperazine | S | H | Br | H | Br |
| 2 | morpholine | S | Br | H | Br | H |
| 2 | piperidine | S | Br | H | H | Br |
| 2 | N-methylpiperazine | S | H | I | H | I |
| 2 | 4-hydroxypiperidine | S | I | H | I | H |

TABLE 2B-continued

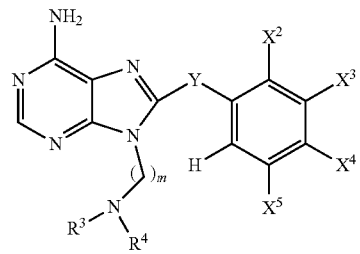

and pharmaceutically acceptable salts thereof, where:

| m | R³, R⁴ | Y | X² | X³ | X⁴ | X⁵ |
|---|---|---|---|---|---|---|
| 2 | 3-hydroxypiperidine | S | I | H | H | I |
| 2 | 4-aminopiperidine | S | H | CH₃ | H | CH₃ |
| 2 | 3-aminopiperidine | S | CH₃ | H | CH₃ | H |
| 2 | 3-hydroxypyrrolidine | S | CH₃ | H | H | CH₃ |
| 3 | 3-aminopyrrolidne | S | H | C₂H₅ | H | C₂H₅ |
| 3 | aziridine | S | C₂H₅ | H | C₂H₅ | H |
| 3 | azetidine | S | C₂H₅ | H | H | C₂H₅ |
| 3 | pyrrolidine | S | H | i-C₃H₇ | H | i-C₃H₇ |
| 3 | piperazine | S | i-C₃H₇ | H | i-C₃H₇ | H |
| 3 | morpholine | S | i-C₃H₇ | H | H | i-C₃H₇ |
| 3 | piperidine | O | H | Cl | H | Cl |
| 3 | N-methylpiperazine | O | Cl | H | Cl | H |
| 3 | 4-hydroxypiperidine | O | Cl | H | H | Cl |
| 3 | 3-hydroxypiperidine | O | H | Br | H | Br |
| 3 | 4-aminopiperidine | O | Br | H | Br | H |
| 3 | 3-aminopiperidine | O | Br | H | H | Br |
| 3 | 3-hydroxypyrrolidne | O | H | I | H | I |
| 3 | 3-aminopyrrolidne | O | I | H | I | H |
| 2 | aziridine | O | I | H | H | I |
| 2 | azetidine | O | H | CH₃ | H | CH₃ |
| 2 | pyrrolidine | O | CH₃ | H | CH₃ | H |
| 2 | piperazine | O | CH₃ | H | H | CH₃ |
| 2 | morpholine | O | H | C₂H₅ | H | C₂H₅ |
| 2 | piperidine | O | C₂H₅ | H | C₂H₅ | H |
| 2 | N-methylpiperazine | O | C₂H₅ | H | H | C₂H₅ |
| 2 | 4-hydroxypiperidine | O | H | i-C₃H₇ | H | i-C₃H₇ |
| 2 | 3-hydroxypiperidine | O | i-C₃H₇ | H | i-C₃H₇ | H |
| 2 | 4-aminopiperidine | O | i-C₃H₇ | H | H | i-C₃H₇ |
| 3 | 3-aminopiperidine | S=O | H | Cl | H | Cl |
| 3 | 3-hydroxypyrrolidine | S=O | Cl | H | Cl | H |
| 3 | 3-aminopyrrolidne | S=O | Cl | H | H | Cl |
| 3 | aziridine | S=O | H | Br | H | Br |
| 3 | azetidine | S=O | Br | H | Br | H |
| 3 | pyrrolidine | S=O | Br | H | H | Br |
| 3 | piperazine | S=O | H | I | H | I |
| 3 | morpholine | S=O | I | H | I | H |
| 3 | piperidine | S=O | I | H | H | I |
| 3 | N-methylpiperazine | S=O | H | CH₃ | H | CH₃ |
| 3 | 4-hydroxypiperidine | S=O | CH₃ | H | CH₃ | H |
| 3 | 3-hydroxypiperidine | S=O | CH₃ | H | H | CH₃ |
| 2 | 4-aminopiperidine | S=O | H | C₂H₅ | H | C₂H₅ |
| 2 | 3-aminopiperidine | S=O | C₂H₅ | H | C₂H₅ | H |
| 2 | 3-hydroxypyrrolidine | S=O | C₂H₅ | H | H | C₂H₅ |
| 2 | 3-aminopyrrolidne | S=O | H | i-C₃H₇ | H | i-C₃H₇ |
| 2 | aziridine | S=O | i-C₃H₇ | H | i-C₃H₇ | H |
| 2 | azetidine | S=O | i-C₃H₇ | H | H | i-C₃H₇ |
| 2 | pyrrolidine | O=S=O | H | Cl | H | Cl |
| 2 | piperazine | O=S=O | Cl | H | Cl | H |
| 2 | morpholine | O=S=O | Cl | H | H | Cl |
| 2 | piperidine | O=S=O | H | Br | H | Br |
| 2 | N-methylpiperazine | O=S=O | Br | H | Br | H |
| 2 | 4-hydroxypiperidine | O=S=O | Br | H | H | Br |
| 3 | 3-hydroxypiperidine | O=S=O | H | I | H | I |
| 3 | 4-aminopiperidine | O=S=O | I | H | I | H |
| 3 | 3-aminopiperidine | O=S=O | I | H | H | I |
| 3 | 3-hydroxypyrrolidne | O=S=O | H | CH₃ | H | CH₃ |
| 3 | 3-aminopyrrolidne | O=S=O | CH₃ | H | CH₃ | H |
| 3 | aziridine | O=S=O | CH₃ | H | H | CH₃ |
| 3 | azetidine | O=S=O | H | C₂H₅ | H | C₂H₅ |
| 3 | pyrrolidine | O=S=O | C₂H₅ | H | C₂H₅ | H |
| 3 | piperazine | O=S=O | C₂H₅ | H | H | C₂H₅ |
| 3 | morpholine | O=S=O | H | i-C₃H₇ | H | i-C₃H₇ |
| 3 | piperidine | O=S=O | i-C₃H₇ | H | i-C₃H₇ | H |

TABLE 2B-continued

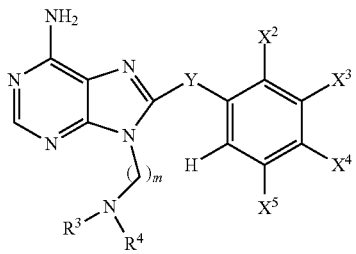

and pharmaceutically acceptable salts thereof, where:

| m | R³, R⁴ | Y | X² | X³ | X⁴ | X⁵ |
|---|---|---|---|---|---|---|
| 3 | N-methylpiperazine | O=S=O | i-C₃H₇ | H | H | i-C₃H₇ |
| 2 | 4-hydroxypiperidine | NH | H | Cl | H | Cl |
| 2 | 3-hydroxypiperidine | NH | Cl | H | Cl | H |
| 2 | 4-aminopiperidine | NH | Cl | H | H | Cl |
| 2 | 3-aminopiperidine | NH | H | Br | H | Br |
| 2 | 3-hydroxypyrrolidne | NH | Br | H | Br | H |
| 2 | 3-aminopyrrolidne | NH | Br | H | H | Br |
| 2 | aziridine | NH | H | I | H | I |
| 2 | azetidine | NH | I | H | I | H |
| 2 | pyrrolidine | NH | I | H | H | I |
| 2 | piperazine | NH | H | CH₃ | H | CH₃ |
| 2 | morpholine | NH | CH₃ | H | CH₃ | H |
| 2 | piperidine | NH | CH₃ | H | H | CH₃ |
| 3 | N-methylpiperazine | NH | H | C₂H₅ | H | C₂H₅ |
| 2 | 4-hydroxypiperidine | NH | C₂H₅ | H | C₂H₅ | H |
| 2 | 3-hydroxypiperidine | NH | C₂H₅ | H | H | C₂H₅ |
| 3 | 4-aminopiperidine | NH | H | i-C₃H₇ | H | i-C₃H₇ |
| 3 | 3-aminopiperidine | NH | i-C₃H₇ | H | i-C₃H₇ | H |
| 3 | 3-hydroxypyrrolidne | NH | i-C₃H₇ | H | H | i-C₃H₇ |
| 3 | 3-aminopyrrolidne | C=O | H | Cl | H | Cl |
| 3 | aziridine | C=O | Cl | H | Cl | H |
| 3 | azetidine | C=O | Cl | H | H | Cl |
| 3 | pyrrolidine | C=O | H | Br | H | Br |
| 3 | piperazine | C=O | Br | H | Br | H |
| 3 | morpholine | C=O | Br | H | H | Br |
| 3 | piperidine | C=O | H | I | H | I |
| 2 | N-methylpiperazine | C=O | I | H | I | H |
| 2 | 4-hydroxypiperidine | C=O | I | H | H | I |
| 2 | 3-hydroxypiperidine | C=O | H | CH₃ | H | CH₃ |
| 2 | 4-aminopiperidine | C=O | CH₃ | H | CH₃ | H |
| 2 | 3-aminopiperidine | C=O | CH₃ | H | H | CH₃ |
| 2 | 3-hydroxypyrrolidne | C=O | H | C₂H₅ | H | C₂H₅ |
| 2 | 3-aminopyrrolidne | C=O | C₂H₅ | H | C₂H₅ | H |
| 2 | aziridine | C=O | C₂H₅ | H | H | C₂H₅ |
| 2 | azetidine | C=O | H | i-C₃H₇ | H | i-C₃H₇ |
| 2 | pyrrolidine | C=O | i-C₃H₇ | H | i-C₃H₇ | H |
| 2 | piperazine | C=O | i-C₃H₇ | H | H | i-C₃H₇ |
| 3 | morpholine | C=S | H | Cl | H | Cl |
| 3 | piperidine | C=S | Cl | H | Cl | H |
| 3 | N-methylpiperazine | C=S | Cl | H | H | Cl |
| 3 | 4-hydroxypiperidine | C=S | H | Br | H | Br |
| 3 | 3-hydroxypiperidine | C=S | Br | H | Br | H |
| 3 | 4-aminopiperidine | C=S | Br | H | H | Br |
| 3 | 3-aminopiperidine | C=S | H | I | H | I |
| 3 | 3-hydroxypyrrolidne | C=S | I | H | I | H |
| 3 | 3-aminopyrrolidne | C=S | I | H | H | I |
| 3 | aziridine | C=S | H | CH₃ | H | CH₃ |
| 2 | azetidine | C=S | CH₃ | H | CH₃ | H |
| 2 | pyrrolidine | C=S | CH₃ | H | H | CH₃ |
| 2 | piperazine | C=S | H | C₂H₅ | H | C₂H₅ |
| 2 | morpholine | C=S | C₂H₅ | H | C₂H₅ | H |
| 2 | piperidine | C=S | C₂H₅ | H | H | C₂H₅ |
| 2 | N-methylpiperazine | C=S | H | i-C₃H₇ | H | i-C₃H₇ |
| 2 | 4-hydroxypiperidine | C=S | i-C₃H₇ | H | i-C₃H₇ | H |
| 2 | 3-hydroxypiperidine | C=S | i-C₃H₇ | H | H | i-C₃H₇ |
| 3 | 4-aminopiperidine | CH₂ | H | Cl | H | Cl |
| 3 | 3-aminopiperidine | CH₂ | Cl | H | Cl | H |
| 3 | 3-hydroxypyrrolidne | CH₂ | Cl | H | H | Cl |
| 3 | 3-aminopyrrolidne | CH₂ | H | Br | H | Br |
| 3 | aziridine | CH₂ | Br | H | Br | H |
| 3 | azetidine | CH₂ | Br | H | H | Br |
| 2 | pyrrolidine | CH₂ | H | I | H | I |
| 2 | piperazine | CH₂ | I | H | I | H |
| 2 | morpholine | CH₂ | I | H | H | I |
| 2 | piperidine | CH₂ | H | CH₃ | H | CH₃ |
| 2 | N-methylpiperazine | CH₂ | CH₃ | H | CH₃ | H |
| 2 | 4-hydroxypiperidine | CH₂ | CH₃ | H | H | CH₃ |
| 3 | 3-hydroxypiperidine | CH₂ | H | C₂H₅ | H | C₂H₅ |
| 3 | 4-aminopiperidine | CH₂ | C₂H₅ | H | C₂H₅ | H |
| 3 | 3-aminopiperidine | CH₂ | C₂H₅ | H | H | C₂H₅ |
| 3 | 3-hydroxypyrrolidne | CH₂ | H | i-C₃H₇ | H | i-C₃H₇ |
| 3 | 3-aminopyrrolidne | CH₂ | i-C₃H₇ | H | i-C₃H₇ | H |
| 3 | aziridine | CH₂ | i-C₃H₇ | H | H | i-C₃H₇ |
| 2 | azetidine | CH—OH | H | Cl | H | Cl |
| 2 | pyrrolidine | CH—OH | Cl | H | Cl | H |
| 2 | piperazine | CH—OH | Cl | H | H | Cl |
| 2 | morpholine | CH—OH | H | Br | H | Br |
| 2 | piperidine | CH—OH | Br | H | Br | H |
| 2 | N-methylpiperazine | CH—OH | Br | H | H | Br |
| 3 | 4-hydroxypiperidine | CH—OH | H | I | H | I |
| 3 | 3-hydroxypiperidine | CH—OH | I | H | I | H |
| 3 | 4-aminopiperidine | CH—OH | I | H | H | I |
| 3 | 3-aminopiperidine | CH—OH | H | CH₃ | H | CH₃ |
| 3 | 3-hydroxypyrrolidne | CH—OH | CH₃ | H | CH₃ | H |
| 3 | 3-aminopyrrolidne | CH—OH | CH₃ | H | H | CH₃ |
| 2 | aziridine | CH—OH | H | C₂H₅ | H | C₂H₅ |
| 2 | azetidine | CH—OH | C₂H₅ | H | C₂H₅ | H |
| 2 | pyrrolidine | CH—OH | C₂H₅ | H | H | C₂H₅ |
| 2 | piperazine | CH—OH | H | i-C₃H₇ | H | i-C₃H₇ |
| 2 | morpholine | CH—OH | i-C₃H₇ | H | i-C₃H₇ | H |
| 2 | piperidine | CH—OH | i-C₃H₇ | H | H | i-C₃H₇ |
| 3 | N-methylpiperazine | CH—F | H | Cl | H | Cl |
| 3 | 4-hydroxypiperidine | CH—F | Cl | H | Cl | H |
| 3 | 3-hydroxypiperidine | CH—F | Cl | H | H | Cl |
| 3 | 4-aminopiperidine | CH—F | H | Br | H | Br |
| 3 | 3-aminopiperidine | CH—F | Br | H | Br | H |
| 3 | 3-hydroxypyrrolidne | CH—F | Br | H | H | Br |
| 2 | 3-aminopyrrolidne | CH—F | H | I | H | I |
| 2 | aziridine | CH—F | I | H | I | H |
| 2 | azetidine | CH—F | I | H | H | I |
| 2 | pyrrolidine | CH—F | H | CH₃ | H | CH₃ |
| 2 | piperazine | CH—F | CH₃ | H | CH₃ | H |
| 2 | morpholine | CH—F | CH₃ | H | H | CH₃ |
| 3 | piperidine | CH—F | H | C₂H₅ | H | C₂H₅ |
| 3 | N-methylpiperazine | CH—F | C₂H₅ | H | C₂H₅ | H |
| 3 | 4-hydroxypiperidine | CH—F | C₂H₅ | H | H | C₂H₅ |
| 3 | 3-hydroxypiperidine | CH—F | H | i-C₃H₇ | H | i-C₃H₇ |
| 3 | 4-aminopiperidine | CH—F | i-C₃H₇ | H | i-C₃H₇ | H |
| 3 | 3-aminopiperidine | CH—F | i-C₃H₇ | H | H | i-C₃H₇ |
| 2 | 3-hydroxypyrrolidne | S | H | Cl | Cl | Cl |
| 2 | 3-aminopyrrolidne | S | Cl | Cl | H | Cl |
| 2 | aziridine | S | H | Br | Br | Br |
| 2 | azetidine | S | Br | Br | H | Br |
| 2 | pyrrolidine | S | H | I | I | I |
| 2 | piperazine | S | I | I | H | I |
| 3 | morpholine | S | H | CH₃ | CH₃ | CH₃ |
| 3 | piperidine | S | CH₃ | CH₃ | H | CH₃ |
| 3 | N-methylpiperazine | S | H | C₂H₅ | C₂H₅ | C₂H₅ |
| 3 | 4-hydroxypiperidine | S | C₂H₅ | C₂H₅ | H | C₂H₅ |
| 3 | 3-hydroxypiperidine | S | H | i-C₃H₇ | i-C₃H₇ | i-C₃H₇ |
| 3 | 4-aminopiperidine | S | i-C₃H₇ | i-C₃H₇ | H | i-C₃H₇ |
| 2 | 3-aminopiperidine | O | H | Cl | Cl | Cl |
| 2 | 3-hydroxypyrrolidne | O | Cl | Cl | H | Cl |
| 2 | 3-aminopyrrolidne | O | H | Br | Br | Br |
| 2 | aziridine | O | Br | Br | H | Br |
| 2 | azetidine | O | H | I | I | I |

TABLE 2B-continued

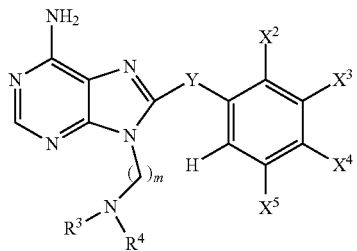

and pharmaceutically acceptable salts thereof, where:

| m | $R^3$, $R^4$ | Y | $X^2$ | $X^3$ | $X^4$ | $X^5$ |
|---|---|---|---|---|---|---|
| 2 | pyrrolidine | O | I | I | H | I |
| 3 | piperazine | O | H | $CH_3$ | $CH_3$ | $CH_3$ |
| 3 | morpholine | O | $CH_3$ | $CH_3$ | H | $CH_3$ |
| 3 | piperidine | O | H | $C_2H_5$ | $C_2H_5$ | $C_2H_5$ |
| 3 | N-methylpiperazine | O | $C_2H_5$ | $C_2H_5$ | H | $C_2H_5$ |
| 3 | 4-hydroxypiperidine | O | H | $i-C_3H_7$ | $i-C_3H_7$ | $i-C_3H_7$ |
| 3 | 3-hydroxypiperidine | O | $i-C_3H_7$ | $i-C_3H_7$ | H | $i-C_3H_7$ |
| 2 | 4-aminopiperidine | S=O | H | Cl | Cl | Cl |
| 2 | 3-aminopiperidine | S=O | Cl | Cl | H | Cl |
| 2 | 3-hydroxypyrrolidne | S=O | H | Br | Br | Br |
| 2 | 3-aminopyrrolidne | S=O | Br | Br | H | Br |
| 2 | aziridine | S=O | H | I | I | I |
| 2 | aziridine | S=O | I | I | H | I |
| 3 | azetidine | S=O | H | $CH_3$ | $CH_3$ | $CH_3$ |
| 3 | pyrrolidine | S=O | $CH_3$ | $CH_3$ | H | $CH_3$ |
| 3 | piperazine | S=O | H | $C_2H_5$ | $C_2H_5$ | $C_2H_5$ |
| 3 | morpholine | S=O | $C_2H_5$ | $C_2H_5$ | H | $C_2H_5$ |
| 3 | piperidine | S=O | H | $i-C_3H_7$ | $i-C_3H_7$ | $i-C_3H_7$ |
| 3 | N-methylpiperazine | S=O | $i-C_3H_7$ | $i-C_3H_7$ | H | $i-C_3H_7$ |
| 2 | 4-hydroxypiperidine | O=S=O | H | Cl | Cl | Cl |
| 2 | 3-hydroxypiperidine | O=S=O | Cl | Cl | H | Cl |
| 2 | 4-aminopiperidine | O=S=O | H | Br | Br | Br |
| 2 | 3-aminopiperidine | O=S=O | Br | Br | H | Br |
| 2 | 3-hydroxypyrrolidne | O=S=O | H | I | I | I |
| 2 | 3-aminopyrrolidne | O=S=O | I | I | H | I |
| 3 | aziridine | O=S=O | H | $CH_3$ | $CH_3$ | $CH_3$ |
| 3 | azetidine | O=S=O | $CH_3$ | $CH_3$ | H | $CH_3$ |
| 3 | pyrrolidine | O=S=O | H | $C_2H_5$ | $C_2H_5$ | $C_2H_5$ |
| 3 | piperazine | O=S=O | $C_2H_5$ | $C_2H_5$ | H | $C_2H_5$ |
| 3 | morpholine | O=S=O | H | $i-C_3H_7$ | $i-C_3H_7$ | $i-C_3H_7$ |
| 3 | piperidine | O=S=O | $i-C_3H_7$ | $i-C_3H_7$ | H | $i-C_3H_7$ |
| 2 | N-methylpiperazine | NH | H | Cl | Cl | Cl |
| 2 | 4-hydroxypiperidine | NH | Cl | Cl | H | Cl |
| 2 | 3-hydroxypiperidine | NH | H | Br | Br | Br |
| 2 | 4-aminopiperidine | NH | Br | Br | H | Br |
| 2 | 3-aminopiperidine | NH | H | I | I | I |
| 2 | 3-hydroxypyrrolidne | NH | I | I | H | I |
| 3 | 3-aminopyrrolidne | NH | H | $CH_3$ | $CH_3$ | $CH_3$ |
| 3 | aziridine | NH | $CH_3$ | $CH_3$ | H | $CH_3$ |
| 3 | azetidine | NH | H | $C_2H_5$ | $C_2H_5$ | $C_2H_5$ |
| 3 | pyrrolidine | NH | $C_2H_5$ | $C_2H_5$ | H | $C_2H_5$ |
| 3 | piperazine | NH | H | $i-C_3H_7$ | $i-C_3H_7$ | $i-C_3H_7$ |
| 3 | morpholine | NH | $i-C_3H_7$ | $i-C_3H_7$ | H | $i-C_3H_7$ |
| 2 | piperidine | C=O | H | Cl | Cl | Cl |
| 2 | N-methylpiperazine | C=O | Cl | Cl | H | Cl |
| 2 | 4-hydroxypiperidine | C=O | H | Br | Br | Br |
| 2 | 3-hydroxypiperidine | C=O | Br | Br | H | Br |
| 2 | 4-aminopiperidine | C=O | H | I | I | I |
| 2 | 3-aminopiperidine | C=O | I | I | H | I |
| 3 | 3-hydroxypyrrolidne | C=O | H | $CH_3$ | $CH_3$ | $CH_3$ |
| 3 | 3-aminopyrrolidne | C=O | $CH_3$ | $CH_3$ | H | $CH_3$ |
| 3 | aziridine | C=O | H | $C_2H_5$ | $C_2H_5$ | $C_2H_5$ |
| 3 | azetidine | C=O | $C_2H_5$ | $C_2H_5$ | H | $C_2H_5$ |
| 3 | pyrrolidine | C=O | H | $i-C_3H_7$ | $i-C_3H_7$ | $i-C_3H_7$ |
| 3 | piperazine | C=O | $i-C_3H_7$ | $i-C_3H_7$ | H | $i-C_3H_7$ |
| 2 | morpholine | C=S | H | Cl | Cl | Cl |
| 2 | piperidine | C=S | Cl | Cl | H | Cl |
| 2 | N-methylpiperazine | C=S | H | Br | Br | Br |
| 2 | 4-hydroxypiperidine | C=S | Br | Br | H | Br |
| 2 | 3-hydroxypiperidine | C=S | H | I | I | I |
| 2 | 4-aminopiperidine | C=S | I | I | H | I |
| 3 | 3-aminopiperidine | C=S | H | $CH_3$ | $CH_3$ | $CH_3$ |
| 3 | 3-hydroxypyrrolidne | C=S | $CH_3$ | $CH_3$ | H | $CH_3$ |

TABLE 2B-continued

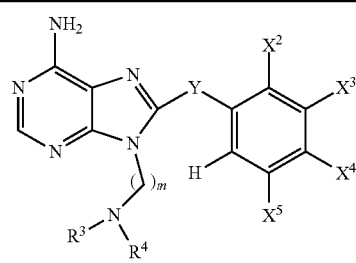

and pharmaceutically acceptable salts thereof, where:

| m | $R^3$, $R^4$ | Y | $X^2$ | $X^3$ | $X^4$ | $X^5$ |
|---|---|---|---|---|---|---|
| 3 | 3-aminopyrrolidne | C=S | H | $C_2H_5$ | $C_2H_5$ | $C_2H_5$ |
| 3 | aziridine | C=S | $C_2H_5$ | $C_2H_5$ | H | $C_2H_5$ |
| 3 | azetidine | C=S | H | $i-C_3H_7$ | $i-C_3H_7$ | $i-C_3H_7$ |
| 3 | pyrrolidine | C=S | $i-C_3H_7$ | $i-C_3H_7$ | H | $i-C_3H_7$ |
| 2 | piperazine | $CH_2$ | H | Cl | Cl | Cl |
| 2 | morpholine | $CH_2$ | Cl | Cl | H | Cl |
| 2 | piperidine | $CH_2$ | H | Br | Br | Br |
| 2 | N-methylpiperazine | $CH_2$ | Br | Br | H | Br |
| 2 | 4-hydroxypiperidine | $CH_2$ | H | I | I | I |
| 2 | 3-hydroxypiperidine | $CH_2$ | I | I | H | I |
| 3 | 4-aminopiperidine | $CH_2$ | H | $CH_3$ | $CH_3$ | $CH_3$ |
| 3 | 3-aminopiperidine | $CH_2$ | $CH_3$ | $CH_3$ | H | $CH_3$ |
| 3 | 3-hydroxypyrrolidne | $CH_2$ | H | $C_2H_5$ | $C_2H_5$ | $C_2H_5$ |
| 3 | 3-aminopyrrolidne | $CH_2$ | $C_2H_5$ | $C_2H_5$ | H | $C_2H_5$ |
| 3 | aziridine | $CH_2$ | H | $i-C_3H_7$ | $i-C_3H_7$ | $i-C_3H_7$ |
| 3 | azetidine | $CH_2$ | $i-C_3H_7$ | $i-C_3H_7$ | H | $i-C_3H_7$ |
| 2 | pyrrolidine | CH—OH | H | Cl | Cl | Cl |
| 2 | piperazine | CH—OH | Cl | Cl | H | Cl |
| 2 | morpholine | CH—OH | H | Br | Br | Br |
| 2 | piperidine | CH—OH | Br | Br | H | Br |
| 2 | N-methylpiperazine | CH—OH | H | I | I | I |
| 2 | 4-hydroxypiperidine | CH—OH | I | I | H | I |
| 3 | 3-hydroxypiperidine | CH—OH | H | $CH_3$ | $CH_3$ | $CH_3$ |
| 3 | 4-aminopiperidine | CH—OH | $CH_3$ | $CH_3$ | H | $CH_3$ |
| 3 | 3-aminopiperidine | CH—OH | H | $C_2H_5$ | $C_2H_5$ | $C_2H_5$ |
| 3 | 3-hydroxypyrrolidne | CH—OH | $C_2H_5$ | $C_2H_5$ | H | $C_2H_5$ |
| 3 | 3-aminopyrrolidne | CH—OH | H | $i-C_3H_7$ | $i-C_3H_7$ | $i-C_3H_7$ |
| 3 | aziridine | CH—OH | $i-C_3H_7$ | $i-C_3H_7$ | H | $i-C_3H_7$ |
| 2 | azetidine | CH—F | H | Cl | Cl | Cl |
| 2 | pyrrolidine | CH—F | Cl | Cl | H | Cl |
| 2 | piperazine | CH—F | H | Br | Br | Br |
| 2 | morpholine | CH—F | Br | Br | H | Br |
| 2 | piperidine | CH—F | H | I | I | I |
| 2 | N-methylpiperazine | CH—F | I | I | H | I |
| 3 | 4-hydroxypiperidine | CH—F | H | $CH_3$ | $CH_3$ | $CH_3$ |
| 3 | 3-hydroxypiperidine | CH—F | $CH_3$ | $CH_3$ | H | $CH_3$ |
| 3 | 4-aminopiperidine | CH—F | H | $C_2H_5$ | $C_2H_5$ | $C_2H_5$ |
| 3 | 3-aminopiperidine | CH—F | $C_2H_5$ | $C_2H_5$ | H | $C_2H_5$ |
| 3 | 3-hydroxypyrrolidne | CH—F | H | $i-C_3H_7$ | $i-C_3H_7$ | $i-C_3H_7$ |
| 3 | 3-aminopyrrolidne | CH—F | $i-C_3H_7$ | $i-C_3H_7$ | H | $i-C_3H_7$ |
| 2 | aziridine | S | I | H | Cl | H |
| 2 | azetidine | S=O | I | H | H | Cl |
| 2 | pyrrolidine | O=S=O | Br | H | Cl | H |
| 2 | piperazine | $CH_2$ | Br | H | H | Cl |
| 2 | morpholine | C=O | Br | H | I | H |
| 3 | piperidine | C=S | Br | H | H | I |
| 3 | N-methylpiperazine | CH—OH | I | H | Br | H |
| 3 | 4-hydroxypiperidine | CH—F | I | H | H | Br |
| 3 | 3-hydroxypiperidine | O | I | Cl | H | Cl |
| 3 | 4-aminopiperidine | NH | Br | Cl | H | Cl |

TABLE 2C

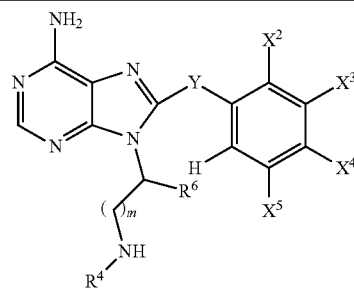

and pharmaceutically acceptable salts thereof, where:

| m | $R^4$ | $R^6$ | Y | $X^2$ | $X^3$ | $X^4$ | $X^5$ |
|---|---|---|---|---|---|---|---|
| 1 | $CH(CH_3)_2$ | $CH_3$ | S | H | Cl | H | Cl |
| 1 | $CH_2CH_2OH$ | $CH_3$ | S | Cl | H | Cl | H |
| 1 | $CH_2CH(CH_3)OH$ | $C_2H_5$ | S | Cl | H | H | Cl |
| 1 | $CH(CH_3)CH_2OH$ | $C_2H_5$ | S | H | Br | H | Br |
| 1 | $CH(CH_3)CH(CH_3)OH$ | $n-C_3H_7$ | S | Br | H | Br | H |
| 1 | $C(CH_3)_2CH_2OH$ | $n-C_3H_7$ | S | Br | H | H | Br |
| 1 | $CH_2C(CH_3)_2OH$ | $i-C_3H_7$ | S | H | I | H | I |
| 1 | $CH_2CHF_2$ | $i-C_3H_7$ | S | I | H | I | H |
| 1 | $CH_2CF_3$ | $c-C_3H_5$ | S | I | H | H | I |
| 2 | $CH_2CH(CH_3)_2$ | $c-C_3H_5$ | S | H | $CH_3$ | H | $CH_3$ |
| 2 | $CH_2C(CH_3)_3$ | $sec-C_4H_9$ | S | $CH_3$ | H | $CH_3$ | H |
| 2 | $H_2C-C\equiv N$ | $sec-C_4H_9$ | S | $CH_3$ | H | H | $CH_3$ |
| 2 | $H_2C-C\equiv CH$ | $i-C_4H_9$ | S | H | $C_2H_5$ | H | $C_2H_5$ |
| 2 | $CH(CH_3)_2$ | $i-C_4H_9$ | S | $C_2H_5$ | H | $C_2H_5$ | H |
| 2 | $CH_2CH_2OH$ | $n-C_4H_9$ | S | $C_2H_5$ | H | H | $C_2H_5$ |
| 2 | $CH_2CH(CH_3)OH$ | $n-C_4H_9$ | S | H | $i-C_3H_7$ | H | $i-C_3H_7$ |
| 2 | $CH(CH_3)CH_2OH$ | $CH_3$ | S | $i-C_3H_7$ | H | $i-C_3H_7$ | H |
| 2 | $CH(CH_3)CH(CH_3)OH$ | $CH_3$ | S | $i-C_3H_7$ | H | H | $i-C_3H_7$ |
| 1 | $C(CH_3)_2CH_2OH$ | $C_2H_5$ | O | H | Cl | H | Cl |
| 1 | $CH_2C(CH_3)_2OH$ | $C_2H_5$ | O | Cl | H | Cl | H |
| 1 | $CH_2CHF_2$ | $n-C_3H_7$ | O | Cl | H | H | Cl |
| 1 | $CH_2CF_3$ | $n-C_3H_7$ | O | H | Br | H | Br |
| 1 | $CH_2CH(CH_3)_2$ | $i-C_3H_7$ | O | Br | H | Br | H |
| 1 | $CH_2C(CH_3)_3$ | $i-C_3H_7$ | O | Br | H | H | Br |
| 1 | $H_2C-C\equiv N$ | $c-C_3H_5$ | O | H | I | H | I |
| 1 | $H_2C-C\equiv CH$ | $c-C_3H_5$ | O | I | H | I | H |
| 1 | $CH(CH_3)_2$ | $sec-C_4H_9$ | O | I | H | H | I |
| 2 | $CH_2CH_2OH$ | $sec-C_4H_9$ | O | H | $CH_3$ | H | $CH_3$ |
| 2 | $CH_2CH(CH_3)OH$ | $i-C_4H_9$ | O | $CH_3$ | H | $CH_3$ | H |
| 2 | $CH(CH_3)CH_2OH$ | $i-C_4H_9$ | O | $CH_3$ | H | H | $CH_3$ |
| 2 | $CH(CH_3)CH(CH_3)OH$ | $n-C_4H_9$ | O | H | $C_2H_5$ | H | $C_2H_5$ |
| 2 | $C(CH_3)_2CH_2OH$ | $n-C_4H_9$ | O | $C_2H_5$ | H | $C_2H_5$ | H |
| 2 | $CH_2C(CH_3)_2OH$ | $CH_3$ | O | $C_2H_5$ | H | H | $C_2H_5$ |
| 2 | $CH_2CHF_2$ | $CH_3$ | O | H | $i-C_3H_7$ | H | $i-C_3H_7$ |
| 2 | $CH_2CF_3$ | $C_2H_5$ | O | $i-C_3H_7$ | H | $i-C_3H_7$ | H |
| 2 | $CH_2CH(CH_3)_2$ | $C_2H_5$ | O | $i-C_3H_7$ | H | H | $i-C_3H_7$ |
| 1 | $CH_2C(CH_3)_3$ | $n-C_3H_7$ | S=O | H | Cl | H | Cl |
| 1 | $H_2C-C\equiv N$ | $n-C_3H_7$ | S=O | Cl | H | Cl | H |
| 1 | $H_2C-C\equiv CH$ | $i-C_3H_7$ | S=O | Cl | H | H | Cl |
| 1 | $CH(CH_3)_2$ | $i-C_3H_7$ | S=O | H | Br | H | Br |
| 1 | $CH_2CH_2OH$ | $c-C_3H_5$ | S=O | Br | H | Br | H |
| 1 | $CH_2CH(CH_3)OH$ | $c-C_3H_5$ | S=O | Br | H | H | Br |
| 1 | $CH(CH_3)CH_2OH$ | $sec-C_4H_9$ | S=O | H | I | H | I |
| 1 | $CH(CH_3)CH(CH_3)OH$ | $sec-C_4H_9$ | S=O | I | H | I | H |
| 1 | $C(CH_3)_2CH_2OH$ | $i-C_4H_9$ | S=O | I | H | H | I |
| 2 | $CH_2C(CH_3)_2OH$ | $i-C_4H_9$ | S=O | H | $CH_3$ | H | $CH_3$ |
| 2 | $CH_2CHF_2$ | $n-C_4H_9$ | S=O | $CH_3$ | H | $CH_3$ | H |
| 2 | $CH_2CF_3$ | $n-C_4H_9$ | S=O | $CH_3$ | H | H | $CH_3$ |
| 2 | $CH_2CH(CH_3)_2$ | $CH_3$ | S=O | H | $C_2H_5$ | H | $C_2H_5$ |
| 2 | $CH_2C(CH_3)_3$ | $CH_3$ | S=O | $C_2H_5$ | H | $C_2H_5$ | H |
| 2 | $H_2C-C\equiv N$ | $C_2H_5$ | S=O | $C_2H_5$ | H | H | $C_2H_5$ |
| 2 | $H_2C-C\equiv CH$ | $C_2H_5$ | S=O | H | $i-C_3H_7$ | H | $i-C_3H_7$ |
| 2 | $CH(CH_3)_2$ | $n-C_3H_7$ | S=O | $i-C_3H_7$ | H | $i-C_3H_7$ | H |
| 2 | $CH_2CH_2OH$ | $n-C_3H_7$ | S=O | $i-C_3H_7$ | H | H | $i-C_3H_7$ |
| 1 | $CH_2CH(CH_3)OH$ | $i-C_3H_7$ | O=S=O | H | Cl | H | Cl |
| 1 | $CH(CH_3)CH_2OH$ | $i-C_3H_7$ | O=S=O | Cl | H | Cl | H |
| 1 | $CH(CH_3)CH(CH_3)OH$ | $c-C_3H_5$ | O=S=O | Cl | H | H | Cl |
| 1 | $C(CH_3)_2CH_2OH$ | $c-C_3H_5$ | O=S=O | H | Br | H | Br |
| 1 | $CH_2C(CH_3)_2OH$ | $sec-C_4H_9$ | O=S=O | Br | H | Br | H |
| 1 | $CH_2CHF_2$ | $sec-C_4H_9$ | O=S=O | Br | H | H | Br |
| 1 | $CH_2CF_3$ | $i-C_4H_9$ | O=S=O | H | I | H | I |

TABLE 2C-continued

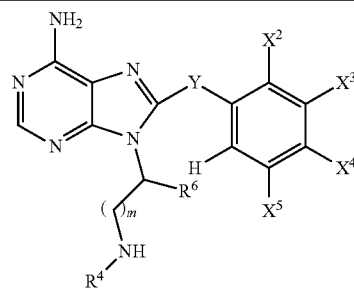

and pharmaceutically acceptable salts thereof, where:

| m | R⁴ | R⁶ | Y | X² | X³ | X⁴ | X⁵ |
|---|---|---|---|---|---|---|---|
| 1 | CH₂CH(CH₃)₂ | i-C₄H₉ | O=S=O | I | H | I | H |
| 1 | CH₂C(CH₃)₃ | n-C₄H₉ | O=S=O | I | H | H | I |
| 2 | H₂C—C≡N | n-C₄H₉ | O=S=O | H | CH₃ | H | CH₃ |
| 2 | H₂C—C≡CH | CH₃ | O=S=O | CH₃ | H | CH₃ | H |
| 2 | CH(CH₃)₂ | CH₃ | O=S=O | CH₃ | H | H | CH₃ |
| 2 | CH₂CH₂OH | C₂H₅ | O=S=O | H | C₂H₅ | H | C₂H₅ |
| 2 | CH₂CH(CH₃)OH | C₂H₅ | O=S=O | C₂H₅ | H | C₂H₅ | H |
| 2 | CH(CH₃)CH₂OH | n-C₃H₇ | O=S=O | C₂H₅ | H | H | C₂H₅ |
| 2 | CH(CH₃)CH(CH₃)OH | n-C₃H₇ | O=S=O | H | i-C₃H₇ | H | i-C₃H₇ |
| 2 | C(CH₃)₂CH₂OH | i-C₃H₇ | O=S=O | i-C₃H₇ | H | i-C₃H₇ | H |
| 2 | CH₂C(CH₃)₂OH | i-C₃H₇ | O=S=O | i-C₃H₇ | H | H | i-C₃H₇ |
| 1 | CH₂CHF₂ | c-C₃H₅ | NH | H | Cl | H | Cl |
| 1 | CH₂CF₃ | c-C₃H₅ | NH | Cl | H | Cl | H |
| 1 | CH₂CH(CH₃)₂ | sec-C₄H₉ | NH | Cl | H | H | Cl |
| 1 | CH₂C(CH₃)₃ | sec-C₄H₉ | NH | H | Br | H | Br |
| 1 | H₂C—C≡N | i-C₄H₉ | NH | Br | H | Br | H |
| 1 | H₂C—C≡CH | i-C₄H₉ | NH | Br | H | H | Br |
| 1 | CH(CH₃)₂ | n-C₄H₉ | NH | H | I | H | I |
| 1 | CH₂CH₂OH | n-C₄H₉ | NH | I | H | I | H |
| 1 | CH₂CH(CH₃)OH | CH₃ | NH | I | H | H | I |
| 2 | CH(CH₃)CH₂OH | CH₃ | NH | H | CH₃ | H | CH₃ |
| 2 | CH(CH₃)CH(CH₃)OH | C₂H₅ | NH | CH₃ | H | CH₃ | H |
| 2 | C(CH₃)₂CH₂OH | C₂H₅ | NH | CH₃ | H | H | CH₃ |
| 2 | CH₂C(CH₃)₂OH | n-C₃H₇ | NH | H | C₂H₅ | H | C₂H₅ |
| 2 | CH₂CHF₂ | n-C₃H₇ | NH | C₂H₅ | H | C₂H₅ | H |
| 2 | CH₂CF₃ | i-C₃H₇ | NH | C₂H₅ | H | H | C₂H₅ |
| 2 | CH₂CH(CH₃)₂ | i-C₃H₇ | NH | H | i-C₃H₇ | H | i-C₃H₇ |
| 2 | CH₂C(CH₃)₃ | c-C₃H₅ | NH | i-C₃H₇ | H | i-C₃H₇ | H |
| 2 | H₂C—C≡N | c-C₃H₅ | NH | i-C₃H₇ | H | H | i-C₃H₇ |
| 1 | H₂C—C≡CH | sec-C₄H₉ | C=O | H | Cl | H | Cl |
| 1 | CH(CH₃)₂ | sec-C₄H₉ | C=O | Cl | H | Cl | H |
| 1 | CH₂CH₂OH | i-C₄H₉ | C=O | Cl | H | H | Cl |
| 1 | CH₂CH(CH₃)OH | i-C₄H₉ | C=O | H | Br | H | Br |
| 1 | CH(CH₃)CH₂OH | n-C₄H₉ | C=O | Br | H | Br | H |
| 1 | CH(CH₃)CH(CH₃)OH | n-C₄H₉ | C=O | Br | H | H | Br |
| 1 | C(CH₃)₂CH₂OH | CH₃ | C=O | H | I | H | I |
| 1 | CH₂C(CH₃)₂OH | CH₃ | C=O | I | H | I | H |
| 1 | CH₂CHF₂ | C₂H₅ | C=O | I | H | H | I |
| 2 | CH₂CF₃ | C₂H₅ | C=O | H | CH₃ | H | CH₃ |
| 2 | CH₂CH(CH₃)₂ | n-C₃H₇ | C=O | CH₃ | H | CH₃ | H |
| 2 | CH₂C(CH₃)₃ | n-C₃H₇ | C=O | CH₃ | H | H | CH₃ |
| 2 | H₂C—C≡N | i-C₃H₇ | C=O | H | C₂H₅ | H | C₂H₅ |
| 2 | H₂C—C≡CH | i-C₃H₇ | C=O | C₂H₅ | H | C₂H₅ | H |
| 2 | CH(CH₃)₂ | c-C₃H₅ | C=O | C₂H₅ | H | H | C₂H₅ |
| 2 | CH₂CH₂OH | c-C₃H₅ | C=O | H | i-C₃H₇ | H | i-C₃H₇ |
| 2 | CH₂CH(CH₃)OH | sec-C₄H₉ | C=O | i-C₃H₇ | H | i-C₃H₇ | H |
| 2 | CH(CH₃)CH₂OH | sec-C₄H₉ | C=O | i-C₃H₇ | H | H | i-C₃H₇ |
| 1 | CH(CH₃)CH(CH₃)OH | i-C₄H₉ | C=S | H | Cl | H | Cl |
| 1 | C(CH₃)₂CH₂OH | i-C₄H₉ | C=S | Cl | H | Cl | H |
| 1 | CH₂C(CH₃)₂OH | n-C₄H₉ | C=S | Cl | H | H | Cl |
| 1 | CH₂CHF₂ | n-C₄H₉ | C=S | H | Br | H | Br |
| 1 | CH₂CF₃ | CH₃ | C=S | Br | H | Br | H |
| 1 | CH₂CH(CH₃)₂ | CH₃ | C=S | Br | H | H | Br |
| 1 | CH₂C(CH₃)₃ | C₂H₅ | C=S | H | I | H | I |
| 1 | H₂C—C≡N | C₂H₅ | C=S | I | H | I | H |
| 1 | H₂C—C≡CH | n-C₃H₇ | C=S | I | H | H | I |
| 2 | CH(CH₃)₂ | n-C₃H₇ | C=S | H | CH₃ | H | CH₃ |
| 2 | CH₂CH₂OH | i-C₃H₇ | C=S | CH₃ | H | CH₃ | H |
| 2 | CH₂CH(CH₃)OH | i-C₃H₇ | C=S | CH₃ | H | H | CH₃ |
| 2 | CH(CH₃)CH₂OH | c-C₃H₅ | C=S | H | C₂H₅ | H | C₂H₅ |
| 2 | CH(CH₃)CH(CH₃)OH | c-C₃H₅ | C=S | C₂H₅ | H | C₂H₅ | H |

TABLE 2C-continued

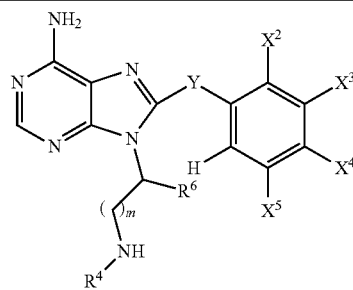

and pharmaceutically acceptable salts thereof, where:

| m | R⁴ | R⁶ | Y | X² | X³ | X⁴ | X⁵ |
|---|---|---|---|---|---|---|---|
| 2 | C(CH₃)₂CH₂OH | sec-C₄H₉ | C=S | C₂H₅ | H | H | C₂H₅ |
| 2 | CH₂C(CH₃)₂OH | sec-C₄H₉ | C=S | H | i-C₃H₇ | H | i-C₃H₇ |
| 2 | CH₂CHF₂ | i-C₄H₉ | C=S | i-C₃H₇ | H | i-C₃H₇ | H |
| 2 | CH₂CF₃ | i-C₄H₉ | C=S | i-C₃H₇ | H | H | i-C₃H₇ |
| 1 | CH₂CH(CH₃)₂ | n-C₄H₉ | CH₂ | H | Cl | H | Cl |
| 1 | CH₂C(CH₃)₃ | n-C₄H₉ | CH₂ | Cl | H | Cl | H |
| 1 | H₂C—C≡N | CH₃ | CH₂ | Cl | H | H | Cl |
| 1 | H₂C—C≡CH | CH₃ | CH₂ | H | Br | H | Br |
| 1 | CH(CH₃)₂ | C₂H₅ | CH₂ | Br | H | Br | H |
| 1 | CH₂CH₂OH | C₂H₅ | CH₂ | Br | H | H | Br |
| 1 | CH₂CH(CH₃)OH | n-C₃H₇ | CH₂ | H | I | H | I |
| 1 | CH(CH₃)CH₂OH | n-C₃H₇ | CH₂ | I | H | I | H |
| 1 | CH(CH₃)CH(CH₃)OH | i-C₃H₇ | CH₂ | I | H | H | I |
| 2 | C(CH₃)₂CH₂OH | i-C₃H₇ | CH₂ | H | CH₃ | H | CH₃ |
| 2 | CH₂C(CH₃)₂OH | c-C₃H₅ | CH₂ | CH₃ | H | CH₃ | H |
| 2 | CH₂CHF₂ | c-C₃H₅ | CH₂ | CH₃ | H | H | CH₃ |
| 2 | CH₂CF₃ | sec-C₄H₉ | CH₂ | H | C₂H₅ | H | C₂H₅ |
| 2 | CH₂CH(CH₃)₂ | sec-C₄H₉ | CH₂ | C₂H₅ | H | C₂H₅ | H |
| 2 | CH₂C(CH₃)₃ | i-C₄H₉ | CH₂ | C₂H₅ | H | H | C₂H₅ |
| 2 | H₂C—C≡N | i-C₄H₉ | CH₂ | H | i-C₃H₇ | H | i-C₃H₇ |
| 2 | H₂C—C≡CH | n-C₄H₉ | CH₂ | i-C₃H₇ | H | i-C₃H₇ | H |
| 2 | CH(CH₃)₂ | n-C₄H₉ | CH₂ | i-C₃H₇ | H | H | i-C₃H₇ |
| 1 | CH₂CH₂OH | CH₃ | CH—OH | H | Cl | H | Cl |
| 1 | CH₂CH(CH₃)OH | CH₃ | CH—OH | Cl | H | Cl | H |
| 1 | CH(CH₃)CH₂OH | C₂H₅ | CH—OH | Cl | H | H | Cl |
| 1 | CH(CH₃)CH(CH₃)OH | C₂H₅ | CH—OH | H | Br | H | Br |
| 1 | C(CH₃)₂CH₂OH | n-C₃H₇ | CH—OH | Br | H | Br | H |
| 1 | CH₂C(CH₃)₂OH | n-C₃H₇ | CH—OH | Br | H | H | Br |
| 1 | CH₂CHF₂ | i-C₃H₇ | CH—OH | H | I | H | I |
| 1 | CH₂CF₃ | i-C₃H₇ | CH—OH | I | H | I | H |
| 1 | CH₂CH(CH₃)₂ | c-C₃H₅ | CH—OH | I | H | H | I |
| 2 | CH₂C(CH₃)₃ | c-C₃H₅ | CH—OH | H | CH₃ | H | CH₃ |
| 2 | H₂C—C≡N | sec-C₄H₉ | CH—OH | CH₃ | H | CH₃ | H |
| 2 | H₂C—C≡CH | sec-C₄H₉ | CH—OH | CH₃ | H | H | CH₃ |
| 2 | CH(CH₃)₂ | i-C₄H₉ | CH—OH | H | C₂H₅ | H | C₂H₅ |
| 2 | CH₂CH₂OH | i-C₄H₉ | CH—OH | C₂H₅ | H | C₂H₅ | H |
| 2 | CH₂CH(CH₃)OH | n-C₄H₉ | CH—OH | C₂H₅ | H | H | C₂H₅ |
| 2 | CH(CH₃)CH₂OH | n-C₄H₉ | CH—OH | H | i-C₃H₇ | H | i-C₃H₇ |
| 2 | CH(CH₃)CH(CH₃)OH | CH₃ | CH—OH | i-C₃H₇ | H | i-C₃H₇ | H |
| 2 | C(CH₃)₂CH₂OH | CH₃ | CH—OH | i-C₃H₇ | H | H | i-C₃H₇ |
| 1 | CH₂C(CH₃)₂OH | C₂H₅ | CH—F | H | Cl | H | Cl |
| 1 | CH₂CHF₂ | C₂H₅ | CH—F | Cl | H | Cl | H |
| 1 | CH₂CF₃ | n-C₃H₇ | CH—F | Cl | H | H | Cl |
| 1 | CH₂CH(CH₃)₂ | n-C₃H₇ | CH—F | H | Br | H | Br |
| 1 | CH₂C(CH₃)₃ | i-C₃H₇ | CH—F | Br | H | Br | H |
| 1 | H₂C—C≡N | i-C₃H₇ | CH—F | Br | H | H | Br |
| 1 | H₂C—C≡CH | c-C₃H₅ | CH—F | H | I | H | I |
| 1 | CH(CH₃)₂ | c-C₃H₅ | CH—F | I | H | I | H |
| 1 | CH₂CH₂OH | sec-C₄H₉ | CH—F | I | H | H | I |
| 2 | CH₂CH(CH₃)OH | sec-C₄H₉ | CH—F | H | CH₃ | H | CH₃ |
| 2 | CH(CH₃)CH₂OH | i-C₄H₉ | CH—F | CH₃ | H | CH₃ | H |
| 2 | CH(CH₃)CH(CH₃)OH | i-C₄H₉ | CH—F | CH₃ | H | H | CH₃ |
| 2 | C(CH₃)₂CH₂OH | n-C₄H₉ | CH—F | H | C₂H₅ | H | C₂H₅ |
| 2 | CH₂C(CH₃)₂OH | n-C₄H₉ | CH—F | C₂H₅ | H | C₂H₅ | H |
| 2 | CH₂CHF₂ | CH₃ | CH—F | C₂H₅ | H | H | C₂H₅ |
| 2 | CH₂CF₃ | CH₃ | CH—F | H | i-C₃H₇ | H | i-C₃H₇ |
| 2 | CH₂CH(CH₃)₂ | C₂H₅ | CH—F | i-C₃H₇ | H | i-C₃H₇ | H |
| 2 | CH₂C(CH₃)₃ | C₂H₅ | CH—F | i-C₃H₇ | H | H | i-C₃H₇ |
| 1 | H₂C—C≡N | n-C₃H₇ | S | H | Cl | Cl | Cl |
| 1 | H₂C—C≡CH | n-C₃H₇ | S | Cl | Cl | H | Cl |
| 1 | CH(CH₃)₂ | i-C₃H₇ | S | H | Br | Br | Br |

TABLE 2C-continued

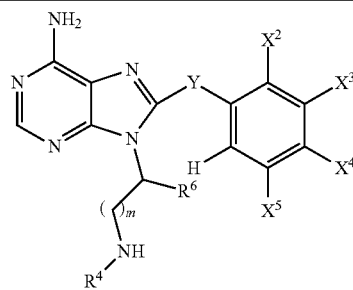

and pharmaceutically acceptable salts thereof, where:

| m | $R^4$ | $R^6$ | Y | $X^2$ | $X^3$ | $X^4$ | $X^5$ |
|---|---|---|---|---|---|---|---|
| 1 | $CH_2CH_2OH$ | i-$C_3H_7$ | S | Br | Br | H | Br |
| 1 | $CH_2CH(CH_3)OH$ | c-$C_3H_5$ | S | H | I | I | I |
| 1 | $CH(CH_3)CH_2OH$ | c-$C_3H_5$ | S | I | I | H | I |
| 1 | $CH(CH_3)CH(CH_3)OH$ | sec-$C_4H_9$ | S | H | $CH_3$ | $CH_3$ | $CH_3$ |
| 1 | $C(CH_3)_2CH_2OH$ | sec-$C_4H_9$ | S | $CH_3$ | $CH_3$ | H | $CH_3$ |
| 1 | $CH_2C(CH_3)_2OH$ | i-$C_4H_9$ | S | H | $C_2H_5$ | $C_2H_5$ | $C_2H_5$ |
| 2 | $CH_2CHF_2$ | i-$C_4H_9$ | S | $C_2H_5$ | $C_2H_5$ | H | $C_2H_5$ |
| 2 | $CH_2CF_3$ | n-$C_4H_9$ | S | H | i-$C_3H_7$ | i-$C_3H_7$ | i-$C_3H_7$ |
| 2 | $CH_2CH(CH_3)_2$ | n-$C_4H_9$ | S | i-$C_3H_7$ | i-$C_3H_7$ | H | i-$C_3H_7$ |
| 2 | $CH_2C(CH_3)_3$ | $CH_3$ | O | H | Cl | Cl | Cl |
| 2 | $H_2C-C\equiv N$ | $CH_3$ | O | Cl | Cl | H | Cl |
| 2 | $H_2C-C\equiv CH$ | $C_2H_5$ | O | H | Br | Br | Br |
| 2 | $CH(CH_3)_2$ | $C_2H_5$ | O | Br | Br | H | Br |
| 2 | $CH_2CH_2OH$ | n-$C_3H_7$ | O | H | I | I | I |
| 2 | $CH_2CH(CH_3)OH$ | n-$C_3H_7$ | O | I | I | H | I |
| 1 | $CH(CH_3)CH_2OH$ | i-$C_3H_7$ | O | H | $CH_3$ | $CH_3$ | $CH_3$ |
| 1 | $CH(CH_3)CH(CH_3)OH$ | i-$C_3H_7$ | O | $CH_3$ | $CH_3$ | H | $CH_3$ |
| 1 | $C(CH_3)_2CH_2OH$ | c-$C_3H_5$ | O | H | $C_2H_5$ | $C_2H_5$ | $C_2H_5$ |
| 1 | $CH_2C(CH_3)_2OH$ | c-$C_3H_5$ | O | $C_2H_5$ | $C_2H_5$ | H | $C_2H_5$ |
| 1 | $CH_2CHF_2$ | sec-$C_4H_9$ | O | H | i-$C_3H_7$ | i-$C_3H_7$ | i-$C_3H_7$ |
| 1 | $CH_2CF_3$ | sec-$C_4H_9$ | O | i-$C_3H_7$ | i-$C_3H_7$ | H | i-$C_3H_7$ |
| 1 | $CH_2CH(CH_3)_2$ | i-$C_4H_9$ | S=O | H | Cl | Cl | Cl |
| 1 | $CH_2C(CH_3)_3$ | i-$C_4H_9$ | S=O | Cl | Cl | H | Cl |
| 1 | $H_2C-C\equiv N$ | n-$C_4H_9$ | S=O | H | Br | Br | Br |
| 2 | $H_2C-C\equiv CH$ | n-$C_4H_9$ | S=O | Br | Br | H | Br |
| 2 | $CH(CH_3)_2$ | $CH_3$ | S=O | H | I | I | I |
| 2 | $CH_2CH_2OH$ | $CH_3$ | S=O | I | I | H | I |
| 2 | $CH_2CH(CH_3)OH$ | $C_2H_5$ | S=O | H | $CH_3$ | $CH_3$ | $CH_3$ |
| 2 | $CH(CH_3)CH_2OH$ | $C_2H_5$ | S=O | $CH_3$ | $CH_3$ | H | $CH_3$ |
| 2 | $CH(CH_3)CH(CH_3)OH$ | n-$C_3H_7$ | S=O | H | $C_2H_5$ | $C_2H_5$ | $C_2H_5$ |
| 2 | $C(CH_3)_2CH_2OH$ | n-$C_3H_7$ | S=O | $C_2H_5$ | $C_2H_5$ | H | $C_2H_5$ |
| 2 | $CH_2C(CH_3)_2OH$ | i-$C_3H_7$ | S=O | H | i-$C_3H_7$ | i-$C_3H_7$ | i-$C_3H_7$ |
| 2 | $CH_2CHF_2$ | i-$C_3H_7$ | S=O | i-$C_3H_7$ | i-$C_3H_7$ | H | i-$C_3H_7$ |
| 1 | $CH_2CF_3$ | c-$C_3H_5$ | O=S=O | H | Cl | Cl | Cl |
| 1 | $CH_2CH(CH_3)_2$ | c-$C_3H_5$ | O=S=O | Cl | Cl | H | Cl |
| 1 | $CH_2C(CH_3)_3$ | sec-$C_4H_9$ | O=S=O | H | Br | Br | Br |
| 1 | $H_2C-C\equiv N$ | sec-$C_4H_9$ | O=S=O | Br | Br | H | Br |
| 1 | $H_2C-C\equiv CH$ | i-$C_4H_9$ | O=S=O | H | I | I | I |
| 1 | $CH(CH_3)_2$ | i-$C_4H_9$ | O=S=O | I | I | H | I |
| 1 | $CH_2CH_2OH$ | n-$C_4H_9$ | O=S=O | H | $CH_3$ | $CH_3$ | $CH_3$ |
| 1 | $CH_2CH(CH_3)OH$ | n-$C_4H_9$ | O=S=O | $CH_3$ | $CH_3$ | H | $CH_3$ |
| 1 | $CH(CH_3)CH_2OH$ | $CH_3$ | O=S=O | H | $C_2H_5$ | $C_2H_5$ | $C_2H_5$ |
| 2 | $CH(CH_3)CH(CH_3)OH$ | $CH_3$ | O=S=O | $C_2H_5$ | $C_2H_5$ | H | $C_2H_5$ |
| 2 | $C(CH_3)_2CH_2OH$ | $C_2H_5$ | O=S=O | H | i-$C_3H_7$ | i-$C_3H_7$ | i-$C_3H_7$ |
| 2 | $CH_2C(CH_3)_2OH$ | $C_2H_5$ | O=S=O | i-$C_3H_7$ | i-$C_3H_7$ | H | i-$C_3H_7$ |
| 2 | $CH_2CHF_2$ | n-$C_3H_7$ | NH | H | Cl | Cl | Cl |
| 2 | $CH_2CF_3$ | n-$C_3H_7$ | NH | Cl | Cl | H | Cl |
| 2 | $CH_2CH(CH_3)_2$ | i-$C_3H_7$ | NH | H | Br | Br | Br |
| 2 | $CH_2C(CH_3)_3$ | i-$C_3H_7$ | NH | Br | Br | H | Br |
| 2 | $H_2C-C\equiv N$ | c-$C_3H_5$ | NH | H | I | I | I |
| 2 | $H_2C-C\equiv CH$ | c-$C_3H_5$ | NH | I | I | H | I |
| 1 | $CH(CH_3)_2$ | sec-$C_4H_9$ | NH | H | $CH_3$ | $CH_3$ | $CH_3$ |
| 1 | $CH_2CH_2OH$ | sec-$C_4H_9$ | NH | $CH_3$ | $CH_3$ | H | $CH_3$ |
| 1 | $CH_2CH(CH_3)OH$ | i-$C_4H_9$ | NH | H | $C_2H_5$ | $C_2H_5$ | $C_2H_5$ |
| 1 | $CH(CH_3)CH_2OH$ | i-$C_4H_9$ | NH | $C_2H_5$ | $C_2H_5$ | H | $C_2H_5$ |
| 1 | $CH(CH_3)CH(CH_3)OH$ | n-$C_4H_9$ | NH | H | i-$C_3H_7$ | i-$C_3H_7$ | i-$C_3H_7$ |
| 1 | $C(CH_3)_2CH_2OH$ | n-$C_4H_9$ | NH | i-$C_3H_7$ | i-$C_3H_7$ | H | i-$C_3H_7$ |
| 1 | $CH_2C(CH_3)_2OH$ | $CH_3$ | C=O | H | Cl | Cl | Cl |
| 1 | $CH_2CHF_2$ | $CH_3$ | C=O | Cl | Cl | H | Cl |
| 1 | $CH_2CF_3$ | $C_2H_5$ | C=O | H | Br | Br | Br |
| 2 | $CH_2CH(CH_3)_2$ | $C_2H_5$ | C=O | Br | Br | H | Br |

TABLE 2C-continued

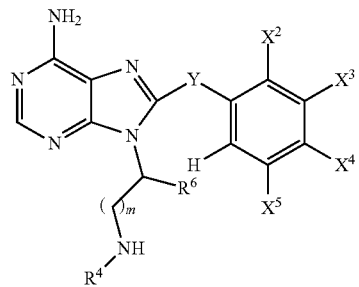

and pharmaceutically acceptable salts thereof, where:

| m | $R^4$ | $R^6$ | Y | $X^2$ | $X^3$ | $X^4$ | $X^5$ |
|---|---|---|---|---|---|---|---|
| 2 | $CH_2C(CH_3)_3$ | $n$-$C_3H_7$ | C=O | H | I | I | I |
| 2 | $H_2C$—C≡N | $n$-$C_3H_7$ | C=O | I | I | H | I |
| 2 | $H_2C$—C≡CH | $i$-$C_3H_7$ | C=O | H | $CH_3$ | $CH_3$ | $CH_3$ |
| 2 | $CH(CH_3)_2$ | $i$-$C_3H_7$ | C=O | $CH_3$ | $CH_3$ | H | $CH_3$ |
| 2 | $CH_2CH_2OH$ | $c$-$C_3H_5$ | C=O | H | $C_2H_5$ | $C_2H_5$ | $C_2H_5$ |
| 2 | $CH_2CH(CH_3)OH$ | $c$-$C_3H_5$ | C=O | $C_2H_5$ | $C_2H_5$ | H | $C_2H_5$ |
| 2 | $CH(CH_3)CH_2OH$ | $sec$-$C_4H_9$ | C=O | H | $i$-$C_3H_7$ | $i$-$C_3H_7$ | $i$-$C_3H_7$ |
| 2 | $CH(CH_3)CH(CH_3)OH$ | $sec$-$C_4H_9$ | C=O | $i$-$C_3H_7$ | $i$-$C_3H_7$ | H | $i$-$C_3H_7$ |
| 1 | $C(CH_3)_2CH_2OH$ | $i$-$C_4H_9$ | C=S | H | Cl | Cl | Cl |
| 1 | $CH_2C(CH_3)_2OH$ | $i$-$C_4H_9$ | C=S | Cl | Cl | H | Cl |
| 1 | $CH_2CHF_2$ | $n$-$C_4H_9$ | C=S | H | Br | Br | Br |
| 1 | $CH_2CF_3$ | $n$-$C_4H_9$ | C=S | Br | Br | H | Br |
| 1 | $CH_2CH(CH_3)_2$ | $CH_3$ | C=S | H | I | I | I |
| 1 | $CH_2C(CH_3)_3$ | $CH_3$ | C=S | I | I | H | I |
| 1 | $H_2C$—C≡N | $C_2H_5$ | C=S | H | $CH_3$ | $CH_3$ | $CH_3$ |
| 1 | $H_2C$—C≡CH | $C_2H_5$ | C=S | $CH_3$ | $CH_3$ | H | $CH_3$ |
| 1 | $CH(CH_3)_2$ | $n$-$C_3H_7$ | C=S | H | $C_2H_5$ | $C_2H_5$ | $C_2H_5$ |
| 2 | $CH_2CH_2OH$ | $n$-$C_3H_7$ | C=S | $C_2H_5$ | $C_2H_5$ | H | $C_2H_5$ |
| 2 | $CH_2CH(CH_3)OH$ | $i$-$C_3H_7$ | C=S | H | $i$-$C_3H_7$ | $i$-$C_3H_7$ | $i$-$C_3H_7$ |
| 2 | $CH_2CH(CH_3)OH$ | $i$-$C_3H_7$ | C=S | $i$-$C_3H_7$ | $i$-$C_3H_7$ | H | $i$-$C_3H_7$ |
| 2 | $CH(CH_3)CH(CH_3)OH$ | $c$-$C_3H_5$ | $CH_2$ | H | Cl | Cl | Cl |
| 2 | $C(CH_3)_2CH_2OH$ | $c$-$C_3H_5$ | $CH_2$ | Cl | Cl | H | Cl |
| 2 | $CH_2C(CH_3)_2OH$ | $sec$-$C_4H_9$ | $CH_2$ | H | Br | Br | Br |
| 2 | $CH_2CHF_2$ | $sec$-$C_4H_9$ | $CH_2$ | Br | Br | H | Br |
| 2 | $CH_2CF_3$ | $i$-$C_4H_9$ | $CH_2$ | H | I | I | I |
| 2 | $CH_2CH(CH_3)_2$ | $i$-$C_4H_9$ | $CH_2$ | I | I | H | I |
| 1 | $CH_2C(CH_3)_3$ | $n$-$C_4H_9$ | $CH_2$ | H | $CH_3$ | $CH_3$ | $CH_3$ |
| 1 | $H_2C$—C≡N | $n$-$C_4H_9$ | $CH_2$ | $CH_3$ | $CH_3$ | H | $CH_3$ |
| 1 | $H_2C$—C≡CH | $CH_3$ | $CH_2$ | H | $C_2H_5$ | $C_2H_5$ | $C_2H_5$ |
| 1 | $CH(CH_3)_2$ | $CH_3$ | $CH_2$ | $C_2H_5$ | $C_2H_5$ | H | $C_2H_5$ |
| 1 | $CH_2CH_2OH$ | $C_2H_5$ | $CH_2$ | H | $i$-$C_3H_7$ | $i$-$C_3H_7$ | $i$-$C_3H_7$ |
| 1 | $CH_2CH(CH_3)OH$ | $C_2H_5$ | $CH_2$ | $i$-$C_3H_7$ | $i$-$C_3H_7$ | H | $i$-$C_3H_7$ |
| 1 | $CH(CH_3)CH_2OH$ | $n$-$C_3H_7$ | CH—OH | H | Cl | Cl | Cl |
| 1 | $CH(CH_3)CH(CH_3)OH$ | $n$-$C_3H_7$ | CH—OH | Cl | Cl | H | Cl |
| 1 | $C(CH_3)_2CH_2OH$ | $i$-$C_3H_7$ | CH—OH | H | Br | Br | Br |
| 2 | $CH_2C(CH_3)_2OH$ | $i$-$C_3H_7$ | CH—OH | Br | Br | H | Br |
| 2 | $CH_2CHF_2$ | $c$-$C_3H_5$ | CH—OH | H | I | I | I |
| 2 | $CH_2CF_3$ | $c$-$C_3H_5$ | CH—OH | I | I | H | I |
| 2 | $CH_2CH(CH_3)_2$ | $sec$-$C_4H_9$ | CH—OH | H | $CH_3$ | $CH_3$ | $CH_3$ |
| 2 | $CH_2C(CH_3)_3$ | $sec$-$C_4H_9$ | CH—OH | $CH_3$ | $CH_3$ | H | $CH_3$ |
| 2 | $H_2C$—C≡N | $i$-$C_4H_9$ | CH—OH | H | $C_2H_5$ | $C_2H_5$ | $C_2H_5$ |
| 2 | $H_2C$—C≡CH | $i$-$C_4H_9$ | CH—OH | $C_2H_5$ | $C_2H_5$ | H | $C_2H_5$ |
| 2 | $CH(CH_3)_2$ | $n$-$C_4H_9$ | CH—OH | H | $i$-$C_3H_7$ | $i$-$C_3H_7$ | $i$-$C_3H_7$ |
| 2 | $CH_2CH_2OH$ | $n$-$C_4H_9$ | CH—OH | $i$-$C_3H_7$ | $i$-$C_3H_7$ | H | $i$-$C_3H_7$ |
| 1 | $CH_2CH(CH_3)OH$ | $CH_3$ | CH—F | H | Cl | Cl | Cl |
| 1 | $CH(CH_3)CH_2OH$ | $CH_3$ | CH—F | Cl | Cl | H | Cl |
| 1 | $CH(CH_3)CH(CH_3)OH$ | $C_2H_5$ | CH—F | H | Br | Br | Br |
| 1 | $C(CH_3)_2CH_2OH$ | $C_2H_5$ | CH—F | Br | Br | H | Br |
| 1 | $CH_2C(CH_3)_2OH$ | $n$-$C_3H_7$ | CH—F | H | I | I | I |
| 1 | $CH_2CHF_2$ | $n$-$C_3H_7$ | CH—F | I | I | H | I |
| 1 | $CH_2CF_3$ | $i$-$C_3H_7$ | CH—F | H | $CH_3$ | $CH_3$ | $CH_3$ |
| 1 | $CH_2CH(CH_3)_2$ | $i$-$C_3H_7$ | CH—F | $CH_3$ | $CH_3$ | H | $CH_3$ |
| 1 | $CH_2C(CH_3)_3$ | $c$-$C_3H_5$ | CH—F | H | $C_2H_5$ | $C_2H_5$ | $C_2H_5$ |
| 2 | $H_2C$—C≡N | $c$-$C_3H_5$ | CH—F | $C_2H_5$ | $C_2H_5$ | H | $C_2H_5$ |
| 2 | $H_2C$—C≡CH | $sec$-$C_4H_9$ | CH—F | H | $i$-$C_3H_7$ | $i$-$C_3H_7$ | $i$-$C_3H_7$ |
| 2 | $CH(CH_3)_2$ | $sec$-$C_4H_9$ | CH—F | $i$-$C_3H_7$ | $i$-$C_3H_7$ | H | $i$-$C_3H_7$ |
| 2 | $CH_2CH_2OH$ | $i$-$C_4H_9$ | S | I | H | Cl | H |
| 2 | $CH_2CH(CH_3)OH$ | $i$-$C_4H_9$ | S=O | I | H | H | Cl |
| 2 | $CH(CH_3)CH_2OH$ | $n$-$C_4H_9$ | O=S=O | Br | H | Cl | H |
| 2 | $CH(CH_3)CH(CH_3)OH$ | $n$-$C_4H_9$ | $CH_2$ | Br | H | H | Cl |
| 2 | $C(CH_3)_2CH_2OH$ | $CH_3$ | C=O | Br | H | I | H |

TABLE 2C-continued

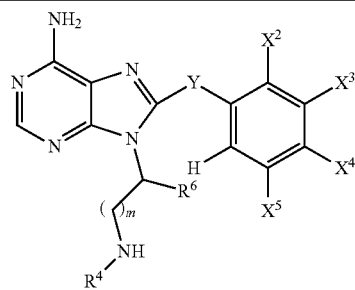

and pharmaceutically acceptable salts thereof, where:

| m | R⁴ | R⁶ | Y | X² | X³ | X⁴ | X⁵ |
|---|---|---|---|---|---|---|---|
| 2 | CH₂C(CH₃)₂OH | CH₃ | C=S | Br | H | H | I |
| 1 | CH₂CHF₂ | C₂H₅ | CH—OH | I | H | Br | H |
| 1 | CH₂CF₃ | C₂H₅ | CH—F | I | H | H | Br |
| 1 | CH₂CH(CH₃)₂ | n-C₃H₇ | O | I | Cl | H | Cl |
| 1 | CH₂C(CH₃)₃ | n-C₃H₇ | NH | Br | Cl | H | Cl |

TABLE 2D

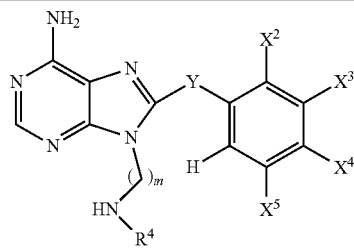

and pharmaceutically acceptable salts thereof, where:

| m | R⁴ | Y | X² | X³ | X⁴ | X⁵ |
|---|---|---|---|---|---|---|
| 2 | CH₂CH(CH₃)OH | S | Furan-2-yl | Cl | H | Cl |
| 2 | CH(CH₃)CH₂OH | S | Furan-3-yl | H | Cl | H |
| 2 | CH(CH₃)CH(CH₃)OH | S | Furan-4-yl | H | H | Cl |
| 2 | C(CH₃)₂CH₂OH | S | Furan-5-yl | Br | H | Br |
| 2 | CH₂C(CH₃)₂OH | S | Pyrrol-2-yl | H | Br | H |
| 2 | CH₂CHF₂ | S | Pyrrol-3-yl | H | H | Br |
| 2 | CH₂CF₃ | S | Pyrrol-4-yl | I | H | I |
| 2 | CH₂CH(CH₃)₂ | S | Pyrrol-5-yl | H | I | H |
| 2 | CH₂C(CH₃)₃ | S | Thiophene-2-yl | H | H | I |
| 2 | H₂C—C≡N | S | Thiophene-3-yl | CH₃ | H | CH₃ |
| 2 | H₂C—C≡CH | S | Thiophene-4-yl | H | CH₃ | H |
| 2 | CH(CH₃)₂ | S | Thiophene-5-yl | H | H | CH₃ |
| 3 | CH₂CH₂OH | S | Oxazol-2-yl | C₂H₅ | H | C₂H₅ |
| 3 | CH₂CH(CH₃)OH | S | Oxazol-4-yl | H | C₂H₅ | H |
| 3 | CH(CH₃)CH₂OH | S | Oxazol-5-yl | H | H | C₂H₅ |
| 3 | CH(CH₃)CH(CH₃)OH | S | Isoxazol-3-yl | i-C₃H₇ | H | i-C₃H₇ |
| 3 | C(CH₃)₂CH₂OH | S | Isoxazol-4-yl | H | i-C₃H₇ | H |
| 3 | CH₂C(CH₃)₂OH | S | Isoxazol-5-yl | H | H | i-C₃H₇ |
| 3 | CH₂CHF₂ | O | Pyrazol-3-yl | Cl | H | Cl |
| 3 | CH₂CF₃ | O | Pyrazol-4-yl | H | Cl | H |
| 3 | CH₂CH(CH₃)₂ | O | Pyrazol-5-yl | H | H | Cl |
| 3 | CH₂C(CH₃)₃ | O | Thiazol-2-yl | Br | H | Br |
| 3 | H₂C—C≡N | O | Thiazol-4-yl | H | Br | H |
| 3 | H₂C—C≡CH | O | Thiazol-5-yl | H | H | Br |
| 2 | CH(CH₃)₂ | O | Furan-2-yl | I | H | I |
| 2 | CH₂CH₂OH | O | Furan-3-yl | H | I | H |
| 2 | CH₂CH(CH₃)OH | O | Furan-4-yl | H | H | I |
| 2 | CH(CH₃)CH₂OH | O | Furan-5-yl | CH₃ | H | CH₃ |
| 2 | CH(CH₃)CH(CH₃)OH | O | Pyrrol-2-yl | H | CH₃ | H |
| 2 | C(CH₃)₂CH₂OH | O | Pyrrol-3-yl | H | H | CH₃ |
| 2 | CH₂C(CH₃)₂OH | O | Pyrrol-4-yl | C₂H₅ | H | C₂H₅ |
| 2 | CH₂CHF₂ | O | Pyrrol-5-yl | H | C₂H₅ | H |
| 2 | CH₂CF₃ | O | Thiophene-2-yl | H | H | C₂H₅ |
| 2 | CH₂CH(CH₃)₂ | O | Thiophene-3-yl | i-C₃H₇ | H | i-C₃H₇ |
| 2 | CH₂C(CH₃)₃ | O | Thiophene-4-yl | H | i-C₃H₇ | H |

TABLE 2D-continued

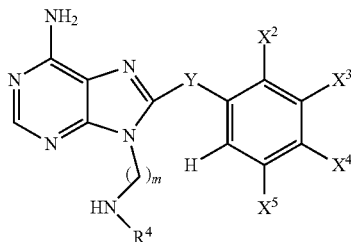

and pharmaceutically acceptable salts thereof, where:

| m | R⁴ | Y | X² | X³ | X⁴ | X⁵ |
|---|---|---|---|---|---|---|
| 2 | H₂C—C≡N | O | Thiophene-5-yl | H | H | i-C₃H₇ |
| 3 | H₂C—C≡CH | S=O | Oxazol-2-yl | Cl | H | Cl |
| 3 | CH(CH₃)₂ | S=O | Oxazol-4-yl | H | Cl | H |
| 3 | CH₂CH₂OH | S=O | Oxazol-5-yl | H | H | Cl |
| 3 | CH₂CH(CH₃)OH | S=O | Isoxazol-3-yl | Br | H | Br |
| 3 | CH(CH₃)CH₂OH | S=O | Isoxazol-4-yl | H | Br | H |
| 3 | CH(CH₃)CH(CH₃)OH | S=O | Isoxazol-5-yl | H | H | Br |
| 3 | C(CH₃)₂CH₂OH | S=O | Pyrazol-3-yl | I | H | I |
| 3 | CH₂C(CH₃)₂OH | S=O | Pyrazol-4-yl | H | I | H |
| 3 | CH₂CHF₂ | S=O | Pyrazol-5-yl | H | H | I |
| 3 | CH₂CF₃ | S=O | Thiazol-2-yl | CH₃ | H | CH₃ |
| 3 | CH₂CH(CH₃)₂ | S=O | Thiazol-4-yl | H | CH₃ | H |
| 3 | CH₂C(CH₃)₃ | S=O | Thiazol-5-yl | H | H | CH₃ |
| 2 | H₂C—C≡N | S=O | Furan-2-yl | C₂H₅ | H | C₂H₅ |
| 2 | H₂C—C≡CH | S=O | Furan-3-yl | H | C₂H₅ | H |
| 2 | CH(CH₃)₂ | S=O | Furan-4-yl | H | H | C₂H₅ |
| 2 | CH₂CH₂OH | S=O | Furan-5-yl | i-C₃H₇ | H | i-C₃H₇ |
| 2 | CH₂CH(CH₃)OH | S=O | Pyrrol-2-yl | H | i-C₃H₇ | H |
| 2 | CH(CH₃)CH₂OH | S=O | Pyrrol-3-yl | H | H | i-C₃H₇ |
| 2 | CH(CH₃)CH(CH₃)OH | O=S=O | Pyrrol-4-yl | Cl | H | Cl |
| 2 | C(CH₃)₂CH₂OH | O=S=O | Pyrrol-5-yl | H | Cl | H |
| 2 | CH₂C(CH₃)₂OH | O=S=O | Thiophene-2-yl | H | H | Cl |
| 2 | CH₂CHF₂ | O=S=O | Thiophene-3-yl | Br | H | Br |
| 2 | CH₂CF₃ | O=S=O | Thiophene-4-yl | H | Br | H |
| 2 | CH₂CH(CH₃)₂ | O=S=O | Thiophene-5-yl | H | H | Br |
| 3 | CH₂C(CH₃)₃ | O=S=O | Oxazol-2-yl | I | H | I |
| 3 | H₂C—C≡N | O=S=O | Oxazol-4-yl | H | I | H |
| 3 | H₂C—C≡CH | O=S=O | Oxazol-5-yl | H | H | I |
| 3 | CH(CH₃)₂ | O=S=O | Isoxazol-3-yl | CH₃ | H | CH₃ |
| 3 | CH₂CH₂OH | O=S=O | Isoxazol-4-yl | H | CH₃ | H |
| 3 | CH₂CH(CH₃)OH | O=S=O | Isoxazol-5-yl | H | H | CH₃ |
| 3 | CH(CH₃)CH₂OH | O=S=O | Pyrazol-3-yl | C₂H₅ | H | C₂H₅ |
| 3 | CH(CH₃)CH(CH₃)OH | O=S=O | Pyrazol-4-yl | H | C₂H₅ | H |
| 3 | C(CH₃)₂CH₂OH | O=S=O | Pyrazol-5-yl | H | H | C₂H₅ |
| 3 | CH₂C(CH₃)₂OH | O=S=O | Thiazol-2-yl | i-C₃H₇ | H | i-C₃H₇ |
| 3 | CH₂CHF₂ | O=S=O | Thiazol-4-yl | H | i-C₃H₇ | H |
| 3 | CH₂CF₃ | O=S=O | Thiazol-5-yl | H | H | i-C₃H₇ |
| 2 | CH₂CH(CH₃)₂ | NH | Furan-2-yl | Cl | H | Cl |
| 2 | CH₂C(CH₃)₃ | NH | Furan-3-yl | H | Cl | H |
| 2 | H₂C—C≡N | NH | Furan-4-yl | H | H | Cl |
| 2 | H₂C—C≡CH | NH | Furan-5-yl | Br | H | Br |
| 2 | CH(CH₃)₂ | NH | Pyrrol-2-yl | H | Br | H |
| 2 | CH₂CH₂OH | NH | Pyrrol-3-yl | H | H | Br |
| 2 | CH₂CH(CH₃)OH | NH | Pyrrol-4-yl | I | H | I |
| 2 | CH(CH₃)CH₂OH | NH | Pyrrol-5-yl | H | I | H |
| 2 | CH(CH₃)CH(CH₃)OH | NH | Thiophene-2-yl | H | H | I |
| 2 | C(CH₃)₂CH₂OH | NH | Thiophene-3-yl | CH₃ | H | CH₃ |
| 2 | CH₂C(CH₃)₂OH | NH | Thiophene-4-yl | H | CH₃ | H |
| 2 | CH₂CHF₂ | NH | Thiophene-5-yl | H | H | CH₃ |
| 3 | CH₂CF₃ | NH | Oxazol-2-yl | C₂H₅ | H | C₂H₅ |
| 3 | CH₂CH(CH₃)₂ | NH | Oxazol-4-yl | H | C₂H₅ | H |
| 3 | CH₂C(CH₃)₃ | NH | Oxazol-5-yl | H | H | C₂H₅ |
| 3 | H₂C—C≡N | NH | Isoxazol-3-yl | i-C₃H₇ | H | i-C₃H₇ |
| 3 | H₂C—C≡CH | NH | Isoxazol-4-yl | H | i-C₃H₇ | H |
| 3 | CH(CH₃)₂ | NH | Isoxazol-5-yl | H | H | i-C₃H₇ |
| 3 | CH₂CH₂OH | C=O | Pyrazol-3-yl | Cl | H | Cl |
| 3 | CH₂CH(CH₃)OH | C=O | Pyrazol-4-yl | H | Cl | H |
| 3 | CH(CH₃)CH₂OH | C=O | Pyrazol-5-yl | H | H | Cl |
| 3 | CH(CH₃)CH(CH₃)OH | C=O | Thiazol-2-yl | Br | H | Br |
| 3 | C(CH₃)₂CH₂OH | C=O | Thiazol-4-yl | H | Br | H |
| 3 | CH₂C(CH₃)₂OH | C=O | Thiazol-5-yl | H | H | Br |
| 3 | CH₂CHF₂ | C=O | Furan-2-yl | I | H | I |
| 2 | CH₂CF₃ | C=O | Furan-3-yl | H | I | H |

TABLE 2D-continued

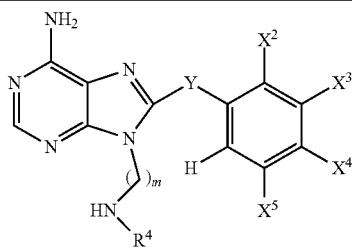

and pharmaceutically acceptable salts thereof, where:

| m | $R^4$ | Y | $X^2$ | $X^3$ | $X^4$ | $X^5$ |
|---|---|---|---|---|---|---|
| 2 | $CH_2CH(CH_3)_2$ | C=O | Furan-4-yl | H | H | I |
| 2 | $CH_2C(CH_3)_3$ | C=O | Furan-5-yl | $CH_3$ | H | $CH_3$ |
| 2 | $H_2C-C\equiv N$ | C=O | Pyrrol-2-yl | H | $CH_3$ | H |
| 2 | $H_2C-C\equiv CH$ | C=O | Pyrrol-3-yl | H | H | $CH_3$ |
| 2 | $CH(CH_3)_2$ | C=O | Pyrrol-4-yl | $C_2H_5$ | H | $C_2H_5$ |
| 2 | $CH_2CH_2OH$ | C=O | Pyrrol-5-yl | H | $C_2H_5$ | H |
| 2 | $CH_2CH(CH_3)OH$ | C=O | Thiophene-2-yl | H | H | $C_2H_5$ |
| 2 | $CH(CH_3)CH_2OH$ | C=O | Thiophene-3-yl | $i-C_3H_7$ | H | $i-C_3H_7$ |
| 2 | $CH(CH_3)CH(CH_3)OH$ | C=O | Thiophene-4-yl | H | $i-C_3H_7$ | H |
| 2 | $C(CH_3)_2CH_2OH$ | C=O | Thiophene-5-yl | H | H | $i-C_3H_7$ |
| 3 | $CH_2C(CH_3)_2OH$ | C=S | Oxazol-2-yl | Cl | H | Cl |
| 3 | $CH_2CHF_2$ | C=S | Oxazol-4-yl | H | Cl | H |
| 3 | $CH_2CF_3$ | C=S | Oxazol-5-yl | H | H | Cl |
| 3 | $CH_2CH(CH_3)_2$ | C=S | Isoxazol-3-yl | Br | H | Br |
| 3 | $CH_2C(CH_3)_3$ | C=S | Isoxazol-4-yl | H | Br | H |
| 3 | $H_2C-C\equiv N$ | C=S | Isoxazol-5-yl | H | H | Br |
| 3 | $H_2C-C\equiv CH$ | C=S | Pyrazol-3-yl | I | H | I |
| 3 | $CH(CH_3)_2$ | C=S | Pyrazol-4-yl | H | I | H |
| 3 | $CH_2CH_2OH$ | C=S | Pyrazol-5-yl | H | H | I |
| 3 | $CH_2CH(CH_3)OH$ | C=S | Thiazol-2-yl | $CH_3$ | H | $CH_3$ |
| 2 | $CH(CH_3)CH_2OH$ | C=S | Thiazol-4-yl | H | $CH_3$ | H |
| 2 | $CH(CH_3)CH(CH_3)OH$ | C=S | Thiazol-5-yl | H | H | $CH_3$ |
| 2 | $C(CH_3)_2CH_2OH$ | C=S | Furan-2-yl | $C_2H_5$ | H | $C_2H_5$ |
| 2 | $CH_2C(CH_3)_2OH$ | C=S | Furan-3-yl | H | $C_2H_5$ | H |
| 2 | $CH_2CHF_2$ | C=S | Furan-4-yl | H | H | $C_2H_5$ |
| 2 | $CH_2CF_3$ | C=S | Furan-5-yl | $i-C_3H_7$ | H | $i-C_3H_7$ |
| 2 | $CH_2CH(CH_3)_2$ | C=S | Pyrrol-2-yl | H | $i-C_3H_7$ | H |
| 2 | $CH_2C(CH_3)_3$ | C=S | Pyrrol-3-yl | H | H | $i-C_3H_7$ |
| 3 | $H_2C-C\equiv N$ | $CH_2$ | Pyrrol-4-yl | Cl | H | Cl |
| 3 | $H_2C-C\equiv CH$ | $CH_2$ | Pyrrol-5-yl | H | Cl | H |
| 3 | $CH(CH_3)_2$ | $CH_2$ | Thiophene-2-yl | H | H | Cl |
| 3 | $CH_2CH_2OH$ | $CH_2$ | Thiophene-3-yl | Br | H | Br |
| 3 | $CH_2CH(CH_3)OH$ | $CH_2$ | Thiophene-4-yl | H | Br | H |
| 3 | $CH(CH_3)CH_2OH$ | $CH_2$ | Thiophene-5-yl | H | H | Br |
| 2 | $CH(CH_3)CH(CH_3)OH$ | $CH_2$ | Oxazol-2-yl | I | H | I |
| 2 | $C(CH_3)_2CH_2OH$ | $CH_2$ | Oxazol-4-yl | H | I | H |
| 2 | $CH_2C(CH_3)_2OH$ | $CH_2$ | Oxazol-5-yl | H | H | I |
| 2 | $CH_2CHF_2$ | $CH_2$ | Isoxazol-3-yl | $CH_3$ | H | $CH_3$ |
| 2 | $CH_2CF_3$ | $CH_2$ | Isoxazol-4-yl | H | $CH_3$ | H |
| 2 | $CH_2CH(CH_3)_2$ | $CH_2$ | Isoxazol-5-yl | H | H | $CH_3$ |
| 3 | $CH_2C(CH_3)_3$ | $CH_2$ | Pyrazol-3-yl | $C_2H_5$ | H | $C_2H_5$ |
| 3 | $H_2C-C\equiv N$ | $CH_2$ | Pyrazol-4-yl | H | $C_2H_5$ | H |
| 3 | $H_2C-C\equiv CH$ | $CH_2$ | Pyrazol-5-yl | H | H | $C_2H_5$ |
| 3 | $CH(CH_3)_2$ | $CH_2$ | Thiazol-2-yl | $i-C_3H_7$ | H | $i-C_3H_7$ |
| 3 | $CH_2CH_2OH$ | $CH_2$ | Thiazol-4-yl | H | $i-C_3H_7$ | H |
| 3 | $CH_2CH(CH_3)OH$ | $CH_2$ | Thiazol-5-yl | H | H | $i-C_3H_7$ |
| 2 | $CH(CH_3)CH_2OH$ | CH—OH | Furan-2-yl | Cl | H | Cl |
| 2 | $CH(CH_3)CH(CH_3)OH$ | CH—OH | Furan-3-yl | H | Cl | H |
| 2 | $C(CH_3)_2CH_2OH$ | CH—OH | Furan-4-yl | H | H | Cl |
| 2 | $CH_2C(CH_3)_2OH$ | CH—OH | Furan-5-yl | Br | H | Br |
| 2 | $CH_2CHF_2$ | CH—OH | Pyrrol-2-yl | H | Br | H |
| 2 | $CH_2CF_3$ | CH—OH | Pyrrol-3-yl | H | H | Br |
| 3 | $CH_2CH(CH_3)_2$ | CH—OH | Pyrrol-4-yl | I | H | I |
| 3 | $CH_2C(CH_3)_3$ | CH—OH | Pyrrol-5-yl | H | I | H |
| 3 | $H_2C-C\equiv N$ | CH—OH | Thiophene-2-yl | H | H | I |
| 3 | $H_2C-C\equiv CH$ | CH—OH | Thiophene-3-yl | $CH_3$ | H | $CH_3$ |
| 3 | $CH(CH_3)_2$ | CH—OH | Thiophene-4-yl | H | $CH_3$ | H |
| 3 | $CH_2CH_2OH$ | CH—OH | Thiophene-5-yl | H | H | $CH_3$ |
| 2 | $CH_2CH(CH_3)OH$ | CH—OH | Oxazol-2-yl | $C_2H_5$ | H | $C_2H_5$ |
| 2 | $CH(CH_3)CH_2OH$ | CH—OH | Oxazol-4-yl | H | $C_2H_5$ | H |
| 2 | $CH(CH_3)CH(CH_3)OH$ | CH—OH | Oxazol-5-yl | H | H | $C_2H_5$ |
| 2 | $C(CH_3)_2CH_2OH$ | CH—OH | Isoxazol-3-yl | $i-C_3H_7$ | H | $i-C_3H_7$ |
| 2 | $CH_2C(CH_3)_2OH$ | CH—OH | Isoxazol-4-yl | H | $i-C_3H_7$ | H |

TABLE 2D-continued

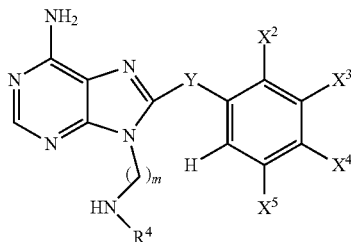

and pharmaceutically acceptable salts thereof, where:

| m | R⁴ | Y | X² | X³ | X⁴ | X⁵ |
|---|---|---|---|---|---|---|
| 2 | $CH_2CHF_2$ | CH—OH | Isoxazol-5-yl | H | H | $i-C_3H_7$ |
| 3 | $CH_2CF_3$ | CH—F | Pyrazol-3-yl | Cl | H | Cl |
| 3 | $CH_2CH(CH_3)_2$ | CH—F | Pyrazol-4-yl | H | Cl | H |
| 3 | $CH_2C(CH_3)_3$ | CH—F | Pyrazol-5-yl | H | H | Cl |
| 3 | $H_2C—C\equiv N$ | CH—F | Thiazol-2-yl | Br | H | Br |
| 3 | $H_2C—C\equiv CH$ | CH—F | Thiazol-4-yl | H | Br | H |
| 3 | $CH(CH_3)_2$ | CH—F | Thiazol-5-yl | H | H | Br |
| 2 | $CH_2CH_2OH$ | CH—F | Furan-2-yl | I | H | I |
| 2 | $CH_2CH(CH_3)OH$ | CH—F | Furan-3-yl | H | I | H |
| 2 | $CH(CH_3)CH_2OH$ | CH—F | Furan-4-yl | H | H | I |
| 2 | $CH(CH_3)CH(CH_3)OH$ | CH—F | Furan-5-yl | $CH_3$ | H | $CH_3$ |
| 2 | $C(CH_3)_2CH_2OH$ | CH—F | Pyrrol-2-yl | H | $CH_3$ | H |
| 2 | $CH_2C(CH_3)_2OH$ | CH—F | Pyrrol-3-yl | H | H | $CH_3$ |
| 3 | $CH_2CHF_2$ | CH—F | Pyrrol-4-yl | $C_2H_5$ | H | $C_2H_5$ |
| 3 | $CH_2CF_3$ | CH—F | Pyrrol-5-yl | H | $C_2H_5$ | H |
| 3 | $CH_2CH(CH_3)_2$ | CH—F | Thiophene-2-yl | H | H | $C_2H_5$ |
| 3 | $CH_2C(CH_3)_3$ | CH—F | Thiophene-3-yl | $i-C_3H_7$ | H | $i-C_3H_7$ |
| 3 | $H_2C—C\equiv N$ | CH—F | Thiophene-4-yl | H | $i-C_3H_7$ | H |
| 3 | $H_2C—C\equiv CH$ | CH—F | Thiophene-5-yl | H | H | $i-C_3H_7$ |
| 2 | $CH(CH_3)_2$ | S | Oxazol-2-yl | Cl | Cl | Cl |
| 2 | $CH_2CH_2OH$ | S | Oxazol-4-yl | Cl | H | Cl |
| 2 | $CH_2CH(CH_3)OH$ | S | Oxazol-5-yl | Br | Br | Br |
| 2 | $CH(CH_3)CH_2OH$ | S | Isoxazol-3-yl | Br | H | Br |
| 2 | $CH(CH_3)CH(CH_3)OH$ | S | Isoxazol-4-yl | I | I | I |
| 2 | $C(CH_3)_2CH_2OH$ | S | Isoxazol-5-yl | I | H | I |
| 3 | $CH_2C(CH_3)_2OH$ | S | Pyrazol-3-yl | $CH_3$ | $CH_3$ | $CH_3$ |
| 3 | $CH_2CHF_2$ | S | Pyrazol-4-yl | $CH_3$ | H | $CH_3$ |
| 3 | $CH_2CF_3$ | S | Pyrazol-5-yl | $C_2H_5$ | $C_2H_5$ | $C_2H_5$ |
| 3 | $CH_2CH(CH_3)_2$ | S | Thiazol-2-yl | $C_2H_5$ | H | $C_2H_5$ |
| 3 | $CH_2C(CH_3)_3$ | S | Thiazol-4-yl | $i-C_3H_7$ | $i-C_3H_7$ | $i-C_3H_7$ |
| 3 | $H_2C—C\equiv N$ | S | Thiazol-5-yl | $i-C_3H_7$ | H | $i-C_3H_7$ |
| 2 | $H_2C—C\equiv CH$ | O | Furan-2-yl | Cl | Cl | Cl |
| 2 | $CH(CH_3)_2$ | O | Furan-3-yl | Cl | H | Cl |
| 2 | $CH_2CH_2OH$ | O | Furan-4-yl | Br | Br | Br |
| 2 | $CH_2CH(CH_3)OH$ | O | Furan-5-yl | Br | H | Br |
| 2 | $CH(CH_3)CH_2OH$ | O | Pyrrol-2-yl | I | I | I |
| 2 | $CH(CH_3)CH(CH_3)OH$ | O | Pyrrol-3-yl | I | H | I |
| 3 | $C(CH_3)_2CH_2OH$ | O | Pyrrol-4-yl | $CH_3$ | $CH_3$ | $CH_3$ |
| 3 | $CH_2C(CH_3)_2OH$ | O | Pyrrol-5-yl | $CH_3$ | H | $CH_3$ |
| 3 | $CH_2CHF_2$ | O | Thiophene-2-yl | $C_2H_5$ | $C_2H_5$ | $C_2H_5$ |
| 3 | $CH_2CF_3$ | O | Thiophene-3-yl | $C_2H_5$ | H | $C_2H_5$ |
| 3 | $CH_2CH(CH_3)_2$ | O | Thiophene-4-yl | $i-C_3H_7$ | $i-C_3H_7$ | $i-C_3H_7$ |
| 3 | $CH_2C(CH_3)_3$ | O | Thiophene-5-yl | $i-C_3H_7$ | H | $i-C_3H_7$ |
| 2 | $H_2C—C\equiv N$ | S=O | Oxazol-2-yl | Cl | Cl | Cl |
| 2 | $H_2C—C\equiv CH$ | S=O | Oxazol-4-yl | Cl | H | Cl |
| 2 | $CH(CH_3)_2$ | S=O | Oxazol-5-yl | Br | Br | Br |
| 2 | $CH_2CH_2OH$ | S=O | Isoxazol-3-yl | Br | H | Br |
| 2 | $CH_2CH(CH_3)OH$ | S=O | Isoxazol-4-yl | I | I | I |
| 2 | $CH(CH_3)CH_2OH$ | S=O | Isoxazol-5-yl | I | H | I |
| 3 | $CH(CH_3)CH(CH_3)OH$ | S=O | Pyrazol-3-yl | $CH_3$ | $CH_3$ | $CH_3$ |
| 3 | $C(CH_3)_2CH_2OH$ | S=O | Pyrazol-4-yl | $CH_3$ | H | $CH_3$ |
| 3 | $CH_2C(CH_3)_2OH$ | S=O | Pyrazol-5-yl | $C_2H_5$ | $C_2H_5$ | $C_2H_5$ |
| 3 | $CH_2CHF_2$ | S=O | Thiazol-2-yl | $C_2H_5$ | H | $C_2H_5$ |
| 3 | $CH_2CF_3$ | S=O | Thiazol-4-yl | $i-C_3H_7$ | $i-C_3H_7$ | $i-C_3H_7$ |
| 3 | $CH_2CH(CH_3)_2$ | S=O | Thiazol-5-yl | $i-C_3H_7$ | H | $i-C_3H_7$ |
| 2 | $CH_2C(CH_3)_3$ | O=S=O | Furan-2-yl | Cl | Cl | Cl |
| 2 | $H_2C—C\equiv N$ | O=S=O | Furan-3-yl | Cl | H | Cl |
| 2 | $H_2C—C\equiv CH$ | O=S=O | Furan-4-yl | Br | Br | Br |
| 2 | $CH(CH_3)_2$ | O=S=O | Furan-5-yl | Br | H | Br |
| 2 | $CH_2CH_2OH$ | O=S=O | Pyrrol-2-yl | I | I | I |
| 2 | $CH_2CH(CH_3)OH$ | O=S=O | Pyrrol-3-yl | I | H | I |
| 2 | $CH(CH_3)CH_2OH$ | O=S=O | Pyrrol-4-yl | $CH_3$ | $CH_3$ | $CH_3$ |
| 2 | $CH(CH_3)CH(CH_3)OH$ | O=S=O | Pyrrol-5-yl | $CH_3$ | H | $CH_3$ |

TABLE 2D-continued

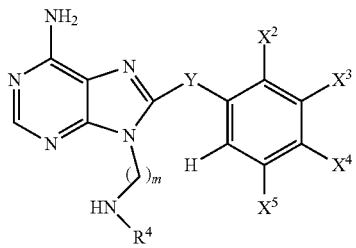

and pharmaceutically acceptable salts thereof, where:

| m | $R^4$ | Y | $X^2$ | $X^3$ | $X^4$ | $X^5$ |
|---|---|---|---|---|---|---|
| 3 | $C(CH_3)_2CH_2OH$ | O=S=O | Thiophene-2-yl | $C_2H_5$ | $C_2H_5$ | $C_2H_5$ |
| 3 | $CH_2C(CH_3)_2OH$ | O=S=O | Thiophene-3-yl | $C_2H_5$ | H | $C_2H_5$ |
| 3 | $CH_2CHF_2$ | O=S=O | Thiophene-4-yl | $i-C_3H_7$ | $i-C_3H_7$ | $i-C_3H_7$ |
| 3 | $CH_2CF_3$ | O=S=O | Thiophene-5-yl | $i-C_3H_7$ | H | $i-C_3H_7$ |
| 2 | $CH_2CH(CH_3)_2$ | NH | Oxazol-2-yl | Cl | Cl | Cl |
| 2 | $CH_2C(CH_3)_3$ | NH | Oxazol-4-yl | Cl | H | Cl |
| 2 | $H_2C-C\equiv N$ | NH | Oxazol-5-yl | Br | Br | Br |
| 2 | $H_2C-C\equiv CH$ | NH | Isoxazol-3-yl | Br | H | Br |
| 2 | $CH(CH_3)_2$ | NH | Isoxazol-4-yl | I | I | I |
| 2 | $CH_2CH_2OH$ | NH | Isoxazol-5-yl | I | H | I |
| 3 | $CH_2CH(CH_3)OH$ | NH | Pyrazol-3-yl | $CH_3$ | $CH_3$ | $CH_3$ |
| 3 | $CH(CH_3)CH_2OH$ | NH | Pyrazol-4-yl | $CH_3$ | H | $CH_3$ |
| 3 | $CH(CH_3)CH(CH_3)OH$ | NH | Pyrazol-5-yl | $C_2H_5$ | $C_2H_5$ | $C_2H_5$ |
| 3 | $C(CH_3)_2CH_2OH$ | NH | Thiazol-2-yl | $C_2H_5$ | H | $C_2H_5$ |
| 3 | $CH_2C(CH_3)_2OH$ | NH | Thiazol-4-yl | $i-C_3H_7$ | $i-C_3H_7$ | $i-C_3H_7$ |
| 3 | $CH_2CHF_2$ | NH | Thiazol-5-yl | $i-C_3H_7$ | H | $i-C_3H_7$ |
| 2 | $CH_2CF_3$ | C=O | Furan-2-yl | Cl | Cl | Cl |
| 2 | $CH_2CH(CH_3)_2$ | C=O | Furan-3-yl | Cl | H | Cl |
| 2 | $CH_2C(CH_3)_3$ | C=O | Furan-4-yl | Br | Br | Br |
| 2 | $H_2C-C\equiv N$ | C=O | Furan-5-yl | Br | H | Br |
| 2 | $H_2C-C\equiv CH$ | C=O | Pyrrol-2-yl | I | I | I |
| 3 | $CH(CH_3)_2$ | C=O | Pyrrol-3-yl | I | H | I |
| 3 | $CH_2CH_2OH$ | C=O | Pyrrol-4-yl | $CH_3$ | $CH_3$ | $CH_3$ |
| 3 | $CH_2CH(CH_3)OH$ | C=O | Pyrrol-5-yl | $CH_3$ | H | $CH_3$ |
| 3 | $CH(CH_3)CH_2OH$ | C=O | Thiophene-2-yl | $C_2H_5$ | $C_2H_5$ | $C_2H_5$ |
| 3 | $CH(CH_3)CH(CH_3)OH$ | C=O | Thiophene-3-yl | $C_2H_5$ | H | $C_2H_5$ |
| 3 | $C(CH_3)_2CH_2OH$ | C=O | Thiophene-4-yl | $i-C_3H_7$ | $i-C_3H_7$ | $i-C_3H_7$ |
| 3 | $CH_2C(CH_3)_2OH$ | C=O | Thiophene-5-yl | $i-C_3H_7$ | H | $i-C_3H_7$ |
| 2 | $CH_2CHF_2$ | C=S | Oxazol-2-yl | Cl | Cl | Cl |
| 2 | $CH_2CF_3$ | C=S | Oxazol-4-yl | Cl | H | Cl |
| 2 | $CH_2CH(CH_3)_2$ | C=S | Oxazol-5-yl | Br | Br | Br |
| 2 | $CH_2C(CH_3)_3$ | C=S | Isoxazol-3-yl | Br | H | Br |
| 2 | $H_2C-C\equiv N$ | C=S | Isoxazol-4-yl | I | I | I |
| 2 | $H_2C-C\equiv CH$ | C=S | Isoxazol-5-yl | I | H | I |
| 3 | $CH(CH_3)_2$ | C=S | Pyrazol-3-yl | $CH_3$ | $CH_3$ | $CH_3$ |
| 3 | $CH_2CH_2OH$ | C=S | Pyrazol-4-yl | $CH_3$ | H | $CH_3$ |
| 3 | $CH_2CH(CH_3)OH$ | C=S | Pyrazol-5-yl | $C_2H_5$ | $C_2H_5$ | $C_2H_5$ |
| 3 | $CH(CH_3)CH_2OH$ | C=S | Thiazol-2-yl | $C_2H_5$ | H | $C_2H_5$ |
| 3 | $CH(CH_3)CH(CH_3)OH$ | C=S | Thiazol-4-yl | $i-C_3H_7$ | $i-C_3H_7$ | $i-C_3H_7$ |
| 3 | $C(CH_3)_2CH_2OH$ | C=S | Thiazol-5-yl | $i-C_3H_7$ | H | $i-C_3H_7$ |
| 2 | $CH_2C(CH_3)_2OH$ | $CH_2$ | Furan-2-yl | Cl | Cl | Cl |
| 2 | $CH_2CHF_2$ | $CH_2$ | Furan-3-yl | Cl | H | Cl |
| 2 | $CH_2CF_3$ | $CH_2$ | Furan-4-yl | Br | Br | Br |
| 2 | $CH_2CH(CH_3)_2$ | $CH_2$ | Furan-5-yl | Br | H | Br |
| 2 | $CH_2C(CH_3)_3$ | $CH_2$ | Pyrrol-2-yl | I | I | I |
| 2 | $H_2C-C\equiv N$ | $CH_2$ | Pyrrol-3-yl | I | H | I |
| 3 | $H_2C-C\equiv CH$ | $CH_2$ | Pyrrol-4-yl | $CH_3$ | $CH_3$ | $CH_3$ |
| 3 | $CH(CH_3)_2$ | $CH_2$ | Pyrrol-5-yl | $CH_3$ | H | $CH_3$ |
| 3 | $CH_2CH_2OH$ | $CH_2$ | Thiophene-2-yl | $C_2H_5$ | $C_2H_5$ | $C_2H_5$ |
| 3 | $CH_2CH(CH_3)OH$ | $CH_2$ | Thiophene-3-yl | $C_2H_5$ | H | $C_2H_5$ |
| 3 | $CH(CH_3)CH_2OH$ | $CH_2$ | Thiophene-4-yl | $i-C_3H_7$ | $i-C_3H_7$ | $i-C_3H_7$ |
| 3 | $CH(CH_3)CH(CH_3)OH$ | $CH_2$ | Thiophene-5-yl | $i-C_3H_7$ | H | $i-C_3H_7$ |
| 2 | $C(CH_3)_2CH_2OH$ | CH—OH | Oxazol-2-yl | Cl | Cl | Cl |
| 2 | $CH_2C(CH_3)_2OH$ | CH—OH | Oxazol-4-yl | Cl | H | Cl |
| 2 | $CH_2CHF_2$ | CH—OH | Oxazol-5-yl | Br | Br | Br |
| 2 | $CH_2CF_3$ | CH—OH | Isoxazol-3-yl | Br | H | Br |
| 2 | $CH_2CH(CH_3)_2$ | CH—OH | Isoxazol-4-yl | I | I | I |
| 2 | $CH_2C(CH_3)_3$ | CH—OH | Isoxazol-5-yl | I | H | I |
| 3 | $H_2C-C\equiv N$ | CH—OH | Pyrazol-3-yl | $CH_3$ | $CH_3$ | $CH_3$ |
| 3 | $H_2C-C\equiv CH$ | CH—OH | Pyrazol-4-yl | $CH_3$ | H | $CH_3$ |
| 3 | $CH(CH_3)_2$ | CH—OH | Pyrazol-5-yl | $C_2H_5$ | $C_2H_5$ | $C_2H_5$ |
| 3 | $CH_2CH_2OH$ | CH—OH | Thiazol-2-yl | $C_2H_5$ | H | $C_2H_5$ |
| 3 | $CH_2CH(CH_3)OH$ | CH—OH | Thiazol-4-yl | $i-C_3H_7$ | $i-C_3H_7$ | $i-C_3H_7$ |

TABLE 2D-continued

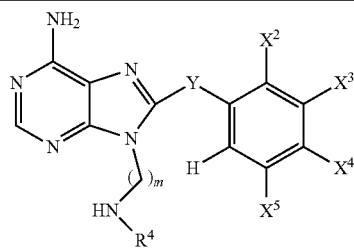

and pharmaceutically acceptable salts thereof, where:

| m | R⁴ | Y | X² | X³ | X⁴ | X⁵ |
|---|---|---|---|---|---|---|
| 3 | CH(CH₃)CH₂OH | CH—OH | Thiazol-5-yl | i-C₃H₇ | H | i-C₃H₇ |
| 2 | CH(CH₃)CH(CH₃)OH | CH—F | Furan-2-yl | Cl | Cl | Cl |
| 2 | C(CH₃)₂CH₂OH | CH—F | Furan-3-yl | Cl | H | Cl |
| 2 | CH₂C(CH₃)₂OH | CH—F | Furan-4-yl | Br | Br | Br |
| 2 | CH₂CHF₂ | CH—F | Furan-5-yl | Br | H | Br |
| 2 | CH₂CF₃ | CH—F | Pyrrol-2-yl | I | I | I |
| 2 | CH₂CH(CH₃)₂ | CH—F | Pyrrol-3-yl | I | H | I |
| 3 | CH₂C(CH₃)₃ | CH—F | Pyrrol-4-yl | CH₃ | CH₃ | CH₃ |
| 3 | H₂C—C≡N | CH—F | Pyrrol-5-yl | CH₃ | H | CH₃ |
| 3 | H₂C—C≡CH | CH—F | Thiophene-2-yl | C₂H₅ | C₂H₅ | C₂H₅ |
| 3 | CH(CH₃)₂ | CH—F | Thiophene-3-yl | C₂H₅ | H | C₂H₅ |
| 3 | CH₂CH₂OH | CH—F | Thiophene-4-yl | i-C₃H₇ | i-C₃H₇ | i-C₃H₇ |
| 3 | CH₂CH(CH₃)OH | CH—F | Thiophene-5-yl | i-C₃H₇ | H | i-C₃H₇ |
| 2 | CH(CH₃)CH₂OH | S | Oxazol-2-yl | H | Cl | H |
| 2 | CH(CH₃)CH(CH₃)OH | S═O | Oxazol-4-yl | H | H | Cl |
| 2 | C(CH₃)₂CH₂OH | O═S═O | Oxazol-5-yl | H | Cl | H |
| 2 | CH₂C(CH₃)₂OH | CH₂ | Isoxazol-3-yl | H | H | Cl |
| 2 | CH₂CHF₂ | C═O | Isoxazol-4-yl | H | I | H |
| 3 | CH₂CF₃ | C═S | Isoxazol-5-yl | H | H | I |
| 3 | CH₂CH(CH₃)₂ | CH—OH | Pyrazol-3-yl | H | Br | H |
| 3 | CH₂C(CH₃)₃ | CH—F | Pyrazol-4-yl | H | H | Br |
| 3 | H₂C—C≡N | O | Pyrazol-5-yl | Cl | H | Cl |
| 3 | H₂C—C≡CH | NH | Thiazol-2-yl | Cl | H | Cl |

TABLE 3

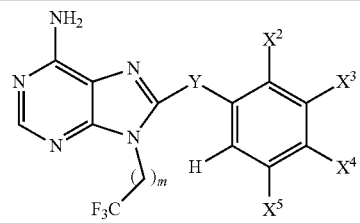

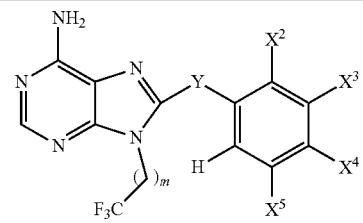

and pharmaceutically acceptable salts thereof, where:

| m | Y | X² | X³ | X⁴ | X⁵ |
|---|---|---|---|---|---|
| 2 | S | H | Cl | H | H |
| 2 | S | H | H | H | Cl |
| 2 | S | H | H | Cl | H |
| 2 | S | Cl | H | H | H |
| 2 | S | H | Br | H | H |
| 2 | S | H | H | H | Br |
| 3 | S | H | H | Br | H |
| 3 | S | Br | H | H | H |
| 3 | S | H | I | H | H |
| 3 | S | H | H | H | I |
| 3 | S | I | H | H | H |
| 4 | S | H | CH₃ | H | H |
| 4 | S | H | H | H | CH₃ |
| 4 | S | CH₃ | H | H | H |
| 4 | S | H | C₂H₅ | H | H |
| 4 | S | H | H | H | C₂H₅ |
| 5 | S | H | H | C₂H₅ | H |
| 5 | S | C₂H₅ | H | H | H |
| 5 | S | H | i-C₃H₇ | H | H |
| 5 | S | H | H | H | i-C₃H₇ |
| 5 | S | H | H | i-C₃H₇ | H |
| 5 | S | i-C₃H₇ | H | H | H |
| 2 | O | H | Cl | H | H |
| 2 | O | H | H | H | Cl |
| 2 | O | H | H | Cl | H |
| 2 | O | Cl | H | H | H |
| 2 | O | H | Br | H | H |
| 2 | O | H | H | H | Br |
| 3 | O | H | H | Br | H |
| 3 | O | Br | H | H | H |
| 3 | O | H | I | H | H |
| 3 | O | H | H | H | I |
| 3 | O | H | H | I | H |
| 3 | O | I | H | H | H |
| 4 | O | H | CH₃ | H | H |
| 4 | O | H | H | H | CH₃ |
| 4 | O | H | H | CH₃ | H |
| 4 | O | CH₃ | H | H | H |

TABLE 3-continued

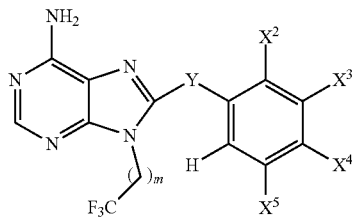

and pharmaceutically acceptable salts thereof, where:

| m | Y | $X^2$ | $X^3$ | $X^4$ | $X^5$ |
|---|---|---|---|---|---|
| 4 | O | H | $C_2H_5$ | H | H |
| 4 | O | H | H | H | $C_2H_5$ |
| 5 | O | H | H | $C_2H_5$ | H |
| 5 | O | $C_2H_5$ | H | H | H |
| 5 | O | H | $i\text{-}C_3H_7$ | H | H |
| 5 | O | H | H | H | $i\text{-}C_3H_7$ |
| 5 | O | H | H | $i\text{-}C_3H_7$ | H |
| 5 | O | $i\text{-}C_3H_7$ | H | H | H |
| 2 | S=O | H | Cl | H | H |
| 2 | S=O | H | H | H | Cl |
| 2 | S=O | H | H | Cl | H |
| 2 | S=O | Cl | H | H | H |
| 2 | S=O | H | Br | H | H |
| 2 | S=O | H | H | H | Br |
| 3 | S=O | H | H | Br | H |
| 3 | S=O | Br | H | H | H |
| 3 | S=O | H | I | H | H |
| 3 | S=O | H | H | H | I |
| 3 | S=O | H | H | I | H |
| 3 | S=O | I | H | H | H |
| 4 | S=O | H | $CH_3$ | H | H |
| 4 | S=O | H | H | H | $CH_3$ |
| 4 | S=O | H | H | $CH_3$ | H |
| 4 | S=O | $CH_3$ | H | H | H |
| 4 | S=O | H | $C_2H_5$ | H | H |
| 4 | S=O | H | H | H | $C_2H_5$ |
| 5 | S=O | H | H | $C_2H_5$ | H |
| 5 | S=O | $C_2H_5$ | H | H | H |
| 5 | S=O | H | $i\text{-}C_3H_7$ | H | H |
| 5 | S=O | H | H | H | $i\text{-}C_3H_7$ |
| 5 | S=O | H | H | $i\text{-}C_3H_7$ | H |
| 5 | S=O | $i\text{-}C_3H_7$ | H | H | H |
| 2 | O=S=O | H | Cl | H | H |
| 2 | O=S=O | H | H | H | Cl |
| 2 | O=S=O | H | H | Cl | H |
| 2 | O=S=O | Cl | H | H | H |
| 2 | O=S=O | H | Br | H | H |
| 2 | O=S=O | H | H | H | Br |
| 3 | O=S=O | H | H | Br | H |
| 3 | O=S=O | Br | H | H | H |
| 3 | O=S=O | H | I | H | H |
| 3 | O=S=O | H | H | H | I |
| 3 | O=S=O | H | H | I | H |
| 3 | O=S=O | I | H | H | H |
| 4 | O=S=O | H | $CH_3$ | H | H |
| 4 | O=S=O | H | H | H | $CH_3$ |
| 4 | O=S=O | H | H | $CH_3$ | H |
| 4 | O=S=O | $CH_3$ | H | H | H |
| 4 | O=S=O | H | $C_2H_5$ | H | H |
| 4 | O=S=O | H | H | H | $C_2H_5$ |
| 5 | O=S=O | H | H | $C_2H_5$ | H |
| 5 | O=S=O | $C_2H_5$ | H | H | H |
| 5 | O=S=O | H | $i\text{-}C_3H_7$ | H | H |
| 5 | O=S=O | H | H | H | $i\text{-}C_3H_7$ |
| 5 | O=S=O | H | H | $i\text{-}C_3H_7$ | H |
| 5 | O=S=O | $i\text{-}C_3H_7$ | H | H | H |
| 2 | NH | H | Cl | H | H |
| 2 | NH | H | H | H | Cl |
| 2 | NH | H | H | Cl | H |
| 2 | NH | Cl | H | H | H |
| 2 | NH | H | Br | H | H |
| 2 | NH | H | H | H | Br |
| 3 | NH | H | H | Br | H |
| 3 | NH | Br | H | H | H |
| 3 | NH | H | I | H | H |

TABLE 3-continued

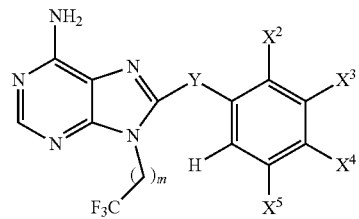

and pharmaceutically acceptable salts thereof, where:

| m | Y | $X^2$ | $X^3$ | $X^4$ | $X^5$ |
|---|---|---|---|---|---|
| 3 | NH | H | H | H | I |
| 3 | NH | H | H | I | H |
| 3 | NH | I | H | H | H |
| 4 | NH | H | $CH_3$ | H | H |
| 4 | NH | H | H | H | $CH_3$ |
| 4 | NH | H | H | $CH_3$ | H |
| 4 | NH | $CH_3$ | H | H | H |
| 4 | NH | H | $C_2H_5$ | H | H |
| 4 | NH | H | H | H | $C_2H_5$ |
| 5 | NH | H | H | $C_2H_5$ | H |
| 5 | NH | $C_2H_5$ | H | H | H |
| 5 | NH | H | $i\text{-}C_3H_7$ | H | H |
| 5 | NH | H | H | H | $i\text{-}C_3H_7$ |
| 5 | NH | H | H | $i\text{-}C_3H_7$ | H |
| 5 | NH | $i\text{-}C_3H_7$ | H | H | H |
| 2 | C=O | H | Cl | H | H |
| 2 | C=O | H | H | H | Cl |
| 2 | C=O | H | H | Cl | H |
| 2 | C=O | Cl | H | H | H |
| 2 | C=O | H | Br | H | H |
| 2 | C=O | H | H | H | Br |
| 3 | C=O | H | H | Br | H |
| 3 | C=O | Br | H | H | H |
| 3 | C=O | H | I | H | H |
| 3 | C=O | H | H | H | I |
| 3 | C=O | H | H | I | H |
| 3 | C=O | I | H | H | H |
| 4 | C=O | H | $CH_3$ | H | H |
| 4 | C=O | H | H | H | $CH_3$ |
| 4 | C=O | H | H | $CH_3$ | H |
| 4 | C=O | $CH_3$ | H | H | H |
| 4 | C=O | H | $C_2H_5$ | H | H |
| 4 | C=O | H | H | H | $C_2H_5$ |
| 5 | C=O | H | H | $C_2H_5$ | H |
| 5 | C=O | $C_2H_5$ | H | H | H |
| 5 | C=O | H | $i\text{-}C_3H_7$ | H | H |
| 5 | C=O | H | H | H | $i\text{-}C_3H_7$ |
| 5 | C=O | H | H | $i\text{-}C_3H_7$ | H |
| 5 | C=O | $i\text{-}C_3H_7$ | H | H | H |
| 2 | C=S | H | Cl | H | H |
| 2 | C=S | H | H | H | Cl |
| 2 | C=S | Cl | H | H | H |
| 2 | C=S | H | Br | H | H |
| 2 | C=S | H | H | H | Br |
| 3 | C=S | H | H | Br | H |
| 3 | C=S | Br | H | H | H |
| 3 | C=S | H | I | H | H |
| 3 | C=S | H | H | H | I |
| 3 | C=S | H | H | I | H |
| 3 | C=S | I | H | H | H |
| 4 | C=S | H | $CH_3$ | H | H |
| 4 | C=S | H | H | H | $CH_3$ |
| 4 | C=S | H | H | $CH_3$ | H |
| 4 | C=S | $CH_3$ | H | H | H |
| 4 | C=S | H | $C_2H_5$ | H | H |
| 4 | C=S | H | H | H | $C_2H_5$ |
| 5 | C=S | H | H | $C_2H_5$ | H |
| 5 | C=S | $C_2H_5$ | H | H | H |
| 5 | C=S | H | $i\text{-}C_3H_7$ | H | H |
| 5 | C=S | H | H | H | $i\text{-}C_3H_7$ |
| 5 | C=S | H | H | $i\text{-}C_3H_7$ | H |
| 5 | C=S | $i\text{-}C_3H_7$ | H | H | H |
| 2 | $CH_2$ | H | Cl | H | H |
| 2 | $CH_2$ | H | H | H | Cl |

TABLE 3-continued

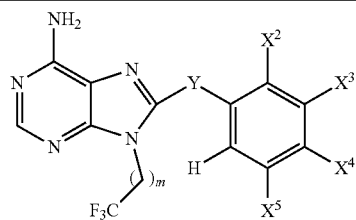

and pharmaceutically acceptable salts thereof, where:

| m | Y | $X^2$ | $X^3$ | $X^4$ | $X^5$ |
|---|---|---|---|---|---|
| 2 | $CH_2$ | H | H | Cl | H |
| 2 | $CH_2$ | Cl | H | H | H |
| 2 | $CH_2$ | H | Br | H | H |
| 2 | $CH_2$ | H | H | H | Br |
| 3 | $CH_2$ | H | H | Br | H |
| 3 | $CH_2$ | Br | H | H | H |
| 3 | $CH_2$ | H | I | H | H |
| 3 | $CH_2$ | H | H | H | I |
| 3 | $CH_2$ | H | H | I | H |
| 3 | $CH_2$ | I | H | H | H |
| 4 | $CH_2$ | H | $CH_3$ | H | H |
| 4 | $CH_2$ | H | H | H | $CH_3$ |
| 4 | $CH_2$ | H | H | $CH_3$ | H |
| 4 | $CH_2$ | $CH_3$ | H | H | H |
| 4 | $CH_2$ | H | $C_2H_5$ | H | H |
| 4 | $CH_2$ | H | H | H | $C_2H_5$ |
| 5 | $CH_2$ | H | H | $C_2H_5$ | H |
| 5 | $CH_2$ | $C_2H_5$ | H | H | H |
| 5 | $CH_2$ | H | i-$C_3H_7$ | H | H |
| 5 | $CH_2$ | H | H | H | i-$C_3H_7$ |
| 5 | $CH_2$ | H | H | i-$C_3H_7$ | H |
| 5 | $CH_2$ | i-$C_3H_7$ | H | H | H |
| 2 | CH—OH | H | Cl | H | H |
| 2 | CH—OH | H | H | H | Cl |
| 2 | CH—OH | H | H | Cl | H |
| 2 | CH—OH | Cl | H | H | H |
| 2 | CH—OH | H | Br | H | H |
| 2 | CH—OH | H | H | H | Br |
| 3 | CH—OH | H | H | Br | H |
| 3 | CH—OH | Br | H | H | H |
| 3 | CH—OH | H | I | H | H |
| 3 | CH—OH | H | H | H | I |
| 3 | CH—OH | H | H | I | H |
| 3 | CH—OH | I | H | H | H |
| 4 | CH—OH | H | $CH_3$ | H | H |
| 4 | CH—OH | H | H | H | $CH_3$ |
| 4 | CH—OH | H | H | $CH_3$ | H |
| 4 | CH—OH | $CH_3$ | H | H | H |
| 4 | CH—OH | H | $C_2H_5$ | H | H |
| 4 | CH—OH | H | H | H | $C_2H_5$ |
| 5 | CH—OH | H | H | $C_2H_5$ | H |
| 5 | CH—OH | $C_2H_5$ | H | H | H |
| 5 | CH—OH | H | i-$C_3H_7$ | H | H |
| 5 | CH—OH | H | H | H | i-$C_3H_7$ |
| 5 | CH—OH | H | H | i-$C_3H_7$ | H |
| 5 | CH—OH | i-$C_3H_7$ | H | H | H |
| 2 | CH—F | H | Cl | H | H |
| 2 | CH—F | H | H | H | Cl |
| 2 | CH—F | Cl | H | H | H |
| 2 | CH—F | H | Br | H | H |
| 2 | CH—F | H | H | H | Br |
| 3 | CH—F | H | H | Br | H |
| 3 | CH—F | Br | H | H | H |
| 3 | CH—F | H | I | H | H |
| 3 | CH—F | H | H | H | I |
| 3 | CH—F | I | H | H | H |
| 4 | CH—F | H | $CH_3$ | H | H |
| 4 | CH—F | H | H | H | $CH_3$ |
| 4 | CH—F | $CH_3$ | H | H | H |
| 4 | CH—F | H | $C_2H_5$ | H | H |
| 4 | CH—F | H | H | H | $C_2H_5$ |
| 5 | CH—F | H | H | $C_2H_5$ | H |
| 5 | CH—F | $C_2H_5$ | H | H | H |
| 5 | CH—F | H | i-$C_3H_7$ | H | H |
| 5 | CH—F | H | H | H | i-$C_3H_7$ |
| 5 | CH—F | H | H | i-$C_3H_7$ | H |
| 5 | CH—F | i-$C_3H_7$ | H | H | H |
| 2 | S | H | Cl | H | Cl |
| 2 | S | Cl | H | H | Cl |
| 2 | S | H | Br | H | Br |
| 2 | S | Br | H | Br | H |
| 2 | S | Br | H | H | Br |
| 3 | S | H | I | H | I |
| 3 | S | I | H | I | H |
| 3 | S | I | H | H | I |
| 3 | S | H | $CH_3$ | H | $CH_3$ |
| 3 | S | $CH_3$ | H | $CH_3$ | H |
| 3 | S | $CH_3$ | H | H | $CH_3$ |
| 4 | S | H | $C_2H_5$ | H | $C_2H_5$ |
| 4 | S | $C_2H_5$ | H | $C_2H_5$ | H |
| 4 | S | $C_2H_5$ | H | H | $C_2H_5$ |
| 4 | S | H | i-$C_3H_7$ | H | i-$C_3H_7$ |
| 4 | S | i-$C_3H_7$ | H | i-$C_3H_7$ | H |
| 4 | S | i-$C_3H_7$ | H | H | i-$C_3H_7$ |
| 5 | O | H | Cl | H | Cl |
| 5 | O | Cl | H | Cl | H |
| 5 | O | Cl | H | H | Cl |
| 5 | O | H | Br | H | Br |
| 5 | O | Br | H | Br | H |
| 5 | O | Br | H | H | Br |
| 2 | O | H | I | H | I |
| 2 | O | I | H | I | H |
| 2 | O | I | H | H | I |
| 2 | O | H | $CH_3$ | H | $CH_3$ |
| 2 | O | $CH_3$ | H | $CH_3$ | H |
| 2 | O | $CH_3$ | H | H | $CH_3$ |
| 3 | O | H | $C_2H_5$ | H | $C_2H_5$ |
| 3 | O | $C_2H_5$ | H | $C_2H_5$ | H |
| 3 | O | $C_2H_5$ | H | H | $C_2H_5$ |
| 3 | O | H | i-$C_3H_7$ | H | i-$C_3H_7$ |
| 3 | O | i-$C_3H_7$ | H | i-$C_3H_7$ | H |
| 3 | O | i-$C_3H_7$ | H | H | i-$C_3H_7$ |
| 4 | S=O | H | Cl | H | Cl |
| 4 | S=O | Cl | H | Cl | H |
| 4 | S=O | Cl | H | H | Cl |
| 4 | S=O | H | Br | H | Br |
| 4 | S=O | Br | H | Br | H |
| 4 | S=O | Br | H | H | Br |
| 5 | S=O | H | I | H | I |
| 5 | S=O | I | H | I | H |
| 5 | S=O | I | H | H | I |
| 5 | S=O | H | $CH_3$ | H | $CH_3$ |
| 5 | S=O | $CH_3$ | H | $CH_3$ | H |
| 5 | S=O | $CH_3$ | H | H | $CH_3$ |
| 2 | S=O | H | $C_2H_5$ | H | $C_2H_5$ |
| 2 | S=O | $C_2H_5$ | H | $C_2H_5$ | H |
| 2 | S=O | $C_2H_5$ | H | H | $C_2H_5$ |
| 2 | S=O | H | i-$C_3H_7$ | H | i-$C_3H_7$ |
| 2 | S=O | i-$C_3H_7$ | H | i-$C_3H_7$ | H |
| 2 | S=O | i-$C_3H_7$ | H | H | i-$C_3H_7$ |
| 3 | O=S=O | H | Cl | H | Cl |
| 3 | O=S=O | Cl | H | Cl | H |
| 3 | O=S=O | Cl | H | H | Cl |
| 3 | O=S=O | H | Br | H | Br |
| 3 | O=S=O | Br | H | Br | H |
| 3 | O=S=O | Br | H | H | Br |

TABLE 3-continued

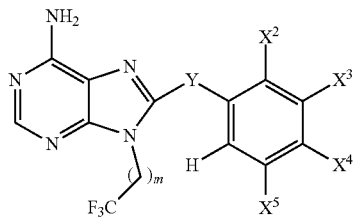

and pharmaceutically acceptable salts thereof, where:

| m | Y | $X^2$ | $X^3$ | $X^4$ | $X^5$ |
|---|---|---|---|---|---|
| 4 | O=S=O | H | I | H | I |
| 4 | O=S=O | I | H | I | H |
| 4 | O=S=O | I | H | H | I |
| 4 | O=S=O | H | $CH_3$ | H | $CH_3$ |
| 4 | O=S=O | $CH_3$ | H | $CH_3$ | H |
| 4 | O=S=O | $CH_3$ | H | H | $CH_3$ |
| 5 | O=S=O | H | $C_2H_5$ | H | $C_2H_5$ |
| 5 | O=S=O | $C_2H_5$ | H | $C_2H_5$ | H |
| 5 | O=S=O | $C_2H_5$ | H | H | $C_2H_5$ |
| 5 | O=S=O | H | $i-C_3H_7$ | H | $i-C_3H_7$ |
| 5 | O=S=O | $i-C_3H_7$ | H | $i-C_3H_7$ | H |
| 5 | O=S=O | $i-C_3H_7$ | H | H | $i-C_3H_7$ |
| 2 | NH | H | Cl | H | Cl |
| 2 | NH | Cl | H | Cl | H |
| 2 | NH | Cl | H | H | Cl |
| 2 | NH | H | Br | H | Br |
| 2 | NH | Br | H | Br | H |
| 2 | NH | Br | H | H | Br |
| 2 | NH | H | I | H | I |
| 3 | NH | I | H | I | H |
| 3 | NH | I | H | H | I |
| 3 | NH | H | $CH_3$ | H | $CH_3$ |
| 3 | NH | $CH_3$ | H | $CH_3$ | H |
| 3 | NH | $CH_3$ | H | H | $CH_3$ |
| 3 | NH | H | $C_2H_5$ | H | $C_2H_5$ |
| 4 | NH | $C_2H_5$ | H | $C_2H_5$ | H |
| 4 | NH | $C_2H_5$ | H | H | $C_2H_5$ |
| 4 | NH | H | $i-C_3H_7$ | H | $i-C_3H_7$ |
| 4 | NH | $i-C_3H_7$ | H | $i-C_3H_7$ | H |
| 4 | NH | $i-C_3H_7$ | H | H | $i-C_3H_7$ |
| 4 | C=O | H | Cl | H | Cl |
| 5 | C=O | Cl | H | Cl | H |
| 5 | C=O | Cl | H | H | Cl |
| 5 | C=O | H | Br | H | Br |
| 5 | C=O | Br | H | Br | H |
| 5 | C=O | Br | H | H | Br |
| 2 | C=O | H | I | H | I |
| 2 | C=O | I | H | I | H |
| 2 | C=O | I | H | H | I |
| 2 | C=O | H | $CH_3$ | H | $CH_3$ |
| 2 | C=O | $CH_3$ | H | $CH_3$ | H |
| 2 | C=O | $CH_3$ | H | H | $CH_3$ |
| 3 | C=O | H | $C_2H_5$ | H | $C_2H_5$ |
| 3 | C=O | $C_2H_5$ | H | $C_2H_5$ | H |
| 3 | C=O | $C_2H_5$ | H | H | $C_2H_5$ |
| 3 | C=O | H | $i-C_3H_7$ | H | $i-C_3H_7$ |
| 3 | C=O | $i-C_3H_7$ | H | $i-C_3H_7$ | H |
| 3 | C=O | $i-C_3H_7$ | H | H | $i-C_3H_7$ |
| 4 | C=S | H | Cl | H | Cl |
| 4 | C=S | Cl | H | Cl | H |
| 4 | C=S | Cl | H | H | Cl |
| 4 | C=S | H | Br | H | Br |
| 4 | C=S | Br | H | Br | H |
| 4 | C=S | Br | H | H | Br |
| 5 | C=S | H | I | H | I |
| 5 | C=S | I | H | I | H |
| 5 | C=S | I | H | H | I |
| 5 | C=S | H | $CH_3$ | H | $CH_3$ |
| 5 | C=S | $CH_3$ | H | $CH_3$ | H |
| 5 | C=S | $CH_3$ | H | H | $CH_3$ |
| 2 | C=S | H | $C_2H_5$ | H | $C_2H_5$ |
| 2 | C=S | $C_2H_5$ | H | $C_2H_5$ | H |
| 2 | C=S | $C_2H_5$ | H | H | $C_2H_5$ |
| 2 | C=S | H | $i-C_3H_7$ | H | $i-C_3H_7$ |
| 2 | C=S | $i-C_3H_7$ | H | $i-C_3H_7$ | H |

TABLE 3-continued

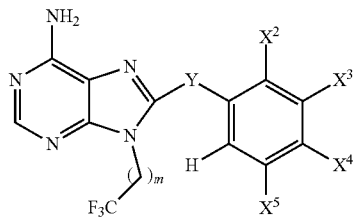

and pharmaceutically acceptable salts thereof, where:

| m | Y | $X^2$ | $X^3$ | $X^4$ | $X^5$ |
|---|---|---|---|---|---|
| 2 | C=S | $i-C_3H_7$ | H | H | $i-C_3H_7$ |
| 3 | $CH_2$ | H | Cl | H | Cl |
| 3 | $CH_2$ | Cl | H | Cl | H |
| 3 | $CH_2$ | Cl | H | H | Cl |
| 3 | $CH_2$ | H | Br | H | Br |
| 3 | $CH_2$ | Br | H | Br | H |
| 3 | $CH_2$ | Br | H | H | Br |
| 4 | $CH_2$ | H | I | H | I |
| 4 | $CH_2$ | I | H | I | H |
| 4 | $CH_2$ | I | H | H | I |
| 4 | $CH_2$ | H | $CH_3$ | H | $CH_3$ |
| 4 | $CH_2$ | $CH_3$ | H | $CH_3$ | H |
| 4 | $CH_2$ | $CH_3$ | H | H | $CH_3$ |
| 5 | $CH_2$ | H | $C_2H_5$ | H | $C_2H_5$ |
| 5 | $CH_2$ | $C_2H_5$ | H | $C_2H_5$ | H |
| 5 | $CH_2$ | $C_2H_5$ | H | H | $C_2H_5$ |
| 5 | $CH_2$ | H | $i-C_3H_7$ | H | $i-C_3H_7$ |
| 5 | $CH_2$ | $i-C_3H_7$ | H | $i-C_3H_7$ | H |
| 5 | $CH_2$ | $i-C_3H_7$ | H | H | $i-C_3H_7$ |
| 2 | CH—OH | H | Cl | H | Cl |
| 2 | CH—OH | Cl | H | Cl | H |
| 2 | CH—OH | Cl | H | H | Cl |
| 2 | CH—OH | H | Br | H | Br |
| 2 | CH—OH | Br | H | Br | H |
| 2 | CH—OH | Br | H | H | Br |
| 3 | CH—OH | H | I | H | I |
| 3 | CH—OH | I | H | I | H |
| 3 | CH—OH | I | H | H | I |
| 3 | CH—OH | H | $CH_3$ | H | $CH_3$ |
| 3 | CH—OH | $CH_3$ | H | $CH_3$ | H |
| 3 | CH—OH | $CH_3$ | H | H | $CH_3$ |
| 4 | CH—OH | H | $C_2H_5$ | H | $C_2H_5$ |
| 4 | CH—OH | $C_2H_5$ | H | $C_2H_5$ | H |
| 4 | CH—OH | $C_2H_5$ | H | H | $C_2H_5$ |
| 4 | CH—OH | H | $i-C_3H_7$ | H | $i-C_3H_7$ |
| 4 | CH—OH | $i-C_3H_7$ | H | $i-C_3H_7$ | H |
| 4 | CH—OH | $i-C_3H_7$ | H | H | $i-C_3H_7$ |
| 5 | CH—F | H | Cl | H | Cl |
| 5 | CH—F | Cl | H | Cl | H |
| 5 | CH—F | Cl | H | H | Cl |
| 5 | CH—F | H | Br | H | Br |
| 5 | CH—F | Br | H | Br | H |
| 5 | CH—F | Br | H | H | Br |
| 2 | CH—F | H | I | H | I |
| 2 | CH—F | I | H | I | H |
| 2 | CH—F | I | H | H | I |
| 2 | CH—F | H | $CH_3$ | H | $CH_3$ |
| 2 | CH—F | $CH_3$ | H | $CH_3$ | H |
| 2 | CH—F | $CH_3$ | H | H | $CH_3$ |
| 3 | CH—F | H | $C_2H_5$ | H | $C_2H_5$ |
| 3 | CH—F | $C_2H_5$ | H | $C_2H_5$ | H |
| 3 | CH—F | $C_2H_5$ | H | H | $C_2H_5$ |
| 3 | CH—F | H | $i-C_3H_7$ | H | $i-C_3H_7$ |
| 3 | CH—F | $i-C_3H_7$ | H | $i-C_3H_7$ | H |
| 3 | CH—F | $i-C_3H_7$ | H | H | $i-C_3H_7$ |
| 4 | S | H | Cl | Cl | Cl |
| 4 | S | Cl | Cl | H | Cl |
| 4 | S | H | Br | Br | Br |
| 4 | S | Br | Br | H | Br |
| 4 | S | H | I | I | I |
| 4 | S | I | I | H | I |
| 5 | S | H | $CH_3$ | $CH_3$ | $CH_3$ |
| 5 | S | $CH_3$ | $CH_3$ | H | $CH_3$ |
| 5 | S | H | $C_2H_5$ | $C_2H_5$ | $C_2H_5$ |
| 5 | S | $C_2H_5$ | $C_2H_5$ | H | $C_2H_5$ |

TABLE 3-continued

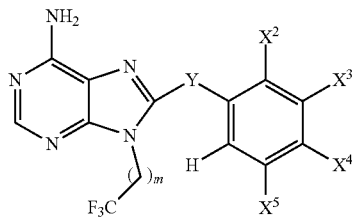

and pharmaceutically acceptable salts thereof, where:

| m | Y | $X^2$ | $X^3$ | $X^4$ | $X^5$ |
|---|---|---|---|---|---|
| 5 | S | H | i-$C_3H_7$ | i-$C_3H_7$ | i-$C_3H_7$ |
| 5 | S | i-$C_3H_7$ | i-$C_3H_7$ | H | i-$C_3H_7$ |
| 2 | O | H | Cl | Cl | Cl |
| 2 | O | Cl | Cl | H | Cl |
| 2 | O | H | Br | Br | Br |
| 2 | O | Br | Br | H | Br |
| 2 | O | H | I | I | I |
| 2 | O | I | I | H | I |
| 3 | O | H | $CH_3$ | $CH_3$ | $CH_3$ |
| 3 | O | $CH_3$ | $CH_3$ | H | $CH_3$ |
| 3 | O | H | $C_2H_5$ | $C_2H_5$ | $C_2H_5$ |
| 3 | O | $C_2H_5$ | $C_2H_5$ | H | $C_2H_5$ |
| 3 | O | H | i-$C_3H_7$ | i-$C_3H_7$ | i-$C_3H_7$ |
| 3 | O | i-$C_3H_7$ | i-$C_3H_7$ | H | i-$C_3H_7$ |
| 4 | S=O | H | Cl | Cl | Cl |
| 4 | S=O | Cl | Cl | H | Cl |
| 4 | S=O | H | Br | Br | Br |
| 4 | S=O | Br | Br | H | Br |
| 4 | S=O | H | I | I | I |
| 4 | S=O | I | I | H | I |
| 5 | S=O | H | $CH_3$ | $CH_3$ | $CH_3$ |
| 5 | S=O | $CH_3$ | $CH_3$ | H | $CH_3$ |
| 5 | S=O | H | $C_2H_5$ | $C_2H_5$ | $C_2H_5$ |
| 5 | S=O | $C_2H_5$ | $C_2H_5$ | H | $C_2H_5$ |
| 5 | S=O | H | i-$C_3H_7$ | i-$C_3H_7$ | i-$C_3H_7$ |
| 5 | S=O | i-$C_3H_7$ | i-$C_3H_7$ | H | i-$C_3H_7$ |
| 2 | O=S=O | H | Cl | Cl | Cl |
| 2 | O=S=O | Cl | Cl | H | Cl |
| 2 | O=S=O | H | Br | Br | Br |
| 2 | O=S=O | Br | Br | H | Br |
| 2 | O=S=O | H | I | I | I |
| 2 | O=S=O | I | I | H | I |
| 3 | O=S=O | H | $CH_3$ | $CH_3$ | $CH_3$ |
| 3 | O=S=O | $CH_3$ | $CH_3$ | H | $CH_3$ |
| 3 | O=S=O | H | $C_2H_5$ | $C_2H_5$ | $C_2H_5$ |
| 3 | O=S=O | $C_2H_5$ | $C_2H_5$ | H | $C_2H_5$ |
| 3 | O=S=O | H | i-$C_3H_7$ | i-$C_3H_7$ | i-$C_3H_7$ |
| 3 | O=S=O | i-$C_3H_7$ | i-$C_3H_7$ | H | i-$C_3H_7$ |
| 4 | NH | H | Cl | Cl | Cl |
| 4 | NH | Cl | Cl | H | Cl |
| 4 | NH | H | Br | Br | Br |
| 4 | NH | Br | Br | H | Br |
| 4 | NH | H | I | I | I |
| 4 | NH | I | I | H | I |
| 5 | NH | H | $CH_3$ | $CH_3$ | $CH_3$ |
| 5 | NH | $CH_3$ | $CH_3$ | H | $CH_3$ |
| 5 | NH | H | $C_2H_5$ | $C_2H_5$ | $C_2H_5$ |
| 5 | NH | $C_2H_5$ | $C_2H_5$ | H | $C_2H_5$ |
| 5 | NH | H | i-$C_3H_7$ | i-$C_3H_7$ | i-$C_3H_7$ |
| 5 | NH | i-$C_3H_7$ | i-$C_3H_7$ | H | i-$C_3H_7$ |
| 2 | C=O | H | Cl | Cl | Cl |
| 2 | C=O | Cl | Cl | H | Cl |
| 2 | C=O | H | Br | Br | Br |
| 2 | C=O | Br | Br | H | Br |
| 2 | C=O | H | I | I | I |
| 2 | C=O | I | I | H | I |
| 3 | C=O | H | $CH_3$ | $CH_3$ | $CH_3$ |
| 3 | C=O | $CH_3$ | $CH_3$ | H | $CH_3$ |
| 3 | C=O | H | $C_2H_5$ | $C_2H_5$ | $C_2H_5$ |
| 3 | C=O | $C_2H_5$ | $C_2H_5$ | H | $C_2H_5$ |
| 3 | C=O | H | i-$C_3H_7$ | i-$C_3H_7$ | i-$C_3H_7$ |
| 3 | C=O | i-$C_3H_7$ | i-$C_3H_7$ | H | i-$C_3H_7$ |
| 4 | C=S | H | Cl | Cl | Cl |
| 4 | C=S | Cl | Cl | H | Cl |
| 4 | C=S | H | Br | Br | Br |
| 4 | C=S | Br | Br | H | Br |
| 4 | C=S | H | I | I | I |
| 4 | C=S | I | I | H | I |
| 5 | C=S | H | $CH_3$ | $CH_3$ | $CH_3$ |
| 5 | C=S | $CH_3$ | $CH_3$ | H | $CH_3$ |
| 5 | C=S | H | $C_2H_5$ | $C_2H_5$ | $C_2H_5$ |
| 5 | C=S | $C_2H_5$ | $C_2H_5$ | H | $C_2H_5$ |
| 5 | C=S | H | i-$C_3H_7$ | i-$C_3H_7$ | i-$C_3H_7$ |
| 5 | C=S | i-$C_3H_7$ | i-$C_3H_7$ | H | i-$C_3H_7$ |
| 2 | $CH_2$ | H | Cl | Cl | Cl |
| 2 | $CH_2$ | Cl | Cl | H | Cl |
| 2 | $CH_2$ | H | Br | Br | Br |
| 2 | $CH_2$ | Br | Br | H | Br |
| 2 | $CH_2$ | H | I | I | I |
| 2 | $CH_2$ | I | I | H | I |
| 3 | $CH_2$ | H | $CH_3$ | $CH_3$ | $CH_3$ |
| 3 | $CH_2$ | $CH_3$ | $CH_3$ | H | $CH_3$ |
| 3 | $CH_2$ | H | $C_2H_5$ | $C_2H_5$ | $C_2H_5$ |
| 3 | $CH_2$ | $C_2H_5$ | $C_2H_5$ | H | $C_2H_5$ |
| 3 | $CH_2$ | H | i-$C_3H_7$ | i-$C_3H_7$ | i-$C_3H_7$ |
| 3 | $CH_2$ | i-$C_3H_7$ | i-$C_3H_7$ | H | i-$C_3H_7$ |
| 4 | CH—OH | H | Cl | Cl | Cl |
| 4 | CH—OH | Cl | Cl | H | Cl |
| 4 | CH—OH | H | Br | Br | Br |
| 4 | CH—OH | Br | Br | H | Br |
| 4 | CH—OH | H | I | I | I |
| 4 | CH—OH | I | I | H | I |
| 5 | CH—OH | H | $CH_3$ | $CH_3$ | $CH_3$ |
| 5 | CH—OH | $CH_3$ | $CH_3$ | H | $CH_3$ |
| 5 | CH—OH | H | $C_2H_5$ | $C_2H_5$ | $C_2H_5$ |
| 5 | CH—OH | $C_2H_5$ | $C_2H_5$ | H | $C_2H_5$ |
| 5 | CH—OH | H | i-$C_3H_7$ | i-$C_3H_7$ | i-$C_3H_7$ |
| 5 | CH—OH | i-$C_3H_7$ | i-$C_3H_7$ | H | i-$C_3H_7$ |
| 2 | CH—F | H | Cl | Cl | Cl |
| 2 | CH—F | Cl | Cl | H | Cl |
| 2 | CH—F | H | Br | Br | Br |
| 2 | CH—F | Br | Br | H | Br |
| 2 | CH—F | H | I | I | I |
| 2 | CH—F | I | I | H | I |
| 3 | CH—F | H | $CH_3$ | $CH_3$ | $CH_3$ |
| 3 | CH—F | $CH_3$ | $CH_3$ | H | $CH_3$ |
| 3 | CH—F | H | $C_2H_5$ | $C_2H_5$ | $C_2H_5$ |
| 3 | CH—F | $C_2H_5$ | $C_2H_5$ | H | $C_2H_5$ |
| 3 | CH—F | H | i-$C_3H_7$ | i-$C_3H_7$ | i-$C_3H_7$ |
| 3 | CH—F | i-$C_3H_7$ | i-$C_3H_7$ | H | i-$C_3H_7$ |
| 4 | S | I | H | Cl | H |
| 4 | S=O | I | H | H | Cl |
| 4 | O=S=O | Br | H | Cl | H |
| 4 | $CH_2$ | Br | H | H | Cl |
| 4 | C=O | Br | H | I | H |
| 4 | C=S | Br | H | H | I |
| 5 | CH—OH | I | H | Br | H |
| 5 | CH—F | I | H | H | Br |
| 5 | O | I | Cl | H | Cl |
| 5 | NH | Br | Cl | H | Cl |

5.3.2 Grp94 Inhibitors of Formula (II)

In one aspect, the disclosure encompasses purine-scaffold compounds that are substituted at the 8-position with a linker group bonded to a 2,4,6-tri-substituted aryl group and are further substituted at the N-9 position. Such compounds are represented schematically in Formula (II):

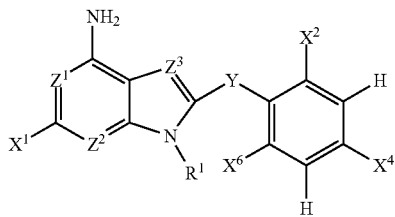 (II)

or a pharmaceutically acceptable salt thereof, wherein:

(a) Y is —C(R$^Y$)$_2$—, —S—, —NR—, —O—,

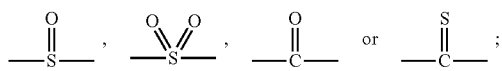

(b) each of $Z^1$ and $Z^3$ are independently —CH— or —N—;

(c) $Z^2$ is —N— or —CR$^{10}$—, wherein R$^{10}$ is H or unsubstituted or substituted —(C$_1$-C$_6$)aliphatic;

(d) $X^1$ is —H, -halo, —N(R)$_2$, —OR, —CN, or unsubstituted or substituted —(C$_1$-C$_6$)aliphatic;

(e) each of $X^2$, $X^4$, and $X^6$ are independently —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered)arylalkyl, and (5- or 6-membered)heterocyclic aromatic or heterocyclic non-aromatic group;

(f) R$^1$ is —(C$_1$-C$_6$)aliphatic-N$^+$—(R$^2$)(R$^3$)(R$^4$), —(C$_1$-C$_6$)aliphatic-N—R$^3$R$^4$, —(C$_1$-C$_6$)aliphatic-C(=O)N—R$^3$R$^4$, —(C$_1$-C$_6$)aliphatic-R$^3$R$^4$, —(C$_1$-C$_6$)aliphatic-R$^2$R$^3$R$^4$, —(C$_1$-C$_6$)aliphatic-N—CR$^2$R$^3$R$^4$, —(C$_1$-C$_6$)aliphatic-C(halo)$_3$, —(C$_1$-C$_6$)aliphatic-alkenyl, —(C$_1$-C$_6$)aliphatic-alkynyl, —(C$_1$-C$_6$)aliphatic-(C$_3$-C$_8$)cycloalkyl, —(C$_1$-C$_6$)aliphatic-(C$_3$-C$_8$)heterocycloalkyl, —(C$_1$-C$_6$)aliphatic-phenyl, —(C$_1$-C$_6$)aliphatic-(5 or 6-membered)heteroaryl, —(C$_1$-C$_6$)aliphatic-cyano, with the proviso that when all of R$^2$-R$^4$ are present the compound further comprises a pharmaceutically acceptable counter ion;

(g) R$^2$ and R$^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$) aliphatic, or R$^3$ and R$^4$ form an unsubstituted or substituted 3- to 7-membered heterocyclic ring when taken together with the nitrogen to which they are attached;

(h) each R$^Y$ is independently R, —OR, or halo;

(i) R$^4$ is hydrogen, halogen, or unsubstituted or substituted —(C$_1$-C$_6$)aliphatic; and (j) each R is independently hydrogen, unsubstituted C$_{1-6}$ aliphatic, or C$_{1-6}$ aliphatic substituted with halo, —OH, —CN, or —NH$_2$;

wherein each substituted group is substituted with one or more groups selected from halo, —N(R)$_2$, —OR, —CN, oxo, unsubstituted C$_{1-6}$ aliphatic, or C$_{1-6}$ aliphatic substituted with halo, —OH, —CN, or —NH$_2$.

In some embodiments, a compound of formula (II) or pharmaceutically acceptable salt thereof is defined wherein:

(a) Y is —CH$_2$—, —S—, —NH—, —O—,

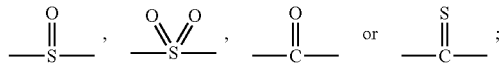

(b) each of $Z^1$ and $Z^3$ are independently —CH— or —N—;

(c) $Z^2$ is —CH—, —N—, or —CR$^{10}$—, wherein R$^{10}$ is —(C$_1$-C$_6$)alkyl;

(d) $X^1$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, or —OCH$_2$(halo);

(e) each of $X^2$, $X^4$ and $X^6$ are independently —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, —OCH$_2$(halo), or a (5- or 6-membered)aryl, heterocyclic aromatic, or non-aromatic group selected from pyridyl, furyl, thiophenyl, pyrrolyl, oxazolyl, imidazolyl, phenyl, benzyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl;

(f) R$^1$ is —(CH$_2$)$_m$—N$^+$—(R$^2$)(R$^3$)(R$^4$), —(CH$_2$)$_m$—N—R$^3$R$^4$, —(CH$_2$)$_m$—C(=O)N—R$^3$R$^4$, —(CH$_2$)$_m$—R$^3$R$^4$, —(CH$_2$)$_m$—C(halo)$_3$, —(CH$_2$)$_m$-alkenyl, —(CH$_2$)$_m$-alkenyl-CH$_3$, —(CH$_2$)$_m$-alkynyl, —(CH$_2$)$_m$-alkynyl-CH$_3$, —(CH$_2$)$_m$—(C$_3$-C$_8$)cycloalkyl, —(CH$_2$)$_m$—(C$_3$-C$_8$)heterocycloalkyl, —(CH$_2$)$_m$-phenyl, —(CH$_2$)$_m$-(5 or 6-membered)heteroaryl, —(CH$_2$)$_m$-cyano, where m is 1, 2, 3, 4 or 5 and where the cyloalkyl, heterocycle or phenyl is unsubstituted or substituted with one or more $X^1$ groups, with the proviso that when all of R$^2$-R$^4$ are present the compound further comprises a pharmaceutically acceptable counter ion;

(g) R$^2$ and R$^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —CH$_2$(halo), —CH$_2$C(halo)$_3$, —CHCH(halo)$_2$, CHCH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)CH$_2$OH, —CH(CH$_3$)CH(OH)R$^4$, —CH$_2$CH(OH)R$^4$, —CH$_2$SO$_2$NHR$^4$, —CH$_2$SO$_2$NHR4, or R$^2$ and R$^3$ form an unsubstituted or substituted aziridine, azetidine, pyrrolidine, piperazine, or piperidine ring when taken together with the nitrogen to which they are attached; and (h) R$^4$ is hydrogen, methyl, ethyl, isopropyl, t-butyl, isobutyl, or —C(halo)$_3$.

In one embodiment, $Z^1$, $Z^2$ and $Z^3$ are —N—. In another embodiment, $Z^1$ and $Z^3$ are —N— and $Z^2$ is —CH—. In another embodiment, $Z^1$ is —CH— and $Z^2$ and $Z^3$ are —N—.

In another embodiment, Y is —S—, —CH$_2$—, or

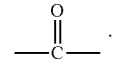

In another embodiment, Y is S or

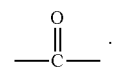

In another embodiment, Y is —S— or —CH$_2$—. In another embodiment, Y is —S— or —O—. In another embodiment, Y is —S—. In another embodiment, Y is —CH$_2$—. In another embodiment, Y is

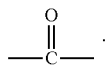

In some embodiments, Y is —C(R$^Y$)$_2$—, wherein each R$^Y$ is independently hydrogen, —OH, or halo.

In certain embodiment, R$^1$ is —(CH$_2$)$_m$—N—(R$^3$)(R$^4$). In one such embodiment, R$^1$ is —(CH$_2$)$_2$—N—(R$^3$)(R$^4$). In another such embodiment, R$^1$ is —(CH$_2$)$_3$—N—(R$^3$)(R$^4$). In another such embodiment, R$^1$ is —(CH$_2$)$_2$—N—(R$^3$)(R$^4$), R$^3$ is H and R$^4$ is isopropyl or isobutyl. In another such embodiment, R$^1$ is —(CH$_2$)$_2$—N—(R$^3$)(R$^4$), R$^3$ is —H and R$^4$ is isopropyl. In another such embodiment, R$^1$ is —(CH$_2$)$_3$—N—(R$^3$)(R$^4$), R$^3$ is —H and R$^4$ is isobutyl. In another such embodiment, R$^1$ is —(CH$_2$)$_3$—N—(R$^3$)(R$^4$), R$^3$ is —H and R$^4$ is isopropyl. It will be understood, that in these embodiments, the amine functionality may exist as a free base or as an acid addition salt. Acid addition salts can be prepared by addition of a suitable acid, as is well understood in the art. In particular embodiments, the acid addition salt may be a hydrochloride salt, a phosphate salt, a sulfate salt, a lactate salt, a citrate salt, a succinate salt, a mesylate salt, a tartrate salt, a lactobionate salt, a benzene sulfonic acid salt, a para-toluenesulfonic acid salt, or a fumaric acid-salt. In another embodiment, the acid addition salt is a hydrochloride salt or a sulfate salt. In another embodiment, the acid addition salt is a hydrochloride salt. In another embodiment, the acid addition salt is a sulfate salt. In another embodiment, the acid addition salt is a phosphate salt.

In certain embodiments, R$^1$ is —(CH$_2$)$_m$—CF$_3$. In one such embodiment, R$^1$ is —(CH$_2$)$_3$—CF$_3$. In another such embodiment, R$^1$ is —(CH$_2$)$_4$—CF$_3$.

In some embodiments, R$^1$ is is —(CH$_2$)$_3$—CCH.

In some embodiments, R$^2$ or R$^3$ is —CH$_2$NHSO$_2$R$^4$.

In some embodiments, R$^2$ and R$^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —CH$_2$(halo), —CH$_2$C(halo)$_3$, —CHCH(halo)$_2$, CHCH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)CH$_2$OH, —CH(CH$_3$)CH(OH)R$^4$, —CH$_2$CH(OH)R$^4$, —CH$_2$SO$_2$NHR$^4$, —CH$_2$NHSO$_2$R$^4$ or R$^2$ and R$^3$ form an unsubstituted or substituted aziridine, azetidine, pyrrolidine, piperazine, or piperidine ring when taken together with the nitrogen to which they are attached.

In other embodiments, the Grp94 inhibitors of Formula (II) have one of the Formula of Table 4, wherein each substituent is as defined above and described in classes and subclasses herein, both singly and in combination.

TABLE 4

| Formula | Compound |
|---|---|
| IIA | (structure) |
| IIB | (structure) |
| IIC | (structure) |
| IID | (structure) |
| IIE | (structure) |
| IIF | (structure) |
| IIG | (structure) |
| IIH | (structure) |

TABLE 4-continued

| Formula | Compound |
|---------|----------|
| III | (adenine-purine with C(=S) linker to phenyl with X², X⁴, X⁶, H substituents; N9-R¹) |
| IIJ | (adenine-purine with CHF linker to phenyl with X², X⁴, X⁶, H substituents; N9-R¹) |
| IIK | (adenine-purine with S linker to phenyl with X², X⁴, X⁶, H substituents; N9-R¹) |
| IIL | (adenine-purine with CH₂ linker to phenyl with X², X⁴, X⁶, H substituents; N9-R¹) |
| IIM | (adenine-purine with C(=O) linker to phenyl with X², X⁴, X⁶, H substituents; N9-R¹) |
| IIN | (adenine-purine with O linker to phenyl with X², X⁴, X⁶, H substituents; N9-R¹) |
| IIO | (adenine-purine with S(=O) linker to phenyl with X², X⁴, X⁶, H substituents; N9-R¹) |
| IIP | (adenine-purine with S(=O)₂ linker to phenyl with X², X⁴, X⁶, H substituents; N9-R¹) |
| IIQ | (adenine-purine with NH linker to phenyl with X², X⁴, X⁶, H substituents; N9-R¹) |
| IIR | (adenine-purine with CH(OH) linker to phenyl with X², X⁴, X⁶, H substituents; N9-R¹) |
| IIS | (adenine-purine with C(=S) linker to phenyl with X², X⁴, X⁶, H substituents; N9-R¹) |
| IIT | (adenine-purine with CHF linker to phenyl with X², X⁴, X⁶, H substituents; N9-R¹) |

Illustrative compounds of Formula (II) are listed below in Table 5.

TABLE 5

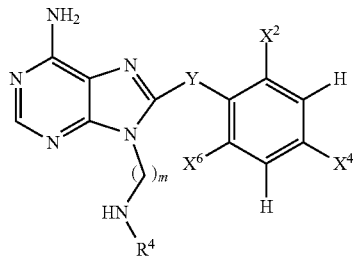

and pharmaceutically acceptable salts thereof, where:

| m | R⁴ | Y | X² | X⁴ | X⁶ |
|---|----|----|----|----|----|
| 2 | CH(CH₃)₂ | S | Cl | Cl | Cl |
| 2 | CH₂CH₂OH | S | CH₃ | CH₃ | CH₃ |
| 2 | CH₂CH(CH₃)OH | S | C₂H₅ | C₂H₅ | C₂H₅ |
| 2 | CH(CH₃)CH₂OH | S | i-C₃H₇ | i-C₃H₇ | i-C₃H₇ |
| 2 | CH(CH₃)CH(CH₃)OH | S | CH₃ | Cl | Cl |
| 2 | C(CH₃)₂CH₂OH | S | CH₃ | CH₃ | Cl |
| 2 | CH₂C(CH₃)₂OH | S | CH₃ | Cl | CH₃ |
| 2 | CH₂CHF₂ | S | C₂H₅ | Cl | Cl |
| 2 | CH₂CF₃ | S | C₂H₅ | C₂H₅ | Cl |
| 3 | CH₂CH(CH₃)₂ | S | C₂H₅ | Cl | C₂H₅ |
| 3 | CH₂C(CH₃)₃ | S | CH₃ | Br | Br |
| 3 | H₂C—C≡N | S | CH₃ | CH₃ | Br |
| 3 | H₂C—C≡CH | S | CH₃ | Br | CH₃ |
| 3 | CH(CH₃)₂ | S | C₂H₅ | I | I |
| 3 | CH₂CH₂OH | S | C₂H₅ | C₂H₅ | I |
| 3 | CH₂CH(CH₃)OH | S | C₂H₅ | I | C₂H₅ |
| 3 | CH(CH₃)CH₂OH | S | C₂H₅ | Br | Cl |
| 3 | CH(CH₃)CH(CH₃)OH | S | C₂H₅ | C₂H₅ | Br |
| 3 | C(CH₃)₂CH₂OH | S | C₂H₅ | Br | C₂H₅ |
| 2 | CH₂C(CH₃)₂OH | S=O | Cl | Cl | Cl |
| 2 | CH₂CHF₂ | S=O | CH₃ | CH₃ | CH₃ |
| 2 | CH₂CF₃ | S=O | C₂H₅ | C₂H₅ | C₂H₅ |
| 2 | CH₂CH(CH₃)₂ | S=O | i-C₃H₇ | i-C₃H₇ | i-C₃H₇ |
| 2 | CH₂C(CH₃)₃ | S=O | CH₃ | Cl | Cl |
| 2 | H₂C—C≡N | S=O | CH₃ | CH₃ | Cl |
| 2 | H₂C—C≡CH | S=O | CH₃ | Cl | CH₃ |
| 2 | CH(CH₃)₂ | S=O | C₂H₅ | Cl | Cl |
| 2 | CH₂CH₂OH | S=O | C₂H₅ | C₂H₅ | Cl |
| 3 | CH₂CH(CH₃)OH | S=O | C₂H₅ | Cl | C₂H₅ |
| 3 | CH(CH₃)CH₂OH | S=O | CH₃ | Br | Br |
| 3 | CH(CH₃)CH(CH₃)OH | S=O | CH₃ | CH₃ | Br |
| 3 | C(CH₃)₂CH₂OH | S=O | CH₃ | Br | CH₃ |
| 3 | CH₂C(CH₃)₂OH | S=O | C₂H₅ | I | I |
| 3 | CH₂CHF₂ | S=O | C₂H₅ | C₂H₅ | I |
| 3 | CH₂CF₃ | S=O | C₂H₅ | I | C₂H₅ |
| 3 | CH₂CH(CH₃)₂ | S=O | C₂H₅ | Br | Cl |
| 3 | CH₂C(CH₃)₃ | S=O | C₂H₅ | C₂H₅ | Br |
| 3 | H₂C—C≡N | S=O | C₂H₅ | Br | C₂H₅ |
| 3 | H₂C—C≡CH | O=S=O | Cl | Cl | Cl |
| 2 | CH(CH₃)₂ | O=S=O | CH₃ | CH₃ | CH₃ |
| 2 | CH₂CH₂OH | O=S=O | C₂H₅ | C₂H₅ | C₂H₅ |
| 2 | CH₂CH(CH₃)OH | O=S=O | i-C₃H₇ | i-C₃H₇ | i-C₃H₇ |
| 2 | CH(CH₃)CH₂OH | O=S=O | CH₃ | Cl | Cl |
| 2 | CH(CH₃)CH(CH₃)OH | O=S=O | CH₃ | CH₃ | Cl |
| 2 | C(CH₃)₂CH₂OH | O=S=O | CH₃ | Cl | CH₃ |
| 2 | CH₂C(CH₃)₂OH | O=S=O | C₂H₅ | Cl | Cl |
| 2 | CH₂CHF₂ | O=S=O | C₂H₅ | C₂H₅ | Cl |
| 2 | CH₂CF₃ | O=S=O | C₂H₅ | Cl | C₂H₅ |
| 3 | CH₂CH(CH₃)₂ | O=S=O | CH₃ | Br | Br |
| 3 | CH₂C(CH₃)₃ | O=S=O | CH₃ | CH₃ | Br |
| 3 | H₂C—C≡N | O=S=O | CH₃ | Br | CH₃ |
| 3 | H₂C—C≡CH | O=S=O | C₂H₅ | I | I |
| 3 | CH(CH₃)₂ | O=S=O | C₂H₅ | C₂H₅ | I |
| 3 | CH₂CH₂OH | O=S=O | C₂H₅ | I | C₂H₅ |
| 3 | CH₂CH(CH₃)OH | O=S=O | C₂H₅ | Br | Cl |
| 3 | CH(CH₃)CH₂OH | O=S=O | C₂H₅ | C₂H₅ | Br |
| 3 | CH(CH₃)CH(CH₃)OH | O=S=O | C₂H₅ | Br | C₂H₅ |
| 2 | C(CH₃)₂CH₂OH | NH | Cl | Cl | Cl |
| 2 | CH₂C(CH₃)₂OH | NH | CH₃ | CH₃ | CH₃ |
| 2 | CH₂CHF₂ | NH | C₂H₅ | C₂H₅ | C₂H₅ |
| 2 | CH₂CF₃ | NH | i-C₃H₇ | i-C₃H₇ | i-C₃H₇ |
| 2 | CH₂CH(CH₃)₂ | NH | CH₃ | Cl | Cl |
| 2 | CH₂C(CH₃)₃ | NH | CH₃ | CH₃ | Cl |
| 2 | H₂C—C≡N | NH | CH₃ | Cl | CH₃ |
| 2 | H₂C—C≡CH | NH | C₂H₅ | Cl | Cl |
| 2 | CH(CH₃)₂ | NH | C₂H₅ | C₂H₅ | Cl |
| 2 | CH₂CH₂OH | NH | C₂H₅ | Cl | C₂H₅ |
| 3 | CH₂CH(CH₃)OH | NH | CH₃ | Br | Br |
| 3 | CH(CH₃)CH₂OH | NH | CH₃ | CH₃ | Br |
| 3 | CH(CH₃)₂ | NH | CH₃ | Br | CH₃ |
| 3 | CH₂CH₂OH | NH | C₂H₅ | I | I |
| 3 | CH₂CH(CH₃)OH | NH | C₂H₅ | C₂H₅ | I |
| 3 | CH(CH₃)CH₂OH | NH | C₂H₅ | I | C₂H₅ |
| 3 | CH(CH₃)CH(CH₃)OH | NH | C₂H₅ | Br | Cl |
| 3 | C(CH₃)₂CH₂OH | NH | C₂H₅ | C₂H₅ | Br |
| 3 | CH₂C(CH₃)₂OH | NH | C₂H₅ | Br | C₂H₅ |
| 3 | CH₂CHF₂ | O | Cl | Cl | Cl |
| 2 | CH₂CF₃ | O | CH₃ | CH₃ | CH₃ |
| 2 | CH₂CH(CH₃)₂ | O | C₂H₅ | C₂H₅ | C₂H₅ |
| 2 | CH₂C(CH₃)₃ | O | i-C₃H₇ | i-C₃H₇ | i-C₃H₇ |
| 2 | H₂C—C≡N | O | CH₃ | Cl | Cl |
| 2 | H₂C—C≡CH | O | CH₃ | CH₃ | Cl |
| 2 | CH(CH₃)₂ | O | CH₃ | Cl | CH₃ |
| 2 | CH₂CH₂OH | O | C₂H₅ | Cl | Cl |
| 2 | CH₂CH(CH₃)OH | O | C₂H₅ | C₂H₅ | Cl |
| 2 | CH(CH₃)CH₂OH | O | C₂H₅ | Cl | C₂H₅ |
| 3 | CH(CH₃)CH(CH₃)OH | O | CH₃ | Br | Br |
| 3 | C(CH₃)₂CH₂OH | O | CH₃ | CH₃ | Br |
| 3 | CH₂C(CH₃)₂OH | O | CH₃ | Br | CH₃ |
| 3 | CH₂CHF₂ | O | C₂H₅ | I | I |
| 3 | CH₂CF₃ | O | C₂H₅ | C₂H₅ | I |
| 3 | CH₂CH(CH₃)₂ | O | C₂H₅ | I | C₂H₅ |
| 3 | CH₂C(CH₃)₃ | O | C₂H₅ | Br | Cl |
| 3 | H₂C—C≡N | O | C₂H₅ | C₂H₅ | Br |
| 3 | H₂C—C≡CH | O | C₂H₅ | Br | C₂H₅ |
| 2 | CH(CH₃)₂ | CH₂ | Cl | Cl | Cl |
| 2 | CH₂CH₂OH | CH₂ | CH₃ | CH₃ | CH₃ |
| 2 | CH₂CH(CH₃)OH | CH₂ | C₂H₅ | C₂H₅ | C₂H₅ |
| 2 | CH(CH₃)CH₂OH | CH₂ | i-C₃H₇ | i-C₃H₇ | i-C₃H₇ |
| 2 | CH(CH₃)CH(CH₃)OH | CH₂ | CH₃ | Cl | Cl |
| 2 | C(CH₃)₂CH₂OH | CH₂ | CH₃ | CH₃ | Cl |
| 2 | CH₂C(CH₃)₂OH | CH₂ | CH₃ | Cl | CH₃ |
| 2 | CH₂CHF₂ | CH₂ | C₂H₅ | Cl | Cl |
| 2 | CH₂CF₃ | CH₂ | C₂H₅ | C₂H₅ | Cl |
| 3 | CH₂CH(CH₃)₂ | CH₂ | C₂H₅ | Cl | C₂H₅ |
| 3 | CH₂C(CH₃)₃ | CH₂ | CH₃ | Br | Br |
| 3 | H₂C—C≡N | CH₂ | CH₃ | CH₃ | Br |
| 3 | H₂C—C≡CH | CH₂ | CH₃ | Br | CH₃ |
| 3 | CH(CH₃)₂ | CH₂ | C₂H₅ | I | I |
| 3 | CH₂CH₂OH | CH₂ | C₂H₅ | C₂H₅ | I |
| 3 | CH₂CH(CH₃)OH | CH₂ | C₂H₅ | I | C₂H₅ |
| 3 | CH(CH₃)CH₂OH | CH₂ | C₂H₅ | Br | Cl |
| 3 | CH(CH₃)CH(CH₃)OH | CH₂ | C₂H₅ | C₂H₅ | Br |
| 3 | C(CH₃)₂CH₂OH | CH₂ | C₂H₅ | Br | C₂H₅ |
| 2 | CH₂C(CH₃)₂OH | C=O | Cl | Cl | Cl |
| 2 | CH₂CHF₂ | C=O | CH₃ | CH₃ | CH₃ |
| 2 | CH₂CF₃ | C=O | C₂H₅ | C₂H₅ | C₂H₅ |
| 2 | CH₂CH(CH₃)₂ | C=O | i-C₃H₇ | i-C₃H₇ | i-C₃H₇ |
| 2 | CH₂C(CH₃)₃ | C=O | CH₃ | Cl | Cl |
| 2 | H₂C—C≡N | C=O | CH₃ | CH₃ | Cl |
| 2 | H₂C—C≡CH | C=O | CH₃ | Cl | CH₃ |
| 2 | CH(CH₃)₂ | C=O | C₂H₅ | Cl | Cl |
| 2 | CH₂CH₂OH | C=O | C₂H₅ | C₂H₅ | Cl |
| 3 | CH₂CH(CH₃)OH | C=O | C₂H₅ | I | C₂H₅ |
| 3 | CH(CH₃)CH₂OH | C=O | CH₃ | Br | Br |
| 3 | CH(CH₃)CH(CH₃)OH | C=O | CH₃ | CH₃ | Br |

TABLE 5-continued

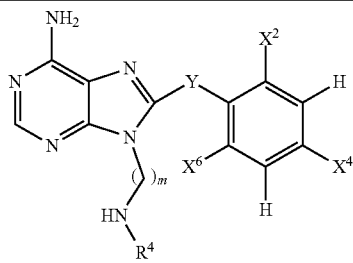

and pharmaceutically acceptable salts thereof, where:

| m | $R^4$ | Y | $X^2$ | $X^4$ | $X^6$ |
|---|---|---|---|---|---|
| 3 | $C(CH_3)_2CH_2OH$ | C=O | $CH_3$ | Br | $CH_3$ |
| 3 | $CH_2C(CH_3)_2OH$ | C=O | $C_2H_5$ | I | I |
| 3 | $CH_2CHF_2$ | C=O | $C_2H_5$ | $C_2H_5$ | I |
| 3 | $CH_2CF_3$ | C=O | $C_2H_5$ | I | $C_2H_5$ |
| 3 | $CH_2CH(CH_3)_2$ | C=O | $C_2H_5$ | Br | Cl |
| 3 | $CH_2C(CH_3)_3$ | C=O | $C_2H_5$ | $C_2H_5$ | Br |
| 3 | $H_2C—C\equiv N$ | C=O | $C_2H_5$ | Br | $C_2H_5$ |
| 3 | $H_2C—C\equiv CH$ | C=S | Cl | Cl | Cl |
| 2 | $CH(CH_3)_2$ | C=S | $CH_3$ | $CH_3$ | $CH_3$ |
| 2 | $CH_2CH_2OH$ | C=S | $C_2H_5$ | $C_2H_5$ | $C_2H_5$ |
| 2 | $CH_2CH(CH_3)OH$ | C=S | i-$C_3H_7$ | i-$C_3H_7$ | i-$C_3H_7$ |
| 2 | $CH(CH_3)CH_2OH$ | C=S | $CH_3$ | Cl | Cl |
| 2 | $CH(CH_3)CH(CH_3)OH$ | C=S | $CH_3$ | $CH_3$ | Cl |
| 2 | $C(CH_3)_2CH_2OH$ | C=S | $CH_3$ | Cl | $CH_3$ |
| 2 | $CH_2C(CH_3)_2OH$ | C=S | $CH_3$ | Cl | Cl |
| 2 | $CH_2CHF_2$ | C=S | $C_2H_5$ | $C_2H_5$ | Cl |
| 2 | $CH_2CF_3$ | C=S | $C_2H_5$ | Cl | $C_2H_5$ |
| 3 | $CH_2CH(CH_3)_2$ | C=S | $CH_3$ | Br | Br |
| 3 | $CH_2C(CH_3)_3$ | C=S | $CH_3$ | $CH_3$ | Br |
| 3 | $H_2C—C\equiv N$ | C=S | $CH_3$ | Br | $CH_3$ |
| 3 | $H_2C—C\equiv CH$ | C=S | $C_2H_5$ | I | I |
| 3 | $CH(CH_3)_2$ | C=S | $C_2H_5$ | $C_2H_5$ | I |
| 3 | $CH_2CH_2OH$ | C=S | $C_2H_5$ | I | $C_2H_5$ |
| 3 | $CH_2CH(CH_3)OH$ | C=S | $C_2H_5$ | Br | Cl |
| 3 | $CH(CH_3)CH_2OH$ | C=S | $C_2H_5$ | $C_2H_5$ | Br |
| 3 | $CH(CH_3)CH(CH_3)OH$ | C=S | $C_2H_5$ | Br | $C_2H_5$ |
| 2 | $C(CH_3)_2CH_2OH$ | CH—OH | Cl | Cl | Cl |
| 2 | $CH_2C(CH_3)_2OH$ | CH—OH | $CH_3$ | $CH_3$ | $CH_3$ |
| 2 | $CH_2CHF_2$ | CH—OH | $C_2H_5$ | $C_2H_5$ | $C_2H_5$ |
| 2 | $CH_2CF_3$ | CH—OH | i-$C_3H_7$ | i-$C_3H_7$ | i-$C_3H_7$ |
| 2 | $CH_2CH(CH_3)_2$ | CH—OH | $CH_3$ | Cl | Cl |
| 2 | $CH_2C(CH_3)_3$ | CH—OH | $CH_3$ | $CH_3$ | Cl |
| 2 | $H_2C—C\equiv N$ | CH—OH | $CH_3$ | Cl | $CH_3$ |
| 2 | $H_2C—C\equiv CH$ | CH—OH | $C_2H_5$ | Cl | Cl |
| 2 | $CH(CH_3)_2$ | CH—OH | $C_2H_5$ | $C_2H_5$ | Cl |
| 3 | $CH_2CH_2OH$ | CH—OH | $C_2H_5$ | Cl | $C_2H_5$ |
| 3 | $CH_2CH(CH_3)OH$ | CH—OH | $CH_3$ | Br | Br |
| 3 | $CH(CH_3)CH_2OH$ | CH—OH | $CH_3$ | $CH_3$ | Br |
| 3 | $CH(CH_3)CH(CH_3)OH$ | CH—OH | $CH_3$ | Br | $CH_3$ |
| 3 | $C(CH_3)_2CH_2OH$ | CH—OH | $C_2H_5$ | I | I |
| 3 | $CH_2C(CH_3)_2OH$ | CH—OH | $C_2H_5$ | $C_2H_5$ | I |
| 3 | $CH_2CHF_2$ | CH—OH | $C_2H_5$ | I | $C_2H_5$ |
| 3 | $CH_2CF_3$ | CH—OH | $C_2H_5$ | Br | Cl |
| 3 | $CH_2CH(CH_3)_2$ | CH—OH | $C_2H_5$ | $C_2H_5$ | Br |
| 3 | $CH_2C(CH_3)_3$ | CH—OH | $C_2H_5$ | Br | $C_2H_5$ |
| 2 | $H_2C—C\equiv N$ | CH—F | Cl | Cl | Cl |
| 2 | $H_2C—C\equiv CH$ | CH—F | $CH_3$ | $CH_3$ | $CH_3$ |
| 2 | $CH(CH_3)_2$ | CH—F | $C_2H_5$ | $C_2H_5$ | $C_2H_5$ |
| 2 | $CH_2CH_2OH$ | CH—F | i-$C_3H_7$ | i-$C_3H_7$ | i-$C_3H_7$ |
| 2 | $CH_2CH(CH_3)OH$ | CH—F | $CH_3$ | Cl | Cl |
| 2 | $CH(CH_3)CH_2OH$ | CH—F | $CH_3$ | $CH_3$ | Cl |
| 2 | $CH(CH_3)CH(CH_3)OH$ | CH—F | $CH_3$ | Cl | $CH_3$ |
| 2 | $C(CH_3)_2CH_2OH$ | CH—F | $C_2H_5$ | Cl | Cl |
| 2 | $CH_2C(CH_3)_2OH$ | CH—F | $C_2H_5$ | $C_2H_5$ | Cl |
| 3 | $CH_2CHF_2$ | CH—F | $C_2H_5$ | Cl | $C_2H_5$ |
| 3 | $CH_2CF_3$ | CH—F | $CH_3$ | Br | Br |
| 3 | $CH_2CH(CH_3)_2$ | CH—F | $CH_3$ | $CH_3$ | Br |
| 3 | $CH_2C(CH_3)_3$ | CH—F | $CH_3$ | Br | $CH_3$ |
| 3 | $H_2C—C\equiv N$ | CH—F | $C_2H_5$ | I | I |
| 3 | $H_2C—C\equiv CH$ | CH—F | $C_2H_5$ | $C_2H_5$ | I |
| 3 | $CH(CH_3)_2$ | CH—F | $C_2H_5$ | I | $C_2H_5$ |
| 3 | $CH_2CH_2OH$ | CH—F | $C_2H_5$ | Br | Cl |
| 3 | $CH_2CH(CH_3)OH$ | CH—F | $C_2H_5$ | $C_2H_5$ | Br |
| 3 | $CH(CH_3)CH_2OH$ | CH—F | $C_2H_5$ | Br | $C_2H_5$ |

TABLE 5-continued

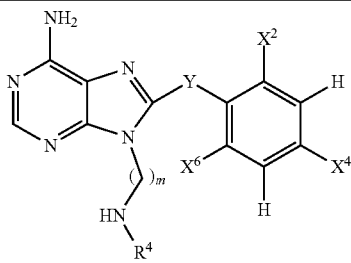

and pharmaceutically acceptable salts thereof, where:

5.3.3 Grp94 Inhibitors of Formula (III)

In one aspect, the disclosure encompasses purine-scaffold compounds that are substituted at the 8-position with a linker group bonded to a bicyclic group and are further substituted at the N-9 position. Such compounds are represented schematically in Formula (III):

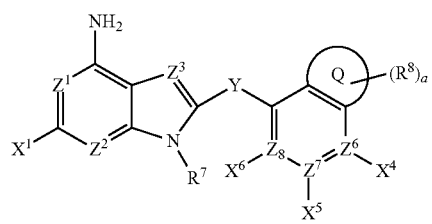

or a pharmaceutically acceptable salt thereof, wherein:

(a) Y is —C($R^Y$)$_2$—, —S—, —NR—, —O—, $$-\overset{O}{\underset{\|}{S}}-, \quad -\overset{O}{\underset{\|}{\underset{\|}{S}}}\overset{O}{-}, \quad -\overset{O}{\underset{\|}{C}}- \quad \text{or} \quad -\overset{S}{\underset{\|}{C}}-;$$

(b) each of $Z^1$ and $Z^3$ are independently —CH— or —N—;

(c) $Z^2$ is —N— or —$CR^{10}$—, wherein $R^{10}$ is H or unsubstituted or substituted —(C$_1$-C$_6$)aliphatic;

(d) each of $Z^6$, $Z^7$ and $Z^8$ are independently —C— or —N—, with the proviso that at least one of $Z^6$-$Z^8$ is —C—;

(e) $X^1$ is —H, -halo, —N(R)$_2$, —OR, —CN, or unsubstituted or substituted —(C$_1$-C$_6$)aliphatic;

(f) each of $X^4$, $X^5$, and $X^6$ are independently —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered)arylalkyl, and (5- or 6-membered)heterocyclic aromatic or heterocyclic non-aromatic group; with the provisos that $X^4$ is absent when $Z^6$ is a nitrogen, $X^5$ is absent when $Z^7$ is a nitrogen and $X^6$ is absent when $Z^8$ is a nitrogen;

(g) $R^7$ is —(C$_1$-C$_6$)aliphatic-N$^+$—(R$^2$)(R$^3$)(R$^4$), —(C$_1$-C$_6$)aliphatic-N—R$^3$R$^4$, —(C$_1$-C$_6$)aliphatic-C(=O)N—R$^3$R$^4$, —(C$_1$-C$_6$)aliphatic-R$^3$R$^4$, —(C$_1$-C$_6$)aliphatic-R$^2$R$^3$R$^4$, —(C$_1$-C$_6$)aliphatic-N—CR$^2$R$^3$R$^4$, —(C$_1$-C$_6$)

aliphatic-C(halo)$_3$, —(C$_1$-C$_6$)aliphatic-alkenyl, —(C$_1$-C$_6$) aliphatic-alkynyl, —(C$_1$-C$_6$)aliphatic-(C$_3$-C$_8$)cycloalkyl, —(C$_1$-C$_6$)aliphatic-(C$_3$-C$_8$)heterocycloalkyl, —(C$_1$-C$_6$)aliphatic-phenyl, —(C$_1$-C$_6$)aliphatic-(5 or 6-membered)heteroaryl, —(C$_1$-C$_6$)aliphatic-cyano, with the proviso that when all of R$^2$-R$^4$ are present the compound further comprises a pharmaceutically acceptable counter ion;

(h) Q is fused benzo, fused (5- or 6-membered)heteroaryl, a fused 4 to 7-membered cyloalkyl ring or a fused 4- to 7-membered non-aromatic heterocyclic ring;

(i) R$^2$ and R$^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$) aliphatic, or R$^3$ and R$^4$ form an unsubstituted or substituted 3- to 7-membered heterocyclic ring when taken together with the nitrogen to which they are attached;

(j) R$^4$ is hydrogen, halogen, or unsubstituted or substituted —(C$_1$-C$_6$)aliphatic;

(k) each R$^8$ is independently —H, -halo, —N(R)$_2$, —OR, —CN, or a unsubstituted or substituted selected from —CH$_2$-phenyl or —(C$_1$-C$_6$)aliphatic;

(l) each R$^Y$ is independently R, —OR, or halo;

(m) a is an integer selected from 0, 1 and 2; and (n) each R is independently hydrogen, unsubstituted C$_{1-6}$ aliphatic, or C$_{1-6}$ aliphatic substituted with halo, —OH, —CN, or —NH$_2$;

wherein each substituted group is substituted with one or more groups selected from halo, —N(R)$_2$, —OR, —CN, oxo, unsubstituted C$_{1-6}$ aliphatic, or C$_{1-6}$ aliphatic substituted with halo, —OH, —CN, or —NH$_2$.

In some embodiments, a compound of formula (III) or pharmaceutically acceptable salt thereof is defined wherein:

(a) Y is —CH$_2$—, —S—, —N—, —O—, $$-\underset{\underset{O}{\|}}{S}-, \quad -\underset{\underset{O}{\|}}{\overset{\overset{O}{\|}}{S}}-, \quad -\underset{\underset{O}{\|}}{C}- \quad \text{or} \quad -\underset{\underset{S}{\|}}{C}-;$$

(b) each of Z$^1$ and Z$^3$ are independently —C— or —N—;

(c) Z$^2$ is —CH—, —N—, or —CR$^{10}$—, wherein R$^{10}$ is —(C$_1$-C$_6$)alkyl;

(d) each of Z$^6$, Z$^7$ and Z$^8$ are independently —C— or —N—, with the proviso that at least one of Z$^6$-Z$^8$ is —C—;

(e) X$^1$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, or —OCH$_2$(halo);

(f) each of X$^4$, X$^5$, and X$^6$ are independently —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, —OCH$_2$(halo), or a (5- or 6-membered)aryl, heterocyclic aromatic, or non-aromatic group selected from pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl, with the provisos that X$^4$ is absent when Z$^6$ is a nitrogen, X$^5$ is absent when Z$^7$ is a nitrogen and X$^6$ is absent when Z$^8$ is a nitrogen;

(g) R$^7$ is —(CH$_2$)$_m$—N$^+$—(R$^2$)(R$^3$)(R$^4$), —(CH$_2$)$_m$—N—R$^3$R$^4$, —(CH$_2$)$_m$—C(=O)N—R$^3$R$^4$, —(CH$_2$)$_m$R$^3$R$^4$, —(CH$_2$)$_m$—C(halo)$_3$, —(CH$_2$)$_m$-alkenyl, —(CH$_2$)$_m$-alkenyl-CH$_3$, —(CH$_2$)$_m$-alkynyl, —(CH$_2$)$_m$-alkynyl-CH$_3$, —(CH$_2$)$_m$—(C$_3$-C$_8$)cycloalkyl, —(CH$_2$)$_m$—(C$_3$-C$_8$)heterocycloalkyl, —(CH$_2$)$_m$-phenyl, —(CH$_2$)$_m$-(5 or 6-membered)heteroaryl, —(CH$_2$)$_m$-cyano, where m is 1, 2, 3, 4 or 5 and where the cyloalkyl, heterocycle or phenyl is unsubstituted or substituted with one or more X$^1$ groups, with the proviso that when all of R$^2$-R$^4$ are present the compound further comprises a pharmaceutically acceptable counter ion;

(h) Q is fused benzo, fused (5- or 6-membered)heteroaryl, a fused 4 to 7-membered cyloalkyl ring or a fused 4- to 7-membered non-aromatic heterocyclic ring selected from pyrrolo, pyridino, pyrimidino, pyrazino, pyridazino, oxadiazolo, thiadiazolo, dioxolano, imidazolo, or imidazo[1,2-a]pyridine;

(i) R$^2$ and R$^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —CH$_2$(halo), —CH$_2$C(halo)$_3$, —CHCH(halo)$_2$, CHCH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)CH$_2$OH, —CH(CH$_3$)CH(OH)R$^4$, —CH$_2$CH(OH)R$^4$, —CH$_2$SO$_2$NHR$^4$, —CH$_3$SO$_2$NHR$^4$ or R$^2$ and R$^3$ form an unsubstituted or substituted aziridine, azetidine, pyrrolidine, piperazine, or piperidine ring when taken together with the nitrogen to which they are attached;

(j) R$^4$ is hydrogen, methyl, ethyl, isopropyl, t-butyl, isobutyl, or —C(halo)$_3$;

(k) R$^8$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, and —OCH$_2$(halo); and (l) a is an integer selected from 0, 1 and 2.

In one embodiment, Z$^1$, Z$^2$ and Z$^3$ are —N—. In another embodiment, Z$^1$ and Z$^3$ are —N— and Z$^2$ is —CH—. In another embodiment, Z$^1$ is —C— and Z$^2$ and Z$^3$ are —N—.

In another embodiment, Z$^6$, Z$^7$ and Z$^8$ are —C—. In another embodiment, Z$^6$ is —N— and Z$^7$ and Z$^8$ are —C—.

In another embodiment, Y is —S—, —CH$_2$—, or $$-\underset{\underset{O}{\|}}{C}-.$$

In another embodiment, Y is S or $$-\underset{\underset{O}{\|}}{C}-.$$

In another embodiment, Y is —S— or —CH$_2$—. In another embodiment, Y is —S— or —O—. In another embodiment, Y is —S—. In another embodiment, Y is —CH$_2$—. In another embodiment, Y is $$-\underset{\underset{O}{\|}}{C}-.$$

In some embodiments, Y is —C(R$^Y$)$_2$—, wherein each R$^Y$ is independently hydrogen, —OH, or halo.

In some embodiments, R$^2$ or R$^3$ is —CH$_2$NHSO$_2$R$^4$.

In some embodiments, R$^2$ and R$^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$)aliphatic, or R$^3$ and R$^4$ form an unsubstituted or substituted 3- to 7-membered heterocyclic ring when taken together with the nitrogen to which they are attached.

In some embodiments, $R^2$ and $R^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —CH$_2$(halo), —CH$_2$C(halo)$_3$, —CHCH(halo)$_2$, CHCH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)CH$_2$OH, —CH(CH$_3$)CH(OH)R$^4$, —CH$_2$CH(OH)R$^4$, —CH$_2$SO$_2$NHR$^4$, —CH$_2$NHSO$_2$R$^4$ or $R^2$ and $R^3$ form an unsubstituted or substituted aziridine, azetidine, pyrrolidine, piperazine, or piperidine ring when taken together with the nitrogen to which they are attached.

In certain embodiments, $R^7$ is —(CH$_2$)$_m$—N—(R$^3$)(R$^4$). In one such embodiment, $R^7$ is —(CH$_2$)$_2$—N—(R$^3$)(R$^4$). In another such embodiment, $R^7$ is —(CH$_2$)$_3$—N—(R$^3$)(R$^4$). In another such embodiment, $R^7$ is —(CH$_2$)$_2$—N—(R$^3$)(R$^4$), $R^3$ is H and $R^4$ is isopropyl or isobutyl. In another such embodiment, $R^7$ is —(CH$_2$)$_3$—N—(R$^3$)(R$^4$), $R^3$ is H and $R^4$ is isopropyl. In another such embodiment, $R^7$ is —(CH$_2$)$_3$—N—(R$^3$)(R$^4$), $R^3$ is H and $R^4$ is isobutyl.

In certain embodiments, $R^7$ is —(CH$_2$)$_m$—CF$_3$. In one such embodiment, $R^7$ is —(CH$_2$)$_3$—CF$_3$. In another such embodiment, $R^7$ is —(CH$_2$)$_4$—CF$_3$.

In certain embodiments, $R^7$ is —(CH$_2$)$_m$-alkenyl. In one such embodiment, $R^7$ is —(CH$_2$)$_3$-alkenyl. In another such embodiment, $R^7$ is —(CH$_2$)$_4$-alkenyl.

In another embodiment, $R^7$ is —(CH$_2$)$_3$-alkynyl. In another embodiment, $R^7$ is —(CH$_2$)$_3$—CCH. In another embodiment, $R^7$ is —(CH$_2$)$_4$-alkynyl. In another embodiment, $R^7$ is —(CH$_2$)$_m$-cyano In another embodiment, $R^7$ is —(CH$_2$)$_3$-cyano. In another embodiment, $R^7$ is —(CH$_2$)$_4$-cyano.

In another embodiment Q is benzo, pyrrolo, pyridino, pyrimidino, pyrazino, or pyridazino. In another embodiment, Q is benzo or pyridino, wherein preferably the 2- and 3-positions of the pyridino are fused to the 6-membered, nitrogen-containing ring. In another embodiment, Q is benzo. In another embodiment, Q is oxadiazolo, thiadiazolo, dioxolano or imidazolo. In another embodiment, Q is fused with an aryl ring to form an imidazo[1,2-a]pyridine ring.

In another embodiment Q is piperazinyl, piperidinyl, 2H-pyranyl, pyrrolidinyl, tetrahydrofuranyl, tetrahydropyranyl, morpholinyl, oxoimidazolidinyl, 2-oxopyrrolidinyl, thiomorpholinyl, or thiazolidinyl.

In another embodiment, Q is cyclobutyl, cyclopentyl, cyclopentenyl, cyclohexyl.

In other embodiments, the Grp94 inhibitors of Formula (III) have one of the Formula of Table 6, wherein each substituent is as defined above and described in classes and subclasses herein, both singly and in combination.

TABLE 6

| Formula | Compound |
|---------|----------|
| IIIA | |
| IIIB | |
| IIIC | |
| IIID | |
| IIIE | |
| IIIF | |
| IIIG | |
| IIIH | |

TABLE 6-continued

| Formula | Compound |
|---|---|
| IIII | |
| IIIJ | |
| IIIK | |
| IIIL | |
| IIIM | |
| IIIN | |
| IIIO | |
| IIIP | |
| IIIQ | |
| IIIR | |
| IIIS | |
| IIIT | |
| IIIU | |

TABLE 6-continued

| Formula | Compound |
|---|---|
| IIIV | (structure) |
| IIIW | (structure) |
| IIIX | (structure) |
| IIIY | (structure) |
| IIIZ | (structure) |
| IIIAA | (structure) |
| IIIAB | (structure) |
| IIIAC | (structure) |
| IIIAD | (structure) |
| IIIAE | (structure) |
| IIIAF | (structure) |
| IIIAG | (structure) |
| IIIAH | (structure) |
| IIIAI | (structure) |

TABLE 6-continued

| Formula | Compound |
|---------|----------|
| IIIAJ | (structure) |
| IIIAK | (structure) |
| IIIAL | (structure) |
| IIIAM | (structure) |
| IIIAN | (structure) |
| IIIAO | (structure) |
| IIIAP | (structure) |
| IIIAQ | (structure) |
| IIIAR | (structure) |
| IIIAS | (structure) |
| IIIAT | (structure) | wherein each $R^9$ is R.

Illustrative compounds of Formula (III) are listed below in Table 7.

TABLE 7

(structure)

and pharmaceutically acceptable salts thereof, where:

| $R^7$ | $X^{10}$ | $X^{11}$ | $X^{12}$ | $X^{13}$ |
|-------|----------|----------|----------|----------|
| (H₂C)₃—≡ | Cl | Cl | Cl | CH |
| (H₂C)₃—≡ | H | H | H | CH |
| (H₂C)₃—≡ | H | Cl | H | CH |
| (H₂C)₃—≡ | H | H | Cl | CH |
| (H₂C)₃—≡ | Cl | H | Cl | CH |
| (H₂C)₃—≡ | Cl | Cl | H | CH |
| (H₂C)₃—≡ | Cl | Cl | Cl | N |
| (H₂C)₃—≡ | H | H | H | N |

TABLE 7-continued

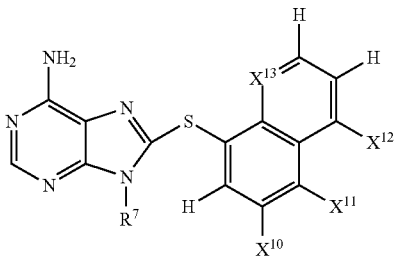

and pharmaceutically acceptable salts thereof, where:

| R$^7$ | X$^{10}$ | X$^{11}$ | X$^{12}$ | X$^{13}$ |
|---|---|---|---|---|
| (H$_2$C)$_3$—≡ | H | Cl | H | N |
| (H$_2$C)$_3$—≡ | H | H | Cl | N |
| (H$_2$C)$_3$—≡ | Cl | H | Cl | N |
| (H$_2$C)$_3$—≡ | Cl | Cl | H | N |
| (CH$_2$)$_3$—NHCH(CH$_3$)$_2$ | Cl | Cl | Cl | CH |
| (CH$_2$)$_3$—NHCH(CH$_3$)$_2$ | H | H | H | CH |
| (CH$_2$)$_3$—NHCH(CH$_3$)$_2$ | H | Cl | H | CH |
| (CH$_2$)$_3$—NHCH(CH$_3$)$_2$ | H | H | Cl | CH |
| (CH$_2$)$_3$—NHCH(CH$_3$)$_2$ | Cl | H | Cl | CH |
| (CH$_2$)$_3$—NHCH(CH$_3$)$_2$ | Cl | Cl | H | CH |
| (CH$_2$)$_3$—NHCH(CH$_3$)$_2$ | Cl | Cl | Cl | N |
| (CH$_2$)$_3$—NHCH(CH$_3$)$_2$ | H | H | H | N |
| (CH$_2$)$_3$—NHCH(CH$_3$)$_2$ | H | Cl | H | N |
| (CH$_2$)$_3$—NHCH(CH$_3$)$_2$ | H | H | Cl | N |
| (CH$_2$)$_3$—NHCH(CH$_3$)$_2$ | Cl | H | Cl | N |
| (CH$_2$)$_3$—NHCH(CH$_3$)$_2$ | Cl | Cl | H | N |

5.3.4 Grp94 Inhibitors of Formula (IV)

In one aspect, the disclosure encompasses purine-scaffold compounds that are represented schematically in Formula (IV):

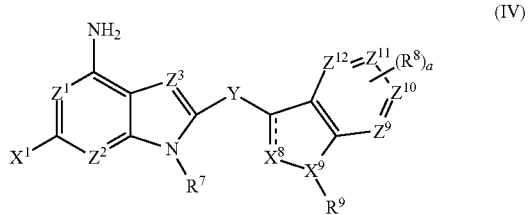

(IV)

or a pharmaceutically acceptable salt thereof, wherein:

(a) Y is —C(R$^Y$)$_2$—, —S—, —NR—, —O—,

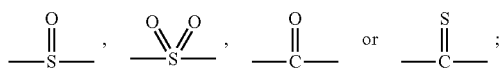

(b) each of Z$^1$, Z$^3$, Z$^9$, Z$^{10}$, Z$^{11}$ and Z$^{12}$ are independently —CH— or —N—;

(c) Z$^2$ is —N— or —CR$^{10}$—, wherein R$^{10}$ is H or unsubstituted or substituted —(C$_1$-C$_6$)aliphatic;

(d) each of X$^8$ and X$^9$ are independently —CH—, —S—, —N—, or —O—;

(e) X$^1$ is —H, -halo, —N(R)$_2$, —OR, —CN, or unsubstituted or substituted —(C$_1$-C$_6$)aliphatic;

(f) R$^7$ is —(C$_1$-C$_6$)aliphatic-N$^+$—(R$^2$)(R$^3$)(R$^4$), —(C$_1$-C$_6$)aliphatic-N—R$^3$R$^4$, —(C$_1$-C$_6$)aliphatic-C(═O)N—R$^3$R$^4$, —(C$_1$-C$_6$)aliphatic-R$^3$R$^4$, —(C$_1$-C$_6$)aliphatic-R$^2$R$^3$R$^4$, —(C$_1$-C$_6$)aliphatic-N—CR$^2$R$^3$R$^4$, —(C$_1$-C$_6$)aliphatic-C(halo)$_3$, —(C$_1$-C$_6$)aliphatic-alkenyl, —(C$_1$-C$_6$)aliphatic-alkynyl, —(C$_1$-C$_6$)aliphatic-(C$_3$-C$_8$)cycloalkyl, —(C$_1$-C$_6$)aliphatic-(C$_3$-C$_8$)heterocycloalkyl, —(C$_1$-C$_6$)aliphatic-phenyl, —(C$_1$-C$_6$)aliphatic-(5 or 6-membered)heteroaryl, —(C$_1$-C$_6$)aliphatic-cyano, with the proviso that when all of R$^2$-R$^4$ are present the compound further comprises a pharmaceutically acceptable counter ion;

(g) R$^2$ and R$^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$) aliphatic, or R$^3$ and R$^4$ form an unsubstituted or substituted 3- to 7-membered heterocyclic ring when taken together with the nitrogen to which they are attached;

(h) R$^4$ is hydrogen, halogen, or unsubstituted or substituted —(C$_1$-C$_6$)aliphatic;

(i) each R$^8$ is independently —H, -halo, —N(R)$_2$, —OR, —CN, or unsubstituted or substituted —(C$_1$-C$_6$)aliphatic;

(j) R$^9$ is —H, (C$_1$-C$_6$)aliphatic-cycloalkyl, —(C$_1$-C$_6$)aliphatic-heterocycloalkyl, —(C$_1$-C$_6$)aliphatic-aryl, —(C$_1$-C$_6$) aliphatic-heteroaryl, or —(C$_1$-C$_6$)aliphatic-cyano, wherein each cycloalkyl, heterocycloalkyl, aryl, or heteroaryl is unsubstituted or substituted, with the proviso that R$^9$ is absent when X$^9$ is —S— or —O—;

(k) each R$^Y$ is independently R, —OR, or halo;

(l) a is an integer selected from 0, 1 and 2; and (m) each R is independently hydrogen, unsubstituted C$_{1-6}$ aliphatic, or C$_{1-6}$ aliphatic substituted with halo, —OH, —CN, or —NH$_2$; and wherein each substituted group is substituted with one or more groups selected from halo, —N(R)$_2$, —OR, —CN, oxo, unsubstituted C$_{1-6}$ aliphatic, or C$_{1-6}$ aliphatic substituted with halo, —OH, —CN, or —NH$_2$.

In some embodiments, a compound of formula (IV) or pharmaceutically acceptable salt thereof is defined wherein:

(a) Y is —CH$_2$—, —S—, —N—, —O—,

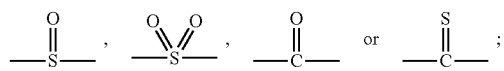

(b) each of Z$^1$, Z$^3$, Z$^9$, Z$^{10}$, Z$^{11}$ and Z$^{12}$ are independently —CH— or —N—;

(c) Z$^2$ is —CH—, —N—, or —CR$^{10}$—, wherein R$^{10}$ is —(C$_1$-C$_6$)alkyl;

(d) each of X$^8$ and X$^9$ are independently —CH—, —S—, —N—, or —O—;

(e) X$^1$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, or —OCH$_2$(halo);

(f) R$^7$ is —(CH$_2$)$_m$—N$^+$—(R$^2$)(R$^3$)(R$^4$), —(CH$_2$)$_m$—N—R$^3$R$^4$, —(CH$_2$)$_m$—C(═O)N—R$^3$R$^4$, —(CH$_2$)$_m$—R$^3$R$^4$, —(CH$_2$)$_m$—C(halo)$_3$, —(CH$_2$)$_m$-alkenyl, (CH$_2$)$_m$-alkenyl-CH$_3$, —(CH$_2$)$_m$-alkynyl, (CH$_2$)$_m$-alkynyl-CH$_3$, (CH$_2$)$_m$—(C$_3$-C$_8$)cycloalkyl, —(CH$_2$)$_m$—(C$_3$-C$_8$)heterocycloalkyl, —(CH$_2$)$_m$-phenyl, —(CH$_2$)$_m$-(5 or 6-membered)heteroaryl, —(CH$_2$)$_m$-cyano, where m is 1, 2, 3, 4 or 5 and where the cyloalkyl, heterocycle or phenyl is unsubstituted or substituted with one or more X$^1$ groups, with the proviso that when all of R$^2$-R$^4$ are present the compound further comprises a pharmaceutically acceptable counter ion;

(g) R$^2$ and R$^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —CH$_2$(halo), —CH$_2$C(halo)$_3$, —CHCH(halo)$_2$, CHCH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)CH$_2$OH or R$^2$ and R³ form an unsubstituted or substituted aziridine, azetidine, pyrrolidine, piperazine, or piperidine ring when taken together with the nitrogen to which they are attached;

(h) R⁴ is hydrogen, methyl, ethyl, isopropyl, t-butyl, isobutyl, or —C(halo)₃;

(i) R⁸ is —H, -halo, —NH₂, —CN, —(C₁-C₆)alkyl, —O(C₁-C₆)alkyl, —CH₂OH, —C(halo)₃, —CH(halo)₂, —CH₂(halo), —OC(halo)₃, —OCH(halo)₂, and —OCH₂(halo);

(j) R⁹ is —H, (CH₂)$_n$-cycloalkyl, —(CH₂)$_n$-heterocycloalkyl, —(CH₂)$_n$-aryl, —(CH₂)$_n$-heteroaryl, or —(CH₂)$_n$-cyano, wherein said cycloalkyl, heterocycloalkyl, aryl or heteroaryl is optionally substituted with one or more X¹ groups;

(k) a is an integer selected from 0, 1 and 2; and (l) n is an integer selected from 1, 2, 3 or 4.

In certain embodiments, Y is —S—, —CH₂—, or

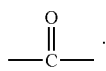

In another embodiment, Y is S or

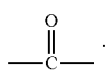

In another embodiment, Y is —S— or —CH₂—. In another embodiment, Y is —S— or —O—. In another embodiment, Y is —S—. In another embodiment, Y is —CH₂—. In another embodiment, Y is

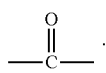

In some embodiments, Y is —C(R$^Y$)₂—, wherein each R$^Y$ is independently hydrogen, —OH, or halo.

In certain embodiments, Z¹ and Z² are —N—. In other embodiments, Z¹ is —N— and Z² is —C—.

In certain embodiments, R⁷ is —(CH₂)$_m$—N—(R³)(R⁴). In one such embodiment, R¹ is —(CH₂)₂—N—(R³)(R⁴). In another such embodiment, R¹ is —(CH₂)₃—N—(R³)(R⁴). In another such embodiment, R⁷ is —(CH₂)₂—N—(R³)(R⁴), R³ is H and R⁴ is isopropyl or isobutyl. In another such embodiment, R⁷ is —(CH₂)₃—N—R³R⁴, R³ is H and R⁴ is isopropyl or isobutyl. In another such embodiment, R⁷ is —(CH₂)₂—N—R³R⁴, R³ is H and R⁴ is isopropyl. It will be understood, that in these embodiments, the amine functionality may exist as a free base or as an acid addition salt. Acid addition salts can be prepared by addition of a suitable acid, as is well understood in the art. In particular embodiments, the acid addition salt may be a hydrochloride salt, a phosphate salt, a sulfate salt, a lactate salt, a citrate salt, a succinate salt, a benzene sulfonic acid salt, a mesylate salt, a tartrate salt, a lactobionate salt, apara-toluenesulfonic acid salt, or a fumaric acid-salt. In another embodiment, the acid addition salt is a hydrochloride salt or a sulfate salt. In another embodiment, the acid addition salt is a hydrochloride salt. In another embodiment, the acid addition salt is a sulfate salt. In another embodiment, the acid addition salt is a phosphate salt. When prepared as an acid addition salt, the purine-scaffold inhibitors are rendered water soluble. Solubility may be increased even further by production of higher order salts, particularly di-salts. For instance, in embodiments where Z₁ is —N—, the nitrogen is ionizable and can be converted to an acid addition salt under strongly acidic conditions (e.g., pH of less than about 3). Accordingly, Grp94 inhibitors of the disclosure in which Z₁ is —N— and the R⁷ group contains an amine functionality can be converted into di-salts. In certain embodiments, the Grp94 inhibitors of the disclosure can be in the form of a di-HCl salt.

In certain embodiments, R⁷ is —(CH₂)$_m$—CF₃. In one such embodiment, R⁷ is —(CH₂)₃—CF₃. In another such embodiment, R⁷ is —(CH₂)₄—CF₃. In another such embodiment, R⁷ is —(CH₂)₂—CF₃.

In another embodiment, R⁷ is —(CH₂)₃-alkynyl. In another embodiment, R⁷ is —(CH₂)₃—CCH. In another embodiment, R⁷ is —(CH₂)₄-alkynyl. In another embodiment, R⁷ is —(CH₂)$_m$-cyano.

In certain embodiments, R⁹ is —(CH₂)$_n$-aryl. In one such embodiment, R⁹ is —(CH₂)$_n$-aryl. In another such embodiment, R⁹ is an unsubstituted benzyl group. In another such embodiment, R⁹ is a substituted benzyl group. In another such embodiment, R⁹ is a para-substituted substituted benzyl group. In another such embodiment, R⁹ is a para-methoxy substituted benzyl group.

In other embodiments, the Grp94 inhibitors of Formula (IV) have one of the Formula of Table 8, wherein each substituent is as defined above and described in classes and subclasses herein, both singly and in combination.

TABLE 8

| Formula | Compound |
|---|---|
| IVA | 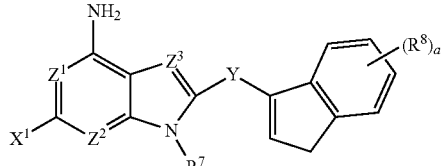 |
| IVB | 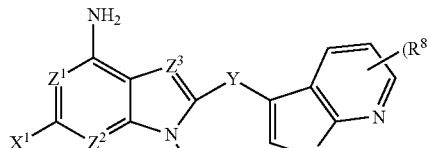 |
| IVC | 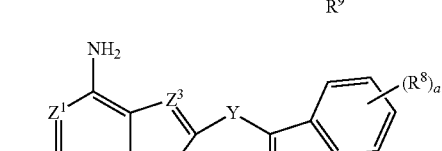 |
| IVD | 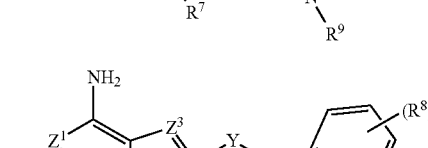 |

TABLE 8-continued

| Formula | Compound |
|---|---|
| IVE | |
| IVF | |
| IVG | |
| IVH | |
| IVI | |
| IVJ | |
| IVK | |
| IVL | |
| IVM | |
| IVN | |

TABLE 8-continued

| Formula | Compound |
|---|---|
| IVO | 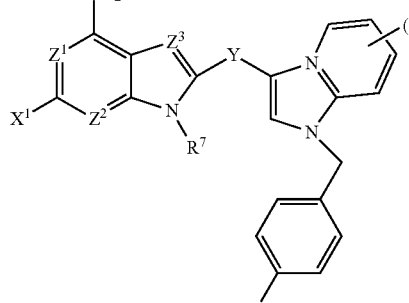 |
| IVP | 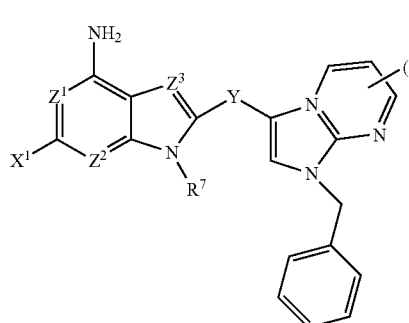 |

Illustrative compounds of Formula (IV) are listed below in Tables 9.

TABLE 9

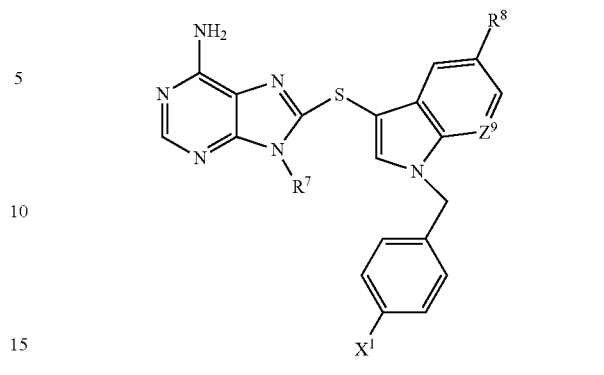

and pharmaceutically acceptable salts thereof, where:

| $R^7$ | $X^1$ | $Z^9$ | $R^8$ |
|---|---|---|---|
| (H$_2$C)$_3$—≡ | H | CH | H |
| (H$_2$C)$_3$—≡ | H | N | H |
| (H$_2$C)$_3$—≡ | H | CH | Br |
| (H$_2$C)$_3$—≡ | H | N | Br |
| (H$_2$C)$_3$—≡ | OCH$_3$ | CH | H |
| (H$_2$C)$_3$—≡ | OCH$_3$ | N | H |
| (H$_2$C)$_3$—≡ | OCH$_3$ | CH | Br |
| (H$_2$C)$_3$—≡ | OCH$_3$ | N | Br |
| (CH$_2$)$_3$—NHCH(CH$_3$)$_2$ | H | CH | H |
| (CH$_2$)$_3$—NHCH(CH$_3$)$_2$ | H | N | H |
| (CH$_2$)$_3$—NHCH(CH$_3$)$_2$ | H | CH | Br |
| (CH$_2$)$_3$—NHCH(CH$_3$)$_2$ | H | N | Br |
| (CH$_2$)$_3$—NHCH(CH$_3$)$_2$ | OCH$_3$ | CH | H |
| (CH$_2$)$_3$—NHCH(CH$_3$)$_2$ | OCH$_3$ | N | H |

TABLE 9-continued

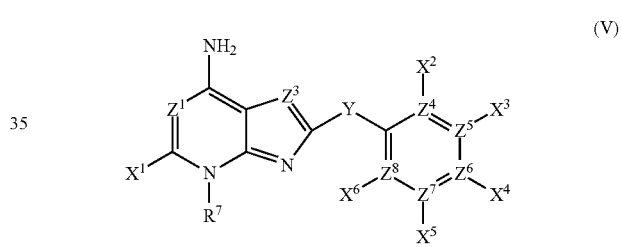

and pharmaceutically acceptable salts thereof, where:

| $R^7$ | $X^1$ | $Z^9$ | $R^8$ |
|---|---|---|---|
| (CH$_2$)$_3$—NHCH(CH$_3$)$_2$ | OCH$_3$ | CH | Br |
| (CH$_2$)$_3$—NHCH(CH$_3$)$_2$ | OCH$_3$ | N | Br |

5.3.5 Grp94 Inhibitors of Formula (V)

In one aspect, the disclosure encompasses purine-scaffold compounds that are substituted at the 8-position with a linker group bonded to aryl or heteroaryl group and are further substituted at the N-3 position. Such compounds are represented schematically in Formula (V):

(V)

or a pharmaceutically acceptable salt thereof, wherein:

(a) Y is —C(R$^Y$)$_2$—, —S—, —NR—, —O—, $$-\overset{O}{\underset{S}{\|}}-, \quad -\overset{O}{\underset{S}{\overset{\|}{\|}}}\overset{O}{-}, \quad -\overset{O}{\underset{C}{\|}}- \text{ or } -\overset{S}{\underset{C}{\|}}-;$$

(b) each of $Z^1$ and $Z^3$ are independently —CH— or —N—;

(c) $Z^2$ is —N— or —CR$^{10}$—, wherein R$^{10}$ is H or unsubstituted or substituted —(C$_1$-C$_6$)aliphatic;

(d) each of $Z^4$, $Z^5$, $Z^6$, $Z^7$ and $Z^8$ are independently —C— or —N—, with the proviso that no three consecutive $Z^4$ through $Z^8$ are N;

(e) $X^1$ is —H, -halo, —N(R)$_2$, —OR, —CN, or unsubstituted or substituted —(C$_1$-C$_6$)aliphatic;

(f) each of $X^4$, $X^5$, and $X^6$ are independently —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered)arylalkyl, and (5- or 6-membered)heterocyclic aromatic or heterocyclic non-aromatic group; with the provisos that at least one of $X^2$, $X^4$ and $X^5$ is —H and that $X^2$ is absent when $Z^4$ is —N—, $X^3$ is absent when $Z^5$ is —N—, $X^4$ is absent when $Z^6$ is —N— and $X^5$ is absent when $Z^7$ is —N—;

(g) each of $X^2$ and $X^3$ are independently selected from
(1) —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered)arylalkyl, and (5- or 6-membered) heterocyclic aromatic or heterocyclic non-aromatic group; or
(2) $X^2$ and $X^3$ taken together form a fused benzo or fused (5- or 6-membered) heteroaryl that may be substituted with one or more $R^8$ groups;

(h) $R^7$ is —(C$_1$-C$_6$)aliphatic-N$^+$—(R$^2$)(R$^3$)(R$^4$), —(C$_1$-C$_6$)aliphatic-N—R$^3$R$^4$, —(C$_1$-C$_6$)aliphatic-C(=O)N—R$^3$R$^4$, —(C$_1$-C$_6$)aliphatic-R$^3$R$^4$, —(C$_1$-C$_6$)aliphatic-R$^2$R$^3$R$^4$, —(C$_1$-C$_6$)aliphatic-N—CR$^2$R$^3$R$^4$, —(C$_1$-C$_6$)aliphatic-C(halo)$_3$, —(C$_1$-C$_6$)aliphatic-alkenyl, —(C$_1$-C$_6$)aliphatic-alkynyl, —(C$_1$-C$_6$)aliphatic-(C$_3$-C$_8$)cycloalkyl, —(C$_1$-C$_6$)aliphatic-(C$_3$-C$_8$)heterocycloalkyl, —(C$_1$-C$_6$)aliphatic-phenyl, —(C$_1$-C$_6$)aliphatic-(5 or 6-membered)heteroaryl, —(C$_1$-C$_6$)aliphatic-cyano, with the proviso that when all of $R^2$-$R^4$ are present the compound further comprises a pharmaceutically acceptable counter ion;

(i) $R^2$ and $R^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$) aliphatic, or $R^3$ and $R^4$ form an unsubstituted or substituted 3- to 7-membered heterocyclic ring when taken together with the nitrogen to which they are attached;

(j) $R^8$ is —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered) arylalkyl, and (5- or 6-membered)heterocyclic aromatic or heterocyclic non-aromatic group;

(k) each $R^Y$ is independently R, —OR, or halo;

(l) $R^4$ is hydrogen, halogen, or unsubstituted or substituted —(C$_1$-C$_6$)aliphatic; and (m) each R is independently hydrogen, unsubstituted C$_{1-6}$ aliphatic, or C$_{1-6}$ aliphatic substituted with halo, —OH, —CN, or —NH$_2$;

wherein each substituted group is substituted with one or more groups selected from halo, —N(R)$_2$, —OR, —CN, oxo, unsubstituted C$_{1-6}$ aliphatic, or C$_{1-6}$ aliphatic substituted with halo, —OH, —CN, or —NH$_2$.

In some embodiments, a compound of formula (V) or pharmaceutically acceptable salt thereof is defined wherein:
(a) Y is —CH$_2$—, —S—, —N—, —O—,

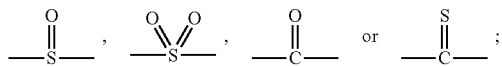

(b) each of $Z^1$ and $Z^3$ are independently —CH— or —N—;

(c) $Z^2$ is —CH—, —N—, or —CR$^{10}$—, wherein $R^{10}$ is —(C$_1$-C$_6$)alkyl;

(d) each of $Z^4$, $Z^5$, $Z^6$, $Z^7$ and $Z^8$ are independently —CH— or —N—, with the proviso that no three consecutive $Z^4$ through $Z^8$ are N;

(e) $X^1$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, or —OCH$_2$(halo);

(f) each of $X^4$, $X^5$, and $X^6$ are independently —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, —OCH$_2$(halo), pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl (g) each of $X^2$ and $X^3$ are independently selected from
(1) —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, —OCH$_2$(halo), pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl; and
(2) $X^2$ and $X^3$ taken together form a fused benzo or fused (5- or 6-membered) heteroaryl that may be substituted with one or more $R^8$ groups;

(h) $R^7$ is —(CH$_2$)$_m$—N$^+$—(R$^2$)(R$^3$)(R$^4$), —(CH$_2$)$_m$—N—R$^3$R$^4$, —(CH$_2$)$_m$—C(=O)N—R$^3$R$^4$, —(CH$_2$)$_m$—C(halo)$_3$, —(CH$_2$)$_m$-alkenyl, (CH$_2$)$_m$-alkenyl-CH$_3$, —(CH$_2$)$_m$-alkynyl, (CH$_2$)$_m$-alkynyl-CH$_3$, (CH$_2$)$_m$—(C$_3$-C$_8$)cycloalkyl, —(CH$_2$)$_m$—(C$_3$-C$_8$)heterocycloalkyl, —(CH$_2$)$_m$-phenyl, —(CH$_2$)$_m$—(5 or 6-membered)heteroaryl, —(CH$_2$)$_m$-cyano, where m is 1, 2, 3, 4 or 5 and where the cyloalkyl, heterocycle or phenyl is unsubstituted or substituted with one or more $X^1$ groups, with the proviso that when all of $R^2$-$R^4$ are present the compound further comprises a pharmaceutically acceptable counter ion;

(i) $R^2$ and $R^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —CH$_2$(halo), —CH$_2$C(halo)$_3$, —CHCH(halo)$_2$, CHCH$_2$(halo), —CH$_2$OH, —CH$_2$CH$_2$OH, —CH$_2$C(CH$_3$)$_2$OH, —CH$_2$CH(CH$_3$)OH, —C(CH$_3$)$_2$CH$_2$OH, —CH(CH$_3$)CH$_2$OH or $R^2$ and $R^3$ form an unsubstituted or substituted aziridine, azetidine, pyrrolidine, piperazine, or piperidine ring when taken together with the nitrogen to which they are attached;

(j) $R^4$ is hydrogen, methyl, ethyl, isopropyl, t-butyl, isobutyl, or —C(halo)$_3$; and (k) $R^8$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, and —OCH$_2$ (halo), and $X^3$, $X^4$, $X^5$, and $X^6$ are independently selected from —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, —OCH$_2$(halo), pyridyl, furyl, phenyl, benzyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl.

In one embodiment, $Z^1$ and $Z^3$ are —N—. In another embodiment, $Z^1$ is —N— and $Z^3$ is —C—. In another embodiment, $Z^1$ is —C— and $Z^3$ is —N—.

In another embodiment, $Z^4$, $Z^5$, $Z^6$, $Z^7$ and $Z^8$ are —C—. In another embodiment, $Z^4$ is —N— and $Z^5$, $Z^6$, $Z^7$ and $Z^8$ are —C—. In another embodiment, $Z^5$ is —N— and $Z^4$, $Z^6$, $Z^7$ and $Z^8$ are —C—. In another embodiment, $Z^6$ is —N— and $Z^4$, $Z^5$, $Z^7$ and $Z^8$ are —C—. In another embodiment, $Z^7$ is —N— and $Z^4$, $Z^5$, $Z^6$ and $Z^8$ are —C—. In another embodiment, $Z^8$ is —N— and $Z^4$, $Z^5$, $Z^6$ and $Z^7$ are —C—. In another embodiment, $Z^7$ and $Z^4$ are —N— and $Z^5$, $Z^6$ and $Z^8$ are —C—. In another embodiment, $Z^5$ and $Z^8$ are —N— and $Z^4$, $Z^6$ and $Z^7$ are —C—.

In another embodiment, Y is —S—, —CH$_2$—, or

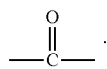

In another embodiment, Y is S or

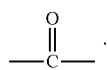

In another embodiment, Y is —S— or —CH$_2$—. In another embodiment, Y is —S— or —O—. In another embodiment, Y is —S—. In another embodiment, Y is —CH$_2$—. In another embodiment, Y is

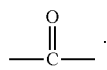

In some embodiments, Y is —C(R$^Y$)$_2$—, wherein each R$^Y$ is independently hydrogen, —OH, or halo.

In certain embodiment, $R^7$ is —(CH$_2$)$_m$—N—(R$^3$)(R$^4$). In one such embodiment, $R^1$ is —(CH$_2$)$_2$—N—(R$^3$)(R$^4$). In another such embodiment, $R^1$ is —(CH$_2$)$_3$—N—(R$^3$)(R$^4$). In another such embodiment, $R^7$ is —(CH$_2$)$_2$—N—(R$^3$)(R$^4$), R$^3$ is H and R$^4$ is isopropyl or isobutyl. In another such embodiment, $R^7$ is —(CH$_2$)$_3$—N—(R$^3$)(R$^4$), R$^3$ is H and R$^4$ is isopropyl or isobutyl. In another such embodiment, $R^7$ is —(CH$_2$)$_3$—N—(R$^3$)(R$^4$), R$^3$ is H and R$^4$ is isopropyl. In another such embodiment, $R^7$ is —(CH$_2$)$_3$—N—(R$^3$)(R$^4$), R$^3$ is H and R$^4$ is isobutyl. It will be understood, that in these embodiments, the amine functionality may exist as a free base or as an acid addition salt. Acid addition salts can be prepared by addition of a suitable acid, as is well understood in the art. In particular embodiments, the acid addition salt may be a hydrochloride salt, a phosphate salt, a sulfate salt, a lactate salt, a citrate salt, a succinate salt, a mesylate salt, a tartrate salt, a lactobionate salt, a benzene sulfonic acid salt, a para-toluenesulfonic acid salt, or a fumaric acid-salt. In another embodiment, the acid addition salt is a hydrochloride salt or a sulfate salt. In another embodiment, the acid addition salt is a hydrochloride salt. In another embodiment, the acid addition salt is a sulfate salt. In another embodiment, the acid addition salt is a phosphate salt. When prepared as an acid addition salt, the purine-scaffold inhibitors are rendered water soluble. Solubility may be increased even further by production of higher order salts, particularly di-salts. For instance, in embodiments where $Z_1$ is —N—, the nitrogen is ionizable and can be converted to an acid addition salt under strongly acidic conditions (e.g., pH of less than 3). Accordingly, Grp94 inhibitors of the disclosure in which $Z_1$ is —N—and the $R^7$ group contains an amine functionality can be converted into di-salts. In certain embodiments, the Grp94 inhibitors of the disclosure can be in the form of a di-HCl salt.

In certain embodiments, $R^7$ is —(CH$_2$)$_m$—CF$_3$. In one such embodiment, $R^7$ is —(CH$_2$)$_3$—CF$_3$. In another such embodiment, $R^7$ is —(CH$_2$)$_4$—CF$_3$.

In another embodiment, $R^7$ is —(CH$_2$)$_2$-alkenyl. In another embodiment, $R^7$ is —(CH$_2$)$_3$—CCH. In another embodiment, $R^7$ is —(CH$_2$)$_4$-alkenyl.

In some embodiments, $R^7$ is CH$_2$CCCH$_3$.

In another embodiment, $R^7$ is —(CH$_2$)$_2$-alkynyl. In another embodiment, $R^7$ is —(CH$_2$)$_3$-alkynyl. In another embodiment, $R^7$ is —(CH$_2$)$_3$—CCH. In another embodiment, $R^7$ is —(CH$_2$)$_4$-alkynyl. In another embodiment, $R^7$ is —(CH$_2$)$_4$—CCH. In another embodiment, $R^7$ is —(CH$_2$)$_m$-cyano.

In some embodiments, $R^7$ is benzyl.

In another embodiment, $X^1$ is —H. In another embodiment, $X^1$ is a halogen atom. In another embodiment, $X^1$ is —F. In another embodiment, $X^1$ is —Cl.

In another embodiment, $X^2$ is a halogen atom and $X^3$, $X^4$, $X^5$ and $X^6$ are hydrogen. In another embodiment $X^2$ is —Cl and $X^3$, $X^4$, $X^5$ and $X^6$ are hydrogen. In another embodiment $X^2$ is —OCH$_3$ and $X^3$, $X^4$, $X^5$ and $X^6$ are hydrogen. In another embodiment $X^2$ is —OCF$_3$ and $X^3$, $X^4$, $X^5$ and $X^6$ are hydrogen.

In another embodiment, $X^4$ is a halogen atom and $X^2$, $X^3$, $X^5$ and $X^6$ are hydrogen. In another embodiment $X^4$ is —Cl and $X^2$, $X^3$, $X^5$ and $X^6$ are hydrogen. In another embodiment $X^4$ is —OCH$_3$ and $X^2$, $X^3$, $X^5$ and $X^6$ are hydrogen. In another embodiment $X^4$ is —OCF$_3$ and $X^2$, $X^3$, $X^5$ and $X^6$ are hydrogen.

In certain embodiments, $Z^4$ and $Z^6$ are —C—, $X^2$ and $X^4$ are independently selected from —H, -halo, —(C$_1$-C$_3$)alkyl and —O(C$_1$-C$_3$)alkyl and $Z^5$, $Z^7$ and $Z^8$ are either an unsubstituted carbon or a nitrogen atom. In one such embodiment, at least one of $X^2$ and $X^4$ are -halo. In another such embodiment, both $X^2$ and $X^4$ are —Cl. In another such embodiment, at least one of $X^2$ and $X^4$ are alkyl groups. In another such embodiment, both $X^2$ and $X^4$ are —CH$_3$. In another such embodiment, at least one of $X^2$ and $X^4$ are —OCH$_3$. In another such embodiment, at least one of $X^2$ and $X^4$ are —CF$_3$.

In certain embodiments, $Z^4$ and $Z^7$ are —C—, $X^2$ and $X^5$ are independently selected from —H, -halo, —(C$_1$-C$_3$)alkyl, —(C$_1$-C$_3$)haloalkyl, —(C$_1$-C$_3$)haloalkyl, and —O(C$_1$-C$_3$)alkyl and $Z^5$, $Z^6$ and $Z^8$ are either an unsubstituted carbon or a nitrogen atom. In one such embodiment, at least one of $X^2$ and $X^5$ are halogen atoms. In another such embodiment, both $X^2$ and $X^5$ are —Cl. In another such embodiment, at least one of $X^2$ and $X^4$ are alkyl groups. In another such embodiment, both $X^2$ and $X^5$ are —CH$_3$. In another such embodiment, at least one of $X^2$ and $X^4$ are —CF$_3$ In certain embodiments, $Z^5$ and $Z^7$ are —C—, $X^3$ and $X^5$ are independently selected from —H, -halo, —(C$_1$-C$_3$)alkyl, —(C$_1$-C$_3$)haloalkyl, —O(C$_1$-C$_3$)haloalkyl, and —O(C$_1$-C$_3$)alkyl and $Z^4$, $Z^6$ and $Z^8$ are either an unsubstituted carbon or a nitrogen atom. In one such embodiment, at least one of $X^3$ and $X^5$ are halogen atoms. In another such embodiment, both $X^3$ and $X^5$ are —Cl. In another such embodiment, at least one of $X^3$ and $X^5$ are alkyl groups. In another such embodiment, both $X^3$ and $X^5$ are —CH$_3$. In another such embodiment, at least one of $X^3$ and $X^5$ are —CF$_3$.

In some embodiments, $X^3$ and $X^4$ are halo and $X^2$, $X^5$, and $X^6$ are hydrogen.

In some embodiments, $X^2$, $X^4$ and $X^5$ are halo and $X^3$ and $X^6$ are hydrogen. In some embodiments, $X^2$, $X^3$ and $X^5$ are halo and $X^4$ and $X^6$ are hydrogen. In some embodiments, $X^2$, $X^3$ and $X^4$ are halo and $X^5$ and $X^6$ are hydrogen.

In some embodiments, $X^2$, $X^4$, and $X^6$ are methyl and $X^3$ and $X^5$ are hydrogen.

In another embodiment, $X^2$ and $X^3$ taken together form a fused benzo. In another embodiment, $X^2$ and $X^3$ taken together form a substituted or unsubstituted fused pyridyl.

In some embodiments, the Grp94 inhibitors of Formula (V) are of Formula (Va):

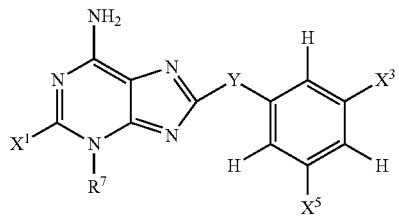

Va or a pharmaceutically acceptable salt thereof, wherein each of $X^1$, $R^7$, Y, $X^3$, and $X^5$ is as defined above and described in classes and subclasses herein, both singly and in combination.

In some embodiments, the Grp94 inhibitors of Formula (V) are of Formula (Vb):

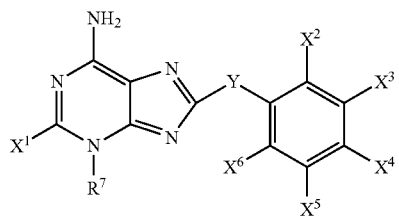

Vb or a pharmaceutically acceptable salt thereof, wherein $R^7$ is as defined above where i) the —($C_1$-$C_6$)aliphatic group attached to the ring nitrogen is —$(CH_2)_3$— or ii) m is 3; and each of $X^1$, Y, $X^2$, $X^3$, $X^4$, $X^5$ and $X^6$ is as defined above and described in classes and subclasses herein, both singly and in combination.

In other embodiments, the Grp94 inhibitors of Formula (V) have one of the Formula of Table 10, wherein each substituent is as defined above and described in classes and subclasses herein, both singly and in combination.

TABLE 10

| Formula | Compound |
|---|---|
| VA | |
| VB | |
| VC | |
| VD | |
| VE | |
| VF | |
| VG | |
| VH | |

TABLE 10-continued
| Formula | Compound |
|---|---|
| VV | 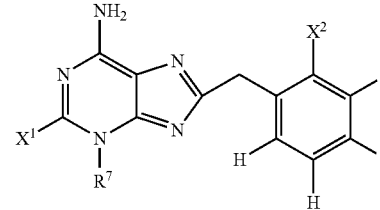 |
| VJ | 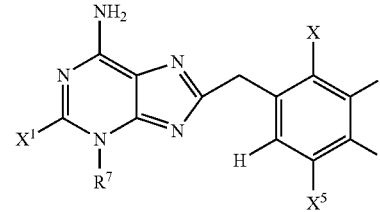 |
| VK | 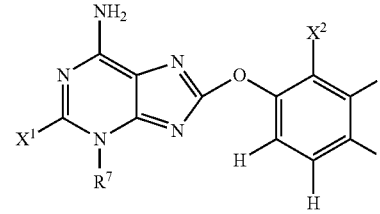 |
| VL | 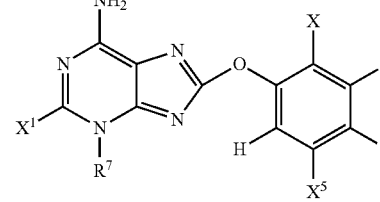 |
| VM | 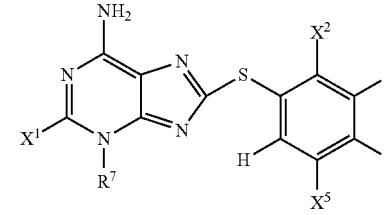 |
| VN | 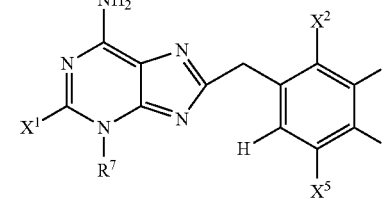 |
| VO | 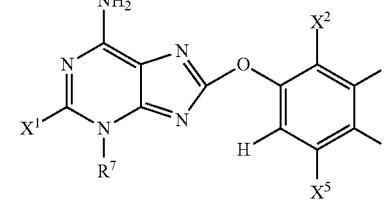 |
| VP | 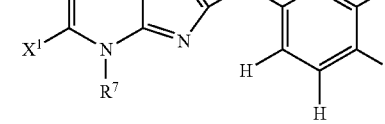 |
| VQ | 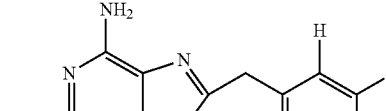 |
| VR |  |
| VS | 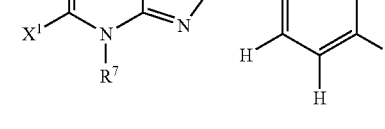 |
| VT | 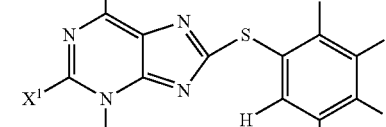 |
| VU | 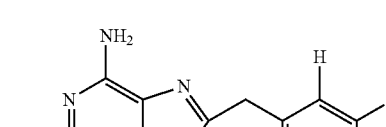 |

TABLE 10-continued

| Formula | Compound |
|---|---|
| VV | (structure) |
| VW | (structure) |
| VX | (structure) |
| VY | (structure) |
| VZ | (structure) |
| VAA | (structure) |
| VAB | (structure) |
| VAC | (structure) |
| VAD | (structure) |
| VAE | (structure) |

TABLE 10-continued

| Formula | Compound |
|---|---|
| VAF | 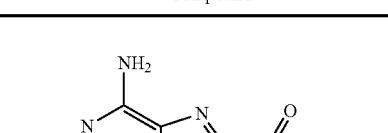 |

TABLE 11

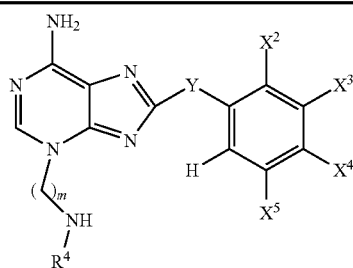

and pharmaceutically acceptable salts thereof, where:

| m | R⁴ | Y | X² | X³ | X⁴ | X⁵ |
|---|---|---|---|---|---|---|
| 3 | CH(CH₃)₂ | S | H | Cl | H | H |
| 3 | CH(CH₃)₂ | S | H | H | H | Cl |
| 3 | CH(CH₃)₂ | S | H | H | Cl | H |
| 3 | CH(CH₃)₂ | S | H | Cl | H | Cl |
| 3 | CH(CH₃)₂ | S | H | Cl | Cl | Cl |
| 3 | CH(CH₃)₂ | O | H | Cl | H | H |
| 3 | CH(CH₃)₂ | O | H | H | H | Cl |
| 3 | CH(CH₃)₂ | O | H | H | Cl | H |
| 3 | CH(CH₃)₂ | O | H | Cl | H | Cl |
| 3 | CH(CH₃)₂ | O | H | Cl | Cl | Cl |
| 3 | CH(CH₃)₂ | CH₂ | H | Cl | H | H |
| 3 | CH(CH₃)₂ | CH₂ | H | H | H | Cl |
| 3 | CH(CH₃)₂ | CH₂ | H | H | Cl | H |
| 3 | CH(CH₃)₂ | CH₂ | H | Cl | H | Cl |
| 3 | CH(CH₃)₂ | CH₂ | H | Cl | Cl | Cl |
| 3 | CH(CH₃)₂ | C=O | H | H | H | Cl |
| 3 | CH(CH₃)₂ | C=O | H | H | Cl | H |
| 3 | CH(CH₃)₂ | C=O | H | Cl | H | Cl |
| 3 | CH(CH₃)₂ | C=O | H | Cl | Cl | Cl |
| 3 | CH(CH₃)₂ | S | H | Cl | H | H |
| 3 | CH(CH₃)₂ | S | H | H | H | Cl |
| 3 | CH(CH₃)₂ | S | H | H | Cl | H |
| 3 | CH(CH₃)₂ | S | H | Cl | H | Cl |
| 3 | CH(CH₃)₂ | S | H | Cl | Cl | Cl |
| 3 | CH(CH₃)₂ | O | H | Cl | H | H |
| 3 | CH(CH₃)₂ | O | H | H | H | Cl |
| 3 | CH(CH₃)₂ | O | H | H | Cl | H |
| 3 | CH(CH₃)₂ | O | H | Cl | H | Cl |
| 3 | CH(CH₃)₂ | O | H | Cl | Cl | Cl |
| 3 | CH(CH₃)₂ | CH₂ | H | Cl | H | H |
| 3 | CH(CH₃)₂ | CH₂ | H | H | H | Cl |
| 3 | CH(CH₃)₂ | CH₂ | H | H | Cl | H |
| 3 | CH(CH₃)₂ | CH₂ | H | Cl | H | Cl |
| 3 | CH(CH₃)₂ | CH₂ | H | Cl | Cl | Cl |
| 3 | CH(CH₃)₂ | C=O | H | H | H | Cl |
| 3 | CH(CH₃)₂ | C=O | H | H | Cl | H |
| 3 | CH(CH₃)₂ | C=O | H | Cl | H | Cl |
| 3 | CH(CH₃)₂ | C=O | H | Cl | Cl | Cl |
| 2 | CH₂CH(OH)CH₃ | S | H | Cl | H | H |
| 2 | CH₂CH(OH)CH₃ | S | H | H | H | Cl |

TABLE 11-continued

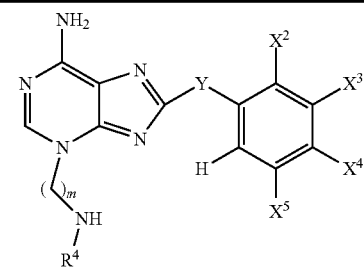

and pharmaceutically acceptable salts thereof, where:

| m | R⁴ | Y | X² | X³ | X⁴ | X⁵ |
|---|---|---|---|---|---|---|
| 2 | CH₂CH(OH)CH₃ | S | H | H | Cl | H |
| 2 | CH₂CH(OH)CH₃ | S | H | Cl | H | Cl |
| 2 | CH₂CH(OH)CH₃ | S | H | Cl | Cl | Cl |
| 2 | C(CH₃)₂CH₂OH | S | H | Cl | H | H |
| 2 | C(CH₃)₂CH₂OH | S | H | H | H | Cl |
| 2 | C(CH₃)₂CH₂OH | S | H | H | Cl | H |
| 2 | C(CH₃)₂CH₂OH | S | H | Cl | H | Cl |
| 2 | C(CH₃)₂CH₂OH | S | H | Cl | Cl | Cl |
| 2 | CH₂CHF₂ | S | H | Cl | H | H |
| 2 | CH₂CHF₂ | S | H | H | H | Cl |
| 2 | CH₂CHF₂ | S | H | H | Cl | H |
| 2 | CH₂CHF₂ | S | H | Cl | H | Cl |
| 2 | CH₂CHF₂ | S | H | Cl | Cl | Cl |
| 3 | CH₂C(CH₃)₂ | S | H | Cl | H | H |
| 3 | CH₂C(CH₃)₂ | S | H | H | H | Cl |
| 3 | CH₂C(CH₃)₂ | S | H | H | Cl | H |
| 3 | CH₂C(CH₃)₂ | S | H | Cl | H | Cl |
| 3 | CH₂C(CH₃)₂ | S | H | Cl | Cl | Cl |
| 3 | CH(CH₃)₂ | S | H | CH₃ | H | H |
| 3 | CH(CH₃)₂ | S | H | H | H | CH₃ |
| 3 | CH(CH₃)₂ | S | H | H | CH₃ | H |
| 3 | CH(CH₃)₂ | S | H | CH₃ | H | CH₃ |
| 3 | CH(CH₃)₂ | S | H | CH₃ | CH₃ | CH₃ |
| 3 | CH(CH₃)₂ | O | H | CH₃ | H | H |
| 3 | CH(CH₃)₂ | O | H | H | H | CH₃ |
| 3 | CH(CH₃)₂ | O | H | H | CH₃ | H |
| 3 | CH(CH₃)₂ | O | H | CH₃ | H | CH₃ |
| 3 | CH(CH₃)₂ | O | H | CH₃ | CH₃ | CH₃ |
| 3 | CH(CH₃)₂ | CH₂ | H | CH₃ | H | H |
| 3 | CH(CH₃)₂ | CH₂ | H | H | H | CH₃ |
| 3 | CH(CH₃)₂ | CH₂ | H | H | CH₃ | H |
| 3 | CH(CH₃)₂ | CH₂ | H | CH₃ | H | CH₃ |
| 3 | CH(CH₃)₂ | CH₂ | H | CH₃ | CH₃ | CH₃ |
| 3 | CH(CH₃)₂ | C=O | H | H | H | CH₃ |
| 3 | CH(CH₃)₂ | C=O | H | H | CH₃ | H |
| 3 | CH(CH₃)₂ | C=O | H | CH₃ | H | CH₃ |
| 3 | CH(CH₃)₂ | C=O | H | CH₃ | CH₃ | CH₃ |
| 3 | CH(CH₃)₂ | S | H | CH₃ | H | H |
| 3 | CH(CH₃)₂ | S | H | H | H | CH₃ |
| 3 | CH(CH₃)₂ | S | H | H | CH₃ | H |
| 3 | CH(CH₃)₂ | S | H | CH₃ | H | CH₃ |
| 3 | CH(CH₃)₂ | S | H | CH₃ | CH₃ | CH₃ |
| 3 | CH(CH₃)₂ | O | H | CH₃ | H | H |
| 3 | CH(CH₃)₂ | O | H | H | H | Cl |
| 3 | CH(CH₃)₂ | O | H | H | CH₃ | H |
| 3 | CH(CH₃)₂ | O | H | CH₃ | H | CH₃ |
| 3 | CH(CH₃)₂ | O | H | CH₃ | CH₃ | CH₃ |
| 3 | CH(CH₃)₂ | CH₂ | H | CH₃ | H | H |
| 3 | CH(CH₃)₂ | CH₂ | H | H | H | CH₃ |
| 3 | CH(CH₃)₂ | CH₂ | H | H | CH₃ | H |
| 3 | CH(CH₃)₂ | CH₂ | H | CH₃ | H | CH₃ |
| 3 | CH(CH₃)₂ | CH₂ | H | CH₃ | CH₃ | CH₃ |
| 3 | CH(CH₃)₂ | C=O | H | H | H | CH₃ |
| 3 | CH(CH₃)₂ | C=O | H | H | CH₃ | H |
| 3 | CH(CH₃)₂ | C=O | H | CH₃ | H | CH₃ |
| 3 | CH(CH₃)₂ | C=O | H | CH₃ | CH₃ | CH₃ |
| 2 | CH₂CH(OH)CH₃ | S | H | CH₃ | H | H |
| 2 | CH₂CH(OH)CH₃ | S | H | H | H | CH₃ |
| 2 | CH₂CH(OH)CH₃ | S | H | H | CH₃ | H |
| 2 | CH₂CH(OH)CH₃ | S | H | CH₃ | H | CH₃ |
| 2 | CH₂CH(OH)CH₃ | S | H | CH₃ | CH₃ | CH₃ |
| 2 | C(CH₃)₂CH₂OH | S | H | CH₃ | H | H |
| 2 | C(CH₃)₂CH₂OH | S | H | H | H | CH₃ |

TABLE 11-continued

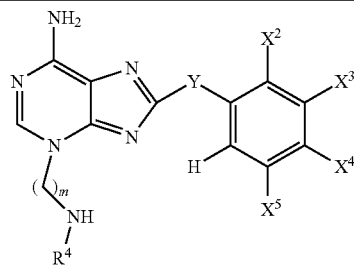

and pharmaceutically acceptable salts thereof, where:

| m | R⁴ | Y | X² | X³ | X⁴ | X⁵ |
|---|---|---|---|---|---|---|
| 2 | C(CH₃)₂CH₂OH | S | H | H | CH₃ | H |
| 2 | C(CH₃)₂CH₂OH | S | H | CH₃ | H | CH₃ |
| 2 | C(CH₃)₂CH₂OH | S | H | CH₃ | CH₃ | CH₃ |
| 2 | CH₂CHF₂ | S | H | CH₃ | H | H |
| 2 | CH₂CHF₂ | S | H | H | H | CH₃ |
| 2 | CH₂CHF₂ | S | H | H | CH₃ | H |
| 2 | CH₂CHF₂ | S | H | CH₃ | H | CH₃ |
| 3 | CH₂CHF₂ | S | H | CH₃ | CH₃ | CH₃ |
| 3 | CH₂C(CH₃)₂ | S | H | CH₃ | H | CH3 |
| 3 | CH₂C(CH₃)₂ | S | H | H | H | H |
| 3 | CH₂C(CH₃)₂ | S | H | H | CH₃ | CH₃ |
| 3 | CH₂C(CH₃)₂ | S | H | CH₃ | H | CH₃ |
| 2 | CH₂C(CH₃)₂ | S | H | CH₃ | CH₃ | H |
| 2 | H₂C—C≡C | S | H | CH₃ | H | H |
| 2 | H₂C—C≡C | S | H | H | H | CH₃ |
| 2 | H₂C—C≡C | S | H | H | CH₃ | H |
| 2 | H₂C—C≡C | S | H | CH₃ | H | CH₃ |
| 2 | H₂C—C≡C | S | H | CH₃ | CH₃ | CH₃ |
| 2 | CH(CH₃)₂ | S | H | Cl | H | H |
| 2 | CH₂CH₂OH | S | H | H | H | Cl |
| 2 | CH₂CH(CH₃)OH | S | H | H | Cl | H |
| 2 | CH(CH₃)CH₂OH | S | Cl | H | H | H |
| 2 | CH(CH₃)CH(CH₃)OH | S | H | Br | H | H |
| 2 | C(CH₃)₂CH₂OH | S | H | H | H | Br |
| 2 | CH₂C(CH₃)₂OH | S | H | Br | H | H |
| 2 | CH₂CHF₂ | S | Br | H | H | H |
| 2 | CH₂CF₃ | S | H | I | H | H |
| 2 | CH₂CH(CH₃)₂ | S | H | H | H | I |
| 2 | CH₂C(CH₃)₃ | S | H | H | I | H |
| 3 | H₂C—C≡N | S | I | H | H | H |
| 3 | H₂C—C≡CH | S | H | CH₃ | H | H |
| 3 | CH(CH₃)₂ | S | H | H | H | CH₃ |
| 3 | CH₂CH₂OH | S | H | H | CH₃ | H |
| 3 | CH₂CH(CH₃)OH | S | CH₃ | H | H | H |
| 3 | CH(CH₃)CH₂OH | S | H | C₂H₅ | H | H |
| 3 | CH(CH₃)CH(CH₃)OH | S | H | H | H | C₂H₅ |
| 3 | C(CH₃)₂CH₂OH | S | H | H | C₂H₅ | H |
| 3 | CH₂C(CH₃)₂OH | S | C₂H₅ | H | H | H |
| 3 | CH₂CHF₂ | S | H | i-C₃H₇ | H | H |
| 3 | CH₂CF₃ | S | H | H | H | i-C₃H₇ |
| 3 | CH₂CH(CH₃)₂ | S | H | H | i-C₃H₇ | H |
| 3 | CH₂C(CH₃)₃ | S | i-C₃H₇ | H | H | H |
| 3 | H₂C—C≡N | O | H | Cl | H | H |
| 2 | H₂C—C≡CH | O | H | H | H | Cl |
| 2 | CH(CH₃)₂ | O | H | H | Cl | H |
| 2 | CH₂CH₂OH | O | Cl | H | H | H |
| 2 | CH₂CH(CH₃)OH | O | H | Br | H | H |
| 2 | CH(CH₃)CH₂OH | O | H | H | H | Br |
| 2 | CH(CH₃)CH(CH₃)OH | O | H | H | Br | H |
| 2 | C(CH₃)₂CH₂OH | O | Br | H | H | H |
| 2 | CH₂C(CH₃)₂OH | O | H | H | I | H |
| 2 | CH₂CHF₂ | O | H | H | H | I |
| 2 | CH₂CF₃ | O | H | H | I | H |
| 2 | CH₂CH(CH₃)₂ | O | I | H | H | H |
| 3 | CH₂C(CH₃)₃ | O | H | CH₃ | H | H |
| 3 | H₂C—C≡N | O | H | H | H | CH₃ |
| 3 | H₂C—C≡CH | O | H | H | CH₃ | H |
| 3 | CH(CH₃)₂ | O | CH₃ | H | H | H |
| 3 | CH₂CH₂OH | O | H | C₂H₅ | H | H |
| 3 | CH₂CH(CH₃)OH | O | H | H | H | C₂H₅ |
| 3 | CH(CH₃)CH₂OH | O | H | H | C₂H₅ | H |
| 3 | CH(CH₃)CH(CH₃)OH | O | C₂H₅ | H | H | H |
| 3 | C(CH₃)₂CH₂OH | O | H | i-C₃H₇ | H | H |
| 3 | CH₂C(CH₃)₂OH | O | H | H | H | i-C₃H₇ |
| 3 | CH₂CHF₂ | O | H | H | i-C₃H₇ | H |
| 3 | CH₂CF₃ | O | i-C₃H₇ | H | H | H |
| 2 | CH₂CH(CH₃)₂ | S=O | H | Cl | H | H |
| 2 | CH₂C(CH₃)₃ | S=O | H | H | H | Cl |
| 2 | H₂C—C≡N | S=O | H | H | Cl | H |
| 2 | H₂C—C≡CH | S=O | Cl | H | H | H |
| 2 | CH(CH₃)₂ | S=O | H | Br | H | H |
| 2 | CH₂CH₂OH | S=O | H | H | H | Br |
| 2 | CH₂CH(CH₃)OH | S=O | H | H | Br | H |
| 2 | CH(CH₃)CH₂OH | S=O | Br | H | H | H |
| 2 | CH(CH₃)CH(CH₃)OH | S=O | H | I | H | H |
| 2 | C(CH₃)₂CH₂OH | S=O | H | H | H | I |
| 2 | CH₂C(CH₃)₂OH | S=O | H | H | I | H |
| 2 | CH₂CHF₂ | S=O | I | H | H | H |
| 3 | CH₂CF₃ | S=O | H | CH₃ | H | H |
| 3 | CH₂CH(CH₃)₂ | S=O | H | H | H | CH₃ |
| 3 | CH₂C(CH₃)₃ | S=O | H | H | CH₃ | H |
| 3 | H₂C—C≡N | S=O | CH₃ | H | H | H |
| 3 | H₂C—C≡CH | S=O | H | C₂H₅ | H | H |
| 3 | CH(CH₃)₂ | S=O | H | H | H | C₂H₅ |
| 3 | CH₂CH₂OH | S=O | H | H | C₂H₅ | H |
| 3 | CH₂CH(CH₃)OH | S=O | C₂H₅ | H | H | H |
| 3 | CH(CH₃)CH₂OH | S=O | H | i-C₃H₇ | H | H |
| 3 | CH(CH₃)₂ | S=O | H | H | H | i-C₃H₇ |
| 3 | CH₂CH₂OH | S=O | H | H | i-C₃H₇ | H |
| 3 | CH₂CH(CH₃)OH | S=O | i-C₃H₇ | H | H | H |
| 2 | CH(CH₃)CH₂OH | O=S=O | H | Cl | H | H |
| 2 | CH(CH₃)CH(CH₃)OH | O=S=O | H | H | H | Cl |
| 2 | C(CH₃)₂CH₂OH | O=S=O | H | H | Cl | H |
| 2 | CH₂C(CH₃)₂OH | O=S=O | Cl | H | H | H |
| 2 | CH₂CHF₂ | O=S=O | H | Br | H | H |
| 2 | CH₂CF₃ | O=S=O | H | H | H | Br |
| 2 | CH₂CH(CH₃)₂ | O=S=O | H | H | Br | H |
| 2 | CH₂C(CH₃)₃ | O=S=O | Br | H | H | H |
| 2 | H₂C—C≡N | O=S=O | H | I | H | H |
| 2 | H₂C—C≡CH | O=S=O | H | H | H | I |
| 2 | CH(CH₃)₂ | O=S=O | H | H | I | H |
| 2 | CH₂CH₂OH | O=S=O | I | H | H | H |
| 3 | CH₂CH(CH₃)OH | O=S=O | H | CH₃ | H | H |
| 3 | CH(CH₃)CH₂OH | O=S=O | H | H | H | CH₃ |
| 3 | CH(CH₃)CH(CH₃)OH | O=S=O | H | H | CH₃ | H |
| 3 | C(CH₃)₂CH₂OH | O=S=O | CH₃ | H | H | H |
| 3 | CH₂C(CH₃)₂OH | O=S=O | H | C₂H₅ | H | H |
| 3 | CH₂CHF₂ | O=S=O | H | H | H | C₂H₅ |
| 3 | CH₂CF₃ | O=S=O | H | H | C₂H₅ | H |
| 3 | CH₂CH(CH₃)₂ | O=S=O | C₂H₅ | H | H | H |
| 3 | CH₂C(CH₃)₃ | O=S=O | H | i-C₃H₇ | H | H |
| 3 | H₂C—C≡N | O=S=O | H | H | H | i-C₃H₇ |
| 3 | H₂C—C≡CH | O=S=O | H | H | i-C₃H₇ | H |
| 3 | CH(CH₃)₂ | O=S=O | i-C₃H₇ | H | H | H |
| 2 | CH₂CH₂OH | NH | H | Cl | H | H |
| 2 | CH₂CH(CH₃)OH | NH | H | H | H | Cl |
| 2 | CH(CH₃)CH₂OH | NH | H | H | Cl | H |
| 2 | CH(CH₃)CH(CH₃)OH | NH | Cl | H | H | H |
| 2 | C(CH₃)₂CH₂OH | NH | H | Br | H | H |
| 2 | CH₂C(CH₃)₂OH | NH | H | H | H | Br |
| 2 | CH₂CHF₂ | NH | H | H | Br | H |
| 2 | CH₂CF₃ | NH | Br | H | H | H |

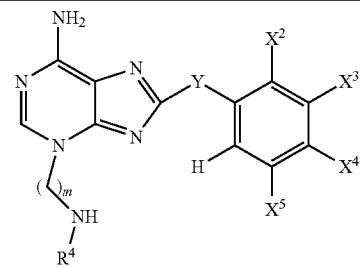

TABLE 11-continued

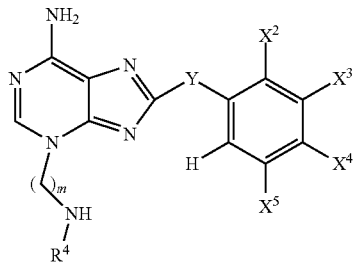

and pharmaceutically acceptable salts thereof, where:

| m | R⁴ | Y | X² | X³ | X⁴ | X⁵ |
|---|---|---|---|---|---|---|
| 2 | CH₂CH(CH₃)₂ | NH | H | I | H | H |
| 2 | CH₂C(CH₃)₃ | NH | H | H | H | I |
| 2 | H₂C—C≡N | NH | H | H | I | H |
| 2 | H₂C—C≡CH | NH | I | H | H | H |
| 3 | CH(CH₃)₂ | NH | H | CH₃ | H | H |
| 3 | CH₂CH₂OH | NH | H | H | H | CH₃ |
| 3 | CH₂CH(CH₃)OH | NH | H | H | CH₃ | H |
| 3 | CH(CH₃)CH₂OH | NH | CH₃ | H | H | H |
| 3 | CH(CH₃)CH(CH₃)OH | NH | H | C₂H₅ | H | H |
| 3 | C(CH₃)₂CH₂OH | NH | H | H | H | C₂H₅ |
| 3 | CH₂C(CH₃)₂OH | NH | H | H | C₂H₅ | H |
| 3 | CH₂CHF₂ | NH | C₂H₅ | H | H | H |
| 3 | CH₂CF₃ | NH | H | i-C₃H₇ | H | H |
| 3 | CH₂CH(CH₃)₂ | NH | H | H | H | i-C₃H₇ |
| 3 | CH₂C(CH₃)₃ | NH | H | H | i-C₃H₇ | H |
| 3 | H₂C—C≡N | NH | i-C₃H₇ | H | H | H |
| 2 | H₂C—C≡CH | C=O | H | Cl | H | H |
| 2 | CH(CH₃)₂ | C=O | H | H | H | Cl |
| 2 | CH₂CH₂OH | C=O | H | H | Cl | H |
| 2 | CH₂CH(CH₃)OH | C=O | Cl | H | H | H |
| 2 | CH(CH₃)CH₂OH | C=O | H | Br | H | H |
| 2 | CH(CH₃)CH(CH₃)OH | C=O | H | H | H | Br |
| 2 | C(CH₃)₂CH₂OH | C=O | H | H | Br | H |
| 2 | CH₂C(CH₃)₂OH | C=O | Br | H | H | H |
| 2 | CH₂CHF₂ | C=O | H | I | H | H |
| 2 | CH₂CF₃ | C=O | H | H | H | I |
| 2 | CH₂CH(CH₃)₂ | C=O | H | H | I | H |
| 2 | CH₂C(CH₃)₃ | C=O | I | H | H | H |
| 3 | H₂C—C≡N | C=O | H | CH₃ | H | H |
| 3 | H₂C—C≡CH | C=O | H | H | H | CH₃ |
| 3 | CH(CH₃)₂ | C=O | H | H | CH₃ | H |
| 3 | CH₂CH₂OH | C=O | CH₃ | H | H | H |
| 3 | CH₂CH(CH₃)OH | C=O | H | C₂H₅ | H | H |
| 3 | CH(CH₃)CH₂OH | C=O | H | H | H | C₂H₅ |
| 3 | CH(CH₃)CH(CH₃)OH | C=O | H | H | C₂H₅ | H |
| 3 | C(CH₃)₂CH₂OH | C=O | C₂H₅ | H | H | H |
| 3 | CH₂C(CH₃)₂OH | C=O | H | i-C₃H₇ | H | H |
| 3 | CH₂CHF₂ | C=O | H | H | H | i-C₃H₇ |
| 3 | CH₂CF₃ | C=O | H | H | i-C₃H₇ | H |
| 3 | CH₂CH(CH₃)₂ | C=O | i-C₃H₇ | H | H | H |
| 2 | CH₂C(CH₃)₃ | C=S | H | Cl | H | H |
| 2 | H₂C—C≡N | C=S | H | H | H | Cl |
| 2 | H₂C—C≡CH | C=S | H | H | Cl | H |
| 2 | CH(CH₃)₂ | C=S | Cl | H | H | H |
| 2 | CH₂CH₂OH | C=S | H | Br | H | H |
| 2 | CH₂CH(CH₃)OH | C=S | H | H | H | Br |
| 2 | CH(CH₃)CH₂OH | C=S | H | H | Br | H |
| 2 | CH(CH₃)CH(CH₃)OH | C=S | Br | H | H | H |
| 2 | C(CH₃)₂CH₂OH | C=S | H | I | H | H |
| 2 | CH₂C(CH₃)₂OH | C=S | H | H | H | I |
| 2 | CH₂CHF₂ | C=S | H | H | I | H |
| 2 | CH₂CF₃ | C=S | I | H | H | H |
| 3 | CH₂CH(CH₃)₂ | C=S | H | CH₃ | H | H |
| 3 | CH₂C(CH₃)₃ | C=S | H | H | H | CH₃ |
| 3 | H₂C—C≡N | C=S | H | H | CH₃ | H |
| 3 | H₂C—C≡CH | C=S | CH₃ | H | H | H |
| 3 | CH(CH₃)₂ | C=S | H | C₂H₅ | H | H |
| 3 | CH₂CH₂OH | C=S | H | H | H | C₂H₅ |
| 3 | CH₂CH(CH₃)OH | C=S | H | H | C₂H₅ | H |
| 3 | CH(CH₃)CH₂OH | C=S | C₂H₅ | H | H | H |
| 3 | CH(CH₃)CH(CH₃)OH | C=S | H | i-C₃H₇ | H | H |
| 3 | C(CH₃)₂CH₂OH | C=S | H | H | H | i-C₃H₇ |
| 3 | CH₂C(CH₃)₂OH | C=S | H | H | i-C₃H₇ | H |
| 3 | CH₂CHF₂ | C=S | i-C₃H₇ | H | H | H |
| 2 | CH₂CF₃ | CH₂ | H | Cl | H | H |
| 2 | CH₂CH(CH₃)₂ | CH₂ | H | H | H | Cl |
| 2 | CH₂C(CH₃)₃ | CH₂ | H | H | Cl | H |
| 2 | H₂C—C≡N | CH₂ | Cl | H | H | H |
| 2 | H₂C—C≡CH | CH₂ | H | Br | H | H |
| 2 | CH(CH₃)₂ | CH₂ | H | H | H | Br |
| 2 | CH₂CH₂OH | CH₂ | H | H | Br | H |
| 2 | CH₂CH(CH₃)OH | CH₂ | Br | H | H | H |
| 2 | CH(CH₃)CH₂OH | CH₂ | H | I | H | H |
| 2 | CH(CH₃)CH(CH₃)OH | CH₂ | H | H | H | I |
| 2 | C(CH₃)₂CH₂OH | CH₂ | H | H | I | H |
| 2 | CH₂C(CH₃)₂OH | CH₂ | I | H | H | H |
| 3 | CH₂CHF₂ | CH₂ | H | CH₃ | H | H |
| 3 | CH₂CF₃ | CH₂ | H | H | H | CH₃ |
| 3 | CH₂CH(CH₃)₂ | CH₂ | H | H | CH₃ | H |
| 3 | CH₂C(CH₃)₃ | CH₂ | CH₃ | H | H | H |
| 3 | H₂C—C≡N | CH₂ | H | C₂H₅ | H | H |
| 3 | H₂C—C≡CH | CH₂ | H | H | H | C₂H₅ |
| 3 | CH(CH₃)₂ | CH₂ | H | H | C₂H₅ | H |
| 3 | CH₂CH₂OH | CH₂ | C₂H₅ | H | H | H |
| 3 | CH₂CH(CH₃)OH | CH₂ | H | i-C₃H₇ | H | H |
| 3 | CH(CH₃)CH₂OH | CH₂ | H | H | H | i-C₃H₇ |
| 3 | CH(CH₃)CH(CH₃)OH | CH₂ | H | H | i-C₃H₇ | H |
| 3 | C(CH₃)₂CH₂OH | CH₂ | i-C₃H₇ | H | H | H |
| 2 | CH₂C(CH₃)₂OH | CH—OH | H | Cl | H | H |
| 2 | CH₂CHF₂ | CH—OH | H | H | H | Cl |
| 2 | CH₂CF₃ | CH—OH | H | H | Cl | H |
| 2 | CH₂CH(CH₃)₂ | CH—OH | Cl | H | H | H |
| 2 | CH₂C(CH₃)₃ | CH—OH | H | Br | H | H |
| 2 | H₂C—C≡N | CH—OH | H | H | H | Br |
| 2 | H₂C—C≡CH | CH—OH | H | H | Br | H |
| 2 | CH(CH₃)₂ | CH—OH | Br | H | H | H |
| 2 | CH₂CH₂OH | CH—OH | H | I | H | H |
| 2 | CH₂CH(CH₃)OH | CH—OH | H | H | H | I |
| 2 | CH(CH₃)CH₂OH | CH—OH | H | H | I | H |
| 2 | CH(CH₃)CH(CH₃)OH | CH—OH | I | H | H | H |
| 3 | C(CH₃)₂CH₂OH | CH—OH | H | CH₃ | H | H |
| 3 | CH₂C(CH₃)₂OH | CH—OH | H | H | H | CH₃ |
| 3 | CH₂CHF₂ | CH—OH | H | H | CH₃ | H |
| 3 | CH₂CF₃ | CH—OH | CH₃ | H | H | H |
| 3 | CH₂CH(CH₃)₂ | CH—OH | H | C₂H₅ | H | H |
| 3 | CH₂C(CH₃)₃ | CH—OH | H | H | H | C₂H₅ |
| 3 | H₂C—C≡N | CH—OH | H | H | C₂H₅ | H |
| 3 | H₂C—C≡CH | CH—OH | C₂H₅ | H | H | H |
| 3 | CH(CH₃)₂ | CH—OH | H | i-C₃H₇ | H | H |
| 2 | CH₂CH₂OH | CH—OH | H | H | H | i-C₃H₇ |
| 3 | CH₂CH(CH₃)OH | CH—OH | H | H | i-C₃H₇ | H |
| 3 | CH(CH₃)CH₂OH | CH—OH | i-C₃H₇ | H | H | H |
| 2 | CH(CH₃)CH(CH₃)OH | CH—F | H | Cl | H | H |
| 2 | C(CH₃)₂CH₂OH | CH—F | H | H | H | Cl |
| 2 | CH₂C(CH₃)₂OH | CH—F | H | H | Cl | H |
| 2 | CH₂CHF₂ | CH—F | Cl | H | H | H |
| 2 | CH₂CF₃ | CH—F | H | H | Br | H |
| 2 | CH₂CH(CH₃)₂ | CH—F | H | H | H | Br |
| 2 | CH₂C(CH₃)₃ | CH—F | H | H | Br | H |
| 2 | H₂C—C≡N | CH—F | Br | H | H | H |
| 2 | H₂C—C≡CH | CH—F | H | I | H | H |

TABLE 11-continued

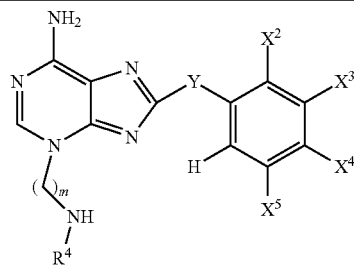

and pharmaceutically acceptable salts thereof, where:

| m | R⁴ | Y | X² | X³ | X⁴ | X⁵ |
|---|---|---|---|---|---|---|
| 2 | CH(CH₃)₂ | CH—F | H | H | H | I |
| 2 | CH₂CH₂OH | CH—F | H | H | I | H |
| 2 | CH₂CH(CH₃)OH | CH—F | I | H | H | H |
| 3 | CH(CH₃)CH₂OH | CH—F | H | CH₃ | H | H |
| 3 | CH(CH₃)CH(CH₃)OH | CH—F | H | H | H | CH₃ |
| 3 | C(CH₃)₂CH₂OH | CH—F | H | H | CH₃ | H |
| 3 | CH₂C(CH₃)₂OH | CH—F | CH₃ | H | H | H |
| 3 | CH₂CHF₂ | CH—F | H | C₂H₅ | H | H |
| 3 | CH₂CF₃ | CH—F | H | H | H | C₂H₅ |
| 3 | CH₂CH(CH₃)₂ | CH—F | H | H | C₂H₅ | H |
| 3 | CH₂C(CH₃)₃ | CH—F | C₂H₅ | H | H | H |
| 3 | H₂C—C≡N | CH—F | H | i-C₃H₇ | H | H |
| 3 | H₂C—C≡CH | CH—F | H | H | H | i-C₃H₇ |
| 3 | CH(CH₃)₂ | CH—F | H | H | i-C₃H₇ | H |
| 3 | CH₂CH₂OH | CH—F | i-C₃H₇ | H | H | H |
| 2 | CH₂CH(CH₃)OH | S | H | Cl | H | Cl |
| 2 | CH(CH₃)CH₂OH | S | Cl | H | Cl | H |
| 2 | CH(CH₃)CH(CH₃)OH | S | Cl | H | H | Cl |
| 2 | C(CH₃)₂CH₂OH | S | H | Br | H | Br |
| 2 | CH₂C(CH₃)₂OH | S | Br | H | Br | H |
| 2 | CH₂CHF₂ | S | Br | H | H | Br |
| 2 | CH₂CF₃ | S | H | I | H | I |
| 2 | CH₂CH(CH₃)₂ | S | I | H | I | H |
| 2 | CH₂C(CH₃)₃ | S | I | H | H | I |
| 2 | H₂C—C≡N | S | H | CH₃ | H | CH₃ |
| 2 | H₂C—C≡CH | S | CH₃ | H | CH₃ | H |
| 2 | CH(CH₃)₂ | S | CH₃ | H | H | CH₃ |
| 3 | CH₂CH₂OH | S | H | C₂H₅ | H | C₂H₅ |
| 3 | CH₂CH(CH₃)OH | S | C₂H₅ | H | C₂H₅ | H |
| 3 | CH(CH₃)CH₂OH | S | C₂H₅ | H | H | C₂H₅ |
| 3 | CH(CH₃)CH(CH₃)OH | S | H | i-C₃H₇ | H | i-C₃H₇ |
| 3 | C(CH₃)₂CH₂OH | S | i-C₃H₇ | H | i-C₃H₇ | H |
| 3 | CH₂C(CH₃)₂OH | S | i-C₃H₇ | H | H | i-C₃H₇ |
| 3 | CH₂CHF₂ | O | H | Cl | H | Cl |
| 3 | CH₂CF₃ | O | Cl | H | H | H |
| 3 | CH₂CH(CH₃)₂ | O | Cl | H | H | Cl |
| 3 | CH₂C(CH₃)₃ | O | H | Br | H | Br |
| 3 | H₂C—C≡N | O | Br | H | Br | H |
| 3 | H₂C—C≡CH | O | Br | H | H | Br |
| 2 | CH(CH₃)₂ | O | H | I | H | I |
| 2 | CH₂CH₂OH | O | I | H | I | H |
| 2 | CH₂CH(CH₃)OH | O | I | H | H | I |
| 2 | CH(CH₃)CH₂OH | O | H | CH₃ | H | CH₃ |
| 2 | CH(CH₃)CH(CH₃)OH | O | CH₃ | H | CH₃ | H |
| 2 | C(CH₃)₂CH₂OH | O | CH₃ | H | H | CH₃ |
| 2 | CH₂C(CH₃)₂OH | O | H | C₂H₅ | H | C₂H₅ |
| 2 | CH₂CHF₂ | O | C₂H₅ | H | C₂H₅ | H |
| 2 | CH₂CF₃ | O | C₂H₅ | H | H | C₂H₅ |
| 2 | CH₂CH(CH₃)₂ | O | H | i-C₃H₇ | H | i-C₃H₇ |
| 2 | CH₂C(CH₃)₃ | O | i-C₃H₇ | H | i-C₃H₇ | H |
| 2 | H₂C—C≡N | O | i-C₃H₇ | H | H | i-C₃H₇ |
| 3 | H₂C—C≡CH | S=O | H | Cl | H | Cl |
| 3 | CH(CH₃)₂ | S=O | Cl | H | Cl | H |
| 3 | CH₂CH₂OH | S=O | Cl | H | H | Cl |
| 3 | CH₂CH(CH₃)OH | S=O | H | Br | H | Br |
| 3 | CH(CH₃)CH₂OH | S=O | Br | H | Br | H |
| 3 | CH(CH₃)CH(CH₃)OH | S=O | Br | H | H | Br |
| 3 | C(CH₃)₂CH₂OH | S=O | H | I | H | I |
| 3 | CH₂C(CH₃)₂OH | S=O | I | H | I | H |
| 3 | CH₂CHF₂ | S=O | I | H | H | I |
| 3 | CH₂CF₃ | S=O | H | CH₃ | H | CH₃ |
| 3 | CH₂CH(CH₃)₂ | S=O | CH₃ | H | CH₃ | H |
| 3 | CH₂C(CH₃)₃ | S=O | CH₃ | H | H | CH₃ |
| 2 | H₂C—C≡N | S=O | H | C₂H₅ | H | C₂H₅ |
| 2 | H₂C—C≡CH | S=O | C₂H₅ | H | C₂H₅ | H |
| 2 | CH(CH₃)₂ | S=O | C₂H₅ | H | H | C₂H₅ |
| 2 | CH₂CH₂OH | S=O | H | i-C₃H₇ | H | i-C₃H₇ |
| 2 | CH₂CH(CH₃)OH | S=O | i-C₃H₇ | H | i-C₃H₇ | H |
| 2 | CH(CH₃)CH₂OH | S=O | i-C₃H₇ | H | H | i-C₃H₇ |
| 2 | CH(CH₃)CH(CH₃)OH | O=S=O | H | Cl | H | Cl |
| 2 | C(CH₃)₂CH₂OH | O=S=O | Cl | H | Cl | H |
| 2 | CH₂C(CH₃)₂OH | O=S=O | Cl | H | H | Cl |
| 2 | CH₂CHF₂ | O=S=O | H | Br | H | Br |
| 2 | CH₂CF₃ | O=S=O | Br | H | Br | H |
| 2 | CH₂CH(CH₃)₂ | O=S=O | Br | H | H | Br |
| 3 | CH₂C(CH₃)₃ | O=S=O | H | I | H | I |
| 3 | H₂C—C≡N | O=S=O | I | H | I | H |
| 3 | H₂C—C≡CH | O=S=O | I | H | H | I |
| 3 | CH(CH₃)₂ | O=S=O | H | CH₃ | H | CH₃ |
| 3 | CH₂CH₂OH | O=S=O | CH₃ | H | CH₃ | H |
| 3 | CH₂CH(CH₃)OH | O=S=O | CH₃ | H | H | CH₃ |
| 3 | CH(CH₃)CH₂OH | O=S=O | H | C₂H₅ | H | C₂H₅ |
| 3 | CH(CH₃)CH(CH₃)OH | O=S=O | C₂H₅ | H | C₂H₅ | H |
| 3 | C(CH₃)₂CH₂OH | O=S=O | C₂H₅ | H | H | C₂H₅ |
| 3 | CH₂C(CH₃)₂OH | O=S=O | H | i-C₃H₇ | H | i-C₃H₇ |
| 3 | CH₂CHF₂ | O=S=O | i-C₃H₇ | H | i-C₃H₇ | H |
| 3 | CH₂CF₃ | O=S=O | i-C₃H₇ | H | H | i-C₃H₇ |
| 2 | CH₂CH(CH₃)₂ | NH | H | Cl | H | Cl |
| 2 | CH₂C(CH₃)₃ | NH | Cl | H | Cl | H |
| 2 | H₂C—C≡N | NH | Cl | H | H | Cl |
| 2 | H₂C—C≡CH | NH | H | Br | H | Br |
| 2 | CH(CH₃)₂ | NH | Br | H | Br | H |
| 2 | CH₂CH₂OH | NH | Br | H | H | Br |
| 2 | CH₂CH(CH₃)OH | NH | H | I | H | I |
| 2 | CH(CH₃)CH₂OH | NH | I | H | I | H |
| 2 | CH(CH₃)CH(CH₃)OH | NH | I | H | H | I |
| 2 | C(CH₃)₂CH₂OH | NH | H | CH₃ | H | CH₃ |
| 2 | CH₂C(CH₃)₂OH | NH | CH₃ | H | CH₃ | H |
| 2 | CH₂CHF₂ | NH | CH₃ | H | H | CH₃ |
| 3 | CH₂CF₃ | NH | H | C₂H₅ | H | C₂H₅ |
| 3 | CH₂CH(CH₃)₂ | NH | C₂H₅ | H | C₂H₅ | H |
| 3 | CH₂C(CH₃)₃ | NH | C₂H₅ | H | H | C₂H₅ |
| 3 | H₂C—C≡N | NH | H | i-C₃H₇ | H | i-C₃H₇ |
| 3 | H₂C—C≡CH | NH | i-C₃H₇ | H | i-C₃H₇ | H |
| 3 | CH(CH₃)₂ | NH | i-C₃H₇ | H | H | i-C₃H₇ |
| 3 | CH₂CH₂OH | C=O | H | Cl | H | Cl |
| 3 | CH₂CH(CH₃)OH | C=O | Cl | H | Cl | H |
| 3 | CH(CH₃)CH₂OH | C=O | Cl | H | H | Cl |
| 3 | CH(CH₃)CH(CH₃)OH | C=O | H | Br | H | Br |
| 3 | C(CH₃)₂CH₂OH | C=O | Br | H | Br | H |
| 3 | CH₂CHF₂ | C=O | Br | H | H | I |
| 3 | CH₂CF₃ | C=O | I | H | I | H |
| 2 | CH₂CH(CH₃)₂ | C=O | I | H | H | I |
| 2 | CH₂C(CH₃)₃ | C=O | H | CH₃ | H | CH₃ |

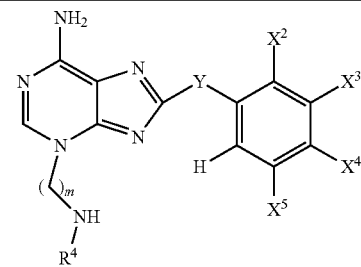

TABLE 11-continued

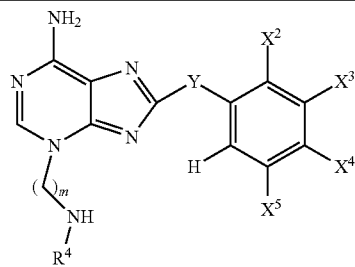

and pharmaceutically acceptable salts thereof, where:

| m | R⁴ | Y | X² | X³ | X⁴ | X⁵ |
|---|---|---|---|---|---|---|
| 2 | H₂C—C≡N | C=O | CH₃ | H | CH₃ | H |
| 2 | H₂C—C≡CH | C=O | CH₃ | H | H | CH₃ |
| 2 | CH(CH₃)₂ | C=O | H | C₂H₅ | H | C₂H₅ |
| 2 | CH₂CH₂OH | C=O | C₂H₅ | H | C₂H₅ | H |
| 2 | CH₂CH(CH₃)OH | C=O | C₂H₅ | H | H | C₂H₅ |
| 2 | CH(CH₃)CH₂OH | C=O | H | i-C₃H₇ | H | i-C₃H₇ |
| 2 | CH(CH₃)CH(CH₃)OH | C=O | i-C₃H₇ | H | i-C₃H₇ | H |
| 2 | C(CH₃)₂CH₂OH | C=O | i-C₃H₇ | H | H | i-C₃H₇ |
| 3 | CH₂C(CH₃)₂OH | C=S | H | Cl | H | Cl |
| 3 | CH₂CHF₂ | C=S | Cl | H | Cl | H |
| 3 | CH₂CF₃ | C=S | Cl | H | H | Cl |
| 3 | CH₂CH(CH₃)₂ | C=S | H | Br | H | Br |
| 3 | CH₂C(CH₃)₃ | C=S | Br | H | Br | H |
| 3 | H₂C—C≡N | C=S | Br | H | H | Br |
| 3 | H₂C—C≡CH | C=S | H | I | H | I |
| 3 | CH(CH₃)₂ | C=S | I | H | I | H |
| 3 | CH₂CH₂OH | C=S | I | H | H | I |
| 3 | CH₂CH(CH₃)OH | C=S | H | CH₃ | H | CH₃ |
| 2 | CH(CH₃)CH₂OH | C=S | CH₃ | H | CH₃ | H |
| 2 | CH(CH₃)CH(CH₃)OH | C=S | CH₃ | H | H | CH₃ |
| 2 | C(CH₃)₂CH₂OH | C=S | H | C₂H₅ | H | C₂H₅ |
| 2 | CH₂C(CH₃)₂OH | C=S | C₂H₅ | H | C₂H₅ | H |
| 2 | CH₂CHF₂ | C=S | C₂H₅ | H | H | C₂H₅ |
| 2 | CH₂CF₃ | C=S | H | i-C₃H₇ | H | i-C₃H₇ |
| 2 | CH₂CH(CH₃)₂ | C=S | i-C₃H₇ | H | i-C₃H₇ | H |
| 2 | CH₂C(CH₃)₃ | C=S | i-C₃H₇ | H | H | i-C₃H₇ |
| 3 | H₂C—C≡N | CH₂ | H | Cl | H | Cl |
| 3 | H₂C—C≡CH | CH₂ | Cl | H | Cl | H |
| 3 | CH(CH₃)₂ | CH₂ | Cl | H | H | Cl |
| 3 | CH₂CH₂OH | CH₂ | H | Br | H | Br |
| 3 | CH₂CH(CH₃)OH | CH₂ | Br | H | Br | H |
| 3 | CH(CH₃)CH₂OH | CH₂ | Br | H | H | Br |
| 2 | CH(CH₃)CH(CH₃)OH | CH₂ | H | I | H | I |
| 2 | C(CH₃)₂CH₂OH | CH₂ | I | H | I | H |
| 2 | CH₂C(CH₃)₂OH | CH₂ | I | H | H | I |
| 2 | CH₂CHF₂ | CH₂ | H | CH₃ | H | CH₃ |
| 2 | CH₂CF₃ | CH₂ | CH₃ | H | CH₃ | H |
| 2 | CH₂CH(CH₃)₂ | CH₂ | CH₃ | H | H | CH₃ |
| 3 | CH₂C(CH₃)₃ | CH₂ | H | C₂H₅ | H | C₂H₅ |
| 3 | H₂C—C≡N | CH₂ | C₂H₅ | H | C₂H₅ | H |
| 3 | H₂C—C≡CH | CH₂ | C₂H₅ | H | H | C₂H₅ |
| 3 | CH(CH₃)₂ | CH₂ | H | i-C₃H₇ | H | i-C₃H₇ |
| 3 | CH₂CH₂OH | CH₂ | i-C₃H₇ | H | i-C₃H₇ | H |
| 3 | CH₂CH(CH₃)OH | CH₂ | i-C₃H₇ | H | H | i-C₃H₇ |
| 2 | CH(CH₃)CH₂OH | CH—OH | H | Cl | H | Cl |
| 2 | CH(CH₃)CH(CH₃)OH | CH—OH | Cl | H | Cl | H |
| 2 | C(CH₃)₂CH₂OH | CH—OH | Cl | H | H | Cl |
| 2 | CH₂C(CH₃)₂OH | CH—OH | H | Br | H | Br |
| 2 | CH₂CHF₂ | CH—OH | Br | H | Br | H |
| 2 | CH₂CF₃ | CH—OH | Br | H | H | Br |
| 3 | CH₂CH(CH₃)₂ | CH—OH | H | I | H | I |
| 3 | CH₂C(CH₃)₃ | CH—OH | I | H | I | H |
| 3 | H₂C—C≡N | CH—OH | I | H | H | I |
| 3 | H₂C—C≡CH | CH—OH | H | CH₃ | H | CH₃ |
| 3 | CH(CH₃)₂ | CH—OH | CH₃ | H | CH₃ | H |
| 3 | CH₂CH₂OH | CH—OH | CH₃ | H | H | CH₃ |
| 2 | CH₂CH(CH₃)OH | CH—OH | H | C₂H₅ | H | C₂H₅ |
| 2 | CH(CH₃)CH₂OH | CH—OH | C₂H₅ | H | C₂H₅ | H |
| 2 | CH(CH₃)CH(CH₃)OH | CH—OH | C₂H₅ | H | H | C₂H₅ |
| 2 | C(CH₃)₂CH₂OH | CH—OH | H | i-C₃H₇ | H | i-C₃H₇ |
| 2 | CH₂C(CH₃)₂OH | CH—OH | i-C₃H₇ | H | i-C₃H₇ | H |
| 2 | CH₂CHF₂ | CH—OH | i-C₃H₇ | H | H | i-C₃H₇ |
| 3 | CH₂CF₃ | CH—F | H | Cl | H | Cl |
| 3 | CH₂CH(CH₃)₂ | CH—F | Cl | H | Cl | H |
| 3 | CH₂C(CH₃)₃ | CH—F | Cl | H | H | Cl |
| 3 | H₂C—C≡N | CH—F | H | Br | H | Br |
| 3 | H₂C—C≡CH | CH—F | Br | H | Br | H |
| 3 | CH(CH₃)₂ | CH—F | Br | H | H | Br |
| 2 | CH₂CH₂OH | CH—F | H | I | H | I |
| 2 | CH₂CH(CH₃)OH | CH—F | I | H | I | H |
| 2 | CH(CH₃)CH₂OH | CH—F | I | H | H | I |
| 2 | CH(CH₃)CH(CH₃)OH | CH—F | H | CH₃ | H | CH₃ |
| 2 | C(CH₃)₂CH₂OH | CH—F | CH₃ | H | CH₃ | H |
| 2 | CH₂C(CH₃)₂OH | CH—F | CH₃ | H | H | CH₃ |
| 3 | CH₂CHF₂ | CH—F | H | C₂H₅ | H | C₂H₅ |
| 3 | CH₂CF₃ | CH—F | C₂H₅ | H | C₂H₅ | H |
| 3 | CH₂CH(CH₃)₂ | CH—F | C₂H₅ | H | H | C₂H₅ |
| 3 | CH₂C(CH₃)₃ | CH—F | H | i-C₃H₇ | H | i-C₃H₇ |
| 3 | H₂C—C≡N | CH—F | i-C₃H₇ | H | i-C₃H₇ | H |
| 3 | H₂C—C≡CH | CH—F | i-C₃H₇ | H | H | i-C₃H₇ |
| 2 | CH(CH₃)₂ | S | H | Cl | Cl | Cl |
| 2 | CH₂CH₂OH | S | Cl | H | Cl | H |
| 2 | CH₂CH(CH₃)OH | S | H | Br | Br | Br |
| 2 | CH(CH₃)CH₂OH | S | Br | Br | H | Br |
| 2 | CH(CH₃)CH(CH₃)OH | S | H | I | I | I |
| 2 | C(CH₃)₂CH₂OH | S | I | I | H | I |
| 3 | CH₂C(CH₃)₂OH | S | H | CH₃ | CH₃ | CH₃ |
| 3 | CH₂CHF₂ | S | CH₃ | CH₃ | H | CH₃ |
| 3 | CH₂CF₃ | S | H | C₂H₅ | C₂H₅ | C₂H₅ |
| 3 | CH₂CH(CH₃)₂ | S | C₂H₅ | C₂H₅ | H | C₂H₅ |
| 3 | CH₂C(CH₃)₃ | S | H | i-C₃H₇ | i-C₃H₇ | i-C₃H₇ |
| 3 | H₂C—C≡N | S | i-C₃H₇ | i-C₃H₇ | H | i-C₃H₇ |
| 2 | H₂C—C≡CH | O | H | Cl | Cl | Cl |
| 2 | CH(CH₃)₂ | O | Cl | Cl | H | Cl |
| 2 | CH₂CH₂OH | O | H | Br | Br | Br |
| 2 | CH₂CH(CH₃)OH | O | Br | Br | H | Br |
| 2 | CH(CH₃)CH₂OH | O | H | I | I | I |
| 2 | CH(CH₃)CH(CH₃)OH | O | I | I | H | I |
| 3 | C(CH₃)₂CH₂OH | O | H | CH₃ | CH₃ | CH₃ |
| 3 | CH₂C(CH₃)₂OH | O | CH₃ | CH₃ | H | CH₃ |
| 3 | CH₂CHF₂ | O | H | C₂H₅ | C₂H₅ | C₂H₅ |
| 3 | CH₂CF₃ | O | C₂H₅ | C₂H₅ | H | C₂H₅ |
| 3 | CH₂CH(CH₃)₂ | O | H | i-C₃H₇ | i-C₃H₇ | i-C₃H₇ |
| 3 | CH₂C(CH₃)₃ | O | i-C₃H₇ | i-C₃H₇ | H | i-C₃H₇ |
| 2 | H₂C—C≡N | S=O | H | Cl | Cl | Cl |
| 2 | H₂C—C≡CH | S=O | Cl | Cl | H | Cl |
| 2 | CH(CH₃)₂ | S=O | H | Br | Br | Br |
| 2 | CH₂CH₂OH | S=O | Br | Br | H | Br |
| 2 | CH₂CH(CH₃)OH | S=O | H | I | I | I |
| 2 | CH(CH₃)CH₂OH | S=O | I | I | H | I |
| 3 | CH(CH₃)CH(CH₃)OH | S=O | H | CH₃ | CH₃ | CH₃ |
| 3 | C(CH₃)₂CH₂OH | S=O | CH₃ | CH₃ | H | CH₃ |

TABLE 11-continued

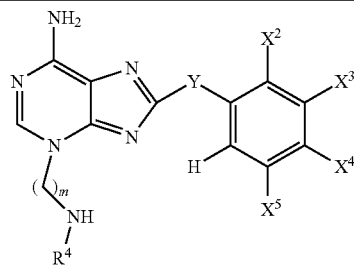

and pharmaceutically acceptable salts thereof, where:

| m | R⁴ | Y | X² | X³ | X⁴ | X⁵ |
|---|---|---|---|---|---|---|
| 3 | CH₂C(CH₃)₂OH | S=O | H | C₂H₅ | C₂H₅ | C₂H₅ |
| 3 | CH₂CHF₂ | S=O | C₂H₅ | C₂H₅ | H | C₂H₅ |
| 3 | CH₂CF₃ | S=O | H | i-C₃H₇ | i-C₃H₇ | i-C₃H₇ |
| 3 | CH₂CH(CH₃)₂ | S=O | i-C₃H₇ | i-C₃H₇ | H | i-C₃H₇ |
| 2 | CH₂C(CH₃)₃ | O=S=O | H | Cl | Cl | Cl |
| 2 | H₂C—C≡N | O=S=O | Cl | Cl | H | Cl |
| 2 | H₂C—C≡CH | O=S=O | H | Br | Br | Br |
| 2 | CH(CH₃)₂ | O=S=O | Br | Br | H | Br |
| 2 | CH₂CH₂OH | O=S=O | H | I | I | I |
| 2 | CH₂CH(CH₃)OH | O=S=O | I | I | H | I |
| 3 | CH(CH₃)CH₂OH | O=S=O | H | CH₃ | CH₃ | CH₃ |
| 3 | CH(CH₃)CH(CH₃)OH | O=S=O | CH₃ | CH₃ | H | CH₃ |
| 3 | C(CH₃)₂CH₂OH | O=S=O | H | C₂H₅ | C₂H₅ | C₂H₅ |
| 3 | CH₂C(CH₃)₂OH | O=S=O | C₂H₅ | C₂H₅ | H | C₂H₅ |
| 3 | CH₂CHF₂ | O=S=O | H | i-C₃H₇ | i-C₃H₇ | i-C₃H₇ |
| 3 | CH₂CF₃ | O=S=O | i-C₃H₇ | i-C₃H₇ | H | i-C₃H₇ |
| 2 | CH₂CH(CH₃)₂ | NH | H | Cl | Cl | Cl |
| 2 | CH₂C(CH₃)₃ | NH | Cl | Cl | H | Cl |
| 2 | H₂C—C≡N | NH | H | Br | Br | Br |
| 2 | H₂C—C≡CH | NH | Br | Br | H | Br |
| 2 | CH(CH₃)₂ | NH | H | I | I | I |
| 2 | CH₂CH₂OH | NH | I | I | H | I |
| 3 | CH₂CH(CH₃)OH | NH | H | CH₃ | CH₃ | CH₃ |
| 3 | CH(CH₃)CH₂OH | NH | CH₃ | CH₃ | H | CH₃ |
| 3 | CH(CH₃)CH(CH₃)OH | NH | H | C₂H₅ | C₂H₅ | C₂H₅ |
| 3 | C(CH₃)₂CH₂OH | NH | C₂H₅ | C₂H₅ | H | C₂H₅ |
| 3 | CH₂C(CH₃)₂OH | NH | H | i-C₃H₇ | i-C₃H₇ | i-C₃H₇ |
| 3 | CH₂CHF₂ | NH | i-C₃H₇ | i-C₃H₇ | H | i-C₃H₇ |
| 2 | CH₂CF₃ | C=O | H | Cl | Cl | Cl |
| 2 | CH₂CH(CH₃)₂ | C=O | Cl | Cl | H | Cl |
| 2 | CH₂C(CH₃)₃ | C=O | H | Br | Br | Br |
| 2 | H₂C—C≡N | C=O | Br | Br | H | Br |
| 2 | H₂C—C≡CH | C=O | H | I | I | I |
| 3 | CH(CH₃)₂ | C=O | I | I | H | I |
| 3 | CH₂CH₂OH | C=O | H | CH₃ | CH₃ | CH₃ |
| 3 | CH₂CH(CH₃)OH | C=O | CH₃ | CH₃ | H | CH₃ |
| 3 | CH(CH₃)CH₂OH | C=O | H | C₂H₅ | C₂H₅ | C₂H₅ |
| 3 | CH(CH₃)CH(CH₃)OH | C=O | C₂H₅ | C₂H₅ | H | C₂H₅ |
| 3 | C(CH₃)₂CH₂OH | C=O | H | i-C₃H₇ | i-C₃H₇ | i-C₃H₇ |
| 3 | CH₂C(CH₃)₂OH | C=O | i-C₃H₇ | i-C₃H₇ | H | i-C₃H₇ |
| 2 | CH₂CHF₂ | C=S | H | Cl | Cl | Cl |
| 2 | CH₂CF₃ | C=S | Cl | Cl | H | Cl |
| 2 | CH₂CH(CH₃)₂ | C=S | H | Br | Br | Br |
| 2 | CH₂C(CH₃)₃ | C=S | Br | Br | H | Br |
| 2 | H₂C—C≡N | C=S | H | I | I | I |
| 2 | H₂C—C≡CH | C=S | I | I | H | I |
| 3 | CH(CH₃)₂ | C=S | H | CH₃ | CH₃ | CH₃ |
| 3 | CH₂CH₂OH | C=S | CH₃ | CH₃ | H | CH₃ |
| 3 | CH₂CH(CH₃)OH | C=S | H | C₂H₅ | C₂H₅ | C₂H₅ |
| 3 | CH(CH₃)CH₂OH | C=S | C₂H₅ | C₂H₅ | H | C₂H₅ |
| 3 | CH(CH₃)CH(CH₃)OH | C=S | H | i-C₃H₇ | i-C₃H₇ | i-C₃H₇ |
| 3 | C(CH₃)₂CH₂OH | C=S | i-C₃H₇ | i-C₃H₇ | H | i-C₃H₇ |
| 2 | CH₂C(CH₃)₂OH | CH₂ | H | Cl | Cl | Cl |
| 2 | CH₂CHF₂ | CH₂ | Cl | Cl | H | Cl |
| 2 | CH₂CF₃ | CH₂ | H | Br | Br | Br |
| 2 | CH₂CH(CH₃)₂ | CH₂ | Br | Br | H | Br |
| 2 | CH₂C(CH₃)₃ | CH₂ | H | I | I | I |
| 2 | H₂C—C≡N | CH₂ | I | I | H | I |
| 3 | H₂C—C≡CH | CH₂ | H | CH₃ | CH₃ | CH₃ |
| 3 | CH(CH₃)₂ | CH₂ | CH₃ | CH₃ | H | CH₃ |
| 3 | CH₂CH₂OH | CH₂ | H | C₂H₅ | C₂H₅ | C₂H₅ |
| 3 | CH₂CH(CH₃)OH | CH₂ | C₂H₅ | C₂H₅ | H | C₂H₅ |
| 3 | CH(CH₃)CH₂OH | CH₂ | H | i-C₃H₇ | i-C₃H₇ | i-C₃H₇ |
| 3 | CH(CH₃)CH(CH₃)OH | CH₂ | i-C₃H₇ | i-C₃H₇ | H | i-C₃H₇ |
| 2 | C(CH₃)₂CH₂OH | CH—OH | H | Cl | Cl | Cl |
| 2 | CH₂C(CH₃)₂OH | CH—OH | Cl | Cl | H | Cl |
| 2 | CH₂CHF₂ | CH—OH | H | Br | Br | Br |
| 2 | CH₂CF₃ | CH—OH | Br | Br | H | Br |
| 2 | CH₂CH(CH₃)₂ | CH—OH | H | I | I | I |
| 2 | CH₂C(CH₃)₃ | CH—OH | I | I | H | I |
| 3 | H₂C—C≡N | CH—OH | H | CH₃ | CH₃ | CH₃ |
| 3 | H₂C—C≡CH | CH—OH | CH₃ | CH₃ | H | CH₃ |
| 3 | CH(CH₃)₂ | CH—OH | H | C₂H₅ | C₂H₅ | C₂H₅ |
| 3 | CH₂CH₂OH | CH—OH | C₂H₅ | C₂H₅ | H | C₂H₅ |
| 3 | CH₂CH(CH₃)OH | CH—OH | H | i-C₃H₇ | i-C₃H₇ | i-C₃H₇ |
| 3 | CH(CH₃)CH₂OH | CH—OH | i-C₃H₇ | i-C₃H₇ | H | i-C₃H₇ |
| 2 | CH(CH₃)CH(CH₃)OH | CH—F | H | Cl | Cl | Cl |
| 2 | C(CH₃)₂CH₂OH | CH—F | Cl | Cl | H | Cl |
| 2 | CH₂C(CH₃)₂OH | CH—F | H | Br | Br | Br |
| 2 | CH₂CHF₂ | CH—F | Br | Br | H | Br |
| 2 | CH₂CF₃ | CH—F | H | I | I | I |
| 2 | CH₂CH(CH₃)₂ | CH—F | I | I | H | I |
| 3 | CH₂C(CH₃)₃ | CH—F | H | CH₃ | CH₃ | CH₃ |
| 3 | H₂C—C≡N | CH—F | CH₃ | CH₃ | H | CH₃ |
| 3 | H₂C—C≡CH | CH—F | H | C₂H₅ | C₂H₅ | C₂H₅ |
| 3 | CH(CH₃)₂ | CH—F | C₂H₅ | C₂H₅ | H | C₂H₅ |
| 3 | CH₂CH₂OH | CH—F | H | i-C₃H₇ | i-C₃H₇ | i-C₃H₇ |
| 3 | CH₂CH(CH₃)OH | CH—F | i-C₃H₇ | i-C₃H₇ | H | i-C₃H₇ |
| 2 | CH(CH₃)CH₂OH | S | I | H | Cl | H |
| 2 | CH(CH₃)CH(CH₃)OH | S=O | I | H | Cl | H |
| 2 | C(CH₃)₂CH₂OH | O=S=O | Br | H | Cl | H |
| 2 | CH₂C(CH₃)₂OH | CH₂ | Br | H | H | Cl |
| 2 | CH₂CHF₂ | C=O | Br | H | I | H |
| 3 | CH₂CF₃ | C=S | Br | H | H | I |
| 3 | CH₂CH(CH₃)₂ | CH—OH | I | H | Br | H |
| 3 | CH₂C(CH₃)₃ | CH—F | I | H | H | Br |
| 3 | H₂C—C≡N | O | I | Cl | H | Cl |
| 3 | H₂C—C≡CH | NH | Br | Cl | H | Cl |

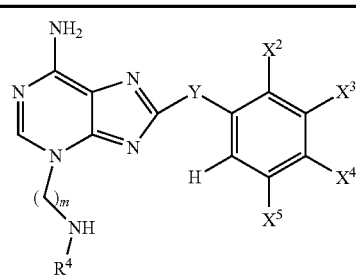

TABLE 12

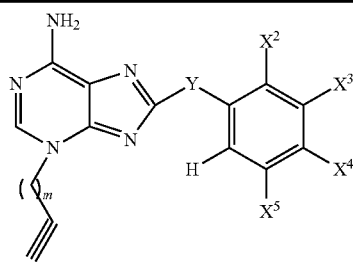

and pharmaceutically acceptable salts thereof, where:

| m | Y | X² | X³ | X⁴ | X⁵ |
|---|---|---|---|---|---|
| 2 | S | H | Cl | H | H |
| 2 | S | H | H | H | Cl |
| 2 | S | H | H | Cl | H |
| 2 | S | H | Cl | H | Cl |
| 2 | S | H | Cl | Cl | Cl |
| 2 | O | H | Cl | H | H |
| 2 | O | H | H | H | Cl |
| 2 | O | H | H | Cl | H |
| 2 | O | H | Cl | H | Cl |
| 2 | O | H | Cl | Cl | Cl |
| 2 | CH₂ | H | Cl | H | H |
| 2 | CH₂ | H | H | H | Cl |
| 2 | CH₂ | H | H | Cl | H |
| 2 | CH₂ | H | Cl | H | Cl |
| 2 | CH₂ | H | Cl | Cl | Cl |
| 2 | C=O | H | H | H | Cl |
| 2 | C=O | H | H | Cl | H |
| 2 | C=O | H | Cl | H | Cl |
| 2 | C=O | H | Cl | Cl | Cl |
| 3 | S | H | Cl | H | H |
| 3 | S | H | H | H | Cl |
| 3 | S | H | H | Cl | H |
| 3 | S | H | Cl | H | Cl |
| 3 | S | H | Cl | Cl | Cl |
| 3 | O | H | Cl | H | H |
| 3 | O | H | H | H | Cl |
| 3 | O | H | H | Cl | H |
| 3 | O | H | Cl | H | Cl |
| 3 | O | H | Cl | Cl | Cl |
| 3 | CH₂ | H | Cl | H | H |
| 3 | CH₂ | H | H | H | Cl |
| 3 | CH₂ | H | H | Cl | H |
| 3 | CH₂ | H | Cl | H | Cl |
| 3 | CH₂ | H | Cl | Cl | Cl |
| 3 | C=O | H | H | H | Cl |
| 3 | C=O | H | H | Cl | H |
| 3 | C=O | H | Cl | H | Cl |
| 3 | C=O | H | Cl | Cl | Cl |
| 2 | S | H | CH₃ | H | H |
| 2 | S | H | H | H | CH₃ |
| 2 | S | H | H | CH₃ | H |
| 2 | S | H | CH₃ | H | CH₃ |
| 2 | S | H | CH₃ | CH₃ | CH₃ |
| 2 | O | H | CH₃ | H | H |
| 2 | O | H | H | H | CH₃ |
| 2 | O | H | H | CH₃ | H |
| 2 | O | H | CH₃ | H | CH₃ |
| 2 | O | H | CH₃ | CH₃ | CH₃ |
| 2 | CH₂ | H | CH₃ | H | H |
| 2 | CH₂ | H | H | H | CH₃ |
| 2 | CH₂ | H | H | CH₃ | H |
| 2 | CH₂ | H | CH₃ | H | CH₃ |
| 2 | CH₂ | H | CH₃ | CH₃ | CH₃ |
| 2 | C=O | H | H | H | CH₃ |
| 2 | C=O | H | H | CH₃ | H |
| 2 | C=O | H | CH₃ | H | CH₃ |
| 2 | C=O | H | CH₃ | CH₃ | CH₃ |
| 3 | S | H | CH₃ | H | H |
| 3 | S | H | H | H | CH₃ |
| 3 | S | H | H | CH₃ | H |
| 3 | S | H | CH₃ | H | CH₃ |
| 3 | S | H | CH₃ | CH₃ | CH₃ |
| 3 | O | H | CH₃ | H | H |

TABLE 12-continued

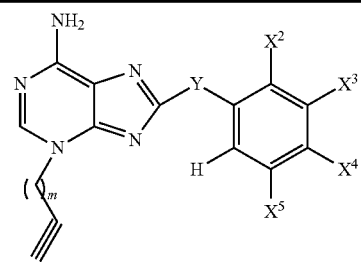

and pharmaceutically acceptable salts thereof, where:

| m | Y | X² | X³ | X⁴ | X⁵ |
|---|---|---|---|---|---|
| 3 | O | H | H | H | Cl |
| 3 | O | H | H | CH₃ | H |
| 3 | O | H | CH₃ | H | CH₃ |
| 3 | O | H | CH₃ | CH₃ | CH₃ |
| 3 | CH₂ | H | CH₃ | H | H |
| 3 | CH₂ | H | H | H | CH₃ |
| 3 | CH₂ | H | H | CH₃ | H |
| 3 | CH₂ | H | CH₃ | H | CH₃ |
| 3 | CH₂ | H | CH₃ | CH₃ | CH₃ |
| 3 | C=O | H | H | H | CH₃ |
| 3 | C=O | H | H | CH₃ | H |
| 3 | C=O | H | CH₃ | H | CH₃ |
| 3 | C=O | H | CH₃ | CH₃ | CH₃ |
| 3 | S | H | Cl | H | Br |
| 3 | S | H | CH₂CH₃ | CH₃ | Br |
| 3 | S | H | OCH₃ | H | OCH₃ |
| 2 | S | H | Cl | H | H |
| 2 | S | H | H | H | Cl |
| 2 | S | H | H | Cl | H |
| 2 | S | Cl | H | H | H |
| 2 | S | H | Br | H | H |
| 2 | S | H | H | H | Br |
| 3 | S | H | H | Br | H |
| 3 | S | Br | H | H | H |
| 3 | S | H | I | H | H |
| 3 | S | H | H | H | I |
| 3 | S | H | H | I | H |
| 3 | S | I | H | H | H |
| 4 | S | H | CH₃ | H | H |
| 4 | S | H | H | H | CH₃ |
| 4 | S | H | H | CH₃ | H |
| 4 | S | CH₃ | H | H | H |
| 4 | S | H | C₂H₅ | H | H |
| 4 | S | H | H | H | C₂H₅ |
| 5 | S | H | H | C₂H₅ | H |
| 5 | S | C₂H₅ | H | H | H |
| 5 | S | H | i-C₃H₇ | H | H |
| 5 | S | H | H | H | i-C₃H₇ |
| 5 | S | H | H | i-C₃H₇ | H |
| 5 | S | i-C₃H₇ | H | H | H |
| 2 | O | H | Cl | H | H |
| 2 | O | H | H | H | Cl |
| 2 | O | Cl | H | H | H |
| 2 | O | H | Br | H | H |
| 2 | O | H | H | H | Br |
| 3 | O | H | H | Br | H |
| 3 | O | Br | H | H | H |
| 3 | O | H | I | H | H |
| 3 | O | H | H | H | I |
| 3 | O | H | H | I | H |
| 3 | O | I | H | H | H |
| 4 | O | H | CH₃ | H | H |
| 4 | O | H | H | H | CH₃ |
| 4 | O | H | H | CH₃ | H |
| 4 | O | CH₃ | H | H | H |
| 4 | O | H | C₂H₅ | H | H |
| 4 | O | H | H | H | C₂H₅ |
| 5 | O | H | H | C₂H₅ | H |
| 5 | O | C₂H₅ | H | H | H |
| 5 | O | H | i-C₃H₇ | H | H |
| 5 | O | H | H | H | i-C₃H₇ |
| 5 | O | H | H | i-C₃H₇ | H |

TABLE 12-continued

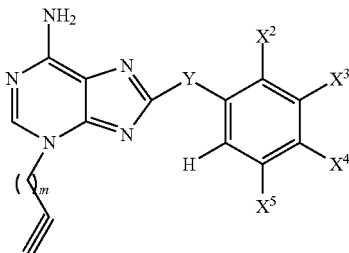

and pharmaceutically acceptable salts thereof, where:

| m | Y | $X^2$ | $X^3$ | $X^4$ | $X^5$ |
|---|---|---|---|---|---|
| 5 | O | i-$C_3H_7$ | H | H | H |
| 2 | S=O | H | Cl | H | H |
| 2 | S=O | H | H | H | Cl |
| 2 | S=O | H | H | Cl | H |
| 2 | S=O | Cl | H | H | H |
| 2 | S=O | H | Br | H | H |
| 2 | S=O | H | H | H | Br |
| 3 | S=O | H | H | Br | H |
| 3 | S=O | Br | H | H | H |
| 3 | S=O | H | I | H | H |
| 3 | S=O | H | H | H | I |
| 3 | S=O | H | H | I | H |
| 3 | S=O | I | H | H | H |
| 4 | S=O | H | $CH_3$ | H | H |
| 4 | S=O | H | H | H | $CH_3$ |
| 4 | S=O | H | H | $CH_3$ | H |
| 4 | S=O | $CH_3$ | H | H | H |
| 4 | S=O | H | $C_2H_5$ | H | H |
| 4 | S=O | H | H | H | $C_2H_5$ |
| 5 | S=O | H | H | $C_2H_5$ | H |
| 5 | S=O | $C_2H_5$ | H | H | H |
| 5 | S=O | H | i-$C_3H_7$ | H | H |
| 5 | S=O | H | H | H | i-$C_3H_7$ |
| 5 | S=O | H | H | i-$C_3H_7$ | H |
| 5 | S=O | i-$C_3H_7$ | H | H | H |
| 2 | O=S=O | H | Cl | H | H |
| 2 | O=S=O | H | H | H | Cl |
| 2 | O=S=O | H | H | Cl | H |
| 2 | O=S=O | Cl | H | H | H |
| 2 | O=S=O | H | Br | H | H |
| 2 | O=S=O | H | H | H | Br |
| 3 | O=S=O | H | H | Br | H |
| 3 | O=S=O | Br | H | H | H |
| 3 | O=S=O | H | I | H | H |
| 3 | O=S=O | H | H | H | I |
| 3 | O=S=O | H | H | I | H |
| 3 | O=S=O | I | H | H | H |
| 4 | O=S=O | H | $CH_3$ | H | H |
| 4 | O=S=O | H | H | H | $CH_3$ |
| 4 | O=S=O | H | H | $CH_3$ | H |
| 4 | O=S=O | $CH_3$ | H | H | H |
| 4 | O=S=O | H | $C_2H_5$ | H | H |
| 4 | O=S=O | H | H | H | $C_2H_5$ |
| 5 | O=S=O | H | H | $C_2H_5$ | H |
| 5 | O=S=O | $C_2H_5$ | H | H | H |
| 5 | O=S=O | H | i-$C_3H_7$ | H | H |
| 5 | O=S=O | H | H | H | i-$C_3H_7$ |
| 5 | O=S=O | H | H | i-$C_3H_7$ | H |
| 5 | O=S=O | i-$C_3H_7$ | H | H | H |
| 2 | NH | H | Cl | H | H |
| 2 | NH | H | H | H | Cl |
| 2 | NH | H | H | Cl | H |
| 2 | NH | Cl | H | H | H |
| 2 | NH | H | Br | H | H |
| 2 | NH | H | H | H | Br |
| 3 | NH | H | H | Br | H |
| 3 | NH | Br | H | H | H |
| 3 | NH | H | I | H | H |
| 3 | NH | H | H | H | I |
| 3 | NH | H | H | I | H |
| 3 | NH | I | H | H | H |
| 4 | NH | H | $CH_3$ | H | H |
| 4 | NH | H | H | H | $CH_3$ |

TABLE 12-continued

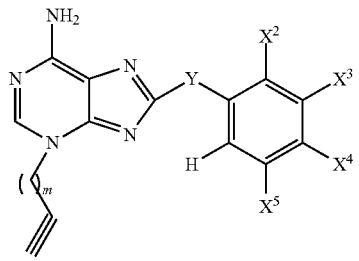

and pharmaceutically acceptable salts thereof, where:

| m | Y | $X^2$ | $X^3$ | $X^4$ | $X^5$ |
|---|---|---|---|---|---|
| 4 | NH | H | H | $CH_3$ | H |
| 4 | NH | $CH_3$ | H | H | H |
| 4 | NH | H | $C_2H_5$ | H | H |
| 4 | NH | H | H | H | $C_2H_5$ |
| 5 | NH | H | H | $C_2H_5$ | H |
| 5 | NH | $C_2H_5$ | H | H | H |
| 5 | NH | H | i-$C_3H_7$ | H | H |
| 5 | NH | H | H | H | i-$C_3H_7$ |
| 5 | NH | H | H | i-$C_3H_7$ | H |
| 5 | NH | i-$C_3H_7$ | H | H | H |
| 2 | C=O | H | Cl | H | H |
| 2 | C=O | H | H | H | Cl |
| 2 | C=O | H | H | Cl | H |
| 2 | C=O | Cl | H | H | H |
| 2 | C=O | H | Br | H | H |
| 2 | C=O | H | H | H | Br |
| 3 | C=O | H | H | Br | H |
| 3 | C=O | Br | H | H | H |
| 3 | C=O | H | I | H | H |
| 3 | C=O | H | H | H | I |
| 3 | C=O | H | H | I | H |
| 3 | C=O | I | H | H | H |
| 4 | C=O | H | $CH_3$ | H | H |
| 4 | C=O | H | H | H | $CH_3$ |
| 4 | C=O | H | H | $CH_3$ | H |
| 4 | C=O | $CH_3$ | H | H | H |
| 4 | C=O | H | $C_2H_5$ | H | H |
| 4 | C=O | H | H | H | $C_2H_5$ |
| 5 | C=O | H | H | $C_2H_5$ | H |
| 5 | C=O | $C_2H_5$ | H | H | H |
| 5 | C=O | H | i-$C_3H_7$ | H | H |
| 5 | C=O | H | H | H | i-$C_3H_7$ |
| 5 | C=O | H | H | i-$C_3H_7$ | H |
| 5 | C=O | i-$C_3H_7$ | H | H | H |
| 2 | C=S | H | Cl | H | H |
| 2 | C=S | H | H | H | Cl |
| 2 | C=S | H | H | Cl | H |
| 2 | C=S | Cl | H | H | H |
| 2 | C=S | H | Br | H | H |
| 2 | C=S | H | H | H | Br |
| 3 | C=S | H | H | Br | H |
| 3 | C=S | Br | H | H | H |
| 3 | C=S | H | I | H | H |
| 3 | C=S | H | H | H | I |
| 3 | C=S | H | H | I | H |
| 3 | C=S | I | H | H | H |
| 4 | C=S | H | $CH_3$ | H | H |
| 4 | C=S | H | H | H | $CH_3$ |
| 4 | C=S | H | H | $CH_3$ | H |
| 4 | C=S | $CH_3$ | H | H | H |
| 4 | C=S | H | $C_2H_5$ | H | H |
| 4 | C=S | H | H | H | $C_2H_5$ |
| 5 | C=S | H | H | $C_2H_5$ | H |
| 5 | C=S | $C_2H_5$ | H | H | H |
| 5 | C=S | H | i-$C_3H_7$ | H | H |
| 5 | C=S | H | H | H | i-$C_3H_7$ |
| 5 | C=S | H | H | i-$C_3H_7$ | H |
| 5 | C=S | i-$C_3H_7$ | H | H | H |
| 2 | $CH_2$ | H | Cl | H | H |
| 2 | $CH_2$ | H | H | H | Cl |
| 2 | $CH_2$ | H | H | Cl | H |
| 2 | $CH_2$ | Cl | H | H | H |
| 2 | $CH_2$ | H | Br | H | H |

TABLE 12-continued

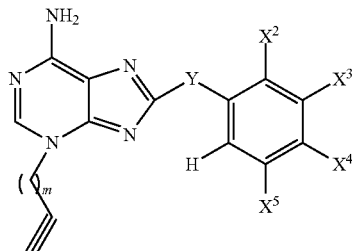

and pharmaceutically acceptable salts thereof, where:

| m | Y | $X^2$ | $X^3$ | $X^4$ | $X^5$ |
|---|---|---|---|---|---|
| 2 | $CH_2$ | H | H | H | Br |
| 3 | $CH_2$ | H | H | Br | H |
| 3 | $CH_2$ | Br | H | H | H |
| 3 | $CH_2$ | H | I | H | H |
| 3 | $CH_2$ | H | H | H | I |
| 3 | $CH_2$ | H | H | I | H |
| 3 | $CH_2$ | I | H | H | H |
| 4 | $CH_2$ | H | $CH_3$ | H | H |
| 4 | $CH_2$ | H | H | H | $CH_3$ |
| 4 | $CH_2$ | H | H | $CH_3$ | H |
| 4 | $CH_2$ | $CH_3$ | H | H | H |
| 4 | $CH_2$ | H | $C_2H_5$ | H | H |
| 4 | $CH_2$ | H | H | H | $C_2H_5$ |
| 5 | $CH_2$ | H | H | $C_2H_5$ | H |
| 5 | $CH_2$ | $C_2H_5$ | H | H | H |
| 5 | $CH_2$ | H | $i$-$C_3H_7$ | H | H |
| 5 | $CH_2$ | H | H | H | $i$-$C_3H_7$ |
| 5 | $CH_2$ | H | H | $i$-$C_3H_7$ | H |
| 5 | $CH_2$ | $i$-$C_3H_7$ | H | H | H |
| 2 | CH—OH | H | Cl | H | H |
| 2 | CH—OH | H | H | H | Cl |
| 2 | CH—OH | H | H | Cl | H |
| 2 | CH—OH | Cl | H | H | H |
| 2 | CH—OH | H | Br | H | H |
| 2 | CH—OH | H | H | H | Br |
| 3 | CH—OH | H | H | Br | H |
| 3 | CH—OH | Br | H | H | H |
| 3 | CH—OH | H | I | H | H |
| 3 | CH—OH | H | H | H | I |
| 3 | CH—OH | H | H | I | H |
| 3 | CH—OH | I | H | H | H |
| 4 | CH—OH | H | $CH_3$ | H | H |
| 4 | CH—OH | H | H | H | $CH_3$ |
| 4 | CH—OH | H | H | $CH_3$ | H |
| 4 | CH—OH | $CH_3$ | H | H | H |
| 4 | CH—OH | H | $C_2H_5$ | H | H |
| 4 | CH—OH | H | H | H | $C_2H_5$ |
| 5 | CH—OH | H | H | $C_2H_5$ | H |
| 5 | CH—OH | $C_2H_5$ | H | H | H |
| 5 | CH—OH | H | $i$-$C_3H_7$ | H | H |
| 5 | CH—OH | H | H | H | $i$-$C_3H_7$ |
| 5 | CH—OH | H | H | $i$-$C_3H_7$ | H |
| 5 | CH—OH | $i$-$C_3H_7$ | H | H | H |
| 2 | CH—F | H | Cl | H | H |
| 2 | CH—F | H | H | H | Cl |
| 2 | CH—F | H | H | Cl | H |
| 2 | CH—F | Cl | H | H | H |
| 2 | CH—F | H | Br | H | H |
| 2 | CH—F | H | H | H | Br |
| 3 | CH—F | H | H | Br | H |
| 3 | CH—F | Br | H | H | H |
| 3 | CH—F | H | I | H | H |
| 3 | CH—F | H | H | H | I |
| 3 | CH—F | H | H | I | H |
| 3 | CH—F | I | H | H | H |
| 4 | CH—F | H | $CH_3$ | H | H |
| 4 | CH—F | H | H | H | $CH_3$ |
| 4 | CH—F | H | H | $CH_3$ | H |
| 4 | CH—F | $CH_3$ | H | H | H |
| 4 | CH—F | H | $C_2H_5$ | H | H |
| 4 | CH—F | H | H | H | $C_2H_5$ |
| 5 | CH—F | H | H | $C_2H_5$ | H |
| 5 | CH—F | $C_2H_5$ | H | H | H |

TABLE 12-continued

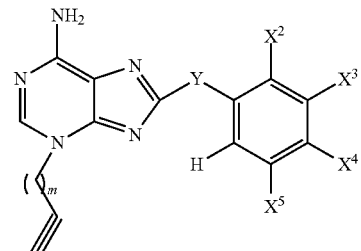

and pharmaceutically acceptable salts thereof, where:

| m | Y | $X^2$ | $X^3$ | $X^4$ | $X^5$ |
|---|---|---|---|---|---|
| 5 | CH—F | H | $i$-$C_3H_7$ | H | H |
| 5 | CH—F | H | H | H | $i$-$C_3H_7$ |
| 5 | CH—F | H | H | $i$-$C_3H_7$ | H |
| 5 | CH—F | $i$-$C_3H_7$ | H | H | H |
| 2 | S | H | Cl | H | Cl |
| 2 | S | Cl | H | Cl | H |
| 2 | S | Cl | H | H | Cl |
| 2 | S | H | Br | H | Br |
| 2 | S | Br | H | Br | H |
| 2 | S | Br | H | H | Br |
| 3 | S | H | I | H | I |
| 3 | S | I | H | I | H |
| 3 | S | I | H | H | I |
| 3 | S | H | $CH_3$ | H | $CH_3$ |
| 3 | S | $CH_3$ | H | $CH_3$ | H |
| 3 | S | $CH_3$ | H | H | $CH_3$ |
| 4 | S | H | $C_2H_5$ | H | $C_2H_5$ |
| 4 | S | $C_2H_5$ | H | $C_2H_5$ | H |
| 4 | S | $C_2H_5$ | H | H | $C_2H_5$ |
| 4 | S | H | $i$-$C_3H_7$ | H | $i$-$C_3H_7$ |
| 4 | S | $i$-$C_3H_7$ | H | $i$-$C_3H_7$ | H |
| 4 | S | $i$-$C_3H_7$ | H | H | $i$-$C_3H_7$ |
| 5 | O | H | Cl | H | Cl |
| 5 | O | Cl | H | Cl | H |
| 5 | O | Cl | H | H | Cl |
| 5 | O | H | Br | H | Br |
| 5 | O | Br | H | Br | H |
| 5 | O | Br | H | H | Br |
| 2 | O | H | I | H | I |
| 2 | O | I | H | I | H |
| 2 | O | I | H | H | I |
| 2 | O | H | $CH_3$ | H | $CH_3$ |
| 2 | O | $CH_3$ | H | $CH_3$ | H |
| 2 | O | $CH_3$ | H | H | $CH_3$ |
| 3 | O | H | $C_2H_5$ | H | $C_2H_5$ |
| 3 | O | $C_2H_5$ | H | $C_2H_5$ | H |
| 3 | O | $C_2H_5$ | H | H | $C_2H_5$ |
| 3 | O | H | $i$-$C_3H_7$ | H | $i$-$C_3H_7$ |
| 3 | O | $i$-$C_3H_7$ | H | $i$-$C_3H_7$ | H |
| 3 | O | $i$-$C_3H_7$ | H | H | $i$-$C_3H_7$ |
| 4 | S=O | H | Cl | H | Cl |
| 4 | S=O | Cl | H | Cl | H |
| 4 | S=O | Cl | H | H | Cl |
| 4 | S=O | H | Br | H | Br |
| 4 | S=O | Br | H | Br | H |
| 4 | S=O | Br | H | H | Br |
| 5 | S=O | H | I | H | I |
| 5 | S=O | I | H | I | H |
| 5 | S=O | I | H | H | I |
| 5 | S=O | H | $CH_3$ | H | $CH_3$ |
| 5 | S=O | $CH_3$ | H | $CH_3$ | H |
| 5 | S=O | $CH_3$ | H | H | $CH_3$ |
| 2 | S=O | H | $C_2H_5$ | H | $C_2H_5$ |
| 2 | S=O | $C_2H_5$ | H | $C_2H_5$ | H |
| 2 | S=O | $C_2H_5$ | H | H | $C_2H_5$ |
| 2 | S=O | H | $i$-$C_3H_7$ | H | $i$-$C_3H_7$ |
| 2 | S=O | $i$-$C_3H_7$ | H | $i$-$C_3H_7$ | H |
| 2 | S=O | $i$-$C_3H_7$ | H | H | $i$-$C_3H_7$ |
| 3 | O=S=O | H | Cl | H | Cl |
| 3 | O=S=O | Cl | H | Cl | H |
| 3 | O=S=O | Cl | H | H | Cl |
| 3 | O=S=O | H | Br | H | Br |
| 3 | O=S=O | Br | H | Br | H |

TABLE 12-continued

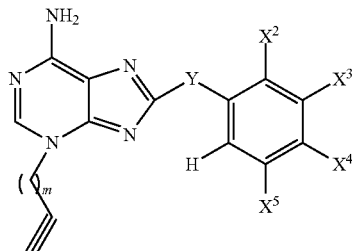

and pharmaceutically acceptable salts thereof, where:

| m | Y | $X^2$ | $X^3$ | $X^4$ | $X^5$ |
|---|---|---|---|---|---|
| 3 | O=S=O | Br | H | H | Br |
| 4 | O=S=O | H | I | H | I |
| 4 | O=S=O | I | H | I | H |
| 4 | O=S=O | I | H | H | I |
| 4 | O=S=O | H | $CH_3$ | H | $CH_3$ |
| 4 | O=S=O | $CH_3$ | H | $CH_3$ | H |
| 4 | O=S=O | $CH_3$ | H | H | $CH_3$ |
| 5 | O=S=O | H | $C_2H_5$ | H | $C_2H_5$ |
| 5 | O=S=O | $C_2H_5$ | H | $C_2H_5$ | H |
| 5 | O=S=O | $C_2H_5$ | H | H | $C_2H_5$ |
| 5 | O=S=O | H | $i-C_3H_7$ | H | $i-C_3H_7$ |
| 5 | O=S=O | $i-C_3H_7$ | H | $i-C_3H_7$ | H |
| 5 | O=S=O | $i-C_3H_7$ | H | H | $i-C_3H_7$ |
| 2 | NH | H | Cl | H | Cl |
| 2 | NH | Cl | H | Cl | H |
| 2 | NH | Cl | H | H | Cl |
| 2 | NH | H | Br | H | Br |
| 2 | NH | Br | H | Br | H |
| 2 | NH | Br | H | H | Br |
| 2 | NH | H | I | H | I |
| 3 | NH | I | H | I | H |
| 3 | NH | I | H | H | I |
| 3 | NH | H | $CH_3$ | H | $CH_3$ |
| 3 | NH | $CH_3$ | H | $CH_3$ | H |
| 3 | NH | $CH_3$ | H | H | $CH_3$ |
| 3 | NH | H | $C_2H_5$ | H | $C_2H_5$ |
| 4 | NH | $C_2H_5$ | H | $C_2H_5$ | H |
| 4 | NH | $C_2H_5$ | H | H | $C_2H_5$ |
| 4 | NH | H | $i-C_3H_7$ | H | $i-C_3H_7$ |
| 4 | NH | $i-C_3H_7$ | H | $i-C_3H_7$ | H |
| 4 | NH | $i-C_3H_7$ | H | H | $i-C_3H_7$ |
| 4 | C=O | H | Cl | H | Cl |
| 5 | C=O | Cl | H | Cl | H |
| 5 | C=O | Cl | H | H | Cl |
| 5 | C=O | H | Br | H | Br |
| 5 | C=O | Br | H | Br | H |
| 5 | C=O | Br | H | H | Br |
| 2 | C=O | H | I | H | I |
| 2 | C=O | I | H | I | H |
| 2 | C=O | I | H | H | I |
| 2 | C=O | H | $CH_3$ | H | $CH_3$ |
| 2 | C=O | $CH_3$ | H | $CH_3$ | H |
| 2 | C=O | $CH_3$ | H | H | $CH_3$ |
| 3 | C=O | H | $C_2H_5$ | H | $C_2H_5$ |
| 3 | C=O | $C_2H_5$ | H | $C_2H_5$ | H |
| 3 | C=O | $C_2H_5$ | H | H | $C_2H_5$ |
| 3 | C=O | H | $i-C_3H_7$ | H | $i-C_3H_7$ |
| 3 | C=O | $i-C_3H_7$ | H | $i-C_3H_7$ | H |
| 3 | C=O | $i-C_3H_7$ | H | H | $i-C_3H_7$ |
| 4 | C=S | H | Cl | H | Cl |
| 4 | C=S | Cl | H | Cl | H |
| 4 | C=S | Cl | H | H | Cl |
| 4 | C=S | H | Br | H | Br |
| 4 | C=S | Br | H | Br | H |
| 4 | C=S | Br | H | H | Br |
| 5 | C=S | H | I | H | I |
| 5 | C=S | I | H | I | H |
| 5 | C=S | I | H | H | I |
| 5 | C=S | H | $CH_3$ | H | $CH_3$ |
| 5 | C=S | $CH_3$ | H | $CH_3$ | H |
| 5 | C=S | $CH_3$ | H | H | $CH_3$ |
| 2 | C=S | H | $C_2H_5$ | H | $C_2H_5$ |
| 2 | C=S | $C_2H_5$ | H | $C_2H_5$ | H |

TABLE 12-continued

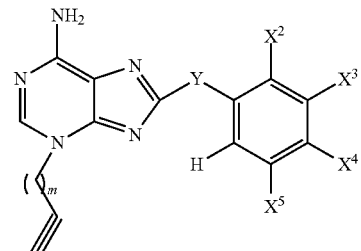

and pharmaceutically acceptable salts thereof, where:

| m | Y | $X^2$ | $X^3$ | $X^4$ | $X^5$ |
|---|---|---|---|---|---|
| 2 | C=S | $C_2H_5$ | H | H | $C_2H_5$ |
| 2 | C=S | H | $i-C_3H_7$ | H | $i-C_3H_7$ |
| 2 | C=S | $i-C_3H_7$ | H | $i-C_3H_7$ | H |
| 2 | C=S | $i-C_3H_7$ | H | H | $i-C_3H_7$ |
| 3 | $CH_2$ | H | Cl | H | Cl |
| 3 | $CH_2$ | Cl | H | Cl | H |
| 3 | $CH_2$ | Cl | H | H | Cl |
| 3 | $CH_2$ | H | Br | H | Br |
| 3 | $CH_2$ | Br | H | Br | H |
| 3 | $CH_2$ | Br | H | H | Br |
| 4 | $CH_2$ | H | I | H | I |
| 4 | $CH_2$ | I | H | I | H |
| 4 | $CH_2$ | I | H | H | I |
| 4 | $CH_2$ | H | $CH_3$ | H | $CH_3$ |
| 4 | $CH_2$ | $CH_3$ | H | $CH_3$ | H |
| 4 | $CH_2$ | $CH_3$ | H | H | $CH_3$ |
| 5 | $CH_2$ | H | $C_2H_5$ | H | $C_2H_5$ |
| 5 | $CH_2$ | $C_2H_5$ | H | $C_2H_5$ | H |
| 5 | $CH_2$ | $C_2H_5$ | H | H | $C_2H_5$ |
| 5 | $CH_2$ | H | $i-C_3H_7$ | H | $i-C_3H_7$ |
| 5 | $CH_2$ | $i-C_3H_7$ | H | $i-C_3H_7$ | H |
| 5 | $CH_2$ | $i-C_3H_7$ | H | H | $i-C_3H_7$ |
| 2 | CH—OH | H | Cl | H | Cl |
| 2 | CH—OH | Cl | H | Cl | H |
| 2 | CH—OH | Cl | H | H | Cl |
| 2 | CH—OH | H | Br | H | Br |
| 2 | CH—OH | Br | H | Br | H |
| 2 | CH—OH | Br | H | H | Br |
| 2 | CH—OH | H | I | H | I |
| 3 | CH—OH | I | H | I | H |
| 3 | CH—OH | I | H | H | I |
| 3 | CH—OH | H | $CH_3$ | H | $CH_3$ |
| 3 | CH—OH | $CH_3$ | H | $CH_3$ | H |
| 3 | CH—OH | $CH_3$ | H | H | $CH_3$ |
| 3 | CH—OH | H | $C_2H_5$ | H | $C_2H_5$ |
| 4 | CH—OH | $C_2H_5$ | H | $C_2H_5$ | H |
| 4 | CH—OH | $C_2H_5$ | H | H | $C_2H_5$ |
| 4 | CH—OH | H | $i-C_3H_7$ | H | $i-C_3H_7$ |
| 4 | CH—OH | $i-C_3H_7$ | H | $i-C_3H_7$ | H |
| 4 | CH—OH | $i-C_3H_7$ | H | H | $i-C_3H_7$ |
| 5 | CH—F | H | Cl | H | Cl |
| 5 | CH—F | Cl | H | Cl | H |
| 5 | CH—F | Cl | H | H | Cl |
| 5 | CH—F | H | Br | H | Br |
| 5 | CH—F | Br | H | Br | H |
| 5 | CH—F | Br | H | H | Br |
| 2 | CH—F | H | I | H | I |
| 2 | CH—F | I | H | I | H |
| 2 | CH—F | I | H | H | I |
| 2 | CH—F | H | $CH_3$ | H | $CH_3$ |
| 2 | CH—F | $CH_3$ | H | $CH_3$ | H |
| 2 | CH—F | $CH_3$ | H | H | $CH_3$ |
| 3 | CH—F | H | $C_2H_5$ | H | $C_2H_5$ |
| 3 | CH—F | $C_2H_5$ | H | $C_2H_5$ | H |
| 3 | CH—F | $C_2H_5$ | H | H | $C_2H_5$ |
| 3 | CH—F | H | $i-C_3H_7$ | H | $i-C_3H_7$ |
| 3 | CH—F | $i-C_3H_7$ | H | $i-C_3H_7$ | H |
| 3 | CH—F | $i-C_3H_7$ | H | H | $i-C_3H_7$ |
| 4 | S | H | Cl | Cl | Cl |
| 4 | S | Cl | Cl | H | Cl |
| 4 | S | H | Br | Br | Br |
| 4 | S | Br | Br | H | Br |
| 4 | S | H | I | I | I |

TABLE 12-continued

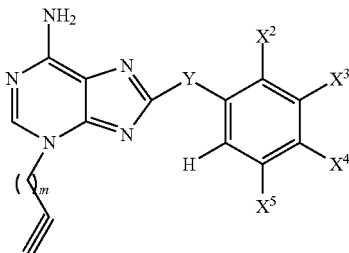

and pharmaceutically acceptable salts thereof, where:

| m | Y | X² | X³ | X⁴ | X⁵ |
|---|---|---|---|---|---|
| 4 | S | I | I | H | I |
| 5 | S | H | CH₃ | CH₃ | CH₃ |
| 5 | S | CH₃ | CH₃ | H | CH₃ |
| 5 | S | H | C₂H₅ | C₂H₅ | C₂H₅ |
| 5 | S | C₂H₅ | C₂H₅ | H | C₂H₅ |
| 5 | S | H | i-C₃H₇ | i-C₃H₇ | i-C₃H₇ |
| 5 | S | i-C₃H₇ | i-C₃H₇ | H | i-C₃H₇ |
| 2 | O | H | Cl | Cl | Cl |
| 2 | O | Cl | Cl | H | Cl |
| 2 | O | H | Br | Br | Br |
| 2 | O | Br | Br | H | Br |
| 2 | O | H | I | I | I |
| 2 | O | I | I | H | I |
| 3 | O | H | CH₃ | CH₃ | CH₃ |
| 3 | O | CH₃ | CH₃ | H | CH₃ |
| 3 | O | H | C₂H₅ | C₂H₅ | C₂H₅ |
| 3 | O | C₂H₅ | C₂H₅ | H | C₂H₅ |
| 3 | O | H | i-C₃H₇ | i-C₃H₇ | i-C₃H₇ |
| 3 | O | i-C₃H₇ | i-C₃H₇ | H | i-C₃H₇ |
| 4 | S=O | H | Cl | Cl | Cl |
| 4 | S=O | Cl | Cl | H | Cl |
| 4 | S=O | H | Br | Br | Br |
| 4 | S=O | Br | Br | H | Br |
| 4 | S=O | H | I | I | I |
| 4 | S=O | I | I | H | I |
| 5 | S=O | H | CH₃ | CH₃ | CH₃ |
| 5 | S=O | CH₃ | CH₃ | H | CH₃ |
| 5 | S=O | H | C₂H₅ | C₂H₅ | C₂H₅ |
| 5 | S=O | C₂H₅ | C₂H₅ | H | C₂H₅ |
| 5 | S=O | H | i-C₃H₇ | i-C₃H₇ | i-C₃H₇ |
| 5 | S=O | i-C₃H₇ | i-C₃H₇ | H | i-C₃H₇ |
| 2 | O=S=O | H | Cl | Cl | Cl |
| 2 | O=S=O | Cl | Cl | H | Cl |
| 2 | O=S=O | H | Br | Br | Br |
| 2 | O=S=O | Br | Br | H | Br |
| 2 | O=S=O | H | I | I | I |
| 2 | O=S=O | I | I | H | I |
| 3 | O=S=O | H | CH₃ | CH₃ | CH₃ |
| 3 | O=S=O | CH₃ | CH₃ | H | CH₃ |
| 3 | O=S=O | H | C₂H₅ | C₂H₅ | C₂H₅ |
| 3 | O=S=O | C₂H₅ | C₂H₅ | H | C₂H₅ |
| 3 | O=S=O | H | i-C₃H₇ | i-C₃H₇ | i-C₃H₇ |
| 3 | O=S=O | i-C₃H₇ | i-C₃H₇ | H | i-C₃H₇ |
| 4 | NH | H | Cl | Cl | Cl |
| 4 | NH | Cl | Cl | H | Cl |
| 4 | NH | H | Br | Br | Br |
| 4 | NH | Br | Br | H | Br |
| 4 | NH | H | I | I | I |
| 4 | NH | I | I | H | I |
| 5 | NH | H | CH₃ | CH₃ | CH₃ |
| 5 | NH | CH₃ | CH₃ | H | CH₃ |
| 5 | NH | H | C₂H₅ | C₂H₅ | C₂H₅ |
| 5 | NH | C₂H₅ | C₂H₅ | H | C₂H₅ |
| 5 | NH | H | i-C₃H₇ | i-C₃H₇ | i-C₃H₇ |
| 5 | NH | i-C₃H₇ | i-C₃H₇ | H | i-C₃H₇ |
| 2 | C=O | H | Cl | Cl | Cl |
| 2 | C=O | Cl | Cl | H | Cl |
| 2 | C=O | H | Br | Br | Br |
| 2 | C=O | Br | Br | H | Br |
| 2 | C=O | H | I | I | I |
| 2 | C=O | I | I | H | I |
| 3 | C=O | H | CH₃ | CH₃ | CH₃ |
| 3 | C=O | CH₃ | CH₃ | H | CH₃ |
| 3 | C=O | H | C₂H₅ | C₂H₅ | C₂H₅ |
| 3 | C=O | C₂H₅ | C₂H₅ | H | C₂H₅ |
| 3 | C=O | H | i-C₃H₇ | i-C₃H₇ | i-C₃H₇ |
| 3 | C=O | i-C₃H₇ | i-C₃H₇ | H | i-C₃H₇ |
| 4 | C=S | H | Cl | Cl | Cl |
| 4 | C=S | Cl | Cl | H | Cl |
| 4 | C=S | H | Br | Br | Br |
| 4 | C=S | Br | Br | H | Br |
| 4 | C=S | H | I | I | I |
| 4 | C=S | I | I | H | I |
| 5 | C=S | H | CH₃ | CH₃ | CH₃ |
| 5 | C=S | CH₃ | CH₃ | H | CH₃ |
| 5 | C=S | H | C₂H₅ | C₂H₅ | C₂H₅ |
| 5 | C=S | C₂H₅ | C₂H₅ | H | C₂H₅ |
| 5 | C=S | H | i-C₃H₇ | i-C₃H₇ | i-C₃H₇ |
| 5 | C=S | i-C₃H₇ | i-C₃H₇ | H | i-C₃H₇ |
| 2 | CH₂ | H | Cl | Cl | Cl |
| 2 | CH₂ | Cl | Cl | H | Cl |
| 2 | CH₂ | H | Br | Br | Br |
| 2 | CH₂ | Br | Br | H | Br |
| 2 | CH₂ | H | I | I | I |
| 2 | CH₂ | I | I | H | I |
| 3 | CH₂ | H | CH₃ | CH₃ | CH₃ |
| 3 | CH₂ | CH₃ | CH₃ | H | CH₃ |
| 3 | CH₂ | H | C₂H₅ | C₂H₅ | C₂H₅ |
| 3 | CH₂ | C₂H₅ | C₂H₅ | H | C₂H₅ |
| 3 | CH₂ | H | i-C₃H₇ | i-C₃H₇ | i-C₃H₇ |
| 3 | CH₂ | i-C₃H₇ | i-C₃H₇ | H | i-C₃H₇ |
| 4 | CH—OH | H | Cl | Cl | Cl |
| 4 | CH—OH | Cl | Cl | H | Cl |
| 4 | CH—OH | H | Br | Br | Br |
| 4 | CH—OH | Br | Br | H | Br |
| 4 | CH—OH | H | I | I | I |
| 4 | CH—OH | I | I | H | I |
| 5 | CH—OH | H | CH₃ | CH₃ | CH₃ |
| 5 | CH—OH | CH₃ | CH₃ | H | CH₃ |
| 5 | CH—OH | H | C₂H₅ | C₂H₅ | C₂H₅ |
| 5 | CH—OH | C₂H₅ | C₂H₅ | H | C₂H₅ |
| 5 | CH—OH | H | i-C₃H₇ | i-C₃H₇ | i-C₃H₇ |
| 5 | CH—OH | i-C₃H₇ | i-C₃H₇ | H | i-C₃H₇ |
| 2 | CH—F | H | Cl | Cl | Cl |
| 2 | CH—F | Cl | Cl | H | Cl |
| 2 | CH—F | H | Br | Br | Br |
| 2 | CH—F | Br | Br | H | Br |
| 2 | CH—F | H | I | I | I |
| 2 | CH—F | I | I | H | I |
| 3 | CH—F | H | CH₃ | CH₃ | CH₃ |
| 3 | CH—F | CH₃ | CH₃ | H | CH₃ |
| 3 | CH—F | H | C₂H₅ | C₂H₅ | C₂H₅ |
| 3 | CH—F | C₂H₅ | C₂H₅ | H | C₂H₅ |
| 3 | CH—F | H | i-C₃H₇ | i-C₃H₇ | i-C₃H₇ |
| 3 | CH—F | i-C₃H₇ | i-C₃H₇ | H | i-C₃H₇ |
| 4 | S | I | H | Cl | H |
| 4 | S=O | I | H | H | Cl |
| 4 | O=S=O | Br | H | Cl | H |
| 4 | CH₂ | Br | H | H | Cl |
| 4 | C=O | Br | H | I | H |
| 4 | C=S | Br | H | H | I |
| 5 | CH—OH | I | H | Br | H |
| 5 | CH—F | I | H | H | Br |
| 5 | O | I | Cl | H | Cl |
| 5 | NH | Br | Cl | H | Cl |

5.4 Grp94 Inhibitors of the Disclosure Exhibit Selective Paralog Inhibition in Cells Having established that the compounds of the disclosure selectivity inhibit Grp94, we next investigated the effect of Grp94 specific inhibitors in cells. As a test compound, we used the selective Grp94 inhibitor PU-WS13, which has the following chemical structure:

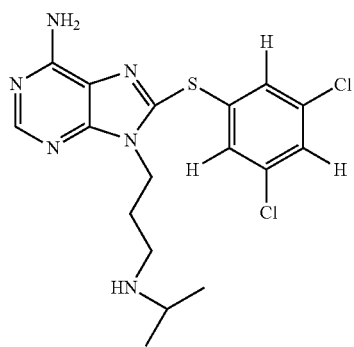

PU-WS13

We compared the in vitro effects of PU-WS13 with a selective Hsp90α/β inhibitor referred to as (PU-29F), which has the following chemical structure:

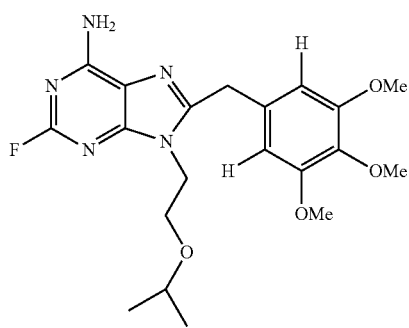

PU-29F

Selective target modulation of these compounds in cells was tested by several different readouts (FIG. 5). Specifically, we demonstrated that PU-WS13 inhibited IGF-II secretion (FIG. 5a) and Toll-like receptor 9 (TLR9) trafficking (FIG. 5e) in a dose-dependent manner Both of these are well-defined Grp94-mediated cellular events (Duerfeldt, A. S., et al. Development of a Grp94 inhibitor. *J. Am. Chem. Soc.* 134, 9796-9804 (2012); Ostrovsky, O., Ahmed, N. T. & Argon, Y. The chaperone activity of GRP94 toward insulin-like growth factor II is necessary for the stress response to serum deprivation. *Mol. Biol. Cell* 20, 1855-1864 (2009); At concentrations of PU-WS13 that inhibited Grp94 activity, we observed no inhibition of Hsp90, as demonstrated by lack of Hsp70 induction and AKT degradation (FIGS. 5b, f, g), both of which are hallmarks of cytolosic Hsp90α inhibition. (Workman, P., Burrows, F., Neckers, L. & Rosen, N. Drugging the cancer chaperone Hsp90: combinatorial therapeutic exploitation of oncogene addiction and tumor stress. *Ann. N.Y. Acad. Sci.* 1113, 202-216 (2007); Pearl, L. H., Prodromou, C. & Workman, P. The Hsp90 molecular chaperone: an open and shut case for treatment. *Biochem. J.* 410, 439-453 (2008)) Conversely, treatment with the selective Hsp90α/β inhibitor PU-29F led to a dose-dependent increase in Hsp90 levels and degradation of AKT (FIGS. 5b, f, g), while minimally effecting the Grp94 hallmarks (FIGS. 5a, e, f). Importantly, PU-WS13 was not toxic to two non-malignant cell lines, C2C12 (mouse skeletal myoblasts) and HEK293 (human embryonic kidney cells) (FIGS. 5c, f).

5.5 Therapeutic Uses of Grp94 Inhibitors of the Disclosure

The Grp94 inhibitors of the disclosure can be used to treat or prevent any condition treatable or preventable by inhibiting the activity of Grp94. Such conditions include, but are not limited to cancer, autoimmune diseases, neurodegenerative diseases and inflammatory diseases. Due to their activity, the Grp94 inhibitors of the disclosure are advantageously useful in human medicine. When administered to an animal, the Grp94 inhibitors of the disclosure can be administered as a component of a composition that comprises a pharmaceutically acceptable carrier or excipient. The compositions of the disclosure can be administered orally, intradermally, intramuscularly, intraperitoneally, parenterally, intravenously, subcutaneously, intranasaly, epidurally, orally, sublingually, intracerebrally, intravaginally, transdermally, rectally or topically.

When a Grp94 inhibitor of the disclosure is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Grp94 inhibitor of the disclosure can also be in the form of a powder for reconstitution as an injectable formulation.

When a Grp94 inhibitor of the disclosure is formulated for oral administration, the formulation can be in the in the form of tablets, capsules, gelcaps, caplets, lozenges, aqueous or oily solutions, suspensions, granules, powders, emulsions, or syrups. The oral formulation can include one or more pharmaceutically acceptable excipients such as diluent, suspending agent, solubilizer, binder, disintegrant, preservative, coloring agent, lubricant. The Grp94 inhibitors can be administered in a vesicle, and in particular, a liposome.

The Grp94 inhibitors of the disclosure are provided at doses that do not inhibit Hsp90α, Hsp90β and Trap-1. For instance, the Grp94 inhibitors of the disclosure can be administered at a dose in the range between 1 mg/m$^2$ and 260 mg/m$^2$. In particular embodiments, the Grp94 inhibitors of the disclosure can be administered at a dose in the range between 2 mg/m$^2$ and 100 mg/m$^2$. In other embodiments, the Grp94 inhibitors of the disclosure can be administered at a dose in the range between 5 mg/m$^2$ and 50 mg/m$^2$. In still other embodiments, the Grp94 inhibitors of the disclosure can be administered at a dose in the range between 5 mg/m$^2$ and 20 mg/m$^2$ or between 10 m g/m$^2$ and 20 mg/m$^2$.

5.5.1 Cancer

The Grp94 inhibitors of the disclosure can be used treat a variety of cancers that are dependent on Hsp90 including but not limited to colorectal cancer, pancreatic cancer, thyroid cancer, basal cell carcinoma, melanoma, renal cell carcinoma, bladder cancer, prostate cancer, a lung cancer including small cell lung cancer and non-small cell lung cancer, breast cancer, neuroblastoma, gastrointestinal cancers including gastrointestinal stromal tumors, esophageal cancer, stomach cancer, liver cancer, gallbladder cancer, anal cancer, brain tumors including gliomas, lymphomas including follicular lymphoma and diffuse large B-cell lymphoma, leukemias, myelomas, myeloproliferative neoplasms and gynecologic cancers including ovarian, cervical, and endometrial cancers.

The precise dose of the Grp94 inhibitor to be employed will depend on, e.g., the route of administration and the stage of the cancer. In accordance with the disclosure, the Grp94 inhibitors of the disclosure can be administered to a patient such that the other Hsp90 paralogs are not affected or affected to a minimal extent. Minimizing the inhibition of the other Hsp90 paralogs can be achieved by an amount sufficient to inhibit binding of Grp94 to its client proteins without inhibiting binding of the other Hsp90 paralogs. Accordingly, in one embodiment, a Grp94 inhibitor of the disclosure can be administered to a cancer patient in an amount sufficient to inhibit binding of Grp94 to its client proteins without inhibition of the other HSP90 paralogs, including Hsp90α, HSP90β and Trap-1. As discussed herein, a particular advantage of administering the Grp94 inhibitors of the disclosure at such a dosage range is that feed-back upregulation of antiapoptotic and resistance-mediating heat shock proteins (e.g., Hsp70) can be substantially avoided. As such, the Grp94 inhibitors of the disclosure can be administered to a patient without concomitant administration of an Hsp70 inhibitor. Hence, in accordance with one aspect of the disclosure, methods of treating cancer by treating a human patient suffering from cancer without up-regulation of Hsp70 are provided. Such methods involve administration of a Grp94 inhibitor of the disclosure in an amount sufficient to inhibit binding of Grp94 to its client proteins without inhibiting binding of the other Hsp90 paralogs (i.e., Hsp90α, Hsp90β and/or Trap-1). In one embodiment, a Grp94 inhibitor of the disclosure can be administered to a cancer patient in an amount sufficient to inhibit binding of Grp94 to its client proteins without inhibiting binding of client protein to other Hsp90 paralogs. In another embodiment, a Grp94 inhibitor of the disclosure can be administered to a cancer patient in an amount sufficient to inhibit binding of Grp94 to its client proteins without up-regulation of Hsp70. Moreover, as discussed below, the Grp94 inhibitors of the disclosure are capable of inducing apoptosis in cancer cells that express oncogenic proteins that are dependent on Grp94 for survival and/or maintaining their function in the survival or proliferation of cancer cells. For instance, as discussed below, Grp94 plays an important role in stabilizing particular receptor tyrosine kinases (RTKs) at the plasma membrane, which allows the RTKs to be active in the development and progression of the tumors. The Grp94 inhibitors of the disclosure are capable of destabilizing the membrane RTKs, thereby inhibiting their signaling properties.

In certain embodiments, the Grp94 inhibitors of the disclosure can be combined with one or more other therapeutic agents for treating cancer. The therapeutic agents of the combination therapy may be administered at the same time or may be administered sequentially. In particular embodiments, the Grp94 inhibitor can be administered with a chemotherapeutic agent such as a toxin or a radioactive molecule. In other embodiments, the Grp94 inhibitor can be administered together with an anti-angiogenic agent such as a VEGF antagonist. In yet other embodiments, the Grp94 inhibitor can be administered together with a TNF-α antagonist. Specific examples of combination therapy will be discussed below.

5.5.2 HER2 Dependent Tumors

With the Grp94 inhibitors of the disclosure, we investigated the specific roles of Hsp90 paralogs on a classical Hsp90 client protein, HER2. HER2 is a receptor tyrosine kinase, which, when activated, leads to the stimulation of many cancer-driving signaling pathways. The expression of HER2 is altered in many epithelial tumors such as breast, ovarian, gastric, and non-small-cell lung cancers, and HER2 levels have been shown to be inversely correlated with the prognosis of breast cancer. HER2 is also one of the most studied oncoprotein clients of Hsp90 and is one of the most sensitive to pan-Hsp90 inhibition.

The current view of the regulation of HER2 by Hsp90 chaperones comes from studies using pan-Hsp90 inhibitors. These suggest that the effect of these agents on HER2 is mediated by disrupting interactions between Hsp90 and the HER2 cytoplasmic domain (Xu, W., Mimnaugh, E. G., Kim, J. S., Trepel, J. B. & Neckers, L. M. Hsp90, not Grp94, regulates the intracellular trafficking and stability of nascent ErbB2. *Cell Stress Chaperones* 7, 91-96 (2002)) leading to the poly-ubiquitination and degradation of HER2 via the 26S proteasome. Pan-Hsp90 inhibitors also appear to act on Grp94 as it regulates the newly synthesized HER2 in the ER, leading to HER2 instability and retention in the ER, with only trace ubiquitination (Yarden, Y. & Sliwkowski, M. X. Untangling the ErbB signaling network. *Nat. Rev. Mol. Cell Biol.* 2, 127-137 (2001).

The Grp94 inhibitors of the disclosure can be used to treat HER2 dependent cancers such as breast cancer, ovarian cancer, gastric cancer, esophageal cancer and non-small-cell lung cancers. As discussed in greater detail below, we have found that inhibition or depletion of Grp94 in cells that overexpress HER2 results in apoptosis of the cells along with a mitigation or termination of the signaling event mediated by HER2. Moreover, inhibition of Grp94 is not associated with feed-back upregulation of anti-apoptotic proteins, such as heat shock protein 70 (Hsp70). As a result, the selective Grp94 inhibitors are capable of inducing apoptosis of HER2 overexpressing cancer cells to a far greater extent than pan-Hsp90 inhibitors, where upregulation of Hsp70 lessens the anti-apoptotic effects of the inhibitor and may lead to resistance. Accordingly, the disclosure provides methods for selectively inducing apoptosis in HER2 overexpressing cancer cells. Moreover, the disclosure provides methods of treating HER2 overexpressing cancers by administering a therapeutically effective amount of a selective Grp94 inhibitor.

In particular embodiments, the disclosure provides methods of treating HER2 overexpressing breast cancers by administering a therapeutically effective amount of a selective Grp94 inhibitor. In other embodiments, the disclosure provides methods of treating HER2 overexpressing ovarian cancers by administering a therapeutically effective amount of a selective Grp94 inhibitor. In still other embodiments, the disclosure provides methods of treating HER2 overexpressing gastric cancers by administering a therapeutically effective amount of a selective Grp94 inhibitor.

In some embodiments, the Grp94 inhibitors of the disclosure can be used in combination with a therapeutic reagent that interferes with the HER2 receptor (e.g., trastuzumab (herceptin)).

5.5.2.1 Hsp90 Paralogs Regulate HER2 in a Tumor-Specific Manner

To assess the role of the Hsp90 paralogs in HER2 dependent cancers, we used the Grp94 selective PU-WS13 and PU-H39 (FIG. 1), and the Hsp90α/β selective inhibitors PU-20F, PU-29F and PU-11, which have the following chemical structures:

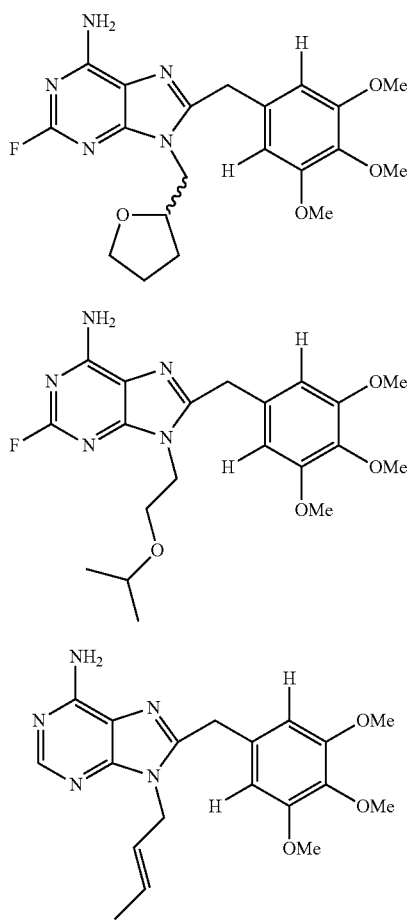

For comparison, we also employed the pan-Hsp90 inhibitor PU-H71 (FIG. 1a) to mimic, when relevant, the combined phenotypes observed with individual selective Grp94 and Hsp90α/β inhibitors. In addition, we confirmed relevant phenotypes by the use of at least three paralog-specific siRNA constructs. We also performed confirmatory paralog-selective affinity purifications with solid-support immobilized probes. For each compound, we controlled for selective target modulation in cells by several functional readouts, including Hsp70 induction and Raf-1 and/or AKT degradation, as well as other cellular compartment specific effects as will be discussed below. Combined, these controls provide an independent measure of the cellular effects of selective paralog inhibition and allowed us to test the cellular effects of Grp94 and Hsp90α/β inhibitors at concentrations that gave validated selective target inhibition.

Figure 6A:
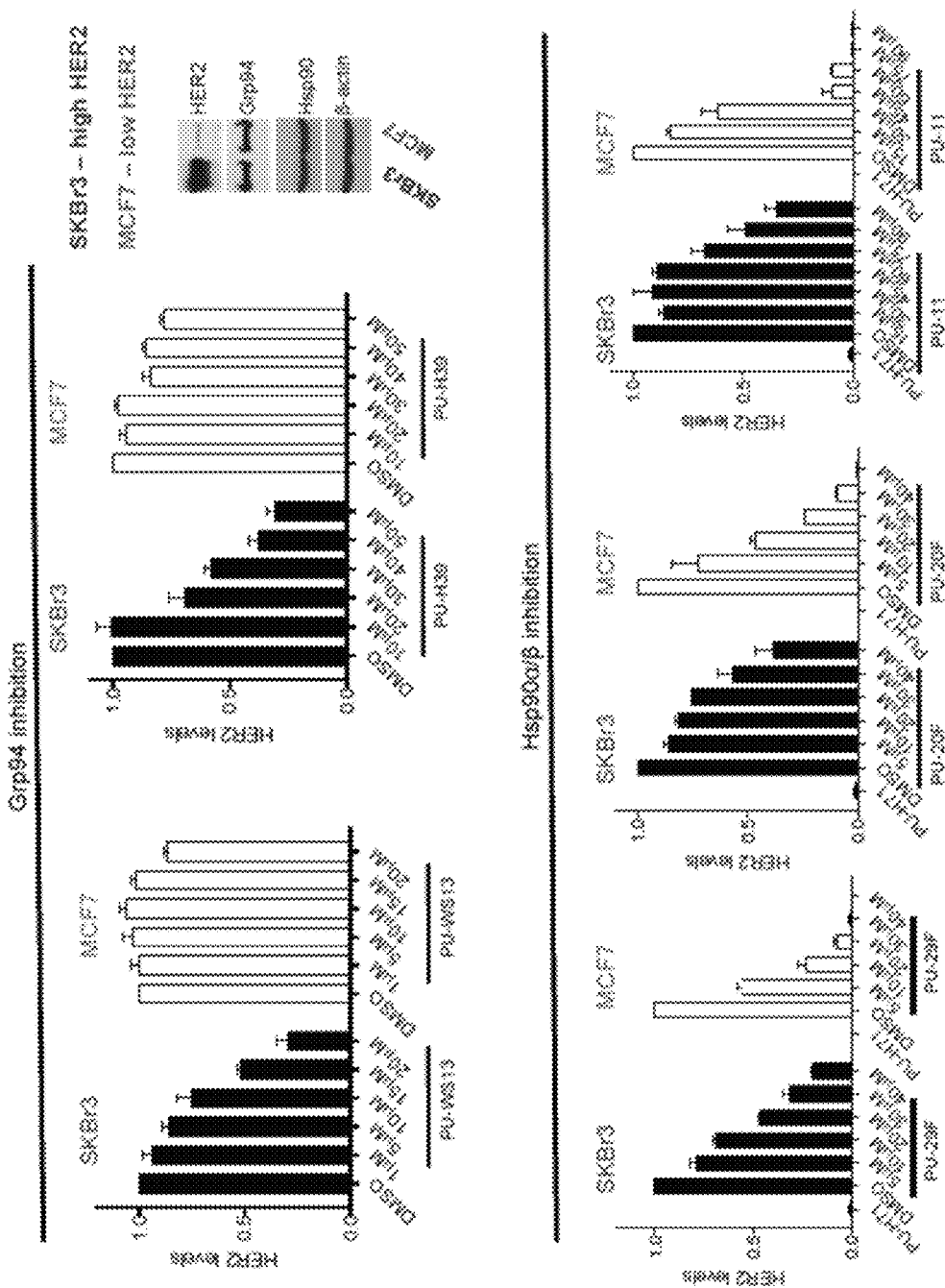
FIG. 6a shows HER2 levels, quantified and normalized, were plotted against the inhibitor concentration in SKBr3 and MCF7 cells treated for 24 h with vehicle (DMSO) or the indicated concentrations of the Grp94-selective inhibitors PU-WS13 and PU-H39 (top) or the Hsp90α/β-selective inhibitors PU-29F, PU-20F and PU-11 (bottom).
Figure 6B:
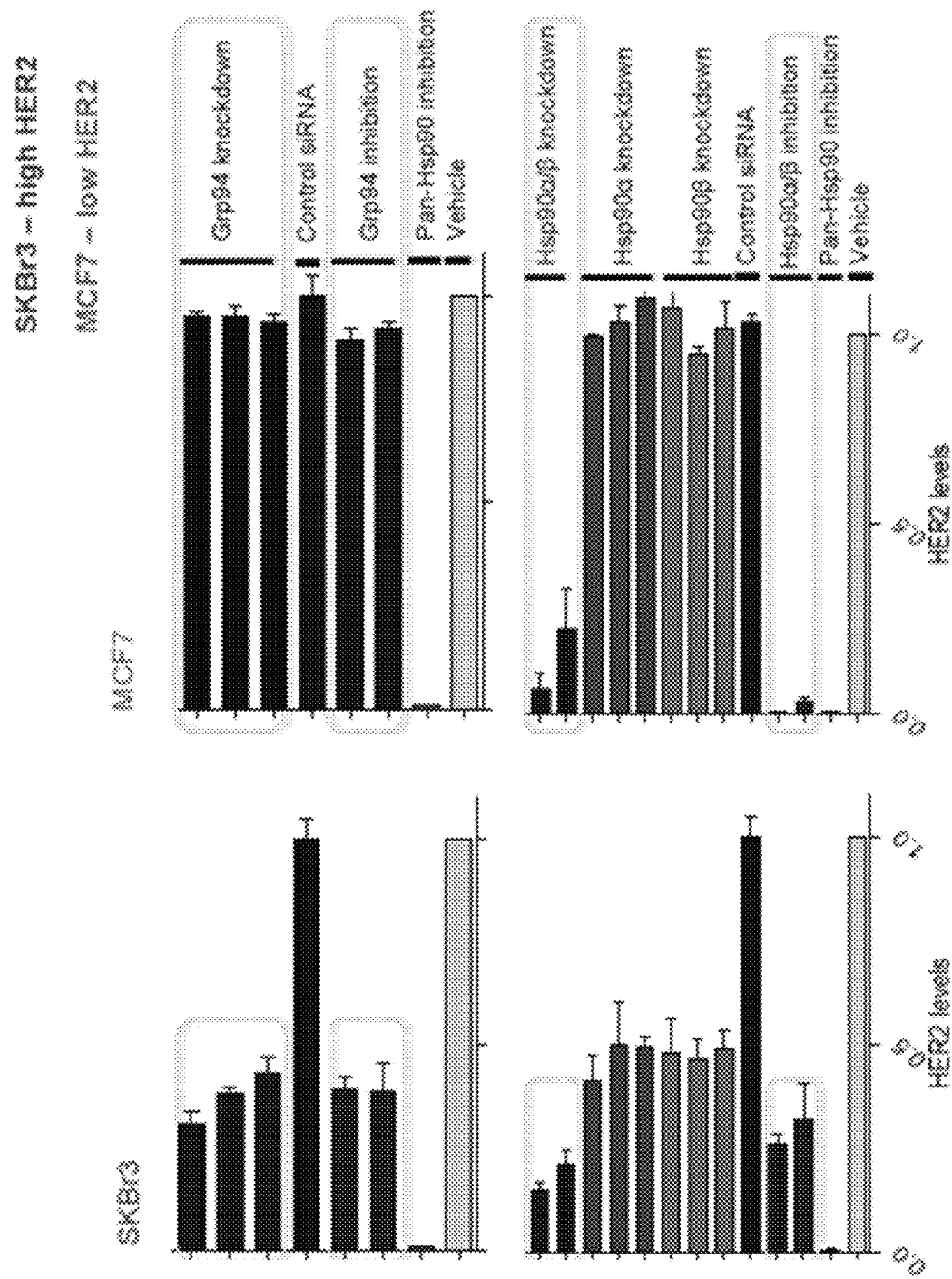
FIG. 6b shows the same as in FIG. 6a but for cells in which Grp94 (top) or Hsp90α/β (bottom) was knocked-down by means of siRNA.
Figure 7B:
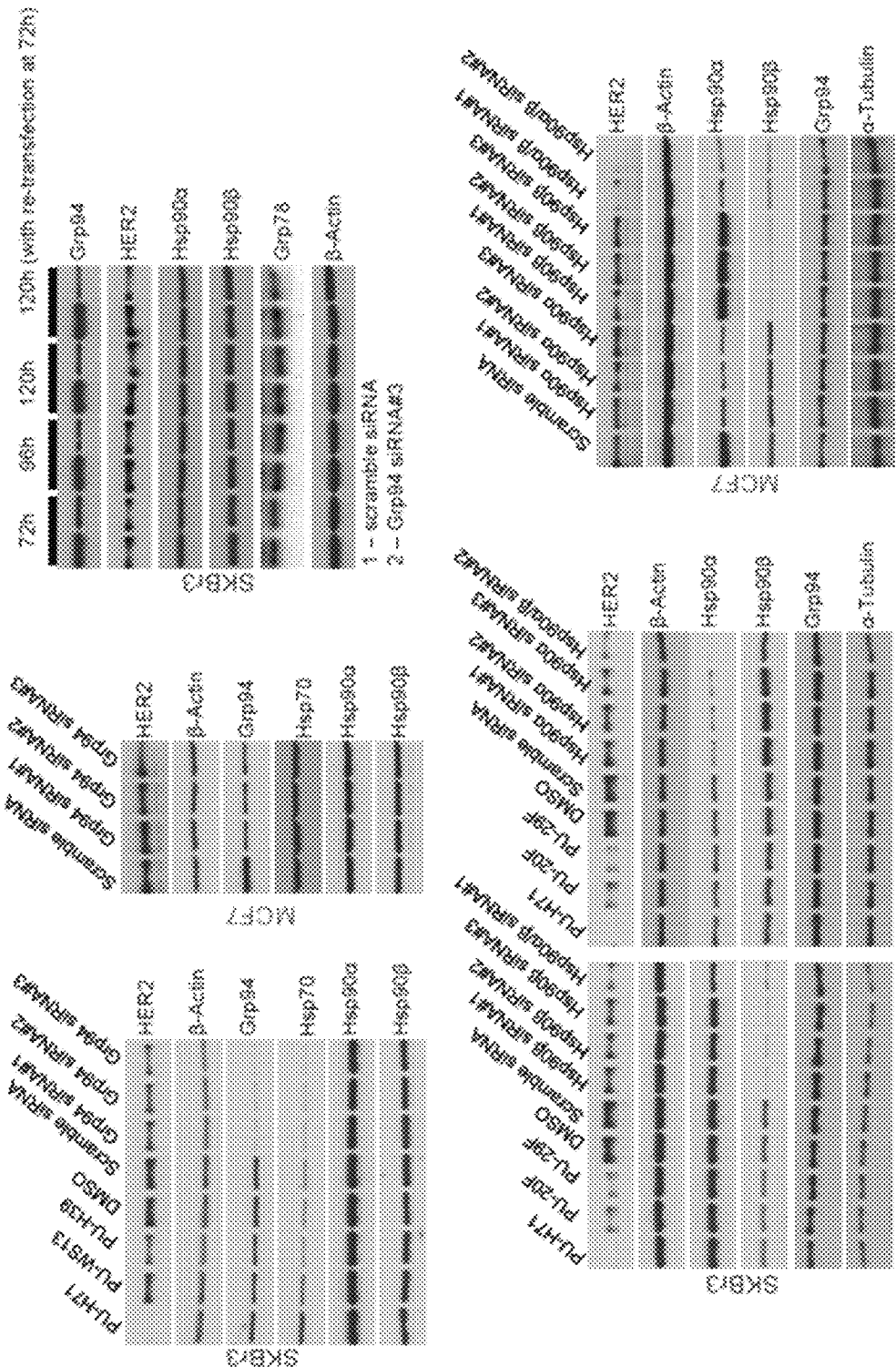
FIG. 7b shows that Grp94 knockdown leads to reduced steady-state levels of HER2 in SKBr3 but not in MCF7 cells, whereas Hsp90 knockdown downregulates HER2 in both SKBr3 and MCF7 cells.
Figure 7C:
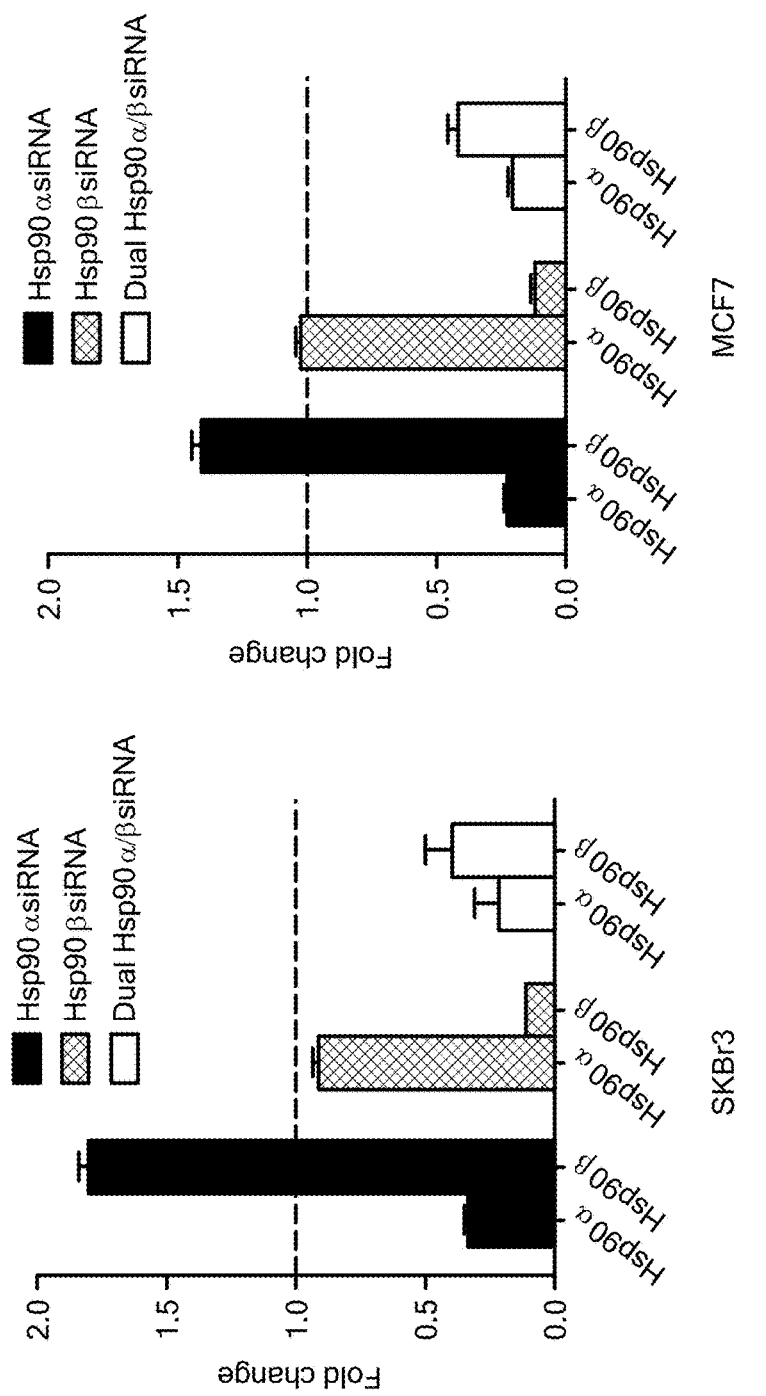
FIG. 7c shows the same as in FIG. 7b but with Hsp90 paralog levels being normalized to β-actin and changes in cytosolic Hsp90 paralogs being graphed as "fold change". Note feed-back induction of Hsp90β upon Hsp90α knockdown.

With this tool set in hand we probed two breast cancer cell lines, SKBr3 (high HER2 expression) and MCF7 (low HER2 expression), for the individual roles of Hsp90 paralogs in HER2 regulation. Surprisingly, we found that the steady-state levels of HER2 were sensitive to selective inhibition of Grp94 in SKBr3 cells but not in MCF7 cells (FIG. 6a, top and FIG. 7a). Knockdown of Grp94 levels by siRNA mimicked the effect of the Grp94 inhibitors. In both cases a similar reduction in the steady-state levels of HER2 in SKBr3 cells, but not in MCF7 cells, was observed (FIG. 6b, top and FIG. 7b).

Moreover, the Grp94 compounds of the disclosure fail to show substantial binding and inhibition of major oncogenic kinases. For instance, both PU-WS13 and PU-H39 were screened in the Discoverx scanEDGE. When tested at 10 uM, these compounds had no significant effect on any of the tested 97 kinases. The tested kinases were distributed throughout the AGC, CAMK, CMGC, CK1, STE, TK, TKL, lipid, and atypical kinase families, plus important mutant forms. Furthermore, the effect of the Grp94 inhibitory compounds is not directly on HER2 because lapatinib, a small molecule that binds to the kinase domain of HER2, fails to mimic the phenotype seen with PU-WS13 on SKBr3 cells. As seen, lapatinib does not disrupt the HER2 architecture at the plasma membrane. In contrast, our results clearly show that upon Grp94 inhibition both signaling and HER2-plasma structures are disturbed. Collectively, these data link the biological effects of the Grp94 inhibitors of the disclosure to their inhibition of Grp94-mediated HER2 function.

Figure 6C:
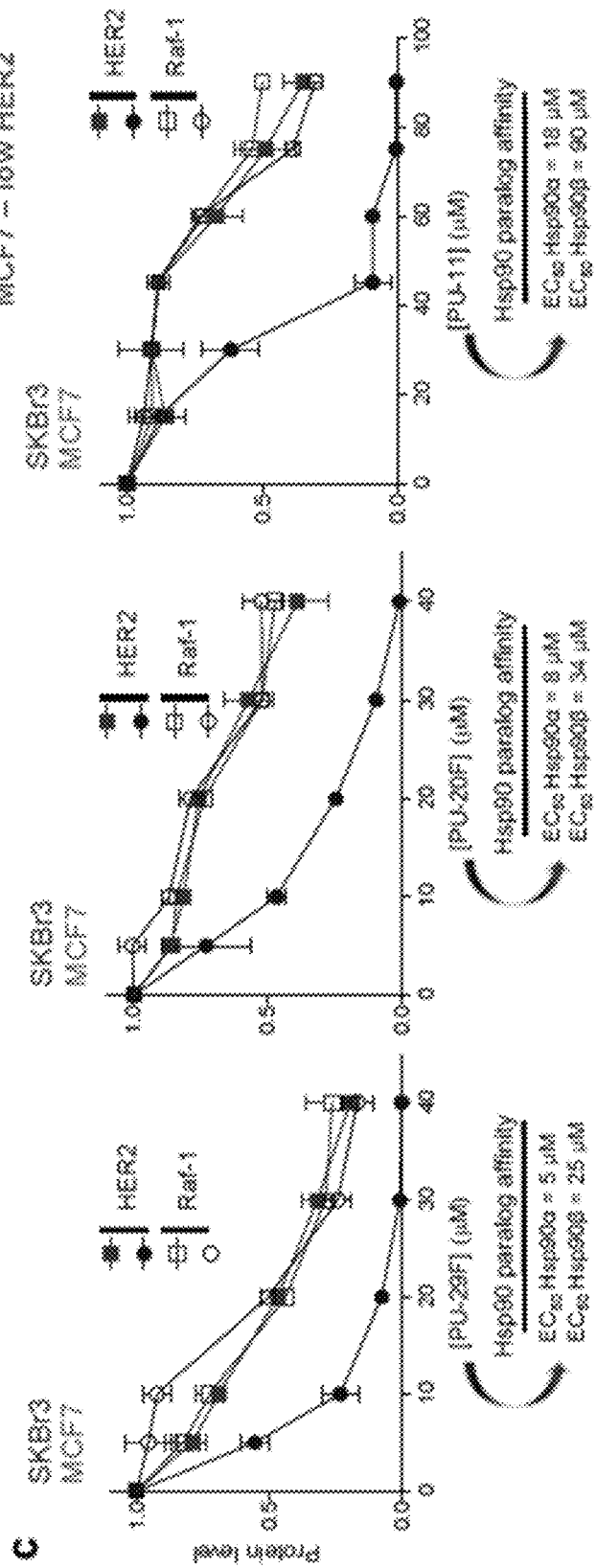
FIG. 6c shows the same as in FIG. 6a but for HER2 and Raf-1 levels. Data for Hsp90 paralog binding affinity is presented under each panel.
Figures 6D, 6E:
FIG. 6d shows correlative analysis of Hsp90 paralog affinity versus HER2 degradation activity for select compounds (n=7). Data were analyzed in GraphPad Prism software.
FIG. 6e shows representative Western blots (WB) of HER2 complexes in MCF7 extracts isolated by precipitation with an anti-HER2 antibody or a nonspecific IgG.

In contrast, steady-state levels of HER2 were sensitive to Hsp90α/β inhibition (FIG. 6a and FIG. 7a) and Hsp90α/β knockdown (FIG. 6b and FIG. 7b) in both cell types. In high HER2 SKBr3 cells, HER2 levels decreased only at inhibitor concentrations that were indicative of simultaneous Hsp90α and Hsp90β inhibition (FIG. 6c), mimicking the case for another Hsp90α/β client protein, Raf-1 (Workman, P., Burrows, F., Neckers, L. & Rosen, N. Drugging the cancer chaperone Hsp90: combinatorial therapeutic exploitation of oncogene addiction and tumor stress. Ann. N.Y. Acad. Sci. 1113, 202-216 (2007)) (FIG. 6c). This was confirmed by siRNA knockdowns, where only dual Hsp90α/β siRNA knockdown mimicked the effect of Hsp90α/β inhibitors in this cell line (FIG. 6b and FIG. 7b). Selective siRNA knockdown of either Hsp90α or Hsp90β led to only a partial reduction in HER2 levels (FIG. 6b). In low HER2 MCF7 cells however, HER2 levels decreased at lower inhibitor concentrations that were characteristic of selective binding to Hsp90α but not Hsp90β (FIG. 6a,c). We also found a significant correlation in MCF7 cells between HER2 degradation and Hsp90α- but not Hsp90β-, Grp94- and Trap-1-affinity (FIG. 6d, $r^2$=0.83, 0.137, 0.217 and 0.005, respectively) (FIG. 6d, $r^2$=0.83, 0.137, 0.217 and 0.005, respectively). HER2 also co-purified specifically with Hsp90α in these cells (FIG. 6e). Selective reduction of Hsp90α by means of siRNA, however, failed to decrease the level of HER2 in MCF7 cells (FIG. 6b and FIG. 7b), possibly due to a feed-back induction of Hsp90β when Hsp90α is suppressed (FIG. 7b.c).

Because HER2 is located in a membrane compartment associated with either the ER and Golgi network or the plasma membrane, or is trafficked through the cytosol, we proceeded to investigate the effect of Hsp90 specific inhibitors on HER2 in these locations. We found that in MCF7 cells, the cytosolic HER2 protein levels as well as the activity of other Hsp90-validated kinases, such as Raf-1 and ERK were rapidly reduced by the Hsp90α/β inhibitor, but not by the Grp94 selective inhibitor (FIG. 6f), further confirming that Hsp90 is the major regulator of cytosolic HER2 in MCF7 cells.

To summarize, inhibition or downregulation of Grp94 leads to reduced steady state levels of HER2 in high-HER2 SKBr3 cells, but not in low-HER2 MCF7 cells. Similarly, inhibition or downregulation of both Hsp90α and Hsp90β reduces HER2 levels in high-HER2 SKBr3 cells, but not in low-HER2 MCF7 cells, where inhibition of the Hsp90α paralog alone substantially impairs HER2 stability. These data suggest a tumor-specific involvement of the Hsp90 paralogs in the chaperoning of HER2. Specifically, they propose the Hsp90α paralog to be sufficient for HER2 function in low-HER2 cells such as MCF7. On the other hand, in cells with excessive amounts of HER2, such as SKBr3, all three Hsp90 paralogs appear to play an important role.

5.5.2.2 Grp94 Regulates Plasma Membrane HER2 in SKBr3 Cells

Figure 8A:
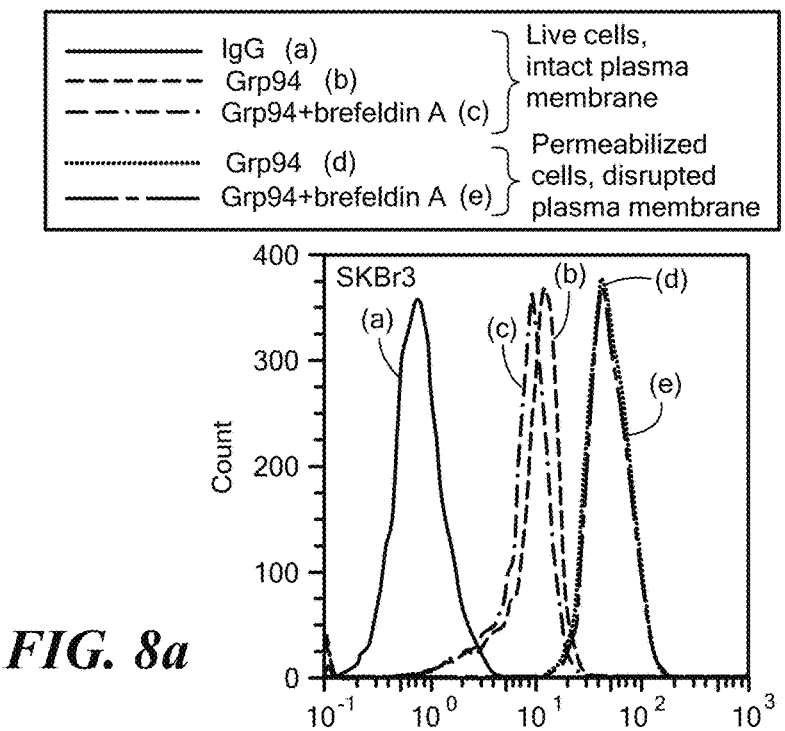
FIG. 8a shows representative flow cytometry of SKBr3 cells stained with a Grp94-specific antibody or an isotype control antibody shows cell surface localization of Grp94 that is reduced by the protein trafficking inhibitor Brefeldin A.
Figure 8B:
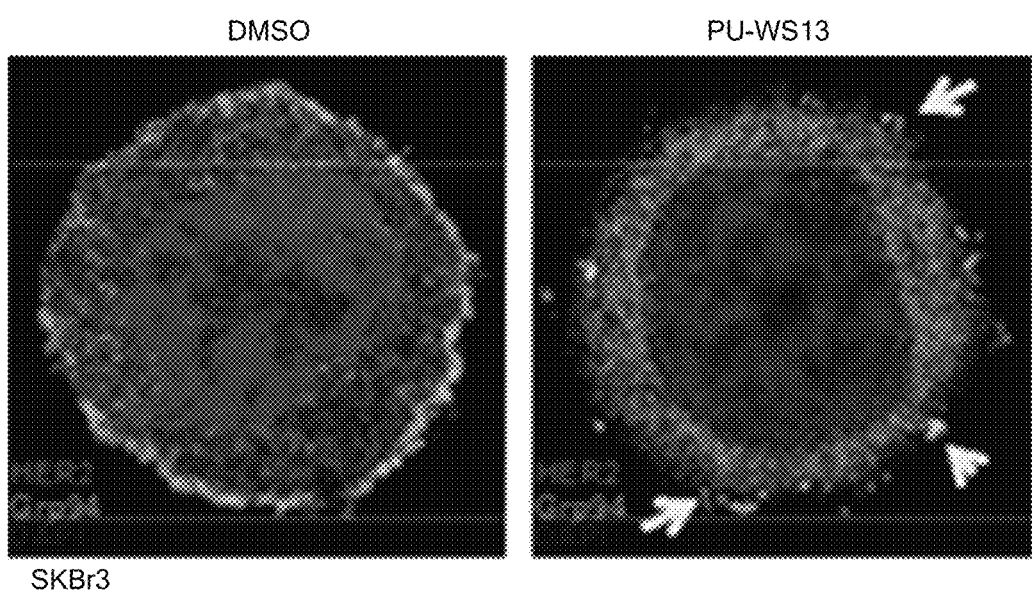
FIG. 8b shows a fluorescence microscopy image of SKBr3 cells treated for 4 h with DMSO or PU-WS13 (15 µM) and then stained with the indicated markers upon fixation and permeabilization.
Figure 8C:
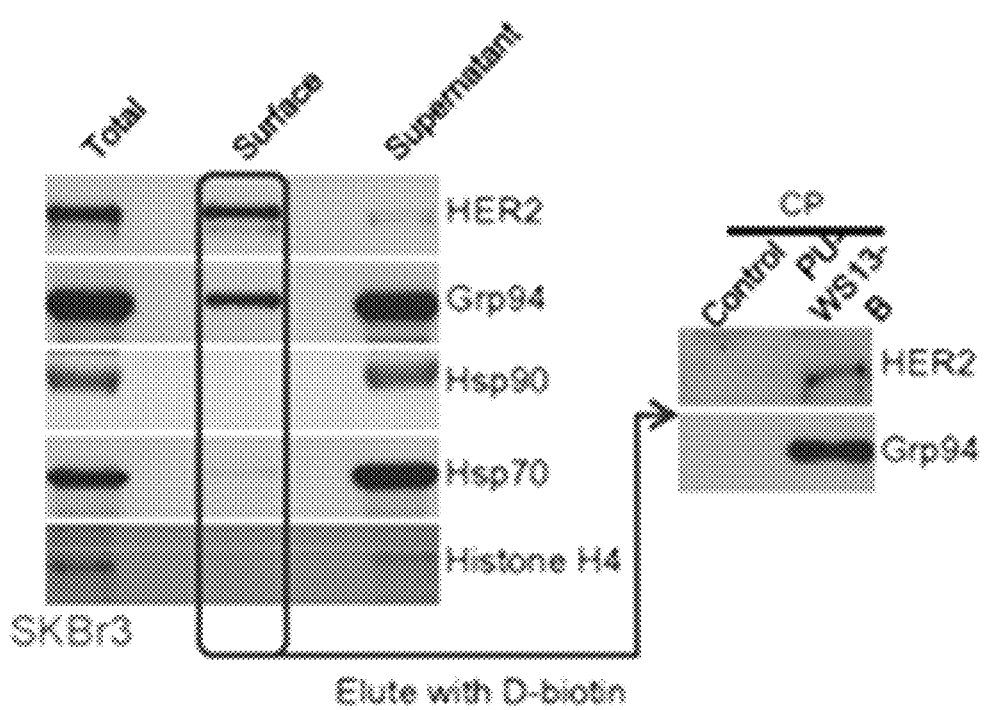
FIG. 8c shows representative blot of surface exposed proteins chemically labeled with biotin and purified using streptavidin columns. Histone H4 was blotted to control for membrane impermeability. Total cell extracts; Total, Supernatant; non-surface proteins. Proteins eluted from the streptavidin column were affinity purified and analyzed by WB as indicated.
Figure 8D:
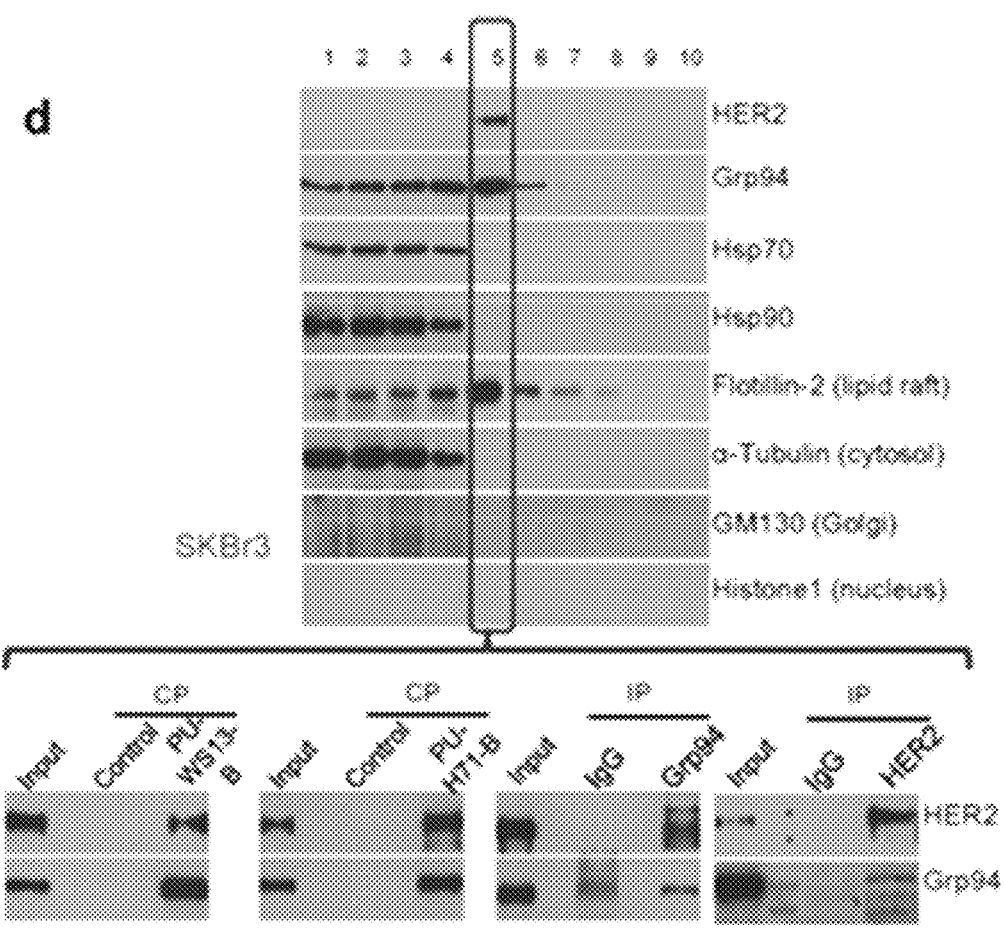
FIG. 8d shows representative WB of Grp94 and HER2 complexes isolated from plasma membrane extracts (Fraction 5) as indicated. CP and IP, chemical and immuno-precipitation, respectively.

We next investigated the unusual requirement for the involvement of multiple Hsp90 paralogs in regulating HER2 in SKBr3 cells. Unlike MCF7, SKBr3 cells express a high density of the HER2 protein at the plasma membrane (Chavany, C. et al. p185erbB2 binds to GRP94 in vivo. Dissociation of the p185erbB2/GRP94 heterocomplex by benzoquinone ansamycins precedes depletion of p185erbB2. *J. Biol. Chem.* 271, 4974-4977 (1996)), where interestingly we also detected Grp94 (FIG. 8*a-d*) but not Hsp90 (FIG. 8*c,d*). Plasma membrane associated Grp94 represents a small but substantial fraction of the total cellular Grp94 (FIG. 8*a-c*). We found that plasma membrane-associated Grp94 co-localized (FIG. 8*b*, DMSO; FIG. 8*c,d*) and co-precipitated with HER2 (FIG. 8*c,d*). Specific complex formation was confirmed both by chemical and reciprocal immunopurification of Grp94/HER2 complexes (FIG. 8*c,d*) and by affinity purification performed with the Grp94 specific chemical tool in cell lysates in which Grp94 levels were reduced by immunopurification with Grp94 specific antibodies (FIG. 8*e*)

We next investigated the biological significance of the unique association of HER2 with Grp94 at the plasma membrane of SKBr3 cells. Because the Grp94 inhibitors described here target the ATP-binding pocket of Grp94, they affect Grp94 chaperone activity. Therefore we hypothesized that Grp94 may act on HER2 at the plasma membrane to stabilize the protein and to regulate its function. Indeed, brief treatment of SKBr3 cells with Grp94-selective compounds led to the disruption of the circular architecture of HER2 at the plasma membrane, resulting in a "shredded" HER2 pattern (FIG. 8*b,f* PU-WS13). No such effect was observed upon direct HER2 inhibition with lapatinib (FIG. 8*f*, Lapatinib), a small molecule that binds to the ATP-regulatory pocket of HER2 (Kim, T. E. & Murren, J. R. Lapatinib ditosylate GlaxoSmithKline. *IDrugs* 6, 886-893 (2003)), further confirming that the effect of PU-WS13 on HER2 was mediated through Grp94.

Figure 7D:
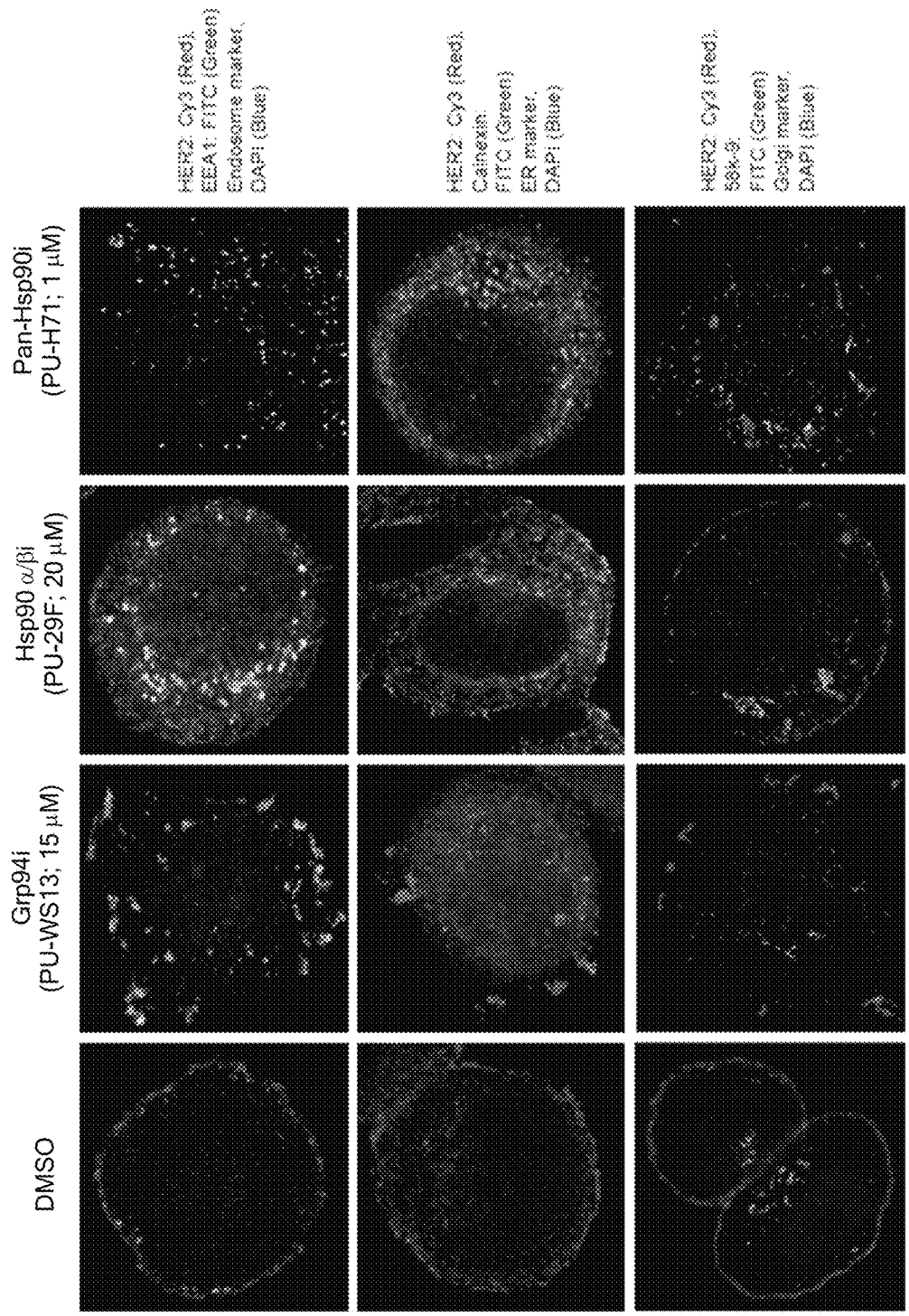
FIG. 7d shows fluorescence microscopy image of SKBr3 cells treated for 4 h with DMSO, PU-WS13 (15 µM), PU-29F (20 µM) or PU-H71 (1 µM) and then stained with the indicated markers upon fixation and permeabilization Inhibitor destabilized HER2 co-localizes with endosomal structures adjoining the plasma membrane (for Grp94 inhibition) or with those found inside the cytosol (for Hsp90 inhibition).
Figure 8H:
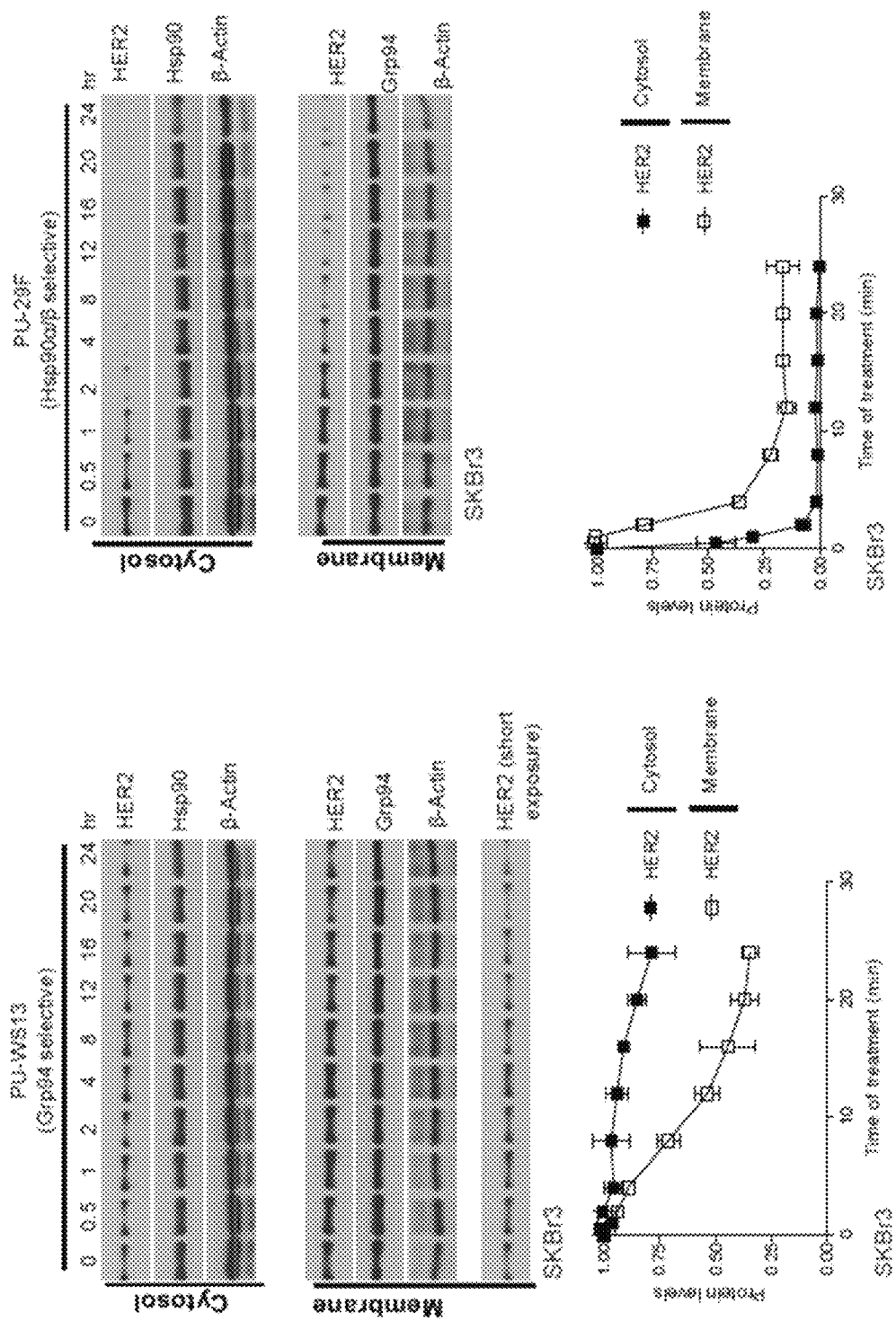

We found that upon Grp94 inhibition, HER2 molecules translocated to early endosomes and plasma membrane-adjacent lysosomes (FIG. 8*g*, LAMP-1 stain and FIG. 7*d*, EEA1 stain). Grp94-inhibited HER2 did not co-localize with ER and Golgi structures (FIG. 7*d*, Calnexin and 58 k-9 stains). The membrane but not the cytosolic HER2 molecules were substantially reduced in a time-dependent manner upon Grp94 inhibition in SKBr3 cells (FIG. 8*h*), altogether, further demonstrating that Grp94 regulates HER2 specifically at the plasma membrane in SKBr3 cells.

In SKBr3 cells and other HER2-overexpressing breast cancer cells, the high-density HER2 tyrosine kinase formations at the cell membrane result in increased signaling and activation of several survival and proliferation-inducing signaling pathways, such as those channeled by Raf-MAPK, AKT and STAT3 (Yarden, Y. & Sliwkowski, M. X. Untangling the ErbB signaling network. *Nat. Rev. Mol. Cell Biol.* 2, 127-137 (2001)). For the case of the Raf-MAPK axis, HER2 promotes retention of Raf-1 in the plasma membrane, resulting in prolonged activation of the MAP kinase cascade (Zhang, L., Bewick, M. & Lafrenie, R. M. EGFR and ErbB2 differentially regulate Raf-1 translocation and activation. *Lab. Invest.* 82, 71-78 (2002)). In further accord with a role for Grp94 in regulating HER2 function at the plasma membrane, we found that pharmacologic inactivation of Grp94 in SKBr3 cells resulted in a rapid inhibition of Raf-1-MAPK signaling at the membrane but not in the cytosol (FIG. 8*i*).

Collectively, these findings indicate that in SKBr3 cells, Grp94 chaperoning is needed to maintain a high-density HER2 architecture and an effective streamlining of its signaling at the plasma membrane but not in the cytosol (FIG. 8*j*). Without Grp94 chaperoning, the plasma membrane architecture of HER2 becomes disrupted, leading to the shutdown of its signaling capacity. Altered HER2 molecules from plasma membranes become engulfed by lysosomes and endosomal structures, ultimately resulting in HER2 clearance.

5.5.2.3 Hsp90α/β Regulate Cytosolic HER2 Species

Figure 6F:
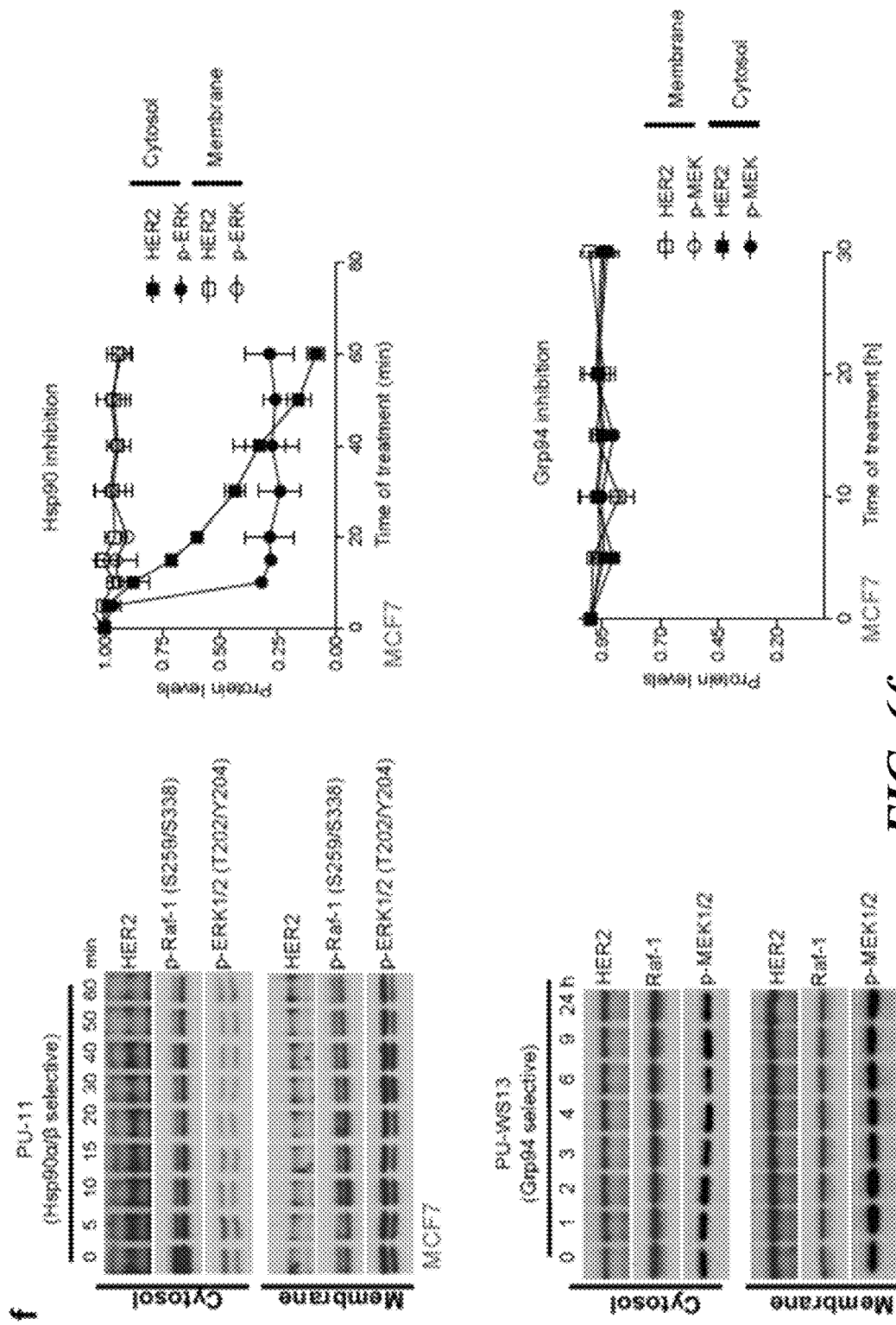
FIG. 6f shows representative WB of MCF7 cells treated for the indicated times with PU-WS13 (15 µM) or PU-11 (40 µM). Protein levels in membrane and cytosolic fractions were plotted against the time of treatment. Data are presented as mean±SEM (n=3).

Using our paralog-specific chemical toolset, we have shown that Grp94 plays a key role in regulating HER2 at the plasma membrane of high-HER2 SKBr3 cells. We next wanted to investigate the role of Hsp90 in regulating the cytosolic HER2. In agreement with the previously proposed specialized role of Hsp90 on cytosolic HER2, Hsp90α/β inhibitors failed to disturb the membrane HER2 architecture in SKBr3 cells, and modified primarily the cytosolic HER2 species (FIG. 8*g*; PU-29F). As such, upon Hsp90α/β inhibition, we observed a marked HER2 redistribution towards lysosomal and early endosomal structures that were distributed throughout the cytosol (FIG. 8*g*, LAMP-1 stain and FIG. 7*d*, EEA1 stain; PU-29F). In addition, by 30 min following Hsp90α/β inhibition, steady-state levels of cytosolic but not membrane-associated HER2 greatly decreased (FIG. 8*h*), similar to what we have seen in MCF7 cells (FIG. 6*f*). Following cytosolic HER2 depletion, we noted a decrease in plasma membrane associated HER2 (FIG. 8*h*), confirming the previously proposed role of Hsp90 in the trafficking and regulation of the cytosolic HER2 species (Xu, W., Mimnaugh, E. G., Kim, J. S., Trepel, J. B. & Neckers, L. M. Hsp90, not Grp94, regulates the intracellular trafficking and stability of nascent ErbB2. *Cell Stress Chaperones* 7, 91-96 (2002)).

Figure 9:
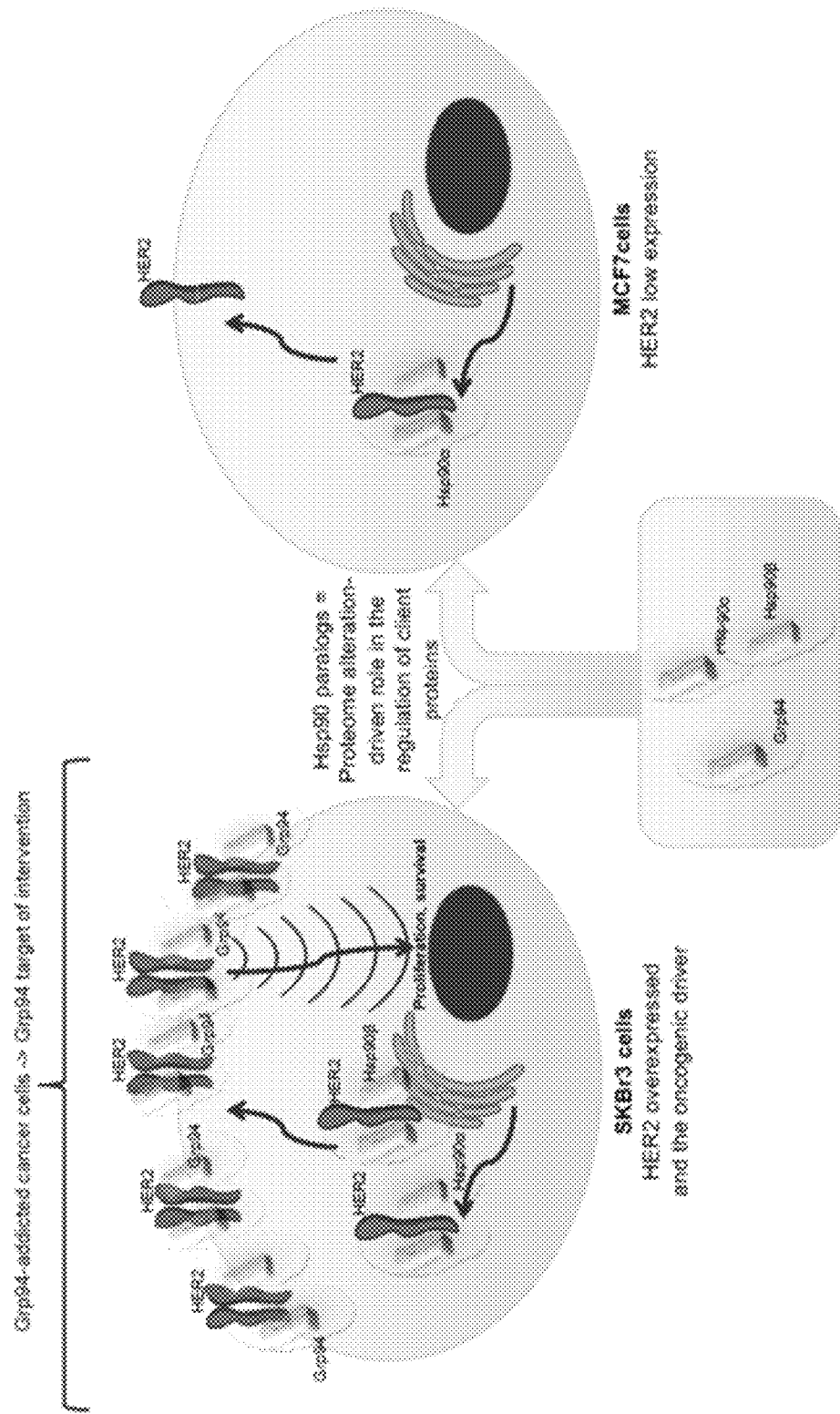
FIG. 9 shows schematic representation summarizing the tumor-specific regulation of HER2 by the Hsp90 paralogs. All epithelial cells contain two copies of the HER2-encoding gene and express small amounts of the HER2 receptor on the cell surface. During oncogenic transformation, the number of gene copies per cell may increase, as in the SKBr3 cell line, leading to an increase in mRNA transcription and a 100- to 1,000-fold increase in the number of HER2 receptors on the cell surface. Hsp90 is sufficient for HER2 function in most cells with low to medium-HER2 expression. Under conditions in which the stress imposed on the cell by proteome alterations (i.e. HER2 plasma overexpression) Grp94 also comes into play, and, the chaperoning function of Grp94 is vital for proper HER2 functioning in these conditions. Because HER2 is the major oncogene in these cells, its dependence on Grp94 renders cells addicted to proper Grp94 functioning. Grp94 therefore becomes a target in such cancers.

To summarize, our data point to distinct Hsp90 paralog requirements for HER2 regulation that are dictated by proteome alterations in the cell (FIG. 9). To chaperone the altered expression and activity of HER2 in HER2-overexpressing cells, where maintenance of a high-density/high-signaling HER2 species is a mechanism for its oncogenic properties, the cell appears to utilize Hsp90α, Hsp90β and Grp94. Cytosolic HER2 requires both Hsp90α and Hsp90β. The aberrantly high levels of plasma membrane HER2 require Grp94. In cells with low HER2 expression, by contrast, the activity of Hsp90α alone appears sufficient to sustain HER2 function, although our knockdown studies indicate that Hsp90β may compensate for the loss of Hsp90α expression in these cells (FIG. 7*b,c*).

Figure 10A:
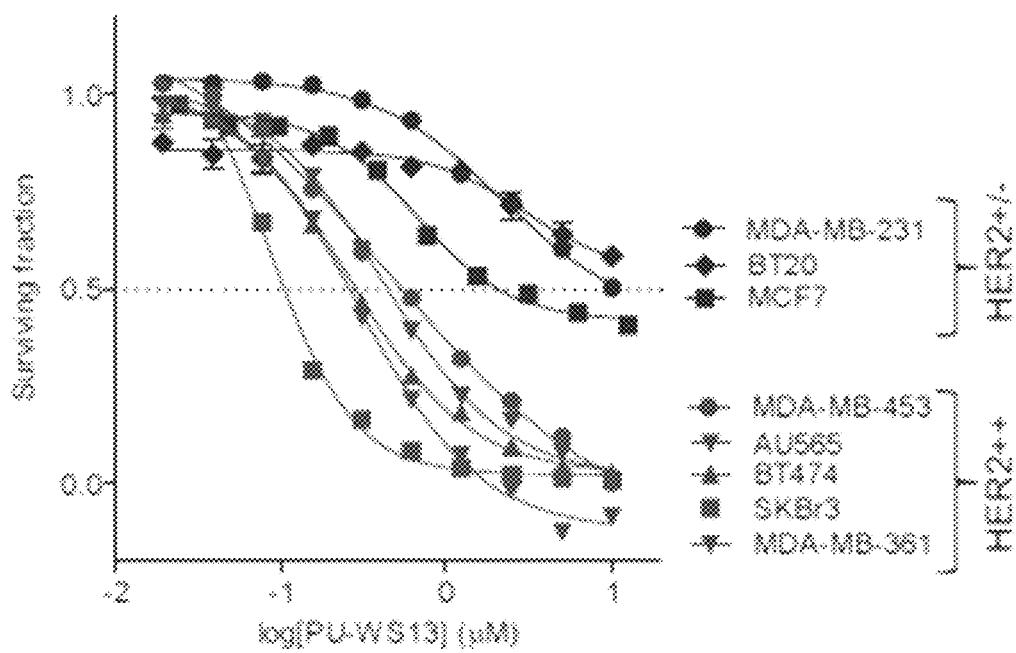
FIG. 10a and FIG. 10b show viability of breast cancer cells in which Grp94 was inhibited with PU-WS13 or knocked-down by means of siRNA. Cell viability was assessed using an assay that quantifies ATP levels.
Figure 10B:
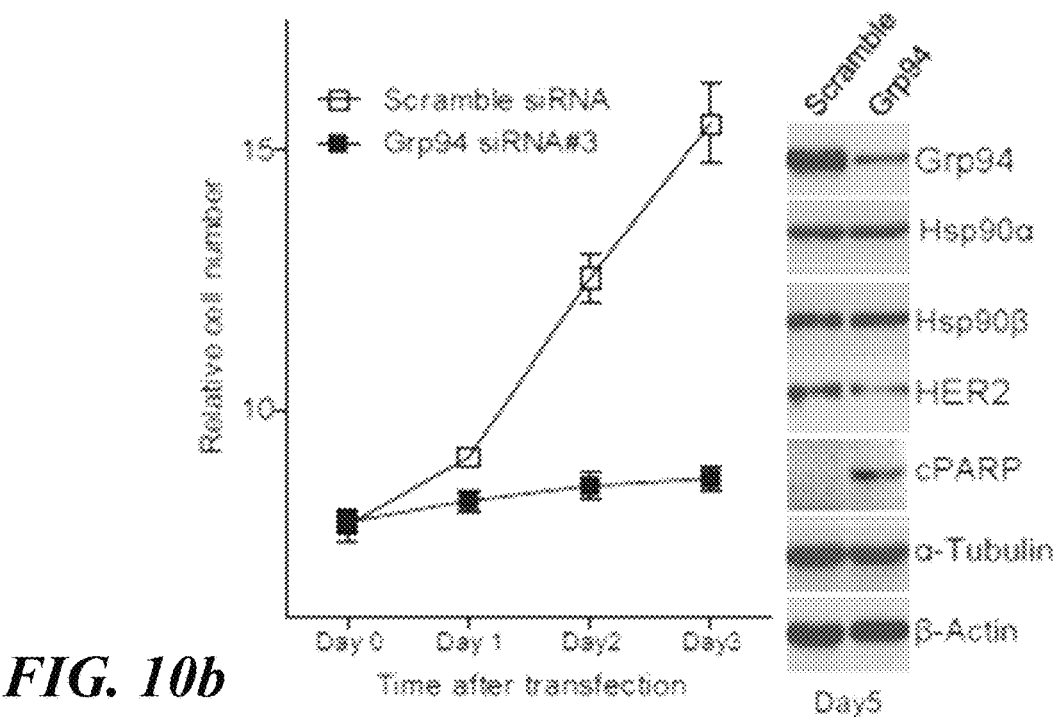
Figure 10F:
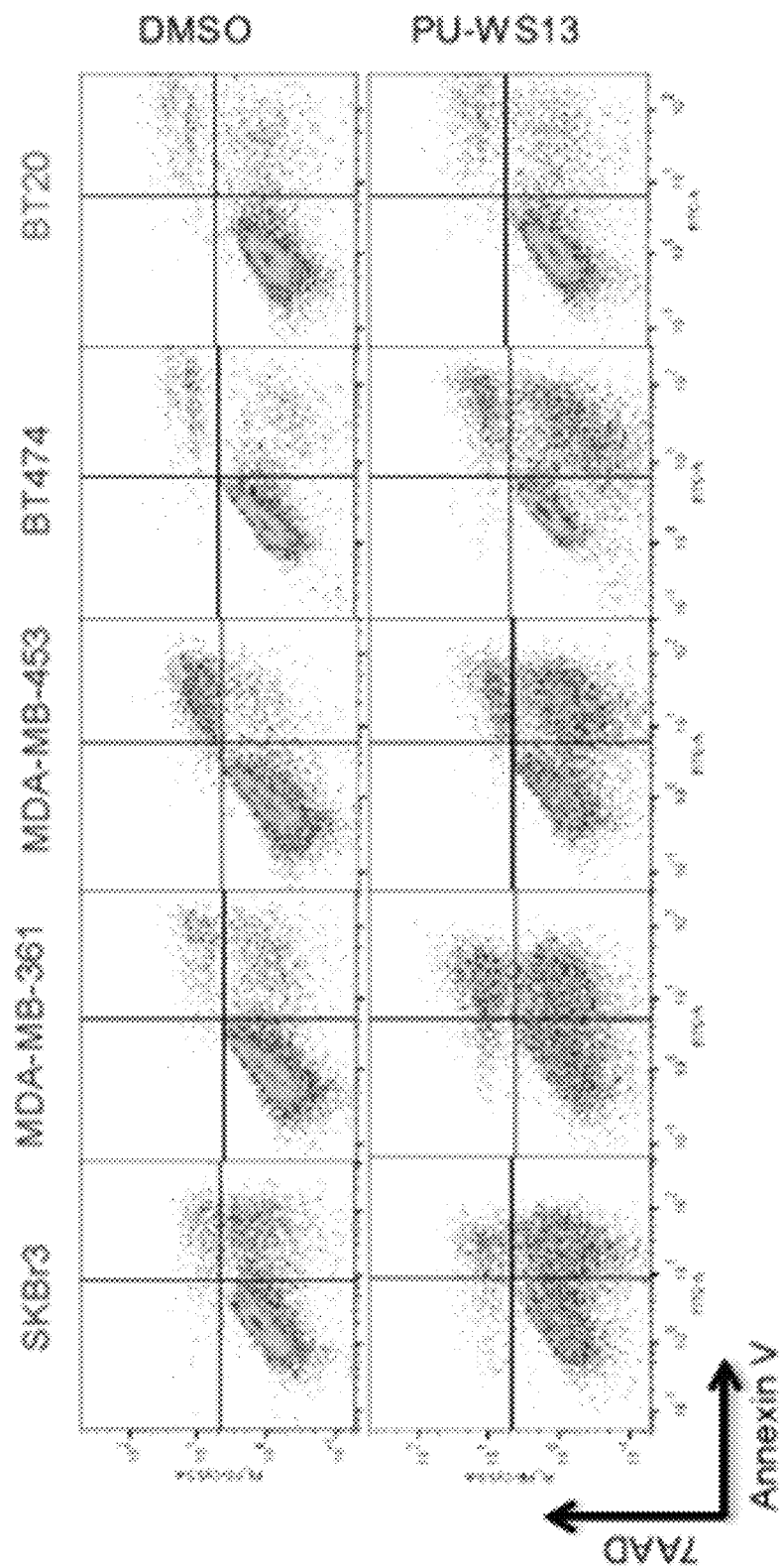
FIG. 10f shows double staining with Annexin V and 7AAD indicates induction of apoptosis following treatment of the indicated breast cancer cells for 48 h with PU-WS13 (10 µM).

5.5.2.4 Inhibition of Grp94 Alone is Sufficient to Reduce the Viability of HER2-Overexpressing Cells Given the important role we identified for Grp94 in plasma membrane HER2 stability and function in high-HER2 SKBr3 cells, we next asked whether inactivating Grp94 reduced SKBr3 cancer cell viability. Indeed, both Grp94 inhibition (FIG. 10*a*) and Grp94 knockdown (FIG. 10*b*) impaired SKBr3 viability. This effect was not limited to the SKBr3 cell line, since we observed that all other tested HER2-overexpressing breast cancer cells, such as AU565, BT474, MDA-MB-453 and MDA-MB-361, were sensitive to Grp94 inhibition (FIG. 10*a*). Specifically, upon treatment of these cells with PU-WS13, we noted a rapid accumulation of cells in sub-G1 phase, observed as early as 1-2 h post-treatment (FIG. 10*c*), cleavage of PARP (FIG. 10*d,e* and FIG. 11a) and a substantial increase in cells exhibiting markers of early- and late-stage apoptosis (FIG. 10f).

Annexin V Apoptosis with 7-AAD has been specifically designed for the identification of apoptotic and necrotic cells. Annexin V (or Annexin A5) is a member of the annexin family of intracellular proteins that binds to phosphatidylserine (PS) in a calcium-dependent manner. PS is normally only found on the intracellular leaflet of the plasma membrane in healthy cells, but during early apoptosis, membrane asymmetry is lost and PS translocates to the external leaflet. Fluorochrome-labeled Annexin V can then be used to specifically target and identify apoptotic cells. Annexin V binding alone cannot differentiate between apoptotic and necrotic cells. To help distinguish between the necrotic and apoptotic cells 7-amino-actinomycin D (7-AAD) is used. Early apoptotic cells will exclude 7-AAD, while late stage apoptotic cells will stain positively, due to the passage of these dyes into the nucleus where they bind to DNA. 7-AAD (7-amino-actinomycin D) has a high DNA binding constant and is efficiently excluded by intact cells. It is useful for DNA analysis and dead cell discrimination during flow cytometric analysis. When excited by 488 laser light, 7-AAD fluorescence is detected in the far red range of the spectrum (650 nm long-pass filter).

Figure 11A:
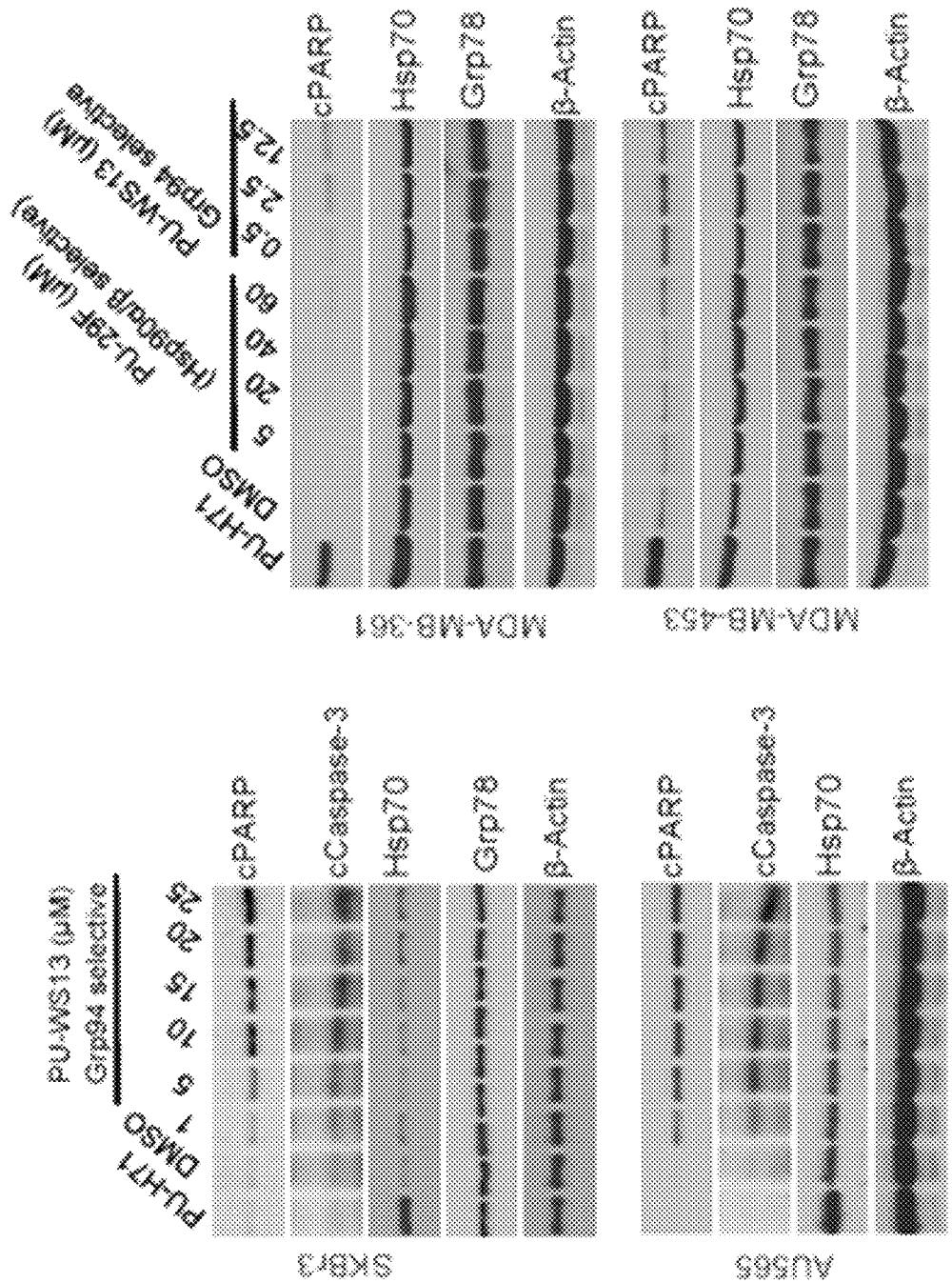

As shown in FIG. 11 both the pan-Hsp90 inhibitor and the cytosolic Hsp90 inhibitors failed to induce apoptosis in two HER2++ cells lines, SKBr3 and AU565 as evidenced by no PARP cleavage (FIG. 11a,b) and little to no apoptosis (FIG. 11d).

Importantly, unlike the pan-Hsp90 and the cytosolic Hsp90 inhibitors, PU-WS13 failed to activate a feed-back heat shock response, as evidenced by little to no Hsp70 induction (FIG. 10d,e and FIG. 11). Hsp90α/β inhibition alone, despite substantially depleting HER2, was less effective at killing these cells and instead elicited a mostly cytostatic effect (FIG. 11b,c). Neither inhibitor led to a substantial increase in Grp78, the ER Hsp70 paralog, in these cells (FIG. 5b, FIG. 11). Downregulation of Grp94 levels also failed to induce Grp78 in SKBr3 cells (FIG. 7b).

5.5.2.5 Grp94 Inhibitors can be Used to Treat HER2 Overexpressing Gastric Cancers Gastric cancer shows a poor prognosis and is the second leading cause of cancer-related deaths. Its incidence is estimated at 934,000 cases, 56% of new cases are in Eastern Asia, 41% in China, and 11% in Japan. Although fluoropyrimidine- and platinum-based combination chemotherapy is the most widely accepted in the world at present, its benefit does not translate into higher overall survival rates. Despite recent advances in the molecular understanding of gastric cancer, there is a noticeable lack of targeted therapies in clinical development for this malignancy. Therefore, more effective therapies for gastric cancer are required. In gastric cancer, EGFR, HER2, and HER3 overexpression has been identified and a relationship with prognosis is suggested. Therefore, inhibiting the signal transduction through heterodimers including HER2 possibly provides more benefit to patients with gastric cancer. Recently, the ToGA trial [a phase III study of trastuzumab (Herceptin) in HER2-positive advanced and inoperable gastric cancer] showed a survival benefit when trastuzumab was added to chemotherapy in HER2-overexpressing gastric cancer patients and the Food and Drug Administration has approved trastuzumab for HER2-positive metastatic gastric and gastroesophageal junction cancer. Thus, anti-HER2 therapy has been identified to be of clinical significance. Amplification of HER2 has been associated with the intestinal pathologic subtype of gastric cancer as well as with tumors arising from the gastroesophageal junction. The largest analysis to date of the incidence of HER2 amplification in gastric cancer was from the recently reported phase III clinical trial evaluating the combination of trastuzumab with chemotherapy in patients with metastatic gastric cancer. In this study, the overall rate of HER2 amplification was reported to be 22%, with a higher percentage (34%) in patients with gastroesophageal junction tumors.

Figure 12A:
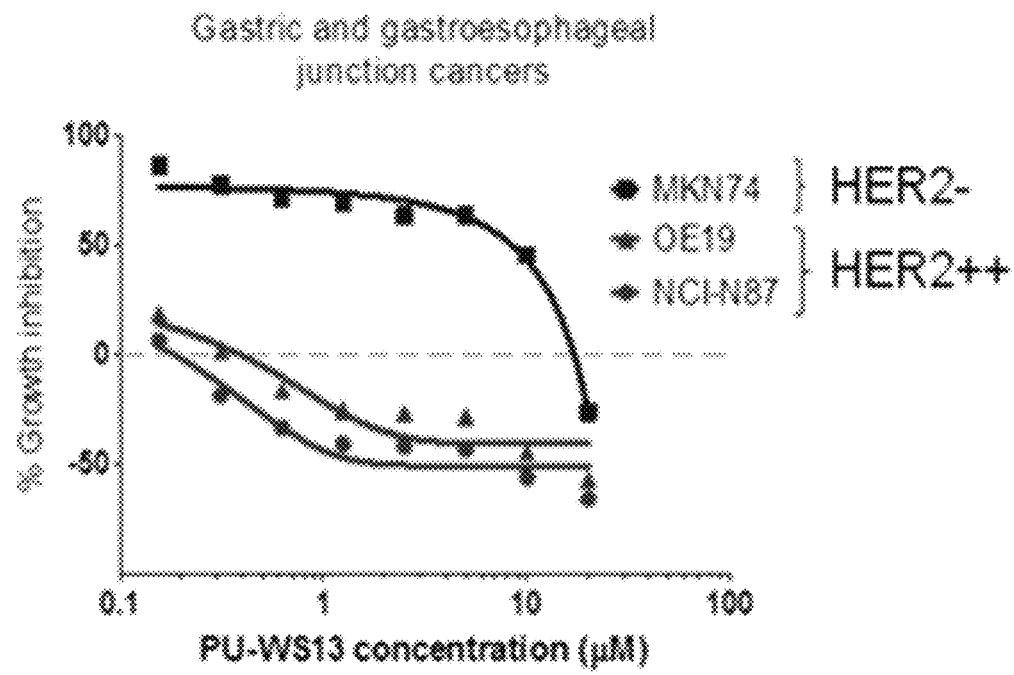
FIG. 12a shows the sensitivity of gastric cancers and esophageal cancer cells to a selective Grp94 inhibitor. The OE19 and NCI-N87 cells, which overexpress high levels of HER2, were susceptible to Grp94 inhibition. The MNK74 cells, which do not overexpress HER2, were not susceptible to Grp94 inhibition.
Figure 12B:
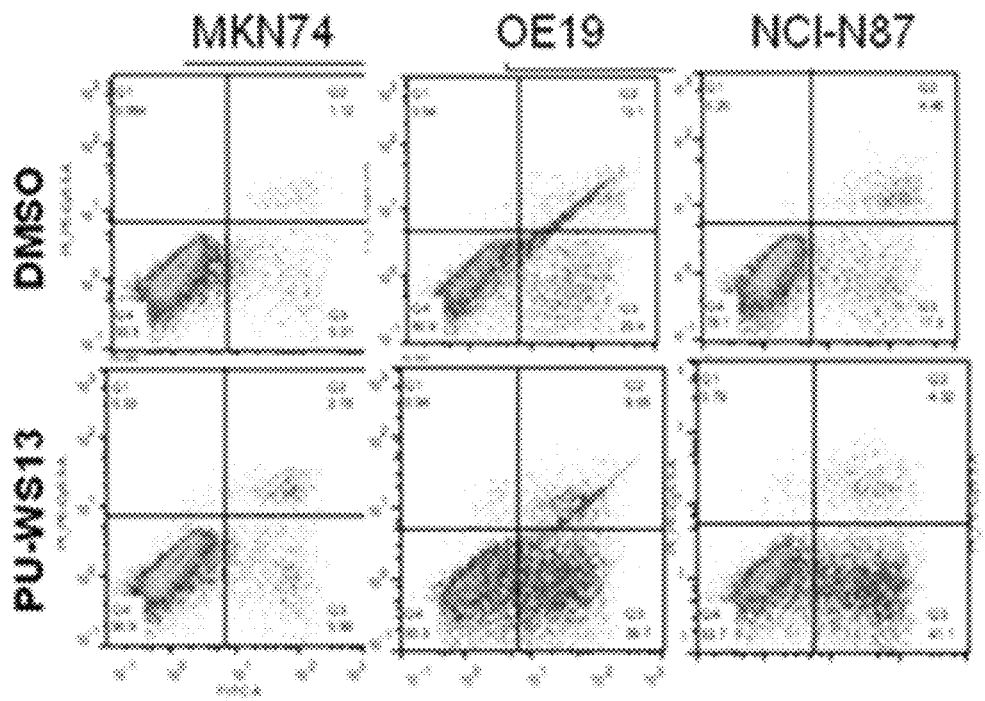
FIG. 12b shows double staining with Annexin V and 7AAD indicates induction of apoptosis following treatment of the indicated gastric and esophageal cancer cells for 48 h with PU-WS13 (10 µM).

We have found that gastric carcinomas expressing high levels of HER2 are particularly sensitive to Grp94 inhibition. On the other hand, gastric carcinomas that do not overexpress HER2 are not susceptible to Grp94 inhibition therapy. The sensitivity of OE19, an esophageal adenocarcinoma with 100-fold amplification of the HER2 gene, to Grp94 inhibition was tested using the Grp94 selective inhibitor PU-WS13. Likewise, the sensitivity of NCI-N87, a gastric carcinoma expressing high levels of HER2, was tested for sensitivity to Grp94 inhibition with the Grp94 selective inhibitor PU-WS13. As shown in FIG. 12a, both the OE19 and NCI-N87 cells were highly susceptible to Grp94 inhibition. On the other hand, MKN74, a gastric adenocarcinoma with no HER2 amplification was not sensitive to Grp94 inhibition. Moreover, as shown in FIG. 12b, there was a substantial increase in cells exhibiting markers of early- and late-stage apoptosis observed for the OE19 and NCI-N87 cells but not for the MKN74 cells.

5.5.3 EGFR Dependent Tumors

The epidermal growth factor receptor (EGFR) gene, located on chromosome 7p12, encodes a 170 kDa membrane glycoprotein. Upon activation by specific ligands such as EGF, its intrinsic kinase is activated and initiates a number of signaling pathways. Upregulated EGFR signaling has been correlated in a wide variety of tumors with progression to invasion and metastasis. EGFR was purified initially from the human squamous cell carcinoma cell line A431, which overexpresses EGFR from 2- to 100-fold, resulting from a commensurate 3- to 110-fold increase in EGFR gene copy number. Since then, many types of epithelial malignancies have been shown to express increased levels of EGFR expression on the cell membrane, with or without gene amplification. EGFR has been identified as a strong prognostic indicator in head and neck, breast, ovarian, cervical, bladder, and esophageal cancers. High EGFR expression has been shown to correlate with poor survival in a range of tumors including nasopharyngeal, NSCLC, ovarian, and breast. In patients with nasopharyngeal carcinoma, a significant correlation between high levels of EGFR and poor survival has also been noted. In ovarian cancer specimens, 61% scored positive for EGFR, and a significant correlation was observed between EGFR expression and shorter overall and progression-free survival. This study also correlated EGFR status with resistance to platinum-containing chemotherapy. In addition, several studies have reported that EGFR expression predicts for a significantly shorter disease-free and overall survival in patients with breast cancer. Potentially explaining the association with poor patient outcome, the expression of EGFR has been linked with resistance to both hormonal therapies and chemotherapeutic agents. There is increasing evidence demonstrating that growth factor pathways are highly interactive with estrogen receptor signaling in the control of breast cancer growth. In tamoxifen-resistant breast cancer cell lines, antiestrogenic resistance is associated with upregulation of the EGFR pathway.

The Grp94 inhibitors of the disclosure can be used to treat EGFR dependent cancers such as pancreatic cancer, neck cancer, breast cancer, ovarian cancer, cervical cancer, bladder and esophageal cancers. We have found that inhibition or depletion of Grp94 in cells that overexpress EGFR results in apoptosis of the cells along with a mitigation or termination of the signaling event mediated by EGFR. Moreover, inhibition of Grp94 is not associated with feed-back upregulation of anti-apoptotic proteins, including heat shock protein 70 (Hsp70). As a result, the selective EGFR inhibitors are capable of inducing apoptosis of HER2 overexpressing cancer cells to a far greater extent than pan-Hsp90 inhibitors, where upregulation of Hsp70 mitigates the anti-apoptotic effects of the inhibitor. Accordingly, the disclosure provides methods for selectively inducing apoptosis in EGFR overexpressing cancer cells. Moreover, the disclosure provides methods of treating EGFR overexpressing cancers by administering a therapeutically effective amount of a selective Grp94 inhibitor.

In particular embodiments, the disclosure provides methods of treating EGFR overexpressing breast cancers by administering a therapeutically effective amount of a selective Grp94 inhibitor. In some such embodiments, the breast cancer is triple negative breast cancer. In other embodiments, the disclosure provides methods of treating EGFR overexpressing pancreatic cancers by administering a therapeutically effective amount of a selective Grp94 inhibitor. In still other embodiments, the disclosure provides methods of treating HER2 overexpressing ovarian cancers by administering a therapeutically effective amount of a selective Grp94 inhibitor.

In some embodiments, the Grp94 inhibitors of the disclosure can be used to treat endocrine-resistant breast and ovarian cancers (e.g., tumors resistant to tamoxifen). The Grp94 inhibitors of the disclosure may be used in combination with am antiestrogen such as a selective estrogen receptor modulator (e.g., tamoxifen) or an aromatase inhibitor (e.g., exemestone or anastrozole).

Figures 13A, 13B, 13C:
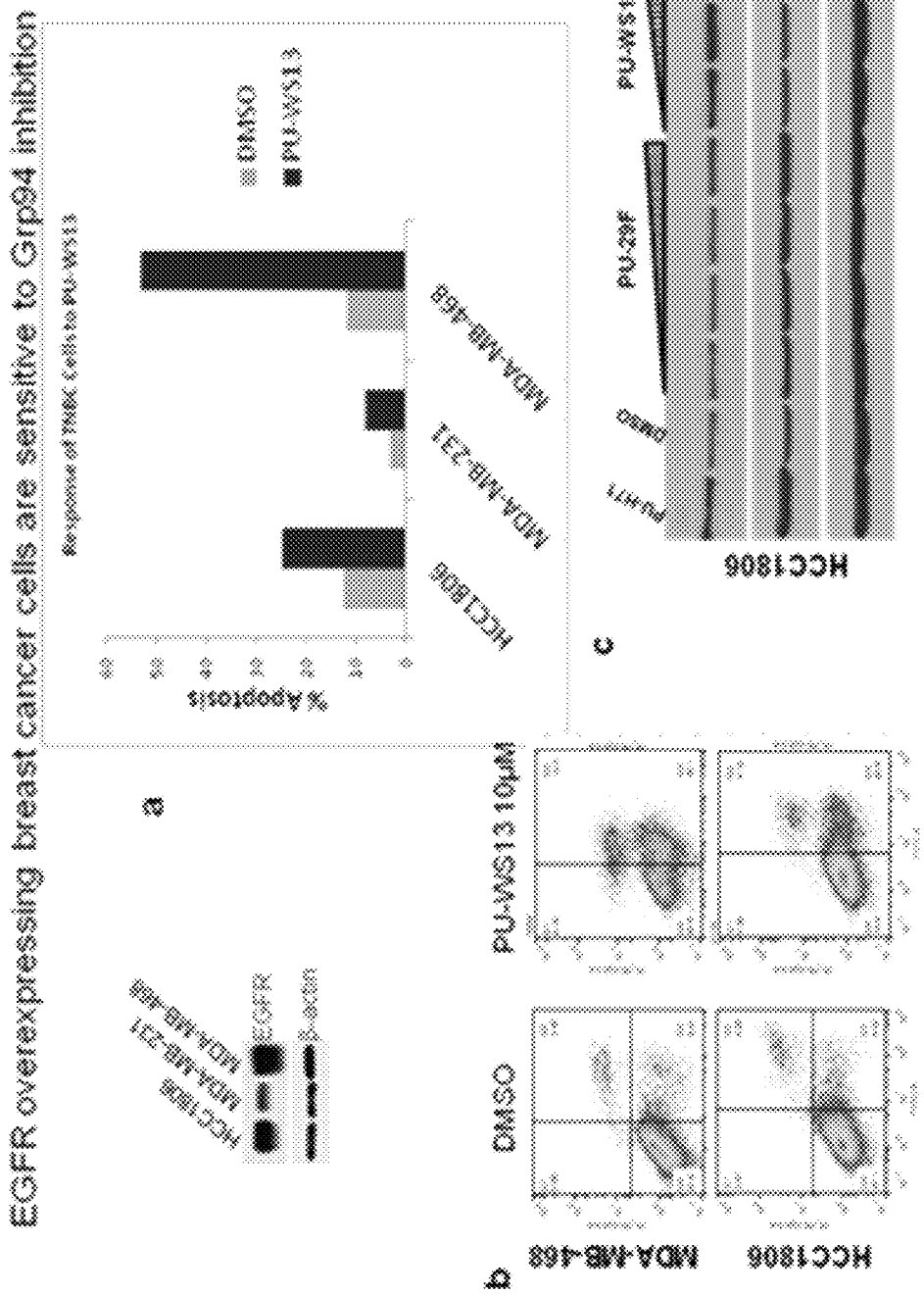
FIG. 13 shows that EGFR overexpressing triple negative breast cancer cells are sensitive to the selective Grp94 inhibitor PU-WS13. The sensitivity of the EGFR overexpressing triple negative breast cancer cells was tested for the presence of apoptotic cells double staining with Annexin V and 7AAD (FIGS. 13a, 13b) and by immunoblotting for the presence of cleaved PARP (FIG. 13c).

The Grp94 inhibitors of the disclosure can be used to treat patients with EGFR overexpressing triple negative breast cancer. As shown in FIGS. 13a-c, EGFR overexpressing triple negative breast cancer cells are sensitive to the selective Grp94 inhibitor PU-WS13. The sensitivity of the EGFR overexpressing triple negative breast cancer cells was tested for the presence of apoptotic cells by Annexin V staining (13a, 13b) and by immunoblotting for the presence of cleaved PARP (13c). There was a substantial increase in the triple negative breast cancer cells exhibiting markers of early- and late-stage apoptosis (FIG. 13a,b) and an increase in PARP cleavage following Grp94 but not Hsp90 inhibition (FIG. 13c) Hence, Grp94 inhibition resulted in apoptosis of the triple negative breast cancer cells. The Grp94 inhibitors of the disclosure can be used to treat patients with EGFR overexpressing pancreatic cancer. Ligand activation of EGFR-family proteins (EGFR is a member of the receptor tyrosine kinase superfamily of transmembrane proteins) results in perturbation of a variety of downstream signaling cascades. Based on studies described herein, we have uncovered that Grp94 maintains the architecture of high density EGFR formations at the plasma membrane, particularly in cells where EGFR is required to channel the amplified signaling through the receptor (e.g., EGFR overexpressing pancreatic cells). Hence, Grp94 inhibition results in a significant attenuation of EGFR signaling.

Figure 14B:
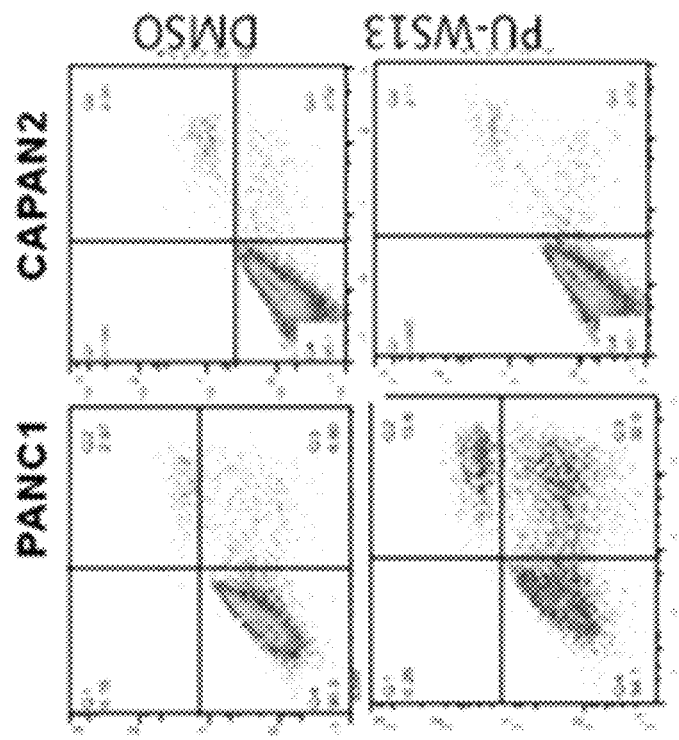
FIG. 14b shows there was a substantial increase in cells exhibiting markers of early- and late-stage apoptosis observed for the PANC-1 cells but not for the Capan-2 cells, as indicated by double staining with Annexin V and 7AAD.
Figure 14A:
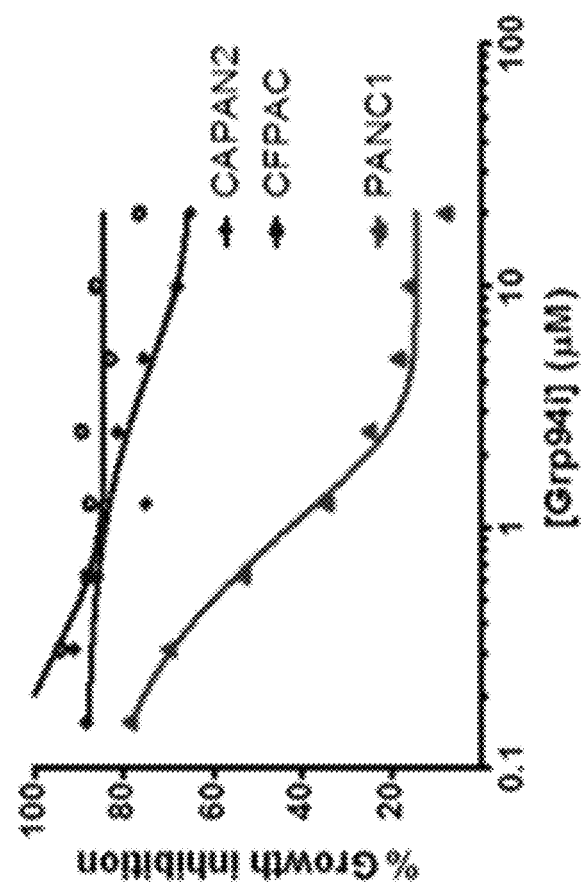
FIG. 14a shows that the selective Grp94 inhibitor PU-WS13 effectively inhibited the growth of the EGFR overexpressing PANC-1 cells but had no effect on the Capan-2 cells and a modest effect on the growth of the CFPAC cells (FIG. 14a).
Figure 15:
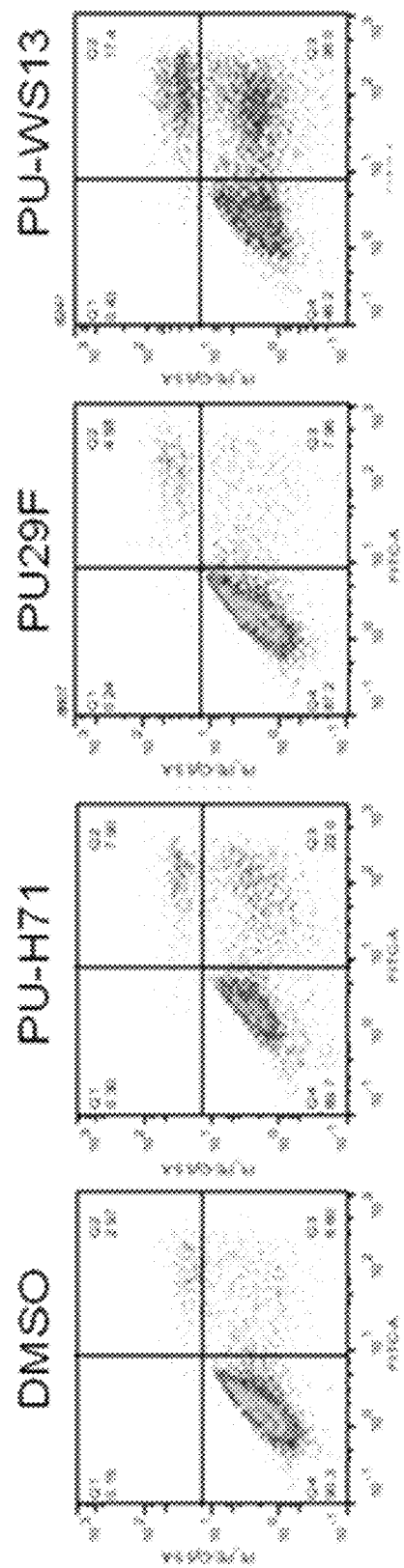
FIG. 15 shows that treatment of EGFR-overexpressing PANC-1 cells with the Grp94 selective inhibitor PU-WS13 was more potent at killing cells through apoptosis than were the pan-HSP90 inhibitor PU-H71 and the HSP90α inhibitor PU-29F. Double staining with Annexin V and 7AAD indicates induction of apoptosis.
Figure 17:
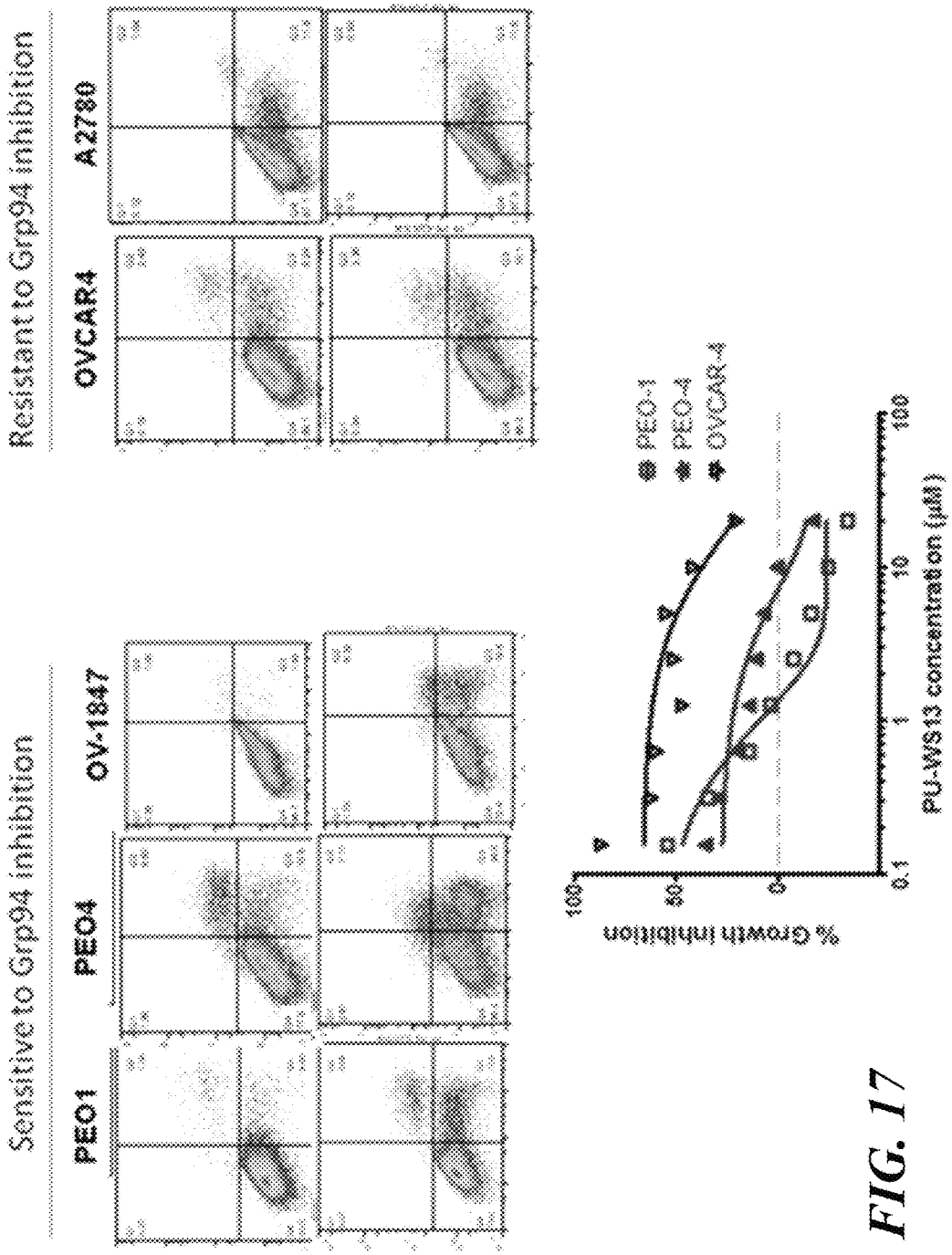
FIG. 17 shows that the Grp94 selective inhibitor PU-WS13 induces apoptosis in IGF1R and TGFbeta expressing ovarian cancer cell lines derived from a poorly differentiated serous adenocarcinoma.

As shown in FIG. 14, EGFR overexpressing cancer cells are sensitive to the Grp94 inhibitor PU-WS13. EGFR levels are 10-17-fold higher in the PANC-1 cells relative to that observed in the Capan-2 cells. CFPAC also express low EGFR levels. HER2 levels are similar among the cell lines. The selective Grp94 inhibitor PU-WS13 effectively inhibited the growth of the EGFR overexpressing PANC-1 cells but had no effect on the Capan-2 cells (FIG. 14a). The Grp94 selective inhibitor had a modest effect on the growth of the CFPAC cells (FIG. 14a). Moreover, as shown in FIG. 14b, there was a substantial increase in cells exhibiting markers of early- and late-stage apoptosis observed for the PANC-1 cells but not for the Capan-2 cells. In contrast, the pan-Hsp90 inhibitor PU-H71 (FIG. 1a) and the HSP90α inhibitor PU29F had very little effect on inducing apoptosis of the PANC-1 cells (FIG. 15).

Of note, PANC1 EGFR-overexpressing cells are reported to be resistant to the EGFR inhibitor erlotinib (*Mol Cancer Ther* 2006; 5:2051-2059) suggesting that inhibition of EGFR signaling by Grp94 inhibitors may be more efficacious in pancreatic cancer than inhibition of EGFR by EGFR kinase inhibitors. Erlotinib (Tarceva, OSI-774, OSI Pharmaceuticals, Inc.) is a low molecular weight, orally bioavailable inhibitor of EGFR and exhibits >100-fold selectivity for EGFR over other receptor tyrosine kinases, including PDGFR, insulin-like growth factor-I receptor, and HER-2.

The Grp94 inhibitors of the disclosure can be used to treat EGFR dependent cancers that are resistant to therapy with EGFR inhibitors. In one such embodiment, the cancer is pancreatic cancer that is resistant to therapy with EGFR inhibitors. The Grp94 inhibitor can be used in combination with an EGFR inhibitor. In particular embodiments, a Grp94 inhibitor is used in combination with the EGFR inhibitor erlotinib in the treatment of pancreatic cancer.

Aberrant epidermal growth factor receptor (EGFR) expression is detected in up to 60% of ovarian cancers and occurs in all histologic subtypes. Further, aberrant EGFR expression is associated with poor outcome of ovarian cancer patients. Overexpression of the EGFR protein has been detected in 9%-62% of human ovarian cancers; the differences in frequencies from these studies likely reflect utilization of different antibodies and cutoffs for overexpression. EGFR gene amplification or protein overexpression occurs across all epithelial ovarian cancer histotypes. Increased EGFR expression has been associated with high tumor grade, high cell proliferation index, aberrant P53 expression, and poor patient outcome (Siwak et al Journal of Oncology 2010; doi:10.1155/2010/568938). The Grp94 inhibitors of the disclosure can be used to treat EGFR dependent ovarian cancers.

Figure 24A:
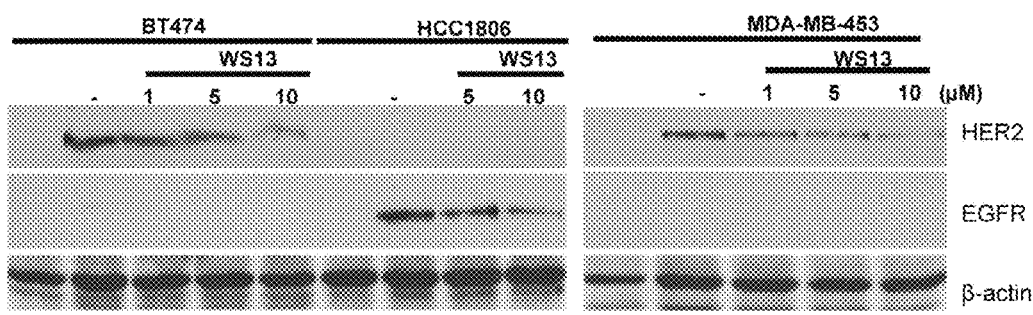
FIG. 24a shows Western blot analysis of the activity of PU-WS13 in a panel of cancer cells.
Figure 24B:
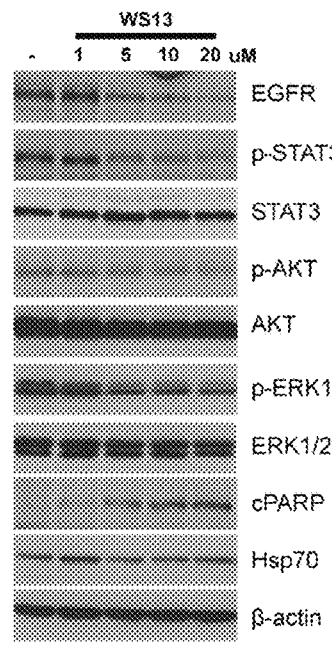
(FIG. 24b) MDA-MB-468 cells were treated for 24 h with the indicated concentration of PU-WS13 or with vehicle (−)
Figure 24C:
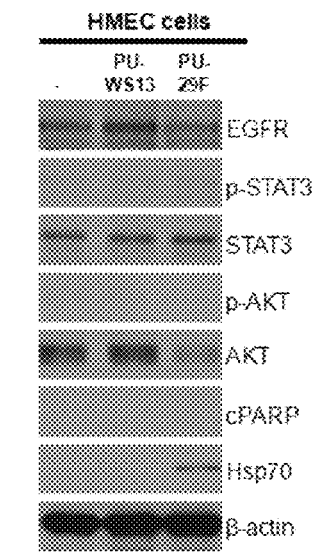
(FIG. 24c) HMEC cells were treated for 24 h with the indicated concentration of PU-WS13, PU29F or with vehicle (−). The expression of HER2 and EGFR, as well as the expression and activity of proteins involved in downstream signaling through these receptors (STAT, AKT ERK) were analyzed by Western blot.

5.5.4 the Grp94 Inhibitor does not Affect RTK Expression and Activity in Normal Cells FIG. 24 shows the activity of PU-WS13 in a panel of cancer cell lines driven by overexpression of either HER2 or EGFR receptor tyrosine kinases. For comparison, the agent was also tested in a normal cell line, human mammary epithelial cells (HMECs). Note that the Grp94 inhibitor PU-WS13 does not affect EGFR and its downstream signaling in normal cells characterized by normal expression and function of EGFR, such as in the HMEC cells. Without wishing to be bound by any particular theory, it is believed that a Grp94 selective inhibitor may therefore have a better therapeutic index than a direct RTK modulator (i.e. TKI or antibody) because it will act on the RTK only in conditions of oncogenic overexpression (see EGFR in TNBC cell lines vs HMEC). Hence it should be devoid of the side effects commonly associated with therapies directly inhibiting RTKs (cardiac toxicity for trastuzumab and lapatinib, diarrhea, asthenia, and stomatitis for Canertinib, an irreversible pan-HER TKI; diarrhea and rash for EGFR/HER2 TKIs due to RTK inhibition in normal tissues). Grp94 inhibition should also be more active in EGFR+ tumors than direct TKI. Approximately half of cases of triple-negative breast cancer (TNBC) and inflammatory breast cancer (IBC) overexpress EGFR, nonetheless clinical trials testing EGFR inhibitors reported lack of or limited benefit (Masuda H. et al. Breast Cancer Res Treat. 2012 November; 136(2):331-45). Without wishing to be bound by any particular theory, it is believed that such ineffectiveness is due to a crosstalk between EGFR and c-Met or other RTKs, because strategies that knocked down EGFR either by siRNA or by mixtures of antibodies that induces robust degradation of EGFR, led to reduced viability of TNBC cells (Mueller et al., Breast Cancer Res. 2012 Jul. 12; 14(4):R104; Ferraro et al., Proc Natl Acad Sci USA. 2013 Jan. 29; 110(5):1815-20. PMID: 23319610). As per our findings, Grp94 inhibition also induces robust EGFR degradation and apoptosis in TNBC cells, and this effect may provide a therapeutic advantage over TKIs. This indicates that in certain tumors, such as in those addicted on survival on plasma RTK-overexpression, Grp94 inhibition may provide better tumor suppression than a pan-HSP90 inhibitor. While Grp94 inhibition downregulates RTK levels and their downstream signaling, similarly to pan-HSP90 inhibitors, it fails to upregulate a feed-back stress response (i.e. Hsp70 induction).

Cell Lines

The cells, SKBr3, BT474, MDA-MB-468, HCC1806 and MDA-MB-453, were obtained from the American Type Culture Collection (ATCC). Cells were cultured routinely in McCoy's 5A (10% FBS, SKBr3), DME/F12 (10% FBS, BT474 and MDA-MB-468), RPMI (10% FBS, HCC1806) and L-15 (20% FBS, MDA-MB-453) supplemented with 1% Glutamax and 1% penicillin and streptomycin (Pen/Strep). HMEC cells were purchased from Lonza and cultured using Clonetics MEGM Bulletkit. When cultured, cells in L-15 medium were kept in a humidified atmosphere without $CO_2$ at 37° C. and all other cell lines were incubated in the humidified cell incubators with $CO_2$ at 37° C.

Growth Inhibition Assay

We evaluated the antiproliferative effects of inhibitors using the dye Alamar blue. This reagent offers a rapid objective measure of cell viability in cell culture, and it uses the indicator dye resazurin to measure the metabolic capacity of cells, an indicator of cell viability. Briefly, MDA-MB-468 cells were plated on Costar 96-well plates at 1500 cells/well. Cells were allowed to incubate for 24 h at 37° C. before drug treatment. Drugs were added in triplicate at the indicated concentrations, and the plate was incubated for 72 h. Alamar Blue (440 µM) was added, and the plate read 6 h later using Softmax Pro 6 software (Fluorescence intensity mode, excitation 530 nm, emission 580 nm, with 560 nm dichroic mirror). Results were analyzed using GraphPad Prism 5. The percentage cell growth inhibition was calculated by comparing fluorescence readings obtained from treated versus control cells, accounting for initial cell population (time zero). The $IC_{50}$ was calculated as the drug concentration that inhibits cell growth by 50%.

Figures 25A, 25B:
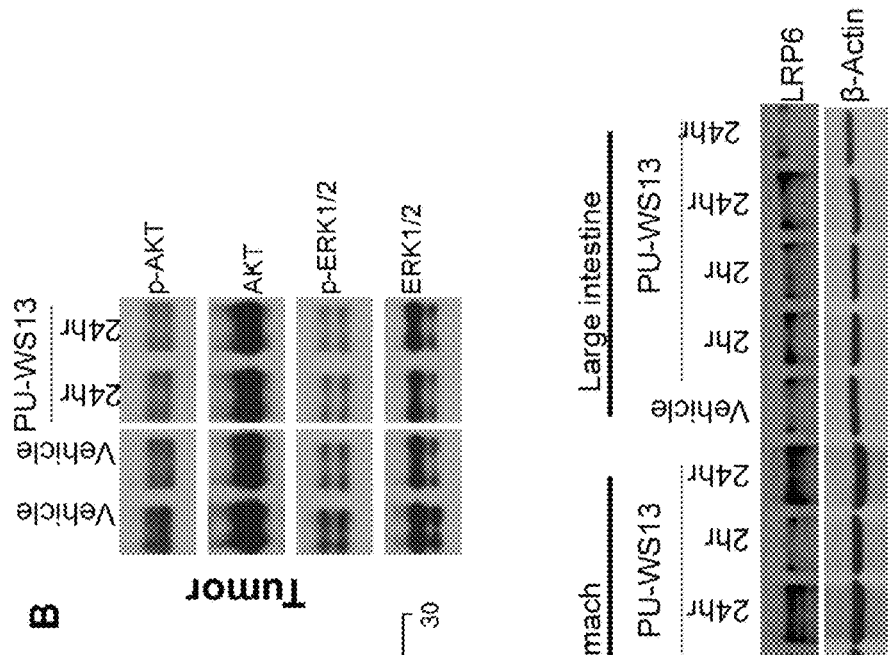
FIG. 25 shows a PK/PD analysis for PU-WS13 tumor retention and selective targeting of Grp94 cancer functions. Mice bearing tumors were injected ip 75 mg/kg of PU-WS13. Mice were sacrificed at the indicated times post-PU-WS13 injection and tissues, tumors, and plasma were harvested. PU-WS13 levels were analyzed by LCMSMS in the indicated tumors (FIG. 25a) or tissues (FIG. 25c). Proteins in the indicated tumors (FIG. 25b) or tissues (FIG. 25d) were analyzed by Western blot.
Figures 25C, 25D:
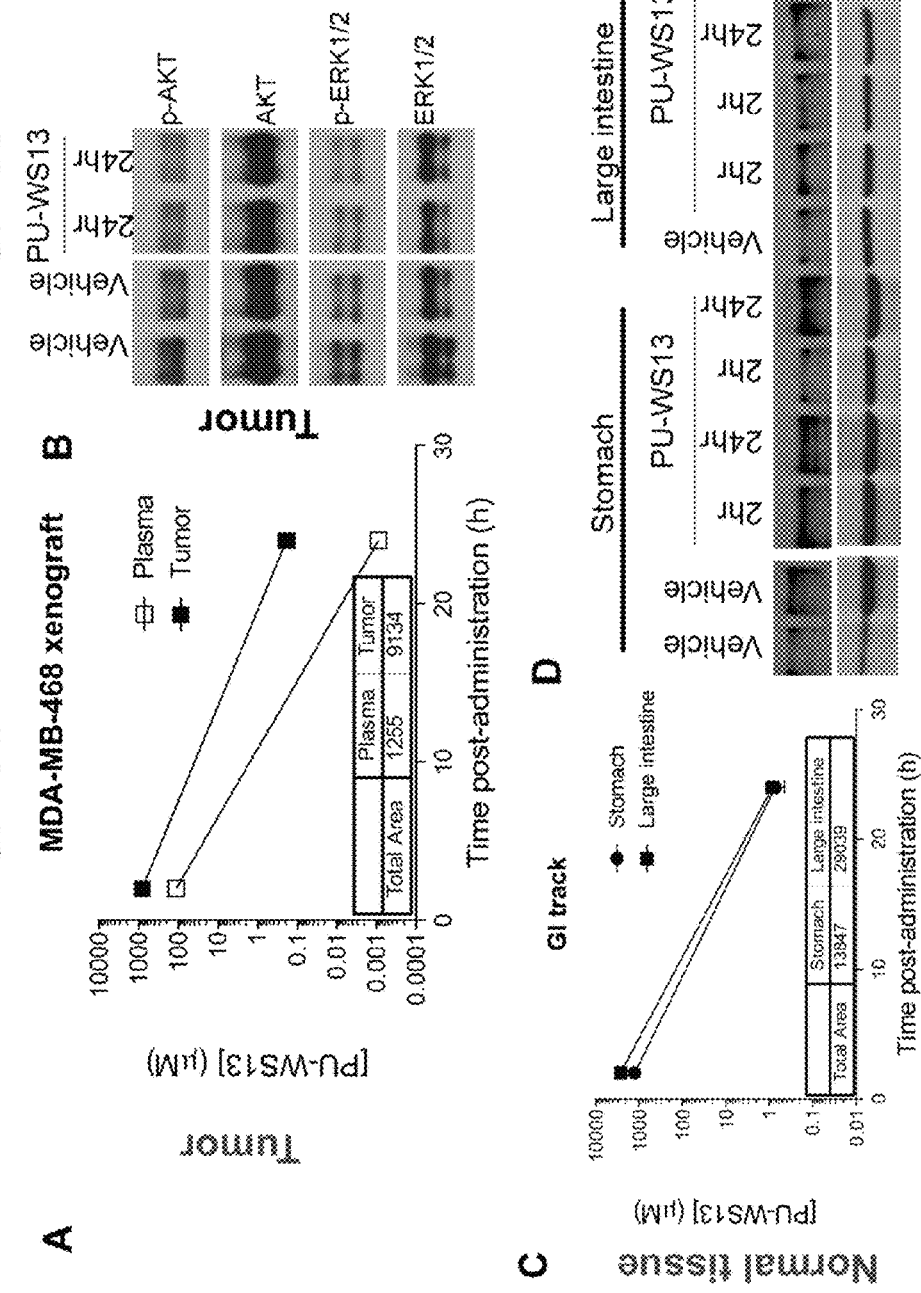

5.5.5 the Grp94 Inhibitors have a Higher Activity Against Tumor-related Grp94 Function Versus Housekeeping (i.e. Normal, Physiological) Functions FIG. 25 shows the activity of the Grp94 inhibitor PU-WS13 against housekeeping and tumor-related Grp94 functions. For this purpose we used mice bearing MDA-MB-468 tumors (a triple-negative breast tumor with EGFR-overexpression). Because of the specific affinity of the provided Grp94 inhibitors for tumor Grp94, we performed PK/PD studies that are tailored for this purpose. In this PK/PD study we incorporated two time points, a 2 h and a 24 h time of sacrifice post-administration. The early time point is incorporated to test the biodistribution of the agent to the site of its action, the tumor; PU-WS13 was readily distributed to tumor mass with ~850 µM noted in tumor at 2 h versus 100 µM in the plasma (FIG. 25A). At 24 h, the ratio of agent in tumor vs plasma increased to 200:1 from 7:1 at 2 h post administration of a single dose, and the $AUC^{0-24h}$ tumor/plasma was 9134/1255, indicating specific retention of PU-WS13 in the tumor mass (FIG. 25A; AUC units are $µM \times h^{-1}$). The concentration of PU-WS13 in the tumor at 24 h post-administration of single dose of 75 mg/kg was 0.5 µM. The associated PD effect correlated with the tumor PK, i.e. was reflective of the tumor concentration of PU-WS13 and indicated partial suppression of downstream EGFR signaling (FIG. 25B, see p-AKT and p-ERK inhibition), demonstrating that PU-WS13 engaged tumor Grp94 at this concentration. We also analyzed the potential suppression by PU-WS13 of normal Grp94 functions. A "housekeeping" function for Grp94 was identified using a conditional knockout mouse model; that study found a role for Grp94 in normal GI cells, i.e. regulation of the Wnt receptor LRP6 (Liu et al., Proc Natl Acad Sci USA. 2013 Apr. 23; 110(17): 6877-82). Because most small molecules such as PU-WS13 are largely cleared via the GI track, the GI is the normal organ most exposed to agent over the time it spends in the body. The $AUC^{0-24h}$ for stomach and the large intestine was indeed 1.4 and 2-fold, respectively, higher than the tumor $AUC^{0-24h}$ (FIG. 25C); nonetheless, we could not detect a significant decrease in LRP6 (the Wnt receptor regulated in the normal GI by "housekeeping" Grp94) (FIG. 25D). We increased the administered dose of PU-WS13 to 150 mg/kg; the $AUC^{0-24h}$ for the GI track increased by ~6-fold, nonetheless we observed no acute tox or change in LRP6 levels.

Four- to 6-week-old nu/nu athymic female mice were obtained from Taconic Farms. Experiments were carried out under an Institutional Animal Care and Use Committee approved protocol, and institutional guidelines for the proper and humane use of animals in research were followed. MDA-MB-468 ($1 \times 10^7$ cells) were subcutaneously implanted in the right flank of mice using a 20-gauge needle and allowed to grow. All mice received Augmentin (amoxicillin/clavulanate potassium; SmithKline Beecham) in their drinking water while on therapy.

For pharmacodynamic and pharmacokinetic assays, mice with established MDA-MB-468 tumors were given assigned doses of inhibitors or vehicle (intraperitoneally). Mice were euthanized by $CO_2$ asphyxiation and all relevant tissues were harvested at a designated time after inhibitor administration (formulated in 30% captisol in 60 mM citrate buffer). Tissues were flash frozen in liquid nitrogen, and divided into two halves. One-half of the frozen tissues were dried and weighed prior to homogenization in 750 µl water/acetonitrile (70:30) solution. Samples were extracted with 600 µl of methylene chloride twice from tissues and then dried in the genevac. Later, samples were dissolved in solvent (75% water: 25% acetonitrile+0.1% formic acid), spun down at 4° C. and concentrations of the inhibitors in tissue were determined by high-performance LC-MS/MS using haloperidol as the internal standard. Compound analysis was performed on the 6410 LC-MS/MS system (Agilent Technologies). A Zorbax Eclipse XDB-C18 column (2.1×50 mm, 3.5 µm) was used for the LC separation, and the analyte was eluted under an isocratic condition (65% $H_2O$+0.1% HCOOH: 35% $CH_3CN$) for 5 minutes at a flow rate of 0.35 ml/min.

The other half of tumor tissues were evaluated for changes in EGFR and other PD markers as established in our laboratory. Briefly, tumor tissues were mixed with steel beads and tissue extraction buffer (50 mM Tris-HCl, pH 8.0, 150 mM NaCl, 2 mM EDTA, 0.25% sodium deoxycholate, 0.5% NP40, 0.25% Triton X-100, protease inhibitors). The samples were homogenized by the Bullet Blender (Next Advance, Inc) at 4° C. The lysates were then transferred to a clean tube and centrifuge at 13,200 rpm for 5 min at 4° C. After quantifying the protein concentrations by BCA, 25-100 ug proteins were loaded into SDS-PAGE and subjected to immunoblotting.

Immunoblotting

Cells were either treated with DMSO (vehicle) or indicated compounds for 24 hr and lysed in RIPA buffer (50 mM Tris-HCl, pH 8.0, 150 mM NaCl, 0.5% sodium deoxycholate and 0.5% NP40) supplemented with cocktail protease inhibitors (Roche) to produce whole cell lysates. Protein concentrations were determined using BCA kit (Pierce) according to the manufacturer's instructions. The protein lysates (10-50 μg) were electrophoretically resolved by SDS-PAGE, transferred onto nitrocellulose membranes and probed with the indicated primary antibodies against: HER2 (Zymed, 28004), EGFR (Cell Signaling, 4267), β-actin (Sigma, A1978), phospho-STAT3 (Cell Signaling, 9145), STAT3 (Cell Signaling, 12640), Hsp70 (Stressgen, SPA-810), ERK1/2 (Cell Signaling, 4695), phospho-ERK1/2 (Cell Signaling, 4370), phospho-AKT (Cell Signaling, 4060), AKT (Cell Signaling, 9272), cleaved PARP (Promega, G7341) and LRP6 (Cell Signaling, 2560). After washing off the excess antibodies, the membranes were incubated with the corresponding horseradish peroxidase (HRP) conjugated secondary antibody. Blots were visualized by autoradiography using the Enhanced Chemiluminescence Detection System (GE Healthcare) according to manufacturer's instructions. For all gels β-actin was used as a protein loading control.

5.5.6 IGF1R Dependent Tumors

The Grp94 inhibitors of the disclosure can be used to treat Insulin growth factor 1 receptor (IGF1R) dependent tumors. In particular, the Grp94 inhibitors of the disclosure can be used in treating cancers with altered expression of the IGFIR where the receptor is necessary for pathogenesis and tumor progression.

In addition to playing an important role in normal cell growth, maintenance and development, insulin-like growth factor receptor (IGF1R) and its ligands are also important in the establishment and maintenance of the malignant phenotype. Binding of IGF-1 and IGF-II ligands to the IGF1R initiates a cascade of events leading to activation of mitogenic signaling pathway (Ras/Raf/MAPK) and antiapoptotic/survival pathway (PI3K-Akt/mTOP), resulting in proliferation, transformation and survival in tumor cells (D. LeRoith, et al., Cancer Lett., 195(2):127-37 (2003), R. Baserga, et al., Int. J. Cancer; 107:873-7 (2003)). IGF1R overexpression and/or enhanced activity have been observed in diverse tumor types suggesting that the potential therapeutic use of agents targeting this pathway is broad. IGF1R provides a critical survival signal in multiple tumor types. The expression of this receptor is an indicator of poor prognosis, thus, it has emerged as an attractive and compelling target for cancer therapy to inhibit the progression of multiple tumor types in cancer patients. Various drug discovery approaches have been explored in recent years to modulate the function of IGF1R. Approaches aimed at the reduction of receptor number or enzymatic activity using a variety of strategies in preclinical models have been shown to reverse the malignant phenotype in tumor cells. These strategies include antisense (L. Long, et al., Cancer Res, 55(5): 1006-9 (1995), D. Andrews et al., J. Clin. Oncol., 19(8):2189-200 (2001)), monoclonal antibody (C. Arteaga, et al., Cancer Res., 49(22):6237-41 (1989)), small molecule inhibitors (M. Wittman, et al., J. Med. Chem., September 8; 48(18):5639-43 (2005), C. Garcia-Echeverria, et al., Cancer Cell, 5(3):231-9 (2004)), IGF-1 mimetic peptides (Z. Pietrzkowski, et al., Cancer Res., 53(5):1102-6 (1993)) as well as dominant negative mutants that lack enzyme activity (C. D'Ambrosio, et al., Cancer Res, 56(17): 4013-20 (1996)).

The disclosure provides evidence that Grp94 inhibitors are efficacious in treating cancer with altered expression of the IGFIR and where the receptor is necessary for pathogenesis and tumor progression. In particular, Grp94 inhibitors of the disclosure are capable of inducing apoptosis in IGFIR overexpressing cells. For instance, FIG. 16 shows that the Grp94 selective inhibitor PU-WS13 is capable of inducing apoptosis in two IGFIR overexpressing Ewing sarcoma cell lines (A673 and TC71), Specifically, there was a substantial increase in the Ewing sarcoma cells exhibiting markers of early- and late-stage apoptosis.

5.5.7 TGFbeta Dependent Tumors

Transforming growth factor-beta (TGF-β) is a pleiotropic cytokine that regulates cell proliferation, apoptosis, differentiation, migration and invasion. TCF-β signals through transmembrane type I (TβRI) and type II (TβRII) receptors to initiate downstream signaling. In the canonical pathway, TGF-β binding to TβRII recruits and phosphorylates TβRI, which results in TβRI activation. Activated TβRI phosphorylates the receptor-regulated Smad proteins Smad2 and Smad3. Phosphorylated Smad2 and Smad3 then co-associate with Smad4, translocate into the nucleus and regulate gene expression by binding to Smad-specific binding elements in the promoters of TGF-β-regulated genes. In humans, TGF-β overexpression has been detected in many cancer types and correlates with tumor metastasis, progression and prognosis. Many studies have indicated that TGF-β can function as a tumor suppressor and promoter depending on the context. TGF-β acts as a tumor suppressor by inhibiting cell proliferation, while as a tumor promoter, TGF-β induces an epithelial-mesenchymal transition (EMT), cell motility and invasion.

EMT has been recognized as a key process for embryonic development and metastasis. Cells undergoing EMT downregulate the expression of the E-cadherin epithelial marker and increase the expression of N-cadherin, a mesenchymal marker. This process has been shown proceed through a set of transcription factors including the Snail and Slug zinc-finger proteins, the Twist bHLH factor and the ZEB1 zinc-finger protein. TGF-β is a potent inducer of EMT, which was first recognized in cultured normal mammary epithelial cells. TGF-β can induce EMT by activating Smad-dependent and Smad-independent pathways. Ectopic expression of Smad2 or Smad3 with Smad4 enhances EMT, whereas ectopic expression of dominant-negative Smad2, Smad3 or Smad4 blocks TGF-β-induced EMT.

TGF-β acts as a tumor suppressor in the early stages of cancer progression, and it becomes a tumor promoter in later stages. TGF-β1, TGF-β2 and TGF-β3 overexpression has been reported in human ovarian tumors. Ovarian cancer is thought to arise from normal ovarian surface epithelium (OSE). TGF-β has been shown to inhibit human OSE proliferation and induce apoptosis, which may prevent the over-proliferation of cells during a normal ovulatory cycle. In the later stages of ovarian cancer, TGF-β enhances tumor cell proliferation and promotes metastasis by inducing an EMT.

It has recently been recognized that high-grade serous ovarian carcinoma (HGC) and low-grade serous ovarian carcinoma (LGC) are fundamentally different types of tumors that develop from distinct molecular pathways. Compared with HGC, LGC accounts for a small proportion (9%) of all serous ovarian carcinomas. Invasive LGC is developed from non-invasive borderline serous ovarian tumors (SBOT). In ovarian cancer, TGF-β-induced EMT is believed to play an important role in the regulation of cell invasion and metastasis. It has been shown that TGF-β and TβRII are expressed in primary human borderline ovarian tumors. Recent studies demonstrate that E-cadherin downregulation induces SBOT cell invasion, suggesting that EMT is involved in the progression from non-invasive SBOT to invasive LGC and that TGF-β induces SBOT invasion by activating EMT (Cheng J-C, (2012) TGF-Beta Induces Serous Borderline Ovarian Tumor Cell Invasion by Activating EMT but Triggers Apoptosis in Low-Grade Serous Ovarian Carcinoma Cells. PLoS ONE 7(8): e42436. doi:10.1371).

PEO1 is an adherent cell line derived from a malignant effusion from the peritoneal ascites of a patient with a poorly differentiated serous adenocarcinoma. Cisplatin-sensitive ovarian cancer cell line PEO1 and -resistant PEO4 were established from the same patient before treatment and after developing resistance to platinum-based chemotherapy. PEO1 and PEO4 express mRNA for IGF-I and mRNA for the IGF type I, IGF type II and insulin receptors; the presence of type I IGF receptors was confirmed by immunocytochemistry. IGF-I and insulin markedly stimulated the proliferation of PEO1 and PEO4. Both expressed mRNA for TGF beta 1 and 3 (Bartlett et al. Brit J. Cancer. 1992 May; 65(5):655-60). The TGF beta receptor pathway is also altered in these cells.

5.5.8 Anti-Angiogenic Effects of Grp94 Inhibitors

Recently, Finotti et al demonstrated that Grp94 promotes the angiogenic transformation of Human Umbilical Vein Endothelial Cells (HUVECs) by a cytokine-like mechanism, and that this effect is more pronounced when Grp94 is in complexes with human IgG (Tramentozzi et al., 2008; Tramentozzi et al., 2009). A similar, strong angiogenic-transforming property has been observed with complexes of IgG with Grp94 purified from the plasma of type 1 diabetic subjects, a finding that indirectly proved the capacity of these complexes to promote and sustain in vivo the inflammatory reactions predicting the development of stable vascular alterations. As discussed below, we show that the proliferative and angiogenic-transforming capacity of Grp94 was affected by the Grp94 inhibition.

Figure 18A:
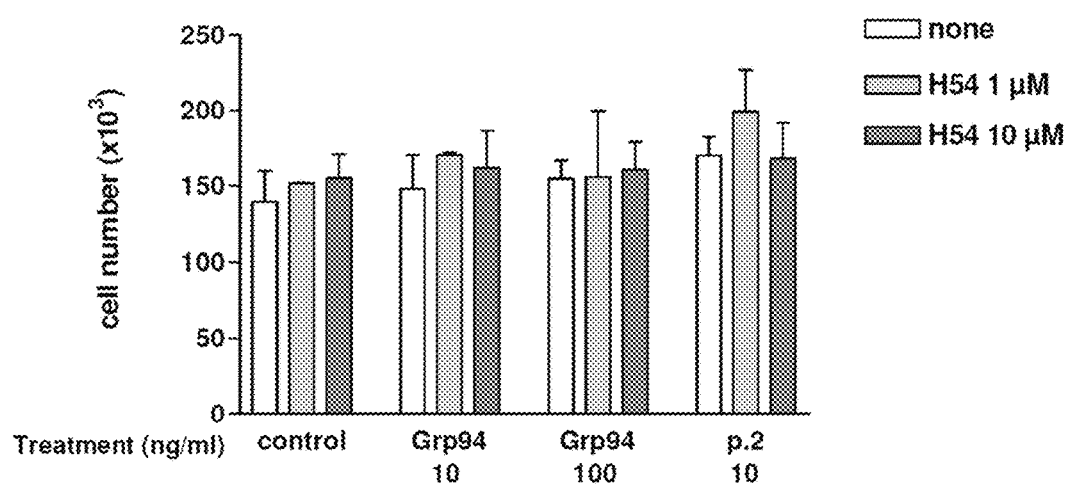
FIG. 18 shows that the angiogenic effect of both native Grp94 and the IgG-containing fraction purified from plasma of diabetic subjects, referred to as peak 2 (p2mQ) is inhibited by the Grp94 inhibitor PU-H54 (FIG. 18a). Grp94 promotes the angiogenic transformation of Human Umbilical Vein Endothelial Cells (HUVECs) by a cytokine-like mechanism. Overall, the morphologic changes observed in the presence of PU-H54 demonstrate that Grp94 inhibition displays an anti-angiogenic effect on HUVECs while it does not affect substantially cell proliferation (FIG. 18b).
Figure 18B:
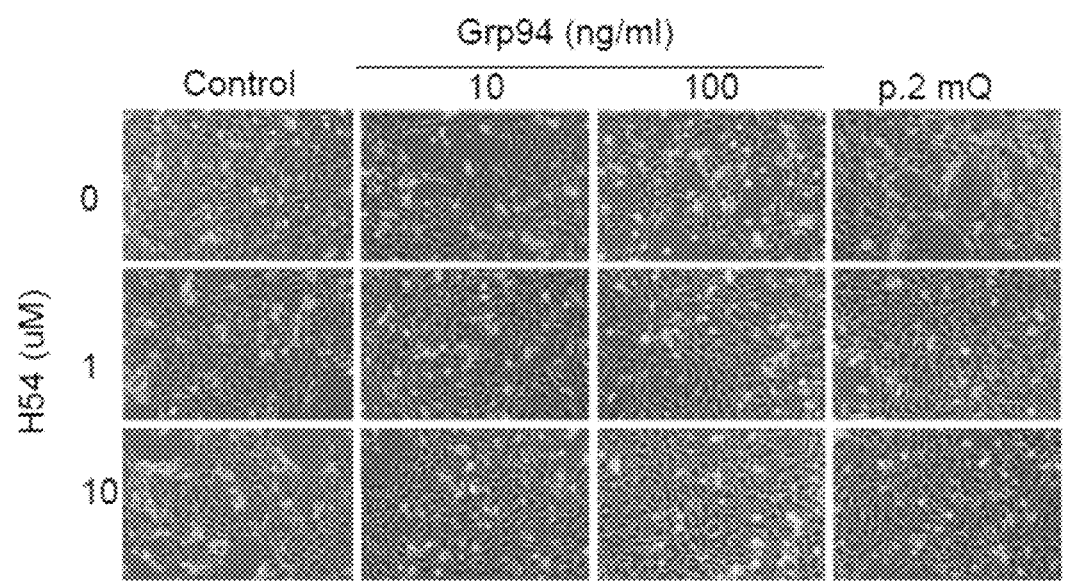

Both native Grp94 and the IgG-containing fraction purified from plasma of diabetic subjects, referred further as peak 2, were tested in cultures of HUVECs in both absence and presence of the Grp94 inhibitor PU-H54. As shown in FIG. 18b, morphological changes observed with Grp94 and peak 2 resembled those typically characterizing the differentiation of endothelial cells into capillary-like structures, in which long cytoplasmic protrusions of enlarged cells connect with each other to border the cavity of new tubes, interspersed with clusters of smaller cells. PU-H54 especially at the highest concentration of 10 μM was able to change the angiogenic-like transformation of HUVECs induced by Grp94 and by peak 2. Overall, the morphologic changes observed in the presence of PU-H54 show that PU-H54 at its $IC_{50}$ displays an anti-angiogenic effect on HUVECs while it does not affect substantially the cell proliferation (see FIG. 18a).

5.5.9 Inflammatory Diseases

Toll-like receptors (TLRs) play an important role in inflammatory responses. Grp94 chaperones multiple TLRs, and is required for the function of these receptors. TLR9 detects an un-methylated DNA and is known to play a role in systemic lupus erythematosus or rheumatoid arthritis. A recent study demonstrated a role for Grp94 in TLR9 stability and conformation. Based on experiments described below, we have found that the Grp94 inhibitors of the disclosure are capable of modulating inflammatory responses through the inhibition of the Grp94 chaperoning of Toll-like receptors (TLRs), particularly TLR9. In particular embodiments, the Grp94 inhibitors of the disclosure can be used in the treatment of inflammatory diseases such as lupus erythematosus and rheumatoid arthritis.

Figure 19A:
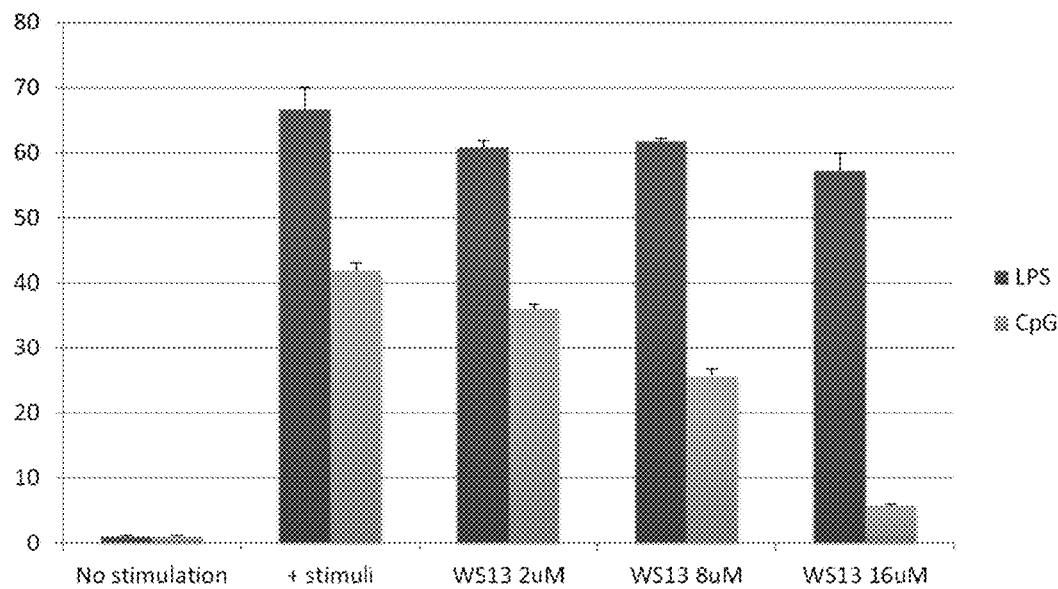
FIG. 19 shows that the Grp94 selective inhibitors PU-WS13 (FIG. 19a) and PU-H54 (FIG. 19b) inhibit TLR9 ligand, CpG DNA, induced TNF-α production in mouse macrophages.
Figure 19B:
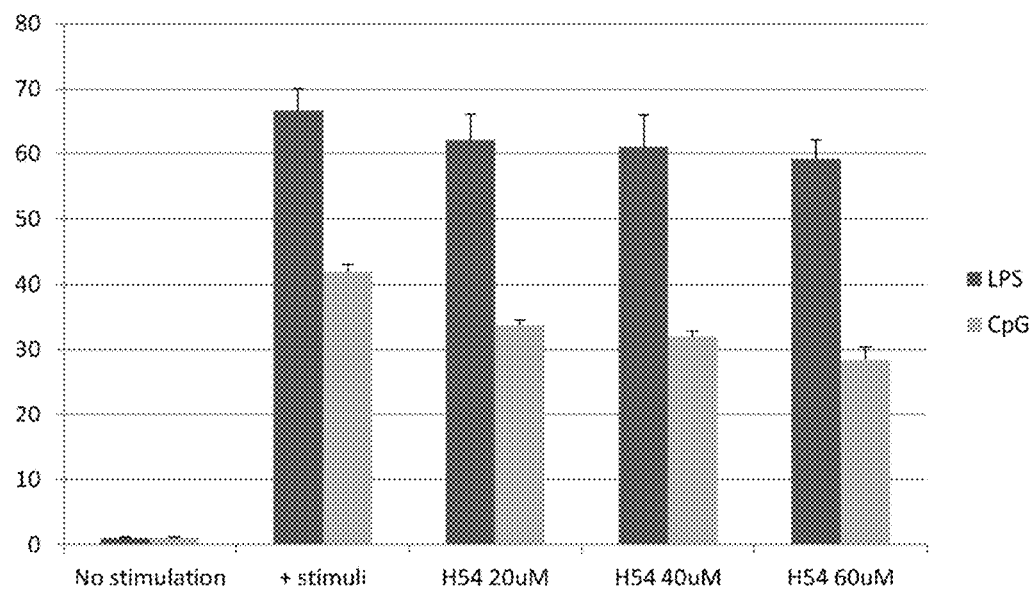

In order to evaluate the effect of Grp94 inhibitors on TLR9 response to stimulus, we treated cells with selective Grp94 inhibitors PU-WS13 (FIG. 19a) and PU-H54 (FIG. 19b). The TLR9 ligand, CpG DNA, induced TNF-α production from mouse macrophages (RAW 264.7). Treatment with PU-WS13 (FIG. 19A) and PU-H54 (FIG. 19B) inhibited this response in a concentration dependent manner. Treatment with vehicle alone did not inhibit signaling (not shown). Hence, these studies suggest selective Grp94 inhibitors improve inflammatory symptoms in diseases in which TLR9 plays a role.

5.6 Fluorescence Polarization Assays

The disclosure provides a versatile experimental fluorescence polarization (FP) assay that can test rapidly and accurately the binding affinity of all major Hsp90 paralogs and has a testing range that spans low nanomolar to millimolar binding affinities.

5.6.1 Development of FP Probes

Most assays published to date and used to assess binding of small molecules to the four Hsp90 paralogs, such as intrinsic tryptophan fluorescence, affinity-resin competitive binding and isothermal titration calorimetry, are laborious and costly as they make use of significant amounts of proteins. For the cytosolic Hsp90, the FP assay has become one of the most extensively used to identify and test Hsp90 inhibitors. There are numerous reasons why FP is an ideal method for measuring protein-ligand interactions and why it has become a favorite tool for Hsp90. First, it is a quick, homogeneous, i.e. there is no necessity for separation of free and bound ligand, high reproducibility and facility for automation assay. By simply mixing a protein with a fluorescently labeled ligand, FP is able to measure real-time protein-ligand interactions in solution where binding of the fluorescently labeled ligand, also referred to as an FP probe, to a protein results in increased polarization values and is directly proportional to the fraction of bound ligand. Its theory, first described in 1926 by Perrin, is based on the observation that fluorescent molecules in solution, excited with plane-polarized light, will emit light back into a fixed plane (i.e. the light remains polarized) if the molecules remain still during the excitation of the fluorophore. Molecules, however, rotate and tumble and the planes into which light is emitted differ from the plane used for initial excitation. Nonetheless, upon binding of the small probe to a protein (i.e. a large, slowly rotating molecule) motility is reduced leading to higher FP. Unlabeled ligands that bind to the protein will compete with the probe, leading to lower FP. FP therefore provides a direct readout of the extent of probe binding to a protein. Second, FP is also well suited for Hsp90 because it is an assay that requires no engineering of the protein. As reported, Hsp90 is a highly flexible molecular chaperone whose function is very sensitive to interference with its conformational modality, such as the attachment of labels may lead to, and thus, FP is best suited for this class of proteins. Third, there are numerous Hsp90 inhibitor chemotypes for which extensive chemistry has been developed and binding to Hsp90 revealed by crystallography, and therefore the choice for the FP probe and knowledge over the site of its fluorescence labeling is available. To date however, no FP assay that efficiently tests for affinity and selectivity of small molecules to all four Hsp90 paralogs has been reported.

Several FP tracers for Hsp90 that bind to the NBD have been reported and include a number based on geldanamycin (GM), GM-BODIPY, GM-Cy3b, and two carboxyfluorescein (FAM) probes based on the pyrazole scaffold (VER-00045864 and VER-00051001. More recently, an FP probe of a derivative of Sansalvamide A-amide has been reported, which, in contrast to other probes binds Hsp90 at the N-terminal/middle domains.

None of the aforementioned probes have been systematically assessed for their suitability as tracers in FP assays with each of the paralogs. While the GM and pyrazole probes have been extensively used to measure binding to Hsp90α, Hsp90β as well as to total Hsp90 in a cancer cell lysate, their use in measuring binding to Grp94 and Trap-1 is more limited. In our own hands we have found GM-Cy3b to be inadequate as a tracer for Trap-1. In order to get a suitable assay window, its use requires a considerable amount of protein and is therefore less suitable for large structure-activity relationship studies.

Figure 20:
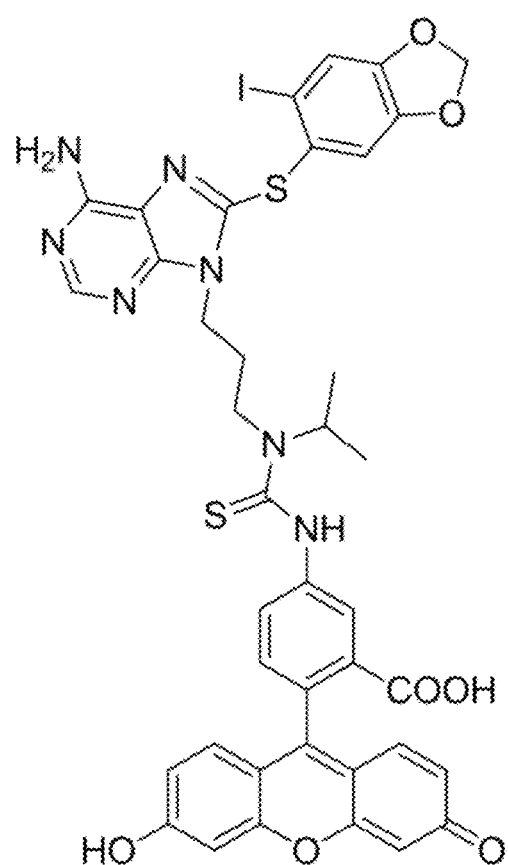
FIG. 20 shows the chemical structure of Compound 40.

We therefore proceeded here to design FP probes based on the Hsp90 inhibitor PU-H71 labeled through different linkers with fluorescein (FITC). We hypothesized that due to its known binding mode and well-established chemistry, useful FP probes amenable for paralog-selectivity testing may be created around this ligand. Compound 40, a FITC derivative of PU-H71 with optimal properties for flow cytometry and fluorescence microscopy, was also included in our analysis (FIG. 20). See Taldone, T.; Gomes-DaGama, E. M.; Zong, H.; Sen, S.; Alpaugh, M. L.; Zatorska, D.; Alonso-Sabadell, R.; Guzman, M. L.; Chiosis, G. Synthesis of purine-scaffold fluorescent probes for heat shock protein 90 with use in flow cytometry and fluorescence microscopy. *Bioorg. Med. Chem. Lett.* 2011, 21, 5347-5352

The linker and its attachment mode, both important in the synthesis of FP chemical probes because they can affect binding to the target protein, can be predicted for PU-H71 from the available structural studies. For the preparation of a suitable FP probe it is also important that the linker not be excessively long or flexible because of the propeller effect. Depolarization due to flexibility in the attachment of the dye, referred to as the "propeller effect", distorts the relationship between fluorescence polarization and molecular weight. For this reason, it is generally preferable to use dyes without long aliphatic linkers between the fluorophore and the reactive group in the preparation of fluorescence polarization assay probes.

In order to determine a linker length optimal for binding to all Hsp90 paralogs, we docked the linker-modified PU-H71 ligands into the respective paralogs of Hsp90, i.e. Hsp90α (PDB ID: 2FWZ_ENREF_32 (Immormino, R. M.; Kang, Y.; Chiosis, G.; Gewirth, D. T. Structural and quantum chemical studies of 8-aryl-sulfanyl adenine class Hsp90 inhibitors. *J. Med. Chem.* 2006, 49, 4953-4960.)), Hsp90β (PDB ID: 3NMQ (Yun, T. J.; Harning, E. K.; Giza, K.; Rabah, D.; Li, P.; Arndt, J. W.; Luchetti, D.; Biamonte, M. A.; Shi, J.; Lundgren, K.; Manning, A.; Kehry, M. R. EC144, a Synthetic Inhibitor of Heat Shock Protein 90, Blocks Innate and Adaptive Immune Responses in Models of Inflammation and Autoimmunity. *The Journal of Immunology* 2011, 186, 563-575)), Grp94 (PDB ID: 3O2F, 2EXL (Immormino, R. M.; Metzger, L. E.; Reardon, P. N.; Dollins, D. E.; Blagg, B. S.; Gewirth, D. T. Different poses for ligand and chaperone in inhibitor-bound Hsp90 and GRP94: implications for paralog-specific drug design. *J. Mol. Biol.* 2009, 388, 1033-1042)) and Trap-1 (Homology Model). FITC was covalently bonded to the N-9 position of the purine-scaffold via at least a three carbon linker as this would orient the probe towards solvent without affecting binding to the target protein (FIG. 21a). A shorter linker would lead to clashes between the probe and a leucine residue positioned in all paralogs at the exit of the binding site (Leu107 in Hsp90α and Hsp90β, Leu163 in Grp94 and Leu172 in Trap-1) (FIG. 21b for Hsp90α).

To determine the optimal chain length for FP properties we synthesized a number of probes with linkers ranging from 3 to 8 carbons (Scheme 20). These were prepared by a three-step sequence from 112, commencing with N9-alkylation with ω-bromophthalimides to yield 113a-113d (Scheme 20). Following unmasking of the amine with hydrazine and attachment of FITC, 114a-114d were obtained after HPLC purification (Scheme 20).

5.6.2 Binding of FP Probes to Hsp90 Paralogs

Figure 22A:
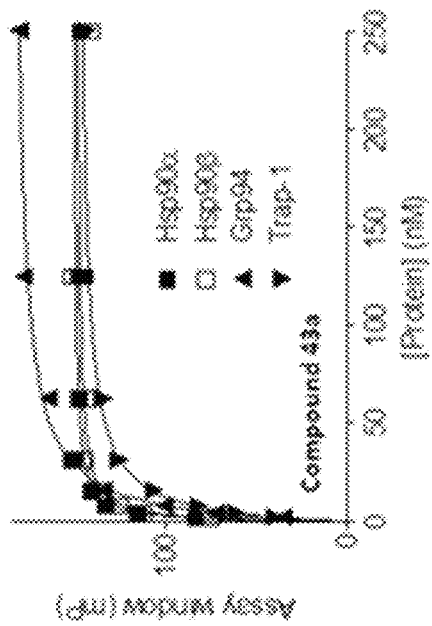
FIG. 22 shows the dose-response curve for the binding of indicated probes to the Hsp90 paralogs from a cancer cell extract (FIG. 22a) or to individual Hsp90 paralogs (FIG. 22b-FIG. 22c). Different amounts of protein (were incubated with the ligand at 4° C. and the response measured at equilibrium (24 h). The assay window data were obtained by subtracting free probe values from values recorded in the presence of specified protein concentrations. Data were analyzed and plotted in Prism 4.0. Average values from duplicate experiments are presented.

The synthesized FITC-derivatives were first evaluated for their potential as FP tracers for binding to Hsp90 in a cancer cell homogenate (FIG. 22a). The potential tracers were initially evaluated by titration with increasing amounts of lysate up to 50 μg of total protein (FIG. 22a). To be useful in FP, the binding affinity of the probe should be high and the binding range (i.e. assay window), defined as the mP value at saturation minus the mP recorded for probe alone should be large. As observed in FIG. 22a, as the amount of lysate, and thus of Hsp90, increased so did the assay window. Good performance was observed for all probes, with an excellent assay window of >100 mP for Compound 115a. Similar to other Hsp90 FP assay probes, when measured at 4° C. to maintain proper folding of Hsp90, the binding assay between Compound 115a and Hsp90 reached equilibrium by 8 h and remained stable for more than 24 h (not shown). While Compound 115a, the analog with a 3-carbon linker, was optimal, Compound 40, the N-isopropyl analog of Compound 115a, and Compounds 115b and 115c, the 4- or 6-carbon linker compounds respectively, performed acceptably well (FIG. 22a).

Figure 22B:
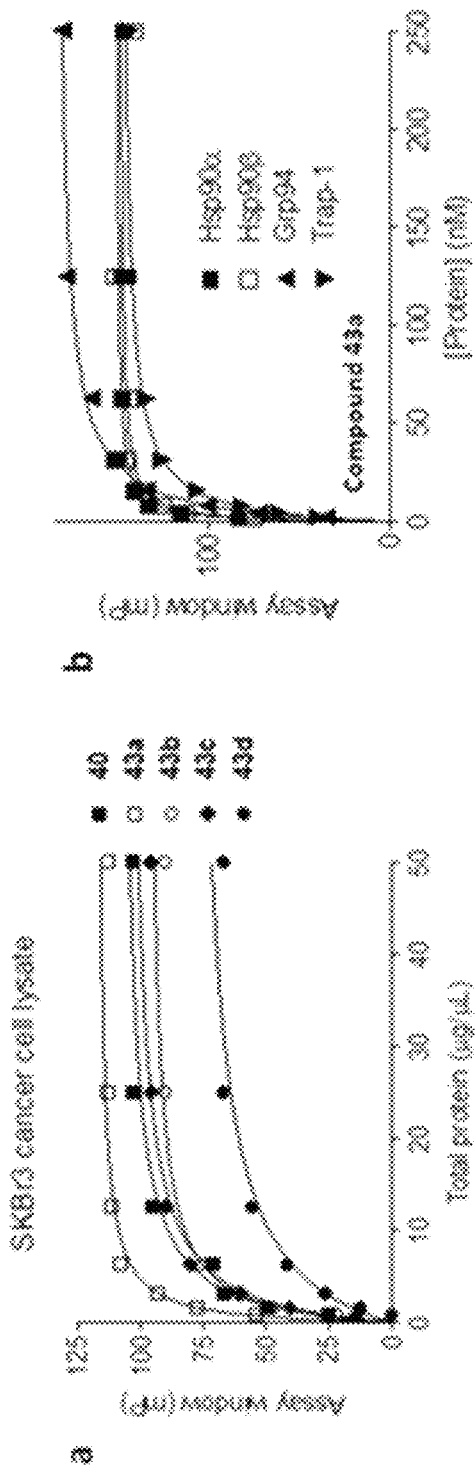
Figure 22C:
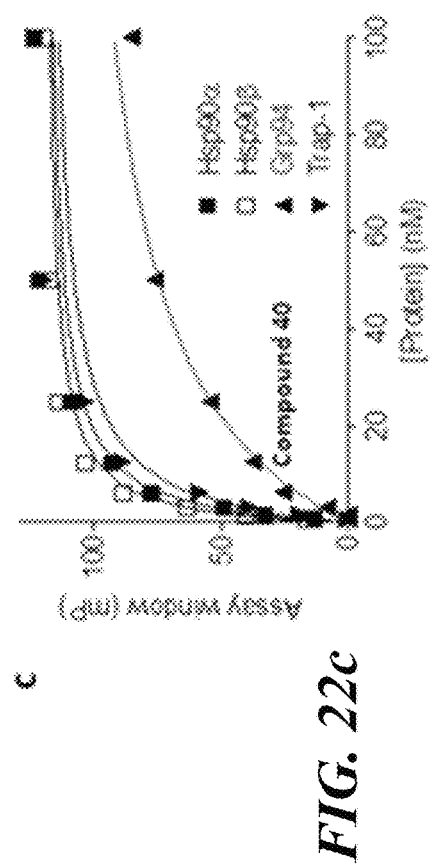

We next determined, in a standard saturation binding experiment that measures ligand binding in the presence of varying concentration of protein, the ability of these ligands as probes for the Hsp90 paralogs (FIGS. 22b-c). Taken as a whole, saturation binding experiments with Compound 115a showed it to be an excellent tracer for each Hsp90 paralog with an assay window of >150mP and an apparent $K_d$=1.4, 1.6, 6.6, and 5.9 nM for Hsp90α, Hsp90β, Grp94 and Trap-1, respectively (FIG. 22b) and we proceed further here to use it as a probe in evaluating the paralog-selective binding of Hsp90 inhibitors and Hsp90 endogenous ligands. Interestingly, Compound 40 showed a 1-log preference for Hsp90α, Hsp90β and Trap-1 over Grp94 (apparent $K_d$=3.9, 2.8, 30.7, and 5.8 nM for Hsp90α, Hsp90β, Grp94 and Trap-1, respectively) with a poor assay window, i.e. less than 100 mP, for Grp94 (FIG. 22c).

5.6.3. Suitability of the FP Assay for Evaluating the Selectivity and Affinity of Small Molecules for the Hsp90 Paralogs Having found a probe that binds effectively to all four Hsp90 paralogs, we next validated its ability to evaluate paralog affinity and selectivity for small molecule ligands. Specifically, we evaluated the binding of ATP and ADP, the two endogenous Hsp90 paralog ligands, for which paralog binding affinity has been extensively explored by means of intrinsic tryptophan fluorescence and isothermal titration calorimetry. We observe for these ligands relative affinities in line with what has been reported previously for each paralog (Table 13). Specifically, the ADP interaction with Hsp90 was reported to be much tighter than that of ATP (41 µM versus 840 µM), (McLaughlin, S. H.; Ventouras, L. A.; Lobbezoo, B.; Jackson, S. E. Independent ATPase activity of Hsp90 subunits creates a flexible assembly platform. *J. Mol. Biol.* 2004, 344, 813-826) which is very much in line with our findings (Table 13). ADP was reported to be a slightly weaker binder of Hsp90α than of Hsp90β (51 µM versus 34 µM), (Richter, K.; Soroka, J.; Skalniak, L.; Leskovar, A.; Hessling, M.; Reinstein, J.; Buchner, J. Conserved conformational changes in the ATPase cycle of human hsp90. *J. Biol. Chem.* 2008, 283, 17757-17765), which is what we find (59 µM versus 42 µM, Table 13). Additionally, as previously reported, we show Grp94 and Trap-1 to show little discrimination between both nucleotides. Grp94 binds both nucleotides relatively well, with binding affinities reported ranging from 2.3 to 3.4 µM to 5 µM (Frey, S.; Leskovar, A.; Reinstein, J.; Buchner, J. The ATPase cycle of the endoplasmic chaperone Grp94. *J. Biol. Chem.* 2007, 282, 35612-35620), which compares well with 3.2 µM and 11.4 µM we record for ATP and ADP, respectively (Table 13). As in our study, ATP was found to be a slightly tighter binder of Grp94 than ADP. Trap-1, which most closely resembles the bacterial Hsp90, HtpG, is reported to bind ATP with approximately 10-fold greater affinity than does Hsp90.

Figure 23:
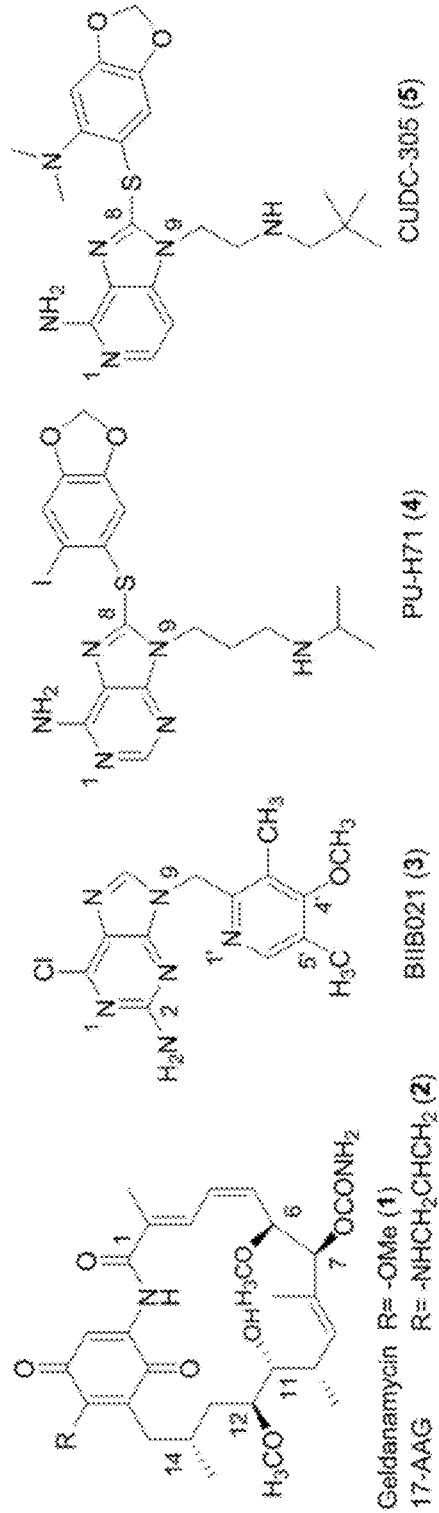
FIG. 23 shows the structures of known Hsp90 inhibitors which were analyzed using fluorescence polarization methods of the disclosure.
Figure 23:
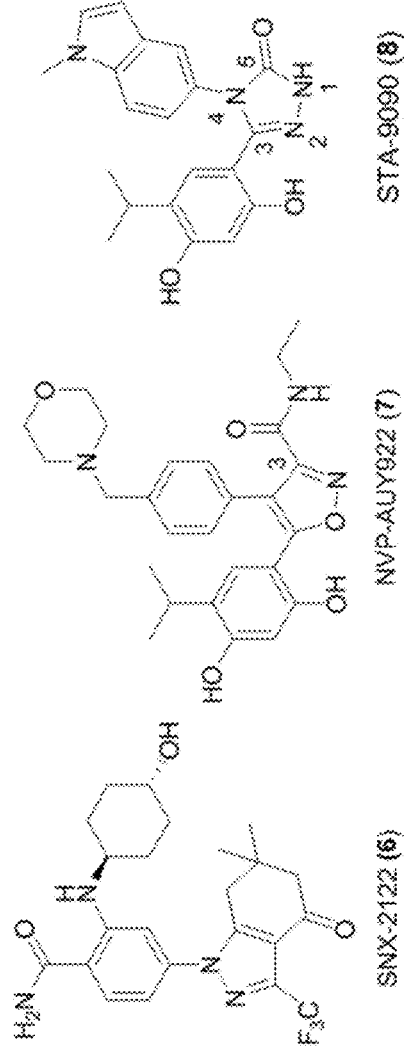

We next used the newly developed FP assay to evaluate the paralog affinity and selectivity of Hsp90 NBD inhibitors encompassing a variety of chemical classes (FIG. 23). All but GM have been or still are in clinical evaluation for cancers. The results for each paralog of Hsp90 are summarized in Table 13 and show that all inhibitors effectively compete with Compound 115a, demonstrating specificity of binding for the probe. The low nanomolar binding affinities for Hsp90α/β that we measured for these inhibitors correlate well with their biological activity determined in several cancer cells.

TABLE 13

Hsp90 paralog affinity determined for Hsp90 inhibitors in clinical development using 43a as a FP probe. The paralog binding affinity of Hsp90-regulatory nucleotides is also presented.

| | Hsp90α $IC_{50}$ (nM) | Hsp90β $IC_{50}$ (nM) | Grp94 $IC_{50}$ (nM) | Trap-1 $IC_{50}$ (nM) |
|---|---|---|---|---|
| GM | 28 | 22 | 10 | 661 |
| 17-AAG | 46 | 45 | 31 | 1,496 |
| BIIB021 | 19 | 17 | 124 | 90 |
| PU-H71 | 43 | 42 | 30 | 205 |
| CUDC-305 | 33 | 38 | 190 | 1,586 |
| SNX-2112 | 29 | 25 | 578 | 726 |
| NVP-AUY922 | 20 | 16 | 12 | 38 |
| STA-9090 | 5 | 5 | 10 | 51 |
| ADP | 59,308 | 42,159 | 11,447 | 55,594 |
| ATP | 861,330 | 893,677 | 3,241 | 31,303 |

Interestingly, while it is believed that the clinical Hsp90 inhibitors bind equally well to all paralogs, we determined a spectrum of paralog binding preferences (Table 13). Of note, all these inhibitors bound approximately equally well and with low nanomolar affinity to the cytosolic Hsp90s, as indicated previously by the extensive interactions they form with the pocket.

In contrast, we found a significant difference among the several agents with regards to their affinity for Grp94 and Trap-1. Most striking was an almost 2-log loss of affinity for Trap-1 recorded for 17-AAG and CUDC-305/Debio092 (Hsp90 vs Trap-1: 46 nM vs 1.5 µM for 17-AAG, 35 nM vs 1.5 µM for CUDC-305/Debio092). Lower binding efficacy for Trap-1 was also seen for the other agents, with a decrease ranging from 25-fold for GM and SNX-2112, 10-fold for STA-9090 to 5-fold for BIIB021 and PU-H71 and 2-fold for NVP-AUY922. The affinity of these agents for Grp94, while comparable to Hsp90 for most agents, was substantially lower for a few inhibitors. Specifically, an approximately 10-fold loss of affinity was noted for BIIB021, CUDC-305 and SNX-2112 (Hsp90 vs Grp94: 19 nM vs 124 nM, 33 nM vs 190 nM and 29 nM vs 578 nM, respectively).

TABLE 14

Solubility of WS-13 salts in water.

| Type of Salt | | Solubility | Appearance | pH |
|---|---|---|---|---|
| Hydrochloride | Mono | 6.25 mg/mL | Clear solution | 5.0 |
| | Di | 12.5 mg/mL | Clear solution | 3.5 |
| Mesylate | Mono | 25.0 mg/mL | Clear solution | 6.5 |
| | Di | 50.0 mg/mL | Clear solution | 3.0 |
| Lactbionate | Mono | 6.25 mg/mL | Clear solution | 6.5 |
| | Di | 25.0 mg/mL | Clear solution | 4.5 |
| Succinate | Mono | <5.0 mg/mL | Insoluble | |
| | Di | 5.0 mg/mL | Hazy solution | |
| Citrate | Mono | <5.0 mg/mL | Insoluble | |
| | Di | 9.4 mg/mL | Hazy solution | |

Mesylate salt of WS-13 had higher solubility in water.

TABLE 15

Solubility of WS-13 salts in Phosphate Buffer Saline (PBS, pH = 7.4).

| Type of Salt | | Solubility | Appearance | pH |
|---|---|---|---|---|
| Hydrochloride | Mono | <5.0 mg/mL | Insoluble | |
| | Di | <5.0 mg/mL | Insoluble | |
| Mesylate | Mono | 5.0 mg/mL | Clear solution | 6.6 |
| | Di | 12.5 mg/mL | Clear solution | 3.5 |
| Lactbionate | Mono | <5.0 mg/mL | Hazy solution | 3 |
| | Di | 5.0 mg/mL | Clear solution | |
| Succinate | Mono | <5.0 mg/mL | Insoluble | |
| | Di | <5.0 mg/mL | Hazy solution | |
| Citrate | Mono | <5.0 mg/mL | Insoluble | |
| | Di | <5.0 mg/mL | Insoluble | |
| Oxalate | Mono | <5.0 mg/mL | Insoluble | |
| | Di | 9.4 mg/mL | Hazy solution | |
| Tosylate | Mono | <5.0 mg/mL | Slight Hazy solution | |
| | Di | 9.4 mg/mL | Slight Hazy solution | |
| Phosphate | Mono | <5.0 mg/mL | Insoluble | |
| | Di | <5.0 mg/mL | Insoluble | |
| Tartarate | Mono | <5.0 mg/mL | Insoluble | |
| | Di | <5.0 mg/mL | Hazy solution | |
| Maleate | Mono | <5.0 mg/mL | Insoluble | |
| | Di | <5.0 mg/mL | Insoluble | |
| Acetate | Mono | <5.0 mg/mL | Insoluble | |
| | Di | <5.0 mg/mL | Insoluble | |
| Trifluoroacetate | Mono | <5.0 mg/mL | Insoluble | |
| | Di | <5.0 mg/mL | Insoluble | |

Mesylate salt of WS-13 had higher solubility in PBS.

EXAMPLES 6.1 Materials and Methods

Biochemical and Cellular Assays. Expression and phosphorylation of proteins was analyzed by immunoblotting. Chemical precipitation and immunoprecipitation assays were performed to determine the interaction between the Hsp90 paralogs and proteins. Analysis of cell cycle and of cell surface expression of Grp94 was carried out by flow cytometry.

X-ray structure determination. Complexes were formed by adding a 2-3 fold molar excess of PU-H54 to a concentrated Hsp90 αN or Grp94N solution prior to crystallization. The Hsp90 and Grp94 complex structures were determined by X-ray diffraction to a resolution of 1.5 Å and 2.0 Å, respectively, and were solved by molecular replacement.

Molecular modeling. All computations were carried out on a HP workstation xw8200 with the Ubuntu 8.10 operating system. The protein structure was prepared using the protein preparation wizard in the Schrodinger software graphical user interface Maestro (version 8.5). Protein sequences and crystal structures were downloaded from the NCBI (www.ncbi.nlm.nih.gov) and the RCSB (www.rcsb.org) database, respectively. The Trap-1 homology model was constructed in Prime (version 2.0) and the crude homology model was further refined by minimization using Macromodel (version 9.6). SiteMap (version 2.2) analysis was performed on the protein structures, as indicated. All docking studies were performed with Glide (version 5.0).

Statistical Analysis. The results were analyzed by unpaired 2-tailed t-tests in Prism5 (GraphPad). Data are presented as the mean±SD or SEM of duplicates or triplicates. Error bars represent the mean SD or SEM. When a single panel is presented it is representative of two or three individual experiments.

Reagents. Recombinant Hsp90α (ADI-SPP-776), Hsp90β (ADI-SPP-777) and Trap-1 (ADI-SPP-848) were purchased from Enzo Life Sciences. Grp94 was generated as previously reported (Dollins, D. E., Immormino, R. M. & Gewirth, D. T. Structure of unliganded GRP94, the endoplasmic reticulum Hsp90. Basis for nucleotide-induced conformational change. J. Biol. Chem. 280, 30438-47 (2005); Dollins, D. E., Warren, J. J., Immormino, R. M. & Gewirth, D. T. Structures of GRP94-nucleotide complexes reveal mechanistic differences between the hsp90 chaperones. Mol. Cell 28, 41-56 (2007)). The synthesis and characterization of the purine-scaffold compounds and chemical tools was reported elsewhere (Llauger, L. et al. Evaluation of 8-arylsulfanyl, 8-arylsulfoxyl, and 8-arylsulfonyl adenine derivatives as inhibitors of the heat shock protein 90. J. Med. Chem. 48, 2892-905 (2005); He, H. et al. Identification of potent water soluble purine-scaffold inhibitors of the heat shock protein 90. J. Med. Chem. 49, 381-90 (2006); Moulick, K. et al. Affinity-based proteomics reveal cancer-specific networks coordinated by Hsp90. Nat. Chem. Biol. 7, 818-26 (2011). Geldanamycin was purchased from Sigma-Aldrich and lapatinib from Selleck Chemicals. The synthesized compounds were fully characterized and structures confirmed by direct comparison to previous reports and determined to have a purity of >98%.

Cell lines. The HER2 overexpressing breast cancer cells SKBr3, BT474, MDA-MB-361, MDA-MB-453 and AU565, as well as the low HER2 breast cancer cells MCF7, BT20 and MDA-MB-231, were obtained from the American Type Culture Collection (ATCC). Cells were cultured routinely in McCoy's 5A (10% FBS, SKBr3), DME/F12 (10% FBS, BT474 and MDA-MB-231), RPMI (10% FBS, AU565), MEM (10% FBS, MCF7 and BT20) and L-15 (20% FBS, MDA-MB-361 and MDA-MB-453) supplemented with 1% Glutamax and 1% penicillin and streptomycin (Pen/Strep). C2C12 and HEK293 cells were purchased from ATCC and cultured in DMEM in the presence of 10% FBS and 1% penicillin/streptomycin. Gastric carcinoma cell lines OE19, NCI-N87 and MKN74 were grown in DME media (MKN74), or RPMI media supplemented with 10% FBS and 1% penicillin/streptomycin. Ovarian cancer cell lines PEO-1, PEO-4, OV-1847, OVCAR4 and A2780, Ewing's sarcoma cell lines TC71 and A673 were generous gift from Dr. Malcolm A. S. Moore lab. All cell lines were grown in M-5 media supplemented with 10% FBS, 1% GlutaMax (Gibco, cat #35050-061) and 1% penicillin/streptomycin. Pancreatic cancer cell lines PANC-1, CAPAN2 and CFPAC were purchased from ATCC and grown in DME (PANC-1), McCoy's 5a Medium Modified (CAPAN-2) and IMDM media supplemented with 10% FBS and 1% penicillin/streptomycin. Breast cancer cell lines HCC1806, MDA-MB-231 and MDA-MB-468 were purchased from ATCC and grown in RPMI (HCC1806) and DME (MDA-MB-231 and MDA-MB-468) media supplemented with 10% FBS and 1% penicillin/streptomycin. When cultured, cells in L-15 medium were kept in a humidified atmosphere without CO2 at 37° C. and all other cell lines were incubated in the humidified cell incubators with CO2 at 37° C.

Crystallization of Grp94 and hHsp90 PU-H54 complexes. Recombinant canine Grp94N A41 and human Hsp90αN were purified as described previously. Prior to crystallization, protein-inhibitor complexes were formed by the addition of a two-fold molar excess of PU-H54 to Grp94 or a three-fold molar excess of PU-H54 to human Hsp90 at 30 mg/ml in 10 mM Tris, pH 7.6, 100 mM NaCl, and 1 mM DTT. Grp94 crystals were grown by hanging-drop vapor diffusion at 18° C. by mixing a 1:1 ratio of protein to reservoir solution containing 14-17% isopropanol, 300-375 mM MgCl2, 0.1-1.0% glycerol, and 100 mM Hepes, pH 7.4. Grp94 crystals were cryo-protected by rapid passage through a solution containing 30% glycerol, 5% isopropanol, and 100 mM Hepes, pH 7.4 before flash freezing in liquid nitrogen. Hsp90 crystals were grown by hanging-drop vapor diffusion at 4° C. by mixing a 1:1 ratio of protein to reservoir solution containing (11-15% PEG 2K MME, 200 mM MgCl2, and 100 mM sodium cacodylate, pH 6.5). Hsp90 crystals were cryo-protected by sequentially passing through reservoir solution rapidly followed by a cryoprotectant solution containing 35% PEG 2K MME, 200 mM MgCl2, and 100 mM sodium cacodylate, pH 6.5 before flash freezing in liquid nitrogen.

Data collection, structure determination and refinement. X-ray diffraction data for the Grp94NA41+PU-H54 and human Hsp90N+PU-H54 co-crystals were collected on a MAR-325 CCD detector at SSRL beamline 11-1 using an X-ray wavelength of 0.979 Å. Data were indexed and scaled using HKL2000. Initial phases for the co-crystals were obtained by molecular replacement using Phaser software in the CCP4 software suite. The search model for Grp94NA41 was the core region (residues 100-166 and 200-337) of Grp94NA41+ATP (PDB ID 1TC0), and the search model for hHsp90 was Hsp90+PU-H71 (PDB ID 2FWZ). Initial molecular replacement models were manually rebuilt in Coot and refined using Refmac 5.5 in CCP4. Ligand topology files for PU-H54 were generated using the Dundee PRODRG server. For the Grp94NA41+PU-H54 structure, density modification was carried out using DM software in CCP4 and TLS parameters generated using TLSMD[‡]were applied in the final stage of refinement. Final models contained no Ramachandran outliers, and 95.1 and 97.6% of the residues fell in Ramachandran favored regions for the Grp94NA41+PU-H54 and Hsp90N+PU-H54 structures, respectively.

Sequence alignment. Sequences were aligned and shown as Percentage Identity view using the program of T-Coffee Multiple Sequence Alignment in Jalview 2.7 (http://www.t-coffee.org/Projects/tcoffee/).

Homology model for Trap-1. The protein structures of the Hsp90α NTD (PDB ID: 2FWZ), Grp94 NTD (PDB ID:

3O2F) and the amino acid sequence of Trap-1 protein (Accession number: Q12931) were used for model building. To create the model, the protein sequence of Trap-1 protein (Accession number: Q12931) was entered as an input sequence in Prime's Structure Preparation wizard. The homologous protein Hsp90α (PDB ID: 2FWZ) with 31% identities, 47% positives, 20% gaps and Grp94 (PDB ID: 3O2F) with 28% identities, 45% positives and 28% gaps were imported. The NTD Trap-1 sequence and the templates were aligned and then edited using parameters as implemented in Prime. In the "Build structure" option of Prime, amino acids 179-196 (Grp94) were selected from PDP ID 3O2F whereas the remaining amino acids from Hsp90α (PDB ID: 2FWZ). The structure was then built using selected sequence alignment of the template(s), taking solvent, ligand, force field, and other contributions into account via a series of algorithms implemented in Prime. Structural discontinuities were optimized by inserting template gaps for more than twenty residues. All loops were refined with the default parameter settings of Prime. The obtained homology model of Trap-1 was further refined using the protein preparation wizard available in Maestro (version 8.5). Partial atomic charges were assigned according to the OLPS-AA force field. To obtain a more reliable 3D structure of Trap-1, the homology model was further subjected to a series of energy minimization steps that consisted of 5,000 iterations of steepest descent (SD) and conjugate gradient (CG), until the root mean-square deviation (rmsd) was lower than 0.001 kcal mol$^{-1}$ Å$^{-1}$.

Ligand preparation. All the compounds were constructed using the fragment dictionary of Maestro (version 8.5). The geometry of compounds was optimized using the Macromodel program (version 9.6) and the OLPS-AA force field[7]. Resulting ligands were further prepared using Ligprep (version 2.2) utility provided by Schrodinger LLC., New York.

Docking. The x-ray crystal structure of Hsp90α NTD in complex with PU-H71 (PDB ID: 2FWZ), Hsp90β NTD in complex with EC44 (PDB ID: 3NMQ), Grp94 NTD in complex with PU-H54 (PDB ID: 3O2F), ADP (PDB ID: 1TC6) and unliganded (PDB ID: 1YTO) and Trap-1 homology model were first aligned using the protein structure alignment tool, then were optimized for subsequent grid generation and docking using the default parameters in Protein Preparation Wizard provided by Schrödinger LLC. Grids were then prepared using the Receptor Grid Generation tool in Glide (version 5.0) (Friesner, R. A. et al. Glide: a new approach for rapid, accurate docking and scoring. 1. Method and assessment of docking accuracy. J. Med. Chem. 47, 1739-49 (2004); Halgren, T. A. et al. Glide: a new approach for rapid, accurate docking and scoring. 2. Enrichment factors in database screening. J Med Chem 47, 1750-9 (2004); Friesner, R. A. et al. Extra precision glide: Docking and scoring incorporating a model of hydrophobic enclosure for protein-ligand complexes. J. Med. Chem 49, 6177-6196 (2006)) Next, the extra precision (XP) Glide docking method was used to dock compounds flexibly into the ATP binding site of the Hsp90 paralogs. Upon completion of each docking calculation, at most 100 poses per docking were run and at most 10 poses per ligand were allowed to be generated. Top-scored docking poses (orientation plus conformation) based on the Glide scoring (GScore) function were analyzed. To validate docking parameters and experimental set-up, endogenous ligands (PU-H71, PDB ID: 2FWZ; EC44, PDB ID: 3NMQ; PU-H54, PDB ID: 3O2F; ADP, PDB ID: 1TC6) were removed from the binding site and re-docked. Very good agreement was found between inhibitor pose as obtained from docking analyses and as captured in the crystal structure (RMSD of 0.7 Å; PDB ID: 2FWZ, 0.9 Å; PDB ID: 3NMQ, 0.04 Å; PDB ID: 3O2F and 1.2 Å; PDB ID: 1TC6) between the predicted conformation and the observed x-ray crystallographic conformation, validating the docking strategy.

Binding site analysis: SiteMap (Halgren, T. A. Identifying and Characterizing Binding Sites and Assessing Druggability. J. Chem. Information and Modeling 49, 377-389 (2009); Halgren, T. New method for fast and accurate binding-site identification and analysis. Chemical Biology & Drug Design 69, 146-148 (2007)) analysis was carried out on the x-ray crystal structures of Hsp90α (PDB ID: 2FWZ), Hsp90β (PDB ID: 3NMQ) and Grp94 (PDB ID: 3O2F) and the refined homology model of Trap-1 using "Evaluate a single binding site region" using default parameters implemented in SiteMap (version 2.2). Next, to investigate the ATP binding site, hydrophobic and hydrophilic contour maps were constructed using default parameters as implemented in the "Manage surfaces" function.

Hsp90 saturation binding assay. The Hsp90 FP saturation assays were performed on an Analyst GT instrument (Molecular Devices, Sunnyvale, Calif.) and carried out in black 96-well microplates (Corning #3650) in a total volume of 100 µL in each well. A stock of 10 µM 40 or 115a-115d was prepared in DMSO and diluted with Felts buffer (20 mM Hepes (K), pH 7.3, 50 mM KCl, 2 mM DTT, 5 mM MgCl$_2$, 20 mM Na$_2$MoO$_4$, and 0.01% NP40 with 0.1 mg/mL BGG). To determine the equilibrium binding of 112 or 115a-115d, increasing amounts of Hsp90α, Hsp90β, Grp94 or Trap-1 (up to 250 nM), or SKBr3 lysate (up to 50 µg of total protein) were incubated with 3 nM of 40 or 115a-115d. The assay plate was incubated on a shaker at 4° C. for the indicated times and the FP values in mP were measured. The assay window was calculated as the difference between the FP value recorded for the bound fluorescent tracer and the FP value recorded for the free fluorescent tracer (defined as mP–mP$_f$).

Fluorescence polarization (FP) measurements on Grp94 inhibitors of the disclosure. The Hsp90 FP competition assays on Grp94 inhibitors of the disclosure were performed as described below.

Fluorescence polarization (FP) measurements using new probes. The Hsp90 FP competition assays were performed on an Analyst GT instrument (Molecular Devices, Sunnyvale, Calif.) and carried out in black 96-well microplates (Corning #3650) in a total volume of 100 µL in each well. A stock of 10 µM 112 or 115a-115d was prepared in DMSO and diluted with Felts buffer (20 mM Hepes (K), pH 7.3, 50 mM KCl, 2 mM DTT, 5 mM MgCl$_2$, 20 mM Na$_2$MoO$_4$, and 0.01% NP40 with 0.1 mg/mL BGG). To each well was added 3 nM fluorescent 40 or 115a-115d, protein (25 nM Hsp90α, 25 nM Hsp90β, 25 nM Grp94, 30 nM Trap-1) or SKBr3 lysate (4.5 µg total protein), and tested inhibitor (initial stock in DMSO) in a final volume of 100 µL HFB buffer. Compounds were added in triplicate wells. For each assay, background wells (buffer only), probe controls (free, probe only) and bound probe controls (probe in the presence of protein or SKBr3 lysate) were included on each assay plate. The assay plate was incubated on a shaker at 4° C. for 24 h and the FP values in mP were measured. The fraction of probe bound to Hsp90 was correlated to the mP value and plotted against values of competitor concentrations. The inhibitor concentration at which 50% of bound probe was displaced was obtained by fitting the data. All experimental data were analyzed using SOFTmax Pro 4.3.1 and plotted using Prism 4.0 (Graphpad Software Inc., San Diego, Calif.).

Cell fractionation and immunoblotting. Cells were either treated with DMSO (vehicle) or indicated compounds for 24 hr and lysed in RIPA buffer (50 mM Tris-HCl, pH 7.4, 150 mM NaCl, 0.5% sodium deoxycholate and 0.5% NP40) supplemented with cocktail protease inhibitors (Roche) to produce whole cell lysates. Lysates for cytosol and membrane fractions were harvested using ProteoExtract Subcellular Proteome Extraction Kit (Calbiochem) following the manufacturer's instructions. Protein concentrations were determined using BCA kit (Pierce) according to the manufacturer's instructions. The protein lysates (5-50 pg) were electrophoretically resolved by SDS-PAGE, transferred onto nitrocellulose membranes and probed with the indicated primary antibodies against: HER2 (Zymed, 28004), Hsp70 (Stressgen, SPA-810), Grp94 (Stressgen, SPA-850), Hsp90α (Abcam, Ab2928), Hsp90β (StressMarq, SMC-107B), Grp78 (Cell Signaling, 3183), Raf-1 (Santa Cruz, sc-133), phospho-Raf-1 (Cell Signaling, 9421), MEK1/2 (Cell Signaling, 8727), phospho-MEK1/2 (Cell Signaling, 9154), ERK1/2 (Cell Signaling, 4695), phospho-ERK1/2 (Cell Signaling, 4370), AKT (Cell Signaling, 9272), GM130 (Cell Signaling, 2296), Flotillin 2 (Cell Signaling, 3436), Histone H4 (Cell Signaling, 2592), Histone H1 (Santa Cruz, sc-8030), Caspase 3 (Cell Signaling, 9665), cleaved PARP (Promega, G7341), α-tubulin (Sigma, T5168) and 3-actin (Sigma, A1978). After washing off the excess antibodies, the membranes were incubated with the corresponding horseradish peroxidase (HRP) conjugated secondary antibody. Blots were visualized by autoradiography using the Enhanced Chemiluminescence Detection System (GE Healthcare) according to manufacturer's instructions. For all gels 3-actin was used as a protein loading control.

Densitometry analysis. Films were scanned in Adobe Photoshop CS5 and quantitative densitometric analysis was performed using ImageJ (NIH).

Protein level quantification. In all instances when protein quantification was performed, protein levels were first normalized to 3-actin then to the levels of the vehicle only treated experimental conditions. All quantified protein levels are reported as a fraction of control (i.e. the value obtained in the experimental condition was divided by the value obtained in the vehicle treated cells).

Chemical precipitation (CP). Agarose beads conjugated with Hsp90 inhibitors were washed three times with and finally suspended in Felts buffer (20 mM HEPES, 50 mM KCl, 5 mM MgCl2, 0.01% NP40, 20 mM Na2MoO4, pH 7.2~7.3) (Moulick, K. et al. Affinity-based proteomics reveal cancer-specific networks coordinated by Hsp90. Nat. Chem. Biol. 7, 818-26 (2011)). The bead conjugates (50 μL) were then incubated for 4 hrs at 4° C. with the indicated amounts of cell lysate, and the volume was adjusted to 500 pl with Felts buffer. The complexes were then washed three times with Felts buffer and proteins in the pull-down were analyzed by immunoblotting. For PU-WS13-biotin pull-down assays, the cell lysate was first incubated overnight at 4° C. with biotinylated PU-WS13, then for 2 hrs with 50 μL High Capacity Streptavidin Beads (Thermosci). The beads were washed three times with Felts buffer and the proteins in the pull-downs identified by immunoblotting. Control beads containing 2-methoxyethylamine, an Hsp90-inert molecule, or D-biotin were used to control for non-specific binding Immunoprecipitation (IP). The HER2 antibody (Cell Signaling, 2165), the Grp94 antibody (Abcam, Ab13509) or a normal rabbit IgG (Santa Cruz Biotechnology) were incubated with the indicated amount of cell lysate and with 40 pL protein A agarose beads (Roche). The mixture was incubated overnight on a rotator at 4° C. The beads were washed three times with RIPA buffer and separated by SDS-PAGE, followed by a standard immunoblotting procedure.

Grp94 depletion assay. The Grp94 antibodies (Abcam, Ab13509; Bioss, bs-0194R) or a normal rabbit IgG (Santa Cruz Biotechnology) were incubated with the indicated amount of cell lysate and with 40 pL protein A agarose beads (Roche). The mixture was incubated for 4 hours on a rotator at 4° C. The supernatants were collected after centrifugation, then incubated with the Grp94 antibody or a normal rabbit IgG and then with 40 μL protein A agarose beads to further deplete Grp94 in the cell lysate. After three rounds of antibody depletions, the supernatants were collected and incubated overnight with the PU-WS13-biotin beads at 4° C. The beads were washed three times with Felts buffer and separated by SDS-PAGE, followed by a standard immunoblotting procedure.

siRNA knock-down of Hsp90α, Hsp90β and Grp94. Transient transfections were carried out by using Lipofectamine RNAiMax reagent (Invitrogen, for SKBr3 cells) or electroporation with Neon transfection system (Life Technologies, for MCF7 cells.) according to manufacturer's instructions. For each target, four different siRNAs were purchased from Qiagen and designed against the open reading frame of Hsp90α (Gene Hsp90AA1), Hsp90β (Gene Hsp90AB1) or Grp94 (Gene Hsp90B1). Control cells were transfected with scramble siRNA. Cells were transfected with 20 nM siRNA and knock-down efficiency was evaluated at the indicated time by immunoblotting. Electroporation in MCF7 was optimized and the experiments were performed using two 1230 v 20 ms pulses on Neon transfection system (Life Technologies). SKBr3 cells were transfected with 20 nM siRNAs for 72 hrs, then re-transfected with 20 nM siRNAs for another 48 hrs before WB analysis.

Kinase screen. For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 min). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μm non-biotinylated affinity ligand) and incubated at room temperature with shaking for 30 minutes. The kinase concentration in the eluates was measured by qPCR. KINOMEscan's selectivity score (S) is a quantitative measure of compound selectivity. It is calculated by dividing the number of kinases that bind to the compound by the total number of distinct kinases tested, excluding mutant variants. TREEspot™ is a proprietary data visualization software tool developed by KINOMEscan. Kinases found to bind are marked with red circles, where larger circles indicate higher-affinity binding. The kinase dendrogram was adapted and is reproduced with permission from Science and Cell Signaling Technology, Inc.

Cell viability assessment. Cells were treated for 72 h with the indicated inhibitors or transfected for 72 h with Grp94 siRNA or control siRNA and their viability was assessed using CellTiter-Glo luminescent Cell Viability Assay (Promega) as previously described (Rodina, A. et al. Selective compounds define Hsp90 as a major inhibitor of apoptosis in small-cell lung cancer. Nat. Chem. Biol. 3, 498-507 (2007); Caldas-Lopes, E. et al. Hsp90 inhibitor PU-H71, a multimodal inhibitor of malignancy, induces complete responses in triple-negative breast cancer models. Proc. Natl. Acad. Sci. USA 106, 8368-73 (2009)). The method determines the number of viable cells in culture based on quantitation of the ATP present, which signals the presence of metabolically active cells.

Immunofluorescence. Cells were seeded and grown onto culture slides (BD Falcon) for 24 hrs. After washing with cold PBS, cells were fixed by treating at 4° C. for 20 min with 4% paraformaldehyde in PBS, permeabilized with 0.1% Triton X-100 in PBS containing 10% FBS for 10 min, and blocked with 2% BSA for 1hr. After washing for four times with PBS, primary antibodies were added onto the chambers and cell were incubated overnight at 4° C., washed again with PBS followed by incubation with the secondary antibody for 1hr at room temperature. Cell were washed and then mounted and observed under microscope (Leica Upright Confocal SP5). The primary antibodies used in the assay are against: HER2 (Zymed, 28004), Grp94 (Stressgen, SPA-850), Hsp70 (Stressgen, SPA-810), LAMP1-FITC (Abcam, ab25406), EEA1 (Abcam, ab70521), 58K Golgi-FITC (Abcam, ab27043) and Calnexin (BD, 610523).

Flow cytometry. Flow cytometry analysis was performed using MACSQuant analyzer (Miltenyi Biotec). $5 \times 10^4$ to $5 \times 10^5$ cells were seeded in 35 mm dishes and centrifuged at 500 g for 5 mins Excess medium was removed and the cell pellet was resuspended in cold medium containing human AB serum for blocking. Then the primary antibody Grp94-PE (Enzo, SPA-850PE) or an isotype control was added to each tube. Cells were incubated on ice for 60 mins then washed with cold PBS. Cells were then stained on ice with 7-AAD for 15 minutes and washed once with cold PBS. Cells were finally resuspended in 1% paraformaldehyde and subjected to flow cytometry analysis. Data were further analyzed by FlowJo (Ashland). Dead cells with positive 7-AAD staining were excluded from the analysis. For the Brefeldin A trafficking assay, cells were treated with GolgiPlug (BD biosciences, 555029) for 4 h according to the manufacturer's instructions. Cells were then either processed for live cell staining or first permeabilized with 0.1% Triton-X100 before flow analysis using the MACSQuant analyzer.

Assessment of cell surface proteins. Cell surface protein isolation kit (Pierce) was used to biotinylate proteins on the cell surface according to the manufacturer's instructions. Briefly, four 75 cm (Dollins, D. E., Warren, J. J., Immormino, R. M. & Gewirth, D. T. Structures of GRP94-nucleotide complexes reveal mechanistic differences between the hsp90 chaperones. Mol. Cell 28, 41-56 (2007)) flasks of cells were incubated with Sulfo-NHS-SS-biotin for 30 min at 4° C., the reaction was then quenched and cells were lyzed. The biotinylated proteins were isolated using NeutrAvidin Agarose beads, then eluted with Laemmli buffer and subjected to SDS-PAGE analysis and immunoblotting. Alternatively, after biotin labeling of the cell surface proteins, the biotinylated proteins were purified by using monomeric Avidin beads, followed by elution of proteins from the beads by incubation with 2 mM biotin for 6 hours at 4° C.

Cell cycle and apoptosis assessment. Cell cycle and apoptosis were assessed by flow cytometry after single staining with propidium iodide (PI, BD Pharmingen) or double staining with AnnexinV-FITC (BD Pharmingen) and 7AAD (BD Pharmingen), respectively. Specifically, for cell cycle analysis, cells were washed twice with cold PBS and fixed in 70% ethanol overnight at 4° C. Fixed cells were collected at 1800 rpm for 10 min and stained with PBS containing PI and DNase-free RNase A (Sigma-Aldrich) for 1 h at room temperature in the dark. DNA content was measured by BD LSRII flow cytometer and cell further analyzed using program of cell cycle analysis in FloJo (Ashland, Oreg.). The chicken erythrocyte nuclei singlets (CEN, Biosure) were used as the reference. For apoptosis assessment, live cells were collected, washed twice with cold PBS, resuspended in Binding Buffer and stained with AnnexinV-FITC and 7AAD for 15 min at room temperature in the dark. Signals from FL1 and FL3 channels were collected by MACSQuant analyzer and further analyzed using FloJo. Early apoptosis was defined as AnnexinV+/7AAD−, and late apoptosis was observed as AnnexinV+/7AAD+.

C2C12 differentiation and IGF-II secretion assay (Wanderling, S. et al. GRP94 is essential for mesoderm induction and muscle development because it regulates insulin-like growth factor secretion. Mol. Biol. Cell 18, 3764-75 (2007); Ostrovsky, O., Ahmed, N. T. & Argon, Y. The chaperone activity of GRP94 toward insulin-like growth factor II is necessary for the stress response to serum deprivation. Mol. Biol. Cell 20, 1855-64 (2009)). C2C12 cells were maintained and cultured in DMEM in the presence of 10% FBS and 1% penicillin/streptomycin (Culture medium). C2C12 is an immortal line of mouse skeletal myoblasts originally derived from satellite cells from the thigh muscle of a two month old female mouse donor. These cells differentiate well into myocytes under appropriate culture conditions. Here, cells were induced to differentiate by replacing the culture medium with DMEM supplemented with 2% horse serum and 1% penicillin/streptomycin (Differentiation medium) for 36-48 hours. Secreted IGF-II was quantified by using IGF-II mouse ELISA kit (Abcam, AB100696) according to the manufacturer's instructions. Briefly, after shifting the culture medium to differentiation medium, C2C12 cells were treated for 24 hrs with the indicated compounds. Media from each experimental condition was then transferred into ELISA plates coated with anti-IGF-II and incubated overnight at 4° C. The bound IGF-II was detected with a biotinylated anti-IGF-II antibody. After the sequential incubation with HRP conjugated streptavidin, TMB One-step substrate reagent and the Stop solution, the absorbance was measured at 450 nm. The secreted IGF-II was quantified against a standard curve generated with recombinant IGF-II provided by the kit.

TLR9-trafficking assay (Yang, Y. et al. Heat shock protein gp96 is a master chaperone for toll-like receptors and is important in the innate function of macrophages Immunity 26, 215-26 (2007)). HEK 293T cells were transfected with pUNO-hTLR9-HA (Invivogen) using X-tremgene HP (Roche) according to the manufacturer's instructions. At 24 hrs post-transfection, cells were split onto cell culture chamber slides (Lab-Tek). Cells were then treated for 24 hrs with indicated compound at varying concentrations. After treatment, cells were fixed for 20 min in 4% paraformaldehyde in PBS, permeabilized with 0.1% Triton-X 100 in PBS for 10 min, blocked with 3% BSA in PBS for 30 min, followed by staining for 1hr with an anti-HA antibody (Abcam, ab9110) or a normal rabbit IgG. Cells were washed with PBS, stained with an anti-rabbit-Cy3 antibody (Invitrogen) and finally mounted in the dark at 4° C. with Prolong Gold Antifade reagent (with DAPI). Cells were visualized under a confocal microscope (Leica Upright Confocal SP5). Fluorescence intensity was quantified using MetaMorph Microscopy Automation and Image Analysis Software (Molecular Devices Inc.) and normalized to the cell number.

Preparation of crude plasma membranes (Sokolowska, I. et al. Proteomic analysis of plasma membranes isolated from undifferentiated and differentiated HepaRG cells. Proteome Sci. 10, 47 (2012)). All the steps were performed at 4° C. and all the buffers were chilled on ice before use. The cells were gently scraped in PBS, pelleted by centrifugation at 600×g for 5 min and resuspended in 1mL 1× Hypotonic Extraction Buffer (Sigma, H8412, 10 mM HEPES, pH7.8, 1 mM EGTA, 25 mM KCl) for 20 min to allow the cells to swell. Then, cells were collected at 1000×g for 5 min, resuspended in 0.5 mL 1× Isotonic Extraction Buffer (Sigma, 13533, 10 mM HEPES, pH 7.8, 0.25M sucrose, 1 mM EGTA, 25 mM KCl), homogenized with 20 strokes of the Dounce homogenizer and then centrifuged for 10 min at 1000 g. The supernatant with the floating lipid layer was carefully collected and layered on top of 12 mL of 30% Percoll (Sigma, P4937) in Isotonic Extraction Buffer, followed by ultracentrifugation at 28,184 rpm in a TH641 rotor (Thermo Scientific) for 45 min. The crude plasma membrane fraction was visible as a ring at 5.4 cm from the bottom of the tube.

Angiogenesis studies with HUVEC cells purified from the plasma of diabetic patients: HUVECs were isolated from freshly collected umbilical veins by collagenase treatment (Jaffe et al., 1973) applied to at least three different cords. Cells were maintained in endothelial basal medium (EBM) supplemented with 10% (v/v) FBS, 100 units/ml penicillin, 10 µg/ml streptomycin, 0.1% (v/v) rHEGF, 01% (v/v) hydrocortisone and 0.4% bovine brain extract, at 37° C. in a humidified 95% air, 5% $CO_2$ atmosphere, until the cells reached sub-confluence. HUVECs at the $4^{th}$-$5^{th}$ passage were seeded at the density of 25×10$^4$/well in 12-well (2 ml each) plates in EBM supplemented with 10% FBS, and allowed to attach to well plastics for 24 h. A fresh aliquot (2 ml) of serum-free medium was added with native Grp94 (10 and 100 ng/ml, final concentrations), peak 2 from the mono-Q column (10 ng/ml), both with and without the inhibitors in triplicate wells. The inhibitors were added to cells immediately before the addition of Grp94 and peak 2. Wells with inhibitors alone and with the diluent (DMSO) in which inhibitors were dissolved served as controls. After 18 h-incubation, morphologic examination of cells was performed with the Leica DMI 4000B microscope. The medium was then collected and cells washed with PBS, detached from the wells with a solution of 0.05% trypsin and 0.2% EDTA and counted in a hemocytometer. PU-H54 was used at the final concentrations of 1 and 10 µM. Pictures of HUVECs are representative and show overlapping features for each condition.

TNFα ELISA protocol: Mouse macrophage cells, RAW264.7, were cultured in DMEM medium (Invitrogen) with 2 mM Glutamax, 50 U/mL penicillin/streptomycin, 10 mM HEPES, 1 mM sodium pyruvate and 10% low endotoxin FBS. The cells were kept in a humidified cell incubator with CO2 at 37° C. Lipopolysaccharides (LPS, Sigma) and CpG DNA ODN1585 (5'-G*G*GGTCAACGTTGAGG*G*G*G*G-3' (SEQ ID NO: 5), IDT) were used to stimulate TNF-α production in RAW264.7 cells. TNFα production was determined using the mouse TNF-α ELISA MAX Set (Biolegend) from supernatants of cells pretreated with inhibitors. Briefly, RAW264.7 cells were pretreated for 2 hours with the indicated concentrations of the inhibitors, then stimulated with 10 ng/mL LPS or 2.5 uM CpG DNA for 18 hours. Media from each experimental condition was then transferred into ELISA plates (pre-coated with Capture Antibody and blocked) and incubated at room temperature (RT) for 2 hour with shaking. The captured TNF-α was detected with Detection Antibody in the kit. After the sequential incubation with HRP conjugated streptavidin, TMB substrate reagent and the Stop solution, the absorbance was measured at 450 nm. The produced TNF-α was finally quantified against a standard curve generated with recombinant TNF-α provided by the kit.

6.2 Preparation of Grp94 Inhibitors 6.2.1 Synthesis of Compounds of Formula 4a-t (Scheme 1)

Scheme 1:

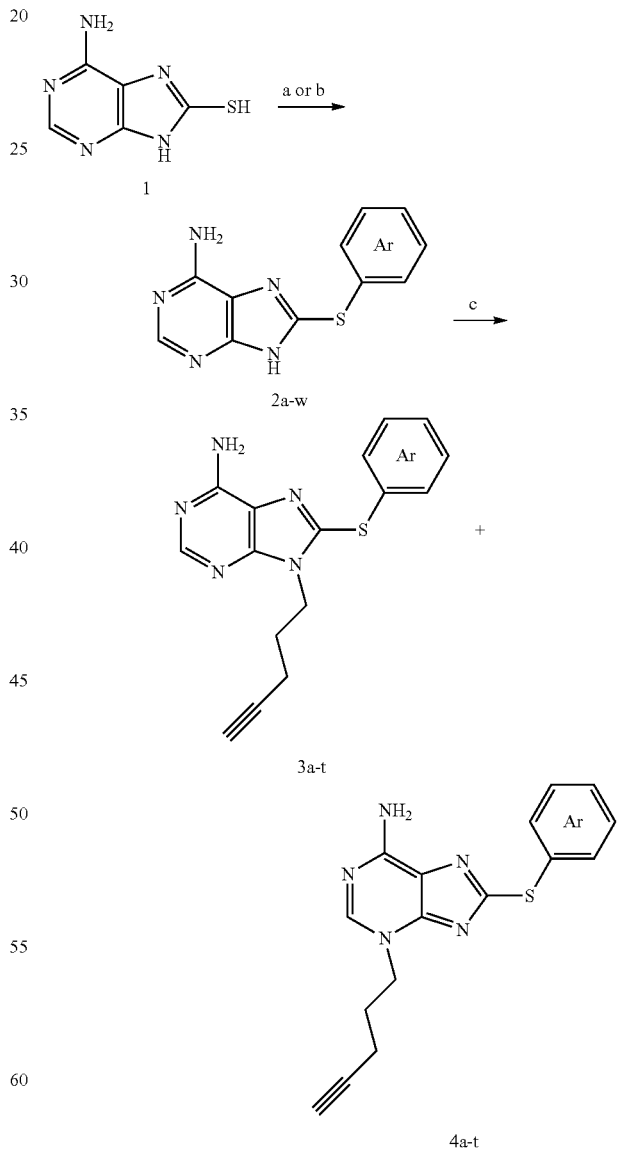

Reagents and conditions: (a) ArI, neocuproine, CuI, NaOt-Bu, DMF, 110° C., 24-36 h; (b) ArI, t-butyl ammonium bromide, CuI, NaOt-Bu, DMF, MW, 190° C., 1.5-2 h; (c) 5-bromopent-1-yne, Cs$_2$CO$_3$, DMF, rt-60° C., 2-6 h.

General Procedure for Synthesis of 8-aryl Sulfanyl Derivatives 2a-w

Method A: Conventional Heating Reaction. 8-Mercaptoadenine (3.6 mmol), neocuproine hydrate (0.36 mmol), CuI (0.36 mmol), NaO-t-Bu (7.2 mmol), respective aryl iodide (10.8 mmol), and anhydrous DMF (24 mL) were taken in a round bottom flask flushed with nitrogen. The flask was sealed with Teflon tape, heated at 110° C., and magnetically stirred for 24-36 h under nitrogen. Solvent was removed under reduced pressure and the resulting residue was chromatographed ($CH_2Cl_2$:MeOH:AcOH, 20:1:0.5).

Method B: Microwave Coupling Reaction. In a conical-bottomed microwave vial, the mixture of 8 mercaptoadenine (0.1 mmol), respective aryl iodide (0.1 mmol), CuI (0.02 mmol), NaOt-Bu (0.3 mmol) and t-butyl ammonium bromide (0.02 mmol) in DMF (2 mL) was charged. The sealed vial was irradiated in the microwave for 1.5 h at 150° C. After cooling, the reaction mixture was condensed under reduced pressure and purified by flash chromatography ($CH_2Cl_2$:MeOH:AcOH, 20:1:0.5).

8-((4-Bromo-2-ethylphenyl)thio)-9H-purin-6-amine (2a). Obtained by method B as a light yellow solid in 49% yield. MS (ESI): m/z 351.8 $[M+H]^+$.

8-((4-Bromo-2-chlorophenyl)thio)-9H-purin-6-amine (2b). Obtained by method B as a light yellow solid in 42% yield. MS (ESI): m/z 357.6 $[M+H]^+$.

8-((4-Chloro-2-(trifluoromethyl)phenyl)thio)-9H-purin-6-amine (2c). Obtained by method B as a light yellow solid in 43% yield. MS (ESI): m/z 343.9 $[M-H]^-$.

8-((2,4-Bis(trifluoromethyl)phenyl)thio)-9H-purin-6-amine (2d). Obtained by method B as a light yellow solid in 45% yield. MS (ESI): m/z 380.0 $[M+H]^+$.

8-((3-Bromo-5-chlorophenyl)thio)-9H-purin-6-amine (2e). Obtained by method B as a light yellow solid in 42% yield. MS (ESI): m/z 358.1 $[M+H]^+$.

8-((3,5-Dibromophenyl)thio)-9H-purin-6-amine (2f). Obtained by method B as a light yellow solid in 40% yield. MS (ESI): m/z 401.9 $[M+H]^+$.

8-((3-Bromo-5-iodophenyl)thio)-9H-purin-6-amine (2g). Obtained by method B as a light yellow solid in 16% yield. MS (ESI): m/z 449.8 $[M+H]^+$.

8-((3-Bromo-5-(trifluoromethoxy)phenyl)thio)-9H-purin-6-amine (2h). Obtained by method A as a light yellow solid in 41% yield. MS (ESI): m/z 407.8 $[M+H]^+$.

8-((2,3-Dichlorophenyl)thio)-9H-purin-6-amine (2i). Obtained by method A as a yellow solid in 47% yield. MS (ESI): m/z 311.9 $[M+H]^+$.

8-((3,4-Dichlorophenyl)thio)-9H-purin-6-amine (2j). Obtained by method B as a yellow solid in 69% yield. MS (ESI): m/z 312.0 $[M+H]^+$.

8-((3,4,5-Trichlorophenyl)thio)-9H-purin-6-amine (2k). Obtained by method A as a light yellow solid in 42% yield. MS (ESI): m/z 347.8 $[M+H]^+$.

8-((2,3,4-Trichlorophenyl)thio)-9H-purin-6-amine (2l). Obtained by method A a yellow solid in 43% yield. MS (ESI): m/z 347.7 $[M+H]^+$.

8-((2,3,5-Trichlorophenyl)thio)-9H-purin-6-amine (2m). Obtained by method A as a light yellow solid in 49% yield. MS (ESI): m/z 347.4 $[M+H]^+$.

8-((5-Bromopyridin-2-yl)thio)-9H-purin-6-amine (2n). Obtained by method B as a light yellow solid in 40% yield. MS (ESI): m/z 324.9 $[M+H]^+$.

8-(Naphthalen-1-ylthio)-9H-purin-6-amine (2o). Obtained by method A as a yellow solid in 39% yield. MS (ESI): m/z 294.0 $[M+H]^+$.

8-((4-Chloronaphthalen-1-yl)thio)-9H-purin-6-amine (2p). Obtained by method B as a light yellow solid in 39% yield. MS (ESI): m/z 328.4 $[M+H]^+$.

8-((4,6-Dichloroquinolin-8-yl)thio)-9H-purin-6-amine (2q). Obtained by method B as a light yellow solid in 39% yield. MS (ESI): m/z 362.9 $[M+H]^+$.

8-((4-(1H-Pyrrol-1-yl)phenyl)thio)-9H-purin-6-amine (2r). Obtained by method B as a yellow solid in 58% yield. MS (ESI): m/z 309.3 $[M+H]^+$.

8-((5-Bromo-1-(4-methoxybenzyl)-1H-indol-7-yl)thio)-9H-purin-6-amine (2s).

Obtained by method B as a white solid in 53% yield. MS (ESI): m/z 483.3 $[M+H]^+$.

8-((5-Bromo-1-(4-methoxybenzyl)-1H-pyrrolo[2,3-b]pyridin-3-yl)thio)-9H-purin-6-amine (2t). Obtained by method B as a light yellow solid in 47% yield. MS (ESI): m/z 483.1 $[M+H]^+$.

8-(2,4-Dimethyl-phenylsulfanyl)adenine (2u). Obtained by method B as a white solid in 62% yield. $^1$H NMR (400 MHz, DMSO) δ 13.2 (br s, 1H), 8.05 (s, 1H), 7.03-7.26 (m, 5H), 2.30 (s, 3H), 2.26 (s, 3H); $^{13}$C NMR (100 MHz, DMSO) δ 154.6, 152.2, 139.4, 138.5, 133.0, 131.6, 127.7, 20.6, 20.24; MS (ESI): m/z 272.1 $[M+H]^+$.

8-((3,5-Bis(trifluoromethyl)phenyl)thio)-9H-purin-6-amine (2v). Obtained by method A in 57% yield. $^1$H NMR (600 MHz, DMSO) δ 13.6 (br s, 1H), 8.09-8.14 (m, 4H), 7.44 (br s, 2H); MS (ESI): m/z 380.1 $[M+H]^+$.

8-(Mesitylthio)-9H-purin-6-amine (2w). Obtained by method A in 53% yield. $^1$H NMR (400 MHz, DMSO) δ 13.1 (br s, 1H), 8.02 (s, 1H), 6.93-7.04 (m, 5H), 2.33 (s, 6H), 2.25 (s, 3H); MS (ESI): m/z 286.1 $[M+H]^+$.

General Procedure for Synthesis of N9 and N3 alkylated 8-aryl sulfanyl Derivatives 3a-t and 4a-t 8-Arylsulfanyl adenine (2a-r, 1.21 mmol) was dissolved in DMF (15 mL) and $Cs_2CO_3$ (1.45 mmol) and 5-bromopent-1-yne (2.42 mmol) were added and the mixture was stirred under nitrogen at 40° C. for 2-6 h. Solvent was removed under reduced pressure and the resulting residue was chromatographed ($CH_2Cl_2$:MeOH:AcOH, 20:1:0.5) to afford desired compounds 3a-t and 4a-t.

8-((4-Bromo-2-ethylphenyl)thio)-9-(pent-4-yn-1-yl)-9H-purin-6-amine (3a). Obtained as a white solid in 40% yield. $^1$H-NMR (400 MHz, $CDCl_3$) δ 8.30 (1H, s), 7.44 (1H, d, J=2.1 Hz), 7.27-7.29 (1H, m), 7.15 (1H, d, J=8.3 Hz), 5.89 (2H, br s), 4.29 (2H, t, J=7.4 Hz), 2.28 (2H, td, J=6.9, 2.5 Hz), 2.01-2.06 (2H, m), 1.98 (1H, t, J=2.6 Hz); $^{13}$C-NMR ($CDCl_3$) δ 154.3, 152.8, 151.7, 147.3, 145.9, 134.0, 132.3, 130.2, 128.2, 123.4, 114.9, 82.4, 69.5, 42.8, 28.3, 27.2 16.0, 14.5; HRMS (ESI) m/z $[M+H]^+$ calcd. for $C_{18}H_{19}N_5SBr$, 416.0545. found 416.0536.

8-((4-Bromo-2-chlorophenyl)thio)-9-(pent-4-yn-1-yl)-9H-purin-6-amine (3b). Obtained as a white solid in 39% yield. $^1$H-NMR (400 MHz, $CDCl_3$) δ 8.29 (1H, s), 7.54 (1H, d, J=2.0 Hz), 7.24 (1H, dd, J=8.4, 2.0 Hz), 6.99 (1H, d, J=8.5 Hz), 5.72 (2H, br s), 4.26 (2H, t, J=7.3 Hz), 2.20 (2H, td, J=6.9, 2.6 Hz), 1.96 (2H, p, J=7.2 Hz), 1.91 (1H, t, J=2.6 Hz); $^{13}$C-NMR ($CDCl_3$) δ 154.6, 153.5, 151.7, 143.7, 135.1, 132.9, 132.4, 130.9, 130.5, 122.2, 116.5, 82.2, 69.6, 43.1, 28.4, 16.1; HRMS (ESI) m/z $[M+H]^+$ calcd. for $C_{16}H_{14}N_5SBrCl$, 421.9842. found 421.9823.

8-((4-Chloro-2-(trifluoromethyl)phenyl)thio)-9-(pent-4-yn-1-yl)-9H-purin-6-amine (3c). Obtained as a white solid in 41% yield. $^1$H-NMR (400 MHz, $CDCl_3$) δ 8.34 (1H, s), 7.72 (1H, s), 7.41 (1H, d, J=8.1 Hz), 7.33 (1H, d, J=8.3 Hz), 6.23 (2H, br s), 4.29 (2H, t, J=7.1 Hz), 2.21-2.28 (2H, m), 1.95-2.02 (3H, m); $^{13}$C-NMR ($CDCl_3$) δ 154.9, 151.6, 143.7, 134.5, 132.7, 131.4, 131.0, 129.1, 127.7, 124.0, 121.3, 120.3, 82.1, 70.6, 43.0, 28.3, 15.9; HRMS (ESI) m/z [M+H]$^+$ calcd. for C$_{17}$H$_{14}$N$_5$SF$_3$Cl$_2$, 412.0611. found 412.0612.

8-((2,4-Bis(trifluoromethyl)phenyl)thio)-9-(pent-4-yn-1-yl)-9H-purin-6-amine (3d). Obtained as a white solid in 39% yield. $^1$H-NMR (400 MHz, CDCl$_3$) δ 8.36 (1H, s), 7.96 (2H, s), 7.83 (1H, s), 5.70 (2H, br s), 4.37 (2H, t, J=7.2 Hz), 2.27 (2H, td, J=6.9, 2.6 Hz), 1.98-2.07 (3H, m); $^{13}$C-NMR (CDCl$_3$) δ 154.6, 153.5, 151.7, 143.6, 134.3, 132.9, 132.6, 130.7, 124.1, 121.4, 120.3, 82.2, 69.6, 42.9, 28.3, 16.0; MS (ESI): m/z 446.1 [M+H]$^+$.

8-((3-Bromo-5-chlorophenyl)thio)-9-(pent-4-yn-1-yl)-9H-purin-6-amine (3e). Obtained as a white solid in 37% yield. $^1$H-NMR (400 MHz, CDCl$_3$) δ 8.36 (1H, s), 7.42-7.44 (2H, m), 7.33 (1H, s), 6.19 (2H, br s), 4.33 (2H, t, J=7.3 Hz), 2.27 (2H, td, J=6.6, 2.4 Hz), 1.99-2.03 (3H, m); $^{13}$C-NMR (CDCl$_3$) δ 154.9, 153.5, 151.5, 143.5, 135.9, 134.7, 131.2, 131.0, 128.7, 123.4, 120.3, 82.3, 69.7, 43.0, 28.3, 16.0; HRMS (ESI) m/z [M+H]$^+$ calcd. for C$_{16}$H$_{14}$N$_5$SClBr, 423.9821. found 423.9822.

8-((3,5-Dibromophenyl)thio)-9-(pent-4-yn-1-yl)-9H-purin-6-amine (3f). Obtained as a white solid in 37% yield. $^1$H-NMR (400 MHz, CDCl$_3$) δ 8.31 (1H, s), 7.62 (1H, t, J=1.6 Hz), 7.50 (2H, d, J=1.7 Hz), 6.22 (2H, br s), 4.33 (2H, t, J=7.5 Hz), 2.27 (2H, td, J=6.8, 2.6 Hz), 1.99-2.05 (3H, m); $^{13}$C-NMR (CDCl$_3$) δ 154.2, 152.9, 151.6, 145.8, 134.1, 131.8, 128.2, 123.6, 114.5, 82.4, 69.7, 43.0, 28.2, 16.0; HRMS (ESI) m/z [M+H]$^+$ calcd. for C$_{16}$H$_{14}$N$_5$SBr$_2$, 465.9337. found 465.9329.

8-((3,5-Dibromophenyl)thio)-3-(pent-4-yn-1-yl)-3H-purin-6-amine (4f). Obtained as a white solid in 16% yield. $^1$H-NMR (400 MHz, CDCl$_3$) δ 8.04 (1H, s), 7.66 (2H, s), 7.52-7.55 (1H, m), 4.22 (2H, t, J=6.2 Hz), 2.18-2.24 (4H, m), 2.05-2.08 (1H, m); HRMS (ESI) m/z [M+H]$^+$ calcd. for C$_{16}$H$_{14}$N$_5$SBr$_2$, 465.9337. found 465.9331.

8-((3-Bromo-5-iodophenyl)thio)-9-(pent-4-yn-1-yl)-9H-purin-6-amine (3g). Obtained as a white solid in 35% yield. $^1$H-NMR (400 MHz, CDCl$_3$) δ 8.29 (1H, s), 7.79 (1H, s), 7.70 (1H, s), 7.53 (1H, s), 6.57 (2H, bs), 4.33 (2H, t, J=7.4 Hz), 2.27 (2H, td, J=6.6, 2.4 Hz), 1.97-2.04 (3H, m); $^{13}$C-NMR (CDCl$_3$) δ 154.9, 152.8, 151.4, 144.1, 139.6, 137.5, 134.5, 132.5, 123.6, 119.2, 94.8, 82.2, 69.7, 43.1, 28.2, 16.0; HRMS (ESI) m/z [M+H]$^+$ calcd. for C$_{16}$H$_{14}$N$_5$SBrI, 513.9198. found 513.9202.

8-((3-Bromo-5-(trifluoromethoxy)phenyl)thio)-9-(pent-4-yn-1-yl)-9H-purin-6-amine (3h, PDP-120-A). Obtained as a yellow solid in 36% yield. $^1$H-NMR (400 MHz, CDCl$_3$) δ 8.33 (1H, s), 7.49 (1H, t, J=1.5 Hz), 7.33 (1H, s), 7.25 (1H, s), 6.15 (2H, bs), 4.34 (2H, t, J=7.4 Hz), 2.27 (2H, td, J=6.8, 2.6 Hz), 2.02-2.05 (2H, m), 1.99 (1H, t, J=2.5 Hz); $^{13}$C-NMR (CDCl$_3$) δ 161.0, 154.8, 153.2, 151.5, 149.8, 143.6, 135.1, 131.1, 123.9, 123.5, 121.4, 120.2, 82.2, 69.6, 43.0, 28.3, 16.0; HRMS (ESI) m/z [M+H]$^+$ calcd. for C$_{17}$H$_{14}$N$_5$OF$_3$SBr, 474.0034. found 474.0035.

8-((3-Bromo-5-(trifluoromethoxy)phenyl)thio)-3-(pent-4-yn-1-yl)-3H-purin-6-amine (4h). Obtained as a yellow solid in 14% yield. $^1$H-NMR (400 MHz, CDCl$_3$) δ 8.05 (1H, s), 7.63 (1H, s), 7.41 (1H, s), 7.23 (1H, s), 4.50 (2H, t, J=7.4 Hz), 2.20-2.23 (2H, m), 2.04-2.07 (3H, m); $^{13}$C-NMR (CDCl$_3$) δ 158.6, 153.1, 152.0, 149.3, 145.2, 142.5, 138.1, 135.8, 130.9, 122.5, 121.3, 120.1, 81.7, 70.7, 53.5, 26.8, 15.3; HRMS (ESI) m/z [M+H]$^+$ calcd. for C$_{17}$H$_{14}$N$_5$OF$_3$SBr, 474.0034. found 474.0033.

8-((3,4-Dichlorophenyl)thio)-9-(pent-4-yn-1-yl)-9H-purin-6-amine (3i). Obtained as a yellow solid in 54% yield. $^1$H-NMR (400 MHz, CDCl$_3$) δ 8.25 (1H, s), 7.58 (1H, d, J=2.2 Hz), 7.40 (1H, d, J=8.4 Hz), 7.25 (1H, dd, J=8.3, 2.1 Hz), 6.97 (2H, br s), 4.32 (2H, t, J=7.4 Hz), 2.28 (2H, td, J=6.8, 2.6 Hz), 1.97-2.02 (3H, m); $^{13}$C-NMR (CDCl$_3$) δ 154.8, 153.3, 151.5, 144.6, 133.6, 133.0, 132.5, 131.3, 130.6, 130.2, 120.1, 82.3, 69.6, 42.9, 28.2, 16.0; HRMS (ESI) m/z [M+H]$^+$ calcd. for C$_{16}$H$_{14}$N$_5$SCl$_2$, 378.0347. found 378.0353.

8-((3,4-Dichlorophenyl)thio)-3-(pent-4-yn-1-yl)-3H-purin-6-amine (4i). Obtained as a yellow solid in 18% yield. $^1$H-NMR (400 MHz, CDCl$_3$) δ 8.07 (1H, s), 7.70 (1H, d, J=2.2 Hz), 7.42-7.44 (2H, m), 4.46 (2H, t, J=6.6 Hz), 2.23-2.25 (2H, m), 2.16-2.20 (2H, m), 2.08-2.10 (1H, m); $^{13}$C-NMR (CDCl$_3$) δ 159.3, 152.5, 151.1, 142.5, 133.4, 132.9, 132.5, 131.9, 131.0, 130.7, 121.6, 81.7, 70.8, 49.2, 26.9, 15.3; HRMS (ESI) m/z [M+H]$^+$ calcd. for C$_{16}$K$_4$N$_5$SCl$_2$, 378.0347. found 378.0359.

8-((2,3-Dichlorophenyl)thio)-9-(pent-4-yn-1-yl)-9H-purin-6-amine (3j). Obtained as a white solid in 34% yield. $^1$H-NMR (400 MHz, CDCl$_3$) δ 8.38 (1H, s), 7.38 (1H, d, J=8.0 Hz), 7.10 (1H, t, J=7.9 Hz), 6.93 (1H, d, J=8.0 Hz), 5.89 (2H, br s), 4.33 (2H, t, J=7.3 Hz), 2.25 (2H, td, J=6.8, 2.6 Hz), 2.02 (2H, p, J=7.0 Hz), 1.97 (1H, t, J=2.6 Hz); $^{13}$C-NMR (CDCl$_3$) δ 154.8, 153.6, 151.6, 143.4, 134.5, 134.2, 131.5, 129.4, 128.1, 127.9, 120.5, 82.2, 69.6, 43.2, 28.4, 16.0; HRMS (ESI) m/z [M+H]$^+$ calcd. for C$_{16}$H$_{14}$N$_5$SCl$_2$, 378.0347. found 378.0342.

9-(Pent-4-yn-1-yl)-8-((3,4,5-trichlorophenyl)thio)-9H-purin-6-amine (3k). Obtained as a yellow solid in 39% yield. $^1$H-NMR (400 MHz, CDCl$_3$) δ 8.35 (1H, s), 7.47 (2H, s), 5.74 (2H, br s), 4.34 (2H, t, J=7.3 Hz), 2.28 (2H, td, J=6.9, 2.8 Hz), 2.03-2.07 (2H, m), 2.01 (1H, t, J=2.6 Hz); $^{13}$C-NMR (CDCl$_3$) δ 154.8, 153.2, 151.5, 149.8, 143.6, 135.1, 131.1, 123.9, 123.5, 121.4, 120.2, 82.2, 69.6, 43.0, 28.3, 16.0; HRMS (ESI) m/z [M+H]$^+$ calcd. for C$_{16}$K$_3$N$_5$SCl$_3$, 411.9957. found 411.9944.

9-(Pent-4-yn-1-yl)-8-((2,3,5-trichlorophenyl)thio)-9H-purin-6-amine (3l). Obtained as a yellow solid in 41% yield. $^1$H-NMR (400 MHz, CDCl$_3$) δ 8.30 (1H, s), 7.39 (1H, d, J=2.1 Hz), 6.97 (1H, d, J=2.1 Hz); 6.80 (2H, br s), 4.36 (2H, t, J=7.2 Hz), 2.27 (2H, td, J=6.8, 2.5 Hz), 2.03 (2H, pentet, J=6.9 Hz), 1.97 (1H, t, J=2.5 Hz); $^{13}$C-NMR (CDCl$_3$) δ 155.2, 152.9, 151.3, 142.5, 135.4, 134.7, 133.4, 130.0, 129.3, 127.9, 120.3, 82.0, 69.7, 43.3, 28.4, 16.0; HRMS (ESI) m/z [M+H]$^+$ calcd. for C$_{16}$H$_{13}$N$_5$SCl$_3$, 411.9957. found 411.9953.

3-(Pent-4-yn-1-yl)-8-((2,3,5-trichlorophenyl)thio)-3H-purin-6-amine (4l). Obtained as a yellow solid in 16% yield. $^1$H-NMR (400 MHz, CDCl$_3$) δ 8.09 (1H, s), 7.31 (1H, s), 7.25 (1H, s), 6.24 (2H, br s), 4.51 (2H, t, J=6.8 Hz), 2.17-2.23 (2H, m), 2.06-2.09 (3H, m); $^{13}$C-NMR (CDCl$_3$) δ 156.3, 153.9, 150.5, 143.4, 138.0, 133.9, 132.5, 129.8, 128.3, 127.9, 121.3, 81.7, 70.7, 49.3, 26.9, 15.3; HRMS (ESI) m/z [M+H]$^+$ calcd. for C$_{16}$H$_{13}$N$_5$SCl$_3$, 411.9957. found 411.9969.

9-(Pent-4-yn-1-yl)-8-((2,3,4-trichlorophenyl)thio)-9H-purin-6-amine (3m). Obtained as a yellow solid in 39% yield. $^1$H-NMR (400 MHz, CDCl$_3$) δ 8.35 (1H, s), 7.29 (1H, d, J=8.6 Hz), 6.97 (1H, d, J=8.6 Hz), 6.18 (2H, bs), 4.34 (2H, t, J=7.3 Hz), 2.26 (2H, td, J=6.8, 2.4 Hz), 2.03 (2H, pentet, J=6.9 Hz), 1.98 (1H, t, J=2.5 Hz); $^{13}$C-NMR (CDCl$_3$) δ 154.8, 153.6, 151.5, 143.2, 133.5, 133.4, 133.0, 132.4, 128.8, 128.4, 120.5, 82.1, 69.7, 43.1, 28.4, 16.0; HRMS (ESI) m/z [M+H]$^+$ calcd. for C$_{16}$H$_{13}$N$_5$SCl$_3$, 411.9957. found 411.9967.

3-(Pent-4-yn-1-yl)-8-((2,3,4-trichlorophenyl)thio)-3H-purin-6-amine (4m). Obtained as a yellow solid in 15% yield. $^1$H-NMR (400 MHz, CDCl$_3$) δ 8.05 (1H, s), 7.24-7.26 (2H, m), 6.97 (1H, d, J=8.6 Hz), 4.48 (2H, t, J=6.7 Hz), 2.06-2.20 (5H, m); $^{13}$C-NMR (CDCl$_3$) δ 157.7, 153.6, 150.7, 143.0, 134.5, 134.2, 132.4, 132.2, 129.7, 128.1, 121.6, 81.7, 70.7, 49.1, 27.0, 15.3; HRMS (ESI) m/z [M+H]$^+$calcd. for C$_{16}$H$_{13}$N$_5$SCl$_3$, 411.9957. found 411.9963.

8-((5-Bromopyridin-2-yl)thio)-9-(pent-4-yn-1-yl)-9H-purin-6-amine (3n). Obtained as a white solid in 34% yield. $^1$H-NMR (400 MHz, CDCl$_3$) δ 8.44 (1H, d, J=2.2 Hz), 8.39 (1H, s), 7.71 (1H, dd, J=8.4, 2.3 Hz), 7.17 (1H, d, J=8.4 Hz), 5.85 (2H, br s), 4.36 (2H, t, J=7.3 Hz), 2.25 (2H, td, J=6.9, 2.5 Hz), 2.07 (2H, pentet, J=7.0 Hz), 1.93 (2H, t, J=2.6 Hz); $^{13}$C-NMR (CDCl$_3$) δ 155.0, 154.7, 153.7, 151.6, 151.2, 142.1, 139.9, 123.6, 120.7, 118.6, 82.4, 69.4, 43.3, 28.4, 16.0; HRMS (ESI) m/z [M+H]$^+$ calcd. for C$_{15}$H$_{14}$N$_6$SBr, 389.0184. found 389.0201.

8-((5-Bromopyridin-2-yl)thio)-3-(pent-4-yn-1-yl)-3H-purin-6-amine (4n). Obtained as a white solid in 15% yield. $^1$H-NMR (400 MHz, CDCl$_3$) δ 7.97 (1H, s), 7.50 (1H, s), 7.27 (1H, d, J=8.4 Hz), 7.19-7.21 (1H, m), 5.72 (2H, br s), 4.42 (2H, t, J=6.2 Hz), 2.15-2.18 (4H, m), 1.99-2.01 (1H, m); MS (ESI): m/z 391.1 [M+H]$^+$.

8-(Naphthalen-1-ylthio)-9-(pent-4-yn-1-yl)-9H-purin-6-amine (3o). Obtained as a white solid in 33% yield. $^1$H-NMR (400 MHz, CDCl$_3$) δ 8.37 (1H, d, J=8.1 Hz), 8.28 (1H, s), 7.85-7.87 (2H, m), 7.64 (1H, d, J=7.1 Hz), 7.54-7.60 (2H, m), 7.40-7.43 (1H, m), 5.99 (2H, br s), 4.29 (2H, t, J=7.3 Hz), 2.18 (2H, td, J=6.9, 2.6 Hz), 1.97 (2H, pentet, J=7.1 Hz), 1.90 (1H, t, J=2.5 Hz); $^{13}$C NMR (CDCl$_3$) δ 154.4, 152.7, 151.7, 146.5, 134.3, 133.1, 131.9, 129.9, 128.8, 127.4, 127.2, 126.7, 125.9, 124.9, 120.0, 82.4, 69.5, 42.9, 28.1, 16.1; MS (ESI): m/z 360.5 [M+H]$^+$.

8-((4-Chloronaphthalen-1-yl)thio)-9-(pent-4-yn-1-yl)-9H-purin-6-amine (3p). Obtained as a white solid in 35% yield. $^1$H-NMR (500 MHz, CDCl$_3$) δ 8.41 (1H, d, J=7.9 Hz), 8.31 (1H, d, J=8.2 Hz), 7.96 (1H, s), 7.87 (1H, d, J=6.8 Hz), 7.55-7.63 (3H, m), 4.40 (2H, t, J=7.3 Hz), 2.13-2.15 (2H, m), 2.04-2.10 (3H, m); MS (ESI): m/z 394.2 [M+H]$^+$.

8-((4,6-Dichloroquinolin-8-yl)thio)-9-(pent-4-yn-1-yl)-9H-purin-6-amine (3q). Obtained as a white solid in 37% yield. $^1$H-NMR (500 MHz, CDCl$_3$) δ 8.77 (1H, d, J=4.8 Hz), 8.38 (1H, d, J=2.2 Hz), 8.36 (1H, s), 8.28 (1H, d, J=2.2 Hz), 7.11 (1H, J=4.8 Hz), 6.15 (2H, br s), 4.34 (2H, t, J=7.3 Hz), 2.23 (2H, td, J=6.8, 2.6 Hz), 2.02 (2H, pentet, J=6.8 Hz), 1.87 (2H, t, J=2.6 Hz).

8-((4,6-Dichloroquinolin-8-yl)thio)-3-(pent-4-yn-1-yl)-3H-purin-6-amine (4q). Obtained as a white solid in 12% yield. $^1$H-NMR (500 MHz, CDCl$_3$) δ 8.75 (1H, d, J=4.7 Hz), 8.30-8.31 (2H, m), 8.08 (1H, s), 7.52 (1H, J=4.7 Hz), 4.50 (2H, t, J=6.3 Hz), 2.19-2.24 (4H, m), 2.07 (1H, t, J=2.4 Hz).

8-(4-(1H-Pyrrol-1-yl)phenylthio)-9-(pent-4-ynyl)-9H-purin-6-amine (3r). Obtained as a white solid in 52% yield. $^1$H NMR (400 MHz, CDCl$_3$) δ 8.37 (s, 1H), 7.55 (2H, d, J=8.2 Hz), 7.38 (2H, d, J=8.2 Hz), 7.07 (2H, d, J=4.3 Hz), 6.36 (2H, d, J=4.3 Hz), 5.76 (2H, br s), 4.33 (2H, t, J=7.1 Hz), 2.22-2.29 (2H, m), 1.98-2.07 (3H, m); $^{13}$C NMR (CDCl$_3$) δ 154.3, 152.9, 151.7, 146.3, 140.9, 133.1, 126.8, 121.1, 120.4, 119.1, 111.1, 82.4, 69.5, 42.8, 28.2, 16.1; HRMS (ESI) m/z [M+H]$^+$ calcd. for C$_{20}$H$_{19}$N$_6$S, 375.1392. found 375.1397.

8-(4-(1H-Pyrrol-1-yl)phenylthio)-3-(pent-4-ynyl)-3H-purin-6-amine (4r). Obtained as a white solid in 19% yield. $^1$H NMR (400 MHz, CDCl$_3$) δ 8.02 (1H, s), 7.68 (2H, d, J=8.4 Hz), 7.46 (2H, d, J=8.5 Hz), 7.06-7.08 (2H, m), 6.34 (2H, d, J=2.0 Hz), 5.72 (2H, br s), 4.47 (2H, t, J=5.6 Hz), 2.19-2.26 (4H, m), 2.00-2.04 (1H, m); $^{13}$C NMR (CDCl$_3$) δ 159.5, 152.2, 151.6, 142.1, 141.0, 134.8, 121.1, 119.5, 111.2, 82.2, 71.1, 54.1, 27.4, 15.7; HRMS (ESI) m/z [M+H]$^+$ calcd. for C$_{20}$H$_{19}$N$_6$S, 375.1392. found 375.1395.

8-((5-Bromo-1-(4-methoxybenzyl)-1H-indol-7-yl)thio)-9-(pent-4-yn-1-yl)-9H-purin-6-amine (3s). Obtained as a white solid in 25% yield. $^1$H-NMR (400 MHz, CDCl$_3$) δ 8.22 (1H, s), 7.86 (1H, d, J=1.7 Hz), 7.50 (1H, d, J=1.5 Hz), 7.12 (1H, d, J=3.1 Hz), 6.73 (2H, d, J=8.5 Hz), 6.61 (2H, d, J=8.6 Hz), 6.57 (1H, d, J=3.1 Hz), 5.75 (2H, s), 4.14 (2H, t, J=7.2 Hz), 3.63 (3H, s), 2.22 (2H, td, J=6.9, 2.5 Hz), 2.02-2.06 (2H, m), 1.98 (1H, t, J=2.6 Hz); $^{13}$C-NMR (CDCl$_3$) δ 158.7, 153.8, 152.2, 151.6, 147.9, 134.6, 133.9, 132.9, 132.5, 129.8, 126.9, 126.2, 113.7, 113.0, 112.4, 110.3, 102.2, 82.4, 69.6, 55.1, 51.4, 42.5, 28.2, 16.0; HRMS (ESI) m/z [M+H]$^+$ calcd. for C$_{26}$H$_{24}$N$_6$OSBr, 547.0916. found 547.0925.

8-((5-Bromo-1-(4-methoxybenzyl)-1H-indol-7-yl)thio)-3-(pent-4-yn-1-yl)-3H-purin-6-amine (4s). Obtained as a white solid in 12% yield. $^1$H-NMR (400 MHz, CDCl$_3$) δ 7.88 (1H, s), 7.82 (1H, s), 7.65 (1H, s), 7.03 (1H, d, J=3.0 Hz), 6.75 (2H, d, J=8.4 Hz), 6.58 (2H, d, J=8.6 Hz), 6.52 (1H, d, J=3.1 Hz), 5.77 (2H, s), 4.31 (2H, t, J=6.8 Hz), 3.66 (3H, s), 2.05-2.17 (5H, m); MS (ESI): m/z 549.2 [M+H]$^+$.

8-((5-Bromo-1-(4-methoxybenzyl)-1H-pyrrolo[2,3-b]pyridin-3-yl)thio)-9-(pent-4-yn-1-yl)-9H-purin-6-amine (3t). Obtained as a yellow solid in 23% yield. $^1$H-NMR (400 MHz, CDCl$_3$) δ 8.41 (1H, d, J=2.1 Hz), 8.20 (1H, s), 8.12

(1H, d, J=2.1 Hz), 7.56 (1H, s), 7.24 (2H, d, J=8.6 Hz), 6.86 (2H, d, J=8.6 Hz), 6.11 (2H, br s), 5.39 (2H, s), 4.36 (2H, t, J=7.2 Hz), 3.79 (3H, s), 2.32 (2H, td, J=6.9, 2.7 Hz), 2.06-2.09 (2H, m), 2.03 (1H, t, J=2.6 Hz); $^{13}$C-NMR (CDCl$_3$) δ 159.6, 153.9, 151.8, 148.2, 146.3, 144.9, 135.5, 130.0, 129.5, 128.2, 123.5, 119.4, 117.1, 114.3, 113.3, 95.0, 82.5, 69.7, 55.3, 48.0, 42.6, 28.1, 16.1; MS (ESI): m/z 548.1 [M+H]$^+$.

8-((5-Bromo-1-(4-methoxybenzyl)-1H-pyrrolo[2,3-b]pyridin-3-yl)thio)-3-(pent-4-yn-1-yl)-3H-purin-6-amine (4t). Obtained as a yellow solid in 10% yield. $^1$H-NMR (400 MHz, CDCl$_3$) δ 8.37 (1H, s), 8.10 (1H, s), 7.93 (1H, s), 7.49 (1H, s), 7.21 (2H, d, J=8.3 Hz), 6.84 (2H, d, J=8.5 Hz), 5.32 (2H, s), 4.38 (2H, t, J=7.2 Hz), 3.78 (3H, s), 2.06-2.15 (5H, m); $^{13}$C-NMR (CDCl$_3$) δ 159.7, 153.8, 147.9, 146.6, 144.2, 134.8, 130.6, 129.4, 128.6, 127.8, 121.7, 118.3, 115.3, 114.7, 112.6, 94.7, 81.8, 70.6, 55.3, 48.9, 47.8, 28.1, 15.2; MS (ESI): m/z 548.4 [M+H]$^+$.

6.2.1 Synthesis of Compounds of Formula 8a-d and 9 (Scheme 2)

8-Bromo-9H-purin-6-amine (6). Adenine (2.2 g, 16.3 mmol) was added to a solution of bromine (6.0 mL, 117.7 mmol) in water (200 mL), and the resulting mixture was stirred overnight at room temperature. The solvent was evaporated to dryness, and the brominated product 6 was used further without additional purification. MS (ESI): m/z 213.5/215.6 [M+H]$^+$.

8-Bromo-9-(pent-4-yn-1-yl)-9H-purin-6-amine (7). A mixture of 6 (2.0 g, 9.4 mmol), Cs$_2$CO$_3$ (4.6 g, 14.1 mmol) and 5-chloropent-1-yne (1.92 ml, 18.8 mmol) in DMF (25 mL) under nitrogen protection was heated at 80° C. for 3 h. Following solvent removal, the crude material was purified by preparatory TLC (CH$_2$Cl$_3$:MeOH:AcOH, 20:1:0.1) to provide 0.52 g (23%) of 7. $^1$H NMR (500 MHz, CDCl$_3$/MeOH-d$_4$) δ 8.29 (s, 1H), 4.33 (t, J=7.2 Hz, 2H), 2.28-2.33 (m, 2H), 2.09 (pentet, J=7.0 Hz, 2H), 2.02 (t, J=2.6 Hz, 1H); $^{13}$C NMR (125 MHz, CDCl$_3$/MeOH-d$_4$) δ 154.4, 153.1, 151.3, 127.4, 119.9, 82.4, 69.7, 43.8, 28.2, 16.1; MS (ESI): m/z 280.1/282.2 [M+H]$^+$.

General Procedure for the Synthesis of 8a-d and 9.

A mixture of thiophenol or phenol (0.069 mmol) and t-BuOK (0.069 mmol) in DMF (1.5 ml), was stirred for 15 minutes at room temperature. 7 (0.057 mmol) was added and Scheme 2:

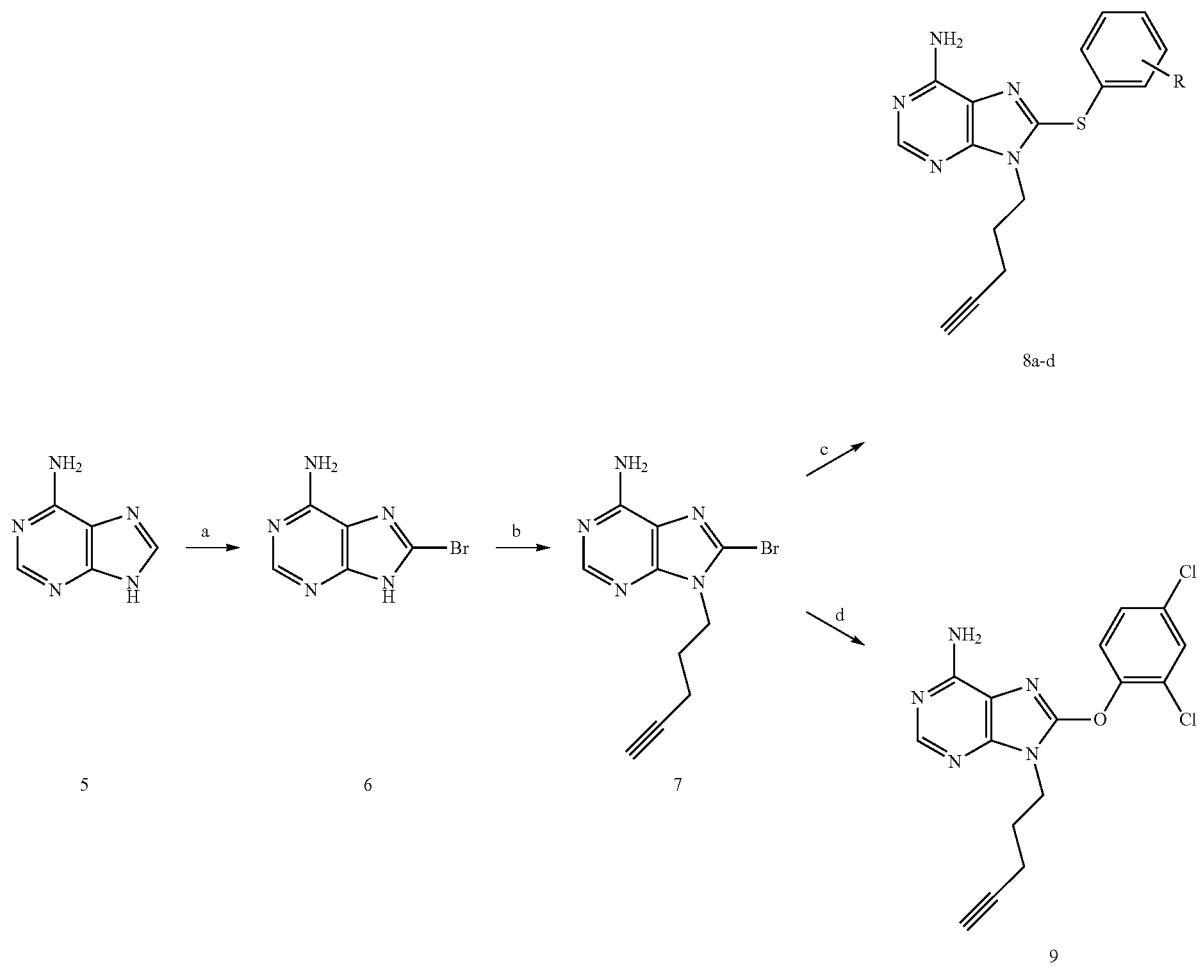

Reagents and conditions: (a) Br$_2$, H$_2$O, rt; (b) 5-chloropent-1-yne, Cs$_2$CO$_3$, DMF, 80° C.; (c) ArSH, t-BuOK, DMF, 130° C.; (d) ArOH, t-BuOK, DMF, 130° C.

the reaction mixture was allowed to stir at 80° C. for 2 h. Following solvent removal, the crude material was purified by preparatory TLC (CH$_2$Cl$_2$:MeOH, 20:1) to afford the corresponding derivatives 8a-d and 9.

5-((6-Amino-9-(pent-4-yn-1-yl)-9H-purin-8-yl)thio) isophthalonitrile (8a; HJP-III-26). Yield, 10.2 mg (51%). $^1$H NMR (600 MHz, CDCl$_3$) δ 8.38 (s, 1H), 7.98 (s, 2H), 7.85 (s, 1H), 4.37 (t, J=7.3 Hz, 2H), 2.27-2.30 (m, 2H), 2.05 (pentet, J=6.9 Hz, 2H), 2.01-2.03 (t, 1H); $^{13}$C NMR (150 MHz, CDCl$_3$/MeOH-d$_4$) δ 154.7, 153.8, 151.7, 142.2, 136.9, 136.1, 134.3, 120.5, 115.8, 115.2, 82.2, 69.8, 43.1, 28.3, 15.9; HRMS (ESI) m/z [M+H]$^+$ calcd. for C$_{18}$H$_{14}$N$_7$S, 360.1031. found 360.1028.

4-((6-Amino-9-(pent-4-yn-1-yl)-9H-purin-8-yl)thio)-2-(trifluoromethyl)benzonitrile (8b; HJP-III-29). Yield, 16.5 mg (42%). $^1$H NMR (600 MHz, CDCl$_3$) δ 8.39 (s, 1H), 7.85 (s, 1H), 7.76 (d, J=8.2 Hz, 1H), 7.59 (d, J=8.1 Hz, 1H), 5.90 (br s, 2H), 4.37 (t, J=7.4 Hz, 2H), 2.26 (td, J=6.8 and 2.6 Hz, 2H), 2.02-2.07 (m, 2H), 1.97 (t, J=2.6 Hz, 1H); $^{13}$C NMR (150 MHz, CDCl$_3$/MeOH-d$_4$) δ 155.1, 154.1, 151.8, 141.9, 140.2, 135.5, 133.9 (q, J=32.9 Hz), 132.1, 126.9 (q, J=4.7 Hz), 124.7, 121.9 (q, J=272.9 Hz), 120.7, 115.1, 108.9, 82.3, 69.9, 43.3, 28.6, 16.1; HRMS (ESI) m/z [M+H]$^+$ calcd. for C$_{18}$H$_{14}$F$_3$N$_6$S, 403.0953. found 403.0956.

4-((6-Amino-9-(pent-4-yn-1-yl)-9H-purin-8-yl)thio)-2-bromobenzonitrile (8c; HJP-III-32). Yield, 6.5 mg (22%). $^1$H NMR (600 MHz, CDCl$_3$ δ) 8.39 (s, 1H), 7.68 (d, J=1.7 Hz, 1H), 7.57 (d, J=8.2 Hz, 1H), 7.33 (dd, J=8.1 and 1.7 Hz, 1H), 5.74 (br s, 2H), 4.35 (t, J=7.4 Hz, 2H), 2.26 (td, J=6.9 and 2.6 Hz, 2H), 2.01-2.06 (m, 2H), 1.98 (t, J=2.6 Hz, 1H); $^{13}$C NMR (150 MHz, CDCl$_3$/MeOH-d$_4$) δ 155.0, 154.1, 151.8, 142.2, 140.6, 134.8, 132.7, 127.8, 126.3, 120.7, 116.8, 114.8, 82.4, 69.9, 43.3, 28.6, 16.2; HRMS (ESI) m/z [M+H]$^+$ calcd. for C$_{17}$H$_{14}$BrN$_6$S, 413.0184. found 413.0192.

4-((6-Amino-9-(pent-4-yn-1-yl)-9H-purin-8-yl)thio)-2-chlorobenzonitrile (8d; HJP-III-33). Yield, 17.8 mg (62%). $^1$H NMR (600 MHz, CDCl$_3$) δ 8.38 (s, 1H), 7.58 (d, J=8.3 Hz, 1H), 7.49 (d, J=1.7 Hz, 1H), 7.28 (dd, J=8.3, 1.7 Hz, 1H), 6.12 (br s, 2H), 4.35 (t, J=7.4 Hz, 2H), 2.26 (td, J=6.9, 2.6 Hz, 2H), 2.00-2.06 (m, 2H), 1.98 (t, J=2.6 Hz, 1H); $^{13}$C NMR (150 MHz, CDCl$_3$/MeOH-d$_4$) δ 155.2, 154.1, 151.7, 141.9, 140.7, 137.9, 134.5, 129.6, 127.2, 120.7, 115.6, 112.3, 82.4, 69.9, 43.3, 28.6, 16.2; HRMS (ESI) m/z [M+H]$^+$ calcd. for C$_{17}$H$_{14}$ClN$_6$S, 369.0689. found 369.0684.

8-(2,4-Dichlorophenoxy)-9-(pent-4-yn-1-yl)-9H-purin-6-amine (9; HJP-V-45). Yield, 16.2 mg, (51%). $^1$H-NMR (600 MHz, CDCl$_3$) δ 8.22 (s, 1H), 7.45 (d, J=2.5 Hz, 1H), 7.43 (d, J=8.7 Hz, 1H), 7.27 (dd, J=8.7, 2.5 Hz, 1H), 5.42 (br s, 2H), 4.26 (t, J=7.1 Hz, 2H), 2.27 (td, J=7.0, 2.6 Hz, 2H), 2.09-2.14 (m, 2H), 1.90 (t, J=2.6 Hz, 1H); $^{13}$C NMR (150 MHz, CDCl$_3$) δ 153.2, 152.7, 151.4, 149.9, 147.4, 132.1, 130.6, 128.9, 128.3, 127.1, 123.7, 115.4, 82.5, 69.4, 41.2, 27.9, 16.1; HRMS (ESI) m/z [M+H]$^+$ calcd. for C$_{16}$H$_{14}$Cl$_2$N$_5$O, 362.0575. found 362.0570.

6.2.3 Synthesis of Compounds of Formula 14a-c (Scheme 3)

Scheme 3:

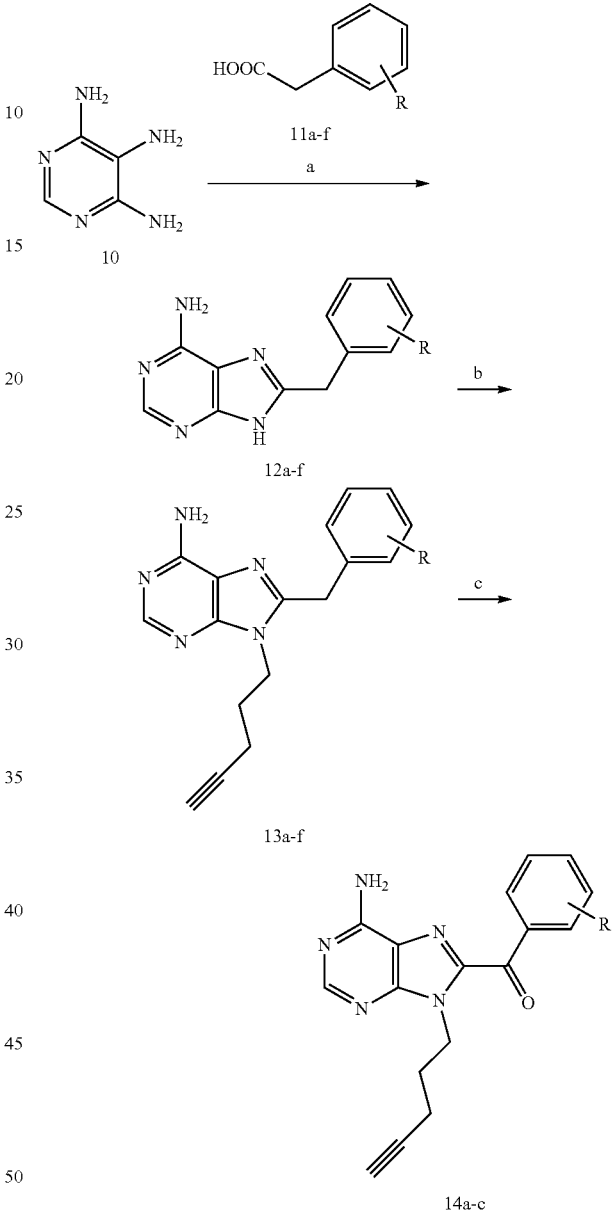

Reagents and conditions: (a) P(OPh)$_3$, pyridine, microwave 220° C., 30 min.; (b) 5-chloropent-1-yne, Cs$_2$CO$_3$, DMF, 80° C.; (c) 2 equiv. Cs$_2$CO$_3$, DMF, 80° C.

General Procedure for the Synthesis of 8-arylmethyl-9H-purin-6-amines (12a-f)

In a conical-bottomed Smith process vial, the mixture of 4,5,6-triaminopyrimidine (10, 0.21 g, 1.7 mmol), aryl acetic acid 11a-f (0.25 g, 1.4 mmol), and triphenyl phosphite (0.52 g, 443 μL, 1.7 mmol) in 1.5 mL anhydrous pyridine were charged. The sealed vial was irradiated in the microwave for 30 min at 220° C. After cooling, the reaction mixture was concentrated under vacuum and the residue purified by column chromatography (CH$_2$Cl$_2$:MeOH, 10:0 to 10:1) to give the desired product 12a-f.

8-(2,4,6-Trimethylbenzyl)-9H-purin-6-amine (12a; HJP-V-32). Yield, 0.24 g (65%). MS (ESI) m/z 268.17 [M+H]$^+$.

8-(2,4-Dichlorobenzyl)-9H-purin-6-amine (12b; HJP-V-33). Yield, 0.33 g (79%). MS (ESI): m/z 294.04 [M+H]+.

8-(2,6-Dichlorobenzyl)-9H-purin-6-amine (12c; HJP-V-34). Yield, 0.18 g (44%). MS (ESI): m/z 294.04 [M+H]+.

8-(3,5-Dichlorobenzyl)-9H-purin-6-amine (12d; HJP-V-35). Yield, 0.21 g (51%). MS (ESI): m/z 294.04 [M+H]+.

8-(2,5-Dichlorobenzyl)-9H-purin-6-amine (12e; HJP-V-50). Yield, 0.18 g (44%). MS (ESI): m/z 294.03 [M+H]+.

8-(2,3-Dichlorobenzyl)-9H-purin-6-amine (12f; HJP-V-51). Yield, 0.24 g (58%). MS (ESI): m/z 294.04 [M+H]+.

General Procedure for the Synthesis of 13a-f

A mixture of 8-benzyladenine 12a-f (100 mmol), $Cs_2CO_3$ (100 mmol) and 1-chloro-pent-4-yne (120 mmol) in DMF (1.3 mL) under nitrogen protection was heated at 80° C. for 1-2 h. Following solvent removal, the crude material was purified by preparatory TLC ($CH_2Cl_2$:$CH_3OH$—$NH_3$ (7N), 20:1 or $CH_2Cl_2$:MeOH:AcOH, 15:1:0.1) to provide the corresponding 9-alkyl-8-benzyladenine derivatives 13a-f.

9-(Pent-4-yn-1-yl)-8-(2,4,6-trimethylbenzyl)-9H-purin-6-amine (13a; HJP-V-36). Yield, 12.2 mg (49%). $^1$H-NMR (600 MHz, $CDCl_3$) δ 8.16 (s, 1H), 6.84 (s, 2H), 6.09 (br s, 2H), 4.23 (t, J=7.3 Hz, 2H), 2.18-2.20 (m, 5H), 2.15 (s, 6H), 1.95-1.98 (m, 3H); $^{13}$C NMR (150 MHz, $CDCl_3$) δ 153.3, 150.2, 150.1, 149.7, 136.1, 135.8, 128.2, 128.1, 117.4, 81.6, 68.8, 40.7, 27.2, 27.1, 19.9, 19.3, 14.8; HRMS (ESI) m/z [M+H]+ calcd. for $C_{20}H_{24}N_5$, 334.2032. found 334.2020.

8-(2,4-Dichlorobenzyl)-9-(pent-4-yn-1-yl)-9H-purin-6-amine (13b; HJP-V-37L). Yield, 3 mg (13%). $^1$H-NMR (600 MHz, $CDCl_3$) δ 8.25 (s, 1H), 7.38 (d, J=2.2 Hz, 1H), 7.13 (dd, J=8.3 and 2.2 Hz, 1H), 7.01 (d, J=8.3 Hz, 1H), 5.86 (br s, 2H), 4.29 (s, 2H), 4.15 (t, J=7.4 Hz, 2H), 2.17 (td, J=6.8 and 2.6 Hz, 2H), 1.90-1.96 (m, 3H); $^{13}$C NMR (150 MHz, $CDCl_3$) δ 154.3, 151.7, 151.4, 150.2, 134.7, 134.1, 132.4, 131.4, 129.8, 127.8, 118.9, 82.5, 70.1, 42.3, 31.3, 28.4, 15.9; HRMS (ESI) m/z [M+H]+ calcd. for $C_{17}H_{16}Cl_2N_5$, 360.0783. found 360.0772.

8-(2,6-Dichlorobenzyl)-9-(pent-4-yn-1-yl)-9H-purin-6-amine (13c; HJP-V-38). Yield, 11.9 mg (48%). $^1$H-NMR (600 MHz, $CDCl_3$/MeOH-$d_4$) δ 8.17 (s, 1H), 7.36 (d, J=8.1 Hz, 1H), 7.21-7.24 (m, 2H), 4.47 (s, 2H), 4.35 (t, J=7.2 Hz, 2H), 2.28 (td, J=6.7 and 2.5 Hz, 2H), 2.05-2.11 (m, 2H), 2.02 (t, J=2.6 Hz, 1H); $^{13}$C NMR (150 MHz, $CDCl_3$/MeOD) δ 153.2, 150.5, 149.7, 147.9, 135.2, 130.7, 128.4, 127.4, 116.9, 81.5, 69.1, 40.8, 28.9, 27.2, 14.8; HRMS (ESI) m/z [M+H]+ calcd. for $C_{17}H_{16}Cl_2N_5$, 360.0783. found 360.0776.

8-(3,5-Dichlorobenzyl)-9-(pent-4-yn-1-yl)-9H-purin-6-amine (13d; HJP-V-39L). Yield, 4.1 mg (17%). $^1$H-NMR (600 MHz, $CDCl_3$/MeOH-$d_4$) δ 8.22 (s, 1H), 7.26 (s, 1H), 7.11 (s, 1H), 4.19 (s, 2H), 4.17 (t, J=6.9 Hz, 2H), 2.20 (td, J=6.4 and 2.1 Hz, 2H), 2.05 (t, J=2.5 Hz, 1H), 1.87-1.95 (m, 2H); $^{13}$C NMR (150 MHz, $CDCl_3$/MeOH-$d_4$) δ 151.7, 149.8, 148.6, 147.9, 136.9, 134.6, 126.9, 126.3, 116.9, 81.3, 69.3, 41.3, 28.7, 26.9, 14.7; HRMS (ESI) m/z [M+H]+ calcd. for $C_{17}H_{16}Cl_2N_5$, 360.0783. found 360.0767.

8-(2,5-Dichlorobenzyl)-9-(pent-4-yn-1-yl)-9H-purin-6-amine (13e; HJP-V-54L). Yield, 5 mg (21%). $^1$H-NMR (600 MHz, $CDCl_3$) δ 8.27 (s, 1H), 7.30 (d, J=8.5 Hz, 1H), 7.17 (dd, J=8.6, 2.4 Hz, 1H), 7.07 (d, J=2.4 Hz, 1H), 5.88 (br s, 2H), 4.30 (s, 2H), 4.17 (t, J=7.3 Hz, 2H), 2.17 (td, J=6.7, 2.6 Hz, 2H), 1.93-1.96 (m, 3H); $^{13}$C NMR (150 MHz, $CDCl_3$) δ 154.1, 151.3, 151.2, 149.8, 135.2, 133.2, 132.1, 130.8, 130.4, 128.9, 118.8, 82.3, 70.0, 42.1, 31.5, 28.2, 15.8; HRMS (ESI) m/z [M+H]+ calcd. for $C_{17}H_{16}Cl_2N_5$, 360.0783. found 360.0776.

8-(2,3-Dichlorobenzyl)-9-(pent-4-yn-1-yl)-9H-purin-6-amine (13l; HJP-V-55). Yield, 8.1 mg (34%). $^1$H-NMR (600 MHz, $CDCl_3$) δ 8.26 (s, 1H), 7.34 (d, J=8.0 Hz, 1H), 7.08 (t, J=7.9, 1H), 6.92 (d, J=7.8 Hz, 1H), 5.87 (br s, 2H), 4.38 (s, 2H), 4.14 (t, J=7.3 Hz, 2H), 2.16 (td, J=6.7, 2.6 Hz, 2H), 1.95 (t, J=2.6 Hz, 1H), 1.89-1.94 (m, 2H); $^{13}$C NMR (150 MHz, $CDCl_3$) δ 154.2, 151.5, 151.2, 150.0, 135.9, 133.6, 132.2, 129.6, 128.3, 127.6, 118.8, 82.2, 70.0, 42.1, 32.5, 28.1, 15.8; HRMS (ESI) m/z [M+H]+ calcd. for $C_{17}H_{16}Cl_2N_5$, 360.0783. found 360.0766.

General Procedure for the Synthesis of 14a-c

A mixture of 13b or 13d or 13e (100 mmol), and $Cs_2CO_3$ (200 mmol) in DMF (1.3 mL) was heated at 80° C. for 3 h. Following solvent removal, the crude material was purified by preparatory TLC ($CH_2Cl_2$:$CH_3OH$—$NH_3$ (7N), 20:1) to provide the corresponding arylketone derivatives 14a-c.

(6-Amino-9-(pent-4-yn-1-yl)-9H-purin-8-yl)(2,4-dichlorophenyl)methanone (14a; HJP-V-37T). Yield, 12 mg (50%). $^1$H-NMR (600 MHz, $CDCl_3$) δ 8.25 (s, 1H), 7.49 (d, J=8.2 Hz, 1H), 7.43 (d, J=1.9 Hz, 1H), 7.33 (dd, J=8.3, 1.9 Hz, 1H), 6.26 (br s, 2H), 4.73 (t, J=7.2 Hz, 2H), 2.28 (td, J=7.0, 2.6 Hz, 2H), 2.07-2.13 (m, 2H), 1.88 (t, J=2.6 Hz, 1H); $^{13}$C NMR (150 MHz, $CDCl_3$) δ 185.5, 155.9, 153.5, 151.3, 144.4, 137.9, 135.5, 133.5, 131.4, 130.3, 127.1, 119.6, 82.4, 69.3, 44.1, 28.9, 16.1; HRMS (ESI) m/z [M+H]+ calcd. for $C_{17}H_{14}Cl_2N_5O$, 374.0575. found 374.0571.

(6-Amino-9-(pent-4-yn-1-yl)-9H-purin-8-yl)(3,5-dichlorophenyl)methanone (14b; HJP-V-39T). Yield, 10 mg (42%). $^1$H-NMR (600 MHz, $CDCl_3$) δ 8.41 (s, 1H), 8.13 (d, J=1.9 Hz, 2H), 7.55 (t, J=1.9 Hz, 1H), 6.13 (br s, 2H), 4.68 (t, J=7.2 Hz, 2H), 2.26 (td, J=6.9 and 2.6 Hz, 2H), 2.05-2.10 (m, 2H), 1.87 (t, J=2.6 Hz, 1H); $^{13}$C NMR (150 MHz, $CDCl_3$) δ 181.2, 155.6, 153.7, 150.3, 142.6, 137.6, 134.2, 132.2, 128.4, 118.4, 81.4, 68.2, 43.2, 27.8, 15.1; HRMS (ESI) m/z [M+H]+ calcd. for $C_{17}H_{14}Cl_2N_5O$, 374.0575. found 374.0567.

(6-Amino-9-(pent-4-yn-1-yl)-9H-purin-8-yl)(2,5-dichlorophenyl)methanone (14c; HJP-V-54T). Yield, 14 mg (58%). $^1$H-NMR (600 MHz, $CDCl_3$) δ 8.37 (s, 1H), 7.49 (d, J=2.5 Hz, 1H), 7.31-7.33 (m, 2H), 6.14 (br s, 2H), 4.72 (t, J=7.2 Hz, 2H), 2.28 (td, J=7.0 and 2.6 Hz, 2H), 2.07-2.13 (m, 2H), 1.90 (t, J=2.6 Hz, 1H); $^{13}$C NMR (150 MHz, $CDCl_3$) δ 184.1, 156.0, 154.4, 150.4, 142.6, 137.6, 131.6, 130.8, 130.2, 129.5, 129.0, 118.9, 81.5, 68.2, 42.9, 27.9, 15.1; HRMS (ESI) m/z [M+H]+ calcd. for $C_{17}H_{14}Cl_2N_5O$, 374.0575. found 374.0560.

6.2.4 Synthesis of Compounds of Formula 17a-I (Scheme 4)

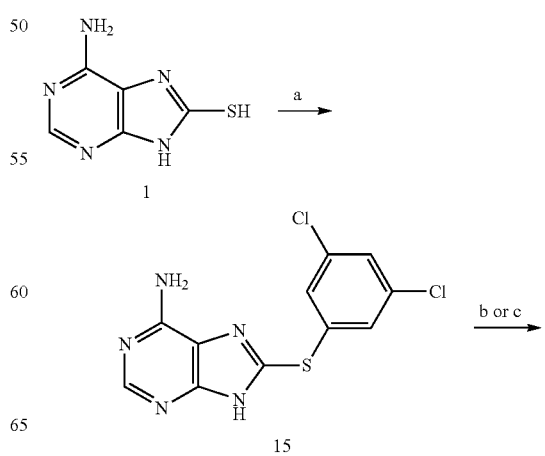

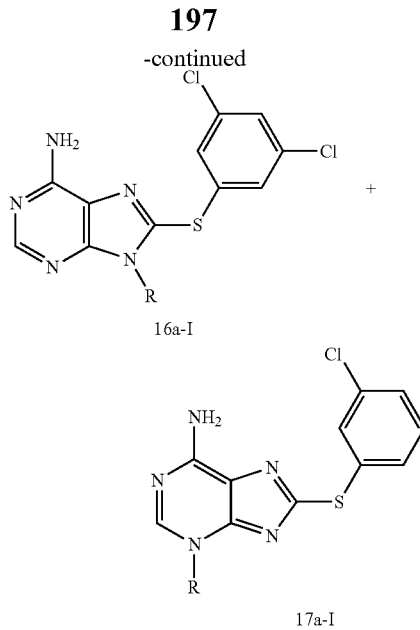

Reagents and conditions: (a) Aryl Iodine, CuI, NaOt-Bu, DMF, MW, 190° C., 1.5-2 h; (b) RBr, Cs$_2$CO$_3$, DMF, rt-60° C., 2-6 h (c) ROH, PPh$_3$, DBAD, CH$_2$Cl$_2$-toluene, rt.

8-((3,5-Dichlorophenyl)thio)-9H-purin-6-amine (15). 8-Mercaptoadenine (3.6 mmol), neocuproine hydrate (0.36 mmol), CuI (0.36 mmol), NaO-t-Bu (7.2 mmol), 3,5-dichloro-iodobenzene (10.8 mmol), and anhydrous DMF (24 mL) were added to a round bottom flask flushed with nitrogen. The flask was sealed with Teflon tape and heated at 110° C. with stirring for 24-36 h under nitrogen. Solvent was removed under reduced pressure and the resulting residue was chromatographed (CH$_2$Cl$_2$:MeOH:AcOH, 20:1: 0.5) to yield 15 as a yellow solid in 44% yield. $^1$H-NMR (400 MHz, DMSO-d$_6$) δ 13.49 (1H, br s), 8.13 (1H, s), 7.59 (1H, s), 7.47 (2H, s), 7.36 (2H, br s); MS (ESI): m/z 312.1 [M+H$^+$].

General Procedure for Synthesis of N9 and N3 Alkylated 8-aryl Sulfanyl Derivatives 16a-l and 17a-l 15 (1.21 mmol) was dissolved in DMF (15 mL). Cs$_2$CO$_3$ (1.45 mmol) and respective bromides (2.42 mmol) were added and the mixture was stirred under nitrogen at rt-60° C. for 2-6 h. Solvent was removed under reduced pressure and the resulting residue was chromatographed (CH$_2$Cl$_2$:MeOH: AcOH, 20:1:0.5) to afford desired compounds 16a-l and 17a-l.

8-((3,5-Dichlorophenyl)thio)-9-(3,3,3-trifluoropropyl)-9H-purin-6-amine (16a, PDP-I-13-A). Obtained as a white solid in 43% yield. $^1$H-NMR (400 MHz, CDCl$_3$) δ 8.33 (1H, s), 7.29 (3H, s), 6.44 (2H, br s), 4.49 (2H, t, J=6.8 Hz), 2.64-2.68 (2H, m); $^{13}$C-NMR (CDCl$_3$) δ 155.0, 153.4, 151.2, 143.5, 136.0, 133.8, 128.8, 128.4, 126.6, 120.2, 37.3, 33.3; HRMS (ESI): m/z [M+H]$^+$ calcd. for C$_{14}$H$_{11}$N$_5$SCl$_2$F$_3$, 408.0064. found 408.0074.

8-((3,5-Dichlorophenyl)thio)-3-(3,3,3-trifluoropropyl)-3H-purin-6-amine (17a, PDP-13B). Obtained as a white solid in 20% yield. $^1$H-NMR (400 MHz, CDCl$_3$) δ 7.99 (1H, s), 7.46 (2H, s), 7.32 (1H, s), 4.55 (2H, t, J=6.3 Hz), 2.86-2.93 (2H, m); $^{13}$C-NMR (CDCl$_3$) δ 159.3, 153.1, 150.3, 142.5, 135.9, 135.2, 129.7, 127.8, 125.3, 121.7, 32.7, 29.6; HRMS (ESI): m/z [M+H]$^+$ calcd. for C$_{14}$H$_{11}$N$_5$SCl$_2$F$_3$, 408.0064. found 408.0065.

8-((3,5-Dichlorophenyl)thio)-9-(4,4,4-trifluorobutyl)-9H-purin-6-amine (16b, PDP-I-15-A). Obtained as a white solid in 44% yield. $^1$H-NMR (400 MHz, CDCl$_3$) δ 8.36 (1H, s), 7.28 (3H, s), 6.16 (2H, br s), 4.30 (2H, t, J=6.6 Hz), 2.10-2.14 (2H, m), 2.03-2.05 (2H, m); $^{13}$C-NMR (CDCl$_3$) δ 154.9, 153.7, 151.5, 143.2, 135.9, 134.2, 128.6, 128.1, 125.1, 120.3, 42.5, 31.3, 22.5; HRMS (ESI): m/z [M+H]$^+$ calcd. for C$_{15}$H$_{13}$N$_5$SCl$_2$F$_3$, 422.0221. found 422.0222.

8-((3,5-Dichlorophenyl)thio)-3-(pent-4-yn-1-yl)-3H-purin-6-amine (17b, PDP-I-15-B). Obtained as a white solid in 15% yield. $^1$H-NMR (400 MHz, CDCl$_3$) δ 8.02 (1H, s), 7.12 (3H, s), 5.89 (2H, s), 4.08 (2H, t, J=6.6 Hz), 2.09-2.11 (4H, m); $^{13}$C-NMR (CDCl$_3$) δ 155.5, 153.1, 150.7, 149.9, 136.1, 134.2, 128.0, 127.1, 125.3, 115.6, 40.1, 31.4, 21.9; MS (ESI): m/z 421.9 [M+H]$^+$.

8-((3,5-Dichlorophenyl)thio)-9-(5,5,5-trifluoropentyl)-9H-purin-6-amine (16c, PDP-109A). Obtained as a white solid in 45% yield. $^1$H-NMR (400 MHz, CDCl$_3$, δ) 8.28 (1H, s), 7.28 (3H, s), 6.82 (2H, br s), 4.25 (2H, t, J=7.2 Hz), 2.07-2.14 (2H, m), 1.85 (2H, pentet, J=7.4 Hz), 1.57 (2H, pentet, J=7.5 Hz); $^{13}$C-NMR (CDCl$_3$) δ 155.1, 152.7, 151.2, 143.5, 135.9, 134.1, 128.6, 128.2, 125.4, 120.1, 43.3, 33.1, 28.8, 19.2; HRMS (ESI): m/z [M+H]$^+$ calcd. for C$_{16}$H$_{15}$N$_5$SF$_3$Cl$_2$, 436.0377. found 436.0363.

8-((3,5-Dichlorophenyl)thio)-3-(5,5,5-trifluoropentyl)-3H-purin-6-amine (17c, PDP-109B). Obtained as a white solid in 16% yield. $^1$H-NMR (400 MHz, CDCl$_3$) δ 7.96 (1H, s), 7.43 (2H, s), 7.17 (1H, s), 4.36 (2H, t, J=6.8 Hz), 2.05-2.17 (4H, m), 1.59-1.67 (2H, m); $^{13}$C-NMR (CDCl$_3$) δ 157.8, 152.9, 150.8, 142.1, 136.2, 135.1, 129.6, 127.7, 122.0, 117.7, 48.8, 33.1, 28.4, 19.0; HRMS (ESI): m/z [M+H]$^+$ calcd. for C$_{16}$H$_{15}$N$_5$F$_3$SCl$_2$, 436.0377. found 436.0398.

8-((3,5-Dichlorophenyl)thio)-9-(6,6,6-trifluorohexyl)-9H-purin-6-amine (16d, PDP-101B). Obtained as a white solid in 47% yield. $^1$H-NMR (400 MHz, CDCl$_3$, δ) 8.35 (1H, s), 7.29 (3H, s), 6.33 (2H, br s), 4.24 (2H, t, J=7.2 Hz), 2.00-2.07 (2H, m), 1.79 (2H, pentet, J=7.4 Hz), 1.57 (2H, pentet, J=7.6 Hz), 1.37 (2H, pentet, J=7.8 Hz); $^{13}$C-NMR (CDCl$_3$) δ 155.1, 152.8, 151.3, 143.4, 135.9, 134.4, 128.5, 128.1, 125.8, 120.0, 43.6, 33.9, 29.4, 25.7, 21.4; HRMS (ESI): m/z [M+H]$^+$ calcd. for C$_{17}$H$_{17}$N$_5$SCl$_2$F$_3$, 450.0534. found 450.0549.

8-((3,5-Dichlorophenyl)thio)-3-(6,6,6-trifluorohexyl)-3H-purin-6-amine (17d, PDP-101-A). Obtained as a white solid in 14% yield. $^1$H-NMR (500 MHz, CDCl$_3$) δ 7.95 (1H, s), 7.43 (2H, s), 7.09 (1H, s), 4.34 (2H, t, J=7.0 Hz), 1.40-1.72 (8H, m); $^{13}$C-NMR (CDCl$_3$) δ 155.0, 153.5, 151.4, 143.1, 135.9, 134.7, 128.3, 127.8, 125.6, 120.3, 43.6, 33.6, 29.4, 25.7, 21.5; HRMS (ESI): m/z [M+H]$^+$ calcd. for C$_{17}$H$_{17}$N$_5$SCl$_2$F$_3$, 450.0534. found 450.0539.

9-(4-Bromopentyl)-8-((3,5-dichlorophenyl)thio)-9H-purin-6-amine (16e, PDP-II-99A). Obtained as a white solid in 43% yield. $^1$H-NMR (400 MHz, CDCl$_3$) δ 8.36 (1H, s), 7.28 (1H, s), 7.24 (2H, s), 6.08 (2H, br s), 4.27 (2H, t, J=7.2 Hz), 4.09 (1H, sextet, J=6.6 Hz), 2.01-2.05 (1H, m), 1.89-1.94 (1H, m), 1.72-1.78 (2H, m), 1.65 (3H, d, J=6.7 Hz); $^{13}$C-NMR (CDCl$_3$, δ) 154.9, 153.6, 151.5, 143.3, 135.9, 134.7, 128.4, 127.9, 120.3, 50.1, 43.1, 37.7, 28.2, 26.4; HRMS (ESI): m/z [M+H]$^+$ calcd. for C$_{16}$H$_{14}$N$_5$SOCl$_2$, 461.9745. found 461.9748.

3-(4-Bromopentyl)-8-((3,5-dichlorophenyl)thio)-3H-purin-6-amine (17e, PDP-99-B). Obtained as a white solid in 16% yield. $^1$H-NMR (400 MHz, CDCl$_3$) δ 7.99 (1H, s), 7.40 (2H, s), 7.16 (1H, s), 4.39 (2H, t, J=7.1 Hz), 4.12 (1H, sextet, J=6.5 Hz), 2.15-2.23 (2H, m), 1.80-1.86 (2H, m), 1.68 (3H, d, J=6.5 Hz); $^{13}$C-NMR (CDCl$_3$, δ) 152.5, 150.7, 148.4, 142.0, 135.9, 134.9, 127.9, 126.9, 117.3, 49.9, 40.3, 37.5, 27.9, 26.4; HRMS (ESI): m/z [M+H]$^+$ calcd. for C$_{16}$H$_{14}$N$_5$SOCl$_2$, 461.9745. found 461.9728.

9-(But-2-yn-1-yl)-8-((3,5-dichlorophenyl)thio)-9H-purin-6-amine OK PDP-102-A). Obtained as a white solid in 40% yield. $^1$H-NMR (500 MHz, CDCl$_3$) δ 8.33 (1H, s), 7.32 (2H, s), 7.28 (1H, s), 6.63 (2H, br s), 4.98-4.99 (2H, m), 1.70 (3H, m); $^{13}$C-NMR (CDCl$_3$) δ 155.1, 153.2, 150.8, 143.3, 135.7, 134.5, 128.5, 128.3, 120.0, 82.1, 71.7, 33.4, 3.5; HRMS (ESI): m/z [M+H]$^+$ calcd. for C$_{15}$H$_{12}$N$_5$SCl$_2$, 364.0190. found 364.0197.

3-(But-2-yn-1-yl)-8-((3,5-dichlorophenyl)thio)-3H-purin-6-amine (171, PDP-102B). Obtained as a white solid in 17% yield. $^1$H-NMR (500 MHz, CDCl$_3$) δ 8.36 (1H, s), 7.40 (2H, s), 7.20 (1H, s), 5.09-5.10 (2H, m), 1.93 (3H, m); $^{13}$C-NMR (CDCl$_3$) δ 158.1, 153.4, 150.5, 141.7, 137.1, 135.0, 128.5, 127.1, 121.4, 86.5, 69.4, 39.7, 3.7; HRMS (ESI): m/z [M+H]$^+$ calcd. for C$_{15}$H$_{12}$N$_5$SCl$_2$, 364.0190. found 364.0190.

9-(But-3-yn-1-yl)-8-((3,5-dichlorophenyl)thio)-9H-purin-6-amine (16g, PDP-I-14-A). Obtained as a white solid in 47% yield. $^1$H-NMR (400 MHz, CDCl$_3$) δ 8.37 (1H, s), 7.28 (3H, s), 6.04 (2H, bs), 4.45 (2H, t, J=7.0 Hz), 2.76 (2H, td, J=6.8, 2.3 Hz), 1.95 (1H, t, J=2.4 Hz); $^{13}$C-NMR (CDCl$_3$) δ 154.9, 153.6, 151.3, 143.7, 135.8, 134.9, 128.3, 127.9, 120.4, 79.4, 71.5, 42.3, 19.5; HRMS (ESI): m/z [M+H]$^+$ calcd. for C$_{15}$H$_{12}$N$_5$SCl$_2$, 364.0190. found 364.0194.

3-(But-3-yn-1-yl)-8-((3,5-dichlorophenyl)thio)-3H-purin-6-amine (17g, PDP-I-14-B). Obtained as a white solid in 18% yield. $^1$H-NMR (400 MHz, CDCl$_3$) δ 8.08 (1H, s), 7.43 (2H, s), 7.30 (1H, s), 4.44 (2H, t, J=6.0 Hz), 2.08-2.10 (3H, m); $^{13}$C-NMR (CDCl$_3$) δ 153.1, 150.3, 142.9, 136.6, 136.2, 135.2, 129.5, 127.7, 121.9, 79.2, 72.5, 47.3, 19.2; HRMS (ESI): m/z [M+H]$^+$ calcd. for C$_{15}$H$_{12}$N$_5$SCl$_2$, 364.0190. found 364.0192.

8-((3,5-Dichlorophenyl)thio)-9-(hex-5-yn-1-yl)-9H-purin-6-amine (16h, PDP-112A). Obtained as a white solid in 41% yield. $^1$H-NMR (400 MHz, CDCl$_3$) δ 8.29 (1H, s), 7.28 (3H, s), 6.71 (2H, bs), 4.26 (2H, t, J=7.2 Hz), 2.22 (2H, td, J=6.8, 2.7 Hz), 1.95 (1H, t, J=2.6 Hz), 1.87-1.93 (2H, m), 1.53 (2H, pentet, J=6.8 Hz); $^{13}$C-NMR (CDCl$_3$) δ 155.0, 151.2, 143.6, 135.9, 134.4, 129.0, 128.5, 128.2, 120.0, 83.3, 69.1, 43.5, 28.8, 25.3, 17.9; HRMS (ESI): m/z [M+H]$^+$ calcd. for C$_{17}$H$_{15}$N$_5$SCl$_2$, 392.0503. found 392.0493.

8-((3,5-Dichlorophenyl)thio)-3-(hex-5-yn-1-yl)-3H-purin-6-amine (17h, PDP-112-B). Obtained as a white solid in 15% yield. $^1$H-NMR (400 MHz, CDCl$_3$) δ 7.99 (1H, s), 7.44 (2H, s), 7.20 (1H, s), 4.38 (2H, t, J=6.9 Hz), 2.27 (2H, td, J=6.8, 2.7 Hz), 2.11-2.15 (2H, m), 1.97 (1H, t, J=2.5 Hz), 1.58 (2H, pentet, J=6.8 Hz); $^{13}$C-NMR (CDCl$_3$) δ 156.3, 152.4, 143.4, 135.0, 134.9, 129.0, 128.4, 127.0, 118.6, 83.2, 69.4, 50.2, 28.5, 25.1, 17.9; HRMS (ESI): m/z [M+H]$^+$ calcd. for C$_{17}$H$_{15}$N$_5$SCl$_2$, 392.0503. found 392.0489.

4-(6-Amino-8-((3,5-dichlorophenyl)thio)-9H-purin-9-yl)butanenitrile (16i, PDP-93). Obtained as a white solid in 41% yield. $^1$H-NMR (400 MHz, CDCl$_3$) δ 8.34 (1H, s), 7.31 (3H, s), 6.04 (2H, bs), 4.36 (2H, t, J=7.0 Hz), 2.42 (2H, t, J=7.1 Hz), 2.18 (2H, pentet, J=7.2 Hz); $^{13}$C-NMR (CDCl$_3$) δ 154.8, 152.7, 151.5, 143.4, 136.0, 133.9, 129.2, 127.5, 120.2, 118.3, 42.4, 25.6, 14.9; HRMS (ESI): m/z [M+H]$^+$ calcd. for C$_{15}$H$_{13}$N$_6$SCl$_2$, 379.0299. found 379.0303.

4-(6-Amino-8-((3,5-dichlorophenyl)thio)-3H-purin-3-yl)butanenitrile (17i, PDP-II-93B) Obtained as a white solid in 16% yield. $^1$H-NMR (400 MHz, CDCl$_3$) δ 8.08 (1H, s), 7.34 (2H, s), 7.31 (1H, s), 4.44 (2H, t, J=6.9 Hz), 2.50 (2H, t, J=7.0 Hz), 2.36 (2H, pentet, J=6.9 Hz); $^{13}$C-NMR (CDCl$_3$) δ 155.1, 152.6, 151.3, 142.6, 136.0, 135.2, 129.5, 127.7, 120.3, 118.2, 39.6, 24.8, 14.3; HRMS (ESI): m/z [M+H]$^+$ calcd. for C$_{15}$H$_{13}$N$_6$SCl$_2$, 379.0299. found 379.0290.

9-(Cyclohexylmethyl)-8-((3,5-dichlorophenyl)thio)-9H-purin-6-amine (16j, PDP-110-A). Obtained as a white solid in 43% yield. $^1$H-NMR (400 MHz, CDCl$_3$) δ 8.29 (1H, s), 7.26 (3H, s), 6.68 (2H, br s), 4.06 (2H, d, J=7.5 Hz), 1.85-1.88 (1H, m), 1.65-1.71 (4H, m), 1.51-1.54 (2H, m), 1.11- 1.16 (2H, m), 1.02-1.06 (2H, m); $^{13}$C-NMR (CDCl$_3$) δ 154.9, 152.6, 151.5, 144.2, 135.8, 134.6, 128.3, 122.8, 120.0, 49.9, 38.2, 30.5, 27.8, 26.1; HRMS (ESI): m/z [M+H]$^+$ calcd. for C$_{18}$H$_{19}$N$_5$SCl$_2$, 408.0816. found 408.0805.

9-Benzyl-8-((3,5-dichlorophenyl)thio)-9H-purin-6-amine (16k, PDP-107-A). Obtained as a white solid in 48% yield. $^1$H-NMR (400 MHz, CDCl$_3$) δ 8.43 (1H, s), 7.23 (3H, s), 7.15-7.19 (3H, m), 7.04-7.05 (2H, m), 5.97 (2H, br s), 5.45 (2H, s); $^{13}$C-NMR (CDCl$_3$) δ 154.9, 153.9, 151.7, 143.6, 135.6, 135.3, 134.5, 128.7, 128.2, 128.1, 127.9, 127.5, 120.8, 47.0; HRMS (ESI): m/z [M+H]$^+$ calcd. for C$_{18}$H$_{14}$N$_5$SCl$_2$, 402.0347. found 402.0335.

3-Benzyl-8-((3,5-dichlorophenyl)thio)-3H-purin-6-amine (17k, PDP-107B). Obtained as a white solid in 16% yield. $^1$H-NMR (400 MHz, CDCl$_3$) δ 8.01 (1H, s), 7.45 (3H, s), 7.34-7.38 (5H, m), 5.48 (2H, s); HRMS (ESI): m/z [M+H]$^+$ calcd. for C$_{18}$H$_{14}$N$_5$SCl$_2$, 402.0347. found 402.0343.

8-((3,5-Dichlorophenyl)thio)-9-phenethyl-9H-purin-6-amine (161, PDP-127-A). Obtained as a yellow solid in 45% yield. $^1$H-NMR (400 MHz, CDCl$_3$) δ 8.35 (1H, s), 7.22-7.26 (4H, m), 7.19-7.20 (2H, m), 7.04-7.06 (2H, m), 6.45 (2H, br s), 4.47 (2H, t, J=7.2 Hz), 3.09 (2H, t, J=7.3 Hz); $^{13}$C-NMR (CDCl$_3$) δ 153.8, 151.5, 151.2, 145.1, 136.8, 135.8, 134.0, 128.9, 128.8, 128.6, 128.5, 127.2, 120.1, 45.5, 35.7; HRMS (ESI): m/z [M+H]$^+$ calcd. for C$_{19}$H$_{16}$N$_5$SCl$_2$, 416.0503. found 416.0508.

General Method for Synthesis of 16m

To a suspension of 8-((2,4-dichlorophenyl)thio)-9H-purin-6-amine (18, 1.0 mmol) in CH$_2$Cl$_2$:toluene (0.5:2.5 mL) were added PPh$_3$ (4.0 mmol) and alcohol (2.0 mmol) under nitrogen protection. After stirring for 10 min. DBAD (6 mmol) was added and reaction mixture was stirred at rt for 2-5 h. Following solvent removal, the crude material was purified by preparative TLC (CH$_2$Cl$_2$:CH$_3$OH:AcOH, 20:1:0.1 or CH$_2$Cl$_2$:NH$_3$—CH$_3$OH (7N), 20:1) to afford desired compounds 16m-.

8-((3,5-Dichlorophenyl)thio)-9-(pentan-2-yl)-9H-purin-6-amine (16m; HJP-V-123). Yield, 7.8 mg (15%). $^1$H NMR (600 MHz, CDCl$_3$+5 drops MeOD, 2 rotamers) δ 8.17-8.21 (m, 1H), 7.40-7.56 (m, 3H), 4.76-4.79 (m, 0.4H), 4.65-4.69 (m, 0.6H), 2.21-2.27 (m, 0.6H), 1.97-2.03 (m, 0.4H), 1.81-1.92 (m, 1H), 1.60-1.63 (m, 3H), 1.03-1.28 (m, 2H), 0.87-0.89 (m, 3H); $^{13}$C NMR (150 MHz, CDCl$_3$+5 drops MeOD) δ 153.3, 151.2, 150.0, 145.6, 135.9, 135.2, 133.5, 130.2, 129.1, 128.1, 120.4, 54.4, 36.7, 19.8, 19.7, 13.6; HRMS (ESI) m/z [M+H]$^+$ calcd. for C$_{16}$H$_{18}$Cl$_2$N$_5$S, 382.0660. found 382.0663.

6.2.5 Synthesis of Compounds of Formula 20a-e (Scheme 5)

Scheme 5:

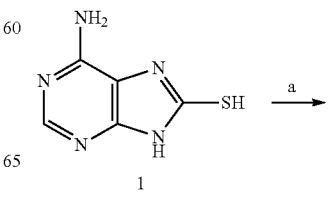

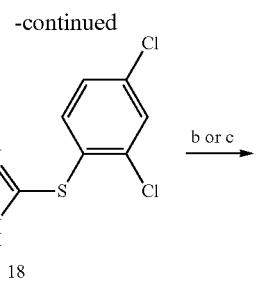

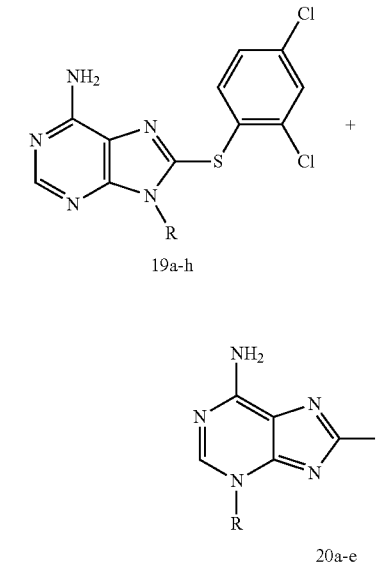

Reagents and conditions: (a) neocuproine, CuI, NaOt-Bu, DMF, 110° C.; (b) ArCH₂CH₂Br or 5-chloropent-1-yne, Cs₂CO₃, DMF, 80° C.; (c) ROH, PPh₃, DBAD, CH₂Cl₂-toluene, rt.

8-((2,4-Dichlorophenyl)thio)-9H-purin-6-amine (18). 8-Mercaptoadenine (1, 1.23 g, 7 mmol), 1-iodo-2,4-dichlorobenzene (3 g, 11 mmol), neocuprine hydrate (0.3 g, 1.4 mmol), CuI (0.28 g, 1.4 mmol), NaOt-Bu (1.4 g, 14 mmol) and DMF (20 mL) were charged in a nitrogen protected dry vessel. The reaction vessel was sealed and placed in an oil bath (110° C.) and stirred for 24 hrs. The reaction mixture was then cooled to room temperature and DMF was removed in vacuo. The crude material was purified by silica gel flash chromatography (CH₂Cl₂:CH₃OH:CH₃COOH, 60:1:0.5 to 20:1:0.5) to afford the 2.0 g (87%) of 18. MS (ESI): m/z 312.0 [M+H]⁺.

General Method for Synthesis of 19a-e and 20a-e

A mixture of 8-((2,4-dichlorophenyl)thio)-9H-purin-6-amine (18, 1.0 mmol), Cs₂CO₃ (1.5 mmol), and arylethylbromide (3.0 mmol) in DMF (1.5 mL) under nitrogen protection was stirred at room temperature for 1-2 h. Following solvent removal, the crude material was purified by preparative TLC (CH₂Cl₂:CH₃OH:AcOH, 20:1:0.1) to afford desired N-9 compounds.

8-((2,4-Dichlorophenyl)thio)-9-(2-(pyridin-2-yl)ethyl)-9H-purin-6-amine (19a; HJP-V-93-N9). Yield, 7.8 mg (15%). ¹H NMR (600 MHz, CDCl₃/MeOH-d₄) δ 8.52 (d, J=4.9 Hz, 1H), 8.25 (s, 1H), 7.58 (t, J=7.7 Hz, 1H), 7.49-7.51 (m, 1H), 7.30 (d, J=8.4 Hz, 1H), 7.18-7.26 (m, 2H), 7.01 (d, J=7.7 Hz, 1H), 4.68 (t, J=6.9 Hz, 2H), 3.35 (t, J=7.0, 2H); ¹³C NMR (150 MHz, CDCl₃/MeOH-d₄) δ 156.8, 153.4, 151.2, 150.9, 149.3, 146.3, 137.1, 136.9, 135.9, 134.5, 130.3, 128.2, 127.7, 123.8, 122.3, 119.5, 43.7, 37.2; HRMS (ESI) m/z [M+H]⁺ calcd. for C₁₈H₁₅Cl₂N₆S, 417.0456. found 417.0447.

8-((2,4-Dichlorophenyl)thio)-9-(2-fluorophenethyl)-9H-purin-6-amine (19b; HJP-V-96). Yield, 7.2 mg (27%). ¹H NMR (600 MHz, CDCl₃) δ 8.25 (s, 1H), 7.38 (d, J=2.0 Hz, 1H), 7.06-7.19 (m, 3H), 6.85-6.94 (m, 3H), 6.05 (br s, 2H), 4.44 (t, J=7.1, 2H), 3.11 (t, J=7.2, 2H); ¹³C NMR (150 MHz, CDCl₃) δ 161.4 (d, J=244.7 Hz), 153.4, 151.3, 151.2, 145.6, 135.7, 135.1, 133.1, 131.1 (d, J=4.5 Hz), 130.2, 129.1 (d, J=8.1 Hz), 128.9, 128.1, 124.3 (d, J=3.7 Hz), 123.8 (d, J=15.9 Hz), 120.1, 115.5 (d, J=21.5 Hz), 43.9, 29.5; HRMS (ESI) m/z [M+H]⁺ calcd. for C₁₉H₁₅Cl₂FN₅S, 434.0409. found 434.0407.

9-(2-Chlorophenethyl)-8-((2,4-dichlorophenyl)thio)-9H-purin-6-amine (19c; HJP-V-97). Yield, 5.2 mg (19%). ¹H NMR (600 MHz, CDCl₃) δ 8.32 (s, 1H), 7.46 (d, J=2.0 Hz, 1H), 7.46 (dd, J=8.0 and 2.0 Hz, 1H), 7.15-7.19 (m, 3H), 7.10 (td, J=7.5 and 1.2 Hz, 1H), 6.94 (dd, J=7.6 and 1.8 Hz, 1H), 6.30 (bs, 2H), 4.55 (t, J=7.0, 2H), 3.29 (t, J=7.0, 2H); ¹³C NMR (150 MHz, CDCl₃) δ 152.9, 151.3, 150.1, 146.3, 135.9, 135.2, 134.5, 134.4, 133.3, 131.1, 130.3, 129.8, 128.8, 128.5, 128.1, 127.1, 119.9, 43.6, 33.6; HRMS (ESI) m/z [M+H]+ calcd. for C₁₉H₁₅Cl₃N₅S, 450.0114. found 450.0099.

8-((2,4-Dichlorophenyl)thio)-9-(2-(trifluoromethyl)phenethyl)-9H-purin-6-amine (19d; HJP-V-98). Yield, 7.7 mg (26%). ¹H NMR (600 MHz, CDCl₃) δ 8.24 (s, 1H), 7.59 (d, J=7.7 Hz, 1H), 7.39 (s, 1H), 7.32 (t, J=7.6 Hz, 1H), 7.28 (t, J=7.4 Hz, 1H), 7.11 (s, 2H), 6.94 (d, J=7.4 Hz, 1H), 6.41 (br s, 2H), 4.45 (t, J=7.1, 2H), 3.25 (t, J=7.2, 2H); ¹³C NMR (150 MHz, CDCl₃) δ 153.2, 151.2, 150.4, 146.1, 136.0, 135.4, 133.4, 132.1, 131.8, 131.4, 130.3, 129.1 (q, J=29.7), 128.3, 128.1, 127.4, 126.4 (q, J=5.5), 124.8 (q, J=272.1), 119.9, 44.9, 32.7; HRMS (ESI) m/z [M+H]⁺ calcd. for C₂₀H₁₅Cl₂F₃N₅S, 484.0377. found 484.0367.

9-(3-(Isopropylamino)propyl)-8-((2,4,5-trichlorophenyl)thio)-9H-purin-6-amine (19e; HJP-V-103-N9). Yield, 7.4 mg (18%). ¹H NMR (600 MHz, CDCl₃/MeOH-d₄) δ 8.20 (s, 1H), 7.58 (s, 1H), 7.45 (s, 1H), 4.29 (t, J=6.9, 2H), 2.76 (septet, J=6.2, 1H), 2.56 (t, J=6.8, 2H), 2.02 (pentet, J=6.8, 2H), 1.05 (d, J=6.4, 6H); ¹³C NMR (150 MHz, CDCl₃/MeOH-d₄) δ 154.6, 152.9, 151.2, 144.1, 134.4, 134.1, 133.8, 132.1, 131.6, 129.4, 119.7, 42.9, 41.4, 29.6, 29.2, 21.7; HRMS (ESI) m/z [M+H]⁺ calcd. for C₁₇H₂₀Cl₃N₆S, 445.0536. found 445.0520.

8-((2,4-Dichlorophenyl)thio)-3-(2-(pyridin-2-yl)ethyl)-3H-purin-6-amine (20a; HJP-V-93-N3). Yield, 7.9 mg (15%). ¹H NMR (600 MHz, CDCl₃/MeOH-d₄) δ 8.59 (d, J=4.8 Hz, 1H), 7.85 (s, 1H), 7.56 (t, J=7.6 Hz, 1H), 7.45 (s, 1H), 7.44 (d, J=6.7 Hz, 1H), 7.14-7.19 (m, 2H), 6.95 (d, J=7.7 Hz, 1H), 4.86 (t, J=6.4, 2H), 3.49 (t, J=6.4, 2H); ¹³C NMR (150 MHz, CDCl₃/MeOH-d₄) δ 158.3, 156.6, 152.8, 150.9, 149.6, 143.0, 136.8, 136.6, 135.2, 133.4, 132.9, 132.1, 129.6, 127.5, 124.1, 122.2, 49.4, 36.3; HRMS (ESI) m/z [M+H]⁺ calcd. for C₁₈H₁₅Cl₂N₆S, 417.0456. found 417.0443.

3-(3-(Isopropylamino)propyl)-8-((2,4,5-trichlorophenyl)thio)-3H-purin-6-amine (20e; HJP-V-103-N3). Yield, 7.3 mg (18%). ¹H NMR (600 MHz, CDCl₃/MeOH-d₄) δ 8.06 (s, 1H), 7.57 (s, 1H), 7.50 (s, 1H), 4.38 (t, J=6.9, 2H), 2.79

(septet, J=6.4, 1H), 2.60 (t, J=6.5, 2H), 2.12 (pentet, J=6.5, 2H), 1.07 (d, J=6.3, 6H); $^{13}$C NMR (150 MHz, CDCl$_3$/MeOH-d$_4$) δ 157.6, 153.1, 150.8, 143.4, 133.9, 133.5, 132.8, 132.2, 131.4, 130.9, 121.9, 47.9, 42.7, 29.7, 28.9, 21.7; HRMS (ESI) m/z [M+H]$^+$ calcd. for C$_{17}$H$_{20}$Cl$_3$N$_6$S, 445.0536. found 445.0523.

General Method for Synthesis of 19f-h

To a suspension of 8-(2,4-dichlorophenyl)thio)-9H-purin-6-amine (18, 1.0 mmol) in CH$_2$Cl$_2$:toluene (0.5:2.5 mL) were added PPh$_3$ (4.0 mmol) and alcohol (2.0 mmol) under nitrogen protection. After stirring for 10 min. DBAD (6 mmol) was added and reaction mixture was stirred at rt for 2-5 h. Following solvent removal, the crude material was purified by preparative TLC (CH$_2$Cl$_2$:CH$_3$OH:AcOH, 20:1:0.1 or CH$_2$Cl$_2$:NH$_3$—CH$_3$OH (7N), 20:1) to afford desired compounds 19f-h.

8-((2,4-Dichlorophenyl)thio)-9-(pentan-2-yl)-9H-purin-6-amine (19f; HJP-V-114). Yield, 7.8 mg (15%). $^1$H NMR (600 MHz, CDCl$_3$) δ 8.22 (s, 1H), 7.43 (d, J=1.8 Hz, 1H), 7.13-7.20 (m, 2H), 6.14 (br s, 2H), 4.65-4.70 (m, 1H), 2.17-2.23 (m, 1H), 1.80-1.86 (m, 1H), 1.54 (d, J=6.9 Hz, 3H), 1.12-1.19 (m, 1H), 0.97-1.02 (m, 1H), 0.79 (t, J=7.4 Hz, 3H); $^{13}$C NMR (150 MHz, CDCl$_3$) δ 153.3, 151.2, 150.0, 145.6, 135.9, 135.2, 133.5, 130.2, 129.1, 128.1, 120.4, 54.4, 36.7, 19.8, 19.7, 13.6; HRMS (ESI) m/z [M+H]$^+$ calcd. for C$_{16}$H$_{18}$Cl$_2$N$_5$S, 382.0660. found 382.0663.

8-((2,4-Dichlorophenyl)thio)-9-(2-(pyridin-3-yl)ethyl)-9H-purin-6-amine (19g; HJP-V-116). Yield, 7.8 mg (15%). $^1$H NMR (600 MHz, CDCl$_3$/MeOH-d$_4$) δ 8.41 (s, 1H), 8.31 (s, 1H), 8.24 (s, 1H), 7.40 (d, J=2.0 Hz, 1H), 7.37 (d, J=7.9 Hz, 1H), 7.08-7.14 (m, 3H), 6.16 (br s, 2H), 4.41 (t, J=7.3, 2H), 3.07 (t, J=7.3, 2H); $^{13}$C NMR (150 MHz, CDCl$_3$) δ 153.0, 151.0, 150.1, 148.9, 147.3, 143.6, 135.6, 134.5, 134.2, 132.1, 131.5, 129.2, 127.7, 127.2, 122.6, 119.0, 43.8, 31.9; HRMS (ESI) m/z [M+H]$^+$ calcd. for C$_{18}$H$_{15}$Cl$_2$N$_6$S, 417.0456. found 417.0448.

8-((2,4-Dichlorophenyl)thio)-9-(2-(pyridin-4-yl)ethyl)-9H-purin-6-amine (19h; HJP-V-118). Yield, 7.8 mg (15%). $^1$H NMR (600 MHz, CDCl$_3$) δ 8.43 (s, 2H), 8.27 (s, 1H), 7.41 (d, J=2.1 Hz, 1H), 7.13 (dd, J=8.5 and 2.2 Hz, 1H), 7.08 (d, J=8.5 Hz, 1H), 7.01 (d, J=5.0 Hz, 2H) 5.89 (br s, 2H), 4.42 (t, J=7.4, 2H), 3.07 (t, J=7.4, 2H); $^{13}$C NMR (150 MHz, CDCl$_3$) δ 154.3, 152.9, 151.3, 149.9, 146.1, 144.3, 135.6, 135.2, 133.1, 128.9, 128.2, 124.3, 120.2, 44.2, 35.1; HRMS (ESI) m/z [M+H]$^+$ calcd. for C$_{18}$H$_{15}$Cl$_2$N$_6$S, 417.0456. found 417.0448.

8-((2,4-dichlorophenyl)thio)-9-(hex-5-yn-3-yl)-9H-purin-6-amine (19i; HJP-V-117). Yield, 3.8 mg (24%). $^1$H NMR (600 MHz, MeOD) δ 8.27 (s, 1H), 7.69 (d, J=2.2 Hz, 1H), 7.63 (d, J=8.5 Hz, 1H), 7.42 (d, J=8.5 and 2.3 Hz, 1H), 4.75-4.79 (m, 1H), 3.24-3.28 (m, 1H), 2.89-2.94 (m, 1H), 2.35-2.41 (m, 1H), 2.25 (t, J=2.6 Hz, 1H), 2.05-2.10 (m, 1H), 0.84 (t, J=7.4 Hz, 3H); $^{13}$C NMR (150 MHz, MeOD) δ 153.3, 151.2, 150.0, 145.6, 135.9, 135.2, 133.5, 130.2, 129.1, 128.1, 120.4, 54.4, 36.7, 19.8, 19.7, 13.6; HRMS (ESI) m/z [M+H]$^+$ calcd. for C$_{17}$H$_{16}$Cl$_2$N$_5$S, 392.0660. found 392.0663.

6.2.6 Synthesis of Compounds of Formula 22a-b (Scheme 6)

Scheme 6:

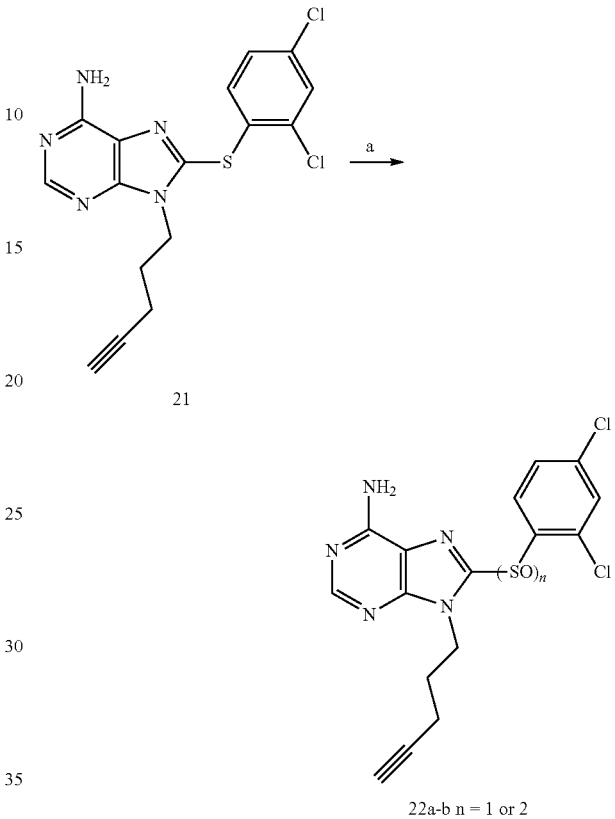

22a-b n = 1 or 2

Reagents and conditions: (a) m-CPBA, 30 min, rt.

Reaction of 21 with m-CPBA to Result in Sulfoxide 22a and Sulfone 22b. A mixture of 21 (20 mg, 0.053 mmol) and m-CPBA (18.2 mg, 0.106 mmol) in THF:CH$_2$Cl$_2$ (2 mL) under nitrogen protection was stirred at room temperature for 30 min. Following solvent removal, the crude material was purified by preparative TLC (CH$_2$Cl$_2$:CH$_3$OH—NH$_3$ (7N), 20:1 to afford desired products 22a and 22b.

8-((2,4-Dichlorophenyl)sulfinyl)-9-(pent-4-yn-1-yl)-9H-purin-6-amine (22a; HJP-V-62M). Yield, 3.4 mg (23%). $^1$H-NMR (600 MHz, CDCl$_3$/MeOH-d$_4$) δ 8.29 (s, 1H), 8.04 (d, J=8.5 Hz, 1H), 7.58 (dd, J=8.5, 2.0 Hz, 1H), 7.41 (d, J=2.0 Hz, 1H), 4.57 (t, J=7.1 Hz, 2H), 2.30 (td, J=7.0, 2.6 Hz, 2H), 2.06-2.20 (m, 2H), 1.98 (t, J=2.6 Hz, 1H); $^{13}$C NMR (150 MHz, CDCl$_3$/MeOH-d$_4$) δ 155.1, 152.6, 150.6, 139.2, 136.3, 131.9, 130.1, 128.7, 128.6, 119.1, 81.9, 70.0, 43.5, 28.7, 16.0; HRMS (ESI) m/z [M+H]$^+$ calcd. for C$_{16}$H$_{14}$Cl$_2$N$_5$OS, 394.0296. found 394.0279.

8-((2,4-Dichlorophenyl)sulfonyl)-9-(pent-4-yn-1-yl)-9H-purin-6-amine (22b; HJP-V-62T). Yield, 5.1 mg (34%). $^1$H-NMR (600 MHz, CDCl$_3$/MeOH-d$_4$) δ 8.39 (s, 1H), 8.24 (d, J=8.4 Hz, 1H), 7.48-7.51 (m, 2H), 6.24 (br s, 2H), 4.88 (t, J=7.6 Hz, 2H), 2.29 (td, J=7.0, 2.6 Hz, 2H), 2.10-2.16 (m, 2H), 1.92 (t, J=2.6 Hz, 1H); $^{13}$C NMR (150 MHz, CDCl$_3$/MeOH-d$_4$) δ 155.4, 153.3, 150.7, 146.2, 142.2, 134.9, 134.8, 132.6, 132.0, 127.9, 119.3, 82.1, 69.6, 44.4, 28.9, 16.1; HRMS (ESI) m/z [M+H]$^+$calcd. for C$_{16}$H$_{14}$Cl$_2$N$_5$O$_2$S, 410.0245. found 410.0228.

6.2.7 Synthesis of Compounds of Formula 24a-o (Scheme 7)

Scheme 7:

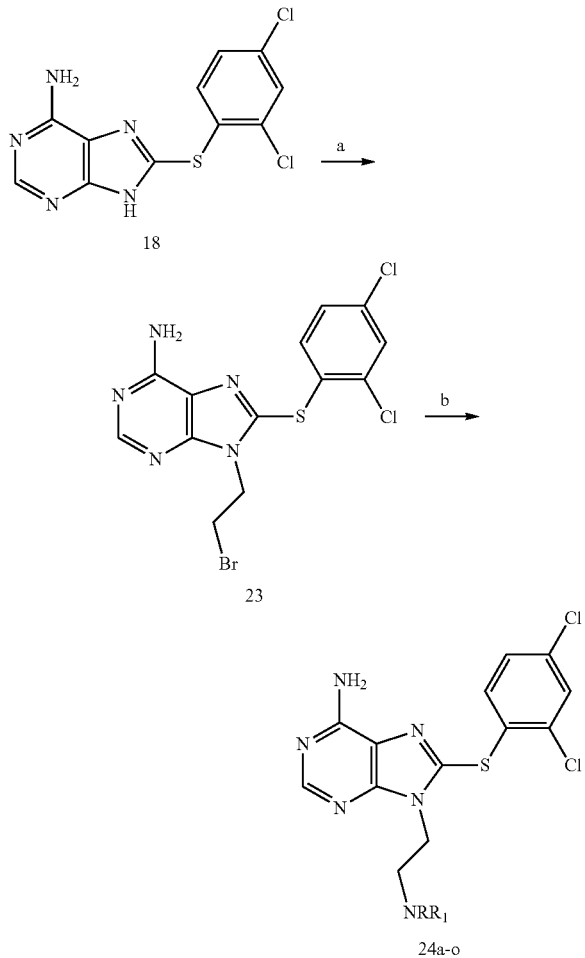

Reagents and conditions: (a) 1,2-dibromoethane, Cs$_2$CO$_3$, DMF; (b) amine, DMF, 16-24 h.

9-(2-Bromoethyl)-8-((2,4-dichlorophenyl)thio)-9H-purin-6-amine (23). A mixture of 8-((2,4-dichlorophenyl)thio)-9H-purin-6-amine (18, 0.4 g, 1.28 mmol), Cs$_2$CO$_3$ (0.63 g, 1.92 mmol), and 1,2-dibromopropane (1.21 g, 0.55 mL, 6.43 mmol) in DMF (10 mL) under nitrogen protection was stirred at room temperature for 30 min. Following solvent removal, the crude material was purified by flash chromatography (CH$_2$Cl$_2$:CH$_3$OH:AcOH, 100:1:0.5 to 20:1:0.5) to afford 23. Yield, 0.19 g (36%). $^1$H-NMR (500 MHz, CDCl$_3$/MeOH-d$_4$) δ 8.27 (s, 1H), 7.52 (d, J=2.2 Hz, 1H), 7.36 (d, J=8.5 Hz, 1H), 7.26 (dd, J=8.4, 2.2 Hz, 1H), 4.68 (d, J=6.5 Hz, 2H), 3.77 (t, J=6.5 Hz, 2H); $^{13}$C NMR (125 MHz, CDCl$_3$/MeOH-d$_4$) δ 154.6, 153.1, 150.9, 145.0, 136.3, 135.7, 133.9, 130.3, 128.4, 128.2, 119.8, 45.0, 28.5.

General Procedure for the Synthesis of 24a-m

A mixture of 23 (10 mg, 0.024 mmol) and amine (1.19 mmol, 50 equiv.) in DMF (1 mL) under nitrogen protection was stirred at room temperature for 16-24 hrs. Following solvent removal, the crude material was purified by preparative TLC (CH$_2$Cl$_2$:CH$_3$OH—NH$_3$ (7N), 20:1 or 15:1) to afford desired product 24a-m.

8-((2,4-Dichlorophenyl)thio)-9-(2-(neopentylamino)ethyl)-9H-purin-6-amine (24a; HJP-V-81). Yield, 10.1 mg (82%). $^1$H-NMR (600 MHz, CDCl$_3$) δ 8.27 (s, 1H), 7.39 (s, 1H), 7.09 (s, 2H), 5.71 (bs, 2H), 4.27-4.29 (m, 2H), 2.93 (t, J=5.8 Hz, 2H), 2.26 (s, 2H), 0.77 (s, 9H); $^{13}$C NMR (150 MHz, CDCl$_3$) δ 154.7, 153.3, 151.6, 144.5, 134.9, 134.5, 132.3, 130.3, 130.1, 128.1, 120.4, 61.9, 49.8, 44.0, 31.6, 27.7; HRMS (ESI) m/z [M+H]$^+$ calcd. for C$_{18}$H$_{23}$Cl$_2$N$_6$S, 425.1082. found 425.1081.

1-((2-(6-Amino-8-((2,4-dichlorophenyl)thio)-9H-purin-9-yl)ethyl)amino)propan-2-ol (24b; HJP-V-82). Yield, 8.2 mg (69%). $^1$H NMR (600 MHz, CDCl$_3$/MeOH-d$_4$) δ 8.25 (s, 1H), 7.53 (s, 1H), 7.35 (d, J=8.3 Hz, 1H), 7.28 (d, J=8.4 Hz, 1H), 4.37 (t, J=5.6 Hz, 2H), 3.73-3.78 (m, 1H), 2.97-3.09 (m, 2H), 2.70-2.73 (m, 1H), 2.45-2.51 (m, 1H), 1.13 (d, J=5.9 Hz, 3H); $^{13}$C NMR (150 MHz, CDCl$_3$/MeOH-d$_4$) δ 154.4, 152.8, 151.1, 145.3, 136.5, 135.8, 134.1, 130.4, 128.2, 128.1, 119.6, 65.6, 56.5, 48.3, 43.8, 20.4; HRMS (ESI) m/z [M+H]$^+$ calcd. for C$_{16}$H$_{19}$Cl$_2$N$_6$OS, 413.0718. found 413.0720.

1-(2-(6-Amino-8-((2,4-dichlorophenyl)thio)-9H-purin-9-yl)ethyl)piperidin-3-ol (24c; HJP-V-83). Yield, 8.7 mg (69%). $^1$H-NMR (600 MHz, CDCl$_3$) δ 8.26 (s, 1H), 7.39 (d, J=2.2 Hz, 1H), 7.17 (d, J=8.5 Hz, 1H), 7.12 (dd, J=8.5, 2.2 Hz, 1H), 5.84 (br s, 2H), 4.23-4.34 (m, 2H), 3.71-3.74 (m, 1H), 2.67 (t, J=4.3 Hz, 2H), 2.45-2.55 (m, 3H), 2.25-2.31 (m, 1H), 1.67-1.70 (m, 1H), 1.39-1.48 (m, 3H); $^{13}$C NMR (150 MHz, CDCl$_3$) δ 154.6, 153.3, 151.5, 144.5, 135.3, 134.9, 132.9, 130.1, 129.7, 128.1, 120.2, 65.8, 60.5, 57.3, 54.0, 41.6, 31.3, 21.3; HRMS (ESI) m/z [M+H]$^+$ calcd. for C$_{18}$H$_{21}$Cl$_2$N$_6$OS, 439.0875. found 439.0867.

2-((2-(6-Amino-8-((2,4-dichlorophenyl)thio)-9H-purin-9-yl)ethyl)amino)-2-methylpropan-1-ol (24d; HJP-V-84). Yield, 7.3 mg (72%). $^1$H-NMR (600 MHz, CDCl$_3$/MeOH-d$_4$) δ 8.25 (s, 1H), 7.53 (d, J=2.2 Hz, 1H), 7.37 (d, J=8.5 Hz, 1H), 7.27 (dd, J=8.4, 2.2 Hz, 1H), 4.38 (t, J=5.9 Hz, 2H), 3.32 (s, 2H), 2.96 (t, J=5.8 Hz, 2H), 1.02 (s, 6H); $^{13}$C NMR (150 MHz, CDCl$_3$) δ 154.6, 154.5, 152.7, 150.9, 145.5, 136.7, 135.8, 134.3, 130.4, 128.2, 119.6, 67.8, 54.8, 44.4, 41.0, 23.1; HRMS (ESI) m/z [M+H]$^+$ calcd. for C$_{17}$H$_{21}$Cl$_2$N$_6$OS, 427.0875. found 427.0884.

1-((2-(6-Amino-8-((2,4-dichlorophenyl)thio)-9H-purin-9-yl)ethyl)amino)-2-methylpropan-2-ol (24e; HJP-V-85). Yield, 6.1 mg (60%). $^1$H-NMR (600 MHz, CDCl$_3$/MeOH-d$_4$) δ 8.24 (s, 1H), 7.53 (d, J=1.7 Hz, 1H), 7.35 (d, J=8.4 Hz, 1H), 7.28 (d, J=8.4, 1.8 Hz, 1H), 4.39 (t, J=5.4 Hz, 2H), 3.09 (t, J=5.3 Hz, 2H), 2.61 (s, 2H), 1.17 (s, 6H); $^{13}$C NMR (150 MHz, CDCl$_3$) δ 154.5, 152.7, 151.1, 145.3, 136.6, 135.9, 134.2, 130.4, 128.3, 128.1, 119.6, 69.4, 59.9, 49.9, 43.8, 26.9; HRMS (ESI) m/z [M+H]$^+$ calcd. for C$_{17}$H$_{21}$Cl$_2$N$_6$OS, 427.0875. found 427.0881.

2-((2-(6-Amino-8-((2,4-dichlorophenyl)thio)-9H-purin-9-yl)ethyl)amino)propan-1-ol (24f; HJP-V-86). Yield, 6.5 mg (66%). $^1$H NMR (600 MHz, CDCl$_3$) δ 8.25 (s, 1H), 7.41 (d, J=1.9 Hz, 1H), 7.11-7.17 (m, 2H), 5.78 (bs, 2H), 4.27-4.38 (m, 2H), 3.51 (dd, J=11.0 and 3.7 Hz, 1H), 3.21 (dd, J=11.0 and 7.4 Hz, 1H), 3.09-3.14 (m, 1H), 2.90-2.95 (m, 1H), 2.74-2.77 (m, 1H), 0.96 (d, J=6.5 Hz, 3H); $^{13}$C NMR (150 MHz, CDCl$_3$) δ 154.7, 153.3, 151.6, 144.4, 135.3, 134.9, 132.8, 130.2, 129.5, 128.2, 120.2, 65.5, 55.1, 46.2, 44.4, 16.9; HRMS (ESI) m/z [M+H]+ calcd. for C$_{16}$H$_{19}$Cl$_2$N$_6$OS, 413.0718. found 413.0707.

8-((2,4-dichlorophenyl)thio)-9-(2-((2,2-difluoroethyl)amino)ethyl)-9H-purin-6-amine (24g; HJP-V-88). Yield, 4.5 mg (57%). $^1$H NMR (600 MHz, MeOD) δ 8.32 (s, 1H), 7.69 (d, J=2.3 Hz, 1H), 7.53 (d, J=8.5 Hz, 1H), 7.41 (dd, J=8.5 and 2.8 Hz, 1H), 6.29 (tt, J=53.8 and 2.8 Hz, 1H), 4.69 (t, J=5.9 Hz, 2H), 3.61-3.68 (m, 4H); $^{13}$C NMR (150 MHz, MeOD) δ 153.8, 152.3, 149.9, 148.2, 137.9, 137.3, 136.2, 131.5, 129.7, 129.1, 120.7, 114.1 (t, J=239.1 Hz), 49.7 (t, J=24.3 Hz), 48.3, 41.9; HRMS (ESI) m/z [M+H]⁺ calcd. for C₁₅H₁₅Cl₂F₂N₆OS, 418.0330. found 418.0331.

8-((2,4-Dichlorophenyl)thio)-9-(2-((2,2,2-trifluoroethyl)amino)ethyl)-9H-purin-6-amine (24h; HJP-V-89). Yield, 6.5 mg (64%). ¹H NMR (600 MHz, CDCl₃) δ 8.27 (s, 1H), 7.40 (d, J=1.9 Hz, 1H), 7.12-7.16 (m, 2H), 5.87 (br s, 2H), 4.28 (t, J=6.1, 2H), 3.05-3.11 (m, 4H); ¹³C NMR (150 MHz, CDCl₃) δ 154.1, 152.1, 151.0, 145.7, 136.5, 135.8, 134.2, 130.3, 128.2, 125.3 (q, J=278.4 Hz), 119.5, 51.8 (q, J=31.2 Hz), 47.9, 43.8; HRMS (ESI) m/z [M+H]⁺ calcd. for C₁₅H₁₄Cl₂F₃N₆OS, 437.0330. found 437.0331.

1-(2-(6-amino-8-((2,4-dichlorophenyl)thio)-9H-purin-9-yl)ethyl)piperidin-4-ol (24i; HJP-V-90). Yield, 4.6 mg (45%). ¹H NMR (600 MHz, MeOD) δ 8.22 (s, 1H), 7.65 (d, J=2.0 Hz, 1H), 7.41 (d, J=8.5 Hz, 1H), 7.38 (dd, J=8.5 and 2.1 Hz, 1H), 4.41-4.63 (m, 3H), 3.71-3.84 (m, 1H), 3.15-3.25 (m, 4H), 1.93-1.98 (m, 2H), 1.61-1.69 (m, 2H); HRMS (ESI) m/z [M+H]⁺ calcd. for C₁₈H₂₁Cl₂N₆OS, 439.0875. found 439.0885.

8-((2,4-Dichlorophenyl)thio)-9-(2-morpholinoethyl)-9H-purin-6-amine (24j; HJP-V-91). Yield, 5.6 mg (55%). ¹H NMR (600 MHz, CDCl₃) δ 8.27 (s, 1H), 7.38 (d, J=2.1 Hz, 1H), 7.14 (d, J=8.5 Hz, 1H), 7.10 (dd, J=8.5 and 2.1 Hz, 1H), 5.77 (br s, 2H), 4.30 (t, J=6.1, 2H), 3.56-3.59 (m, 4H), 2.66 (t, J=6.1, 2H), 2.43-2.45 (m, 4H); ¹³C NMR (150 MHz, CDCl₃) δ 154.5, 153.1, 151.4, 144.7, 134.8, 134.5, 132.2, 130.5, 130.1, 128.0, 120.4, 66.8, 57.6, 53.8, 41.1; HRMS (ESI) m/z [M+H]⁺ calcd. for C₁₇H₁₈Cl₂N₆OS, 425.0718. found 425.0716.

8-((2,4-Dichlorophenyl)thio)-9-(2-(isobutylamino)ethyl)-9H-purin-6-amine (24k; HJP-V-92). Yield, 7.3 mg (81%). ¹H NMR (600 MHz, CDCl₃/MeOH-d₄) δ 8.21 (s, 1H), 7.43 (d, J=2.0 Hz, 1H), 7.22 (d, J=8.0 Hz, 1H), 7.16 (dd, J=8.5, 2.0 Hz, 1H), 4.31 (t, J=5.9 Hz, 2H), 2.94 (t, J=5.7, 2H), 2.34-2.37 (m, 2H), 1.62-1.66 (m, 1H), 0.80 (d, J=6.5, 6H); ¹³C NMR (150 MHz, CDCl₃/MeOH-d₄) δ 154.5, 152.9, 151.2, 145.2, 136.1, 135.4, 133.7, 130.3, 128.9, 128.2, 119.8, 57.3, 48.6, 43.7, 28.0, 20.4; HRMS (ESI) m/z [M+H]⁺ calcd. for C₁₇H₂₁Cl₂N₆S, 411.0925. found 411.0917.

8-((2,4-Dichlorophenyl)thio)-9-(2-(methyl(prop-2-yn-1-yl)amino)ethyl)-9H-purin-6-amine (24l; HJP-V-100). Yield, 6.4 mg (72%). ¹H NMR (600 MHz, CDCl₃) δ 8.25 (s, 1H), 7.40 (d, J=2.0 Hz, 1H), 7.22 (d, J=8.5 Hz, 1H), 7.14 (dd, J=8.5, 2.0 Hz, 1H), 6.29 (br s, 2H), 4.31 (t, J=6.2, 2H), 3.29 (s, 2H), 2.82 (d, J=6.1 Hz, 2H), 2.28 (s, 3H), 2.11 (s, 1H); ¹³C NMR (150 MHz, CDCl₃) δ 153.1, 151.2, 150.2, 146.4, 135.6, 135.1, 133.3, 130.2, 129.4, 128.1, 120.0, 77.6, 73.8, 54.1, 45.8, 41.9, 41.8; HRMS (ESI) m/z [M+H]⁺ calcd. for C₁₇H₁₇Cl₂N₆S, 407.0925. found 407.0917.

1(R)-1-((2-(6-Amino-8-((2,4-dichlorophenyl)thio)-9H-purin-9-yl)ethyl)amino)propan-2-ol (24m; HJP-V-104). Yield, 4.2 mg (53%). ¹H NMR (600 MHz, CDCl₃/MeOH-d₄) δ 8.22 (s, 1H), 7.49 (d, J=2.2 Hz, 1H), 7.31 (d, J=8.5 Hz, 1H), 7.24 (dd, J=8.5, 2.2 Hz, 1H), 4.36-4.40 (m, 2H), 3.78-3.81 (m, 1H), 2.98-3.13 (m, 2H), 2.73-2.76 (m, 1H), 2.46-2.50 (m, 1H), 1.12 (d, J=6.3 Hz, 3H); ¹³C NMR (150 MHz, CDCl₃/MeOH-d₄) δ 154.6, 152.9, 151.1, 145.1, 136.5, 135.8, 134.1, 130.4, 128.3, 128.2, 119.7, 65.2, 56.3, 48.2, 43.6, 20.4; HRMS (ESI) m/z [M+H]⁺ calcd. for C₁₇H₁₉Cl₂N₆OS, 413.0718. found 413.0729.

1(S)-1-((2-(6-Amino-8-((2,4-dichlorophenyl)thio)-9H-purin-9-yl)ethyl)amino)propan-2-ol (24n; HJP-V-105). Yield, 3.8 mg (48%). ¹H NMR (600 MHz, CDCl₃/MeOH-d₄) δ 8.22 (s, 1H), 7.49 (d, J=2.2 Hz, 1H), 7.31 (d, J=8.5 Hz, 1H), 7.24 (dd, J=8.5, 2.2 Hz, 1H), 4.36-4.40 (m, 2H), 3.78-3.81 (m, 1H), 2.98-3.13 (m, 2H), 2.73-2.76 (m, 1H), 2.46-2.50 (m, 1H), 1.12 (d, J=6.3 Hz, 3H); ¹³C NMR (150 MHz, CDCl₃/MeOH-d₄) δ 154.6, 152.9, 151.1, 145.1, 136.5, 135.8, 134.1, 130.4, 128.3, 128.2, 119.7, 65.2, 56.3, 48.2, 43.6, 20.4; HRMS (ESI) m/z [M+H]⁺ calcd. for C₁₇H₁₉Cl₂N₆OS, 413.0718. found 413.0729.

2-((2-(6-Amino-8-((2,4-dichlorophenyl)thio)-9H-purin-9-yl)ethyl)(prop-2-yn-1-yl)amino)ethanol (24o; HJP-V-110). Yield, 8.3 mg (79%). ¹H NMR (600 MHz, CD₃CN) δ 8.32 (s, 1H), 7.67 (d, J=2.1 Hz, 1H), 7.39 (d, J=8.5 Hz, 1H), 7.36 (dd, J=8.5, 2.1 Hz, 1H), 4.56 (t, J=5.9, 2H), 3.94 (d, J=2.2 Hz, 2H), 3.68 (t, J=5.2, 2H), 3.43 (t, J=5.9, 2H), 3.11 (t, J=5.3, 2H), 2.79 (t, J=2.2 Hz, 1H); ¹³C NMR (150 MHz, CD₃CN) δ 151.6, 150.4, 146.4, 146.1, 134.9, 134.4, 133.2, 129.6, 128.8, 127.9, 119.3, 77.1, 73.8, 56.8, 55.4, 51.8, 42.1, 40.5; HRMS (ESI) m/z [M+H]⁺ calcd. for C₁₈H₁₉Cl₂N₆OS, 437.0718. found 437.0709.

6.2.8 Synthesis of Compounds of Formula 26 (Scheme 8)

Scheme 8:

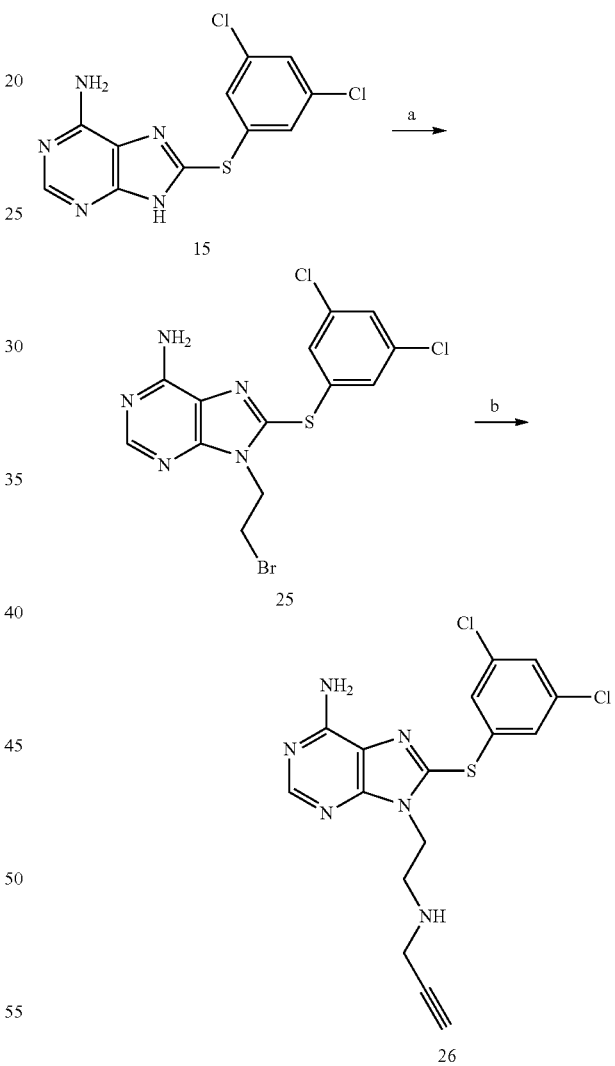

Reagents and conditions: (a) 1,2-dibromoethane, Cs₂CO₃, DMF, rt, 4 h; (b) propargylamine, DMF, rt, 24 h.

9-(2-Bromoethyl)-8-((3,5-dichlorophenyl)thio)-9H-purin-6-amine (25, PDP-129). 15 (1.21 mmol) was dissolved in DMF (15 mL). Cs₂CO₃ (1.45 mmol) and 1,2-dibromoethane (2.42 mmol) were added and the mixture was stirred under nitrogen at rt for 4 h. Solvent was removed under reduced pressure and the resulting residue was chromatographed (CH₂Cl₂:MeOH:AcOH, 20:1:0.5) to afford 25 as a white solid in 38% yield. ¹H-NMR (400 MHz, CDCl₃) δ 8.34 (s, 1H), 7.28 (s, 2H), 7.25 (s, 1H), 6.54 (s, 2H), 4.66 (t, J=6.5 Hz, 2H), 3.74 (t, J=6.5 Hz, 2H); MS (ESI): m/z 420.2 [M+H]⁺.

8-((3,5-Dichlorophenyl)thio)-9-(2-(prop-2-yn-1-ylamino)ethyl)-9H-purin-6-amine (26, PDP-131). 25 (0.09 mmol) was dissolved in DMF (5 mL). Propargylamine (0.9 mmol) was added and the mixture was stirred under nitrogen at rt for 24 h. Solvent was removed under reduced pressure and the resulting residue was chromatographed (CH₂Cl₂: NH₃/MeOH, 30:1) to afford 26 as a white solid in 80% yield. ¹H-NMR (400 MHz, CDCl₃) δ 8.36 (s, 1H), 7.28 (s, 3H), 5.84 (br s, 2H), 4.38 (t, J=6.1 Hz, 2H), 3.40 (d, J=2.2 Hz, 2H), 3.10 (t, J=6.1 Hz, 2H), 2.17-2.19 (m, 2H); ¹³C-NMR (CDCl₃) δ 154.8, 153.5, 151.6, 143.8, 135.8, 135.3, 128.2, 127.8, 120.4, 81.5, 71.8, 47.1, 43.6, 37.7; HRMS (ESI): m/z [M+H]⁺ calcd. for C₁₆H₁₅N₆SCl₂, 393.0456. found 393.0459.

6.2.9 Synthesis of Compounds of Formula 27a-d and 28a-d (Scheme 9)

Scheme 9:

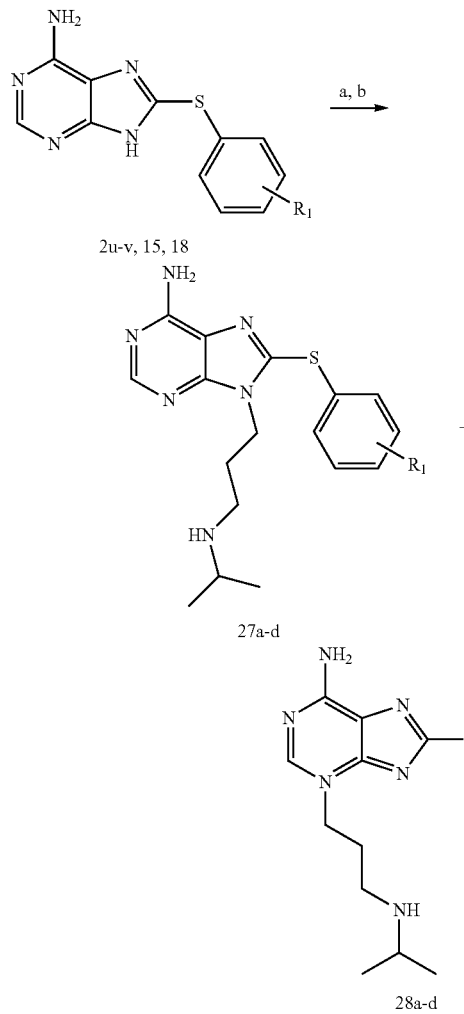

27a-d 28a-d

Reagents and conditions: (a) 3-(tert-Butoxycarbonyl-isopropyl-amino)-propyl tosylate, Cs₂CO₃, DMF, rt; (b) TFA, 0° C.

General procedure for the synthesis of 27a-d and 28a-d: A mixture of 8-arylsulfanyl adenine (100 mmol), Cs₂CO₃ (100 mmol), and 3-(tert-butoxycarbonyl-isopropyl-amino)-propyl tosylate (200 mmol) in DMF (1.3 mL) under nitrogen protection was heated at 80° C. for 30 min. Following solvent removal, the crude material was purified by preparatory TLC with CH₂Cl₂:MeOH:AcOH at 20:1:0.1 to afford the Boc protected N-9 and N-3 alkylated compounds. They were separately treated with TFA (1 ml) at 0° C. for 1.5 h to provide with corresponding 9-alkyl-8-arylsulfanyladenine derivatives and 3-alkyl-8-arylsulfanyladenine derivatives.

8-((2,4-Dichlorophenyl)thio)-9-(3-(isopropylamino)propyl)-9H-purin-6-amine (27a; WS12). ¹H-NMR (600 MHz, CDCl₃/MeOH-d₄) δ 8.23 (s, 1H), 7.55 (s, 1H), 7.38 (d, J=8.3 Hz, 1H), 7.30 (d, J=8.3 Hz, 1H), 4.34 (t, J=6.7 Hz, 2H), 2.92 (septet, J=5.8 Hz, 1H), 2.69 (t, J=6.4 Hz, 2H), 2.13 (pentet, J=6.5 Hz, 2H), 1.16 (d, J=5.7 Hz, 6H); HRMS (ESI) m/z [M+H]⁺ calcd. for C₁₇H₂₁Cl₂N₆S, 411.0925. found 411.0907.

8-((2,4-Dimethylphenyl)thio)-3-(3-(isopropylamino)propyl)-3H-purin-6-amine (28b; WS11). ¹H-NMR (500 MHz, CDCl₃) δ 7.96 (s, 1H), 7.48 (d, J=7.9 Hz, 1H), 7.11 (s, 1H), 7.00 (d, J=7.8 Hz, 1H), 4.48 (t, J=6.3 Hz, 2H), 2.91 (septet, J=6.3 Hz, 1H), 2.65 (t, J=6.1 Hz, 2H), 2.25-2.29 (m, 2H), 1.18 (d, J=6.3 Hz, 6H); HRMS (ESI) m/z [M+H]⁺ calcd. for C₁₉H₂₇N₆S, 371.2018. found 371.2035.

8-((3,5-Dichlorophenyl)thio)-9-(3-(isopropylamino)propyl)-9H-purin-6-amine (27c; WS13). ¹H-NMR (600 MHz, CDCl₃/MeOH-d₄) δ 8.21 (s, 1H), 7.26 (t, J=1.7 Hz, 1H), 7.24 (d, J=1.9 Hz, 2H), 4.23 (t, J=6.9 Hz, 2H), 2.63 (septet, J=6.2 Hz, 1H), 2.46 (t, J=6.4 Hz, 2H), 1.89 (pentet, J=6.9 Hz, 2H), 0.97 (d, J=6.3 Hz, 6H); ¹³C NMR (150 MHz, CDCl₃) δ 154.7, 153.1, 151.3, 144.1, 135.9, 133.7, 128.8, 128.7, 119.7, 48.6, 43.4, 41.6, 29.8, 22.4; HRMS (ESI) m/z [M+H]⁺ calcd. for C₁₇H₂₁Cl₂N₆S, 411.0925. found 411.0917.

8-((3,5-Dichlorophenyl)thio)-3-(3-(isopropylamino)propyl)-3H-purin-6-amine (28c; WS13-N3). ¹H-NMR (600 MHz, CDCl₃/MeOH-d₄) δ 7.98 (s, 1H), 7.33 (d, J=1.8 Hz, 2H), 7.06 (t, J=1.8 Hz, 1H), 4.40 (t, J=6.7 Hz, 2H), 2.66 (septet, J=6.2 Hz, 1H), 2.51 (t, J=6.4 Hz, 2H), 2.06 (pentet, J=6.5 Hz, 2H), 0.96 (d, J=6.2 Hz, 6H); ¹³C NMR (150 MHz, CDCl₃) δ 157.9, 153.4, 151.0, 142.8, 137.8, 134.9, 127.9, 126.8, 122.6, 48.9, 48.1, 43.0, 29.5, 22.9; HRMS (ESI) m/z [M+H]⁺ calcd. for C₁₇H₂₁Cl₂N₆S, 411.0925. found 411.0928.

8-((3,5-Bis(trifluoromethyl)phenyl)thio)-9-(3-(isopropylamino)propyl)-9H-purin-6-amine (27d; WS14). ¹H-NMR (500 MHz, CDCl₃) δ 8.33 (s, 1H), 7.26-7.28 (m, 3H), 5.77 (br s, 2H), 4.33 (t, J=7.0 Hz, 2H), 2.71-2.76 (m, 1H), 2.57 (t, J=6.9 Hz, 2H), 1.96-1.99 (m, 2H), 1.05 (d, J=6.4 Hz, 6H); HRMS (ESI) m/z [M+H]⁺ calcd. for C₁₉H₂₁F₆N₆S, 479.1453. found 479.1444.

6.2.10 Synthesis of Compounds of Formula 30a-n (Scheme 10)

Scheme 10:

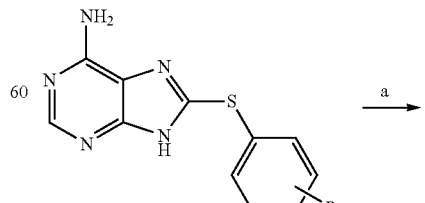

29a-n

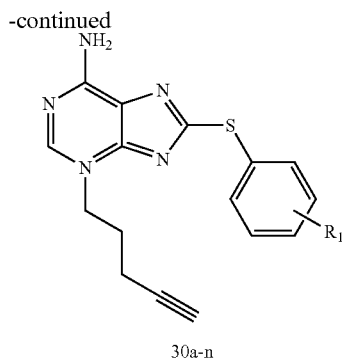

Reagents and conditions: (a) pent-4-yn-1-yl 4-methylbenzenesulfonate, Cs$_2$CO$_3$, DMF, 80° C.

General Procedure for the Synthesis of 30a-n

A mixture of 8-arylsulfanyl adenine (29a-n; 100 mmol), Cs$_2$CO$_3$ (100 mmol), and pent-4-ynyl-4-methylbenzenesulfonate (120 mmol) in DMF (1.3 mL) under nitrogen protection was heated at 80° C. for 30 min. Following solvent removal, the crude material was purified by preparatory TLC (CHCl$_3$:MeOH:NH$_4$OH, 10:1:0.5 or CHCl$_3$:MeOH:AcOH, 10:1:0.5) to provide the corresponding 3-alkyl-8-arylsulfanyladenine derivatives 30a-n.

8-(2-Chlorophenylthio)-3-(pent-4-ynyl)-3H-purin-6-amine (30a). Yield, 10%. $^1$H NMR (400 MHz, CDCl$_3$) δ 8.02 (s, 1H), 7.48-7.51 (m, 1H), 7.40-7.42 (m, 1H), 7.14-7.17 (m, 2H), 4.49-4.51 (m, 2H), 2.17-2.22 (m, 4H), 2.05-2.06 (m, 1H); HRMS (ESI) m/z [M+H]$^+$ calcd. for C$_{16}$H$_{15}$N$_5$ClS, 344.0737. found 344.0720.

8-(2-Methoxyphenylthio)-3-(pent-4-ynyl)-3H-purin-6-amine (30b). Yield, 25%. $^1$H NMR (400 MHz, CDCl$_3$) δ 7.97 (s, 1H), 7.45 (d, J=7.7 Hz, 1H), 7.22 (d, J=7.8 Hz, 1H), 6.86-6.90 (m, 2H), 4.47 (t, J=6.6 Hz, 2H), 3.87 (s, 3H), 2.21-2.26 (m, 4H), 2.05-2.07 (m, 1H); $^{13}$C NMR (100 MHz, CDCl$_3$) δ 157.7, 152.6, 141.8, 132.5, 128.3, 121.1, 111.1, 81.6, 70.5, 55.9, 49.0, 27.0, 15.3; HRMS (ESI) m/z [M+H]$^+$ calcd. for C$_{17}$H$_{18}$N$_5$OS, 340.1232. found 340.1218.

(2-(6-Amino-3-(pent-4-ynyl)-3H-purin-8-ylthio)phenyl)methanol (30c). Yield, 21%. $^1$H NMR (400 MHz, CDCl$_3$) δ 7.96 (s, 1H), 7.74 (d, J=7.6 Hz, 1H), 7.60 (d, J=7.5 Hz, 1H), 7.44 (t, J=7.4 Hz, 1H), 7.29 (t, J=7.5 Hz, 1H), 4.92 (s, 2H), 4.40 (t, J=6.4 Hz, 2H), 3.47 (br s, 1H), 2.11-2.20 (m, 4H), 2.03-2.06 (m, 1H); $^{13}$C NMR (100 MHz, CDCl$_3$) δ 146.2, 142.6, 137.3, 131.5, 130.9, 129.1, 82.1, 71.2, 64.9, 49.6, 27.1, 15.6; HRMS (ESI) m/z [M+H]$^+$ calcd. for C$_{17}$H$_{18}$N$_5$OS, 340.1232. found 340.1242.

3-(Pent-4-ynyl)-8-(2-(trifluoromethoxy)phenylthio)-3H-purin-6-amine (30d). Yield, 19%. $^1$H NMR (400 MHz, CDCl$_3$) δ 8.01 (s, 1H), 7.50 (d, J=7.9 Hz, 1H), 7.21-7.27 (m, 2H), 7.13 (t, J=7.1 Hz, 1H), 4.48 (t, J=6.1 Hz, 2H), 2.17-2.20 (m, 4H), 2.04-2.05 (m, 1H); $^{13}$C NMR (100 MHz, CDCl$_3$) δ 158.3, 153.1, 142.2, 132.1, 128.1, 127.9, 126.9, 122.5, 120.7, 81.8, 70.5, 49.0, 26.9, 15.2; HRMS (ESI) m/z [M+H]$^+$ calcd. for C$_{17}$H$_{15}$N$_5$F$_3$OS, 394.0949. found 394.0946.

8-(2,4-Dichlorophenylthio)-3-(pent-4-ynyl)-3H-purin-6-amine (30e). Yield, 22%. $^1$H NMR (400 MHz, CDCl$_3$/MeOH-d$_4$) δ 8.10 (s, 1H), 7.50 (s, 1H), 7.42 (d, J=8.4 Hz, 1H), 7.23-7.25 (m, 1H), 4.46 (t, J=6.5 Hz, 2H), 2.24-2.27 (m, 2H), 2.14-2.19 (m, 3H); $^{13}$C NMR (100 MHz, CDCl$_3$/MeOH-d$_4$) δ 154.8, 152.9, 150.0, 142.8, 133.9, 132.3, 130.6, 129.3, 128.8, 127.2, 120.4, 81.3, 70.0, 49.8, 26.7, 14.7; HRMS (ESI) m/z [M+H]$^+$ calcd. for C$_{16}$H$_{14}$N$_5$Cl$_2$S, 378.0347. found 378.0335.

8-(2,4-Dimethylphenylthio)-3-(pent-4-ynyl)-3H-purin-6-amine (30f). Yield, 27%. $^1$H NMR (400 MHz, CDCl$_3$) δ 7.94 (s, 1H), 7.48 (d, J=7.7 Hz, 1H), 7.08 (s, 1H), 6.97 (d, J=7.7 Hz, 1H), 4.36 (t, J=6.1 Hz, 2H), 2.51 (s, 3H), 2.39 (s, 3H), 2.15-2.19 (m, 4H), 2.03-2.05 (m, 1H); $^{13}$C NMR (100 MHz, CDCl$_3$) δ 162.6, 151.9, 151.1, 141.5, 141.1, 138.6, 134.5, 131.3, 127.3, 127.2, 121.7, 81.8, 70.5, 48.8, 26.9, 21.1, 20.8, 15.2; HRMS (ESI) m/z [M+H]$^+$ calcd. for C$_{18}$H$_{20}$N$_5$S, 338.1439. found 338.1427.

8-(2,4-Dimethoxyphenylthio)-3-(pent-4-ynyl)-3H-purin-6-amine (30g). Yield, 7%. $^1$H NMR (400 MHz, CDCl$_3$) δ 7.99 (s, 1H), 7.53 (d, J=8.1 Hz, 1H), 6.56-6.59 (m, 2H), 4.43 (t, J=6.8 Hz, 2H), 3.86 (s, 3H), 3.82 (s, 3H), 2.12-2.26 (m, 5H); $^{13}$C NMR (100 MHz, CDCl$_3$) δ 162.2, 160.6, 151.8, 141.6, 137.3, 135.2, 108.8, 105.3, 99.1, 81.5, 70.1, 55.6, 55.1, 26.7, 14.8; HRMS (ESI) m/z [M+H]$^+$calcd. for C$_{18}$H$_{20}$N$_5$O$_2$S, 370.1338. found 370.1350.

8-(2,5-Dichlorophenylthio)-3-(pent-4-ynyl)-3H-purin-6-amine (30h). Yield, 21%. $^1$H NMR (400 MHz, CDCl$_3$) δ 8.06 (s, 1H), 7.43 (s, 1H), 7.26-7.28 (m, 1H), 7.06-7.08 (m, 1H), 4.50-4.52 (m, 2H), 2.21-2.24 (m, 4H), 2.05-2.06 (m, 1H); $^{13}$C NMR (100 MHz, CDCl$_3$) δ 153.6, 142.6, 132.7, 130.3, 129.7, 127.3, 81.7, 70.6, 49.2, 26.9, 15.2; HRMS (ESI) m/z [M+H]$^+$ calcd. for C$_{16}$H$_{14}$N$_5$Cl$_2$S, 378.0347. found 378.0362.

8-(2,5-Dimethylphenylthio)-3-(pent-4-ynyl)-3H-purin-6-amine (30i). Yield, 20%. $^1$H NMR (400 MHz, CDCl$_3$) δ 7.96 (s, 1H), 7.41 (s, 1H), 7.13 (d, J=7.7 Hz, 1H), 7.04 (d, J=7.7 Hz, 1H), 4.45 (t, J=6.3 Hz, 2H), 2.43 (s, 3H), 2.37 (s, 3H), 2.17-2.27 (m, 3H), 2.04 (m, 2H); $^{13}$C NMR (100 MHz, CDCl$_3$) δ 152.0, 151.2, 141.7, 137.7, 135.9, 134.5, 130.9, 130.2, 129.2, 81.8, 70.5, 48.9, 27.0, 20.8, 20.4, 15.3; HRMS (ESI) m/z [M+H]$^+$ calcd. for C$_{18}$H$_{20}$N$_5$S, 338.1439. found 338.1435.

8-(2-Chloro-5-(trifluoromethyl)phenylthio)-3-(pent-4-ynyl)-3H-purin-6-amine (30j). Yield, 18%. $^1$H NMR (400 MHz, CDCl$_3$/MeOH-d$^4$) δ 8.08 (s, 1H), 7.84 (s, 1H), 7.57 (d, J=8.3 Hz, 1H), 7.47 (d, J=8.4 Hz, 1H), 4.48 (t, J=6.5 Hz, 2H), 2.16-2.26 (m, 4H), 2.09-2.10 (m, 1H); $^{13}$C NMR (100 MHz, CDCl$_3$/MeOH-d4) δ 157.4, 153.2, 150.4, 142.8, 138.2, 134.5, 130.1, 129.4, 128.9, 124.8, 121.9, 81.5, 70.4, 28.3, 26.7, 15.0; MS (ESI): m/z 411.8 [M+H]$^+$.

8-(3,5-Dichlorophenylthio)-3-(pent-4-ynyl)-3H-purin-6-amine (30k). Yield, 14%. $^1$H NMR (400 MHz, CDCl$_3$) δ 8.03 (s, 1H), 7.46 (s, 2H), 7.30 (s, 1H), 4.50-4.52 (m, 2H), 2.20-2.24 (m, 3H), 2.04-2.07 (m, 2H); $^{13}$C NMR (100 MHz, CDCl$_3$/MeOH-d$_4$) δ 157.6, 152.6, 150.8, 142.9, 136.3, 134.8, 128.7, 127.1, 120.4, 81.3, 70.1, 43.8, 26.7, 14.7; HRMS (ESI) m/z [M+H]$^+$ calcd. for C$_{14}$H$_{15}$N$_5$Cl$_2$S, 378.0347. found 378.0340.

8-(3,5-Dimethylphenylthio)-3-(pent-4-ynyl)-3H-purin-6-amine (30l). Yield, 16%. $^1$H NMR (400 MHz, CDCl$_3$/MeOH-d$_4$) δ 8.01 (s, 1H), 7.23 (s, 2H), 7.00 (s, 1H), 4.45 (t, J=7.5 Hz, 2H), 2.26 (s, 6H), 2.21-2.25 (m, 4H), 1.94-1.99 (m, 1H); HRMS (ESI) m/z [M+H]$^+$ calcd. for C$_{18}$H$_{20}$N$_5$S, 338.1439. found 338.1426.

3-(Pent-4-ynyl)-8-(2,4,5-trichlorophenylthio)-3H-purin-6-amine (30m). Yield, 23%. $^1$H NMR (400 MHz, CDCl$_3$/MeOH-d$_4$) δ 8.04 (s, 1H), 7.73 (s, 1H), 7.55 (s, 1H), 4.50 (t, J=6.4 Hz, 2H), 2.08-2.29 (m, 4H), 2.06-2.07 (m, 1H); $^{13}$C NMR (100 MHz, CDCl$_3$/MeOH-d$_4$) δ 159.6, 154.7, 152.4, 144.3, 135.3, 134.9, 134.7, 133.5, 132.9, 132.4, 128.8, 83.4, 72.2, 48.6, 28.6, 16.8; HRMS (ESI) m/z [M+H]$^+$ calcd. for C$_{16}$H$_{13}$N$_5$Cl$_3$S, 411.9957. found 411.9947.

8-(Mesitylthio)-3-(pent-4-ynyl)-3H-purin-6-amine (30n). Yield, 15% $^1$H NMR (400 MHz, CDCl$_3$/MeOH-d$_4$) δ 7.93 (s, 1H), 6.97 (s, 2H), 4.38 (t, J=6.5 Hz, 2H), 2.41 (s, 6H), 2.30 (s, 3H), 2.04-2.16 (m, 5H); $^{13}$C NMR (100 MHz, CDCl$_3$/MeOH-d$_4$) δ 157.4, 150.4, 143.0, 142.2, 139.2, 128.9, 124.8, 81.5, 70.1, 26.7, 21.6, 21.3, 20.5, 14.8; HRMS (ESI) m/z [M+H]$^+$ calcd. for C$_{19}$H$_{22}$N$_5$S, 352.1596. found 352.1594.

6.2.11 Synthesis of Compounds of Formula 32-34 (Scheme 11)

Scheme 11:

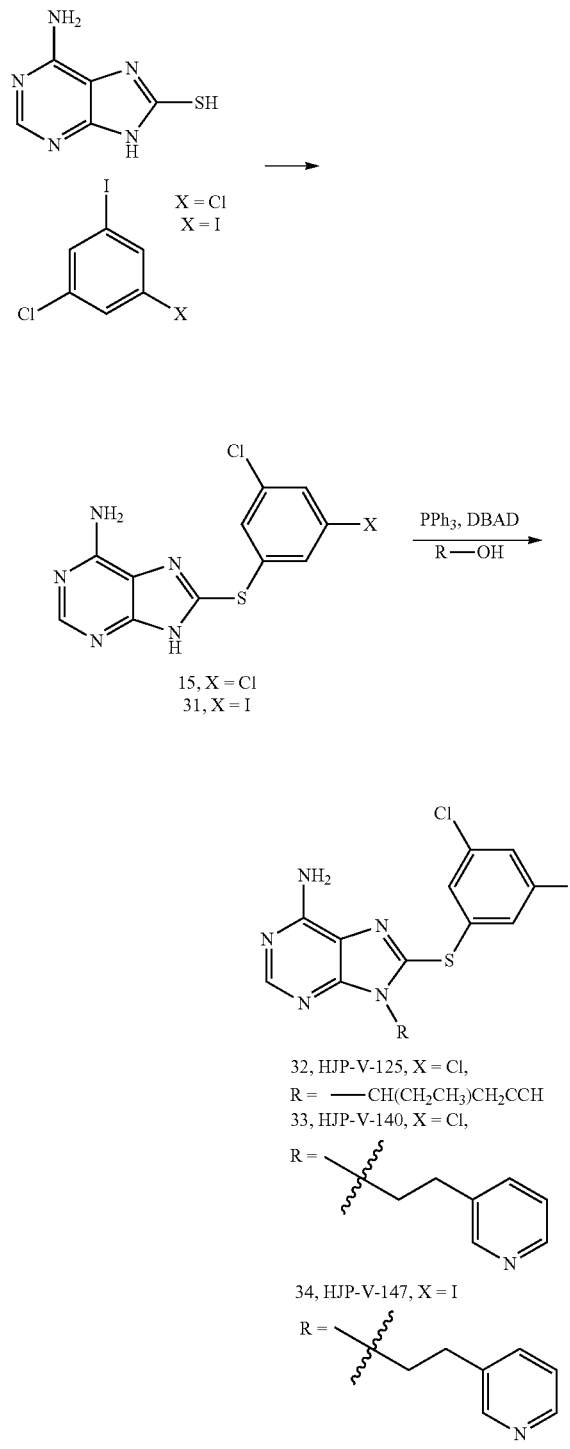

15, X = Cl
31, X = I

32, HJP-V-125, X = Cl,
R = ―CH(CH$_2$CH$_3$)CH$_2$CCH
33, HJP-V-140, X = Cl,

R =

34, HJP-V-147, X = I

R =

8-((3-chloro-5-iodophenyl)thio)-9H-purin-6-amine (31). 8-Mercaptoadenine (3.6 mmol), neocuproine hydrate (0.36 mmol), CuI (0.36 mmol), NaO-t-Bu (7.2 mmol), 1-chloro-3,5-diiodobenzene (10.8 mmol), and anhydrous DMF (24 mL) were taken in a round bottom flask flushed with nitrogen. The flask was sealed with Teflon tape, heated at 110° C., and magnetically stirred for 24 h under nitrogen. Solvent was removed under reduced pressure and the resulting residue was chromatographed (CH$_2$Cl$_2$:MeOH:AcOH, 20:1:0.5). Obtained as a light yellow solid in 67% yield. MS (ESI): m/z 403.7 [M+H]$^+$. Compound 15 was made in a similar manner.

General Procedure for the Synthesis of 32-34

To a suspension of coupled product (15 or 31, 1.0 mmol) in CH$_2$Cl$_2$:toluene (0.5:2.5 mL) were added PPh$_3$ (4.0 mmol) and alcohol (2.0 mmol) under nitrogen protection. After stirring for 10 min. DBAD (6 mmol) was added and reaction mixture was stirred at rt for 2-5 h. Following solvent removal, the crude material was purified by preparative TLC (CH$_2$Cl$_2$:CH$_3$OH:AcOH, 20:1:0.1 or CH$_2$Cl$_2$:NH$_3$—CH$_3$OH (7N), 20:1) to afford desired compounds 32-34.

8-((3,5-dichlorophenyl)thio)-9-(hex-5-yn-3-yl)-9H-purin-6-amine (32, HJP-V-125). Yield, 9.2 mg (37%). $^1$H NMR (600 MHz, CDCl$_3$) δ 8.25 (s, 1H), 7.35-7.37 (m, 2H), 7.33 (t, J=1.7 Hz, 1H), 4.71-4.74 (m, 1H), 3.27-3.33 (m, 1H), 2.80-2.84 (m, 1H), 2.32-2.35 (m, 1H), 2.02-2.05 (m, 1H), 1.84 (t, J=2.5 Hz, 1H), 0.79 (t, J=7.4 Hz, 3H); $^{13}$C NMR (150 MHz, CDCl$_3$) δ 153.6, 150.5, 147.7, 135.8, 133.6, 132.1, 131.9, 129.3, 128.9, 128.4, 79.6, 71.1, 59.9, 26.2, 23.3, 10.9; HRMS (ESI) m/z [M+H]$^+$ calcd. for C$_{17}$H$_{15}$Cl$_2$N$_5$S, 392.0503. found 392.0503.

8-((3,5-dichlorophenyl)thio)-9-(2-(pyridin-3-yl)ethyl)-9H-purin-6-amine (33, HJP-V-140). Yield, 9.6 mg (36.9%). $^1$H NMR (600 MHz, CDCl$_3$) δ 8.33-8.47 (m, 2H), 8.20 (s, 1H), 7.69 (d, J=7.4 Hz, 1H), 7.45-7.55 (m, 1H), 7.39 (t, J=1.7 Hz, 1H), 7.35-7.37 (m, 2H), 4.55 (t, J=7.2 Hz, 2H), 3.27 (t, J=7.0, Hz, 2H); $^{13}$C NMR (150 MHz, CDCl$_3$) δ 150.9, 150.3, 148.8, 146.8, 145.6, 144.9, 139.6, 136.1, 130.9, 130.6, 130.4, 130.0, 119.3, 44.8, 32.8; HRMS (ESI) m/z [M+H]$^+$ calcd. for C$_{18}$H$_{15}$Cl$_2$N$_6$S, 417.0456. found 417.0446.

8-((3-chloro-5-iodophenyl)thio)-9-(2-(pyridin-3-yl)ethyl)-9H-purin-6-amine (34, HJP-V-147). Yield, 8.1 mg (32%). $^1$H NMR (600 MHz, CD$_3$CN) δ 8.57 (d, J=5.5 Hz, 1H), 8.50 (s, 1H), 8.14 (d, J=8.0 Hz, 1H), 7.80 (t, J=1.6 Hz, 1H), 7.70-7.78 (m, 1H), 7.73 (t, J=1.5 Hz, 1H), 7.47 (t, J=1.7 Hz, 1H), 4.58 (t, J=7.4 Hz, 2H), 3.34 (t, J=6.4, Hz, 2H); $^{13}$C NMR (150 MHz, CDCl$_3$) δ 150.5, 150.1, 147.1, 146.1, 144.2, 141.8, 140.4, 137.2, 137.1, 136.8, 134.9, 132.8, 129.8, 126.5, 119.3, 93.8, 44.1, 31.5; HRMS (ESI) m/z [M+H]$^+$ calcd. for C$_{18}$H$_{15}$ICIN$_6$S, 508.9812. found 508.9826.

6.2.12 Synthesis of Compounds of Formula 36-48 (Scheme 12)

Scheme 12:

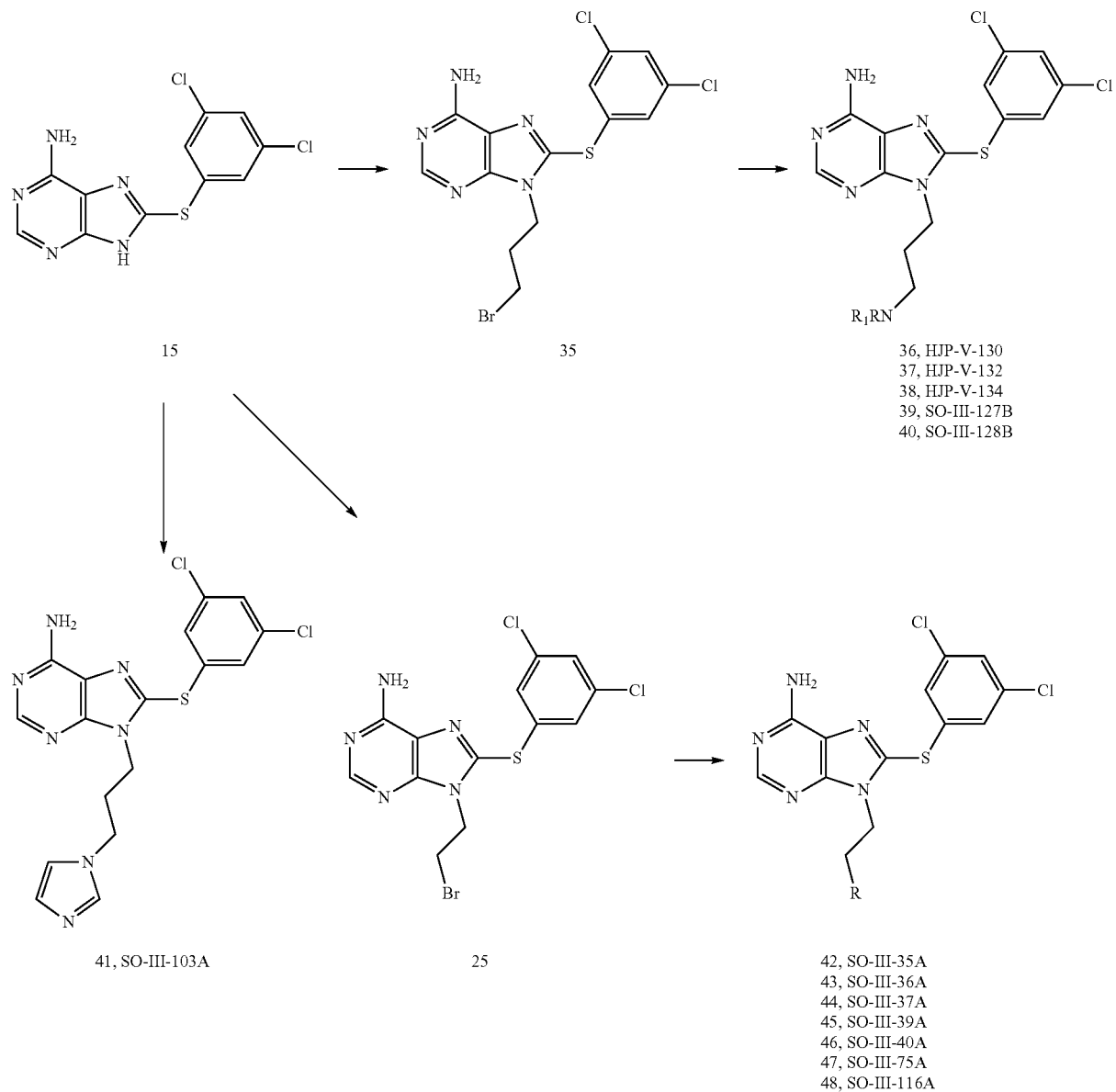

| | |
|---|---|
| 36, HJP-V-130 | |
| 37, HJP-V-132 | |
| 38, HJP-V-134 | |
| 39, SO-III-127B | |
| 40, SO-III-128B | |

41, SO-III-103A

42, SO-III-35A
43, SO-III-36A
44, SO-III-37A
45, SO-III-39A
46, SO-III-40A
47, SO-III-75A
48, SO-III-116A 9-(3-bromopropyl)-8-((3,5-dichlorophenyl)thio)-9H-purin-6-amine (35). Synthesis of compound 35 was done in a manner similar to that of compound 25, except the 1,2-dibromoethane was substituted by 1,3-dibromopropane. Following solvent removal, the crude material was purified by preparatory TLC (CH$_2$Cl$_2$:MeOH:AcOH, 20:1:0.1) to provide desired isomer 35. $^1$H-NMR (600 MHz, CDCl$_3$) δ 8.36 (s, 1H), 7.26-7.31 (m, 3H), 5.68 (br s, 2H), 4.31 (t, J=7.3 Hz, 2H), 3.15 (t, J=6.7 Hz, 2H), 2.28-2.35 (m, 2H); MS (ESI): m/z 432.1 [M+H]$^+$.

General Procedure for the Synthesis of 36-40

A mixture of 35 (0.027 mmol) and amine (1.35 mmol, 50 equiv.) in DMF (1 mL) under nitrogen protection was stirred at room temperature for 16-24 hrs. Following solvent removal, the crude material was purified by preparative TLC (CH$_2$Cl$_2$:CH$_3$OH—NH$_3$ (7N), 20:1 or 15:1) to afford desired products 36-40.

1-((3-(6-amino-8-((3,5-dichlorophenyl)thio)-9H-purin-9-yl)propyl)amino)propan-2-ol (36, HJP-V-130). Yield, 6.1 mg (76%). $^1$H NMR (600 MHz, CDCl$_3$+5 drops CD$_3$OD) δ 8.22 (s, 1H), 7.28-7.33 (m, 3H), 4.27 (t, J=6.9 Hz, 2H), 3.77-3.83 (m, 1H), 2.51-2.62 (m, 3H), 2.37-2.42 (m, 1H), 1.93-1.95 (m, 2H), 1.11 (d, J=6.2 Hz, 3H); $^{13}$C NMR (150 MHz, CDCl$_3$) δ 154.6, 153.1, 151.2, 144.4, 135.9, 133.3, 129.1, 128.9, 119.6, 65.4, 56.5, 45.7, 41.4, 29.4, 20.6; HRMS (ESI) m/z [M+H]$^+$ calcd. for C$_{17}$H$_{21}$Cl$_2$N$_6$OS, 427.0875. found 427.0887.

2-((3-(6-amino-8-((3,5-dichlorophenyl)thio)-9H-purin-9-yl)propyl)(prop-2-yn-1-yl)amino)ethanol (37, HJP-V-132)

Yield, 6.2 mg (60%). ¹H NMR (600 MHz, CD₃CN) δ 8.31 (s, 1H), 7.48 (t, J=1.6 Hz, 1H), 7.49-7.51 (m, 2H), 4.33 (t, J=6.5 Hz, 2H), 3.99-4.05 (m, 2H), 3.78-3.81 (m, 2H), 3.18-3.21 (m, 4H), 2.90 (s, 1H), 2.22-2.28 (m, 2H); ¹³C NMR (150 MHz, CD₃CN) δ 151.3, 150.5, 146.3, 145.9, 135.1, 133.6, 128.7, 128.2, 117.8, 79.1, 71.2, 55.6, 54.9, 50.4, 42.0, 40.8, 23.7; HRMS (ESI) m/z [M+H]⁺ calcd. for C₁₉H₂₁Cl₂N₆OS, 451.0875. found 451.0879.

1-(3-(6-amino-8-((3,5-dichlorophenyl)thio)-9H-purin-9-yl)propyl)azetidin-3-ol (38, HJP-V-134). Yield, 4.2 mg (36%). ¹H NMR (600 MHz, CDCl₃+5 drops CD₃OD) δ 8.27 (s, 1H), 7.37 (t, J=1.7 Hz, 1H), 7.32-7.34 (m, 2H), 4.38-4.44 (m, 1H), 4.28 (t, J=7.2 Hz, 2H), 3.7 (t, J=7.2 Hz, 2H), 3.05 (t, J=7.2 Hz, 2H), 2.59-2.63 (m, 2H), 1.87-1.93 (m, 2H); ¹³C NMR (150 MHz, CDCl₃+5 drops CD₃OD) δ 154.7, 153.2, 151.2, 144.6, 136.0, 122.6, 129.2, 129.0, 119.8, 63.8, 61.4, 55.7, 41.8, 27.2; HRMS (ESI) m/z [M+H]⁺ calcd. for C₁₇H₁₉Cl₂N₆OS, 425.0718. found 425.0718.

(S)-9-(3-((1-cyclopropylethyl)amino)propyl)-8-((3,5-dichlorophenyl)thio)-9H-purin-6-amine (39, SO-III-127B). 9-(3-bromopropyl)-8-((3,5-dichlorophenyl)thio)-9H-purin-6-amine (12 mg, 0.027 mmol) in dry DMF (1 mL) was added (S)-1-cyclopropylethanamine (58.3 μL, 0.554 mmol) and then the reaction mixture was stirred at rt for 4 days. Solvent was removed under reduced pressure and the residue was purified by preparatory TLC (CH₂Cl₂:MeOH—NH₃ (7N), 15:1) to afford 6.0 mg (51%) of SO-III-127B. ¹H NMR (600 MHz, CDCl₃): δ 8.36 (s, 1H), 7.27-7.30 (m, 3H), 5.68 (br s, 2H), 4.31-4.34 (m, 2H), 2.55-2.68 (m, 2H), 1.95-1.99 (m, 2H), 1.75-1.79 (m, 1H), 1.11 (d, J=6.3 Hz, 3H), 0.64-0.69 (m, 1H), 0.46-0.50 (m, 1H), 0.39-0.42 (m, 1H), 0.13-0.17 (m, 1H), 0.02-0.06 (m, 1H). ¹³C NMR (150 MHz, CDCl₃): δ 154.6, 153.4, 151.6, 143.6, 135.8, 134.7, 128.4, 128.0, 120.3, 58.9, 43.9, 41.8, 30.4, 20.6, 17.7, 4.6, 1.7. HRMS (ESI) m/z [M+H]⁺ calcd. for C₁₉H₂₃N₆SCl₂, 437.1082. found 437.1083.

(R)-9-(3-((1-cyclopropylethyl)amino)propyl)-8-((3,5-dichlorophenyl)thio)-9H-purin-6-amine (40, SO-III-128B). 9-(3-bromopropyl)-8-((3,5-dichlorophenyl)thio)-9H-purin-6-amine (12 mg, 0.027 mmol) in dry DMF (1 mL) was added (R)-1-cyclopropylethanamine (58.3 μL, 0.554 mmol) and then the reaction mixture was stirred at rt for 4 days. Solvent was removed under reduced pressure and the residue was purified by preparatory TLC (CH₂Cl₂:MeOH—NH₃ (7N), 15:1) to afford 6.1 mg (52%) of SO-III-128B. ¹H NMR (600 MHz, CDCl₃): δ 8.36 (s, 1H), 7.27-7.30 (m, 3H), 5.68 (br s, 2H), 4.31-4.34 (m, 2H), 2.55-2.68 (m, 2H), 1.95-1.99 (m, 2H), 1.75-1.79 (m, 1H), 1.11 (d, J=6.3 Hz, 3H), 0.64-0.69 (m, 1H), 0.46-0.50 (m, 1H), 0.39-0.42 (m, 1H), 0.13-0.17 (m, 1H), 0.02-0.06 (m, 1H). ¹³C NMR (150 MHz, CDCl₃): δ 154.6, 153.4, 151.6, 143.6, 135.8, 134.7, 128.4, 128.0, 120.3, 58.9, 43.9, 41.8, 30.4, 20.6, 17.7, 4.6, 1.7. HRMS (ESI) m/z [M+H]⁺ calcd. for C₁₉H₂₃N₆SCl₂, 437.1082. found 437.1077.

9-(3-(1H-imidazol-1-yl)propyl)-8-((3,5-dichlorophenyl)thio)-9H-purin-6-amine (41, SO-III-103A). To 8-(3,5-dichlorophenyl)thio)-9H-purin-6-amine (60 mg, 0.192 mmol) in dry DMF (3 mL) was added Cs₂CO₃ (75 mg, 0.230 mmol) and 1-(3-bromopropyl)-1H-imidazole (181 mg, 0.96 mmol) and then the reaction mixture was stirred at rt for 2 hours. Then another portion of Cs₂CO₃ (20 mg) was added to the reaction mixture which was further stirred for one more hour. Solvent was removed under reduced pressure and the residue was purified by preparatory TLC (CH₂Cl₂:MeOH—NH₃ (7N), 10:1) to afford 4.9 mg (6%) of SO-III-103A. ¹H NMR (600 MHz, CDCl₃): δ 8.38 (s, 1H), 7.64 (s, 1H), 7.32 (t, J=1.8 Hz, 1H), 7.24 (d, J=1.8 Hz, 2H), 7.12 (m, 1H), 6.97 (m, 1H), 5.68 (br s, 2H), 4.23 (t, J=7.0 Hz, 2H), 4.02 (t, J=7.0 Hz, 2H), 2.27 (m, 2H). ¹³C NMR (150 MHz, CDCl₃): δ 154.7, 153.7, 151.6, 143.3, 137.1, 135.9, 134.0, 129.6, 128.7, 128.2, 120.2, 118.7, 44.2, 40.9, 31.1. HRMS (ESI) m/z [M+H]⁺calcd. for C₁₇H₁₆N₇SCl₂, 420.0565. found 420.0555.

9-(2-(cyclopropylamino)ethyl)-8-((3,5-dichlorophenyl)thio)-9H-purin-6-amine (42, SO-III-35A). To 9-(2-bromoethyl)-8-((3,5-dichlorophenyl)thio)-9H-purin-6-amine (10 mg, 0.0238 mmol) in dry DMF (1 mL) was added cyclopropylamine (8.26 μL, 0.119 mmol) and then the reaction mixture was stirred at rt for 24 h. Then to the reaction mixture was added more cyclopropylamine (17.3 μL, 0.25 mmol) and the reaction was further stirred at rt for 48 h. Solvent was removed under reduced pressure and the residue was purified by preparatory TLC (CH₂Cl₂:MeOH—NH₃ (7N), 30:1) to afford 6.0 mg (64%) of SO-III-35A. ¹H NMR (600 MHz, CDCl₃): δ 8.37 (s, 1H), 7.27-7.29 (m, 3H), 5.6 (br s, 2H), 4.35 (t, J=6.4 Hz, 2H), 3.08 (t, J=6.4 Hz, 2H), 2.14 (m, 1H), 0.39 (m, 2H), 0.23 (m, 2H). ¹³C NMR (150 MHz, CDCl₃): δ 154.7, 153.5, 151.6, 144.0, 135.7, 135.1, 128.2, 127.9, 120.3, 48.4, 44.1, 30.1, 6.5. HRMS (ESI) m/z [M+H]⁺ calcd. for C₁₆H₁₇N₆SCl₂, 395.0612. found 395.0626.

(R)-9-(2-((1-cyclopropylethyl)amino)ethyl)-8-((3,5-dichlorophenyl)thio)-9H-purin-6-amine (43, SO-III-36A). To 9-(2-bromoethyl)-8-((3,5-dichlorophenyl)thio)-9H-purin-6-amine (10 mg, 0.0238 mmol) in dry DMF (1 mL) was added (R)-1-cyclopropylethanamine (12.7 μL, 0.119 mmol) and then the reaction mixture was stirred at rt for 24 h. Then to the reaction mixture was added more (R)-1-cyclopropylethanamine (12.7 μL, 0.119 mmol) and the reaction was further stirred at rt for 24 h. Solvent was removed under reduced pressure and the residue was purified by preparatory TLC (CH₂Cl₂:MeOH—NH₃ (7N), 30:1) to afford 5.7 mg (57%) of SO-III-36A. ¹H NMR (500 MHz, CDCl₃:CD₃OD): δ 8.27 (s, 1H), 7.33-7.35 (m, 3H), 4.35 (t, J=6.6 Hz, 2H), 3.03-3.07 (m, 1H), 2.95-3.0 (m, 1H), 1.87 (m, 1H), 1.09 (d, J=6.3 Hz, 3H), 0.63 (m, 1H), 0.40-0.47 (m, 2H), 0.13 (m, 1H), 0.04 (m, 1H). ¹³C NMR (150 MHz, CDCl₃:CD₃OD): δ 154.8, 153.2, 151.3, 144.9, 136.0, 134.1, 129.1, 128.9, 119.9, 58.6, 46.1, 44.2, 20.3, 17.3, 4.6, 1.7. HRMS (ESI) m/z [M+H]⁺ calcd. for C₁₈H₂₁N₆SCl₂, 423.0925. found 423.0909.

(S)-9-(2-((1-cyclopropylethyl)amino)ethyl)-8-((3,5-dichlorophenyl)thio)-9H-purin-6-amine (44, SO-III-37A). To 9-(2-bromoethyl)-8-((3,5-dichlorophenyl)thio)-9H-purin-6-amine (10 mg, 0.0238 mmol) in dry DMF (1 mL) was added (S)-1-cyclopropylethanamine (12.7 μL, 0.119 mmol) and then the reaction mixture was stirred at rt for 24 h. Then to the reaction mixture was added more (S)-1-cyclopropylethanamine (12.7 μL, 0.119 mmol) and the reaction was further stirred at rt for 24 h. Solvent was removed under reduced pressure and the residue was purified by preparatory TLC (CH₂Cl₂:MeOH—NH₃ (7N), 30:1) to afford 6.4 mg (64%) of SO-III-37A. ¹H NMR (500 MHz, CDCl₃:CD₃OD): δ 8.27 (s, 1H), 7.33-7.35 (m, 3H), 4.35 (t, J=6.6 Hz, 2H), 3.03-3.07 (m, 1H), 2.95-3.0 (m, 1H), 1.87 (m, 1H), 1.09 (d, J=6.3 Hz, 3H), 0.63 (m, 1H), 0.40-0.47 (m, 2H), 0.13 (m, 1H), 0.04 (m, 1H). ¹³C NMR (150 MHz, CDCl₃:CD₃OD): δ 154.8, 153.2, 151.3, 144.9, 136.0, 134.1, 129.1, 128.9, 119.9, 58.6, 46.1, 44.2, 20.3, 17.3, 4.6, 1.7. HRMS (ESI) m/z [M+H]⁺ calcd. for C₁₈H₂₁N₆SCl₂, 423.0925. found 423.0909.

8-((3,5-dichlorophenyl)thio)-9-(2-(4-methylpiperazin-1-yl)ethyl)-9H-purin-6-amine (45, SO-III-39A). To 9-(2-bromoethyl)-8-((3,5-dichlorophenyl)thio)-9H-purin-6-amine (10 mg, 0.0238 mmol) in dry DMF (1 mL) was added 1-methylpiperazine (51 µL, 0.46 mmol) and then the reaction mixture was stirred at rt for 48 h. Solvent was removed under reduced pressure and the residue was purified by preparatory TLC (CH$_2$Cl$_2$:MeOH—NH$_3$ (7N), 15:1) to afford 8 mg (77%) of SO-III-39A. $^1$H NMR (600 MHz, CDCl$_3$): δ 8.36 (s, 1H), 7.27 (m, 1H), 7.24 (m, 2H), 5.69 (br s, 2H), 4.35 (t, J=6.2 Hz, 2H), 2.71 (t, J=6.2 Hz, 2H), 2.48-2.58 (m, 4H), 2.32-2.42 (m, 4H), 2.26 (s, 3H). $^{13}$C NMR (150 MHz, CDCl$_3$): δ 154.7, 153.4, 151.4, 144.0, 135.8, 135.7, 128.0, 127.6, 120.5, 56.9, 54.9, 53.2, 45.9, 41.4. HRMS (ESI) m/z [M+H]$^+$ calcd. for C$_{18}$H$_{22}$N$_7$SCl$_2$, 438.1034. found 438.1024.

9-(2-((2-cyclopropylpropan-2-yl)amino)ethyl)-8-((3,5-dichlorophenyl)thio)-9H-purin-6-amine (46, SO-III-40A). To 9-(2-bromoethyl)-8-((3,5-dichlorophenyl)thio)-9H-purin-6-amine (10 mg, 0.023 mmol) in dry DMF (1 mL) was added 2-Cyclopropyl-2-propylamine p-toluenesulfonate salt (125 mg, 0.46 mmol) and Et$_3$N (50 µL) then the reaction mixture was stirred at rt for 10 days. Solvent was removed under reduced pressure and the residue was purified by preparatory TLC (CH$_2$Cl$_2$:MeOH—NH$_3$ (7N), 10:1) to afford 3.8 mg (38%) of SO-III-40A. $^1$H NMR (600 MHz, CDCl$_3$:CD$_3$OD): δ 8.26 (s, 1H), 7.35-7.37 (m, 3H), 4.47 (m, 2H), 2.99 (m, 2H), 0.91 (s br, 6H), 0.88 (m, 1H), 0.39 (m, 2H), 0.24 (m, 2H). HRMS (ESI) m/z [M+H]$^+$ calcd. for C$_{19}$H$_{23}$N$_6$SCl$_2$, 437.1082. found 437.1090.

8-((3,5-dichlorophenyl)thio)-9-(2-((2-methoxypropyl)amino)ethyl)-9H-purin-6-amine (47, SO-III-75A). To 9-(2-bromoethyl)-8-((3,5-dichlorophenyl)thio)-9H-purin-6-amine (10 mg, 0.023 mmol) in dry DMF (2 mL) was added 2-methoxy-1-propanamine hydrochloride (24.5 mg, 0.195 mmol), Et$_3$N (50 µL) and the reaction mixture was stirred at rt for 3 days. Solvent was removed under reduced pressure and the residue was purified by preparatory TLC (CH$_2$Cl$_2$:MeOH—NH$_3$ (7N), 20:1) to afford 9.0 mg (92%) of SO-III-75A. $^1$H NMR (600 MHz, CDCl$_3$): δ 8.36 (s, 1H), 7.25-7.28 (m, 3H), 5.93 (br s, 2H), 4.35 (t, J=6.4 Hz, 2H), 3.34-3.37 (m, 1H), 3.29 (s, 3H), 2.95-3.03 (m, 2H), 2.55-2.58 (m, 2H), 1.07 (d, J=6.2 Hz, 3H). $^{13}$C NMR (150 MHz, CDCl$_3$): δ 154.8, 153.4, 151.5, 144.0, 135.7, 135.3, 128.1, 127.8, 120.4, 75.9, 56.2, 55.1, 48.7, 43.9, 16.9. HRMS (ESI) m/z [M+H]$^+$ calcd. for C$_{17}$H$_{21}$N$_6$OSCl$_2$, 427.0875. found 427.0860.

8-((3,5-dichlorophenyl)thio)-9-(2-(isopropylamino)ethyl)-9H-purin-6-amine (48, SO-III-116A). To 9-(2-bromoethyl)-8-((3,5-dichlorophenyl)thio)-9H-purin-6-amine (20 mg, 0.047 mmol) in dry DMF (2 mL) was added isopropylamine (121 µL, 1.41 mmol) and the reaction mixture was stirred at rt for 72 hours. Solvent was removed under reduced pressure and the residue was purified by preparatory TLC (CH$_2$Cl$_2$:MeOH—NH$_3$ (7N), 20:1) to afford 12.6 mg (68%) of SO-III-116A. $^1$H NMR (600 MHz, CDCl$_3$): δ 8.36 (s, 1H), 7.26-7.28 (m, 3H), 5.82 (br s, 2H), 4.34 (t, J=6.5 Hz, 2H), 2.97 (t, J=6.5 Hz, 2H), 2.74-2.76 (m, 1H), 0.96 (d, J=6.2 Hz, 6H). $^{13}$C NMR (150 MHz, CDCl$_3$): δ 154.8, 153.5, 151.5, 144.0, 135.7, 135.3, 128.1, 127.8, 120.4, 48.5, 46.1, 44.5, 22.8. HRMS (ESI) m/z [M+H]$^+$ calcd. for C$_{16}$H$_{19}$N$_6$SCl$_2$, 397.0769. found 397.0765.

6.2.13 Synthesis of Compounds of Formula 51 (Scheme 13a)

Scheme 13a:

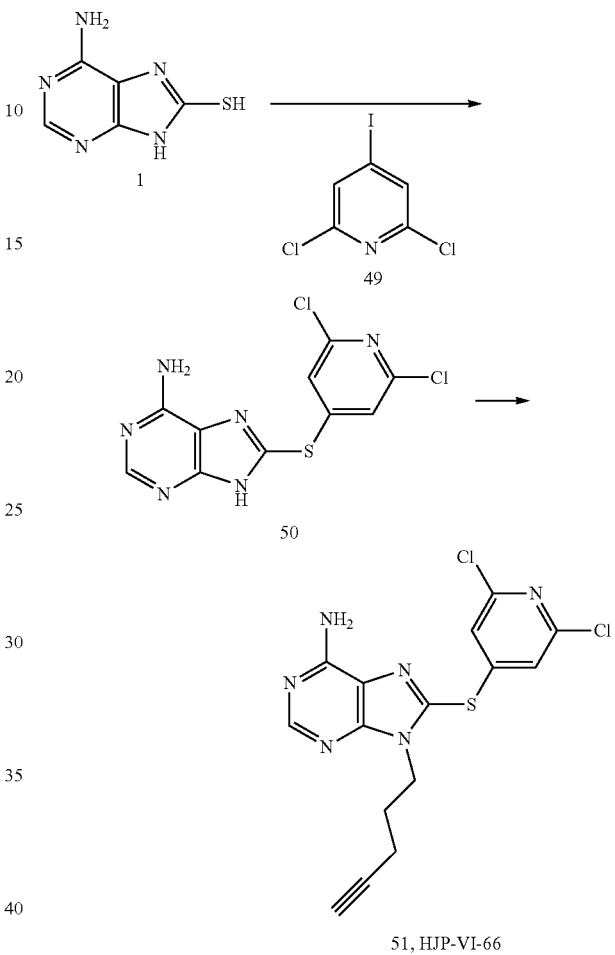

51, HJP-VI-66

8-((2,6-dichloropyridin-4-yl)thio)-9H-purin-6-amine (50). 8-Mercaptoadenine (3.6 mmol), neocuproine hydrate (0.36 mmol), CuI (0.36 mmol), NaO-t-Bu (7.2 mmol), 2,6-dichloro-4-iodopyridine (10.8 mmol), and anhydrous DMF (24 mL) were taken in a round bottom flask flushed with nitrogen. The flask was sealed with Teflon tape, heated at 110° C., and magnetically stirred for 24 h under nitrogen. Solvent was removed under reduced pressure and the resulting residue was chromatographed (CH$_2$Cl$_2$:MeOH:AcOH, 20:1:0.5). Obtained as a light yellow solid in 50% yield. MS (ESI): m/z 312.8 [M+H]$^+$.

8-((2,6-dichloropyridin-4-yl)thio)-9-(pent-4-yn-1-yl)-9H-purin-6-amine (51, HJP-VI-66). 8-Arylsulfanyl adenine (1.21 mmol) was dissolved in DMF (15 mL) and Cs$_2$CO$_3$ (1.45 mmol) and 5-chloropent-1-yne (2.42 mmol) were added and the mixture was stirred under nitrogen at for 3 h. Solvent was removed under reduced pressure and the resulting residue was purified by Preparative chromatography (CH$_2$Cl$_2$:MeOH:AcOH, 20:1:0.5) to afford desired compound HJP-VI-66. Obtained as a solid in 22% yield. $^1$H NMR (600 MHz, CDCl$_3$+5 drops of CD$_3$OD): δ 8.32 (s, 1H), 7.47 (s, 1H), 7.18 (s, 1H), 4.38 (t, J=7.2 Hz, 2H), 2.26-2.29 (m, 2H), 2.03-2.05 (m, 3H), 0.13 (m, 1H), 0.04 (m, 1H). $^{13}$C NMR (150 MHz, CDCl$_3$:CD$_3$OD): δ 159.3, 157.6, 155, 154.9, 153.9, 124.4, 124.3, 85.8, 73.6, 47.3, 41.7, 32.3, 19.7; HRMS (ESI) m/z [M+H]+ calcd. for C$_{15}$H$_{13}$N$_{6}$SCl$_{2}$, 379.0299. found 379.0312.

6.2.13 Synthesis of Compounds of Formula 53-56 (Scheme 13b)

8-((3-chloro-5-iodophenyl)thio)-9-(3-(isopropylamino)propyl)-9H-purin-6-amine (53, HJP-V-149). Yield, 9.5 mg (83%). $^1$H NMR (600 MHz, CDCl$_3$) δ 8.34 (s, 1H), 7.62 (t, J=1.4 Hz, 1H), 7.60 (t, J=1.6 Hz, 1H), 7.34 (t, J=1.7 Hz, 1H), 6.13 (br s, 2H), 4.32 (t, J=7.0 Hz, 2H), 2.67-2.73 (m, 1H), Scheme 13b:

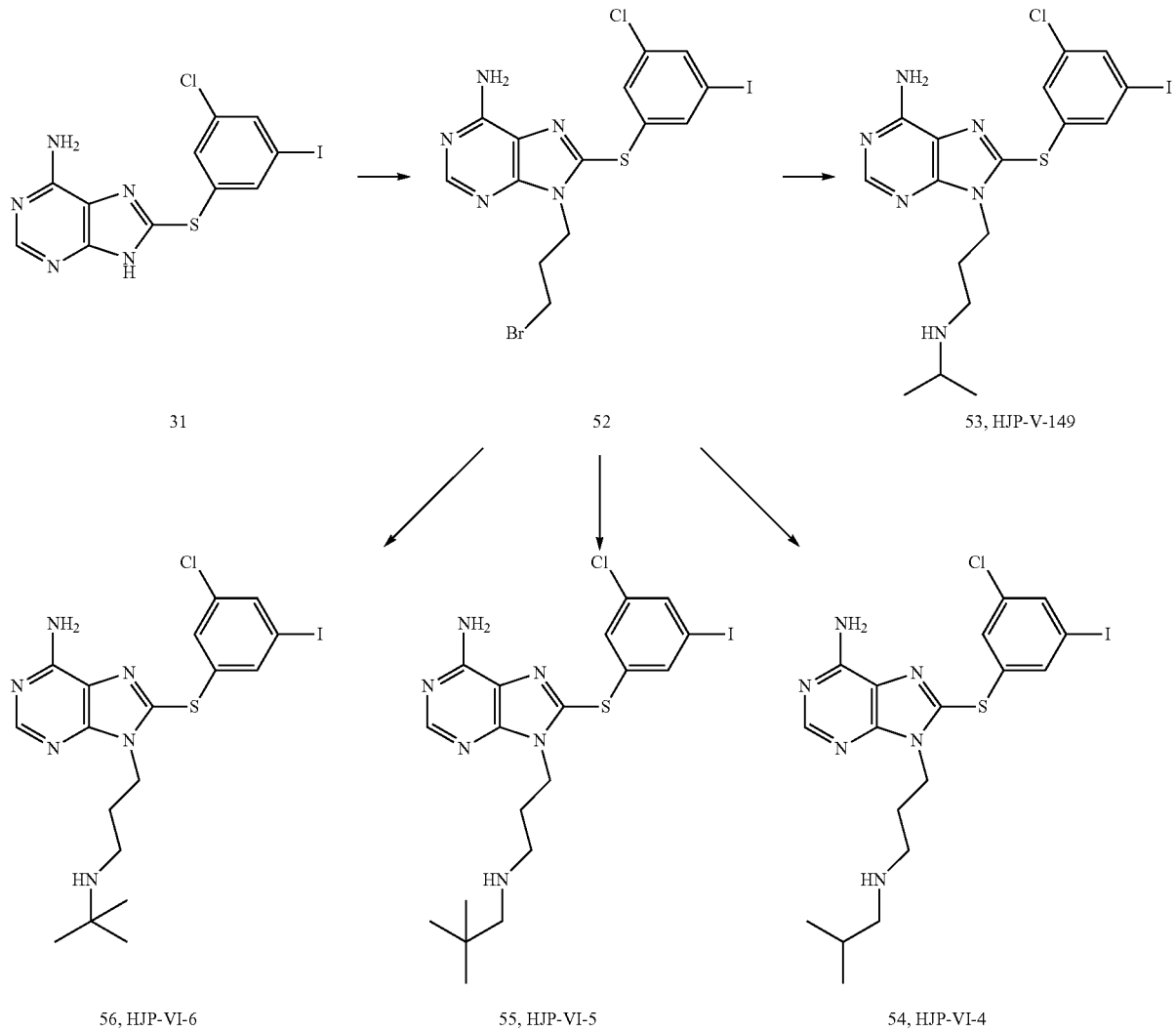

9-(3-bromopropyl)-8-((3-chloro-5-iodophenyl)thio)-9H-purin-6-amine (52). 8-Arylsulfanyl adenine (1.21 mmol) was dissolved in DMF (15 mL) and Cs$_2$CO$_3$ (1.45 mmol) and 1,3-dibromopropane (2.42 mmol) were added and the mixture was stirred under nitrogen at for 2-4 h. Solvent was removed under reduced pressure and the resulting residue was chromatographed (CH$_2$Cl$_2$:MeOH:AcOH, 20:1:0.5) to afford desired compound 52. Obtained as a solid in 25% yield. MS (ESI): m/z 523.9 [M+H]+.

General Procedure for the Synthesis of 53-56

A mixture of 52 (12 mg, 0.028 mmol) and amine (1.40 mmol, 50 equiv.) in DMF (1 mL) under nitrogen protection was stirred at room temperature for 16-24 hrs. Following solvent removal, the crude material was purified by preparative TLC (CH$_2$Cl$_2$:CH$_3$OH—NH$_3$ (7N), 20:1 or 15:1) to afford desired products 53-56.

2.55 (t, J=6.7 Hz, 2H), 1.92-1.98 (m, 2H), 1.03 (d, J=6.2 Hz, 6H); $^{13}$C NMR (150 MHz, CDCl$_3$) δ 154.8, 153.4, 151.6, 143.6, 136.7, 136.6, 135.7, 134.7, 129.3, 120.2, 94.4, 48.7, 43.8, 41.8, 30.3, 22.9; HRMS (ESI) m/z [M+H]+ calcd. for C$_{17}$H$_{21}$ICIN$_6$S, 503.0282. found 503.0260.

8-((3-chloro-5-iodophenyl)thio)-9-(3-(isobutylamino)propyl)-9H-purin-6-amine (54, HJP-VI-4). Yield, 10.2 mg (85%). $^1$H NMR (600 MHz, CDCl$_3$+5 drops CD$_3$OD) δ 8.26 (s, 1H), 7.70 (t, J=1.6 Hz, 1H), 7.68 (t, J=1.6 Hz, 1H), 7.40 (t, J=1.7 Hz, 1H), 4.30 (t, J=7.0 Hz, 2H), 2.55 (t, J=6.9, Hz, 2H), 2.35 (d, J=6.9 Hz, 2H), 1.95-2.01 (m, 2H), 1.72-1.79 (m, 1H), 0.92 (d, J=6.7 Hz, 6H); HRMS (ESI) m/z [M+H]+ calcd. for C$_{18}$H$_{23}$ICIN$_6$S, 517.0438. found 517.0457.

8-((3-chloro-5-iodophenyl)thio)-9-(3-(neopentylamino)propyl)-9H-purin-6-amine (55, HJP-VI-5). Yield, 10.3 mg (85%). $^1$H NMR (600 MHz, CDCl$_3$+5 drops CD$_3$OD) δ 8.24 (s, 1H), 7.72 (t, J=1.5 Hz, 1H), 7.69 (t, J=1.4 Hz, 1H), 7.41

(t, J=1.6 Hz, 1H), 4.31 (t, J=7.0 Hz, 2H), 2.60 (t, J=6.8 Hz, 2H), 2.33 (s, 2H), 1.99-2.05 (m, 2H), 0.95 (s, 9H); $^{13}$C NMR (150 MHz, CDCl$_3$+5 drops CD$_3$OD) δ 158.6, 156.8, 155.1, 148.6, 141.7, 141.3, 139.8, 137.3, 134.3, 123.6, 65.8, 50.8, 45.5, 35.1, 32.9, 31.6; HRMS (ESI) m/z [M+H]$^+$ calcd. for C$_{19}$H$_{25}$ICIN$_6$S, 531.0595. found 531.0587.

9-(3-(tert-butylamino)propyl)-8-((3-chloro-5-iodophenyl)thio)-9H-purin-6-amine (56, HJP-VI-6). Yield, 10.8 mg (91.5%). $^1$H NMR (600 MHz, CDCl$_3$+5 drops CD$_3$OD) δ 8.26 (s, 1H), 7.72 (t, J=1.4 Hz, 1H), 7.70 (t, J=1.4 Hz, 1H), 7.43 (t, J=1.7 Hz, 1H), 4.35 (t, J=6.9 Hz, 2H), 2.64 (t, J=6.5 Hz, 2H), 2.09-2.13 (m, 2H), 1.20 (s, 9H); $^{13}$C NMR (150 MHz, CDCl$_3$+5 drops CD$_3$OD) δ 154.7, 152.8, 151.3, 144.9, 138.0, 137.6, 135.9, 133.1, 130.7, 119.6, 94.6, 53.1, 41.3, 38.4, 29.1, 27.6; HRMS (ESI) m/z [M+H]$^+$ calcd. for C$_{19}$H$_{25}$ICIN$_6$S, 531.0595. found 531.0587.

6.2.14 Synthesis of Compounds of Formula 57-87 (Scheme 14)

Scheme 14:

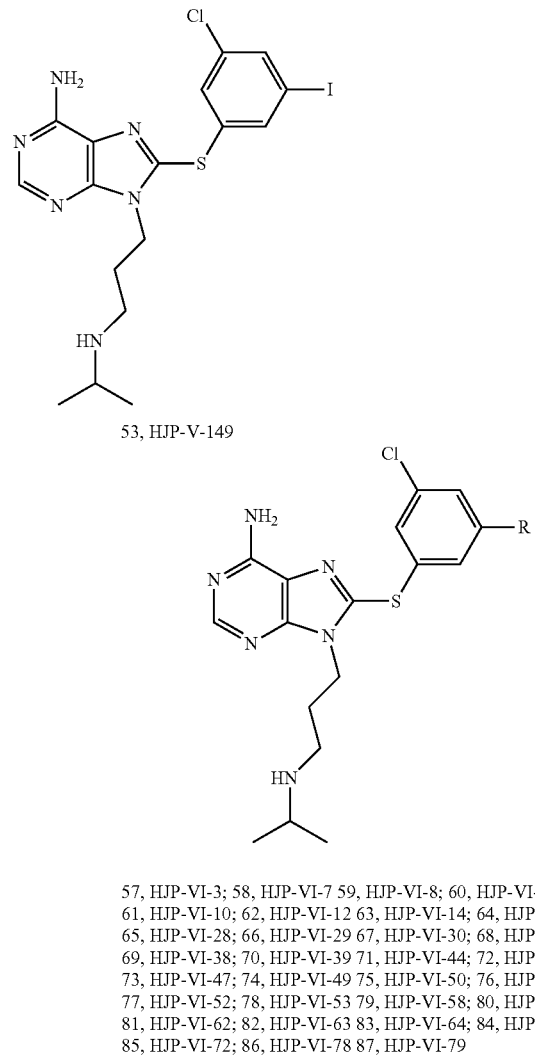

53, HJP-V-149

57, HJP-VI-3; 58, HJP-VI-7 59, HJP-VI-8; 60, HJP-VI-9
61, HJP-VI-10; 62, HJP-VI-12 63, HJP-VI-14; 64, HJP-VI-18
65, HJP-VI-28; 66, HJP-VI-29 67, HJP-VI-30; 68, HJP-VI-31
69, HJP-VI-38; 70, HJP-VI-39 71, HJP-VI-44; 72, HJP-VI-46
73, HJP-VI-47; 74, HJP-VI-49 75, HJP-VI-50; 76, HJP-VI-51
77, HJP-VI-52; 78, HJP-VI-53 79, HJP-VI-58; 80, HJP-VI-59
81, HJP-VI-62; 82, HJP-VI-63 83, HJP-VI-64; 84, HJP-VI-70
85, HJP-VI-72; 86, HJP-VI-78 87, HJP-VI-79

General Conditions:

Method A: Boronic acid or pinacol ester (1.5-3 eq.) was added to HJP-V-149 (53, 15 mg, 0.0298 mmol, 1 eq.) and NaHCO$_3$ (3 eq.) in a 10 mL RBF equipped with a magnetic stir bar and rubber septum. DMF (0.5 mL) was added and the reaction mixture was evacuated and back filled with nitrogen. This was repeated four times then nitrogen was bubbled through the reaction mixture for 10 min. Then H$_2$O (0.1 mL) and PdCl$_2$(PPh$_3$)$_2$ (10-20 mol %) were added and the reaction mixture was heated under nitrogen at 90° C. for 2-24 h. Solvent was removed under reduced pressure and the resulting residue was purified by preparatory TLC to yield desired compounds 57-63, 65-73, 81-85, 87.

Method B: A mixture of HJP-V-149 (15 mg, 0.0298 mmol, 1 eq.), (n-Bu)$_3$SnR (4 eq.), LiCl (2 eq.) and Pd(PPh$_3$)$_4$ (10-20 mol %) in DMF (1 mL) in a 10 mL RBF equipped with a magnetic stir bar and rubber septum was evacuated and back filled with nitrogen. This was repeated four times then the reaction mixture was heated under nitrogen at 90-100° C. for 18 h. Solvent was removed under reduced pressure and the resulting residue was purified by preparatory TLC to yield compounds 74 (HJP-VI-49), and 86 (HJP-VI-78).

Method C: To a solution of HJP-V-149 (15 mg, 0.0298 mmol, 1 eq.) in DMF (2 mL) in a sealed tube flushed with argon was added CuI (0.5 eq.), PdCl$_2$(PPh$_3$)$_2$ (15 mol %), alkyne (2-2.5 eq.) and triethylamine (5 eq.). The reaction mixture was heated at 90-100° C. for 24 h. Solvent was removed under reduced pressure and the resulting residue was purified by preparatory TLC to yield compounds 76 (HJP-VI-51), 77 (HJP-VI-52), 78 (HJP-VI-53), 64 (HJP-VI-18), 75 (HJP-VI-50), 79 (HJP-VI-58), 80 (HJP-VI-59).

8-((5-chloro-4'-methoxy-[1,1'-biphenyl]-3-yl)thio)-9-(3-(isopropylamino)propyl)-9H-purin-6-amine (57, HJP-VI-3). Yield, 9.6 mg (67%). $^1$H NMR (600 MHz, CDCl$_3$+5 drops CD$_3$OD) δ 8.22 (s, 1H), 7.65 (t, J=1.6 Hz, 1H), 7.60 (t, J=1.7 Hz, 1H), 7.52 (d, J=8.8, Hz, 2H), 7.44 (t, J=1.7 Hz, 1H), 7.01 (d, J=8.8, Hz, 2H), 4.42 (t, J=6.9 Hz, 2H), 3.86 (s, 3H), 3.30-3.34 (m, 1H), 3.01 (t, J=7.3 Hz, 2H), 2.27-2.31 (m, 2H), 1.37 (d, J=6.5 Hz, 6H); HRMS (ESI) m/z [M+H]$^+$ calcd. for C$_{24}$H$_{28}$ClN$_6$OS, 483.1734. found 483.1713.

8-((5-chloro-3'-methoxy-[1,1'-biphenyl]-3-yl)thio)-9-(3-(isopropylamino)propyl)-9H-purin-6-amine (58, HJP-VI-7). Yield, 5.1 mg (35%). $^1$H NMR (600 MHz, CDCl$_3$) δ 8.32 (s, 1H), 7.65 (t, J=1.6 Hz, 1H), 7.52 (t, J=1.6 Hz, 1H), 7.50 (t, J=1.7, Hz, 1H), 7.37 (t, J=1.7 Hz, 1H), 7.35 (t, J=7.9, Hz, 1H), 7.08 (d, J=7.6 Hz, 1H), 7.02 (s, 1H), 6.92 (dd, J=8.2 and 1.9 Hz, 1H), 5.72 (br s, 2H), 4.35 (t, J=6.9 Hz, 2H), 3.84 (s, 3H), 2.74-2.79 (m, 1H), 2.58 (t, J=6.7 Hz, 2H), 2.01-2.06 (m, 2H), 1.07 (d, J=6.2 Hz, 6H); $^{13}$C NMR (150 MHz, CDCl$_3$) δ 160.0, 154.6, 153.1, 151.7, 144.9, 144.0, 140.0, 135.6, 132.9, 130.1, 129.0, 127.6, 127.4, 120.1, 119.5, 113.8, 112.8, 55.4, 49.1, 43.4, 41.5, 29.6, 22.3; HRMS (ESI) m/z [M+H]$^+$ calcd. for C$_{24}$H$_{28}$ClN$_6$OS, 483.1734. found 483.1721.

8-((5-chloro-3'-nitro-[1,1'-biphenyl]-3-yl)thio)-9-(3-(isopropylamino)propyl)-9H-purin-6-amine (59, HJP-VI-8). Yield, 11.8 mg (78%). $^1$H NMR (600 MHz, CDCl$_3$) δ 8.40 (s, 1H), 8.33 (s, 1H), 8.25 (d, J=8.0 Hz, 1H), 7.85 (d, J=7.9 Hz, 1H), 7.65 (s, 1H), 7.63 (t, J=8.0 Hz, 1H), 7.54 (s, 1H), 7.46 (s, 1H), 5.82 (br s, 2H), 4.36 (t, J=6.9 Hz, 2H), 2.70-2.74 (m, 1H), 2.58 (t, J=6.8, Hz, 2H), 1.98-2.04 (m, 2H), 1.03 (d, J=6.2 Hz, 6H); $^{13}$C NMR (150 MHz, CDCl$_3$) δ 154.6, 153.2, 151.6, 148.7, 144.5, 141.4, 140.3, 136.0, 133.9, 132.9, 130.1, 130.0, 127.5, 127.2, 123.2, 122.1, 120.1, 48.8, 43.7, 41.7, 30.2, 22.8; HRMS (ESI) m/z [M+H]$^+$ calcd. for C$_{23}$H$_{25}$ClN$_7$O$_2$S, 498.1479. found 498.1483.

8-((5-chloro-3'-(trifluoromethyl)-[1,1'-biphenyl]-3-yl)thio)-9-(3-(isopropylamino)propyl)-9H-purin-6-amine (60, HJP-VI-9). Yield, 9.0 mg (59%). $^1$H NMR (600 MHz, CDCl$_3$) δ 8.33 (s, 1H), 7.76 (s, 1H), 7.69 (d, J=7.7 Hz, 1H), 7.65 (d, J=7.7 Hz, 1H), 7.55-7.59 (m, 2H), 7.51 (t, J=1.7 Hz, 1H), 7.42 (t, J=1.7 Hz, 1H), 5.74 (br s, 2H), 4.35 (t, J=6.9 Hz, 2H), 2.72-2.77 (m, 1H), 2.58 (t, J=6.7 Hz, 2H), 1.99-2.05 (m, 2H), 1.04 (d, J=6.2 Hz, 6H); $^{13}$C NMR (150 MHz, CDCl$_3$) δ 154.6, 153.2, 151.7, 144.7, 142.6, 139.4, 135.8, 133.6, 131.5 (q, J$_{C-F}$=32.1 Hz), 130.4, 129.62, 129.61, 127.5, 127.3, 125.1 (q, J$_{C-F}$=3.5 Hz), 123.94 (q, J$_{C-F}$=3.8 Hz), 123.87 (q, J$_{C-F}$=270.8 Hz) 120.1, 48.9, 43.6, 41.6, 29.9, 22.5; HRMS (ESI) m/z [M+H]$^+$ calcd. for C$_{24}$H$_{25}$ClN$_6$F$_3$S, 521.1502. found 521.1513.

8-((3-chloro-5-(thiophen-2-yl)phenyl)thio)-9-(3-isopropylamino)propyl)-9H-purin-6-amine (61, HJP-VI-10). Yield, 11.0 mg (80%). $^1$H NMR (600 MHz, CDCl$_3$) δ 8.33 (s, 1H), 7.55 (t, J=1.5 Hz, 1H), 7.51 (t, J=1.7 Hz, 1H), 7.33 (d, J=5.1 Hz, 1H), 7.29 (d, J=3.6 Hz, 1H), 7.27 (t, J=1.7 Hz, 1H), 7.07 (t, J=5.0 Hz, 1H), 5.81 (br s, 2H), 4.34 (t, J=6.9 Hz, 2H), 2.71-2.75 (m, 1H), 2.56 (t, J=6.7 Hz, 2H), 1.96-2.03 (m, 2H), 1.04 (d, J=6.2 Hz, 6H); $^{13}$C NMR (150 MHz, CDCl$_3$) δ 154.6, 153.2, 151.6, 144.6, 141.3, 137.1, 135.7, 133.5, 128.7, 128.3, 126.4, 125.9, 125.7, 124.7, 120.1, 48.8, 43.7, 41.7, 30.0, 22.6; HRMS (ESI) m/z [M+H]$^+$ calcd. for C$_{21}$H$_{24}$ClN$_6$S$_2$, 459.1192. found 459.1202.

8-((3-chloro-5-(prop-1-en-2-yl)phenyl)thio)-9-(3-isopropylamino)propyl)-9H-purin-6-amine (62, HJP-VI-12). Yield, 9.2 mg (75%). $^1$H NMR (600 MHz, CDCl$_3$) δ 8.32 (s, 1H), 7.39 (t, J=1.6 Hz, 1H), 7.33 (t, J=1.7 Hz, 1H), 7.26 (t, J=1.8 Hz, 1H), 5.33-5.36 (m, 1H), 5.10-5.15 (m, 1H), 6.16 (br s, 2H), 4.31 (t, J=7.1 Hz, 2H), 2.65-2.72 (m, 1H), 2.53 (t, J=6.8 Hz, 2H), 2.07 (s, 3H), 1.92-1.98 (m, 2H), 1.02 (d, J=6.2 Hz, 6H); $^{13}$C NMR (150 MHz, CDCl$_3$) δ 154.8, 153.2, 151.6, 144.6, 144.1, 141.1, 135.2, 132.8, 128.8, 125.8, 125.7, 120.1, 114.9, 48.7, 43.8, 41.8, 30.3, 22.9, 21.5; HRMS (ESI) m/z [M+H]$^+$ calcd. for C$_{20}$H$_{26}$ClN$_6$S, 417.1628. found 417.1630.

8-((3-chloro-5-(3-methylbut-2-en-2-yl)phenyl)thio)-9-(3-(isopropylamino)propyl)-9H-purin-6-amine (63, HJP-VI-14). Yield, 9.6 mg (72%). $^1$H NMR (600 MHz, CDCl$_3$ δ 8.33 (s, 1H), 7.22 (t, J=1.8 Hz, 1H), 7.05 (t, J=1.5 Hz, 1H), 7.01 (t, J=1.6 Hz, 1H), 5.76 (br s, 2H), 4.30 (t, J=7.0 Hz, 2H), 2.68-2.72 (m, 1H), 2.53 (t, J=6.7 Hz, 2H), 1.92-1.98 (m, 2H), 1.89 (s, 3H), 1.76 (s, 3H), 1.54 (s, 3H), 1.03 (d, J=6.2 Hz, 6H); $^{13}$C NMR (150 MHz, CDCl$_3$) δ 154.6, 153.1, 151.6, 148.1, 144.9, 134.7, 132.4, 129.5, 128.7, 128.5, 127.8, 127.3, 120.1, 48.7, 43.7, 41.7, 30.1, 22.8, 22.1, 20.6, 20.5; HRMS (ESI) m/z [M+H]$^+$ calcd. for C$_{22}$H$_{30}$ClN$_6$S, 445.1941. found 445.1939.

8-((3-chloro-5-ethynylphenyl)thio)-9-(3-(isopropylamino)propyl)-9H-purin-6-amine (64, HJP-VI-18). Yield, 9 mg (76%). $^1$H NMR (600 MHz, CDCl$_3$+5 drops CD$_3$OD) δ 8.26 (s, 1H), 7.46 (t, J=1.5 Hz, 1H), 7.45 (t, J=1.5 Hz, 1H), 7.43 (t, J=1.7 Hz, 1H), 4.31 (t, J=6.9 Hz, 2H), 3.22 (s, 1H), 2.73-2.79 (m, 1H), 2.56 (t, J=6.8 Hz, 2H), 1.98-2.06 (m, 2H), 1.08 (d, J=6.3 Hz, 6H); $^{13}$C NMR (150 MHz, CDCl$_3$+5 drops CD$_3$OD) δ 154.6, 152.9, 151.4, 144.9, 135.4, 132.9, 132.3, 132.2, 131.6, 125.3, 119.7, 80.9, 80.3, 48.9, 43.2, 41.5, 29.5, 22.1; HRMS (ESI) m/z [M+H]$^+$ calcd. for C$_{19}$H$_{22}$ClN$_6$S, 401.1315. found 401.1324.

8-((3-chloro-5-(1H-pyrrol-2-yl)phenyl)thio)-9-(3-(isopropylamino)propyl)-9H-purin-6-amine (65, HJP-VI-28). Yield, 7.4 mg (68%). $^1$H NMR (600 MHz, CDCl$_3$+5 drops CD$_3$OD) δ 8.24 (s, 1H), 7.62 (s, 1H), 7.54 (s, 1H), 7.25 (s, 1H), 6.87-6.90 (m, 1H), 6.53 (d, J=3.4 Hz, 1H), 6.25 (t, J=3.1, Hz, 1H), 4.31 (t, J=7.1 Hz, 2H), 2.75-2.78 (m, 1H), 2.59 (t, J=6.9 Hz, 2H), 1.96-2.01 (m, 2H), 1.07 (d, J=6.3 Hz, 6H); $^{13}$C NMR (150 MHz, CDCl$_3$+5 drops CD$_3$OD) δ 154.5, 152.9, 151.2, 146.1, 136.5, 135.6, 131.5, 129.3, 128.5, 125.6, 124.9, 120.7, 119.4, 110.0, 107.6, 49.0, 43.4, 41.5, 29.2, 21.9; HRMS (ESI) m/z [M+H]$^+$ calcd. for C$_{21}$H$_{25}$ClN$_7$S, 442.1581. found 442.1592.

8-((3-chloro-5-(1H-pyrazol-5-yl)phenyl)thio)-9-(3-(isopropylamino)propyl)-9H-purin-6-amine (66, HJP-VI-29). Yield, 8.2 mg (94%). $^1$H NMR (600 MHz, CDCl$_3$+5 drops CD$_3$OD) δ 8.33 (s, 1H), 7.77 (s, 1H), 7.60 (t, J=1.4 Hz, 1H), 7.56 (d, J=2.2 Hz, 1H), 7.35 (t, J=1.7 Hz, 1H) 6.69 (br s, 2H), 6.53 (d, J=2.2 Hz, 1H), 4.33 (t, J=7.0 Hz, 2H), 2.70-2.75 (m, 1H), 2.58 (t, J=6.8 Hz, 2H), 1.94-1.98 (m, 2H), 1.03 (d, J=6.3 Hz, 6H); $^{13}$C NMR (150 MHz, CDCl$_3$+5 drops CD$_3$OD) δ 154.9, 153.2, 151.4, 147.6, 144.4, 135.8, 133.3, 131.3, 129.1, 125.8, 125.7, 120.0, 102.9, 48.8, 43.6, 41.8, 30.5, 22.5; HRMS (ESI) m/z [M+H]$^+$ calcd. for C$_{20}$H$_{24}$ClN$_8$S, 443.1533. found 443.1522.

8-((3-chloro-5-(furan-2-yl)phenyl)thio)-9-(3-(isopropylamino)propyl)-9H-purin-6-amine (67, HJP-VI-30). Yield, 9.2 mg (69%). $^1$H NMR (600 MHz, CDCl$_3$+5 drops CD$_3$OD) δ 8.26 (s, 1H), 7.66 (t, J=1.4 Hz, 1H), 7.63 (t, J=1.6 Hz, 1H), 7.49 (d, J=1.3 Hz, 1H), 6.72 (d, J=3.4 Hz, 1H), 6.48-6.50 (m, 1H), 4.33 (t, J=6.9 Hz, 2H), 2.78-2.81 (m, 1H), 2.58 (t, J=6.8 Hz, 2H), 2.02-2.07 (m, 2H), 1.09 (d, J=6.3 Hz, 6H); $^{13}$C NMR (150 MHz, CDCl$_3$+5 drops CD$_3$OD) δ 154.6, 153.7, 152.8, 151.4, 149.4, 145.9, 135.8, 134.0, 131.8, 129.2, 124.6, 123.7, 119.5, 108.6, 108.4, 49.9, 43.3, 41.5, 29.3, 22.0, 13.7; HRMS (ESI) m/z [M+H]$^+$ calcd. for C$_{22}$H$_{26}$ClN$_6$OS, 457.1577. found 457.1578.

8-((3-chloro-5-vinylphenyl)thio)-9-(3-(isopropylamino)propyl)-9H-purin-6-amine (68, HJP-VI-31). Yield, 6.7 mg (56%). $^1$H NMR (600 MHz, CDCl$_3$+5 drops CD$_3$OD) δ 8.25 (s, 1H), 7.41 (s, 1H), 7.39 (s, 1H), 7.33 (s, 1H), 6.58-6.65 (m, 1H), 5.79 (d, J=17.5 Hz, 1H), 5.38 (d, J=10.9 Hz, 1H), 4.32 (t, J=6.8 Hz, 2H), 2.81-2.86 (m, 1H), 2.61 (t, J=6.8 Hz, 2H), 2.03-2.05 (m, 2H), 1.13 (d, J=6.3 Hz, 6H); $^{13}$C NMR (150 MHz, CDCl$_3$+5 drops CD$_3$OD) δ 154.6, 152.8, 151.4, 145.9, 140.8, 135.7, 134.4, 131.5, 130.5, 127.9, 126.7, 119.5, 117.2, 49.3, 48.7, 43.0, 41.3, 28.9, 21.7; HRMS (ESI) m/z [M+H]$^+$ calcd. for C$_{19}$H$_{24}$ClN$_6$S, 403.1472. found 403.1461.

8-((3-chloro-5-(5-methylfuran-2-yl)phenyl)thio)-9-(3-(isopropylamino)propyl)-9H-purin-6-amine (69, HJP-VI-38). Yield, 10.1 mg (74%). $^1$H NMR (600 MHz, CDCl$_3$+5 drops CD$_3$OD) δ 8.24 (s, 1H), 7.63 (s, 1H), 7.59 (s, 1H), 7.25 (s, 1H), 6.61 (d, J=3.2 Hz, 1H), 6.08 (d, J=3.1 Hz, 1H), 4.32 (t, J=6.9 Hz, 2H), 2.74-2.78 (m, 1H), 2.57 (t, J=6.8 Hz, 2H), 2.36 (s, 3H), 1.98-2.04 (m, 2H), 1.07 (d, J=6.3 Hz, 6H); $^{13}$C NMR (150 MHz, CDCl$_3$+5 drops CD$_3$OD) δ 154.6, 152.8, 151.4, 151.1, 145.6, 143.4, 135.8, 133.7, 132.1, 129.6, 124.9, 124.1, 119.6, 112.1, 107.5, 49.1, 43.1, 41.4, 29.2, 21.9; HRMS (ESI) m/z [M+H]$^+$ calcd. for C$_{21}$H$_{24}$ClN$_6$OS, 443.1421. found 443.1403.

8-((3-chloro-5-(furan-3-yl)phenyl)thio)-9-(3-(isopropylamino)propyl)-9H-purin-6-amine (70, HJP-VI-39). Yield, 8.8 mg (67%). $^1$H NMR (600 MHz, CDCl$_3$+5 drops CD$_3$OD) δ 8.24 (s, 1H), 7.79 (s, 1H), 7.54 (s, 1H), 7.50 (s, 1H), 7.48 (s, 1H), 7.34 (s, 1H), 6.67 (s, 1H), 4.38 (t, J=6.7 Hz, 2H), 2.99-3.03 (m, 1H), 2.73 (t, J=6.7 Hz, 2H), 2.16-2.21 (m, 2H), 1.24 (d, J=6.4 Hz, 6H); $^{13}$C NMR (150 MHz, CDCl$_3$+5 drops CD$_3$OD) δ 154.6, 152.7, 151.4, 146.1, 144.4, 139.7, 135.9, 131.4, 129.9, 127.6, 126.6, 124.3, 119.4, 108.5, 50.0, 42.4, 40.9, 31.6, 20.6; HRMS (ESI) m/z [M+H]$^+$ calcd. for C$_{21}$H$_{24}$ClN$_6$OS, 443.1421. found 443.1410.

8-((3-chloro-5-(1H-pyrrol-3-yl)phenyl)thio)-9-(3-(isopropylamino)propyl)-9H-purin-6-amine (71, HJP-VI-44). Yield, 4.4 mg (35%). $^1$H NMR (600 MHz, CDCl$_3$) δ 8.32 (s, 1H), 7.45 (t, J=1.5 Hz, 1H), 7.43 (t, J=1.5 Hz, 1H), 7.16 (t, J=1.7 Hz, 1H), 7.05-7.06 (m, 1H), 6.81-6.83 (m, 1H), 6.44-6.46 (m, 1H), 5.68 (br s, 2H), 4.33 (t, J=6.9 Hz, 2H), 2.72-2.76 (m, 1H), 2.56 (t, J=6.7 Hz, 2H), 1.95-2.02 (m, 2H), 1.04 (d, J=6.2 Hz, 6H); $^{13}$C NMR (150 MHz, CDCl$_3$) δ 154.5, 153.1, 151.7, 145.2, 138.9, 135.4, 132.6, 126.9, 125.5, 125.1, 122.6, 120.0, 119.5, 115.5, 106.5, 48.9, 43.6, 41.6, 28.7, 22.5; HRMS (ESI) m/z [M+H]$^+$ calcd. for C$_{21}$H$_{25}$ClN$_7$S, 442.1581. found 442.1586.

8-((3-chloro-5-(1H-pyrazol-4-yl)phenyl)thio)-9-(3-(isopropylamino)propyl)-9H-purin-6-amine (72, HJP-VI-46). Yield, 8.9 mg (67%). $^1$H NMR (600 MHz, CDCl$_3$+5 drops CD$_3$OD) δ 8.24 (s, 1H), 7.83 (s, 2H), 7.54 (s, 1H), 7.49 (s, 1H), 7.29 (s, 1H), 4.33 (t, J=6.8 Hz, 2H), 2.82-2.87 (m, 1H), 2.64 (t, J=6.7 Hz, 2H), 2.05-2.11 (m, 2H), 1.12 (d, J=6.2 Hz, 6H); $^{13}$C NMR (150 MHz, CDCl$_3$+5 drops CD$_3$OD) δ 154.7, 154.6, 152.7, 151.3, 145.9, 136.1, 135.8, 131.7, 129.2, 127.2, 126.2, 119.9, 119.5, 119.4, 49.3, 43.0, 41.3, 28.9, 21.6; HRMS (ESI) m/z [M+H]$^+$ calcd. for C$_{20}$H$_{24}$ClN$_8$S, 443.1533. found 443.1536.

8-((3-chloro-5-(1-methyl-1H-pyrazol-3-yl)phenyl)thio)-9-(3-(isopropylamino)propyl)-9H-purin-6-amine (73, HJP-VI-47). Yield, 10.8 mg (79%). $^1$H NMR (600 MHz, CDCl$_3$+5 drops CD$_3$OD) δ 8.27 (s, 1H), 7.67 (s, 1H), 7.58 (s, 1H), 7.53-7.55 (m, 1H), 7.31 (s, 1H), 6.39 (s, 1H), 4.33 (t, J=6.7 Hz, 2H), 3.27-3.32 (m, 1H), 3.02 (t, J=7.3 Hz, 2H), 2.30-2.33 (m, 2H), 1.33 (d, J=6.5 Hz, 6H); $^{13}$C NMR (150 MHz, CDCl$_3$+5 drops CD$_3$OD) δ 150.5, 150.4, 150.1, 144.7, 140.9, 138.9, 136.0, 133.9, 133.4, 132.2, 130.4, 129.1, 118.9, 107.1, 50.8, 41.9, 41.3, 37.5, 26.1, 18.9; HRMS (ESI) m/z [M+H]$^+$ calcd. for C$_{21}$H$_{26}$ClN$_8$S, 457.1690. found 457.1685.

8-((3-chloro-5-(oxazol-2-yl)phenyl)thio)-9-(3-(isopropylamino)propyl)-9H-purin-6-amine (74, HJP-VI-49). Yield, 7.6 mg (57%). $^1$H NMR (600 MHz, CDCl$_3$+5 drops CD$_3$OD) δ 8.24 (s, 1H), 8.09 (s, 1H), 8.04 (s, 1H), 7.77 (s, 1H), 7.55 (s, 1H), 7.30 (s, 1H), 4.39 (t, J=6.6 Hz, 2H), 3.01-3.06 (m, 1H), 3.74 (t, J=6.7 Hz, 2H), 2.18-2.24 (m, 2H), 1.25 (d, J=6.4 Hz, 6H); $^{13}$C NMR (150 MHz, CDCl$_3$+5 drops CD$_3$OD) δ 159.5, 154.7, 152.7, 151.4, 145.4, 139.8, 136.1, 132.9, 132.5, 130.1, 128.8, 127.5, 126.8, 119.6, 50.1, 42.3, 40.9, 27.8, 20.5; HRMS (ESI) m/z [M+H]$^+$ calcd. for C$_{20}$H$_{23}$ClN$_7$OS, 444.1373. found 444.1362.

8-((3-chloro-5-(prop-1-yn-1-yl)phenyl)thio)-9-(3-(isopropylamino)propyl)-9H-purin-6-amine (75, HJP-VI-50). Yield, 4.8 mg (40%). $^1$H NMR (600 MHz, CD$_3$OD) δ 8.31 (s, 1H), 7.54 (t, J=1.8 Hz, 1H), 7.47 (t, J=1.4 Hz, 1H), 7.42 (t, J=1.6 Hz, 1H), 4.43 (t, J=6.9 Hz, 2H), 3.30-3.34 (m, 1H), 3.06 (t, J=6.9 Hz, 2H), 2.18-2.21 (m, 2H), 2.03 (s, 3H), 1.31 (d, J=6.5 Hz, 6H); $^{13}$C NMR (150 MHz, CD$_3$OD) δ 153.6, 152.2, 149.7, 148.8, 136.4, 134.2, 132.9, 132.8, 132.0, 128.8, 120.7, 90.5, 78.1, 52.2, 43.3, 40.4, 27.7, 19.3, 3.8; HRMS (ESI) m/z [M+H]$^+$ calcd. for C$_{20}$H$_{24}$ClN$_6$S, 415.1472. found 415.1474.

8-((3-chloro-5-(3-methylbut-1-yn-1-yl)phenyl)thio)-9-(3-(isopropylamino)propyl)-9H-purin-6-amine (76, HJP-VI-51). Yield, 9.2 mg (70%). $^1$H NMR (600 MHz, CDCl$_3$) δ 8.33 (s, 1H), 7.30 (t, J=1.6 Hz, 1H), 7.29 (t, J=1.4 Hz, 1H), 7.27 (m, 1H), 5.84 (br s, 2H), 4.30 (t, J=7.1 Hz, 2H), 2.68-2.75 (m, 2H), 2.53 (t, J=6.8 Hz, 2H), 1.93-1.96 (m, 2H), 1.22 (d, J=6.9 Hz, 6H), 1.03 (d, J=6.2 Hz, 6H); $^{13}$C NMR (150 MHz, CDCl$_3$) δ 154.7, 153.3, 151.6, 144.3, 134.9, 132.9, 131.3, 131.2, 129.1, 126.9, 120.2, 98.8, 77.6, 48.7, 43.8, 41.8, 30.2, 22.8, 22.7, 21.1; HRMS (ESI) m/z [M+H]$^+$ calcd. for C$_{22}$H$_{28}$ClN$_6$S, 443.1785. found 443.1774.

8-((3-chloro-5-(cyclopropylethynyl)phenyl)thio)-9-(3-(isopropylamino)propyl)-9H-purin-6-amine (77, HJP-VI-52). Yield, 8.4 mg (64%). $^1$H NMR (600 MHz, CDCl$_3$) δ 8.34 (s, 1H), 7.25-7.27 (m, 2H), 7.24 (t, J=1.4 Hz, 1H), 5.85 (br s, 2H), 4.29 (t, J=7.0 Hz, 2H), 2.68-2.72 (m, 2H), 2.53 (t, J=6.8 Hz, 2H), 1.93-1.96 (m, 2H), 1.40-1.42 (m, 1H), 1.02 (d, J=6.2 Hz, 6H), 0.85-0.89 (m, 2H), 0.78-0.81 (m, 2H); $^{13}$C NMR (150 MHz, CDCl$_3$) δ 154.6, 153.2, 151.5, 144.1, 134.8, 132.9, 131.1, 131.0, 128.8, 126.8, 120.1, 96.5, 73.5, 48.6, 43.7, 41.7, 30.1, 22.7, 8.6; HRMS (ESI) m/z [M+H]$^+$ calcd. for C$_{22}$H$_{26}$ClN$_6$S, 441.1628. found 441.1628.

8-((3-chloro-5-(3,3-dimethylbut-1-yn-1-yl)phenyl)thio)-9-(3-(isopropylamino)propyl)-9H-purin-6-amine (78, HJP-VI-53). Yield, 9.1 mg (67%). $^1$H NMR (600 MHz, CDCl$_3$+5 drops CD$_3$OD) δ 8.26 (s, 1H), 7.35-7.37 (m, 2H), 7.32 (t, J=1.7 Hz, 1H), 4.29 (t, J=6.9 Hz, 2H), 2.65-2.67 (m, 1H), 2.54 (t, J=6.8 Hz, 2H), 1.96-1.99 (m, 2H), 1.29 (s, 9H), 1.06 (d, J=6.3 Hz, 6H); $^{13}$C NMR (150 MHz, CDCl$_3$+5 drops CD$_3$OD) δ 154.6, 152.9, 151.4, 145.3, 135.1, 132.6, 131.9, 131.6, 130.3, 127.3, 119.6, 101.8, 76.8, 48.8, 43.3, 41.5, 30.7, 29.6, 28.0, 22.3; HRMS (ESI) m/z [M+H]$^+$ calcd. for C$_{23}$H$_{30}$ClN$_6$S, 457.1941. found 457.1945.

3-(3-((6-amino-9-(3-(isopropylamino)propyl)-9H-purin-8-yl)thio)-5-chlorophenyl)prop-2-yn-1-ol (79, HJP-VI-58). Yield, 4.5 mg (35%). $^1$H NMR (600 MHz, CDCl$_3$+5 drops CD$_3$OD) δ 8.26 (s, 1H), 7.41 (t, J=1.8 Hz, 1H), 7.37-7.38 (m, 2H), 4.31 (t, J=6.9 Hz, 2H), 2.81-2.84 (m, 1H), 2.61 (t, J=6.8 Hz, 2H), 2.01-2.06 (m, 2H), 1.12 (d, J=6.3 Hz, 6H); $^{13}$C NMR (150 MHz, CDCl$_3$+5 drops CD$_3$OD) δ 154.6, 152.9, 151.3, 145.1, 135.3, 132.6, 131.9, 131.7, 131.1, 126.0, 119.6, 90.9, 82.3, 50.8, 49.2, 43.0, 41.4, 29.0, 21.7; HRMS (ESI) m/z [M+H]$^+$ calcd. for C$_{20}$H$_{24}$ClN$_6$OS, 431.1421. found 431.1431.

4-(3-((6-amino-9-(3-(isopropylamino)propyl)-9H-purin-8-yl)thio)-5-chlorophenyl)but-3-yn-2-ol (80, HJP-VI-59). Yield, 5.6 mg (42%). $^1$H NMR (600 MHz, CD$_3$OD) δ 8.35 (s, 1H), 7.60 (s, 1H), 7.52 (s, 1H), 7.48-7.49 (m, 1H), 4.64-4.68 (m, 1H), 4.43 (t, J=6.9 Hz, 2H), 3.30-3.31 (m, 1H), 3.07 (t, J=7.7 Hz, 2H), 2.19-2.21 (m, 2H), 1.46 (d, J=6.7 Hz, 3H), 1.31 (d, J=6.54 Hz, 6H); $^{13}$C NMR (150 MHz, CD$_3$OD) δ 153.7, 152.2, 149.8, 148.6, 136.5, 134.2, 133.2, 132.9, 132.7, 127.6, 95.7, 81.4, 58.9, 49.6, 43.3, 42.1, 27.7, 24.5, 19.3; HRMS (ESI) m/z [M+H]$^+$ calcd. for C$_{20}$H$_{24}$ClN$_6$OS, 431.1421. found 431.1431.

8-((3-chloro-5-(2-methylprop-1-en-1-yl)phenyl)thio)-9-(3-(isopropylamino)propyl)-9H-purin-6-amine (81, HJP-VI-62). Yield, 5.4 mg (42%). $^1$H NMR (600 MHz, CDCl$_3$+5 drops CD$_3$OD) δ 8.28 (s, 1H), 7.38 (s, 1H), 7.28-7.31 (m, 2H), 6.18 (s, 1H), 4.38 (t, J=6.7 Hz, 2H), 3.27-3.29 (m, 1H), 2.98 (t, J=7.02 Hz, 2H), 2.25-2.29 (m, 2H), 1.92 (s, 3H), 1.85 (s, 3H), 1.33 (d, J=6.5 Hz, 6H); $^{13}$C NMR (150 MHz, CDCl$_3$+5 drops CD$_3$OD) δ 151.4, 150.8, 149.9, 146.9, 142.3, 139.5, 135.2, 132.1, 130.3, 130.2, 128.3, 122.6, 50.9, 41.9, 41.0, 26.9, 26.2, 19.5, 18.9; HRMS (ESI) m/z [M+H]$^+$ calcd. for C$_{21}$H$_{28}$ClN$_6$S, 431.1785. found 431.1794.

(E)-8-((3-chloro-5-(prop-1-en-1-yl)phenyl)thio)-9-(3-(isopropylamino)propyl)-9H-purin-6-amine (82, HJP-VI-63). Yield, 7.3 mg (59%). $^1$H NMR (600 MHz, CDCl$_3$) δ 8.32 (s, 1H), 7.21 (t, J=1.6 Hz, 1H), 7.19 (t, J=1.5 Hz, 1H), 7.18 (t, J=1.7 Hz, 1H), 6.22-6.25 (m, 2H), 6.17 (br s, 2H), 4.64-4.68 (m, 1H), 4.29 (t, J=7.1 Hz, 2H), 2.67-2.71 (m, 1H), 2.52 (t, J=6.8 Hz, 2H), 1.91-1.97 (m, 2H), 1.85 (d, J=4.9 Hz, 3H), 1.02 (d, J=6.2 Hz, 6H); $^{13}$C NMR (150 MHz, CDCl$_3$) δ 154.8, 153.2, 151.6, 144.5, 140.8, 135.3, 132.9, 129.2, 128.9, 127.9, 125.9, 125.5, 120.1, 48.7, 43.8, 41.8, 30.2, 22.8, 18.5; HRMS (ESI) m/z [M+H]$^+$ calcd. for C$_{20}$H$_{26}$ClN$_6$S, 417.1628. found 417.1627.

(E)-8-((3-chloro-5-(2-cyclopropylvinyl)phenyl)thio)-9-(3-(isopropylamino)propyl)-9H-purin-6-amine (83, HJP-VI-64). Yield, 8.2 mg (62%). $^1$H NMR (600 MHz, CDCl$_3$) δ 8.25 (s, 1H), 7.28-7.29 (m, 1H), 7.25-7.26 (m, 1H), 7.21 (t, J=1.7 Hz, 1H), 6.35 (d, J=15.7 Hz, 1H), 5.72-5.78 (m, 1H), 4.28 (t, J=7.0 Hz, 2H), 2.68-2.72 (m, 1H), 2.52 (t, J=6.9 Hz, 2H), 1.95-1.98 (m, 2H), 1.54-1.57 (m, 1H), 1.22 (s, 1H), 1.05 (d, J=6.3 Hz, 6H), 0.84-0.88 (m, 2H), 0.52-0.55 (m, 2H); $^{13}$C NMR (150 MHz, CDCl$_3$) δ 154.5, 152.8, 151.4, 145.9, 141.1, 135.8, 135.5, 131.5, 128.9, 127.2, 125.9, 124.8, 119.5, 48.7, 43.4, 41.5, 29.7, 24.6, 22.4, 14.8, 7.67; HRMS (ESI) m/z [M+H]$^+$ calcd. for C$_{22}$H$_{28}$ClN$_6$S, 443.1785. found 443.1775.

8-((3-chloro-5-(3,3,3-trifluoroprop-1-en-2-yl)phenyl)thio)-9-(3-(isopropylamino)propyl)-9H-purin-6-amine (84, HJP-VI-70). Yield, 8.8 mg (61%). $^1$H NMR (600 MHz, CDCl$_3$+5 drops CD$_3$OD) δ 8.23 (s, 1H), 7.52-7.53 (m, 1H), 7.50 (s, 1H), 7.47 (s, 1H), 6.08 (s, 1H), 5.90 (s, 1H), 4.40 (t, J=6.7 Hz, 2H), 3.18-3.23 (m, 1H), 2.86 (t, J=6.8 Hz, 2H), 2.25-2.31 (m, 2H), 1.35 (d, J=6.5 Hz, 6H); $^{13}$C NMR (150 MHz, CDCl$_3$+5 drops CD$_3$OD) δ 154.8, 152.7, 151.3, 145.9, 136.7 (q, J$_{C-F}$=30.9 Hz), 136.6, 135.9, 132.1, 131.6, 129.2, 128.4, 122.8 (q, J$_{C-F}$=272.2 Hz), 123.1 (q, J$_{C-F}$=5.5 Hz), 119.5, 50.9, 41.9, 40.6, 26.9, 19.5; HRMS (ESI) m/z [M+H]$^+$ calcd. for C$_{20}$H$_{23}$F$_3$ClN$_6$S, 471.1346. found 471.1338.

(E)-8-03-chloro-5-(3,3-dimethylbut-1-en-1-yl)phenyl)thio)-9-(3-(isopropylamino)propyl)-9H-purin-6-amine (85, HJP-VI-72). Yield, 9.2 mg (67%). $^1$H NMR (600 MHz, CDCl$_3$+5 drops CD$_3$OD) δ 8.22 (s, 1H), 7.37-7.39 (m, 2H), 7.29-7.33 (m, 1H), 6.32 (d, J=16.1 Hz, 1H), 6.21 (d, J=16.1 Hz, 1H), 4.37 (t, J=6.3 Hz, 2H), 3.11-3.14 (m, 1H), 2.79 (t, J=6.4 Hz, 2H), 2.21-2.25 (m, 2H), 1.31 (d, J=6.2 Hz, 6H), 1.11 (s, 9H); $^{13}$C NMR (150 MHz, CDCl$_3$+5 drops CD$_3$OD) δ 154.7, 152.5, 151.3, 146.5, 145.4, 141.6, 135.6, 130.7, 129.8, 126.8, 122.4, 119.4, 50.5, 42.1, 40.7, 33.7, 29.33, 27.2, 19.9; HRMS (ESI) m/z [M+H]$^+$ calcd. for C$_{23}$H$_{32}$ClN$_6$S, 459.2098. found 459.2083.

(Z)-8-03-chloro-5-(prop-1-en-1-yl)phenyl)thio)-9-(3-(isopropylamino)propyl)-9H-purin-6-amine (86, HJP-VI-78). Yield, 5.3 mg (43%). $^1$H NMR (600 MHz, CDCl$_3$) δ 8.32 (s, 1H), 7.18-7.26 (m, 3H), 6.25-6.31 (m, 1H), 5.83-5.89 (m, 1H), 5.79 (br s, 2H), 4.33 (t, J=6.8 Hz, 2H), 2.74-2.78 (m, 1H), 2.57 (t, J=6.7 Hz, 2H), 1.97-2.04 (m, 2H), 1.82 (dd, J=7.2 and 1.7 Hz, 3H), 1.08 (d, J=6.3 Hz, 6H); $^{13}$C NMR (150 MHz, CDCl$_3$) δ 154.6, 153.1, 151.6, 145.0, 140.4, 134.9, 132.4, 129.7, 128.9, 128.7, 127.9, 127.6, 120.1, 49.0, 43.5, 41.5, 29.7, 22.4, 18.5; HRMS (ESI) m/z [M+H]$^+$ calcd. for C$_{20}$H$_{26}$ClN$_6$S, 417.1628. found 417.1634.

(E)-8-((3-(but-2-en-2-yl)-5-chlorophenyl)thio)-9-(3-(isopropylamino)propyl)-9H-purin-6-amine (87, HJP-VI-79). Yield, 9.4 mg (73%). $^1$H NMR (600 MHz, CDCl$_3$) δ 8.33 (s, 1H), 7.29-7.30 (m, 1H), 7.26-7.27 (m, 1H), 7.21-7.22 (m, 1H), 5.84-5.89 (m, 1H), 5.82 (br s, 2H), 4.30 (t, J=7.0 Hz, 2H), 2.68-2.73 (m, 1H), 2.54 (t, J=6.8 Hz, 2H), 1.93-1.98 (m, 5H), 1.77 (d, J=6.8 Hz, 3H), 1.02 (d, J=6.2 Hz, 6H); $^{13}$C NMR (150 MHz, CDCl$_3$) δ 154.6, 153.1, 151.6, 145.9, 135.0, 133.5, 132.3, 128.0, 126.1, 125.8, 125.2, 120.1, 48.8, 43.7, 41.7, 30.1, 22.8, 15.3, 14.4; HRMS (ESI) m/z [M+H]$^+$ calcd. for C$_{21}$H$_{28}$ClN$_6$S, 431.1785. found 431.1782.

6.2.15 Synthesis of Compounds of Formula 91-95 (Scheme 15)

Scheme 15:

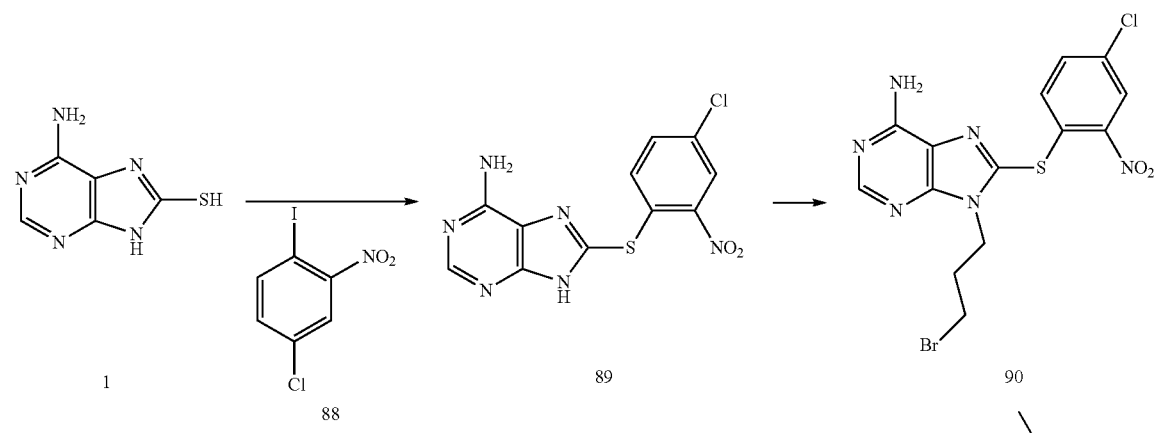

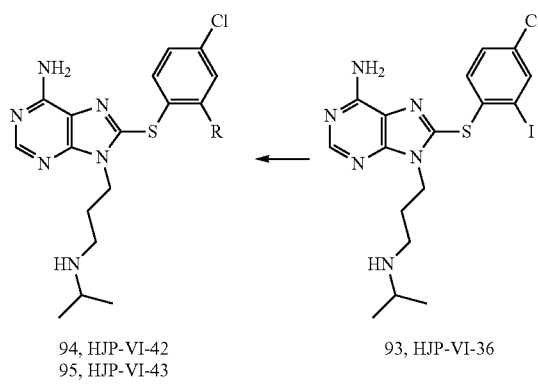
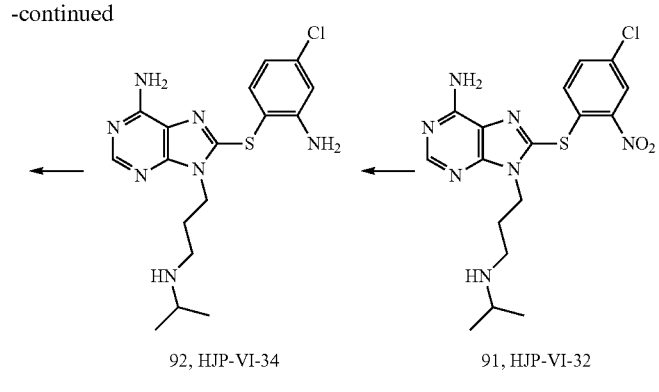

94, HJP-VI-42
95, HJP-VI-43

93, HJP-VI-36

92, HJP-VI-34

91, HJP-VI-32

8-((4-chloro-2-nitrophenyl)thio)-9H-purin-6-amine (89). 8-Mercaptoadenine (3.6 mmol), neocuproine hydrate (0.36 mmol), CuI (0.36 mmol), NaO-t-Bu (7.2 mmol), 4-chloro-1-iodo-2-nitrobenzene (10.8 mmol), and anhydrous DMF (24 mL) were taken in a round bottom flask flushed with nitrogen. The flask was sealed with Teflon tape, heated at 110° C., and magnetically stirred for 18 h under nitrogen. Solvent was removed under reduced pressure and the resulting residue was chromatographed ($CH_2Cl_2$:MeOH:AcOH, 20:1:0.5). Obtained as a yellow solid in 85% yield. MS (ESI): m/z 332.8 $[M+H]^+$.

9-(3-bromopropyl)-8-((4-chloro-2-nitrophenyl)thio)-9H-purin-6-amine (90). 8-Arylsulfanyl adenine (89, 1.21 mmol) was dissolved in DMF (15 mL) and $Cs_2CO_3$ (1.45 mmol) and 1,3-dibromopropane (2.42 mmol) were added and the mixture was stirred under nitrogen at for 2-4 h. Solvent was removed under reduced pressure and the resulting residue was chromatographed ($CH_2Cl_2$:MeOH:AcOH, 20:1:0.5) to afford desired compound 90. Obtained as a solid in 35% yield. MS (ESI): m/z 442.9 $[M+H]^+$.

8-((4-chloro-2-nitrophenyl)thio)-9-(3-(isopropylamino)propyl)-9H-purin-6-amine (91, HJP-VI-32). A mixture of 90 (600 mg, 1.357 mmol) and amine (67.9 mmol, 50 equiv.) in DMF (8 mL) under nitrogen protection was stirred at room temperature for 20 hrs. Following solvent removal, the crude material was purified by column chromatography ($CH_2Cl_2$:$CH_3OH$—$NH_3$ (7N), 100:1 to 20:1) to afford desired product 91. Yield, 510 mg (85%). $^1$H NMR (600 MHz, $CDCl_3$+5 drops $CD_3OD$) δ 8.35 (s, 1H), 8.30 (d, J=2.2 Hz, 1H), 7.43 (dd, J=8.7 and 2.2 Hz, 1H), 6.81 (d, J=8.7 Hz, 1H), 4.29 (t, J=6.9 Hz, 2H), 2.67-2.73 (m, 1H), 2.52 (t, J=6.8 Hz, 2H), 1.93-1.98 (m, 2H), 1.03 (d, J=6.3 Hz, 6H); $^{13}$C NMR (150 MHz, $CDCl_3$+5 drops $CD_3OD$) δ 154.3, 153.9, 151.3, 145.8, 142.0, 134.5, 133.3, 131.9, 129.7, 126.2, 120.4, 48.7, 43.3, 41.9, 30.1, 22.3; HRMS (ESI) m/z $[M+H]^+$ calcd. for $C_{17}H_{21}ClN_7OS$, 422.1166. found 422.1170.

8-((2-amino-4-chlorophenyl)thio)-9-(3-(isopropylamino)propyl)-9H-purin-6-amine (92, HJP-VI-34). A mixture of 91 (510 mg, 1.21 mmol) and iron powder (250 mg.) in acetic acid (6 mL) was stirred at room temperature for 4 hrs. On completion reaction was neutralized by adding solid $Na_2CO_3$ at 0° C. and washed with EtOAc (75 ml×3). Following drying over $MgSO_4$ and solvent removal, the crude material was purified by column chromatography ($CH_2Cl_2$:$CH_3OH$—$NH_3$ (7N), 50:1 to 15:1) to afford desired product 92. Yield, 426.3 mg (90%). $^1$H NMR (600 MHz, $CDCl_3$+5 drops $CD_3OD$) δ 8.16 (s, 1H), 7.39 (d, J=8.3 Hz, 1H), 6.84 (d, J=2.2 Hz, 1H), 6.73 (dd, J=8.3 and 2.2 Hz, 1H), 4.36 (t, J=6.7 Hz, 2H), 3.40-3.41 (m, 1H), 2.83 (t, J=6.8 Hz, 2H), 2.26-2.32 (m, 2H), 1.34 (d, J=6.5 Hz, 6H); $^{13}$C NMR (150 MHz, $CDCl_3$+5 drops $CD_3OD$) δ 154.2, 151.9, 151.4, 150.5, 147.3, 138.3, 138.1, 118.9, 115.7, 107.0, 74.4, 50.6, 42.1, 40.4, 31.1, 19.8; HRMS (ESI) m/z $[M+H]^+$ calcd. for $C_{17}H_{23}ClN_7S$, 392.1424. found 392.1419.

8-((4-chloro-2-iodophenyl)thio)-9-(3-(isopropylamino)propyl)-9H-purin-6-amine (93, HJP-VI-36). A mixture of 92 (426 mg, 1.09 mmol), $NaNO_2$ (1.2 equiv.) and potassium iodide (2 equiv.) in acetic acid (5 mL) was stirred at room temperature for 4 hrs. On completion reaction was neutralized by adding solid $Na_2CO_3$ at 0° C. and washed with EtOAc (75 ml×3). Following drying over $MgSO_4$ and solvent removal, the crude material was purified by column chromatography ($CH_2Cl_2$:$CH_3OH$—$NH_3$ (7N), 80:1 to 20:1) to afford desired product 93. Yield, 436.4 mg (79%). $^1$H NMR (600 MHz, $CDCl_3$+5 drops $CD_3OD$) δ 8.35 (s, 1H), 7.87 (d, J=2.2 Hz, 1H), 7.23 (dd, J=8.5 and 2.2 Hz, 1H), 7.07 (d, J=2.2 Hz, 1H), 5.87 (br s, 2H), 4.30 (t, J=6.9 Hz, 2H), 2.68-2.72 (m, 1H), 2.56 (t, J=6.8 Hz, 2H), 1.95-1.99 (m, 2H), 1.03 (d, J=6.2 Hz, 6H); $^{13}$C NMR (150 MHz, $CDCl_3$+5 drops $CD_3OD$) δ 154.7, 153.3, 151.6, 144.8, 139.3, 135.9, 134.1, 131.1, 129.5, 120.4, 99.8, 48.7, 43.8, 41.9, 30.3, 22.9; HRMS (ESI) m/z $[M+H]^+$ calcd. for $C_{17}H_{21}ICIN_6S$, 503.0282. found 503.0277.

General conditions. Method A: Boronic acid or pinacol ester (1.5-3 eq.) was added to HJP-VI-36 (93, 15 mg, 0.0298 mmol, 1 eq.) and $NaHCO_3$ (3 eq.) in a 10 mL RBF equipped with a magnetic stir bar and rubber septum. DMF (0.5 mL) was added and the reaction mixture was evacuated and back filled with nitrogen. This was repeated four times then nitrogen was bubbled through the reaction mixture for 10 min. Then $H_2O$ (0.1 mL) and $PdCl_2(PPh_3)_2$ (10-20 mol %) were added and the reaction mixture was heated under nitrogen at 90° C. for 2-24 h. Solvent was removed under reduced pressure and the resulting residue was purified by preparatory TLC to yield compounds HJP-VI-42 (94) and HJP-VI-43 (95).

8-((4-chloro-2-(1H-pyrrol-2-yl)phenyl)thio)-9-(3-(isopropylamino)propyl)-9H-purin-6-amine (94, HJP-VI-42). Yield, 2.3 mg (24%). $^1$H NMR (600 MHz, $CD_3OD$) δ 8.29 (s, 1H), 7.57 (d, J=2.3 Hz, 1H), 7.53 (d, J=8.5 Hz, 1H), 7.31 (dd, J=8.4 and 2.3 Hz, 1H), 6.85-6.88 (m, 1H), 6.42-6.44 (m, 1H), 6.13-6.16 (m, 1H), 4.29 (t, J=6.9 Hz, 2H), 3.28-3.32 (m, 1H), 2.99 (t, J=6.2 Hz, 2H), 2.10-2.16 (m, 2H), 1.29 (d, J=6.5 Hz, 6H); $^{13}$C NMR (150 MHz, $CD_3OD$) δ 152.8, 152.0, 150.9, 148.7, 139.9, 137.5, 136.9, 129.2, 128.5, 126.2, 121.3, 121.2, 120.4, 111.7, 110.0, 49.6, 43.3, 41.9, 27.6, 19.3; HRMS (ESI) m/z $[M+H]^+$ calcd. for $C_{21}H_{25}ClN_7S$, 442.1581. found 442.1573.

8-((4-chloro-2-(1H-pyrazol-5-yl)phenyl)thio)-9-(3-(isopropylamino)propyl)-9H-purin-6-amine (95, HJP-VI-43). Yield, 10.4 mg (28%). $^1$H NMR (600 MHz, CD$_3$OD) δ 8.28 (s, 1H), 7.97 (s, 1H), 7.69 (d, J=2.2 Hz, 1H), 7.68 (d, J=2.2 Hz, 1H), 7.46 (d, J=8.5 Hz, 1H), 7.41 (dd, J=8.5 and 2.3 Hz, 1H), 4.28 (t, J=7.0 Hz, 2H), 3.27-3.31 (m, 1H), 2.99 (t, J=8.0 Hz, 2H), 2.05-2.11 (m, 2H), 1.29 (d, J=6.6 Hz, 6H); HRMS (ESI) m/z [M+H]$^+$ calcd. for C$_{20}$H$_{24}$ClN$_8$S, 443.1533. found 443.1520.

6.2.16 Synthesis of Compounds of Formula 100-102 (Scheme 16)

Scheme 16:

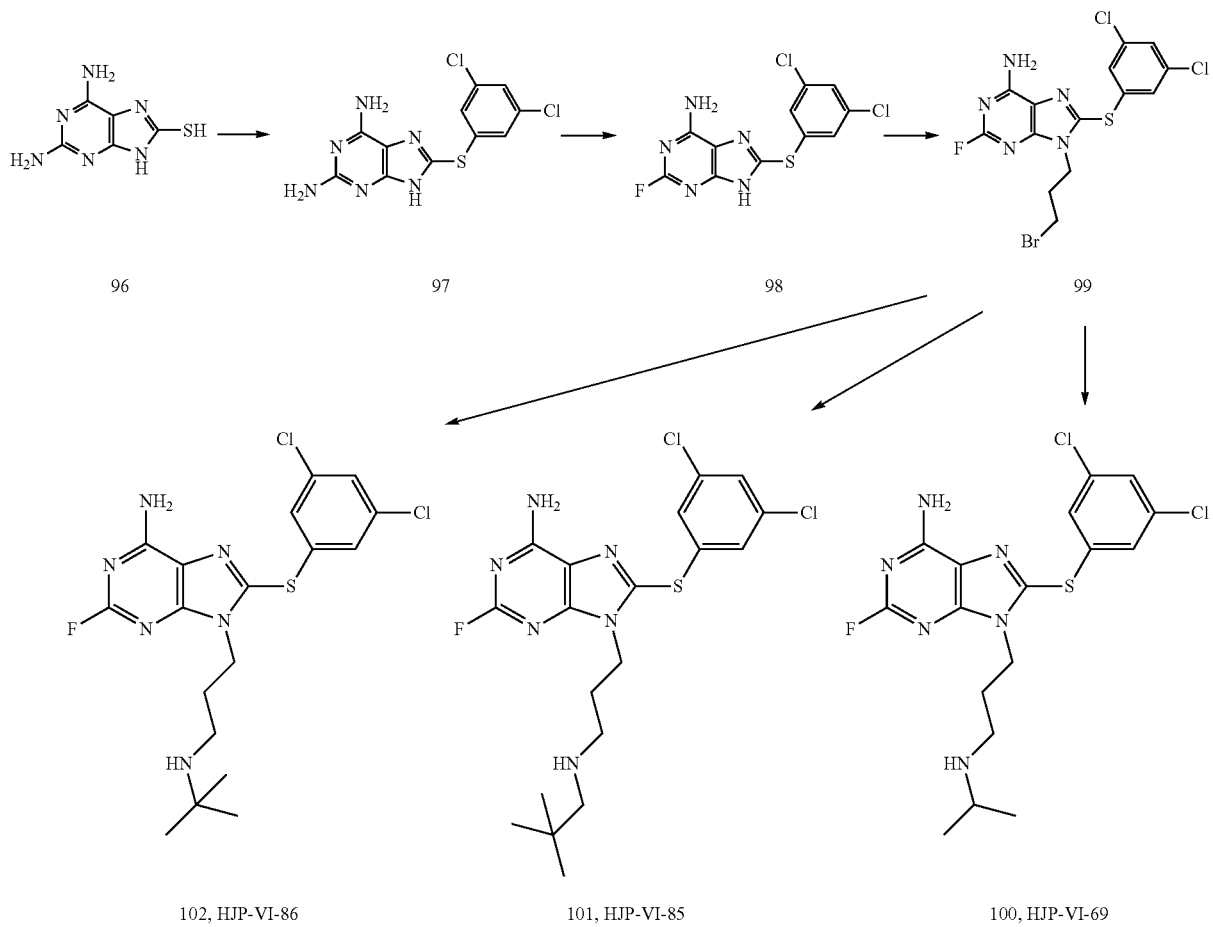

8-((3,5-dichlorophenyl)thio)-9H-purine-2,6-diamine (97). 2,6-diamino-9H-purine-8-thiol (3.6 mmol), neocuproine hydrate (0.36 mmol), CuI (0.36 mmol), NaO-t-Bu (7.2 mmol), 1,3-dichloro-5-iodobenzene (10.8 mmol), and anhydrous DMF (24 mL) were taken in a round bottom flask flushed with nitrogen. The flask was sealed with Teflon tape, heated at 110° C., and magnetically stirred for 20 h under nitrogen. Solvent was removed under reduced pressure and the resulting residue was chromatographed (CH$_2$Cl$_2$:MeOH:AcOH, 20:1:0.5). Obtained as a light yellow solid in 65% yield. MS (ESI): m/z 326.9 [M+H]$^+$.

8-((3,5-dichlorophenyl)thio)-2-fluoro-9H-purin-6-amine (98). To a cooled solution (0° C.) of 97 (350 mg, 1.073 mmol) in HF/pyridine (1.5 mL) was slowly added NaNO$_2$ (126.2 mg, 1.73 mmol). The resulted mixture was stirred at room temperature for 1 h and then quenched by stirring for 1 h with 14 mg of CaCO$_3$ in CH$_2$Cl$_2$ (7.5 mL). The crude material was taken up in CH$_2$Cl$_2$, washed with water, and dried over anhydrous Na$_2$SO$_4$. Following solvent removal, the residue was purified on a preparative silica gel plate (CHCl$_3$:Hexanes:EtOAc:i-PrOH at 2:2:1:0.1) to afford 98 (180 mg, 47% yield). MS (ESI): m/z 329.80 [M+H]$^+$.

9-(3-bromopropyl)-8-((3,5-dichlorophenyl)thio)-2-fluoro-9H-purin-6-amine (99). 8-Arylsulfanyl adenine (98, 0.549 mmol) was dissolved in DMF (15 mL) and Cs$_2$CO$_3$ (0.659 mmol) and 1,3-dibromopropane (1.3752 mmol) were added and the mixture was stirred under nitrogen at for 2 h. Solvent was removed under reduced pressure and the resulting residue was chromatographed (CH$_2$Cl$_2$:MeOH:AcOH, 40:1:0.5-20:1:0.5) to afford desired compound 99. Obtained as a solid in 25% yield. $^1$H NMR (500 MHz, CDCl$_3$+5 drops CD$_3$OD) δ 7.28-7.34 (m, 3H), 4.31 (t, J=7.1 Hz, 2H), 3.40 (t, J=6.1 Hz, 2H), 2.29-2.36 (m, 2H); MS (ESI): m/z 449.9 [M+H]$^+$.

General Procedure for the Synthesis of 100-102

A mixture of 99 (12 mg, 0.0267 mmol) and amine (1.336 mmol, 50 equiv.) in DMF (1 mL) under nitrogen protection was stirred at room temperature for 16-24 hrs. Following solvent removal, the crude material was purified by preparative TLC (CH$_2$Cl$_2$:CH$_3$OH—NH$_3$ (7N), 20:1 or 15:1) to afford desired product 100-102.

8-((3,5-dichlorophenyl)thio)-2-fluoro-9-(3-(isopropylamino)propyl)-9H-purin-6-amine (100, HJP-VI-69). Yield, 9.3 mg (81.6%). $^1$H NMR (600 MHz, CDCl$_3$+5 drops CD$_3$OD) δ 7.30-7.36 (m, 3H), 4.23 (t, J=6.9 Hz, 2H), 2.71-2.76 (m, 1H), 2.54 (t, J=6.8 Hz, 2H), 1.94-1.99 (m, 2H), 1.06 (d, J=6.2 Hz, 6H); $^{13}$C NMR (150 MHz, CDCl$_3$+5 drops CD$_3$OD) δ 159.2 (d, $J_{C-F}$=211.2 Hz), 156.4 (d, $J_{C-F}$=20 Hz), 152.7 (d, $J_{C-F}$=18.9 Hz), 143.9 (d, $J_{C-F}$=2.5 Hz), 136.1, 133.7, 128.9, 128.8, 117.9 (d, $J_{C-F}$=3.5 Hz), 48.9, 43.4, 41.8, 29.7, 22.3; HRMS (ESI) m/z [M+H]$^+$ calcd. for C$_{17}$H$_{20}$Cl$_2$FN$_6$S, 429.0831. found 429.0834.

8-((3,5-dichlorophenyl)thio)-2-fluoro-9-(3-(neopentylamino)propyl)-9H-purin-6-amine (101, HJP-VI-85). Yield, 10.2 mg (84%). $^1$H NMR (600 MHz, CDCl$_3$+5 drops CD$_3$OD) δ 7.35 (t, J=1.7 Hz, 1H), 7.30-7.32 (m, 2H), 4.25 (t, J=7.0 Hz, 2H), 2.60 (t, J=6.8 Hz, 2H), 2.31 (s, 2H), 1.96-2.01 (m, 2H), 0.93 (s, 9H); $^{13}$C NMR (150 MHz, CDCl$_3$+5 drops CD$_3$OD) δ 159.3 (d, $J_{C-F}$=211.1 Hz), 156.4 (d, $J_{C-F}$=20.1 Hz), 152.8 (d, $J_{C-F}$=19.1 Hz), 144.1 (d, $J_{C-F}$=2.4 Hz), 136.1, 133.8, 128.9, 128.8, 117.9 (d, $J_{C-F}$=3.5 Hz), 61.9, 47.1, 42.0, 31.3, 29.2, 27.8; HRMS (ESI) m/z [M+H]$^+$ calcd. for C$_{19}$H$_{24}$Cl$_2$FN$_6$S, 457.1144. found 457.1152.

9-(3-(tert-butylamino)propyl)-8-((3,5-dichlorophenyl)thio)-2-fluoro-9H-purin-6-amine (102, HJP-VI-86). Yield, 9.6 mg (80%). $^1$H NMR (600 MHz, CDCl$_3$+5 drops CD$_3$OD) δ 7.36 (t, J=1.7 Hz, 1H), 7.32-7.34 (m, 2H), 4.28 (t, J=6.8 Hz, 2H), 2.66 (t, J=6.8 Hz, 2H), 2.09-2.12 (m, 2H), 1.21 (s, 9H); $^{13}$C NMR (150 MHz, CDCl$_3$+5 drops CD$_3$OD) δ 159.1 (d, $J_{C-F}$=211.5 Hz), 156.4 (d, $J_{C-F}$=20.1 Hz), 152.7 (d, $J_{C-F}$=18.8 Hz), 144.3 (d, $J_{C-F}$=2.3 Hz), 136.1, 133.3, 129.1, 129.0, 117.9 (d, $J_{C-F}$=3.5 Hz), 53.3, 41.6, 38.5, 28.9, 27.4; HRMS (ESI) m/z [M+H]$^+$ calcd. for C$_{18}$H$_{22}$Cl$_2$FN$_6$S, 443.0988. found 443.1007.

6.2.18 Synthesis of Compounds of Formula 106 (Scheme 18)

Scheme 18:

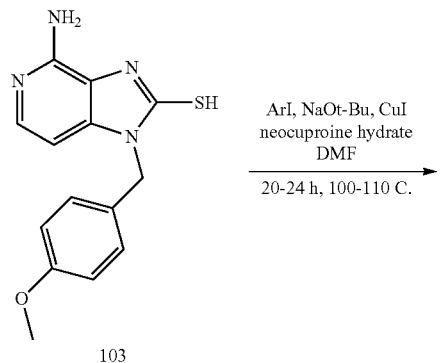

103

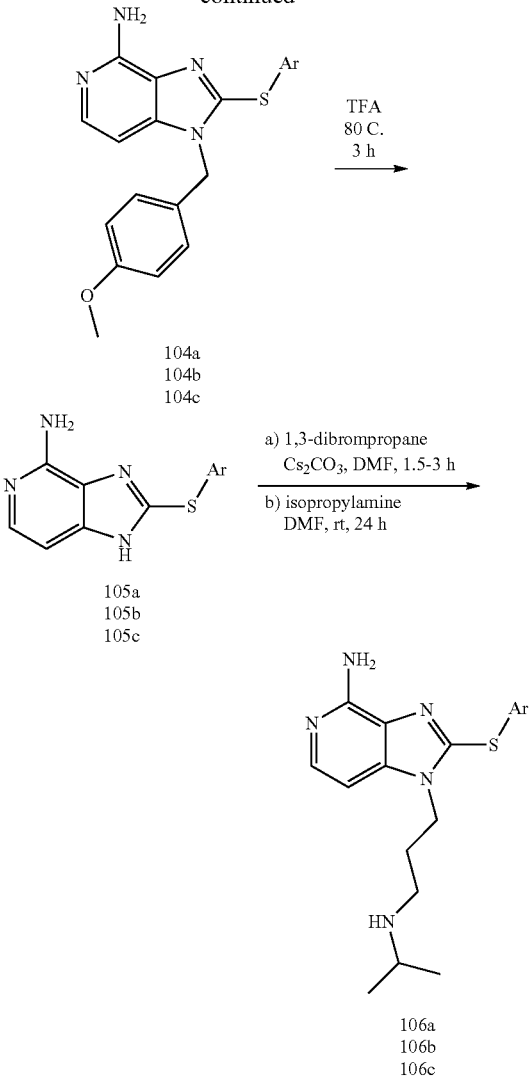

104a
104b
104c 105a
105b
105c 106a
106b
106c

General Procedure for the Synthesis of 104 a-c.

To 4-amino-1-(4-methoxybenzyl)-1H-imidazo[4,5-c]pyridine-2-thiol (103) (50 mg, 0.174 mmol) was added respective iodine (0.348 mmol), neocuproine hydrate (3.6 mg, 0.0174 mmol), CuI (3.3 mg, 0.0174 mmol), sodium tert-butoxide (25 mg, 0.261 mmol) and lastly DMF (5 mL) and the reaction mixture was stirred at 110° C. for 24 hours. Then, the solvent was removed under reduced pressure and the crude product was purified by preparatory TLC (CH$_2$Cl$_2$: MeOH—NH$_3$ (7N), 10:1) to afford desired compounds 104a-c.

2-((3,5-dichlorophenyl)thio)-1-(4-methoxybenzyl)-1H-imidazo[4,5-c]pyridin-4-amine (104a). Obtained as pale yellow solid 39% yield. LCMS found m/z 430.97 [M+H]$^+$.

1-(4-methoxybenzyl)-2-(naphthalen-1-ylthio)-1H-imidazo[4,5-c]pyridin-4-amine (104b). Obtained as white solid in 38% yield. $^1$H NMR (500 MHz, CDCl$_3$): δ 8.33 (d, J=8.1 Hz, 1H), 7.83 (m, 1H), 7.78 (d, J=5.8 Hz, 1H), 7.75 (d, J=8.2 Hz, 1H), 7.51-7.55 (m, 2H), 7.44 (d, J=7.2 Hz, 1H), 7.33 (m, 1H), 6.88 (d, J=8.6 Hz, 2H), 6.68 (d, J=8.6 Hz, 2H), 6.55 (d, J=5.9 Hz, 1H), 5.25 (s, 2H), 5.23 (br s, 2H), 3.73 (s, 3H). LCMS found m/z 413.08 [M+H]$^+$.

2-((2,4-dichlorophenyl)thio)-1-(4-methoxybenzyl)-1H-imidazo[4,5-c]pyridin-4-amine (104c). Obtained as pale yellow solid in 40% yield. $^1$H NMR (500 MHz, CDCl$_3$): δ 7.78 (d, J=5.9 Hz, 1H), 7.36 (d, J=2.1 Hz, 1H), 7.02 (dd, J=8.5, 2.1 Hz, 1H), 6.98 (d, J=8.6 Hz, 2H), 6.91 (d, J=8.6 Hz, 1H), 6.73 (d, J=8.6 Hz, 2H), 6.65 (d, J=6.0 Hz, 1H), 5.30 (s, 2H), 3.75 (s, 3H). LCMS found m/z 430.86 [M+H]$^+$.

Compound (103) may be prepared as described in U.S. Pat. No. 8,017,780 and International Patent Publication No. WO2008115262.

General Procedure for the Synthesis of 105 a-c.

To coupling products (104a-c) (0.067 mmol) were added trifluoroacetic acid (3 mL) and the reaction mixture was stirred at 80° C. for 3 hours. Then, the solvent was removed under reduced pressure and the crude product was purified by preparatory TLC (CH$_2$Cl$_2$:MeOH—NH$_3$ (7N), 15:1) to afford deprotected compounds 105a-c.

2-((3,5-dichlorophenyl)thio)-1H-imidazo[4,5-c]pyridin-4-amine (105a). Obtained as yellow solid in 71% yield. $^1$H NMR (500 MHz, CD$_3$OD): δ 7.47 (d, J=6.7 Hz, 1H), 7.41-7.43 (m, 3H), 6.96 (d, J=6.7 Hz, 1H). LCMS found m/z 310.84 [M+H]$^+$.

2-(naphthalen-1-ylthio)-1H-imidazo[4,5-c]pyridin-4-amine (105b). Obtained as yellow solid in 66% yield. LCMS found m/z 292.95 [M+H]$^+$.

2-((2,4-dichlorophenyl)thio)-1H-imidazo[4,5-c]pyridin-4-amine (105c). Obtained as yellow solid in 92% yield. $^1$H NMR (500 MHz, CDCl$_3$:CD$_3$OD 1:1): δ 7.46-7.48 (m, 2H), 7.30 (d, J=8.5 Hz, 1H), 7.02 (dd, J=8.5, 2.2 Hz, 1H), 6.85 (d, J=6.4 Hz, 1H). MS m/z 310.8 (M+H)$^+$.

2-((3,5-dichlorophenyl)thio)-1-(3-(isopropylamino)propyl)-1H-imidazo[4,5-c]pyridin-4-amine (106a). To 2-((3,5-dichlorophenyl)thio)-1H-imidazo[4,5-c]pyridin-4-amine (105a) (14.9 mg, 0.0477 mmol) in dry DMF (1.5 mL) was added Cs$_2$CO$_3$ (18.6 mg, 0.0572 mmol) and lastly 1,3-dibromopropane (24 μL, 0.0238 mmol) and the reaction mixture was stirred at rt for 2 h. The solvent was removed under reduced pressure and the crude product was purified by preparatory TLC (CH$_2$Cl$_2$:MeOH—NH$_3$ (7N), 20:1) to afford 7.6 mg (37%) of 1-(3-bromopropyl)-2-(3,5-dichlorophenyl)thio)-1H-imidazo[4,5-c]pyridin-4-amine. LCMS found m/z 433.01 [M+H]$^+$. To 1-(3-bromopropyl)-2-(3,5-dichlorophenyl)thio)-1H-imidazo[4,5-c]pyridin-4-amine (7.6 mg, 0.0175 mmol) in dry DMF was added isopropylamine (30 μL, 0.35 mmol) and the reaction mixture was stirred at rt for 24 hours. Then, the solvent was removed under reduced pressure and the crude product was purified by preparatory TLC (CH$_2$Cl$_2$:MeOH—NH$_3$ (7N), 15:1) to afford 5.7 mg (79%) of SO-III-154A (106). $^1$H NMR (500 MHz, CDCl$_3$): δ 7.88 (d, J=5.9 Hz, 1H), 7.21-7.25 (m, 3H), 6.75 (d, J=5.9 Hz, 1H), 5.26 (br s, 2H), 4.26 (t, J=7.1 Hz, 2H), 2.71 (m, 1H), 2.56 (t, J=6.8 Hz, 2H), 1.88 (m, 2H), 1.02 (d, J=6.2 Hz, 3H). $^{13}$C NMR (150 MHz, CDCl$_3$): δ 151.3, 142.7, 141.7, 140.8, 135.9, 135.7, 127.8, 127.5, 127.0, 97.6, 48.8, 44.0, 43.3, 30.5, 22.8. HRMS (ESI) m/z [M+H]$^+$ calcd. for C$_{18}$H$_{22}$N$_5$SCl$_2$, 410.0973. found 410.0978.

1-(3-(isopropylamino)propyl)-2-(naphthalen-1-ylthio)-1H-imidazo[4,5-c]pyridin-4-amine (106b). To 2-(naphthalen-1-ylthio)-1H-imidazo[4,5-c]pyridin-4-amine (105b) (12.6 mg, 0.043 mmol) in dry DMF (1.5 mL) was added Cs$_2$CO$_3$ (16.8 mg, 0.0517 mmol) and lastly 1,3-dibromopropane (17.4 μL, 0.172 mmol) and the reaction mixture was stirred at rt for 1 hour and a half. The solvent was removed under reduced pressure and the crude product was purified by preparatory TLC (CH$_2$Cl$_2$:MeOH—NH$_3$ (7N), 15:1) to afford 9.8 mg (55%) of 1-(3-bromopropyl)-2-(naphthalen-1-ylthio)-1H-imidazo[4,5-c]pyridin-4-amine. LCMS found m/z 412.95 [M+H]$^+$. To 1-(3-bromopropyl)-2-(naphthalen-1-ylthio)-1H-imidazo[4,5-c]pyridin-4-amine (9.8 mg, 0.0237 mmol) in dry DMF was added isopropylamine (50.9 μL, 0.592 mmol) and the reaction mixture was stirred at rt for 24 hours. Then, the solvent was removed under reduced pressure and the crude product was purified by preparatory TLC (CH$_2$Cl$_2$:MeOH—NH$_3$ (7N), 15:1) to afford 5.6 mg (60%) of SO-IV-03A (106b). $^1$H NMR (600 MHz, CDCl$_3$): δ 8.40 (d, J=8.4 Hz, 1H), 7.88 (d, J=8.1 Hz, 1H), 7.82 (m, 2H), 7.55-7.62 (m, 2H), 7.48 (d, J=7.3 Hz, 1H), 7.38 (t, J=7.7 Hz, 1H), 6.69 (d, J=5.9 Hz, 1H), 5.21 (br s, 2H), 4.18 (t, J=7.3 Hz, 2H), 2.62 (m, 1H), 2.42 (t, J=6.9 Hz, 2H), 1.71-1.75 (m, 2H), 0.96 (d, J=6.2 Hz, 6H). $^{13}$C NMR (150 MHz, CDCl$_3$): δ 151.0, 145.3, 141.2, 141.0, 134.1, 132.4, 129.9, 129.1, 128.9, 128.7, 127.3, 127.2, 126.7, 125.9, 124.5, 97.6, 48.7, 44.0, 43.3, 30.3, 22.9. LCMS found m/z 392.13 [M+H]$^+$.

2-((2,4-dichlorophenyl)thio)-1-(3-(isopropylamino)propyl)-1H-imidazo[4,5-c]pyridin-4-amine (106c). To 2-((2,4-dichlorophenyl)thio)-1H-imidazo[4,5-c]pyridin-4-amine (105c) (20 mg, 0.064 mmol) in dry DMF (2 mL) was added Cs$_2$CO$_3$ (25.2 mg, 0.0768 mmol) and lastly 1,3-dibromopropane (32.7 μL, 0.323 mmol) and the reaction mixture was stirred at rt for 2 h. Then another portion of Cs$_2$CO$_3$ (40 mg, 0.122 mmol) and 1,3-dibromopropane (20 μL) were added and the reaction mixture was stirred for 1 more hour. The solvent was removed under reduced pressure and the crude product was purified by preparatory TLC (CH$_2$Cl$_2$:MeOH—NH$_3$ (7N), 20:1, 2×) to afford 11.6 mg (42%) of 1-(3-bromopropyl)-2-((2,4-dichlorophenyl)thio)-1H-imidazo[4,5-c]pyridin-4-amine. LCMS found m/z 432.81 [M+H]$^+$. To 1-(3-bromopropyl)-2-(2,4-dichlorophenyl)thio)-1H-imidazo[4,5-c]pyridin-4-amine (11.6 mg, 0.0268 mmol) in dry DMF was added isopropylamine (110 μL, 1.34 mmol) and the reaction mixture was stirred at rt for 24 hours. Then, the solvent was removed under reduced pressure and the crude product was purified by preparatory TLC (CH$_2$Cl$_2$:MeOH—NH$_3$ (7N), 20:1) to afford 8.3 mg (75%) of HJP-VI-101 (106c). $^1$H NMR (500 MHz, CDCl$_3$): δ 7.86 (d, J=5.9 Hz, 1H), 7.43 (d, J=2.2 Hz, 1H), 7.13 (dd, J=8.5, 2.2 Hz, 1H), 7.02 (d, J=8.6 Hz, 1H), 6.75 (d, J=5.9 Hz, 1H), 5.29 (br s, 2H), 4.25 (t, J=7.1 Hz, 2H), 2.71 (m, 1H), 2.56 (t, J=6.8 Hz, 2H), 1.88 (m, 2H), 1.02 (d, J=6.3 Hz, 6H). LCMS found m/z 410.08 [M+H]$^+$.

6.2.19 Synthesis of Compounds of Formula 110-111 (Scheme 19)

Scheme 19:

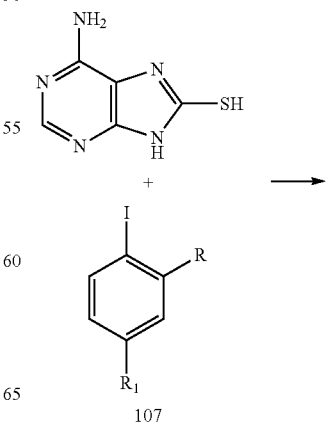

107

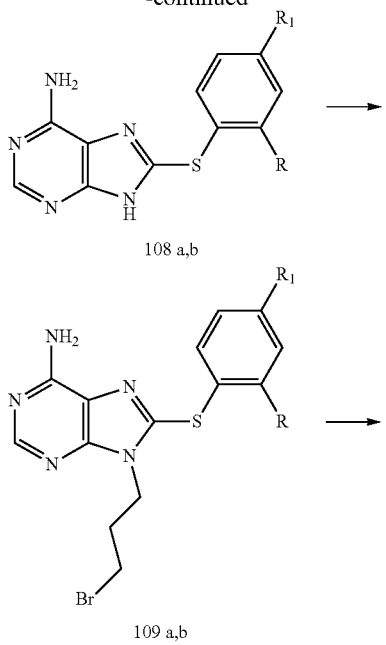

108 a,b 109 a,b

110, HJP-VI-23; R = F, R₁ = Cl
111, HJP-VI-25; R = Cl, R₁ = F

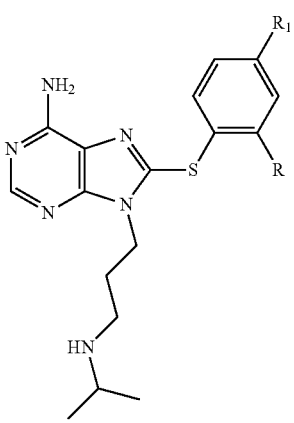

General Procedure for the Synthesis of 108 a and 108 b.

8-Mercaptoadenine (3.6 mmol), neocuproine hydrate (0.36 mmol), CuI (0.36 mmol), NaO-t-Bu (7.2 mmol), respective aryliodide (10.8 mmol), and anhydrous DMF (24 mL) were taken in a round bottom flask flushed with nitrogen. The flask was sealed with Teflon tape, heated at 110° C., and magnetically stirred for 24 h under nitrogen. Solvent was removed under reduced pressure and the resulting residue was chromatographed (CH₂Cl₂:MeOH:AcOH, 20:1:0.5).

8-((4-chloro-2-fluorophenyl)thio)-9H-purin-6-amine (108 a). Obtained as a light yellow solid in 49% yield. MS (ESI): m/z 296.1 [M+H]⁺.

8-((2-chloro-4-fluorophenyl)thio)-9H-purin-6-amine (108 b). Obtained as a light yellow solid in 49% yield. MS (ESI): m/z 296.1 [M+H]⁺.

General Procedure for Synthesis of N9 Alkylated 8-aryl Sulfanyl Derivatives 109a and 109b.

8-Arylsulfanyl adenine (108a or 108b, 1.21 mmol) was dissolved in DMF (15 mL) and Cs₂CO₃ (1.45 mmol) and 1,3-dibromopropane (2.42 mmol) were added and the mixture was stirred under nitrogen at for 2-4 h. Solvent was removed under reduced pressure and the resulting residue was chromatographed (CH₂Cl₂:MeOH:AcOH, 20:1:0.5) to afford desired compounds 109 a and 109b.

9-(3-bromopropyl)-8-((4-chloro-2-fluorophenyl)thio)-9H-purin-6-amine (109a). Obtained as a solid in 35% yield. MS (ESI): m/z 415.9 [M+H]⁺.

9-(3-bromopropyl)-8-((2-chloro-4-fluorophenyl)thio)-9H-purin-6-amine (109b). Obtained as a solid in 29% yield. MS (ESI): m/z 415.9 [M+H]⁺.

General Procedure for the Synthesis of 110 and 111

A mixture of 109a or 109b (12 mg, 0.028 mmol) and amine (1.40 mmol, 50 equiv.) in DMF (1 mL) under nitrogen protection was stirred at room temperature for 16-24 hrs. Following solvent removal, the crude material was purified by preparative TLC (CH₂Cl₂:CH₃OH—NH₃ (7N), 20:1 or 15:1) to afford desired products 110-111.

8-((4-chloro-2-fluorophenyl)thio)-9-(3-(isopropylamino)propyl)-9H-purin-6-amine (110, HJP-VI-23). Yield 15%. ¹H NMR (600 MHz, CDCl₃+5 drops CD₃OD) δ 8.23 (s, 1H), 7.62 (t, J=7.9 Hz, 1H), 7.27-7.32 (m, 2H), 4.42 (t, J=6.7 Hz, 2H), 3.26-3.29 (m, 1H), 3.00 (t, J=7.4 Hz, 2H), 2.31-2.37 (m, 2H), 1.35 (d, J=6.5 Hz, 6H); ¹³C NMR (150 MHz, CDCl₃+5 drops CD₃OD) δ 162.9, 161.2, 150.6, 150.5, 149.5, 145.6, 138.8 (d, $J_{C-F}$=9.8 Hz), 137.3, 126.1 (d, $J_{C-F}$=3.5 Hz), 117.8 (d, $J_{C-F}$=25.5 Hz), 112.4 (d, $J_{C-F}$=18.3 Hz), 50.8, 41.8, 41.1, 26.1, 19.0; HRMS (ESI) m/z [M+H]⁺ calcd. for C₁₇H₂₁ClFN₆S, 395.1221. found 395.1216.

8-((2-chloro-4-fluorophenyl)thio)-9-(3-(isopropylamino)propyl)-9H-purin-6-amine (111, HJP-VI-25). Yield 16%. ¹H NMR (600 MHz, CDCl₃) δ 8.31 (s, 1H), 7.34 (dd, J=8.8 and 5.8 Hz, 1H), 7.23 (dd, J=8.2 and 2.7 Hz, 1H), 6.95 (dt, J=7.9 and 2.7 Hz, 1H), 6.24 (br s, 2H), 4.32 (t, J=7.0 Hz, 2H), 2.68-2.72 (m, 1H), 2.56 (t, J=6.9 Hz, 2H), 1.95-1.99 (m, 2H), 1.02 (d, J=6.2 Hz, 6H); ¹³C NMR (150 MHz, CDCl₃) δ 163.3, 161.6, 154.7, 153.0, 151.6, 144.7, 136.4 (d, $J_{C-F}$=10.4 Hz), 134.2 (d, $J_{C-F}$=8.8 Hz), 125.7 (d, $J_{C-F}$=3.8 Hz), 120.1, 118.1 (d, $J_{C-F}$=25.1 Hz), 115.3 (d, $J_{C-F}$=21.7 Hz), 48.7, 43.7, 41.7, 30.3, 22.9; HRMS (ESI) m/z [M+H]⁺ calcd. for C₁₇H₂₁ClFN₆S, 395.1221. found 395.1222.

6.3 Synthesis of PU-H71-Type Fluorescently Labeled Probes

Scheme 20:

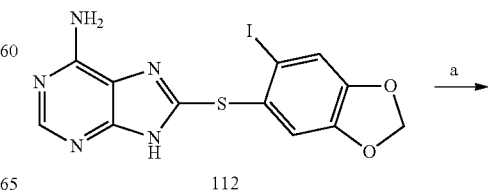

112

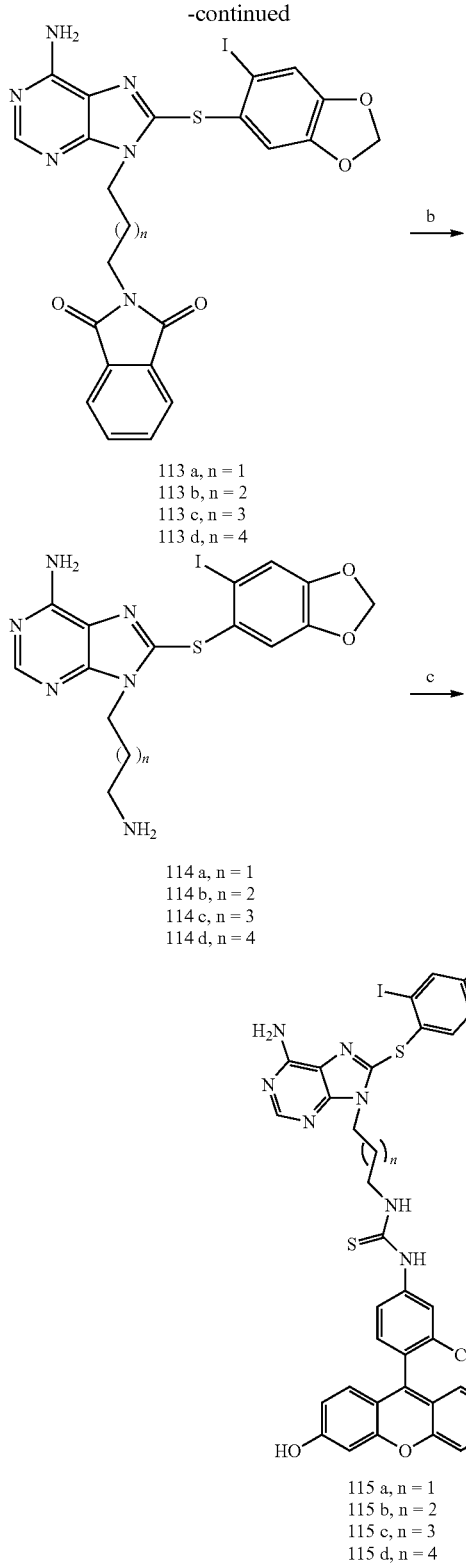

113 a, n = 1
113 b, n = 2
113 c, n = 3
113 d, n = 4

114 a, n = 1
114 b, n = 2
114 c, n = 3
114 d, n = 4

115 a, n = 1
115 b, n = 2
115 c, n = 3
115 d, n = 4

2-(4-(6-Amino-8-((6-iodobenzo[d][1,3]dioxol-5-yl)thio)-9H-purin-9-yl)butyl)isoindoline-1,3-dione (113b). 200 mg (0.484 mmol) of 112 was dissolved in DMF (8 mL). 466 mg (1.43 mmol) of $Cs_2CO_3$ and 683 mg (2.42 mmol) of N-(4-bromobutyl)phthalimide were added and the mixture was sonicated for 30 min. 31.5 mg (0.097 mmol) of $Cs_2CO_3$ was added and the mixture was again sonicated for 30 min. This was repeated two more times for a total reaction time of 2 h. DMF was removed and the resulting residue was purified by preparatory TLC ($CH_2Cl_2$:MeOH:AcOH, 15:1:0.5) to give 134 mg (45%) of 113b. $^1$H NMR (500 MHz, $CDCl_3$) δ 8.18 (s, 1H), 7.84 (dd, J=5.5, 3.1 Hz, 2H), 7.72 (dd, J=5.5, 3.1 Hz, 2H), 7.22 (s, 1H), 6.89 (s, 1H), 6.76 (br s, 2H), 5.99 (s, 2H), 4.23 (t, J=7.1 Hz, 2H), 3.69 (t, J=7.0 Hz, 2H), 1.67-1.83 (m, 4H); MS (ESI) m/z 615.2 [M+H]$^+$.

9-(4-Aminobutyl)-8-((6-iodobenzo[d][1,3]dioxol-5-yl)thio)-9H-purin-6-amine (114b). To a suspension of 113b (38.9 mg, 0.063 mmol) in 2 mL MeOH/$CH_2Cl_2$ (7:1 mL) was added hydrazine hydrate (46 μL, 0.950 mmol) and the mixture was stirred at rt for 12 h. Solvent was removed under reduced pressure and the resulting residue was purified by preparatory TLC ($CH_2Cl_2$:MeOH—$NH_3$ (7N), 10:1) to give 18 mg (59%) of 114b. $^1$H NMR (500 MHz, $CDCl_3$/MeOH-$d_4$) δ 8.22 (s, 1H), 7.38 (s, 1H), 7.04 (s, 1H), 6.05 (s, 2H), 4.23 (t, J=7.4 Hz, 2H), 2.78 (t, J=7.1 Hz, 2H), 1.82-1.91 (m, 2H), 1.55-1.63 (m, 2H); MS (ESI) m/z 485.0 [M+H]$^+$.

PU-C4-FITC (115b). 114b (9.7 mg, 0.020 mmol), FITC (8.57 mg (0.022 mmol) and $Et_3N$ (0.1 mL) in DMF (0.2 mL) was stirred for 3 h at rt. The reaction mixture was directly purified by HPLC to give 5.2 mg (30%) of 115b. $^1$H NMR (600 MHz, MeOH-$d_4$) δ 8.22 (s, 1H), 8.00 (s, 1H), 7.61 (d, J=7.6 Hz, 1H), 7.37 (s, 1H), 7.19 (s, 1H), 7.06 (d, J=8.2 Hz, 1H), 6.58-6.67 (m, 4H), 6.48 (dd, J=8.7, 2.0 Hz, 2H), 5.97 (s, 2H), 4.30 (t, J=7.0 Hz, 2H), 3.58 (br s, 2H), 1.90-2.00 (m, 2H), 1.61-1.70 (m, 2H); HRMS (ESI) m/z [M+H]$^+$ calcd. for $C_{37}H_{29}IN_7O_7S_2$, 874.0615. found 874.0610; HPLC $R_t$=9.57 (98%).

2-(6-(6-Amino-8-((6-iodobenzo[d][1,3]dioxol-5-yl)thio)-9H-purin-9-yl)hexyl)isoindoline-1,3-dione (113c). 200 mg (0.484 mmol) of 112 was dissolved in DMF (8 mL). 466 mg (1.43 mmol) of $Cs_2CO_3$ and 751 mg (2.42 mmol) N-(6-bromohexyl)phthalimide were added and the mixture was sonicated for 2 h. Solvent was removed under reduced pressure and the resulting residue was purified by preparatory TLC ($CH_2Cl_2$:MeOH:AcOH, 15:1:0.5) to give 100 mg (32%) of 113c. $^1$H NMR (500 MHz, $CDCl_3$) δ 8.26 (s, 1H), 7.83 (dd, J=5.4, 3.1 Hz, 2H), 7.70 (dd, J=5.4, 3.0 Hz, 2H), 7.26 (s, 1H), 6.87 (s, 1H), 6.36 (br s, 2H), 5.96 (s, 2H), 4.18 (t, J=7.5 Hz, 2H), 3.66 (t, J=7.2 Hz, 2H), 1.70-1.79 (m, 2H), 1.60-1.68 (m, 2H), 1.32-1.43 (m, 4H); MS (ESI) m/z 643.2 [M+H]$^+$.

9-(6-Aminohexyl)-8-((6-iodobenzo[d][1,3]dioxol-5-yl)thio)-9H-purin-6-amine (114c). To a suspension of 113c (97 mg, 0.1511 mmol) in 4 mL MeOH/$CH_2Cl_2$ (7:1 mL) was added hydrazine hydrate (110 μL, 2.27 mmol) and the mixture was stirred at rt for 12 h. Solvent was removed under reduced pressure and the resulting residue was purified by preparatory TLC ($CH_2Cl_2$:MeOH—$NH_3$ (7N), 10:1) to give 47 mg (61%) of 114c. $^1$H NMR (500 MHz, $CDCl_3$) δ 8.32 (s, 1H), 7.31 (s, 1H), 6.90 (s, 1H), 5.99 (s, 2H), 5.84 (br s, 2H), 4.20 (t, J=7.5 Hz, 2H), 2.67 (t, J=6.5 Hz, 2H), 1.72-1.84 (m, 2H), 1.31-1.45 (m, 6H); MS (ESI) m/z 513.0 [M+H]$^+$.

PU-C6-FITC (115c). 114c (9.7 mg, 0.01894 mmol), FITC (8.11 mg, 0.0208 mmol) and $Et_3N$ (0.1 mL) in DMF (0.2 mL) was stirred for 3 h at rt. The reaction mixture was directly purified by HPLC to give 8.0 mg (47%) of 115c. $^1$H NMR (600 MHz, MeOH-$d_4$) δ 8.23 (s, 1H), 8.09 (s, 1H), 7.65 (d, J=7.9 Hz, 1H), 7.35 (s, 1H), 7.16 (s, 1H), 7.08 (d, J=8.3 Hz, 1H), 6.71 (d, J=8.8 Hz, 2H), 6.67 (d, J=2.2 Hz, 2H), 6.53 (dd, J=8.8, 2.2 Hz, 2H), 5.96 (s, 2H), 4.24 (t, J=7.1 Hz, 2H), 3.50 (br s, 2H), 1.79-1.88 (m, 2H), 1.52-1.61 (m, 2H), 1.31-1.42 (m, 4H); HRMS (ESI) m/z [M+H]+ calcd. for C$_{39}$H$_{33}$IN$_{7}$O$_{7}$S$_{2}$, 902.0928. found 902.0939; HPLC R$_t$=10.02 (99%).

2-(8-(6-Amino-8-((6-iodobenzo[d][1,3]dioxol-5-yl)thio)-9H-purin-9-yl)octyl)isoindoline-1,3-dione (113d). 200 mg (0.484 mmol) of 112 was dissolved in DMF (8 mL). 466 mg (1.43 mmol) of Cs$_2$CO$_3$ and 819 mg (2.42 mmol) N-(8-bromooctyl)phthalimide were added and the mixture was sonicated for 1.5 h. Solvent was removed under reduced pressure and the resulting residue was purified by preparatory TLC (CH$_2$Cl$_2$:MeOH:AcOH, 15:1:0.5) to give 120 mg (34%) of 113d. $^1$H NMR (500 MHz, CDCl$_3$) δ 8.29 (s, 1H), 7.84 (dd, J=5.5, 3.1 Hz, 2H), 7.70 (dd, J=5.5, 3.1 Hz, 2H), 7.28 (s, 1H), 6.87 (s, 1H), 6.29 (br s, 2H), 5.96 (s, 2H), 4.18 (t, J=7.5 Hz, 2H), 3.67 (t, J=7.3 Hz, 2H), 1.62-1.77 (m, 4H), 1.25-1.36 (m, 8H); MS (ESI) m/z 671.3 [M+H]+.

9-(8-Aminooctyl)-8-((6-iodobenzo[d][1,3]dioxol-5-yl)thio)-9H-purin-6-amine (114d). To a suspension of 113d (90.1 mg, 0.1345 mmol) in 4 mL MeOH/CH$_2$Cl$_2$ (7:1 mL) was added hydrazine hydrate (98 µL, 2.017 mmol) and the mixture was stirred at rt for 12 h. Solvent was removed under reduced pressure and the resulting residue was purified by preparatory TLC (CH$_2$Cl$_2$:MeOH—NH$_3$ (7N), 10:1) to give 25 mg (34%) of 114d. $^1$H NMR (500 MHz, CDCl$_3$) δ 8.33 (s, 1H), 7.31 (s, 1H), 6.90 (s, 1H), 5.99 (s, 2H), 5.72 (br s, 2H), 4.20 (t, J=7.5 Hz, 2H), 2.66 (t, J=7.1 Hz, 2H), 1.70-1.80 (m, 2H), 1.36-1.45 (m, 2H), 1.21-1.35 (m, 8H); MS (ESI) m/z 541.1 [M+H]+.

PU-C8-FITC (115d). 114d (15.0 mg, 0.028 mmol), FITC (11.9 mg, 0.031 mmol) and Et$_3$N (0.1 mL) in DMF (0.2 mL) was stirred for 4 h at rt. The reaction mixture was directly purified by HPLC to give 16.9 mg (66%) of 115d. $^1$H NMR (600 MHz, MeOH-d$_4$) δ 8.22 (s, 1H), 8.11 (s, 1H), 7.68 (d, J=7.8 Hz, 1H), 7.34 (s, 1H), 7.12 (s, 1H), 7.09 (d, J=8.2 Hz, 1H), 6.72 (d, J=8.7 Hz, 2H), 6.67 (d, J=2.0 Hz, 2H), 6.53 (dd, J=8.7, 2.0 Hz, 2H), 5.96 (s, 2H), 4.20 (t, J=7.1 Hz, 2H), 3.50 (br s, 2H), 1.74-1.81 (m, 2H), 1.52-1.59 (m, 2H), 1.23-1.35 (m, 8H); HRMS (ESI) m/z [M+H]+ calcd. for C$_{41}$H$_{37}$IN$_{7}$O$_{7}$S$_{2}$, 930.1241. found 930.1231; HPLC R$_t$=10.60 (96%).

6.4. Synthesis of PU-WS13 Beads

Scheme 21:

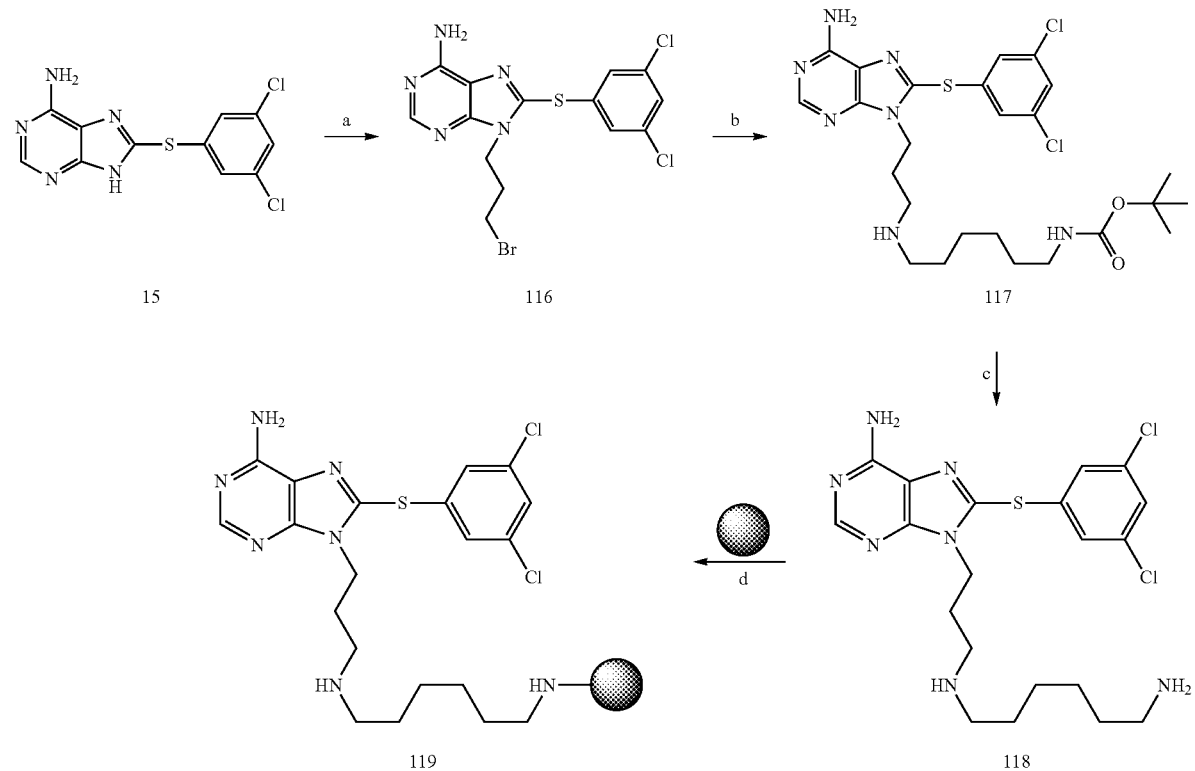

9-(3-Bromopropyl)-8-((3,5-dichlorophenyl)thio)-9H-purin-6-amine (116). To a solution of 15 (0.4 g, 1.29 mmol) in 20 ml of dry DMF was added 0.65 g (2.00 mmol, 1.55 equiv.) of Cs$_2$CO$_3$ and allowed to stir at room temperature for 15 minutes. Then 0.9 g (4.47 mmol, 3.5 equiv.) of 1,3-dibromopropane was added and the reaction mixture was stirred for 2 hrs at room temperature. Solvent was removed under reduced pressure and the residue purified by column chromatography (CH$_2$Cl$_2$:CH$_3$OH:CH$_3$COOH; 20:1:0.1) to yield 0.15 g (27%) of desired N-9 isomer (116). $^1$H NMR (500 MHz, CDCl$_3$) δ 8.36 (s, 1H), 7.31 (m, 3H), 4.31 (t, J=7.1 Hz, 2H), 3.15 (t, J=6.7 Hz, 2H), 2.32 (quintet, J=6.8 Hz, 2H); $^{13}$C NMR (125 MHz, CDCl$_3$) 154.7, 153.6, 151.6, 143.7, 135.9, 134.3, 128.6, 128.3, 120.3, 42.6, 33.0, 29.3. MS (ESI) m/z 432.1 [M+H]+.

tert-Butyl-(6-((3-(6-amino-8-((3,5-dichlorophenyl)thio)-9H-purin-9-yl)propyl)amino)hexyl)carbamate (117): Compound 116 (0.15 g, 0.348 mmol) and tert-Butyl 6-aminohexylcarbamate (0.752 g, 3.48 mmol) in DMF (5 mL) was stirred at rt for 24 h. The reaction mixture was concentrated and the residue purified by preparative TLC [CH$_2$Cl$_2$/

MeOH—NH$_3$ (7 N), 20:1] to give 81 mg (41%) of 117 as a yellow solid. $^1$H NMR (400 MHz, CDCl$_3$/MeOH-d$_4$, δ) 8.19 (s, 1H), 7.46 (d, J=1.7 Hz, 2H), 7.44 (d, J=1.6 Hz, 1H), 4.31 (t, J=6.9 Hz, 2H), 3.05 (m, 2H), 2.56 (t, J=6.7 Hz, 2H), 2.51 (t, J=7.0 Hz, 2H), 1.99 (m, 2H), 1.44 (m, 13H), 1.30 (m, 4H); MS (ESI): m/z 568.2 [M+H]$^+$.

N1-(3-(6-Amino-8-((3,5-dichlorophenyl)thio)-9H-purin-9-yl)propyl)hexane-1,6-diamine (118): Compound 117 (81 mg, 0.143 mmol) was dissolved in 10 mL of CH$_2$Cl$_2$/TFA (4:1) and the solution was stirred at room temperature for 45 min. Solvent was removed under reduced pressure and the residue purified by preparative TLC [CH$_2$Cl$_2$/MeOH—NH$_3$ (7N), 20:1-10:1] to give 41 mg (62% yield) of 118 as a white solid. $^1$H NMR (400 MHz, CDCl$_3$, δ) 8.34 (s, 1H), 7.32 (m, 3H), 6.04 (bs, 2H), 4.31 (t, J=7.0 Hz, 2H), 2.49-2.51 (m, 4H), 1.94-2.03 (m, 2H), 1.31-1.44 (m, 12H); MS (ESI): m/z 468.3 [M+H]$^+$.

Compound-Affi-Gel® 10 Beads (119): 118 (41 mg, 0.087 mmol) was dissolved in DMF (4 mL) and added to 10 mL of Affi-Gel® 10 beads (prewashed, 3×20 mL DMF) in a solid phase peptide synthesis vessel. 75 µL of N,N-diisopropylethylamine and several crystals of DMAP were added and this was shaken at room temperature for 2.5 h. Then 2-methoxyethylamine (17.5 mg, 20 µl, 0.23 mmol) was added and shaking was continued for 30 min. Then the solvent was removed and the beads washed for 10 min each time with CH$_2$Cl$_2$/Et$_3$N (9:1, 4×20 mL), DMF (3×20 mL), Felts buffer (3×20 mL) and i-PrOH (3×20 mL). The beads 119 were stored in i-PrOH (beads/i-PrOH (1:2), v/v) at −80° C.

6.5 Synthesis of PU-WS13 Biotin Analogs and Fluorescently Labeled Probes

Scheme 22:

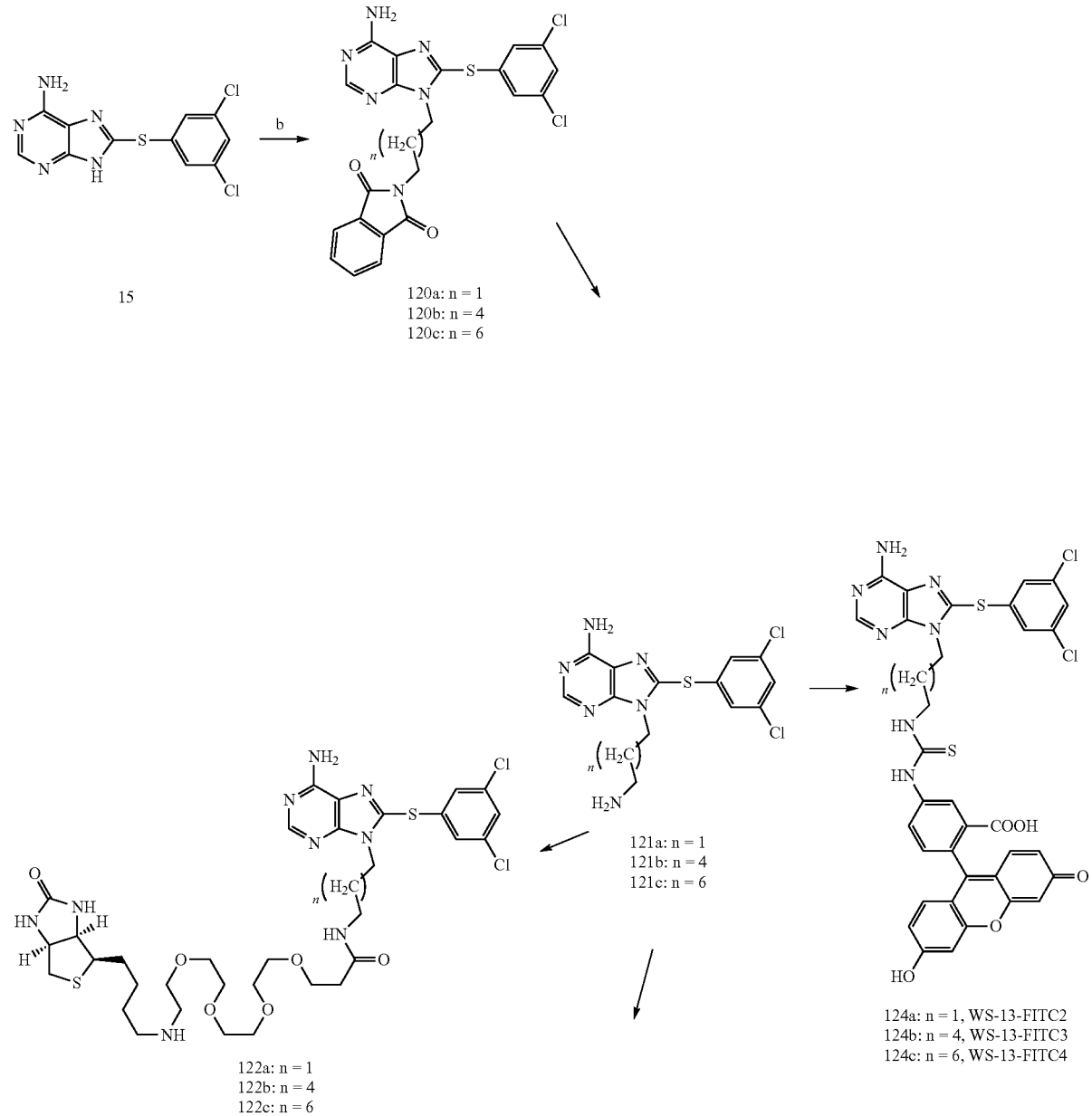

120a: n = 1
120b: n = 4
120c: n = 6

121a: n = 1
121b: n = 4
121c: n = 6

122a: n = 1
122b: n = 4
122c: n = 6

124a: n = 1, WS-13-FITC2
124b: n = 4, WS-13-FITC3
124c: n = 6, WS-13-FITC4

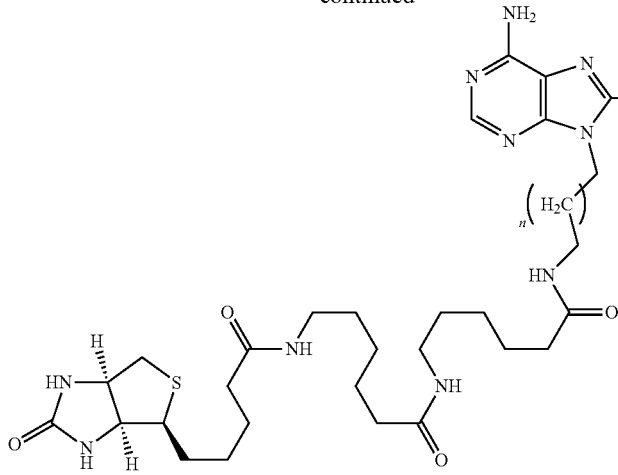

123a: n = 1
123b: n = 4
123c: n = 6

2-(3-(6-Amino-8-((3,5-dichlorophenyl)thio)-9H-purin-9-yl)propyl)isoindoline-1,3-dione (120a): To a solution of 15 (0.4 g, 1.29 mmol) in 20 ml of dry DMF was added 0.65 g (2.00 mmol, 1.55 equiv.) of $Cs_2CO_3$ and allowed to stir at room temperature for 15 minutes. Then 1.2 g (4.47 mmol, 3.5 equiv.) of bromopropyl phthalamide was added and the reaction mixture was stirred for 2 hrs at room temperature. Solvent was removed under reduced pressure and the residue purified by column chromatography ($CH_2Cl_2$:$CH_3OH$:$CH_3COOH$; 20:1:0.1) to yield 0.15 g (25%) of desired N-9 isomer (120a). $^1$H NMR (500 MHz, $CDCl_3$) δ 8.16 (s, 1H), 7.82-7.86 (m, 2H), 7.71-7.75 (m, 2H), 7.24 (t, J=1.65 Hz, 1H), 7.18 (t, J=1.6 Hz, 1H), 4.31 (t, J=7.5 Hz, 2H), 3.37 (t, J=6.7 Hz, 2H), 2.21 (quintet, J=6.8 Hz, 2H); $^{13}$C NMR (125 MHz, $CDCl_3$) 176.1, 168.1, 155.1, 152.2, 150.8, 143.6, 135.8, 134.1, 133.9, 131.8, 128.6, 128.2, 123.3, 41.8, 35.3, 28.6. MS (ESI) m/z 498.95/501.13 [M+H]$^+$.

9-(3-Aminopropyl)-8-((3,5-dichlorophenyl)thio)-9H-purin-6-amine (121a): To a solution of 120a (0.15 g, 0.3 mmol) in 14 ml $CH_2Cl_2$+2 ml $CH_3OH$ was added 194 μL, (4.03 mmol, 15 equiv.) of hydrazine hydrate and allowed to stir at room temperature for 12 h. Solvent was removed under reduced pressure and the residue purified by column chromatography ($CH_2Cl_2$:$CH_3OH$—$NH_3$ (7N); 20:1) to yield 65 mg (66%) of 121a. $^1$H NMR (500 MHz, $CDCl_3$+5 drops $CD_3OD$) δ 8.26 (s, 1H), 7.34-7.39 (m, 3H), 4.31 (t, J=6.9 Hz, 2H), 2.65 (t, J=6.6 Hz, 2H), 1.93 (quintet, J=6.8 Hz, 2H); $^{13}$C NMR (125 MHz, $CDCl_3$) 154.6, 152.9, 151.2, 144.3, 135.9, 133.2, 129.1, 128.9, 119.6, 40.9, 37.9, 32.6. MS (ESI) m/z 369.14/371.22 [M+H]$^+$.

N-(3-(6-Amino-8-((3,5-dichlorophenyl)thio)-9H-purin-9-yl)propyl)-1-(5-((3aS,4R,6aR)-2-oxohexahydro-1H-thieno[3,4-d]imidazol-4-yl)pentanamido)-3,6,9,12-tetraoxapentadecan-15-amide (122a): 121a (18 mg, 0.0487 mmol), EZ-Link® NHS-PEG$_4$-Biotin (31.6 mg, 0.0536 mmol) and DIEA (12.6 mg, 16.9 μL, 0.0974 mmol) in DMF (1.5 ml) was stirred at rt for 1 h. The reaction mixture was concentrated under reduced pressure and resulting residue was purified by preparatory TLC ($CH_2Cl_2$-MeOH—$NH_3$ (7N), 10:1) to give 30 mg (73%) of 122a. $^1$H NMR (600 MHz, $CDCl_3$) δ 8.30 (s, 1H), 7.51 (t, J=5.8 Hz, 1H), 7.26-7.29 (m, 3H), 7.05 (t, J=4.9 Hz, 1H), 6.82 (s, 1H), 6.63 (s, 1H), 6.00 (s, 1H), 4.79-4.50 (m, 1H), 4.29-4.32 (m, 1H), 4.28 (t, J=6.7 Hz, 2H), 3.77 (t, J=6.1 Hz, 2H), 3.59-3.65 (m, 12H), 3.55 (t, J=5.0 Hz, 2H), 3.40-3.43 (m, 2H), 3.18 (q, J=6.1 Hz, 2H), 3.11-3.15 (m, 1H), 2.86-2.90 (m, 2H), 2.52 (t, J=6.0 Hz, 2H), 2.19 (t, J=7.4 Hz, 2H), 1.94 (quintet, J=6.7 Hz, 2H), 1.69-1.76 (m, 2H), 1.58-1.67 (m, 2H), 1.38-1.44 (m, 2H); HRMS (ESI) m/z [M+H]$^+$ calcd. for $C_{35}H_{50}Cl_2N_9O_7S_2$, 842.2652. found 842.2657; HPLC (Method A) $R_t$=8.29.

N-(3-(6-Amino-8-((3,5-dichlorophenyl)thio)-9H-purin-9-yl)propyl)-6-(6-(5-((3aS,4R,6aR)-2-oxohexahydro-1H-thieno[3,4-d]imidazol-4-yl)pentanamido)hexanamido)hexanamide (123a): 121a (5 mg, 0.0128 mmol), EZ-Link® NHS-LC_LC-Biotin (10.2 mg, 0.018 mmol) and DIEA (4.21 mg, 5.7 μL, 0.0326 mmol) in DMF (0.5 ml) was stirred at rt for 1 h. The reaction mixture was concentrated under reduced pressure and resulting residue was purified by preparatory TLC ($CH_2Cl_2$-MeOH—$NH_3$ (7N), 10:1) to give 6.3 mg (60%) of desired compound. $^1$H NMR (500 MHz, $CDCl_3$+3 drops of $CD_3OD$) δ 8.26 (s, 1H), 7.38 (t, J=1.7 Hz, 1H), 7.35 (d, J=1.8 Hz, 2H), 4.48-4.52 (m, 1H), 4.29-4.33 (m, 1H), 4.26 (t, J=6.9 Hz, 2H), 3.09-3.15 (m, 8H), 2.24 (t, J=6.9 Hz, 2H), 2.10-2.20 (m, 8H), 1.94 (quintet, J=6.3 Hz, 2H), 1.58-1.71 (m, 10H), 1.45-1.53 (m, 4H), 1.41-1.44 (m, 3H); HRMS (ESI) m/z [M+H]$^+$ calcd. for $C_{36}H_{51}Cl_2N_{10}O_4S_2$, 821.2913. found 821.2941; HPLC (Method A) $R_t$=9.92.

2-(6-(6-Amino-8-((3,5-dichlorophenyl)thio)-9H-purin-9-yl)hexyl)isoindoline-1,3-dione (120b): To a solution of 15 (0.4 g, 1.29 mmol) in 20 ml of dry DMF was added 0.75 g (2.31 mmol, 1.8 equiv.) of $Cs_2CO_3$ and allowed to stir at room temperature for 15 minutes. Then 1.4 g (4.5 mmol, 3.5 equiv.) of bromohexyl phthalamide was added and the reaction mixture was stirred for 4 hrs at room temperature. Solvent was removed under reduced pressure and the residue purified by column chromatography ($CH_2Cl_2$:$CH_3OH$:$CH_3COOH$; 20:1:0.1) to yield 0.10 g (15%) of desired N-9 isomer (120b). $^1$H NMR (500 MHz, $CDCl_3$) δ 8.25 (s, 1H), 7.83-7.85 (m, 2H), 7.73-7.74 (m, 2H), 7.32 (m, 3H), 4.21 (t, J=7.4 Hz, 2H), 3.66 (t, J=7.2 Hz, 2H), 1.75-1.78 (m, 2H), 1.62-1.65 (m, 2H), 1.32-1.38 (m, 4H). MS (ESI) m/z 541.33/543.24 [M+H]$^+$.

9-(3-Aminohexyl)-8-((3,5-dichlorophenyl)thio)-9H-purin-6-amine (121b): To a solution of 120b (0.10 g, 0.18 mmol) in 10 ml $CH_2Cl_2$+1.5 ml $CH_3OH$ was added 140 µL (2.77 mmol, 15 equiv.) of hydrazine hydrate and allowed to stir at room temperature for 12 h. Solvent was removed under reduced pressure and the residue purified by column chromatography ($CH_2Cl_2$:$CH_3OH$—$NH_3$ (7N); 20:1) to yield 56 mg (74%) of 121b. $^1H$ NMR (600 MHz, $CDCl_3$+5 drops $CD_3OD$) δ 8.31 (s, 1H), 7.31-7.34 (m, 3H), 4.22 (t, J=7.9 Hz, 2H), 2.65 (t, J=7.3 Hz, 2H), 1.76-1.78 (m, 2H), 1.41-1.43 (m, 2H), 1.31-1.36 (m, 4H); $^{13}C$ NMR (150 MHz, $CDCl_3$+5 drops $CD_3OD$) 154.8, 153.2, 151.2, 143.8, 135.9, 134.1, 128.7, 128.6, 119.9, 43.8, 41.6, 33.0, 29.7, 26.4, 26.3. MS (ESI) m/z 411.24/413.24 $[M+H]^+$.

N-(6-(6-Amino-8-((3,5-dichlorophenyl)thio)-9H-purin-9-yl)hexyl)-1-(5-((3aS,4R,6aR)-2-oxohexahydro-1H-thieno[3,4-d]imidazol-4-yl)pentanamido)-3,6,9,12-tetraoxapentadecan-15-amide (122b): 121b (6.4 mg, 0.0156 mmol), EZ-Link® NHS-PEG$_4$-Biotin (10.1 mg, 0.017 mmol) and DIEA (4 mg, 5.5 µL, 0.031 mmol) in DMF (0.5 ml) was stirred at rt for 1 h. The reaction mixture was concentrated under reduced pressure and resulting residue was purified by preparatory TLC ($CH_2Cl_2$-MeOH—$NH_3$ (7N), 10:1) to give 9.6 mg (77%) of 122b. $^1H$ NMR (600 MHz, $CD_2Cl_2$) δ 8.27 (s, 1H), 7.30 (t, J=1.8 Hz, 1H), 7.28 (d, J=1.8 Hz, 2H), 6.76 (t, J=5.2 Hz, 1H), 6.59 (t, J=5.3 Hz, 1H), 6.46 (s, 1H), 6.35 (s, 2H), 5.54 (s, 1H), 4.45-4.49 (m, 1H), 4.27-4.31 (m, 1H), 4.20 (t, J=7.3 Hz, 2H), 3.68 (t, J=5.9 Hz, 2H), 3.55-3.59 (m, 14H), 3.53 (t, J=5.1 Hz, 2H), 3.38 (q, J=5.1 Hz, 2H), 3.14 (q, J=7.1 Hz, 3H), 2.87-2.91 (m, 1H), 2.67-2.73 (m, 1H), 2.39 (t, J=6.0 Hz, 2H), 2.16 (t, J=7.4 Hz, 2H), 1.57-1.76 (m, 7H), 1.37-1.44 (m, 5H); HRMS (ESI) m/z $[M+H]^+$ calcd. for $C_{38}H_{56}Cl_2N_9O_7S_2$, 884.3121. found 884.3157; HPLC (Method A) $R_t$=9.00.

N-(6-(6-Amino-8-((3,5-dichlorophenyl)thio)-9H-purin-9-yl)hexyl)-6-(6-(5-((3aS,4R,6aR)-2-oxohexahydro-1H-thieno[3,4-d]imidazol-4-yl)pentanamido)hexanamido)hexanamide (123b): 121b (5 mg, 0.0122 mmol), EZ-Link® NHS-LC_LC-Biotin (9.65 mg, 0.0146 mmol) and DIEA (4 mg, 5.5 µL, 0.031 mmol) in DMF (0.5 ml) was stirred at rt for 1 h. The reaction mixture was concentrated under reduced pressure and resulting residue was purified by preparatory TLC (CH2Cl2-MeOH—NH3 (7N), 10:1) to give 4.2 mg (42%) of 123b. $^1H$ NMR (600 MHz, $CD_2Cl_2$+5 drops of $CD_3OD$) δ 8.16 (s, 1H), 7.26-7.31 (m, 3H), 4.38-4.42 (m, 1H), 4.20-4.23 (m, 1H), 4.13 (t, J=7.3 Hz, 2H), 3.03-3.09 (m, 8H), 2.80-2.85 (m, 1H), 2.61-2.65 (m, 1H), 2.03-2.11 (m, 7H), 1.25-1.69 (m, 24H); HRMS (ESI) m/z $[M+H]^+$ calcd. for $C_{39}H_{57}Cl_2N_{10}O_4S_2$, 863.3383. found 863.3402; HPLC (Method A) $R_t$=9.47.

2-(6-(6-Amino-8-((3,5-dichlorophenyl)thio)-9H-purin-9-yl)octyl)isoindoline-1,3-dione (120c): To a solution of 15 (0.4 g, 1.29 mmol) in 20 ml of dry DMF was added 0.75 g (2.31 mmol, 1.8 equiv.) of $Cs_2CO_3$ and allowed to stir at room temperature for 15 minutes. Then 1.5 g (4.48 mmol, 3.5 equiv.) of bromooctyl phthalamide was added and the reaction mixture was stirred for 2 hrs at room temperature. Solvent was removed under reduced pressure and the residue purified by column chromatography ($CH_2Cl_2$:$CH_3OH$:$CH_3COOH$; 20:1:0.1) to yield 0.15 g (21%) of desired N-9 isomer (120c). $^1H$ NMR (500 MHz, $CDCl_3$) δ 8.18 (s, 1H), 7.71-7.75 (m, 2H), 7.60-7.64 (m, 2H), 7.21 (m, 3H), 4.13 (t, J=7.3 Hz, 2H), 3.57 (t, J=7.2 Hz, 2H), 1.55-1.64 (m, 4H), 1.19-1.21 (m, 8H); $^{13}C$ NMR (125 MHz, $CDCl_3$) 174.5, 167.6, 153.1, 149.9, 149.6, 144.1, 134.9, 133.0, 132.5, 131.0, 128.1, 127.9, 122.2, 48.9, 43.3, 36.9, 28.6, 27.9, 27.5, 25.7, 25.5. MS (ESI) m/z 569.22/571.13 $[M+H]^+$.

9-(3-Aminohexyl)-8-((3,5-dichlorophenyl)thio)-9H-purin-6-amine (121c): To a solution of 120c (0.15 g, 0.26 mmol) in 10 ml $CH_2Cl_2$+1.5 ml $CH_3OH$ was added 194 µL (3.90 mmol, 15 equiv.) of hydrazine hydrate and allowed to stir at room temperature for 12 h. Solvent was removed under reduced pressure and the residue purified by column chromatography ($CH_2Cl_2$:$CH_3OH$—$NH_3$ (7N); 20:1) to yield 57 mg (50%) of 121c. $^1H$ NMR (600 MHz, $CDCl_3$+5 drops $CD_3OD$) δ 8.26 (s, 1H), 7.12-7.16 (m, 3H), 4.12 (t, J=7.3 Hz, 2H), 2.64 (t, J=6.9 Hz, 2H), 1.62-1.68 (m, 2H), 1.35-1.41 (m, 2H), 1.13-1.20 (m, 8H); $^{13}C$ NMR (125 MHz, $CDCl_3$+5 drops $CD_3OD$) 155.3, 153.4, 151.3, 142.8, 135.7, 134.9, 128.1, 127.8, 120.3, 43.9, 41.5, 30.9, 29.8, 29.1, 28.9, 26.7, 26.5. MS (ESI) m/z 439.16/441.15 $[M+H]^+$.

N-(8-(6-Amino-8-((3,5-dichlorophenyl)thio)-9H-purin-9-yl)octyl)-1-(5-((3aS,4R,6aR)-2-oxohexahydro-1H-thieno[3,4-d]imidazol-4-yl)pentanamido)-3,6,9,12-tetraoxapentadecan-15-amide (122c): 121c (5.7 mg, 0.013 mmol), EZ-Link® NHS-PEG$_4$-Biotin (8.4 mg, 0.014 mmol) and DIEA (3.4 mg, 4.5 µL, 0.026 mmol) in DMF (0.5 ml) was stirred at rt for 1 h. The reaction mixture was concentrated under reduced pressure and resulting residue was purified by preparatory TLC ($CH_2Cl_2$-MeOH—$NH_3$ (7N), 10:1) to give 6.6 mg (56%) of 122c. $^1H$ NMR (600 MHz, $CD_2Cl_2$+5 drops of $CD_3OD$) δ 8.15 (s, 1H), 7.30 (t, J=1.7 Hz, 1H), 7.26 (d, J=1.7 Hz, 2H), 4.38-4.43 (m, 1H), 4.20-4.23 (m, 1H), 4.13 (t, J=7.4 Hz, 2H), 3.61 (t, J=6.0 Hz, 2H), 3.50-3.55 (m, 14H), 3.45 (t, J=5.3 Hz, 2H), 3.27-3.31 (m, 4H), 3.07 (t, J=7.3 Hz, 3H), 2.81-2.85 (m, 1H), 2.60-2.64 (m, 1H), 2.34 (t, J=6.0 Hz, 2H), 2.12 (t, J=7.6 Hz, 2H), 1.49-1.67 (m, 8H), 1.30-1.39 (m, 6H); HRMS (ESI) m/z $[M+H]^+$ calcd. for $C_{40}H_{60}Cl_2N_9O_7S_2$, 912.3410. found 912.3455; HPLC (Method B) $R_t$=4.25.

N-(8-(6-Amino-8-((3,5-dichlorophenyl)thio)-9H-purin-9-yl)octyl)-6-(6-(5-((3aS,4R,6aR)-2-oxohexahydro-1H-thieno[3,4-d]imidazol-4-yl)pentanamido)hexanamido)hexanamide (123c): 121c (5.7 mg, 0.013 mmol), EZ-Link® NHS-LC_LC-Biotin (8.1 mg, 0.014 mmol) and DIEA (3.4 mg, 4.5 µL, 0.026 mmol) in DMF (0.5 ml) was stirred at rt for 1 h. The reaction mixture was concentrated under reduced pressure and resulting residue was purified by preparatory TLC ($CH_2Cl_2$-MeOH—$NH_3$ (7N), 10:1) to give 3.7 mg (34%) of 123c. $^1H$ NMR (600 MHz, $CD_2Cl_2$+5 drops of $CD_3OD$) δ 8.15 (s, 1H), 7.29 (t, J=1.8 Hz, 1H), 7.26 (d, J=1.7 Hz, 2H), 4.40-4.42 (m, 1H), 4.20-4.23 (m, 1H), 4.12 (t, J=7.4 Hz, 2H), 3.03-3.10 (m, 8H), 2.79-2.85 (m, 1H), 2.58-2.64 (m, 1H), 2.03-2.13 (m, 8H), 1.25-1.69 (m, 27H); HRMS (ESI) m/z $[M+H]^+$ calcd. for $C_{41}H_{61}Cl_2N_{10}O_4S_2$, 891.3707. found 891.3696; HPLC (Method B) $R_t$=4.52.

5-(3-(3-(6-Amino-8-((3,5-dichlorophenyl)thio)-9H-purin-9-yl)propyl)thioureido)-2-(6-hydroxy-3-oxo-3H-xanthen-9-yl)benzoic acid, WS-13-FITC2 (124a): 121a (9.4 mg, 0.0255 mmol), FITC (10.7 mg, 0.0281 mmol) and $Et_3N$ (0.1 mL) in DMF (0.5 mL) was stirred for 12 h at rt. The reaction mixture was concentrated under reduced pressure and the residue was purified by HPLC to give 14.8 mg (76%) of 124a. $^1H$ NMR (600 MHz, MeOH-$d_4$) δ 8.26 (s, 1H), 8.17 (s, 1H), 7.72 (d, J=8.2 Hz, 1H), 7.54 (d, J=1.8 Hz, 2H), 7.43 (t, J=1.8 Hz, 1H), 7.11 (d, J=8.2 Hz, 1H), 6.83 (d, J=8.6 Hz, 2H), 6.76 (s, 2H), 6.62 (d, J=8.7 Hz, 2H), 4.35 (t, J=6.8 Hz, 2H), 3.57 (m, 2H), 2.17 (q, J=6.8 Hz, 2H); HRMS (ESI) m/z $[M+H]^+$ calcd. for $C_{35}H_{26}Cl_2N_7O_5S_2$, 758.0814. found 758.0818.

5-(3-(6-(6-Amino-8-((3,5-dichlorophenyl)thio)-9H-purin-9-yl)hexyl)thioureido)-2-(6-hydroxy-3-oxo-3H-xanthen-9-yl)benzoic acid, WS-13-FITC3 (124b): 121b (7.2 mg, 0.0175 mmol), FITC (7.5 mg, 0.0193 mmol) and $Et_3N$ (0.1 mL) in DMF (0.5 mL) was stirred for 12 h at rt. The reaction mixture was concentrated under reduced pressure and the residue was purified by HPLC to give 12.4 mg (86%) of 124b. $^1$H NMR (600 MHz, MeOH-d$_4$) δ 8.26 (s, 1H), 8.13 (s, 1H), 7.67 (d, J=7.7 Hz, 1H), 7.50 (d, J=1.9 Hz, 2H), 7.43 (t, J=1.8 Hz, 1H), 7.09 (d, J=8.2 Hz, 1H), 6.77 (d, J=8.7 Hz, 2H), 6.71 (s, 2H), 6.56 (d, J=8.8 Hz, 2H), 4.25 (t, J=7.1 Hz, 2H), 3.88 (m, 2H), 1.76 (q, J=7.0 Hz, 2H), 1.54 (q, J=6.9 Hz, 2H), 1.25-1.35 (m, 4H); HRMS (ESI) m/z [M+H]$^+$ calcd. for C$_{35}$H$_{32}$Cl$_2$N$_7$O$_5$S$_2$, 800.1324. found 800.1329.

5-(3-(8-(6-Amino-8-((3,5-dichlorophenyl)thio)-9H-purin-9-yl)octyl)thioureido)-2-(6-hydroxy-3-oxo-3H-xanthen-9-yl)benzoic acid, WS-13-FITC4 (124c): 121c (6.4 mg, 0.0146 mmol), FITC (6.0 mg, 0.0153 mmol) and Et$_3$N (0.1 mL) in DMF (0.5 mL) was stirred for 12 h at rt. The reaction mixture was concentrated under reduced pressure and the residue was purified by HPLC to give 8.3 mg (72%) of 124c. $^1$H NMR (600 MHz, MeOH-d$_4$) δ 8.30 (s, 1H), 8.18 (s, 1H), 7.93 (d, J=8.2 Hz, 1H), 7.49 (d, J=1.7 Hz, 2H), 7.48 (t, J=1.7 Hz, 1H), 7.15 (d, J=8.2 Hz, 1H), 6.79-6.83 (m, 4H), 6.64 (d, J=8.7 Hz, 2H), 4.27 (t, J=7.3 Hz, 2H), 3.62 (m, 2H), 1.82 (q, J=6.8 Hz, 2H), 1.65 (q, J=6.9 Hz, 2H), 1.21-1.39 (m, 8H); HRMS (ESI) m/z [M+H]$^+$ calcd. for C$_{40}$H$_{36}$Cl$_2$N$_7$O$_5$S$_2$, 828.1596. found 828.1609.

6.6 Synthesis of [$^{131}$I]-HJP-V-149 of Formula 125 (Scheme 23)

Scheme 23:

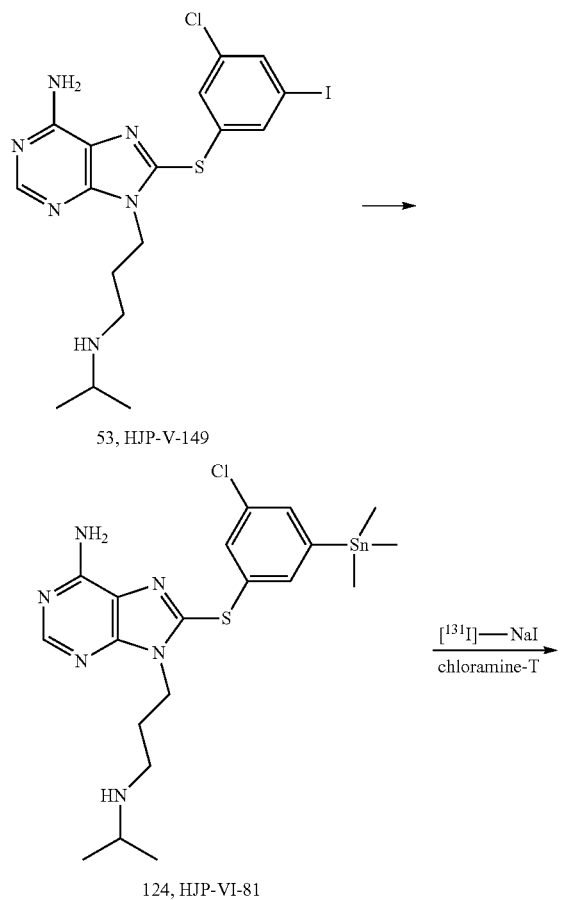

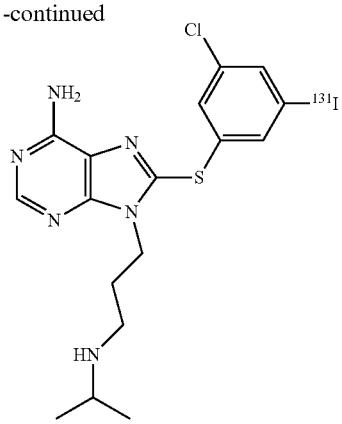

125, [$^{131}$I]-HJP-V-149

8-((3-chloro-5-(trimethylstannyl)phenyl)thio)-9-(3-(isopropylamino)propyl)-9H-purin-6-amine (124, HJP-VI-81). A mixture of 53 (15 mg, 0.0298 mmol, 1 eq.), [(Me)$_3$Sn]$_2$ (4 eq.), LiCl (2 eq.) and Pd(PPh$_3$)$_4$ (10-20 mol %) in dioxane (1 mL) in a 10 mL RBF equipped with a magnetic stir bar and rubber septum was evacuated and back filled with nitrogen. This was repeated four times then the reaction mixture was heated under nitrogen at 90° C. for 15 h. Solvent was removed under reduced pressure and the resulting residue was purified by preparatory TLC (DCM:EtOAc:hexane:MeOH—NH$_3$ (7N) at 4:2:4:1, 2×) to yield compound 124. Yield, 11.2 mg (70%). $^1$H NMR (600 MHz, CDCl$_3$) δ 8.32 (s, 1H), 7.40-7.42 (m, 1H), 7.36-7.37 (m, 1H), 7.30-7.32 (m, 1H), 5.84 (br s, 2H), 4.30 (t, J=6.8 Hz, 2H), 2.74-2.77 (m, 1H), 2.56 (t, J=6.7 Hz, 2H), 1.97-2.03 (m, 2H), 1.07 (d, J=6.2 Hz, 6H), 0.31 (s, 9H); $^{13}$C NMR (150 MHz, CDCl$_3$) δ 154.5, 153.0, 151.6, 146.6, 145.3, 135.5, 135.2, 135.1, 132.1, 130.0, 120.1, 48.9, 43.5, 41.5, 29.8, 22.5, −9.2.

Synthesis of [$^{131}$I]-HJP-V-149 (125). 20 µg of Me$_3$Sn precursor 124 was dissolved in 25 µL methanol in Eppendorf tube and to the resulting solution, [$^{131}$I]-NaI solution was added (0.2 mCi in 2 µl in 0.1N NaOH) and the solution was vortex. To this solution 2 µl of chloramine-T (2 mg/ml acetic acid) was added and vortexed and allowed to react for 1 min and centrifuged at 300 rpm for 15 s. Purification was achieved by passing through C-18 250×4.6 mm, RP Luna HPLC column (Phenomenex Torrance, Calif., C18, 5µ, 110° A), using two solvent system of 0.1% TFA(A) and acetonitrile(B) as eluant under a gradient of 20-80% B (from 3-10 min) with a flow rate of 1 ml/min. The product has a retention time of about 9.7 minutes, under the conditions described above. HPLC profile of purified [$^{131}$I]-Compound HJP-V-149 (125)

6.7 Hsp90 Paralog Competition Assays

The Hsp90 FP competition assays were performed on an Analyst GT instrument (Molecular Devices, Sunnyvale, Calif.) and carried out in black 96-well microplates (Corning #3650) in a total volume of 100 µL, in each well. A stock of 10 µM Cy3B-GM and 115a was prepared in DMSO and diluted with Felts buffer (20 mM Hepes (K), pH 7.3, 50 mM KCl, 2 mM DTT, 5 mM MgCl2, 20 mM Na2MoO4, and 0.01% NP40 with 0.1 mg/mL BGG). To each well was added the fluorescent dye labeled Hsp90 ligand (6 nM Cy3B-GM for Hsp90α, Hsp90β and Grp94 and 3 nM of 115a for Trap-1), protein (10 nM Hsp90α, 10 nM Hsp90β, 10 nM Grp94, 30 nM Trap-1) and tested inhibitor (initial stock in DMSO) in a final volume of 100 μL Felts buffer. Compounds were added in duplicate or triplicate wells. For each assay, background wells (buffer only), tracer controls (free, fluorescent dye labeled Hsp90 ligand only) and bound controls (fluorescent dye labeled Hsp90 ligand in the presence of protein) were included on each assay plate. The assay plate was incubated on a shaker at 4° C. for 24 h and the FP values in mP were measured. The fraction of fluorescent dye labeled Hsp90 ligand bound to Hsp90 was correlated to the mP value and plotted against values of competitor concentrations. The inhibitor concentration at which 50% of bound fluorescent dye labeled Hsp90 ligand was displaced was obtained by fitting the data. For cy3B-GM, an excitation filter at 530 nm and an emission filter at 580 nm were used with a dichroic mirror of 561 nm. For 115a, an excitation filter at 485 nm and an emission filter at 530 nm were used with a dichroic mirror of 505 nm. All experimental data were analyzed using SOFTmax Pro 4.3.1 and plotted using Prism 4.0 (GraphPad Software Inc., San Diego, Calif.) and binding affinity values are given as relative binding affinity values (EC50, concentration at which 50% of fluorescent ligand was competed off by compound).

The results of the competition assays for specific compounds produced in accordance with the present disclosure are shown in Table 16 below:

TABLE 16

| Structure | Compound code | Hsp90α (μM) | Hsp90β (μM) | Grp94 (μM) | TRAP-1 (μM) | MDA-MB-468 |
|---|---|---|---|---|---|---|
| (structure) | PU-H6 | >100 | >100 | 0.35 ± 0.05 | | |
| (structure) | PU-H5 | >>100 | 110 ± 20 | 6.2 ± 2.5 | | |
| (structure) | PU-H34 | >>100 | >>100 | 29 ± 9 | | |
| (structure) | PU-H9 | >>100 | >>100 | 1.4 ± 0.2 | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 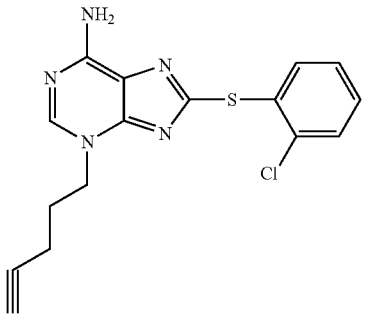 [SMILES: C#CCCCn1cnc(N)c2nc(Sc3ccccc3Cl)nc1-2] | PU-H47 | >>100 | >>100 | 100 ± 10 | | |
| 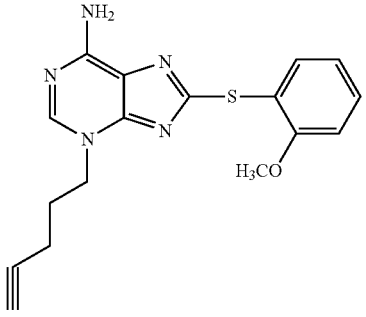 [SMILES: C#CCCCn1cnc(N)c2nc(Sc3ccccc3OC)nc1-2] | PU-H46 | >>100 | >>100 | >100 | | |
| 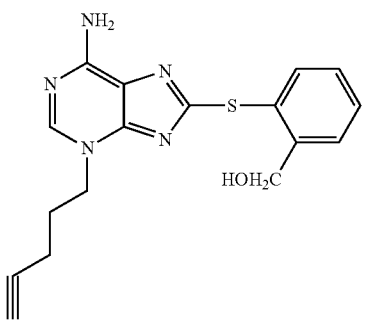 [SMILES: C#CCCCn1cnc(N)c2nc(Sc3ccccc3CO)nc1-2] | PU-H35 | >>100 | >>100 | >100 | | |
| 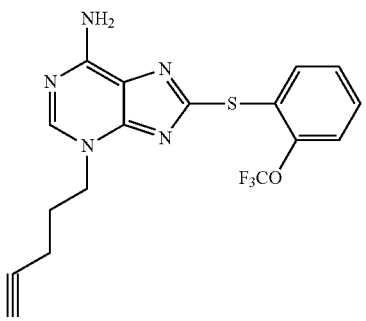 [SMILES: C#CCCCn1cnc(N)c2nc(Sc3ccccc3OC(F)(F)F)nc1-2] | PU-H48 | >>100 | >>100 | 106 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 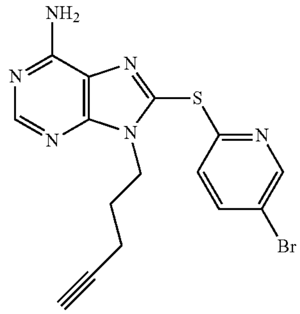 [SMILES: C#CCCCn1c(Sc2ccc(Br)cn2)nc2c(N)ncnc21] | PDP-I-60-N9 | 2.18 ± 0.10 | 2.82 ± 0.14 | 0.53 ± 0.03 | 2.18 ± 0.55 | |
| 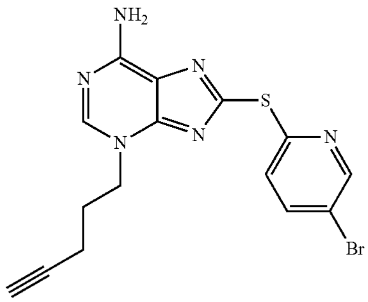 [SMILES: C#CCCCn1cnc(N)c2nc(Sc3ccc(Br)cn3)nc1-2] | PDP-I-60-N3 | | | | | |
| 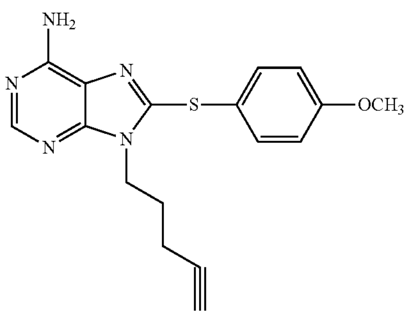 [SMILES: C#CCCCn1c(Sc2ccc(OC)cc2)nc2c(N)ncnc21] | PU-H1 | >100 | >100 | 1.13 ± 0.2 | | |
| 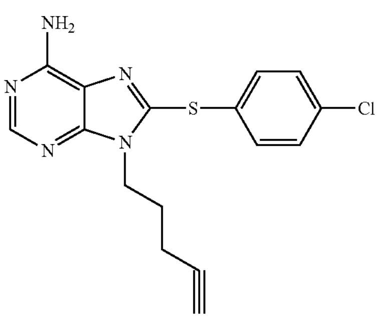 [SMILES: C#CCCCn1c(Sc2ccc(Cl)cc2)nc2c(N)ncnc21] | PU-H7 | >100 | ND | 1.5 ± 0.2 | | |
| 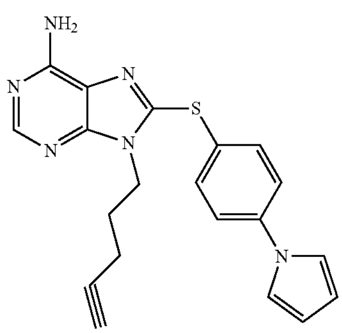 [SMILES: C#CCCCn1c(Sc2ccc(-n3cccc3)cc2)nc2c(N)ncnc21] | PDP-I-51-N9 | >50 | | >10 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| (structure) | PDP-I-51-N3 | >50 | | >5 | | |
| (structure) | PU-H39 | >300 | >300 | 0.12 ± 0.04 | 145.4 ± 13.4 | |
| (structure) | WS-12 | 20.3 ± 1.2 | | 0.41 ± 0.1 0.407 | | |
| (structure) | PDP-I-54-N9 | 13.87 ± 1.3514 | >50 | 0.66 ± 1.10 0.855 | 4.90 ± 0.27 | |
| (structure) | PDP-I-54-N3 | >50 | | >10 | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 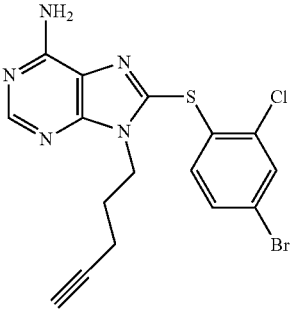 [SMILES: C#CCCCn1c(Sc2ccc(Br)cc2Cl)nc2c(N)ncnc21] | PDP-I-61-N9 | >50 | >50 | 0.28 ± 0.06 | 2.62 ± 0.28 | |
| 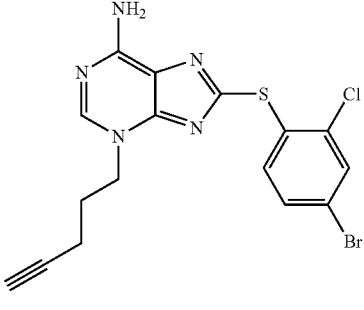 [SMILES: C#CCCCn1cnc(N)c2nc(Sc3ccc(Br)cc3Cl)nc1-2] | PDP-I-61-N3 | | | | | |
| 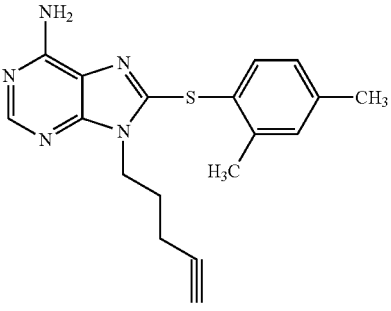 [SMILES: C#CCCCn1c(Sc2ccc(C)cc2C)nc2c(N)ncnc21] | PU-H3 | >300 | >300 | 1.63 ± 0.47 | 13.8 ± 1.8 | |
| 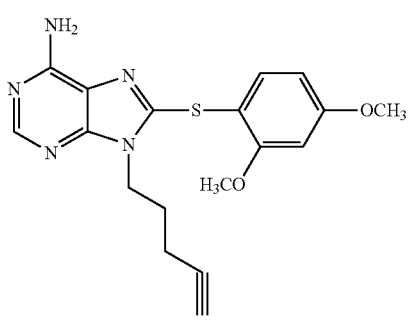 [SMILES: C#CCCCn1c(Sc2ccc(OC)cc2OC)nc2c(N)ncnc21] | PU-H8 | 47.4 ± 2.2 | 22.4 ± 2.8 | 34.5 ± 3.5 | | |
| 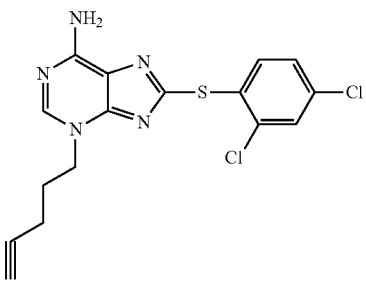 [SMILES: C#CCCCn1cnc(N)c2nc(Sc3ccc(Cl)cc3Cl)nc1-2] | PU-H38 | >500 | >500 | 2.37 ± 0.79 | 9.6 ± 0.8 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 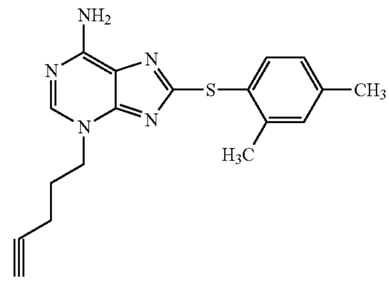 [SMILES: C#CCCCn1cnc(N)c2nc(Sc3ccc(C)cc3C)nc1-2] | PU-H54 | >250 | >250 | 11.77 ± 3.24 | 54.1 ± 4.6 | |
| 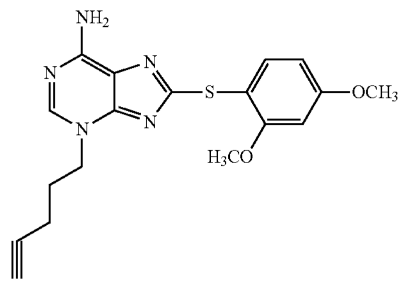 [SMILES: C#CCCCn1cnc(N)c2nc(Sc3ccc(OC)cc3OC)nc1-2] | PU-H44 | >100 | >100 | 46.76 | >100 | |
| 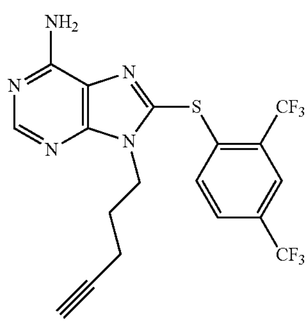 [SMILES: C#CCCCn1c(Sc2ccc(C(F)(F)F)cc2C(F)(F)F)nc2c(N)ncnc21] | PDP-122 | >100 | >100 | 0.5 ± 0.39 | 7.64 ± 2.15 | |
| 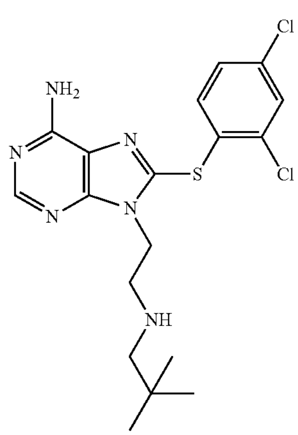 [SMILES: CC(C)(C)CNCCn1c(Sc2ccc(Cl)cc2Cl)nc2c(N)ncnc21] | HJP-V-81 | 2.7 | | 0.78 | 7.5 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 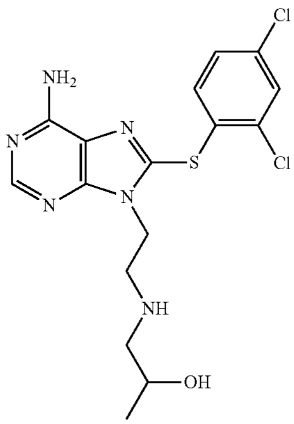 [SMILES: CC(O)CNCCn1c(Sc2ccc(Cl)cc2Cl)nc2c(N)ncnc21] | HJP-V-82 | 31.3 | | 0.23 | | |
| 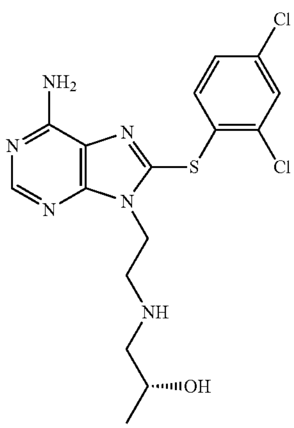 [SMILES: C[C@@H](O)CNCCn1c(Sc2ccc(Cl)cc2Cl)nc2c(N)ncnc21] | HJP-V-104 | 55.8 | | 1.5 | | |
| 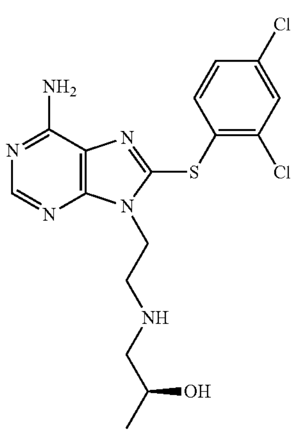 [SMILES: C[C@H](O)CNCCn1c(Sc2ccc(Cl)cc2Cl)nc2c(N)ncnc21] | HJP-V-105 | >50 | | 0.35 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 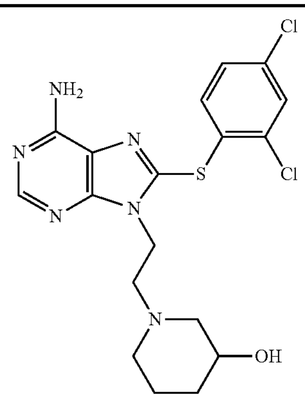 | HJP-V-83 | 33.0 | | 2.9 | 8.8 | |
| 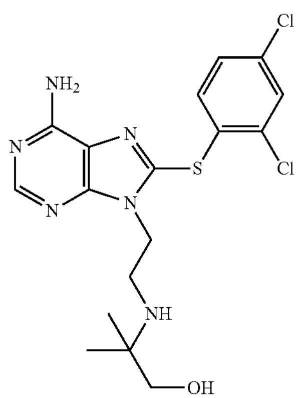 [SMILES: CC(C)(CO)NCCn1c(Sc2ccc(Cl)cc2Cl)nc2c(N)ncnc21] | HJP-V-84 | 28.9 | | 1.9 | 4.4 | |
| 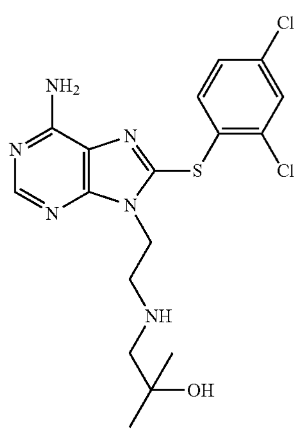 [SMILES: CC(C)(O)CNCCn1c(Sc2ccc(Cl)cc2Cl)nc2c(N)ncnc21] | HJP-V-85 | 9.2 | | 2.3 | 2.6 | |
| 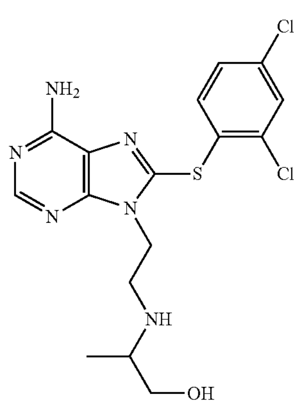 [SMILES: CC(CO)NCCn1c(Sc2ccc(Cl)cc2Cl)nc2c(N)ncnc21] | HJP-V-86 | 7.6 | | 0.21 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 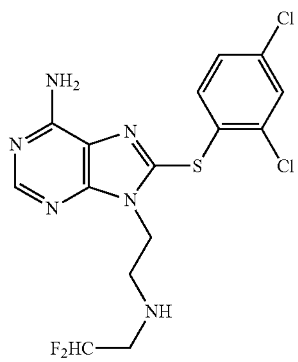 [SMILES: Nc1ncnc2c1nc(Sc1ccc(Cl)cc1Cl)n2CCNCC(F)F] | HJP-V-88 | | | 1.2 | | |
| 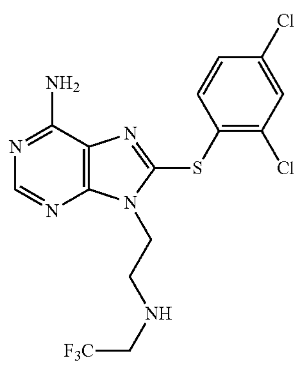 [SMILES: Nc1ncnc2c1nc(Sc1ccc(Cl)cc1Cl)n2CCNCC(F)(F)F] | HJP-V-89 | 39.7 | | 0.82 | | |
| 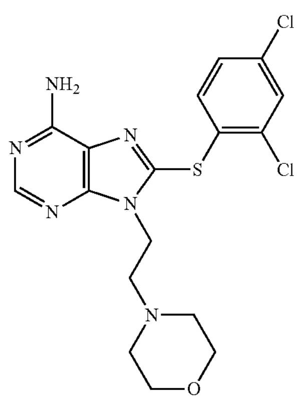 [SMILES: Nc1ncnc2c1nc(Sc1ccc(Cl)cc1Cl)n2CCN1CCOCC1] | HJP-V-91 | 18.9 | | 1.4 | 0.63 | |
| 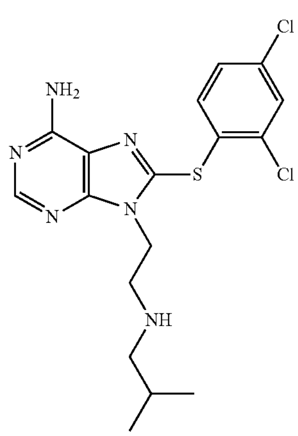 [SMILES: CC(C)CNCCn1c(Sc2ccc(Cl)cc2Cl)nc2c(N)ncnc21] | HJP-V-92 | 3.6 | | 0.18 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 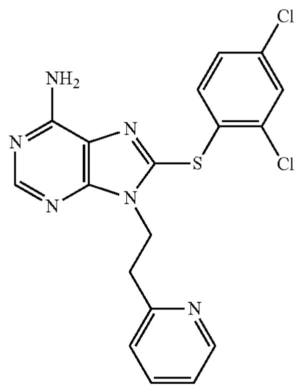 [SMILES: Nc1ncnc2c1nc(Sc1ccc(Cl)cc1Cl)n2CCc1ccccn1] | HJP-V-93 | >50 | | 1.9 | | |
| 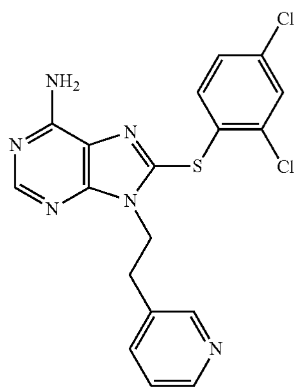 [SMILES: Nc1ncnc2c1nc(Sc1ccc(Cl)cc1Cl)n2CCc1cccnc1] | HJP-V-116 | >50 | | 0.12-0.3 | | |
| 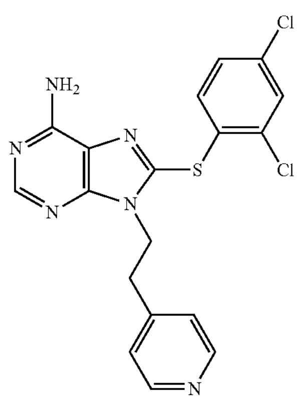 [SMILES: Nc1ncnc2c1nc(Sc1ccc(Cl)cc1Cl)n2CCc1ccncc1] | HJP-V-118 | >50 | | 1.03 | | |
| 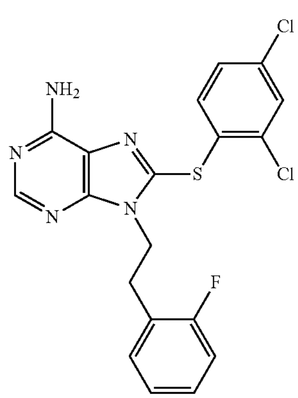 [SMILES: Nc1ncnc2c1nc(Sc1ccc(Cl)cc1Cl)n2CCc1ccccc1F] | HJP-V-96 | >50 | | 1.9 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 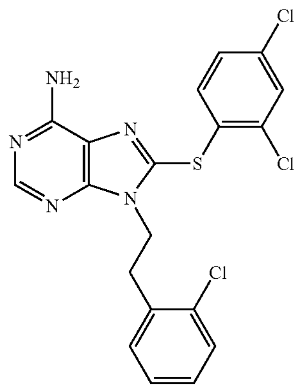 [SMILES: Nc1ncnc2c1nc(Sc1ccc(Cl)cc1Cl)n2CCc1ccccc1Cl] | HJP-V-97 | 186.4 | | 2.2 | | |
| 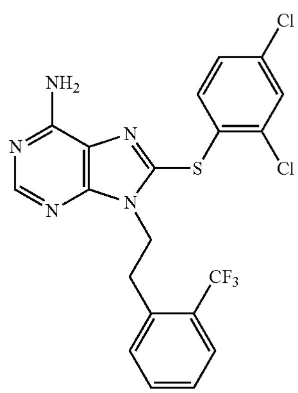 [SMILES: Nc1ncnc2c1nc(Sc1ccc(Cl)cc1Cl)n2CCc1ccccc1C(F)(F)F] | HJP-V-98 | >50 | | 0.71 | | |
| 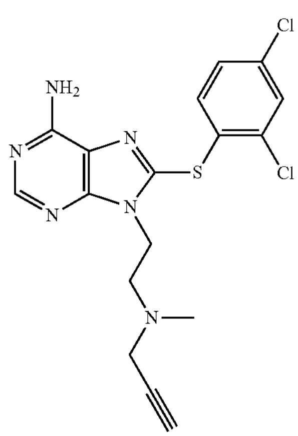 [SMILES: C#CCN(C)CCn1c(Sc2ccc(Cl)cc2Cl)nc2c(N)ncnc21] | HJP-V-100 | 97.9 | | 0.32 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 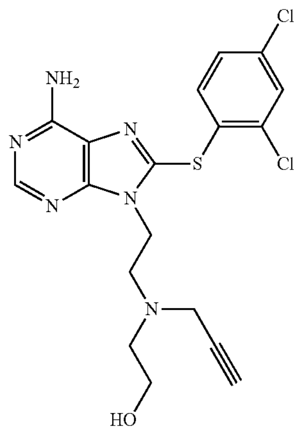 [SMILES: C#CCN(CCO)CCn1c(Sc2ccc(Cl)cc2Cl)nc2c(N)ncnc21] | HJP-V-110 | >50 | | 0.60 | | |
| 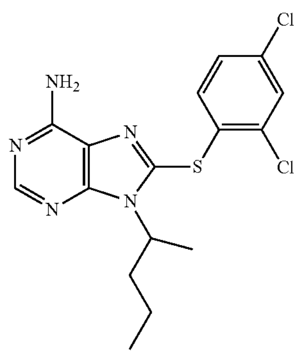 [SMILES: CCCC(C)n1c(Sc2ccc(Cl)cc2Cl)nc2c(N)ncnc21] | HJP-V-114 | >50 | | 2.48 | | |
| 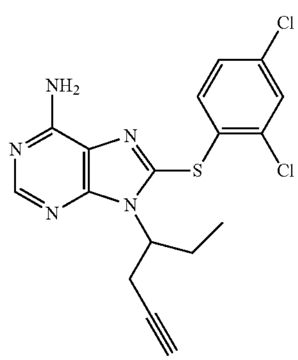 [SMILES: C#CCC(CC)n1c(Sc2ccc(Cl)cc2Cl)nc2c(N)ncnc21] | HJP-V-117 | >50 | | 0.92 | | |
| 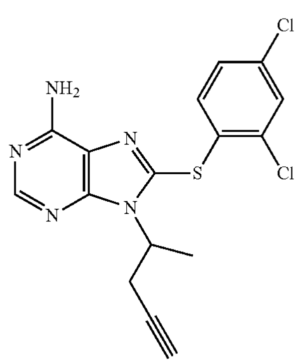 [SMILES: C#CCC(C)n1c(Sc2ccc(Cl)cc2Cl)nc2c(N)ncnc21] | HJP-V-122 | | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 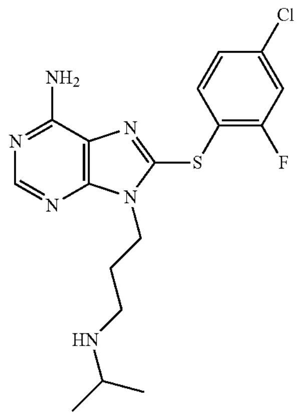 | HJP-VI-23 | >50 | | 1.5 | | |
| 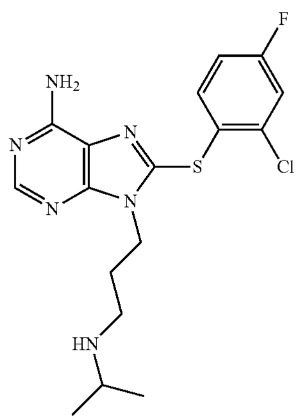 [SMILES: CC(C)NCCCn1c(Sc2ccc(F)cc2Cl)nc2c(N)ncnc21] | HJP-VI-25 | >50 | | | | |
| 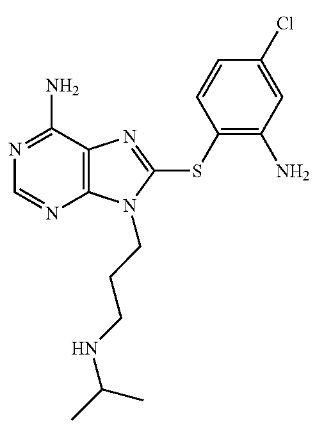 [SMILES: CC(C)NCCCn1c(Sc2ccc(Cl)cc2N)nc2c(N)ncnc21] | HJP-VI-34 | >50 | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 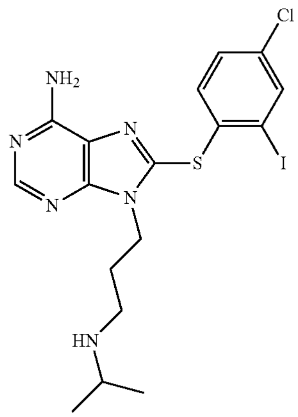 [SMILES: CC(C)NCCCn1c(Sc2ccc(Cl)cc2I)nc2c(N)ncnc21] | HJP-VI-36 | 3.4 | | 0.21 | | 5.85 |
| 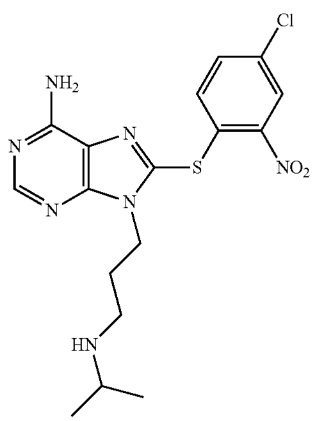 [SMILES: CC(C)NCCCn1c(Sc2ccc(Cl)cc2[N+](=O)[O-])nc2c(N)ncnc21] | HJP-VI-32 | 14.2 | | >5 | | |
| 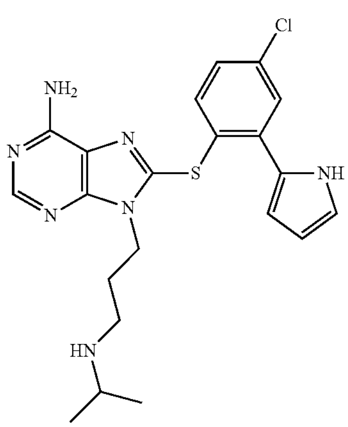 [SMILES: CC(C)NCCCn1c(Sc2ccc(Cl)cc2-c2ccc[nH]2)nc2c(N)ncnc21] | HJP-VI-42 | 66.9 | | 1.1 | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 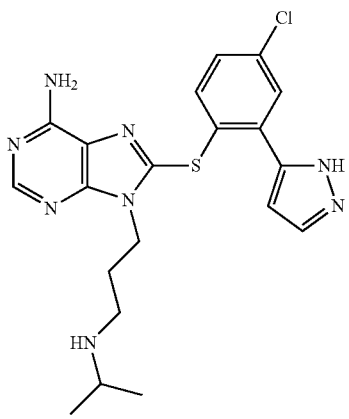 [SMILES: CC(C)NCCCn1c(Sc2ccc(Cl)cc2-c2ccn[nH]2)nc2c(N)ncnc21] | HJP-VI-43 | 1.5 | | 0.45 | | 6.58 |
| 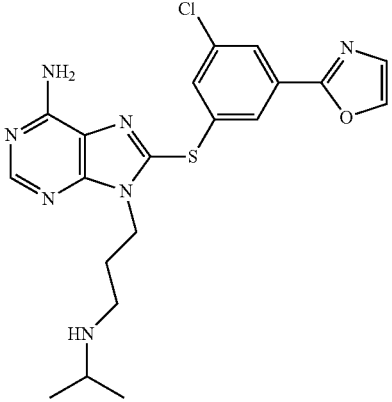 [SMILES: CC(C)NCCCn1c(Sc2cc(Cl)cc(-c3ncco3)c2)nc2c(N)ncnc21] | HJP-VI-49 | 29.6 | | 1.3 | | 3.12 |
| 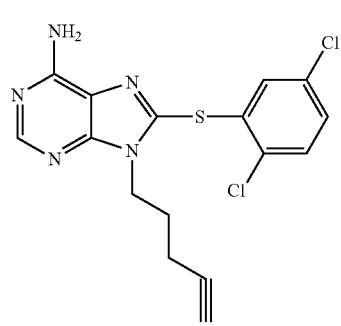 [SMILES: C#CCCCn1c(Sc2cc(Cl)ccc2Cl)nc2c(N)ncnc21] | PU-H42 | 60.4 ± 1.6 | >100 | 0.53 ± 0.10 | 5.1 ± 4.2 | |
| 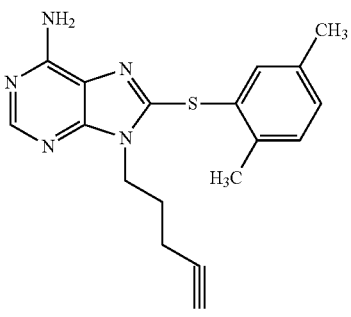 [SMILES: C#CCCCn1c(Sc2cc(C)ccc2C)nc2c(N)ncnc21] | PU-H27 | >300 | >300 | 1.14 ± 0.14 | 203.7 ± 11.0 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| *(structure)* | PU-H2 | 100 ± 7 | 6.5 ± 2.3 | 0.5 ± 0.2 | | |
| *(structure)* | PU-H43 | >>100 | >>100 | 35.3 ± 5 | | |
| *(structure)* | PU-H29 | >>100 | >>100 | 185 ± 15 | | |
| *(structure)* | PU-H53 | >>100 | >>100 | 200 | | |
| *(structure)* | PU-H63 | 5.9 ± 0.5 | 2.5 ± 0.2 | 2.3 ± 0.1 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| [structure] | PU-H4 | >300 | >300 | 11.45 ± 0.92 | 157.9 ± 9.7 | |
| [structure] | PU-H41 | >>100 | 100 ± 11 | 100 ± 8 | | |
| [structure] | PU-H45 | >>100 | >>100 | >>100 | | |
| [structure] | WS-14 | 8.56 | 2.43 | | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 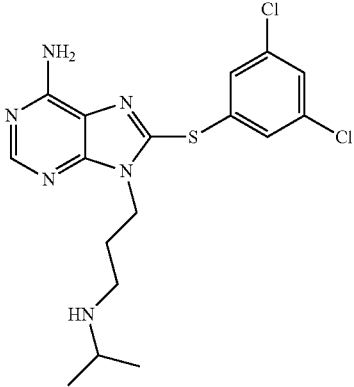 [SMILES: CC(C)NCCCn1c(Sc2cc(Cl)cc(Cl)c2)nc2c(N)ncnc21] | WS-13 | 27.3 ± 3.5 | 41.8 ± 1.3 | 0.22 ± 0.08 | 7.3 | |
| 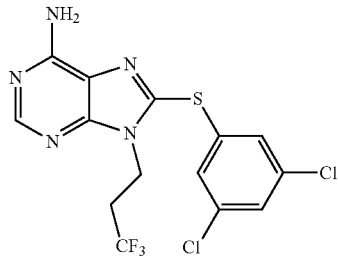 [SMILES: Nc1ncnc2c1nc(Sc1cc(Cl)cc(Cl)c1)n2CCC(F)(F)F] | PDP-I-13-N9 | >50 | >100 | 0.57 ± 0.08 | 10.09 ± 1.13 | |
| 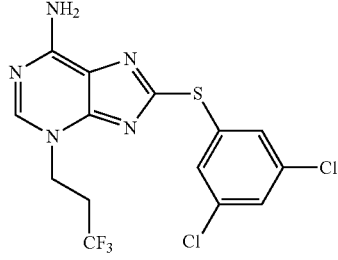 [SMILES: Nc1ncn(CCC(F)(F)F)c2nc(Sc3cc(Cl)cc(Cl)c3)nc1-2] | PDP-I-13-N3 | >50 | >100 | 12.78 ± 0.86 | >100 | |
| 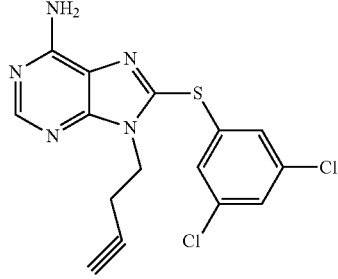 [SMILES: C#CCCn1c(Sc2cc(Cl)cc(Cl)c2)nc2c(N)ncnc21] | PDP-I-14-N9 | >100 | >100 | 0.27 ± 0.02 | >100 | |
| 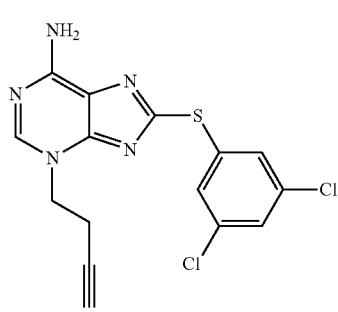 [SMILES: C#CCCn1cnc(N)c2nc(Sc3cc(Cl)cc(Cl)c3)nc1-2] | PDP-I-14-N3 | >50 | | >5 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 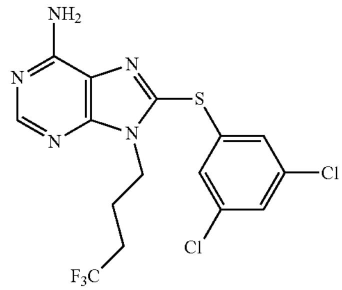 [SMILES: Nc1ncnc2c1nc(Sc1cc(Cl)cc(Cl)c1)n2CCCC(F)(F)F] | PDP-I-15-N9 | >50 | >50 | 0.46 ± 0.04 | >50 | |
| 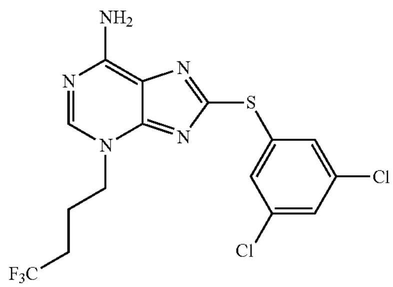 [SMILES: Nc1ncn(CCCC(F)(F)F)c2nc(Sc3cc(Cl)cc(Cl)c3)nc1-2] | PDP-I-15-N3 | >50 | | >10 | | |
| 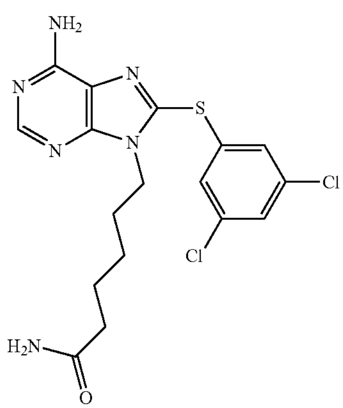 [SMILES: NC(=O)CCCCCn1c(Sc2cc(Cl)cc(Cl)c2)nc2c(N)ncnc21] | PDP-I-83-N9 | | | | | |
| 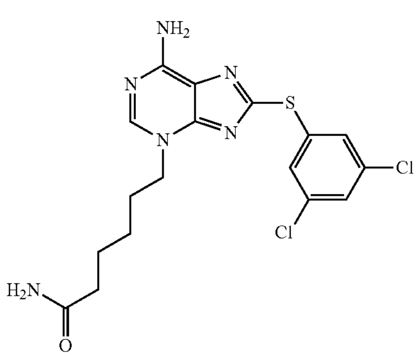 [SMILES: NC(=O)CCCCCn1cnc(N)c2nc(Sc3cc(Cl)cc(Cl)c3)nc1-2] | PDP-I-83-N3 | | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 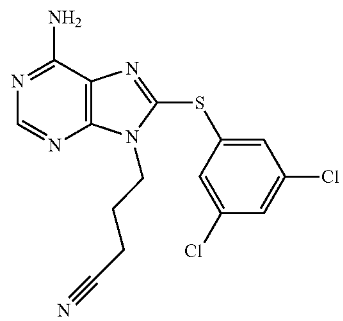 [SMILES: N#CCCCn1c(Sc2cc(Cl)cc(Cl)c2)nc2c(N)ncnc21] | PDP-93A | >50 | >100 | 0.45 ± 0.03 | 4.47 ± 0.31 | |
| 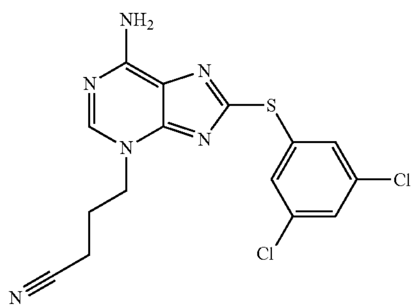 [SMILES: N#CCCCn1cnc(N)c2nc(Sc3cc(Cl)cc(Cl)c3)nc1-2] | PDP-93B | >100 | >100 | >100 | >100 | |
| 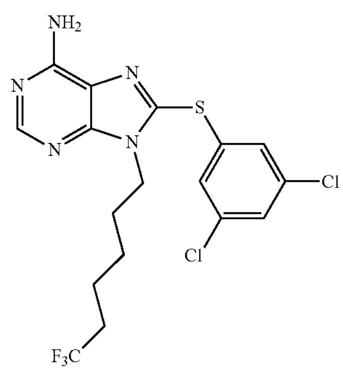 [SMILES: Nc1ncnc2c1nc(Sc1cc(Cl)cc(Cl)c1)n2CCCCCC(F)(F)F] | PDP-101B | >100 | >100 | 1.65 ± 0.31 | >100 | |
| 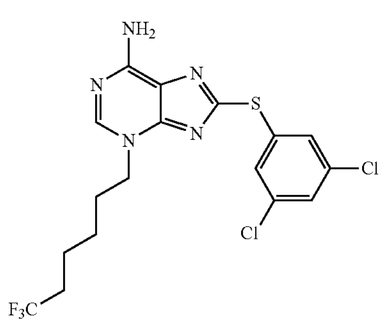 [SMILES: Nc1ncn(CCCCCC(F)(F)F)c2nc(Sc3cc(Cl)cc(Cl)c3)nc1-2] | PDP-101A | >100 | >100 | >100 | >100 | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 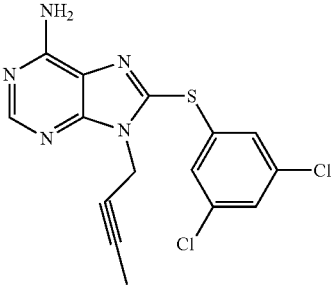 [SMILES: CC#CCn1c(Sc2cc(Cl)cc(Cl)c2)nc2c(N)ncnc21] | PDP-102A | >100 | >100 | >5 | >50 | |
| 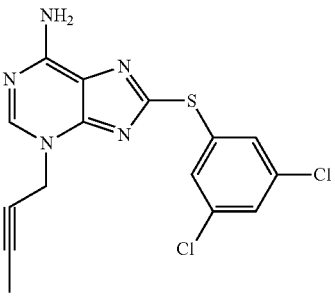 [SMILES: CC#CCn1cnc(N)c2nc(Sc3cc(Cl)cc(Cl)c3)nc1-2] | PDP-102B | >100 | >100 | 10.27 ± 0.82 | >25 | |
| 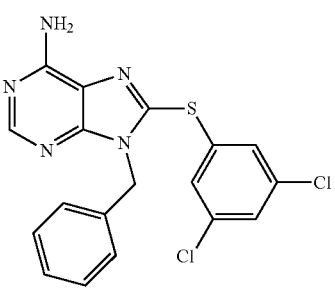 [SMILES: Nc1ncnc2c1nc(Sc1cc(Cl)cc(Cl)c1)n2Cc1ccccc1] | PDP-107A | >100 | >100 | >5 | >50 | |
| 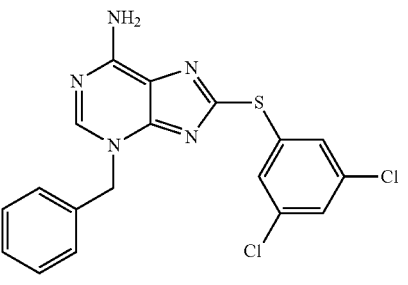 [SMILES: Nc1ncn(Cc2ccccc2)c2nc(Sc3cc(Cl)cc(Cl)c3)nc1-2] | PDP-107B | >100 | >100 | 11.60 | >100 | |
| 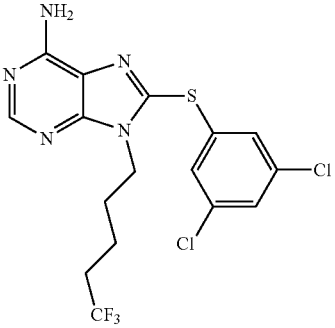 [SMILES: Nc1ncnc2c1nc(Sc1cc(Cl)cc(Cl)c1)n2CCCCC(F)(F)F] | PDP-109A | >100 | >100 | 1.11 ± 0.28 | >100 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 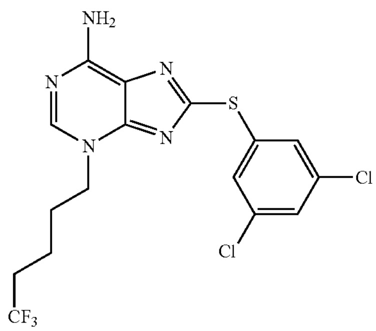 [SMILES: Nc1ncn(CCCCC(F)(F)F)c2nc(Sc3cc(Cl)cc(Cl)c3)nc1-2] | PDP-109B | >100 | >100 | >5 | >100 | |
| 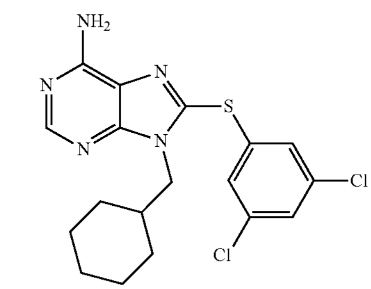 [SMILES: Nc1ncnc2c1nc(Sc1cc(Cl)cc(Cl)c1)n2CC1CCCCC1] | PDP-110A | >100 | >100 | 4.34 ± 0.75 | >100 | |
| 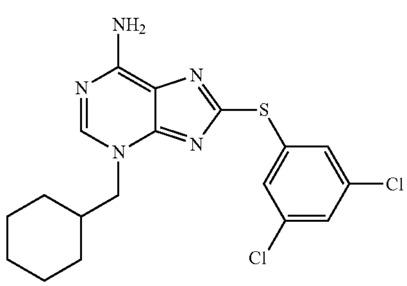 [SMILES: Nc1ncn(CC2CCCCC2)c2nc(Sc3cc(Cl)cc(Cl)c3)nc1-2] | PDP-110B | NA | NA | NA | NA | |
| 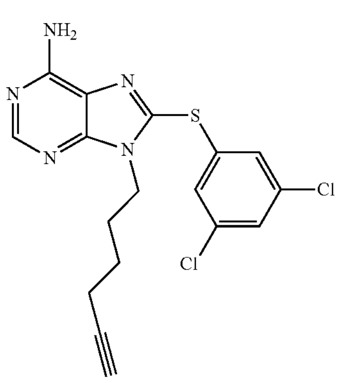 [SMILES: C#CCCCCn1c(Sc2cc(Cl)cc(Cl)c2)nc2c(N)ncnc21] | PDP-112A | >100 | >100 | 0.65 ± 0.05 | >100 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 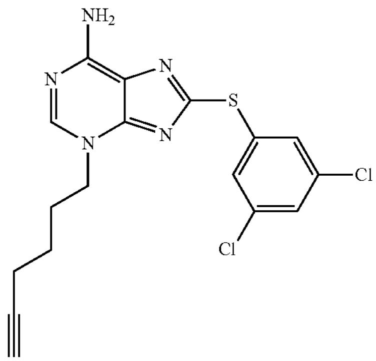 [SMILES: C#CCCCCn1cnc(N)c2nc(Sc3cc(Cl)cc(Cl)c3)nc1-2] | PDP-112B | >100 | >100 | >10 | >100 | |
| 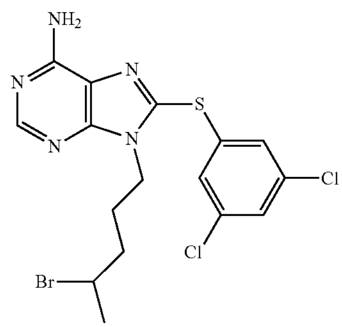 [SMILES: CC(Br)CCCn1c(Sc2cc(Cl)cc(Cl)c2)nc2c(N)ncnc21] | PDP-99A | >100 | >100 | 1.52 ± 0.03 | >100 | |
| 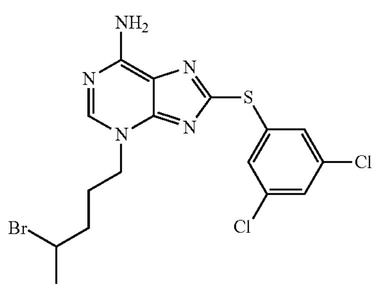 [SMILES: CC(Br)CCCn1cnc(N)c2nc(Sc3cc(Cl)cc(Cl)c3)nc1-2] | PDP-99B | >100 | >100 | >10 | >100 | |
| 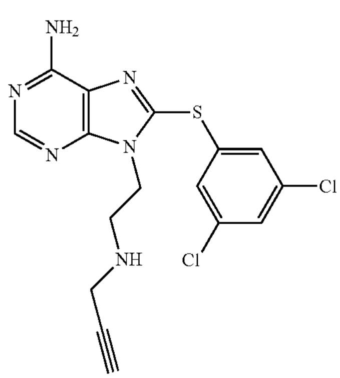 [SMILES: C#CCNCCn1c(Sc2cc(Cl)cc(Cl)c2)nc2c(N)ncnc21] | PDP-132 | >100 | >100 | 0.72 ± 0.02 | 44.38 ± 4.61 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 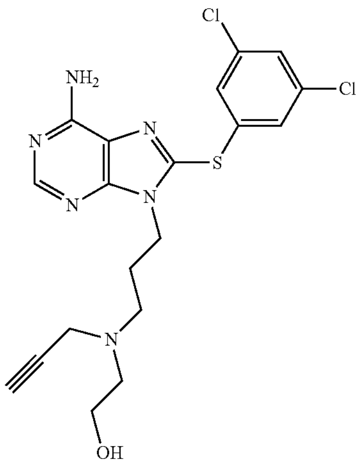 [SMILES: C#CCN(CCO)CCCn1c(Sc2cc(Cl)cc(Cl)c2)nc2c(N)ncnc21] | HJP-V-132 | 26.6 | | 0.81 | | |
| 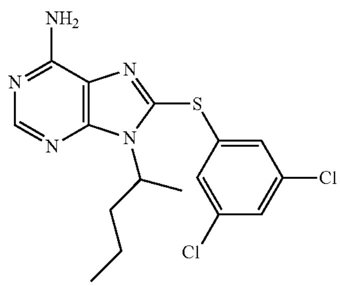 [SMILES: CCCC(C)n1c(Sc2cc(Cl)cc(Cl)c2)nc2c(N)ncnc21] | HJP-V-123 | | | | | |
| 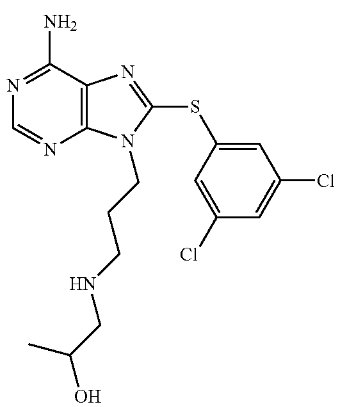 [SMILES: CC(O)CNCCCn1c(Sc2cc(Cl)cc(Cl)c2)nc2c(N)ncnc21] | HJP-V-130 | 51.7 | | 0.37 | | |
| 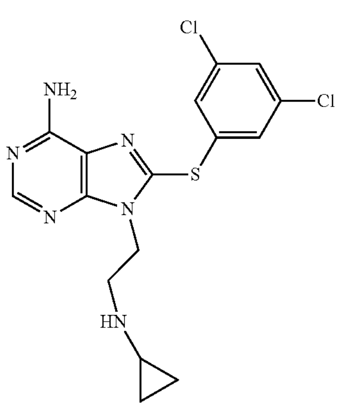 [SMILES: Nc1ncnc2c1nc(Sc1cc(Cl)cc(Cl)c1)n2CCNC1CC1] | SO-III-35A | 87.6 | | 0.776 | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 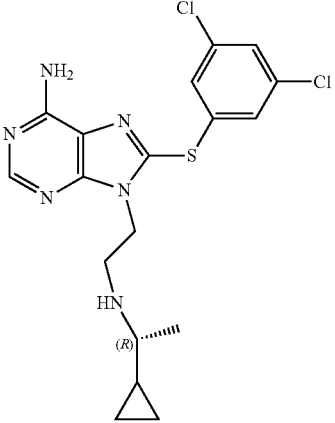 | SO-III-36A | 65.8 | | 0.335 | | |
| 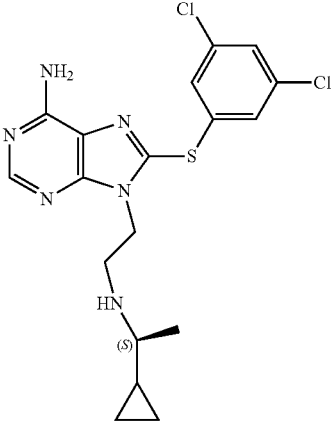 | SO-III-37A | 26.1 | | 0.234 | | |
| 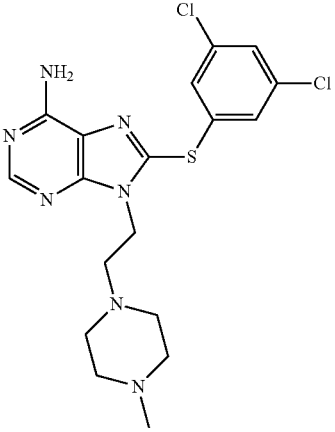 [SMILES: CN1CCN(CCn2c(Sc3cc(Cl)cc(Cl)c3)nc3c(N)ncnc32)CC1] | SO-III-39A | 52.2 | | 0.373 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 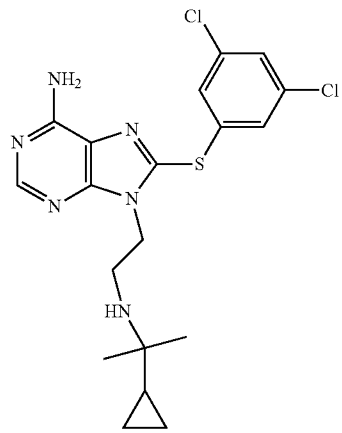 [SMILES: CC(C)(NCCn1c(Sc2cc(Cl)cc(Cl)c2)nc2c(N)ncnc21)C1CC1] | SO-III-40A | 97.2 | | 0.768 | | |
| 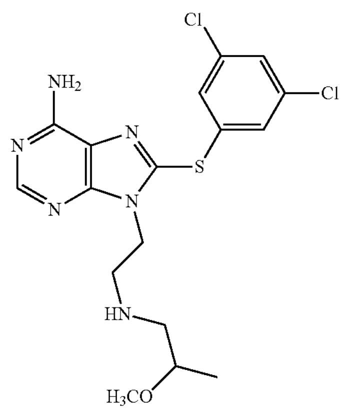 [SMILES: COC(C)CNCCn1c(Sc2cc(Cl)cc(Cl)c2)nc2c(N)ncnc21] | SO-III-75A | 39.92 | | 0.89 | | |
| 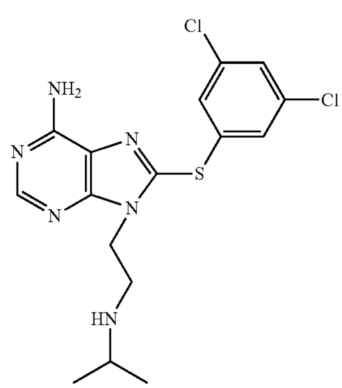 [SMILES: CC(C)NCCn1c(Sc2cc(Cl)cc(Cl)c2)nc2c(N)ncnc21] | SO-III-116A | 47.7 | | 0.44 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 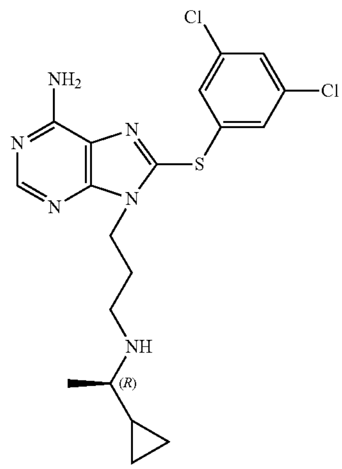 | SO-III-128B | 35.6 | | 0.276 | | 0.84 |
| 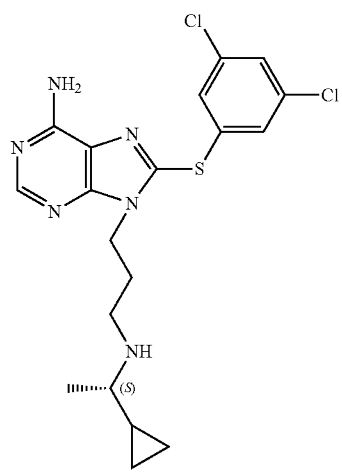 | SO-III-127B | 40.4 | | 0.345 | | 0.83 |
| 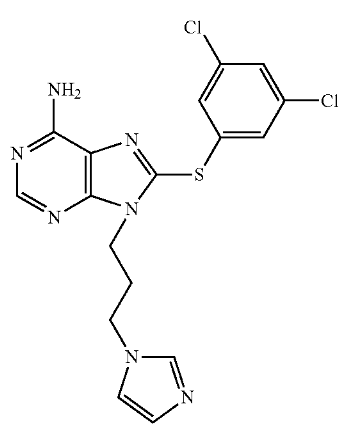 [SMILES: Nc1ncnc2c1nc(Sc1cc(Cl)cc(Cl)c1)n2CCCn1ccnc1] | SO-III-103A | >10 | | 0.203 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 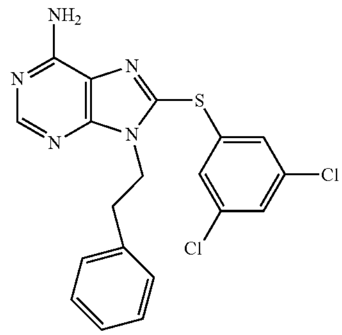 [SMILES: Nc1ncnc2c1nc(Sc1cc(Cl)cc(Cl)c1)n2CCc1ccccc1] | PDP-127 | >100 | >100 | >2.5 | >100 | |
| 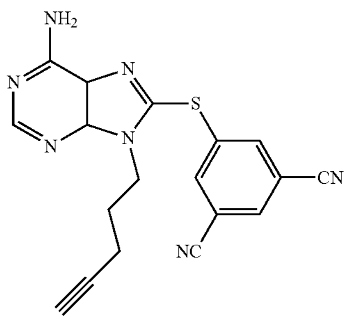 [SMILES: C#CCCCN1C(Sc2cc(C#N)cc(C#N)c2)=NC2C(N)=NC=NC21] | HJP-III-26 | 60.29 | | >3(7.73) | | |
| 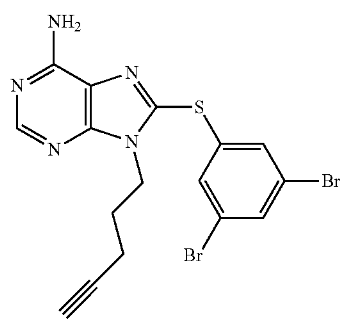 [SMILES: C#CCCCn1c(Sc2cc(Br)cc(Br)c2)nc2c(N)ncnc21] | PDP-I-59-N9 | >100 | >100 | 0.26 ± 0.07 | >100 | |
| 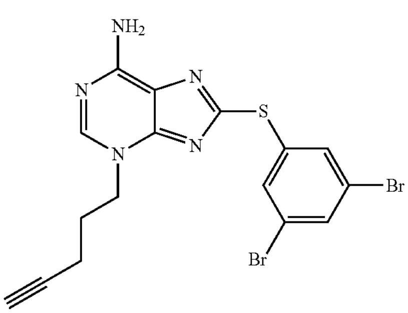 [SMILES: C#CCCCn1cnc(N)c2nc(Sc3cc(Br)cc(Br)c3)nc1-2] | PDP-I-59-N3 | | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 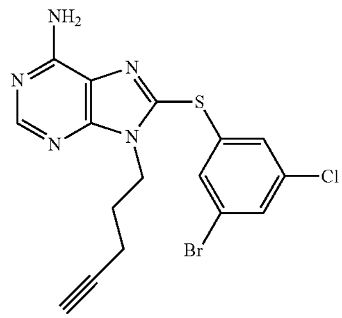 [SMILES: C#CCCCn1c(Sc2cc(Cl)cc(Br)c2)nc2c(N)ncnc21] | PDP-I-53-N9 | >100 | >100 | 0.22 ± 0.02 | >100 | |
| 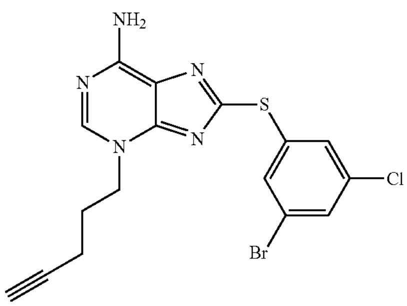 [SMILES: C#CCCCn1cnc(N)c2nc(Sc3cc(Cl)cc(Br)c3)nc1-2] | PDP-I-53-N3 | | | | | |
| 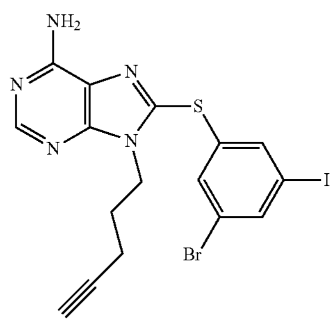 [SMILES: C#CCCCn1c(Sc2cc(Br)cc(I)c2)nc2c(N)ncnc21] | PDP-108A | >50 | >100 | 0.133 | >50 | |
| 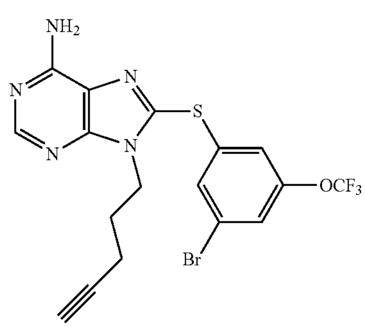 [SMILES: C#CCCCn1c(Sc2cc(Br)cc(OC(F)(F)F)c2)nc2c(N)ncnc21] | PDP-120A | >100 | >100 | 1.207 | 1.873 | |
| 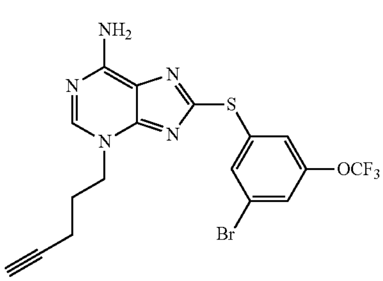 [SMILES: C#CCCCn1cnc(N)c2nc(Sc3cc(Br)cc(OC(F)(F)F)c3)nc1-2] | PDP-120B | >100 | >100 | >10 | >100 | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 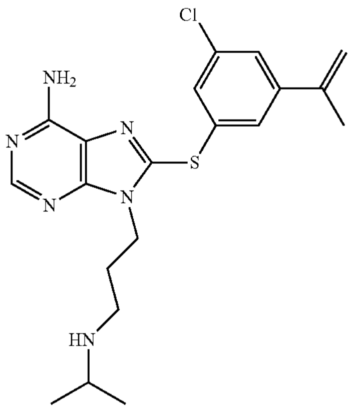 [SMILES: C=C(C)c1cc(Cl)cc(Sc2nc3c(N)ncnc3n2CCCNC(C)C)c1] | HJP-VI-12 | 20 | | 0.21 | | 0.063 |
| 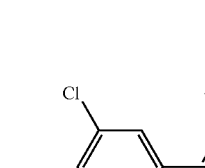 | HJP-VI-14 | >50 | | 0.16 | | 0.122 |
| 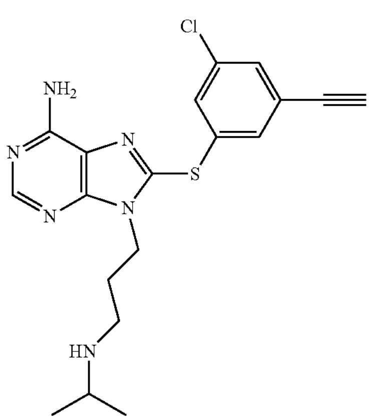 [SMILES: C#Cc1cc(Cl)cc(Sc2nc3c(N)ncnc3n2CCCNC(C)C)c1] | HJP-VI-18 | 152.03 | | 0.9 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 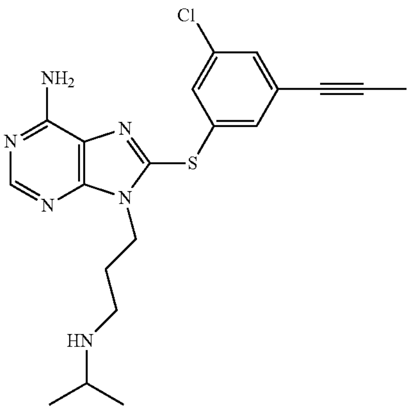 [SMILES: CC#Cc1cc(Cl)cc(Sc2nc3c(N)ncnc3n2CCCNC(C)C)c1] | HJP-VI-50 | >50 | | 2.0 | | |
| 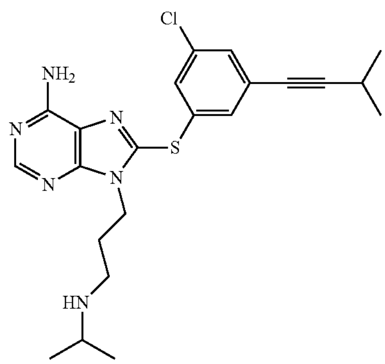 [SMILES: CC(C)C#Cc1cc(Cl)cc(Sc2nc3c(N)ncnc3n2CCCNC(C)C)c1] | HJP-VI-51 | >50 | | 1.2 | | |
| 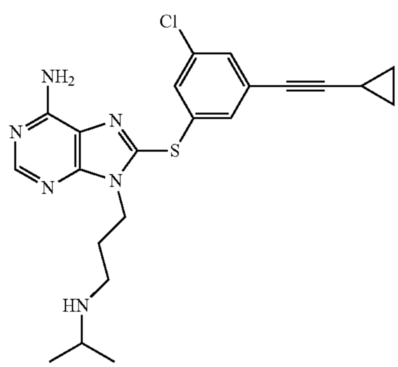 [SMILES: CC(C)NCCCn1c(Sc2cc(Cl)cc(C#CC3CC3)c2)nc2c(N)ncnc21] | HJP-VI-52 | >50 | | 0.18 | | |
| 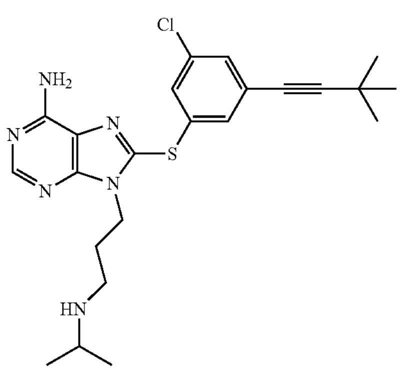 [SMILES: CC(C)NCCCn1c(Sc2cc(Cl)cc(C#CC(C)(C)C)c2)nc2c(N)ncnc21] | HJP-VI-53 | >50 | | 0.63 | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 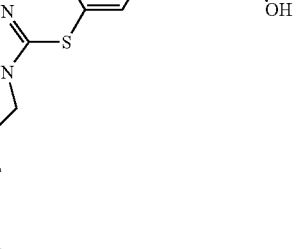 | HJP-VI-58 | >50 | | 5.8 | | |
| 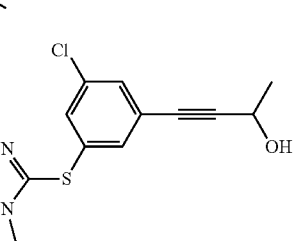 | HJP-VI-59 | >50 | | 7.4 | | |
| 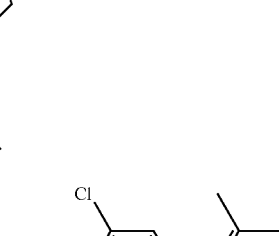 | HJP-VI-62 | >50 | | 0.28 | | |
| 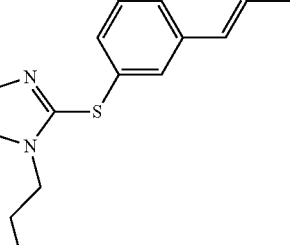 | HJP-VI-63 | >50 | | 0.34 | | 0.226 |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 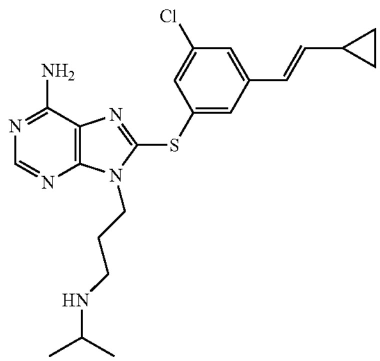 [SMILES: CC(C)NCCCn1c(Sc2cc(Cl)cc(/C=C/C3CC3)c2)nc2c(N)ncnc21] | HJP-VI-64 | >50 | | 0.24 | | |
| 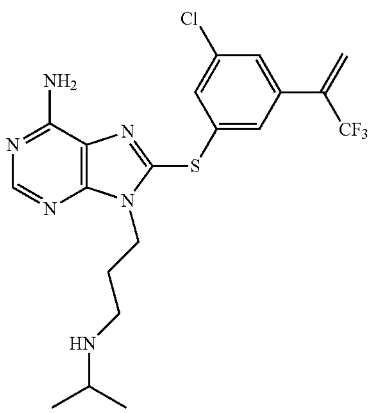 [SMILES: C=C(c1cc(Cl)cc(Sc2nc3c(N)ncnc3n2CCCNC(C)C)c1)C(F)(F)F] | HJP-VI-70 | 13.77 | | 0.153 | | 2.16 |
| 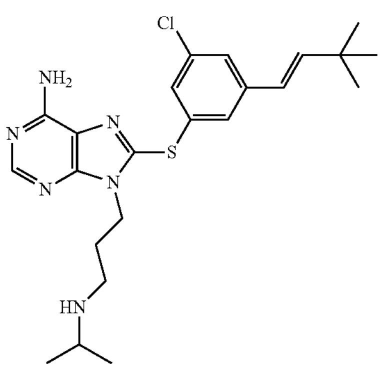 [SMILES: CC(C)NCCCn1c(Sc2cc(Cl)cc(/C=C/C(C)(C)C)c2)nc2c(N)ncnc21] | HJP-VI-72 | 14.23 | | 0.102 | | |
| 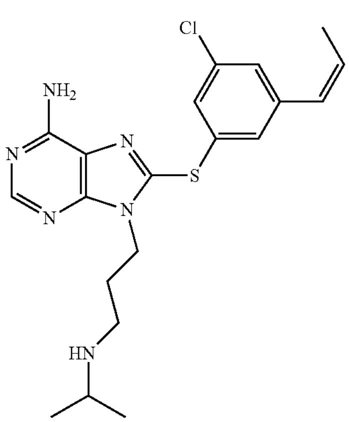 [SMILES: C/C=C\c1cc(Cl)cc(Sc2nc3c(N)ncnc3n2CCCNC(C)C)c1] | HJP-VI-78 | 18.6 | | 0.214 | | 0.58 |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 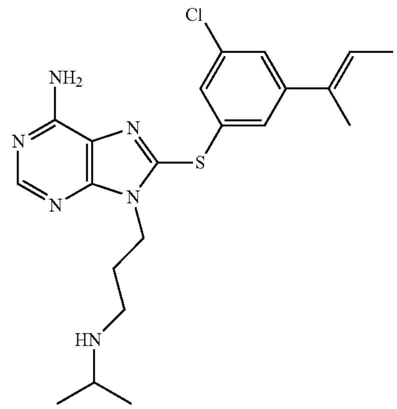 [SMILES: C/C=C(\C)c1cc(Cl)cc(Sc2nc3c(N)ncnc3n2CCCNC(C)C)c1] | HJP-VI-79 | | | 0.124 | | |
| 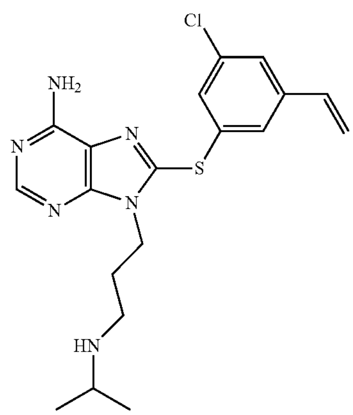 [SMILES: C=Cc1cc(Cl)cc(Sc2nc3c(N)ncnc3n2CCCNC(C)C)c1] | HJP-VI-31 | 48.9 | | 0.63 | | 0.129 |
| 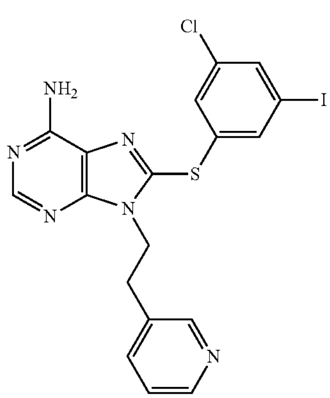 [SMILES: Nc1ncnc2c1nc(Sc1cc(Cl)cc(I)c1)n2CCc1cccnc1] | HJP-V-147 | 72.5 | | 0.86 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 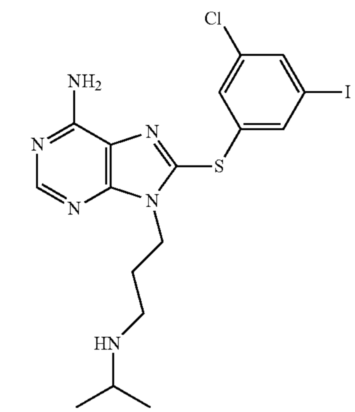 [SMILES: CC(C)NCCCn1c(Sc2cc(Cl)cc(I)c2)nc2c(N)ncnc21] | HJP-V-149 | 43.2 | | 0.24 | | 0.125 |
| 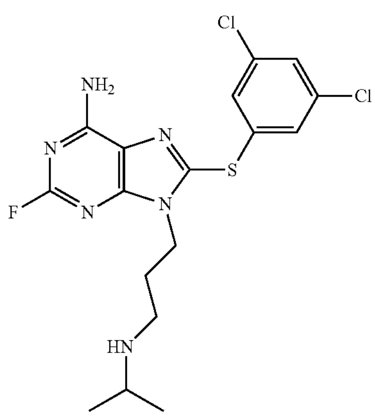 [SMILES: CC(C)NCCCn1c(Sc2cc(Cl)cc(Cl)c2)nc2c(N)nc(F)nc21] | HJP-VI-69 | 10 | | 0.135 | | 0.030 |
| 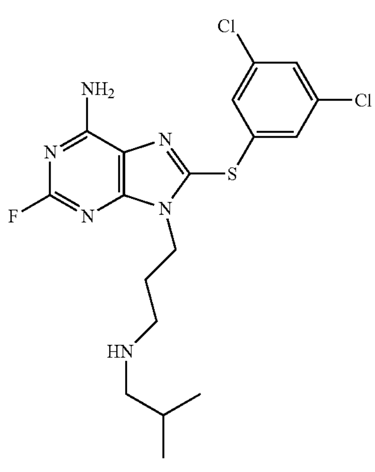 [SMILES: CC(C)CNCCCn1c(Sc2cc(Cl)cc(Cl)c2)nc2c(N)nc(F)nc21] | HJP-VI-84 | | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 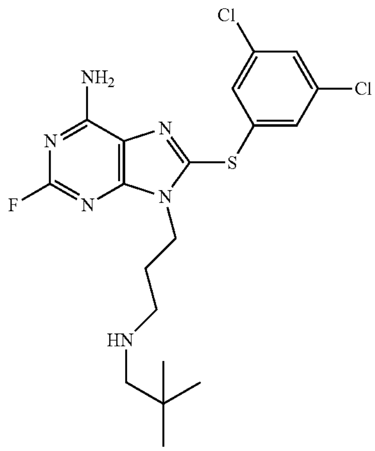 [SMILES: CC(C)(C)CNCCCn1c(Sc2cc(Cl)cc(Cl)c2)nc2c(N)nc(F)nc21] | HJP-VI-85 | >50 | | 0.186 | | 0.164 |
| 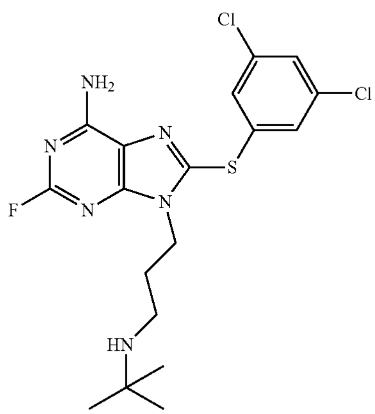 [SMILES: CC(C)(C)NCCCn1c(Sc2cc(Cl)cc(Cl)c2)nc2c(N)nc(F)nc21] | HJP-VI-86 | 20.94 | | 0.156 | | 0.053 |
| 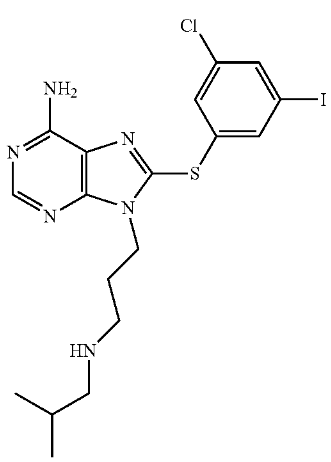 [SMILES: CC(C)CNCCCn1c(Sc2cc(Cl)cc(I)c2)nc2c(N)ncnc21] | HJP-VI-4 | 41.8 | | 0.29 | | 0.212 |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 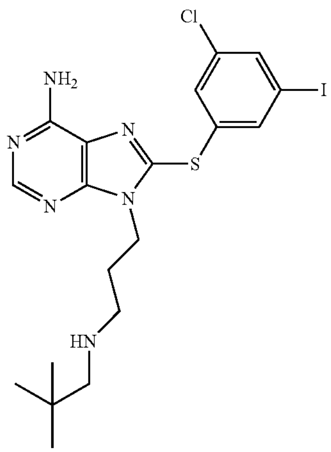 [SMILES: CC(C)(C)CNCCCn1c(Sc2cc(Cl)cc(I)c2)nc2c(N)ncnc21] | HJP-VI-5 | >25 | | 0.49 | | 0.562 |
| 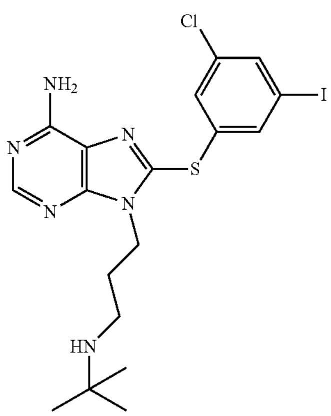 [SMILES: CC(C)(C)NCCCn1c(Sc2cc(Cl)cc(I)c2)nc2c(N)ncnc21] | HJP-VI-6 | 27.8 | | 0.54 | | 0.314 |
| 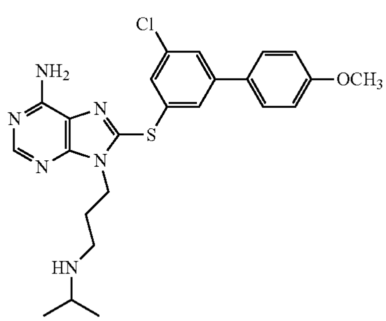 [SMILES: COc1ccc(-c2cc(Cl)cc(Sc3nc4c(N)ncnc4n3CCCNC(C)C)c2)cc1] | HJP-VI-3 | >25 | | 2.7 | | |
| 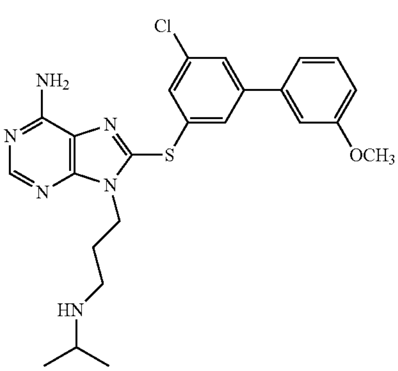 [SMILES: COc1cccc(-c2cc(Cl)cc(Sc3nc4c(N)ncnc4n3CCCNC(C)C)c2)c1] | HJP-VI-7 | 47.5 | | 0.26 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 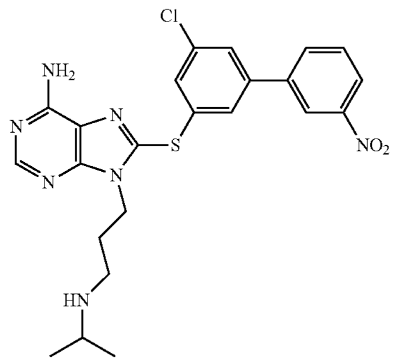 [SMILES: CC(C)NCCCn1c(Sc2cc(Cl)cc(-c3cccc([N+](=O)[O-])c3)c2)nc2c(N)ncnc21] | HJP-VI-8 | 47.3 | | 0.58 | | |
| 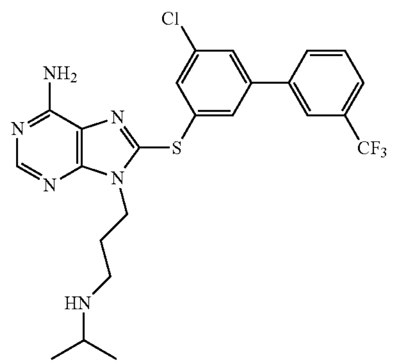 [SMILES: CC(C)NCCCn1c(Sc2cc(Cl)cc(-c3cccc(C(F)(F)F)c3)c2)nc2c(N)ncnc21] | HJP-VI-9 | 13.8 | | 0.26 | | |
| 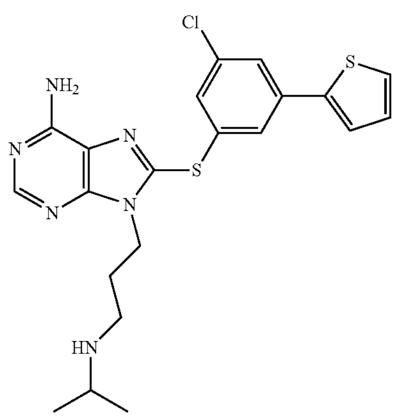 [SMILES: CC(C)NCCCn1c(Sc2cc(Cl)cc(-c3cccs3)c2)nc2c(N)ncnc21] | HJP-VI-10 | 7.9 | | 0.16 | | |
| 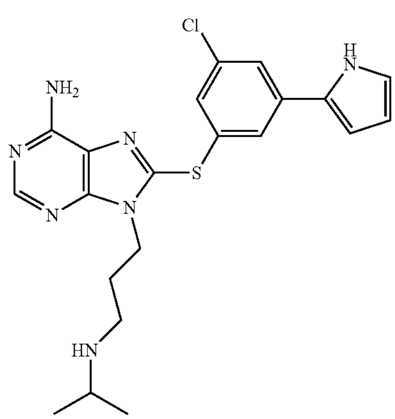 [SMILES: CC(C)NCCCn1c(Sc2cc(Cl)cc(-c3ccc[nH]3)c2)nc2c(N)ncnc21] | HJP-VI-28 | | | 0.22 | | 0.286 |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 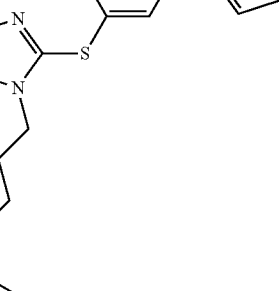 | HJP-VI-29 | 25.9 | | 1.2 | | 0.516 |
| 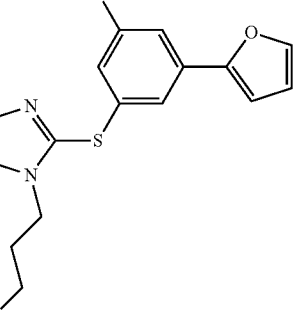 | HJP-VI-30 | 16.7 | | 0.32 | | |
| 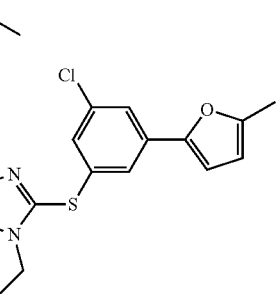 | HJP-VI-38 | 25.9 | | 0.75 | | |
| 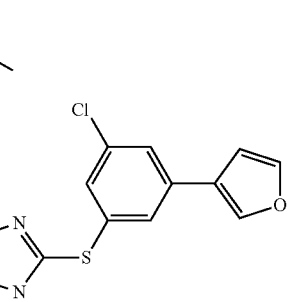 | HJP-VI-39 | 21.3 | | 0.28 | | 0.166 |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 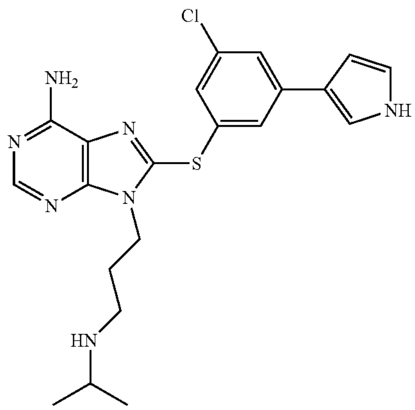 [SMILES: CC(C)NCCCn1c(Sc2cc(Cl)cc(-c3cc[nH]c3)c2)nc2c(N)ncnc21] | HJP-VI-44 | 12.3 | | 0.83 | | 0.917 |
| 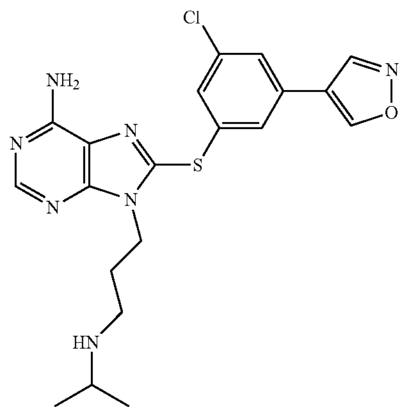 [SMILES: CC(C)NCCCn1c(Sc2cc(Cl)cc(-c3cnoc3)c2)nc2c(N)ncnc21] | HJP-VI-45 | | | | | |
| 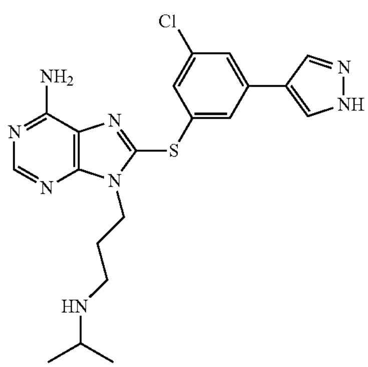 [SMILES: CC(C)NCCCn1c(Sc2cc(Cl)cc(-c3cn[nH]c3)c2)nc2c(N)ncnc21] | HJP-VI-46 | 15.9 | | 1.9 | | |
| 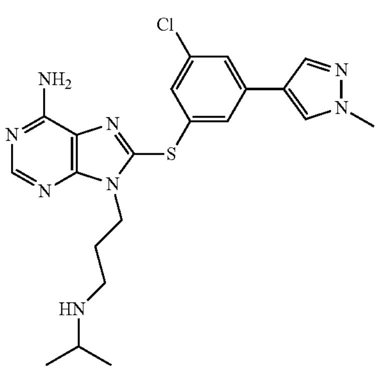 [SMILES: CC(C)NCCCn1c(Sc2cc(Cl)cc(-c3cnn(C)c3)c2)nc2c(N)ncnc21] | HJP-VI-47 | >50 | | 3.3 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 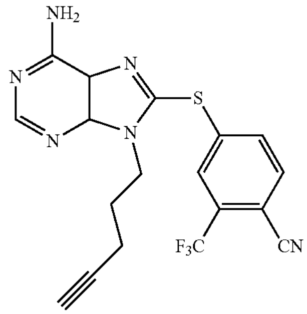 [SMILES: C#CCCCN1C(Sc2ccc(C#N)c(C(F)(F)F)c2)=NC2C(N)=NC=NC21] | HP-III-29 | 4.51 | 2.41 | | | |
| 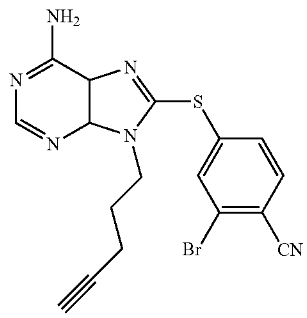 [SMILES: C#CCCCN1C(Sc2ccc(C#N)c(Br)c2)=NC2C(N)=NC=NC21] | HP-III-32 | 14.32 | 4.28 | | | |
| 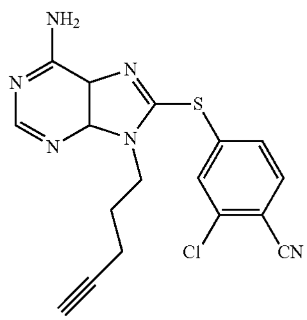 [SMILES: C#CCCCN1C(Sc2ccc(C#N)c(Cl)c2)=NC2C(N)=NC=NC21] | HJP-III-33 | 7.60 | 3.45 | | | |
| 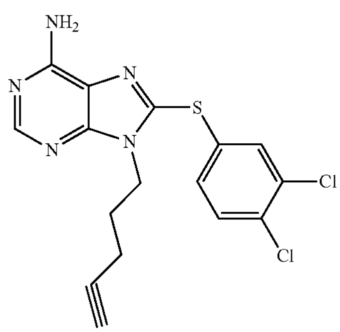 [SMILES: C#CCCCn1c(Sc2ccc(Cl)c(Cl)c2)nc2c(N)ncnc21] | PDP-I-25-N9 | 4.82 ± 1.05 | 10.22 ± 1.62 | 0.42 ± 0.04 | 2.35 ± 0.09 | |
| 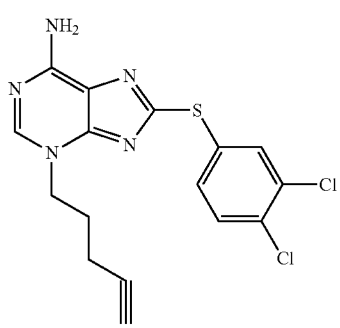 [SMILES: C#CCCCn1cnc(N)c2nc(Sc3ccc(Cl)c(Cl)c3)nc1-2] | PDP-I-25-N3 | >50 | 11.11 | | | |

TABLE 16-continued

| Structure | Compound code | Hsp90α (µM) | Hsp90β (µM) | Grp94 (µM) | TRAP-1 (µM) | MDA-MB-468 |
|---|---|---|---|---|---|---|
| 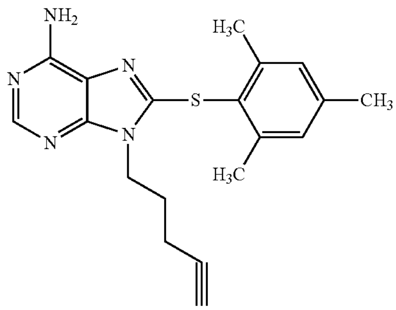 [SMILES: C#CCCCn1c(Sc2c(C)cc(C)cc2C)nc2c(N)ncnc21] | PU-H36 | >250 | >250 | 2.10 ± 0.56 | 65.5 ± 1.3 | |
| 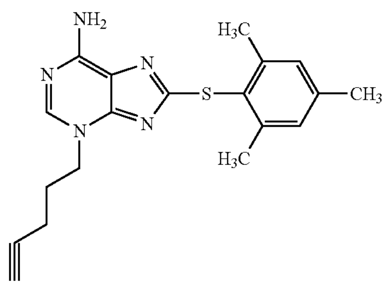 [SMILES: C#CCCCn1cnc(N)c2nc(Sc3c(C)cc(C)cc3C)nc1-2] | PU-H37 | >>100 | >>100 | 20 ± 5 | | |
| 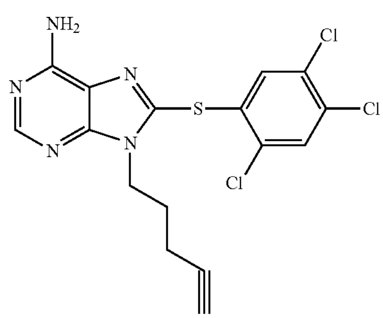 [SMILES: C#CCCCn1c(Sc2cc(Cl)c(Cl)cc2Cl)nc2c(N)ncnc21] | PU-H51 | >200 | >200 | 0.17 ± 0.11 | 78.4 ± 8.9 | |
| 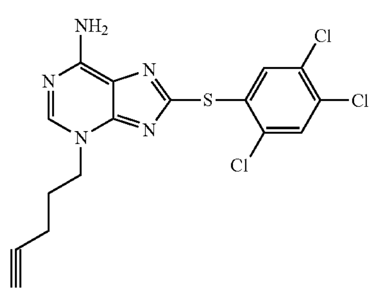 [SMILES: C#CCCCn1cnc(N)c2nc(Sc3cc(Cl)c(Cl)cc3Cl)nc1-2] | PU-H52 | >>100 | >>100 | 2.08 ± 1.49 | 19.5 ± 0.2 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| (structure) | HJP-V-103-N9 | 5.8 | | 0.35 | | |
| (structure) | PDP-121 | >100 | >100 | 1.66 ± 0.48 | 2.20 ± 0.67 | |
| (structure) | PDP-125A | >100 | >100 | 0.19 ± 0.01 | 6.04 ± 0.55 | |
| (structure) | PDP-125B | >100 | >100 | 5.208 | 58.824 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| (structure) | PDP-126A | 15.72 ± 0.35 | 18.26 ± 1.29 | 0.27 ± 0.14 | 4.03 ± 0.89 | |
| (structure) | PDP-126B | >100 | >100 | 8.70 | 34.10 | |
| (structure) | HJP-V-145 | | | | 0.68 | |
| (structure) | PDP-I-55-N9 | >50 | | | >5 | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 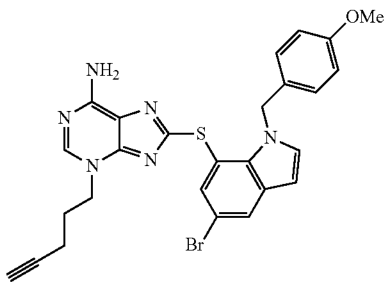 [SMILES: C#CCCCn1cnc(N)c2nc(Sc3cc(Br)cc4ccn(Cc5ccc(OC)cc5)c34)nc1-2] | PDP-I-55-N3 | | | | | |
| 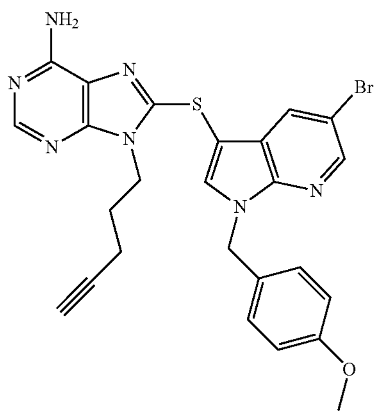 [SMILES: C#CCCCn1c(Sc2cn(Cc3ccc(OC)cc3)c3ncc(Br)cc23)nc2c(N)ncnc21] | PDP-I-58-N9 | >50 | | >10 | | |
| 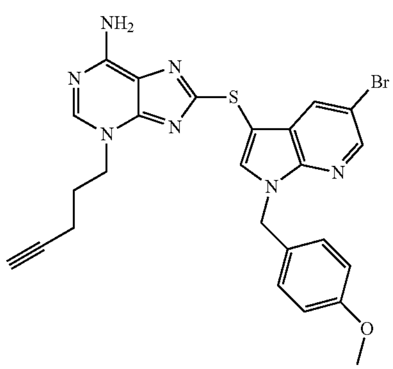 [SMILES: C#CCCCn1cnc(N)c2nc(Sc3cn(Cc4ccc(OC)cc4)c4ncc(Br)cc34)nc1-2] | PDP-I-58-N3 | >50 | | >10 | | |
| 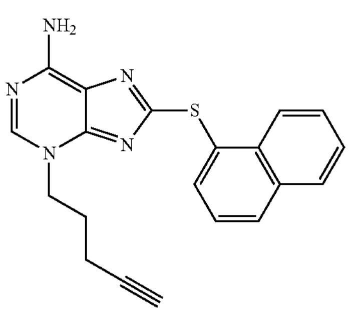 [SMILES: C#CCCCn1cnc(N)c2nc(Sc3cccc4ccccc34)nc1-2] | PDP-I-16-N3 | >100 | | >5 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 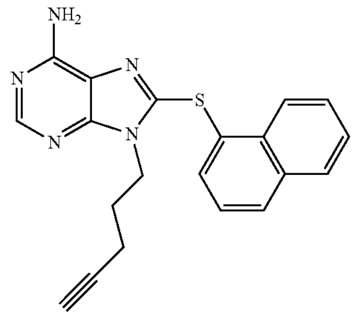 [SMILES: C#CCCCn1c(Sc2cccc3ccccc23)nc2c(N)ncnc21] | PDP-I-16-N9 | >100 | >100 | 2.16 ± 0.21 | >100 | |
| 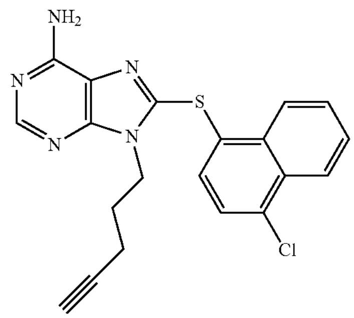 [SMILES: C#CCCCn1c(Sc2ccc(Cl)c3ccccc23)nc2c(N)ncnc21] | PDP-I-77-N9 | >50 | | >2 | | |
| 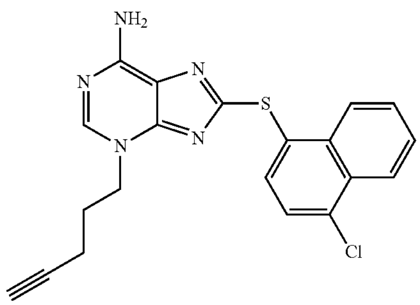 [SMILES: C#CCCCn1cnc(N)c2nc(Sc3ccc(Cl)c4ccccc34)nc1-2] | PDP-I-77-N3 | >50 | | >5 | | |
| 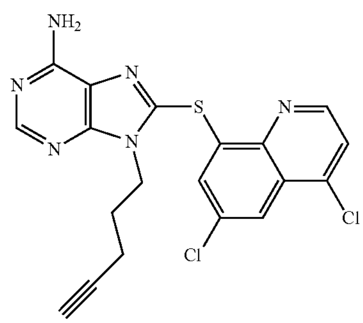 [SMILES: C#CCCCn1c(Sc2cc(Cl)cc3c(Cl)ccnc23)nc2c(N)ncnc21] | PDP-I-79-N9 | >100 | >100 | 2.78 ± 0.21 | >100 | |
| 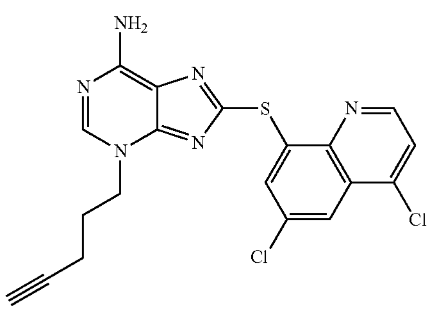 [SMILES: C#CCCCn1cnc(N)c2nc(Sc3cc(Cl)cc4c(Cl)ccnc34)nc1-2] | PDP-I-79-N3 | >50 | | >5 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 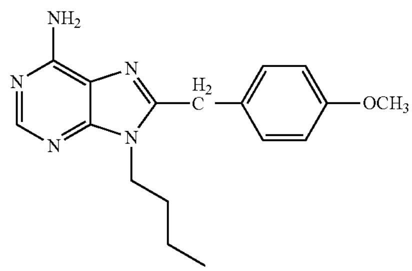 [SMILES: CCCCn1c(Cc2ccc(OC)cc2)nc2c(N)ncnc21] | PU1 | 110 ± 20 | 92 ± 2 | 3.2 ± 0.4 | | |
| 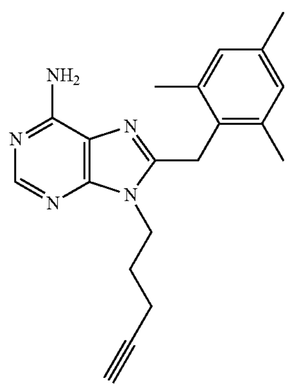 [SMILES: C#CCCCn1c(Cc2c(C)cc(C)cc2C)nc2c(N)ncnc21] | HJP-V-36 | >10 | >10 | >5 | | |
| 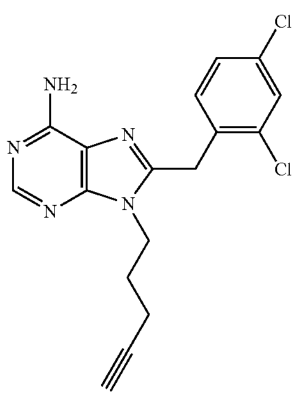 [SMILES: C#CCCCn1c(Cc2ccc(Cl)cc2Cl)nc2c(N)ncnc21] | HJP-V-37 | >10 | | 0.7 | | |
| 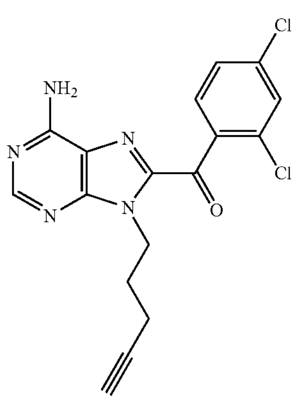 [SMILES: C#CCCCn1c(C(=O)c2ccc(Cl)cc2Cl)nc2c(N)ncnc21] | HJP-V-37T | >25 | | 0.13-0.17 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 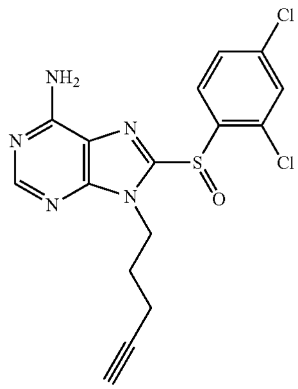 [SMILES: C#CCCCn1c(S(=O)c2ccc(Cl)cc2Cl)nc2c(N)ncnc21] | HJP-V-62M | 24.1 | | 5.4 | | |
| 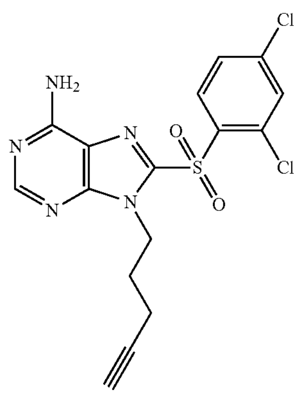 [SMILES: C#CCCCn1c(S(=O)(=O)c2ccc(Cl)cc2Cl)nc2c(N)ncnc21] | HJP-V-62T | >25 | | 4.7 | | |
| 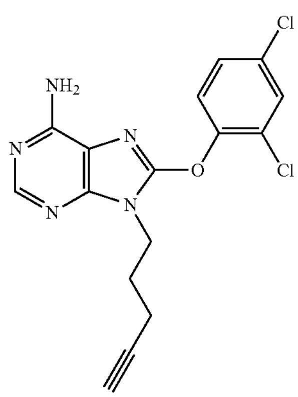 [SMILES: C#CCCCn1c(Oc2ccc(Cl)cc2Cl)nc2c(N)ncnc21] | HJP-V-45 | >10 | | 0.5 | | |
| 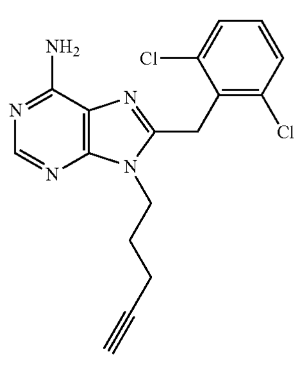 [SMILES: C#CCCCn1c(Cc2c(Cl)cccc2Cl)nc2c(N)ncnc21] | HJP-V-38 | 14.4 | | 13.8 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 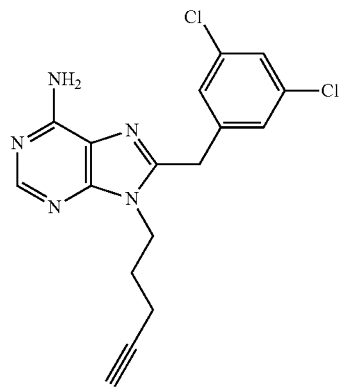 [SMILES: C#CCCCn1c(Cc2cc(Cl)cc(Cl)c2)nc2c(N)ncnc21] | HJP-V-39 | >10 | | 0.5 | | |
| 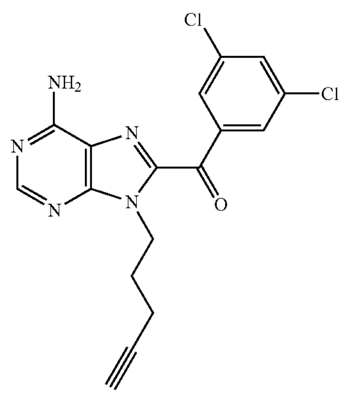 [SMILES: C#CCCCn1c(C(=O)c2cc(Cl)cc(Cl)c2)nc2c(N)ncnc21] | HJP-V-39T | >10 | | 5.0 | | |
| 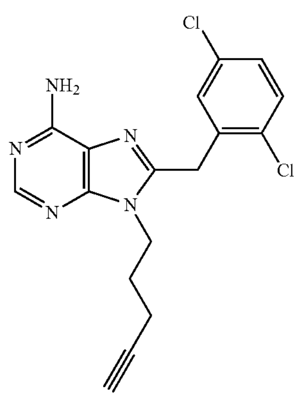 [SMILES: C#CCCCn1c(Cc2cc(Cl)ccc2Cl)nc2c(N)ncnc21] | HJP-V-54 | >10 | | 0.75 | | |
| 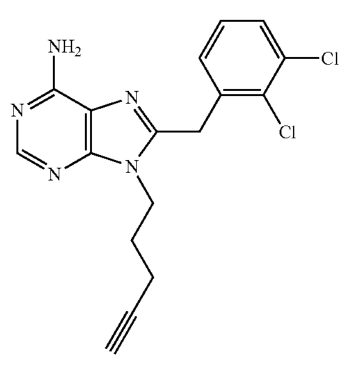 [SMILES: C#CCCCn1c(Cc2cccc(Cl)c2Cl)nc2c(N)ncnc21] | HJP-V-55 | >10 | | 2.0 | | |

TABLE 16-continued
| Structure | Compound code | Hsp90α (μM) | Hsp90β (μM) | Grp94 (μM) | TRAP-1 (μM) | MDA-MB-468 |
|---|---|---|---|---|---|---|
| 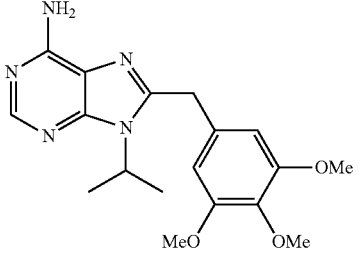 [SMILES: COc1cc(Cc2nc3c(N)ncnc3n2C(C)C)cc(OC)c1OC] | PU-27 | >500 | >250 | 59.30 ± 2.69 | >300 | |
| 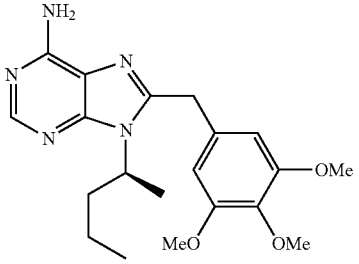 [SMILES: CCC[C@H](C)n1c(Cc2cc(OC)c(OC)c(OC)c2)nc2c(N)ncnc21] | PU-34 | >500 | >250 | 91.33 ± 2.16 | 227.2 ± 6.6 | |
| 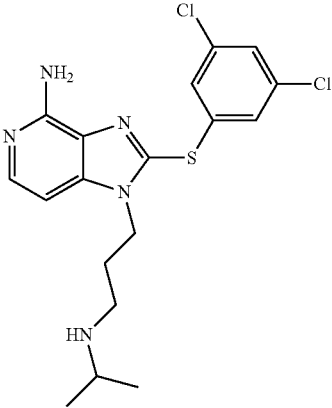 [SMILES: CC(C)NCCCn1c(Sc2cc(Cl)cc(Cl)c2)nc2c(N)nccc21] | SO-III-154 | >50 | | 2.59 | | |
| 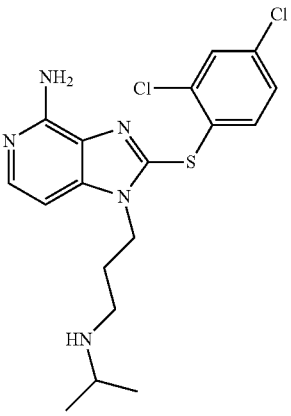 [SMILES: CC(C)NCCCn1c(Sc2ccc(Cl)cc2Cl)nc2c(N)nccc21] | HJP-VI-101 | 9.2 | | >5 | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 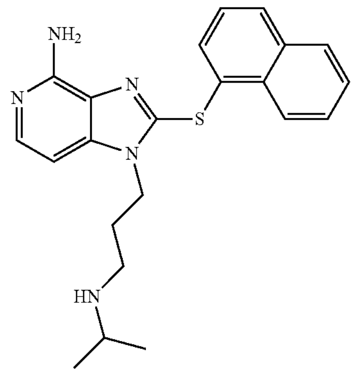 [SMILES: CC(C)NCCCn1c(Sc2cccc3ccccc23)nc2c(N)nccc21] | SO-IV-03 | >50 | | >5 | | |
| 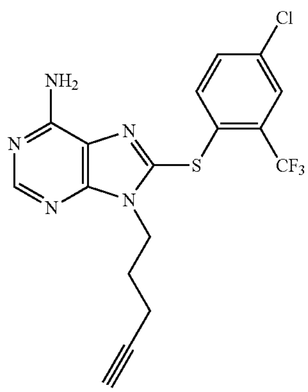 [SMILES: C#CCCCn1c(Sc2ccc(Cl)cc2C(F)(F)F)nc2c(N)ncnc21] | PDP-117A | >100 | >100 | 1.58 | 34.42 | |
| 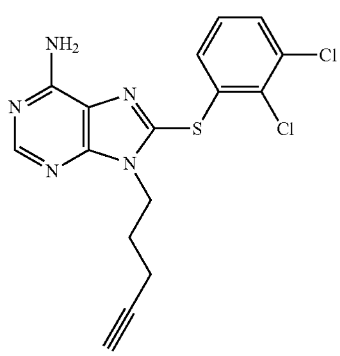 [SMILES: C#CCCCn1c(Sc2cccc(Cl)c2Cl)nc2c(N)ncnc21] | PDP-119A | >100 | >100 | 1.96 | >100 | |
| 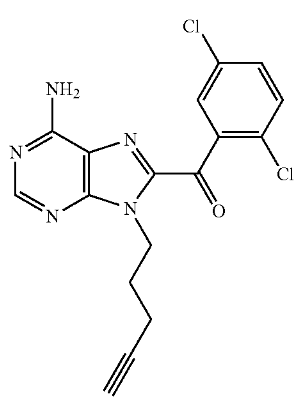 [SMILES: C#CCCCn1c(C(=O)c2cc(Cl)ccc2Cl)nc2c(N)ncnc21] | HJP-V-54T | | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 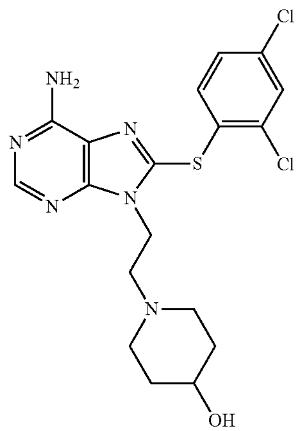 [SMILES: Nc1ncnc2c1nc(Sc1ccc(Cl)cc1Cl)n2CCN1CCC(O)CC1] | HJP-V-90 | | | | | |
| 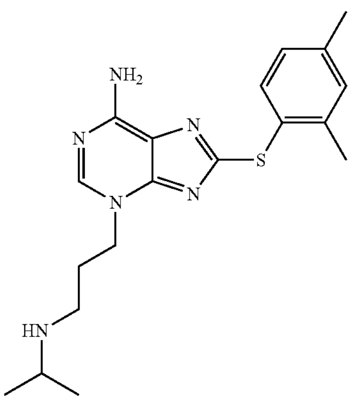 [SMILES: Cc1ccc(Sc2nc3c(N)ncn(CCCNC(C)C)c-3n2)c(C)c1] | WS-11 | >100 | | 25 | | |
| 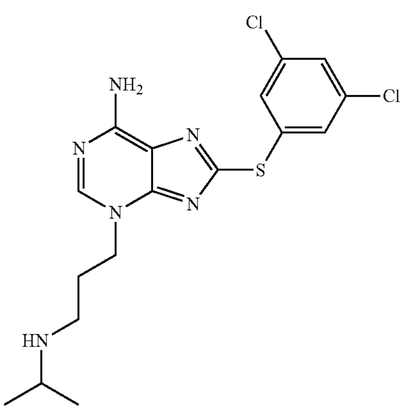 [SMILES: CC(C)NCCCn1cnc(N)c2nc(Sc3cc(Cl)cc(Cl)c3)nc1-2] | WS-13-N3 | >100 | >100 | 2.43 | >100 | |
| 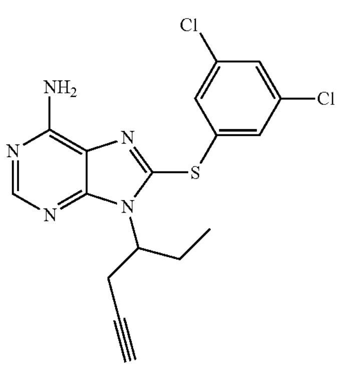 [SMILES: C#CCC(CC)n1c(Sc2cc(Cl)cc(Cl)c2)nc2c(N)ncnc21] | HJP-V-125 | | | | | |

TABLE 16-continued

| Structure | Compound code | Hsp90α (μM) | Hsp90β (μM) | Grp94 (μM) | TRAP-1 (μM) | MDA-MB-468 |
|---|---|---|---|---|---|---|
| 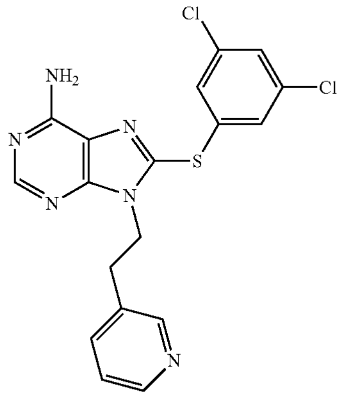 [SMILES: Nc1ncnc2c1nc(Sc1cc(Cl)cc(Cl)c1)n2CCc1cccnc1] | HJP-V-140 | >50 | | 7.9 | | |
| 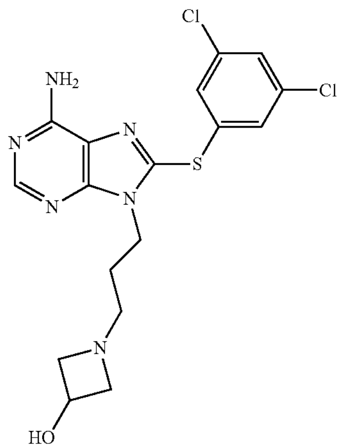 [SMILES: Nc1ncnc2c1nc(Sc1cc(Cl)cc(Cl)c1)n2CCCN1CC(O)C1] | HJP-V-134 | >10 | | 0.38 | | |
| 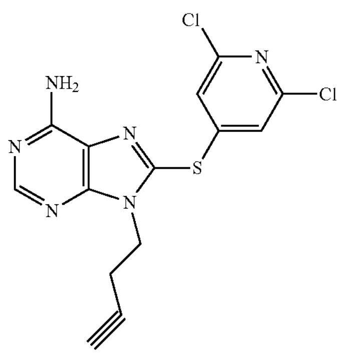 [SMILES: C#CCCn1c(Sc2cc(Cl)nc(Cl)c2)nc2c(N)ncnc21] | HJP-VI-66 | >5 | | 1.9 | | |

What is claimed is:

1. A compound of the Formula (I):

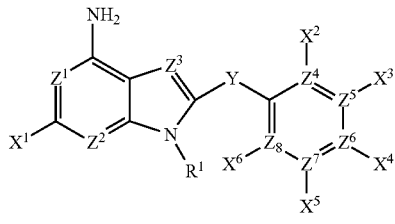

or a pharmaceutically acceptable salt thereof, wherein:

(a) Y is —C(R$^Y$)$_2$—, —S—, —NR—, —O—,

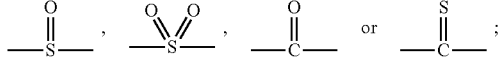

(b) each of Z$^1$ and Z$^3$ are independently —N—;
(c) Z$^2$ is —N—;
(d) each of Z$^4$, Z$^5$, Z$^6$, Z$^7$ and Z$^8$ are independently —C—;
(e) X$^1$ is —H, -halo, —N(R)$_2$, —OR, —CN, or unsubstituted or substituted —(C$_1$-C$_6$)aliphatic;
(f) each of X$^2$ and X$^6$ is independently —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered)arylalkyl, and (5- or 6-membered)heterocyclic aromatic or heterocyclic non-aromatic group; each of X$^3$, X$^4$, and X$^5$ is independently —H, -halo, or unsubstituted —(C$_1$-C$_6$)aliphatic; with the proviso that at least one of X$^2$, X$^4$ and X$^5$ is —H;
(g) R$^1$ is —(C$_1$-C$_6$)aliphatic-N$^+$—(R$^2$)(R$^3$)(R$^4$), —(C$_1$-C$_6$)aliphatic-N—R$^3$R$^4$, —(C$_1$-C$_6$)aliphatic-C(═O)N—R$^3$R$^4$, —(C$_1$-C$_6$)aliphatic-N—CR$^2$R$^3$R$^4$, —(C$_1$-C$_6$)aliphatic-C(halo)$_3$, —(C$_1$-C$_6$)aliphatic-(C$_3$-C$_8$) cycloalkyl, —(C$_1$C$_6$aliphatic-(C$_3$-C$_8$)heterocyclo, —(C$_1$-C$_6$)aliphatic-(5 or 6-membered)heteroaryl, —(C$_1$-C$_6$)aliphatic-cyano, where the cycloalkyl, heterocyclo, or heteroaryl is unsubstituted or substituted, with the proviso that when all of R$^2$-R$^4$ are present the compound further comprises a pharmaceutically acceptable counter ion;
(h) R$^2$ and R$^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$)aliphatic, or R$^3$ and R$^4$ form an unsubstituted or substituted 3- to 7-membered heterocyclic ring when taken together with the nitrogen to which they are attached;
(i) R$^4$ is hydrogen, halogen, or unsubstituted or substituted —(C$_1$-C$_6$)aliphatic;
(j) each R$^Y$ is independently R, —OR, or halo; and
(k) each R is independently hydrogen, unsubstituted C$_{1-6}$ aliphatic, or C$_{1-6}$ aliphatic substituted with halo, —OH, —CN, or —NH$_2$;

wherein each substituted group is substituted with one or more groups selected from halo, —N(R)$_2$, —OR, —CN, oxo, unsubstituted C$_{1-6}$ aliphatic, or C$_{1-6}$ aliphatic substituted with halo, —OH, —CN, or —NH$_2$.

2. The compound of claim 1 or a pharmaceutically acceptable salt thereof, wherein:

(a) Y is —CH$_2$—, —S—, —NH—, —O—,

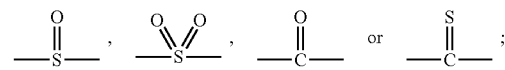

(b) each of Z$^1$ and Z$^3$ are independently —N—;
(c) Z$^2$ is;
(d) each of Z$^4$, Z$^5$, Z$^6$, Z$^7$ and Z$^8$ are independently —C—;
(e) X$^1$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, or —OCH$_2$(halo);
(f) X$^2$ is —H, -halo, —NH$_2$, —CN, —(C$_1$-C$_6$)alkyl, —O(C$_1$-C$_6$)alkyl, —CH$_2$OH, —C(halo)$_3$, —CH(halo)$_2$, —CH$_2$(halo), —OC(halo)$_3$, —OCH(halo)$_2$, —OCH$_2$(halo), or an unsubstituted or substituted (5- or 6-membered)aryl, heterocyclic aromatic, or non-aromatic group selected from pyridyl, furyl, thiophenyl, pyrrolyl, oxazolyl, imidazolyl, phenyl, benzyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl, each of X$^3$, X$^4$, and X$^5$ is independently —H, -halo, or —(C$_1$-C$_6$)alkyl; with the provisos that at least one of X$^2$, X$^4$ and X$^5$ is —H;

(g) $X^6$ is —H;

(h) $R^1$ is —$(CH_2)_m$—$N^+$—$(R^2)(R^3)(R^4)$, —$(CH_2)_m$—N—$R^3R^4$, —$(CH_2)_m$—C(=O)N—$R^3R^4$, —$(CH_2)_m$—C(halo)$_3$, —$(CH_2)_m$—$(C_3$-$C_8)$cycloalkly, —$(CH_2)_m$—$(C_3$-$C_8)$heterocycloalkyl, $(CH_2)_m$-(5 or 6-membered) heteroaryl, —$(CH_2)_m$-cyano, where m is 1, 2, 3, 4 or 5 and where the cycloalkyl or heterocycle is unsubstituted or substituted with one or more $X^1$ groups, with the proviso that when all of $R^2$-$R^4$ are present the compound further comprises a pharmaceutically acceptable counter ion;

(i) $R^2$ and $R^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —$CH_2$(halo), —$CH_2$C(halo)$_3$, —CHCH(halo)$_2$, CHCH$_2$(halo), —$CH_2$OH, —$CH_2CH_2$OH, —$CH_2C(CH_3)_2$OH, —$CH_2CH(CH_3)$OH, —$C(CH_3)_2CH_2$OH, —$CH(CH_3)CH_2$OH, —CH(CH$_3$)CH(OH)$R^4$, —$CH_2$CH(OH)$R^4$, —$CH_2SO_2NHR^4$, —$CH_2NHSO_2R^4$ or $R^4$ and $R^3$ form an unsubstituted or substituted aziridine, azetidine, pyrrolidine or piperidine ring when taken together with the nitrogen to which they are attached; and (j) $R^4$ is hydrogen, methyl, ethyl, isopropyl, t-butyl, isobutyl, or —C(halo)$_3$.

3. The compound of claim 1, having the following formula:

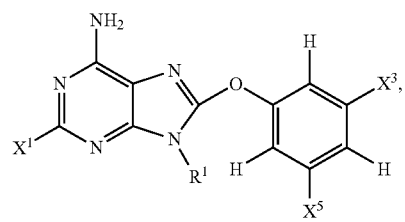

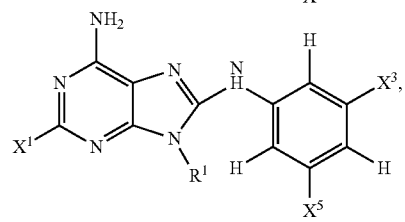

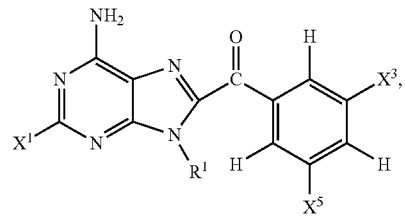

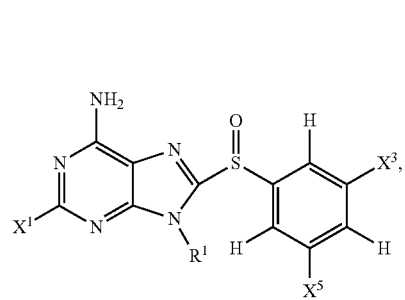

-continued

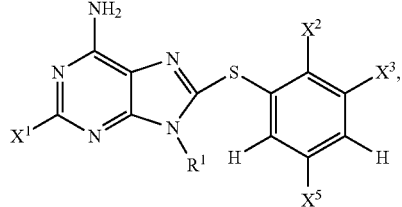

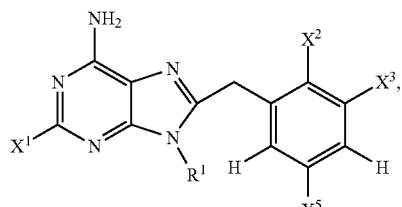

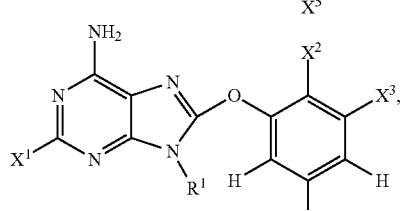

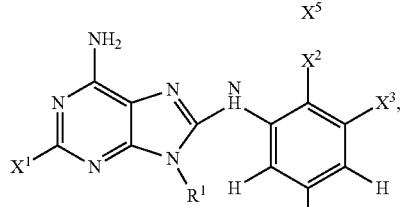

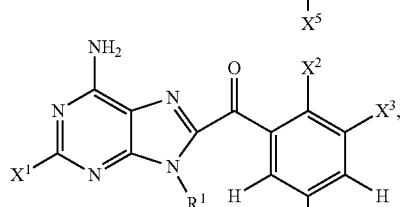

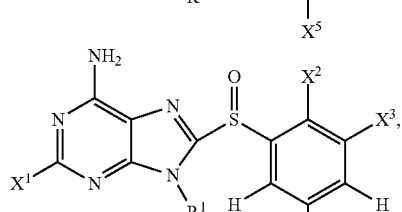

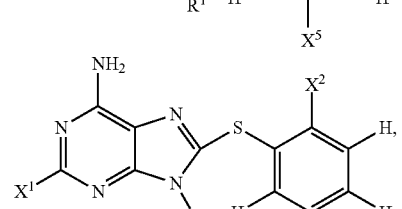

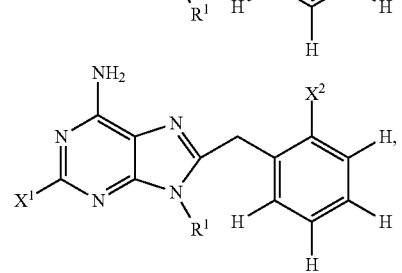

-continued

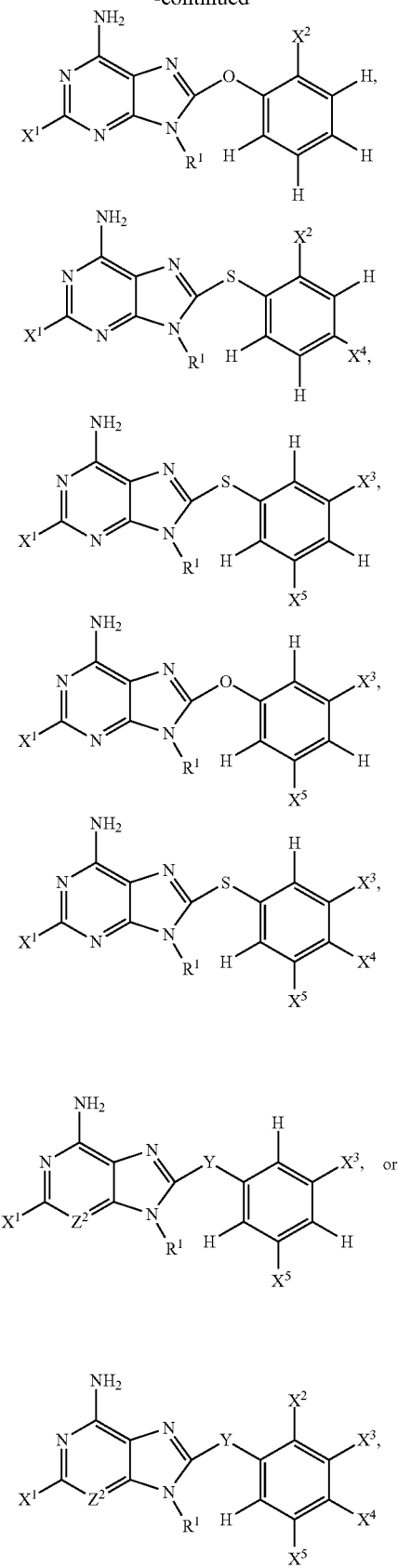

or a pharmaceutically acceptable salt thereof.

4. The compound of claim 1, having Formula(II):

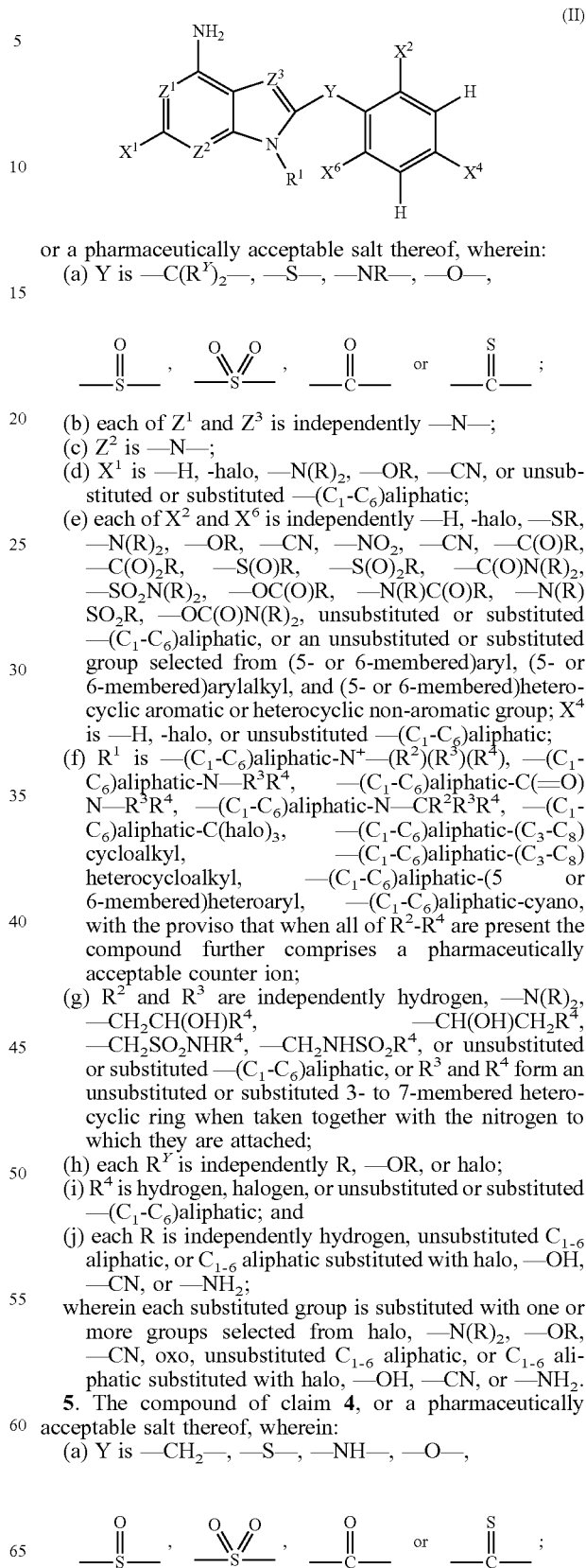

or a pharmaceutically acceptable salt thereof, wherein:
(a) Y is —C($R^Y$)$_2$—, —S—, —NR—, —O—, $$\underset{S}{\overset{O}{\|}},\quad \underset{S}{\overset{O\;\;O}{\|\|}},\quad \underset{C}{\overset{O}{\|}}\;\text{or}\; \underset{C}{\overset{S}{\|}};$$

(b) each of $Z^1$ and $Z^3$ is independently —N—;
(c) $Z^2$ is —N—;
(d) $X^1$ is —H, -halo, —N(R)$_2$, —OR, —CN, or unsubstituted or substituted —(C$_1$-C$_6$)aliphatic;
(e) each of $X^2$ and $X^6$ is independently —H, -halo, —SR, —N(R)$_2$, —OR, —CN, —NO$_2$, —CN, —C(O)R, —C(O)$_2$R, —S(O)R, —S(O)$_2$R, —C(O)N(R)$_2$, —SO$_2$N(R)$_2$, —OC(O)R, —N(R)C(O)R, —N(R)SO$_2$R, —OC(O)N(R)$_2$, unsubstituted or substituted —(C$_1$-C$_6$)aliphatic, or an unsubstituted or substituted group selected from (5- or 6-membered)aryl, (5- or 6-membered)arylalkyl, and (5- or 6-membered)heterocyclic aromatic or heterocyclic non-aromatic group; $X^4$ is —H, -halo, or unsubstituted —(C$_1$-C$_6$)aliphatic;
(f) $R^1$ is —(C$_1$-C$_6$)aliphatic-N$^+$—(R$^2$)(R$^3$)(R$^4$), —(C$_1$-C$_6$)aliphatic-N—R$^3$R$^4$, —(C$_1$-C$_6$)aliphatic-C(=O)N—R$^3$R$^4$, —(C$_1$-C$_6$)aliphatic-N—CR$^2$R$^3$R$^4$, —(C$_1$-C$_6$)aliphatic-C(halo)$_3$, —(C$_1$-C$_6$)aliphatic-(C$_3$-C$_8$)cycloalkyl, —(C$_1$-C$_6$)aliphatic-(C$_3$-C$_8$)heterocycloalkyl, —(C$_1$-C$_6$)aliphatic-(5 or 6-membered)heteroaryl, —(C$_1$-C$_6$)aliphatic-cyano, with the proviso that when all of R$^2$-R$^4$ are present the compound further comprises a pharmaceutically acceptable counter ion;
(g) $R^2$ and $R^3$ are independently hydrogen, —N(R)$_2$, —CH$_2$CH(OH)R$^4$, —CH(OH)CH$_2$R$^4$, —CH$_2$SO$_2$NHR$^4$, —CH$_2$NHSO$_2$R$^4$, or unsubstituted or substituted —(C$_1$-C$_6$)aliphatic, or R$^3$ and R$^4$ form an unsubstituted or substituted 3- to 7-membered heterocyclic ring when taken together with the nitrogen to which they are attached;
(h) each $R^Y$ is independently R, —OR, or halo;
(i) $R^4$ is hydrogen, halogen, or unsubstituted or substituted —(C$_1$-C$_6$)aliphatic; and
(j) each R is independently hydrogen, unsubstituted C$_{1-6}$ aliphatic, or C$_{1-6}$ aliphatic substituted with halo, —OH, —CN, or —NH$_2$;
wherein each substituted group is substituted with one or more groups selected from halo, —N(R)$_2$, —OR, —CN, oxo, unsubstituted C$_{1-6}$ aliphatic, or C$_{1-6}$ aliphatic substituted with halo, —OH, —CN, or —NH$_2$.

5. The compound of claim 4, or a pharmaceutically acceptable salt thereof, wherein:
(a) Y is —CH$_2$—, —S—, —NH—, —O—, $$\underset{S}{\overset{O}{\|}},\quad \underset{S}{\overset{O\;\;O}{\|\|}},\quad \underset{C}{\overset{O}{\|}}\;\text{or}\; \underset{C}{\overset{S}{\|}};$$

(b) each of $Z^1$ and $Z^3$ is independently —N—;

(c) $Z^2$ is —N—;

(d) $X^1$ is —H, -halo, —$NH_2$, —CN, —($C_1$-$C_6$)alkyl, —O($C_1$-$C_6$)alkyl, —$CH_2OH$, —C(halo)$_3$, —CH(halo)$_2$, —$CH_2$(halo), —OC (halo)$_3$, —OCH(halo)$_2$, or —$OCH_2$(halo);

(e) each of $X^2$ and $X^6$ is independently —H, -halo, —$NH_2$, —CN, —($C_1$-$C_6$)alkyl, —O($C_1$-$C_6$)alkyl, —$CH_2OH$, —C(halo)$_3$, —CH(halo)$_2$, —$CH_2$(halo), —OC(halo)$_3$, —OCH(halo)$_2$, —$OCH_2$(halo), or a (5- or 6-membered)aryl, heterocyclic aromatic, or non-aromatic group selected from pyridyl, furyl, thiophenyl, pyrrolyl, oxazolyl, imidazolyl, phenyl, benzyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyridinyl, tetrahydropyridinyl, tetrahydropyrimidinyl, tetrahydrothiophenyl, or tetrahydrothiopyranyl; $X^4$ is —H, -halo, or —($C_1$-$C_6$)alkyl;

(f) $R^1$ is —$(CH_2)_m$—$N^+$—$(R^2)(R^3)(R^4)$, —$(CH_2)_m$—N—$R^3R^4$, —$(CH_2)_m$—C(=O)N—$R^3R^4$, —$(CH_2)_m$—C(halo)$_3$, —$(CH_2)_m$—($C_3$-$C_8$)cycloalkyl, —$(CH_2)_m$—($C_3$-$C_8$)heterocycloalkyl, —$(CH_2)_m$-(5 or 6-membered)heteroaryl, —$(CH_2)_m$-cyano, where m is 1, 2, 3, 4 or 5 and where the cycloalkyl or heterocycle is unsubstituted or substituted with one or more $X^1$ groups, with the proviso that when all of $R^2$-$R^4$ are present the compound further comprises a pharmaceutically acceptable counter ion;

(g) $R^2$ and $R^3$ are independently hydrogen, methyl, ethyl, ethenyl, ethynyl, propyl, butyl, pentyl, hexyl, isopropyl, t-butyl, isobutyl, —C(halo)$_3$, —CH(halo)$_2$, —$CH_2$(halo), —$CH_2$C(halo)$_3$, —CHCH(halo)$_2$, CHCH$_2$(halo), —$CH_2OH$, —$CH_2CH_2OH$, —$CH_2C(CH_3)_2OH$, —$CH_2CH(CH_3)OH$, —$C(CH_3)_2CH_2OH$, —$CH(CH_3)CH_2OH$, —$CH(CH_3)CH(OH)R^4$, —$CH_2CH(OH)R^4$, —$CH_2SO_2NHR^4$, —$CH_2NHSO_2R^4$, or $R^4$ and $R^3$ form an unsubstituted or substituted aziridine, azetidine, pyrrolidine or piperidine ring when taken together with the nitrogen to which they are attached; and (h) $R^4$ is hydrogen, methyl, ethyl, isopropyl, t-butyl, isobutyl, or —C(halo)$_3$.

6. The compound of claim 4, having the following formula:

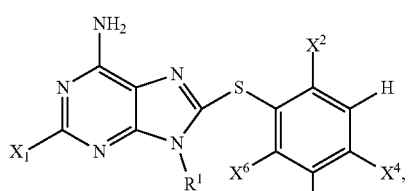

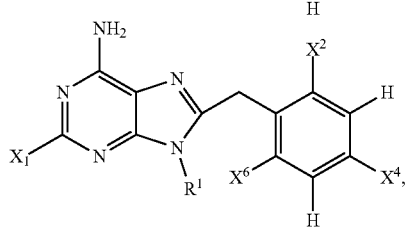

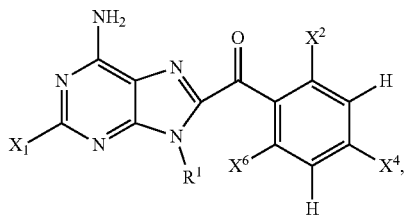

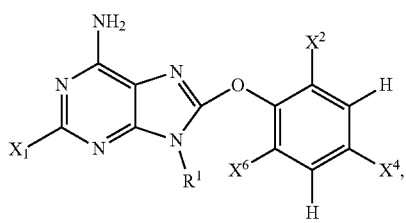

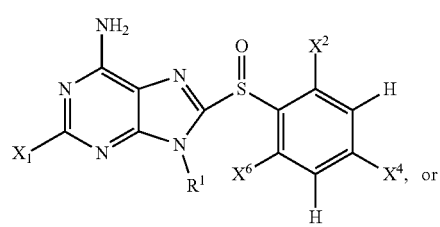

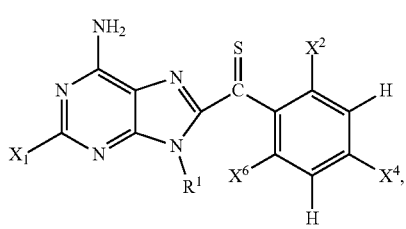

or a pharmaceutically acceptable salt thereof.

7. The compound of claim 1, having the following formula:

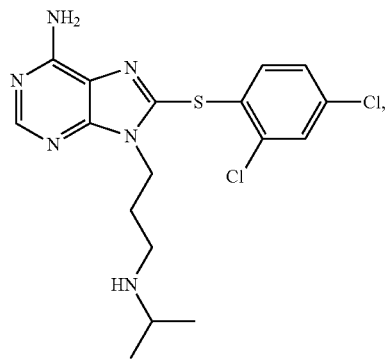

377
-continued
378
-continued
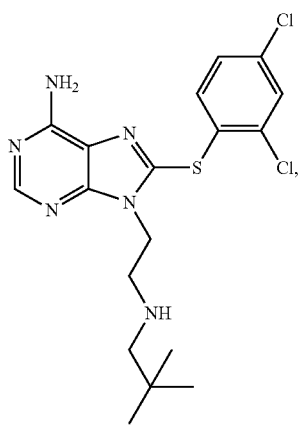
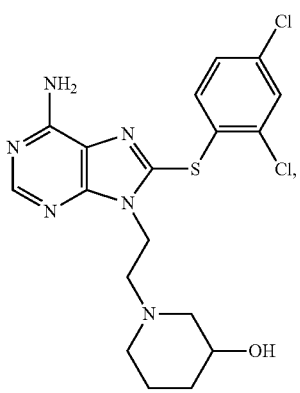

379
-continued
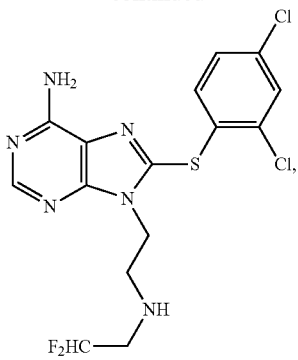
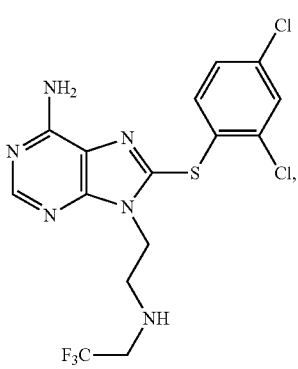
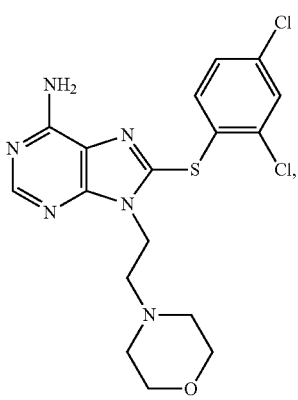
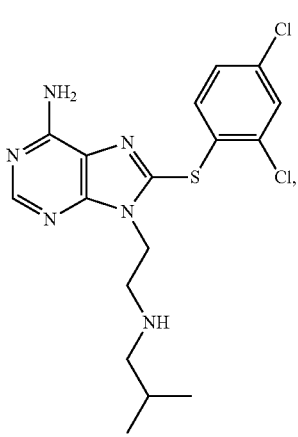
380
-continued
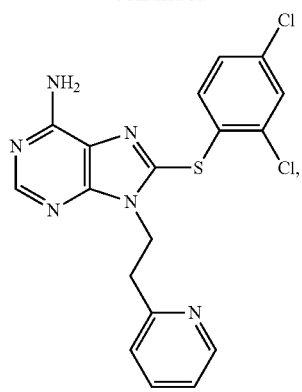
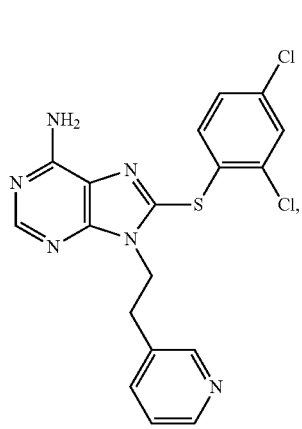
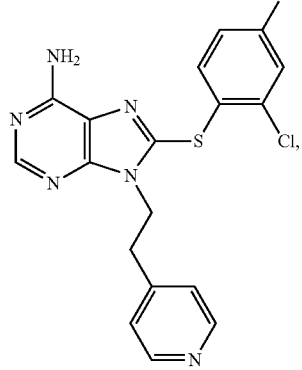
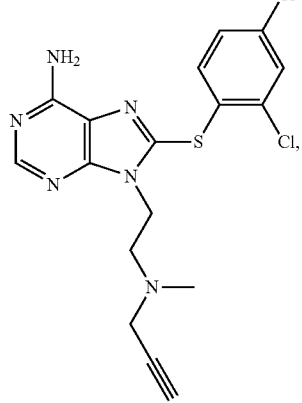

381
-continued
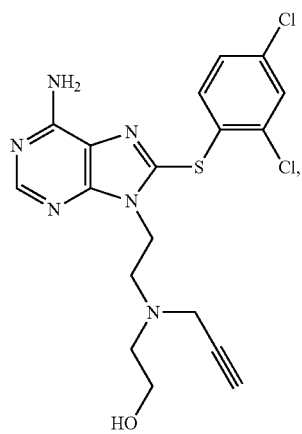
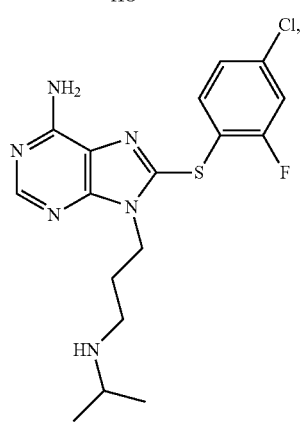
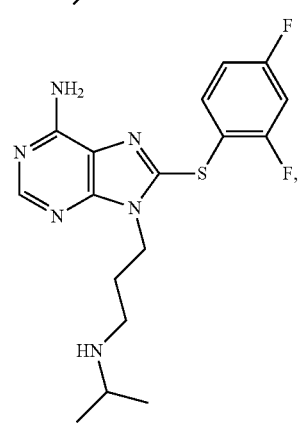
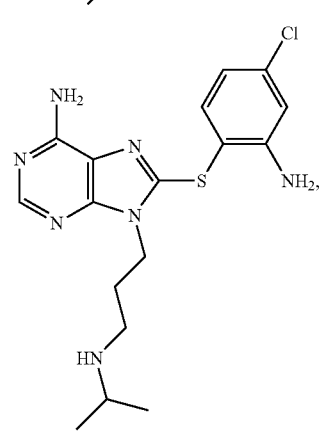
382
-continued
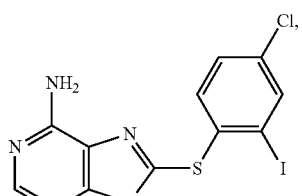
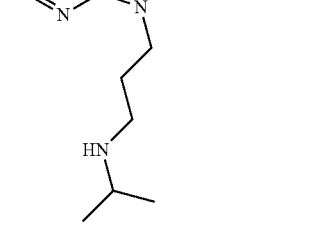
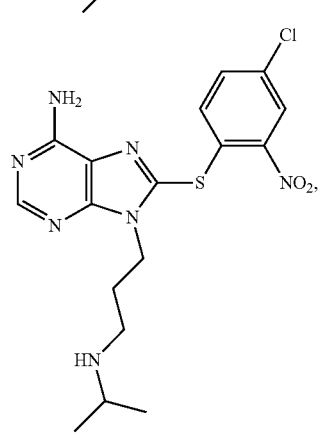
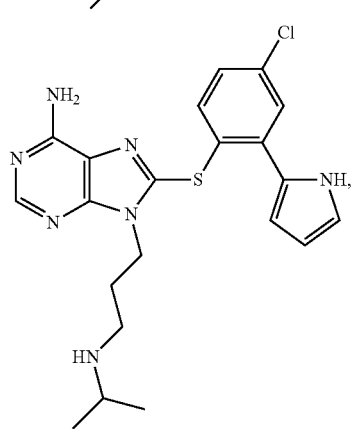
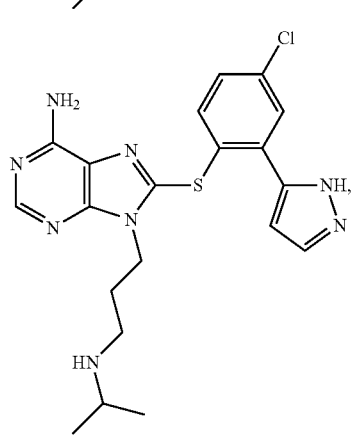

383
-continued
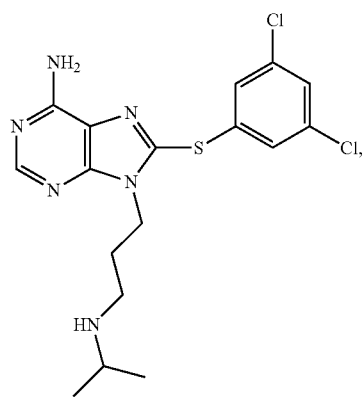
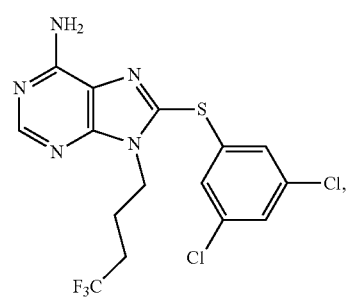
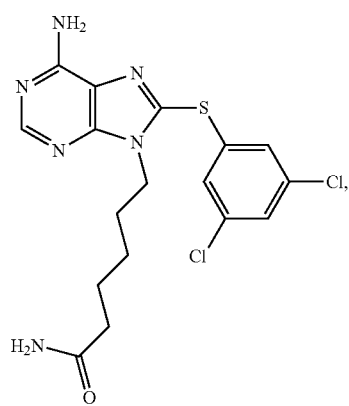
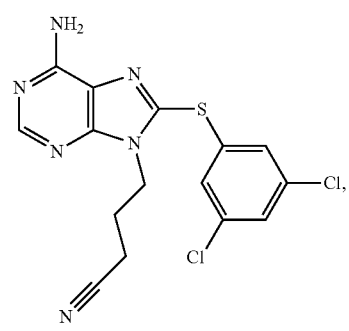
384
-continued
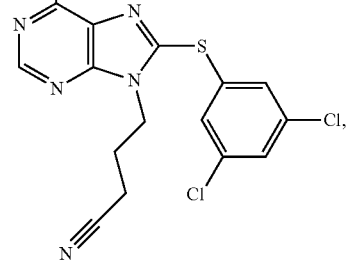
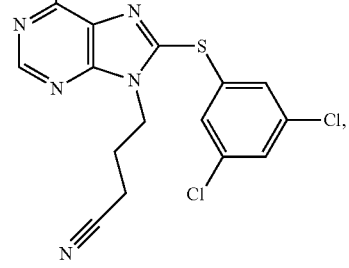
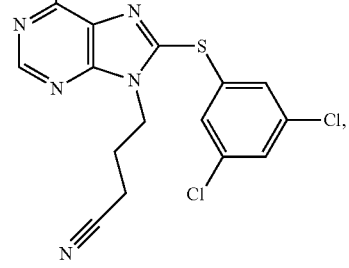
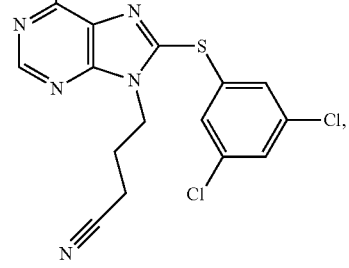

385
-continued
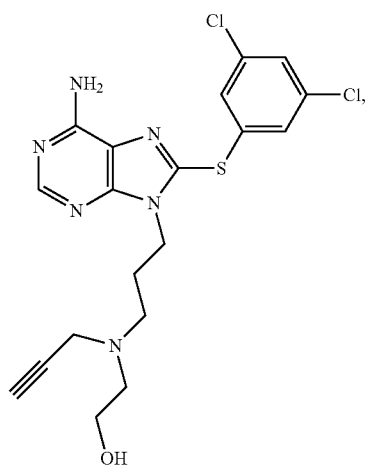
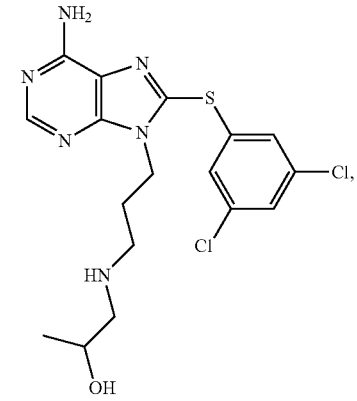
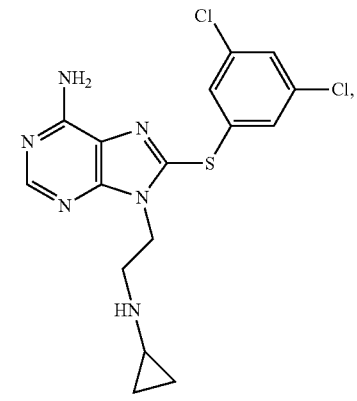
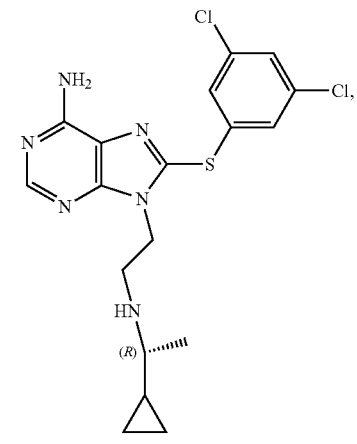
386
-continued
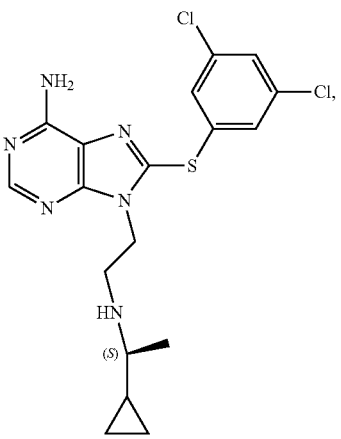
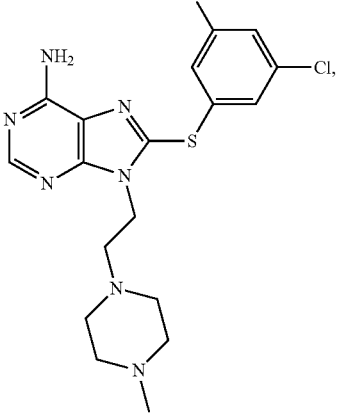
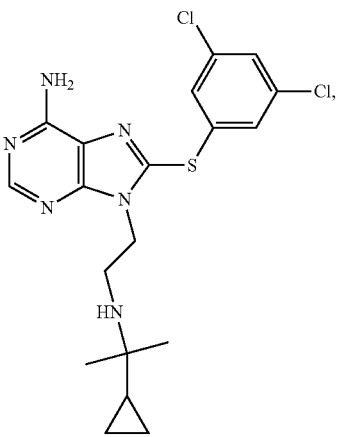
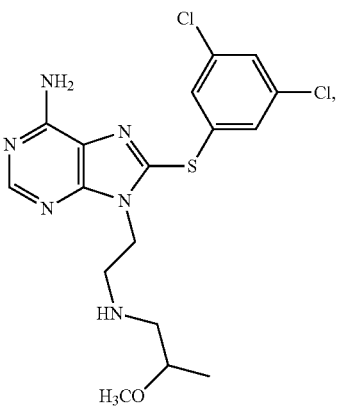

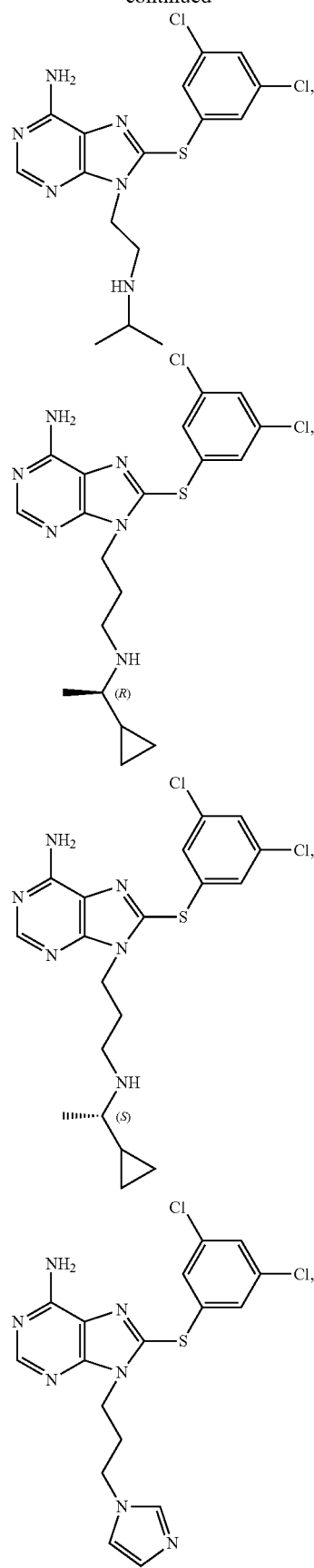
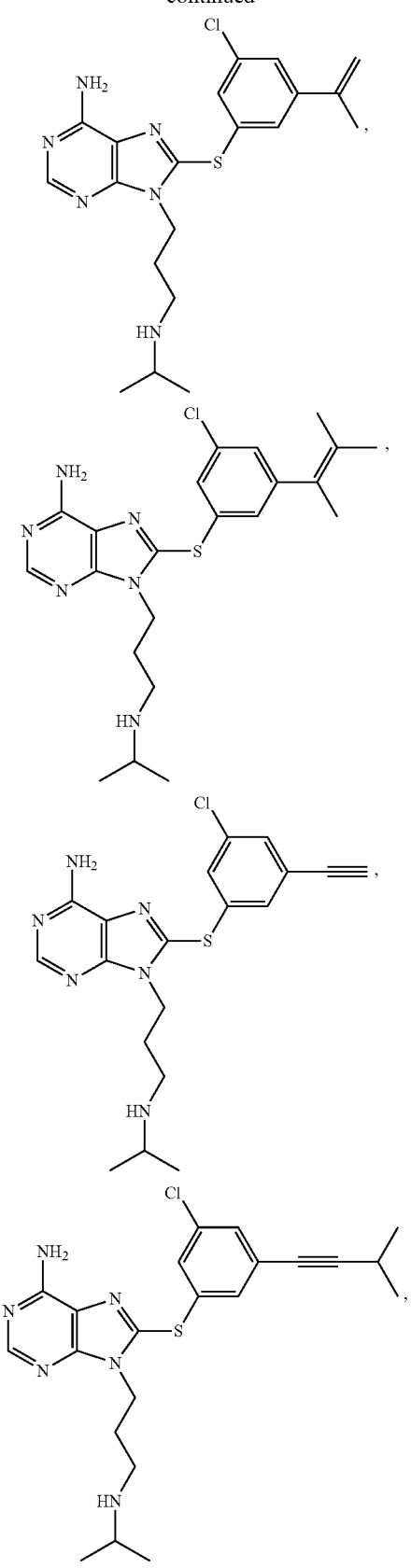

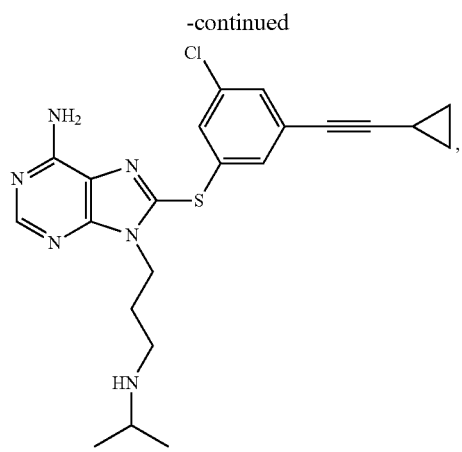
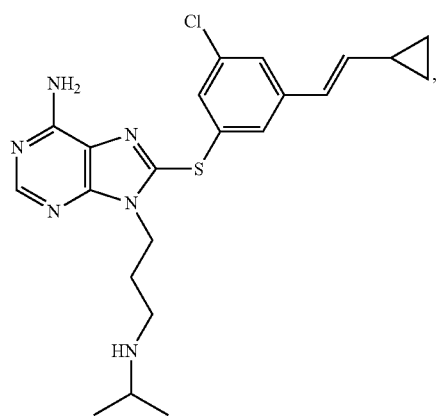

391
-continued
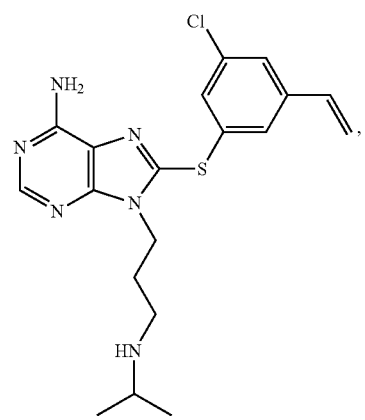
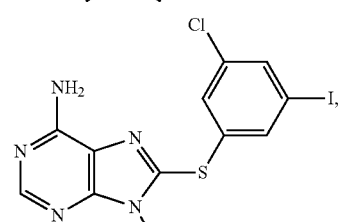
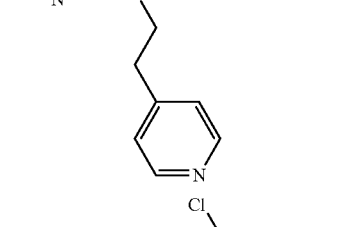
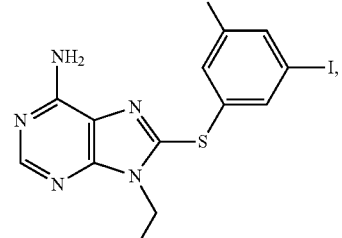
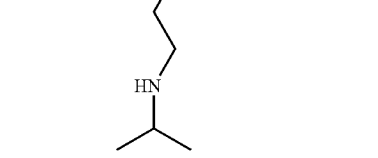
392
-continued
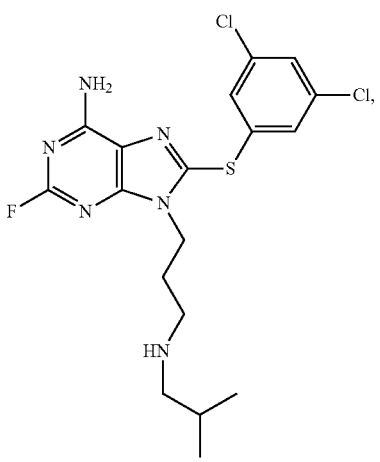
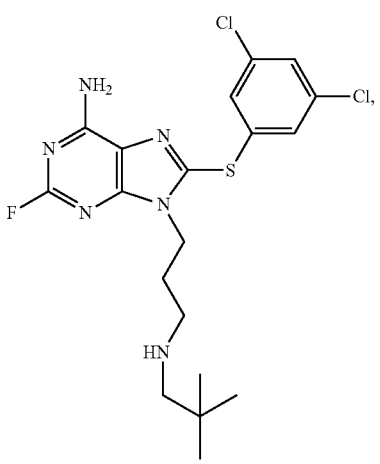
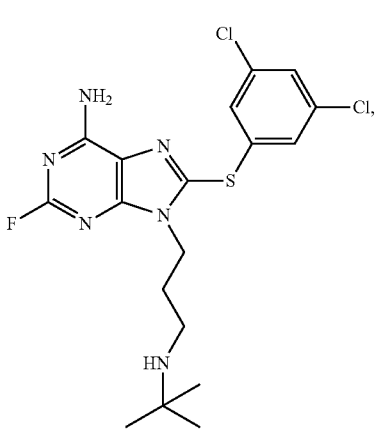

393

-continued

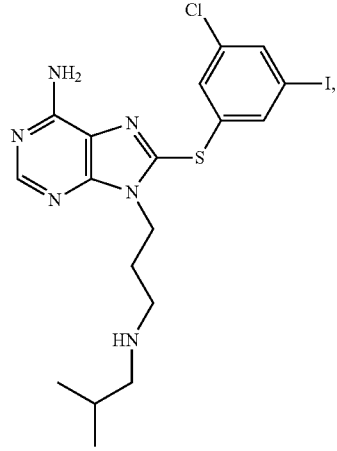

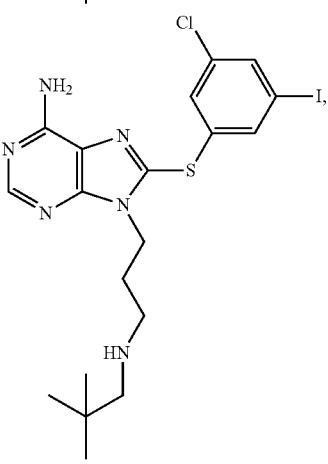

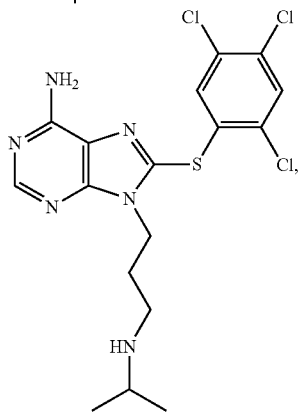

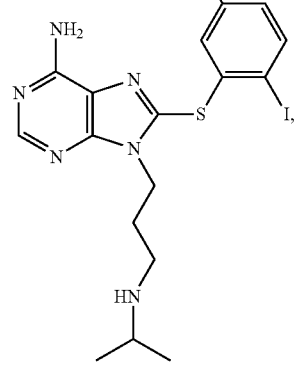

394

-continued

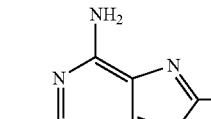
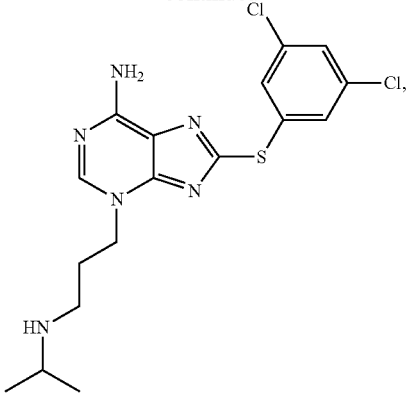

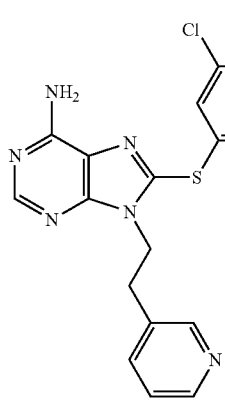

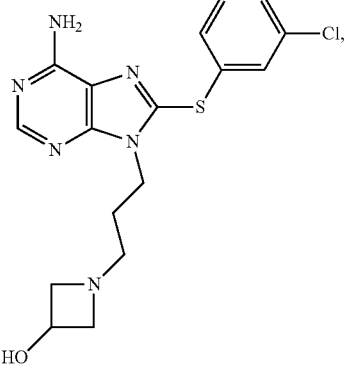

or a pharmaceutically acceptable salt thereof.

8. A pharmaceutical composition comprising a compound of claim 1, or a pharmaceutically acceptable salt thereof, and a pharmaceutically acceptable excipient.

9. A pharmaceutical composition comprising a compound of claim 4, or a pharmaceutically acceptable salt thereof, and a pharmaceutically acceptable excipient.

10. A pharmaceutical composition comprising a compound of claim 3, or a pharmaceutically acceptable salt thereof, and a pharmaceutically acceptable excipient.

11. A pharmaceutical composition comprising a compound of claim 7, or a pharmaceutically acceptable salt thereof, and a pharmaceutically acceptable excipient.

12. The compound of claim 3, having the following formula:

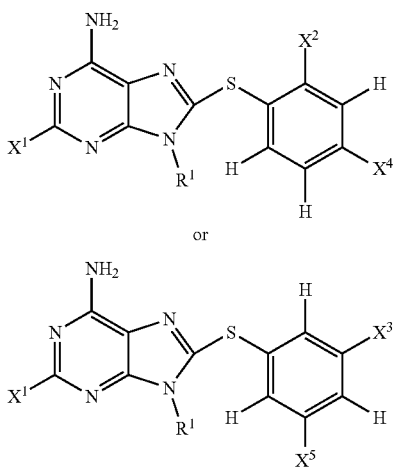

or a pharmaceutically acceptable salt thereof.

13. The compound of claim 3, having the following formula:

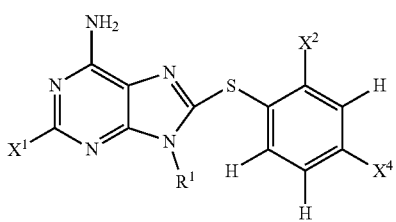

or a pharmaceutically acceptable salt thereof.

14. The compound of claim 3, having the following formula:

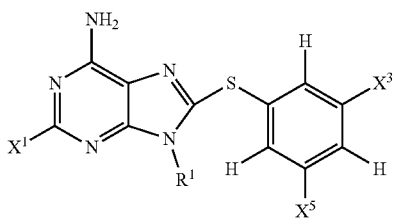

or a pharmaceutically acceptable salt thereof.

15. The compound of claim 6, having the following formula:

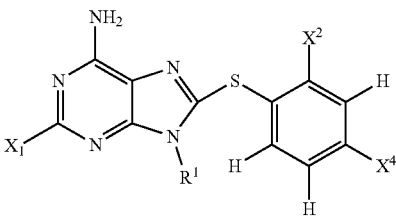

or a pharmaceutically acceptable salt thereof.

16. The compound of claim 13, wherein $X^1$ is —H or -halo.

17. The compound of claim 14, wherein $X^1$ is —H or -halo.

18. The compound of claim 15, wherein $X^1$ is —H or -halo.

19. The compound of claim 16, wherein $X^2$ is -halo, unsubstituted or substituted —$(C_1$-$C_6)$aliphatic, or unsubstituted or substituted (5- or 6-membered)heterocyclic aromatic.

20. The compound of claim 17, wherein each of $X^3$ and $X^5$ is independently -halo or unsubstituted or substituted —$(C_1$-$C_6)$aliphatic.

21. The compound of claim 18, wherein each of $X^2$ and $X^6$ is independently —H, -halo, -unsubstituted or substituted —$(C_1$-$C_6)$aliphatic, or an unsubstituted or substituted (5- or 6-membered)heterocyclic aromatic.

22. The compound of claim 19, wherein $R^1$ is selected from the group consisting of —$(C_1$-$C_6)$aliphatic-N—$R^3R^4$, —$(C_1$-$C_6)$aliphatic-C(halo)$_3$, —$(C_1$-$C_6)$aliphatic-$(C_3$-$C_8)$cycloalkyl, —$(C_1$-$C_6)$aliphatic-$(C_3$-$C_8)$heterocyclo, and —$(C_1$-$C_6)$aliphatic-(5 or 6-membered)heteroaryl.

23. The compound of claim 20, wherein $R^1$ is selected from the group consisting of —$(C_1$-$C_6)$aliphatic-N—$R^3R^4$, —$(C_1$-$C_6)$aliphatic-C(halo)$_3$, —$(C_1$-$C_6)$aliphatic-$(C_3$-$C_8)$cycloalkyl, —$(C_1$-$C_6)$aliphatic-$(C_3$-$C_8)$heterocyclo, and —$(C_1$-$C_6)$aliphatic-(5 or 6-membered)heteroaryl.

24. The compound of claim 21, wherein $R^1$ is selected from the group consisting of —$(C_1$-$C_6)$aliphatic-N—$R^3R^4$, —$(C_1$-$C_6)$aliphatic-C(halo)$_3$, —$(C_1$-$C_6)$aliphatic-$(C_3$-$C_8)$cycloalkyl, —$(C_1$-$C_6)$aliphatic-$(C_3$-$C_8)$heterocyclo, and —$(C_1$-$C_6)$aliphatic-(5 or 6-membered)heteroaryl.

25. The compound of claim 22, wherein $R^1$ is —$(C_1$-$C_6)$aliphatic-N—$R^3R^4$.

26. The compound of claim 22, wherein —$(C_1$-$C_6)$aliphatic-(5 or 6-membered)heteroaryl.

27. The compound of claim 23, wherein $R^1$ is —$(C_1$-$C_6)$aliphatic-N—$R^3R^4$.

28. The compound of claim 23, wherein $R^1$ —$(C_1$-$C_6)$aliphatic-(5 or 6-membered)heteroaryl.

29. The compound of claim 23, wherein $R^1$ —$(C_1$-$C_6)$aliphatic-C(halo)$_3$.

30. The compound of claim 24, wherein $R^1$ is —$(C_1$-$C_6)$aliphatic-N-$R^3R^4$.

31. The compound of claim 24, wherein $R^1$ —$(C_1$-$C_6)$aliphatic-(5 or 6-membered)heteroaryl.

32. The compound of claim 7, selected from the group consisting of:

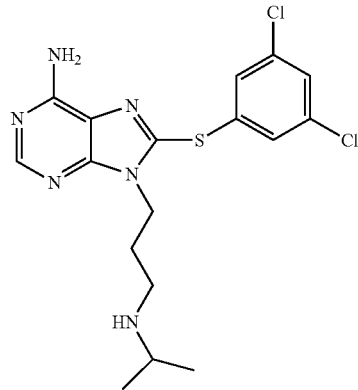

397
-continued
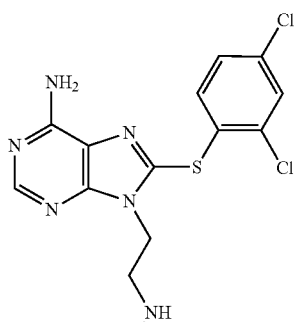
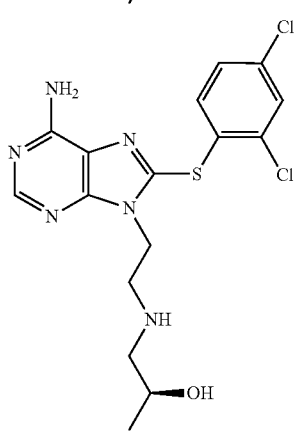
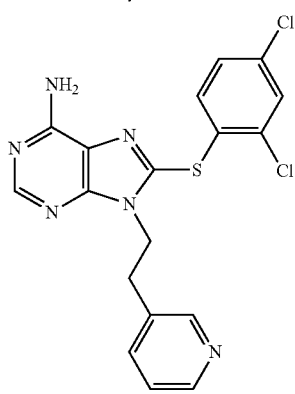
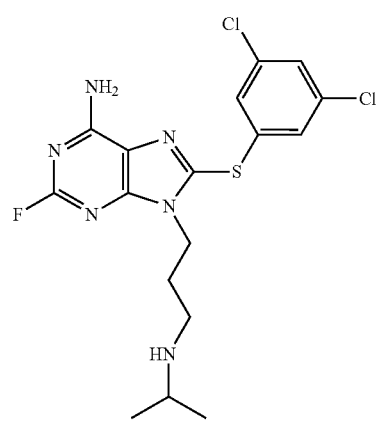
398
-continued
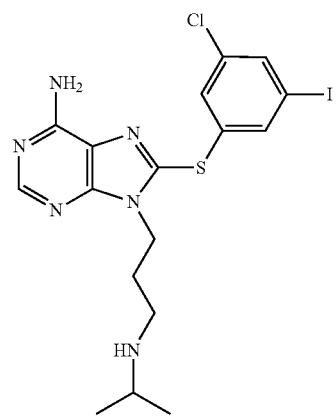
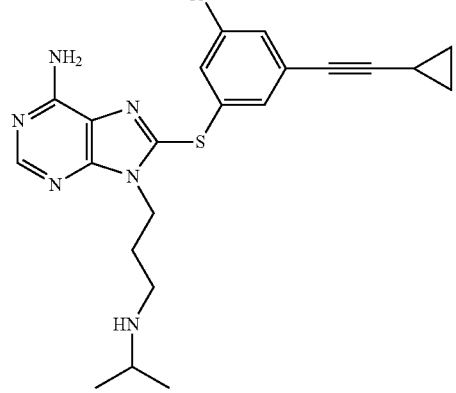
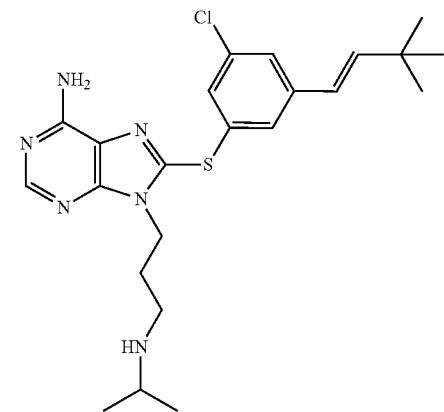
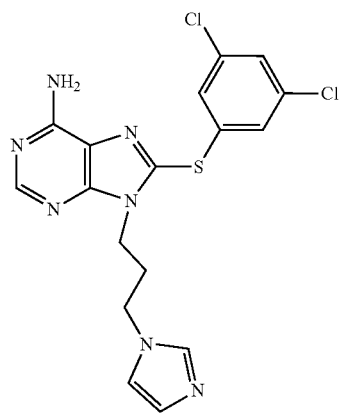 and -continued
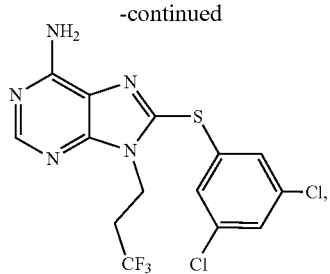
or a pharmaceutically acceptable salt thereof.
* * * * *

SEQUENCE LISTING

<160> NUMBER OF SEQ ID NOS: 5

<210> SEQ ID NO 1
<211> LENGTH: 801
<212> TYPE: PRT
<213> ORGANISM: Homo sapiens

<400> SEQUENCE: 1

Met Arg Ala Leu Trp Val Leu Gly Leu Cys Cys Val Leu Leu Thr Phe
1               5                   10                  15

```
Gly Ser Val Arg Ala Asp Asp Glu Val Asp Val Asp Gly Thr Val Glu
             20                  25                  30

Glu Asp Leu Gly Lys Ser Arg Glu Gly Ser Arg Thr Asp Asp Glu Val
         35                  40                  45

Val Gln Arg Glu Glu Glu Ala Ile Gln Leu Asp Gly Leu Asn Ala Ser
 50                  55                  60

Gln Ile Arg Glu Leu Arg Glu Lys Ser Glu Lys Phe Ala Phe Gln Ala
 65                  70                  75                  80

Glu Val Asn Arg Met Met Lys Leu Ile Ile Asn Ser Leu Tyr Lys Asn
                 85                  90                  95

Lys Glu Ile Phe Leu Arg Glu Leu Ile Ser Asn Ala Ser Asp Ala Leu
             100                 105                 110

Asp Lys Ile Arg Leu Ile Ser Leu Thr Asp Glu Asn Ala Leu Ser Gly
         115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430
```

```
Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
                500                 505                 510

Gln Ser Ser His His Pro Thr Asp Ile Thr Ser Leu Asp Gln Tyr Val
            515                 520                 525

Glu Arg Met Lys Glu Lys Gln Asp Lys Ile Tyr Phe Met Ala Gly Ser
530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Ala Lys
                580                 585                 590

Glu Gly Val Lys Phe Asp Glu Ser Glu Lys Thr Lys Glu Ser Arg Glu
            595                 600                 605

Ala Val Glu Lys Glu Phe Glu Pro Leu Leu Asn Trp Met Lys Asp Lys
                610                 615                 620

Ala Leu Lys Asp Lys Ile Glu Lys Ala Val Val Ser Gln Arg Leu Thr
625                 630                 635                 640

Glu Ser Pro Cys Ala Leu Val Ala Ser Gln Tyr Gly Trp Ser Gly Asn
                645                 650                 655

Met Glu Arg Ile Met Lys Ala Gln Ala Tyr Gln Thr Gly Lys Asp Ile
                660                 665                 670

Ser Thr Asn Tyr Tyr Ala Ser Gln Lys Lys Thr Phe Glu Ile Asn Pro
                675                 680                 685

Arg His Pro Leu Ile Arg Asp Met Leu Arg Arg Ile Lys Glu Asp Glu
690                 695                 700

Asp Asp Lys Thr Val Leu Asp Leu Ala Val Val Leu Phe Glu Thr Ala
705                 710                 715                 720

Thr Leu Arg Ser Gly Tyr Leu Leu Pro Asp Thr Lys Ala Tyr Gly Asp
                725                 730                 735

Arg Ile Glu Arg Met Leu Arg Leu Ser Leu Asn Ile Asp Pro Ala Lys
            740                 745                 750

Val Glu Glu Glu Pro Glu Glu Pro Glu Glu Thr Ala Glu Asp Thr
                755                 760                 765

Thr Glu Asp Thr Glu Gln Asp Glu Asp Glu Glu Met Asp Val Gly Thr
            770                 775                 780

Asp Glu Glu Glu Glu Thr Ala Lys Glu Ser Thr Ala Glu Lys Asp Glu
785                 790                 795                 800

Leu

<210> SEQ ID NO 2
<211> LENGTH: 255
<212> TYPE: PRT
<213> ORGANISM: Homo sapiens

<400> SEQUENCE: 2
```

```
Met Gly Ser Ser His His His His His Ser Ser Gly Leu Val Pro
1               5                   10                  15

Arg Gly Ser His Met Pro Glu Glu Thr Gln Thr Gln Asp Gln Pro Met
            20                  25                  30

Glu Glu Glu Glu Val Glu Thr Phe Ala Phe Gln Ala Glu Ile Ala Gln
        35                  40                  45

Leu Met Ser Leu Ile Ile Asn Thr Phe Tyr Ser Asn Lys Glu Ile Phe
50                  55                  60

Leu Arg Glu Leu Ile Ser Asn Ser Ser Asp Ala Leu Asp Lys Ile Arg
65                  70                  75                  80

Tyr Glu Ser Leu Thr Asp Pro Ser Lys Leu Asp Ser Gly Lys Glu Leu
                85                  90                  95

His Ile Asn Leu Ile Pro Asn Lys Gln Asp Arg Thr Leu Thr Ile Val
            100                 105                 110

Asp Thr Gly Ile Gly Met Thr Lys Ala Asp Leu Ile Asn Asn Leu Gly
        115                 120                 125

Thr Ile Ala Lys Ser Gly Thr Lys Ala Phe Met Glu Ala Leu Gln Ala
130                 135                 140

Gly Ala Asp Ile Ser Met Ile Gly Gln Phe Gly Val Gly Phe Tyr Ser
145                 150                 155                 160

Ala Tyr Leu Val Ala Glu Lys Val Thr Val Ile Thr Lys His Asn Asp
                165                 170                 175

Asp Glu Gln Tyr Ala Trp Glu Ser Ser Ala Gly Gly Ser Phe Thr Val
            180                 185                 190

Arg Thr Asp Thr Gly Glu Pro Met Gly Arg Gly Thr Val Ile Leu His
        195                 200                 205

Leu Lys Glu Asp Gln Thr Glu Tyr Leu Glu Glu Arg Arg Ile Lys Glu
210                 215                 220

Ile Val Lys Lys His Ser Gln Phe Ile Gly Tyr Pro Ile Thr Leu Phe
225                 230                 235                 240

Val Glu Lys Glu Arg Asp Lys Glu Val Ser Asp Asp Glu Ala Glu
                245                 250                 255

<210> SEQ ID NO 3
<211> LENGTH: 239
<212> TYPE: PRT
<213> ORGANISM: Homo sapiens

<400> SEQUENCE: 3

Asp Pro Thr Leu Met Pro Glu Glu Val His His Gly Glu Glu Glu Val
1               5                   10                  15

Glu Thr Phe Ala Phe Gln Ala Glu Ile Ala Gln Leu Met Ser Leu Ile
            20                  25                  30

Ile Asn Thr Phe Tyr Ser Asn Lys Glu Ile Phe Leu Arg Glu Leu Ile
        35                  40                  45

Ser Asn Ala Ser Asp Ala Leu Asp Lys Ile Arg Tyr Glu Ser Leu Thr
50                  55                  60

Asp Pro Ser Lys Leu Asp Ser Gly Lys Glu Leu Lys Ile Asp Ile Ile
65                  70                  75                  80

Pro Asn Pro Gln Glu Arg Thr Leu Thr Leu Val Asp Thr Gly Ile Gly
                85                  90                  95

Met Thr Lys Ala Asp Leu Ile Asn Asn Leu Gly Thr Ile Ala Lys Ser
            100                 105                 110

Gly Thr Lys Ala Phe Met Glu Ala Leu Gln Ala Gly Ala Asp Ile Ser
        115                 120                 125
```

```
Met Ile Gly Gln Phe Gly Val Gly Phe Tyr Ser Ala Tyr Leu Val Ala
        130                 135                 140

Glu Lys Val Val Val Ile Thr Lys His Asn Asp Asp Glu Gln Tyr Ala
145                 150                 155                 160

Trp Glu Ser Ser Ala Gly Gly Ser Phe Thr Val Arg Ala Asp His Gly
                165                 170                 175

Glu Pro Ile Gly Arg Gly Thr Lys Val Ile Leu His Leu Lys Glu Asp
            180                 185                 190

Gln Thr Glu Tyr Leu Glu Arg Arg Val Lys Glu Val Val Lys Lys
        195                 200                 205

His Ser Gln Phe Ile Gly Tyr Pro Ile Thr Leu Tyr Leu Glu Lys Glu
210                 215                 220

Arg Glu Lys Gly Glu Phe Asn Ser Lys Leu Gly Cys Phe Gly Gly
225                 230                 235

<210> SEQ ID NO 4
<211> LENGTH: 704
<212> TYPE: PRT
<213> ORGANISM: Homo sapiens

<400> SEQUENCE: 4

Met Ala Arg Glu Leu Arg Ala Leu Leu Leu Trp Gly Arg Arg Leu Arg
1               5                   10                  15

Pro Leu Leu Arg Ala Pro Ala Leu Ala Ala Val Pro Gly Gly Lys Pro
                20                  25                  30

Ile Leu Cys Pro Arg Arg Thr Thr Ala Gln Leu Gly Pro Arg Arg Asn
            35                  40                  45

Pro Ala Trp Ser Leu Gln Ala Gly Arg Leu Phe Ser Thr Gln Thr Ala
        50                  55                  60

Glu Asp Lys Glu Glu Pro Leu His Ser Ile Ile Ser Ser Thr Glu Ser
65                  70                  75                  80

Val Gln Gly Ser Thr Ser Lys His Glu Phe Gln Ala Glu Thr Lys Lys
                85                  90                  95

Leu Leu Asp Ile Val Ala Arg Ser Leu Tyr Ser Glu Lys Glu Val Phe
            100                 105                 110

Ile Arg Glu Leu Ile Ser Asn Ala Ser Asp Ala Leu Glu Lys Leu Arg
        115                 120                 125

His Lys Leu Val Ser Asp Gly Gln Ala Leu Pro Glu Met Glu Ile His
130                 135                 140

Leu Gln Thr Asn Ala Glu Lys Gly Thr Ile Thr Ile Gln Asp Thr Gly
145                 150                 155                 160

Ile Gly Met Thr Gln Glu Glu Leu Val Ser Asn Leu Gly Thr Ile Ala
                165                 170                 175

Arg Ser Gly Ser Lys Ala Phe Leu Asp Ala Leu Gln Asn Gln Ala Glu
            180                 185                 190

Ala Ser Ser Lys Ile Ile Gly Gln Phe Gly Val Gly Phe Tyr Ser Ala
        195                 200                 205

Phe Met Val Ala Asp Arg Val Glu Val Tyr Ser Arg Ser Ala Ala Pro
210                 215                 220

Gly Ser Leu Gly Tyr Gln Trp Leu Ser Asp Gly Ser Gly Val Phe Glu
225                 230                 235                 240

Ile Ala Glu Ala Ser Gly Val Arg Thr Gly Thr Lys Ile Ile Ile His
                245                 250                 255

Leu Lys Ser Asp Cys Lys Glu Phe Ser Ser Glu Ala Arg Val Arg Asp
```

```
              260                 265                 270
Val Val Thr Lys Tyr Ser Asn Phe Val Ser Phe Pro Leu Tyr Leu Asn
            275                 280                 285

Gly Arg Arg Met Asn Thr Leu Gln Ala Ile Trp Met Met Asp Pro Lys
290                 295                 300

Asp Val Arg Glu Trp Gln His Glu Glu Phe Tyr Arg Tyr Val Ala Gln
305                 310                 315                 320

Ala His Asp Lys Pro Arg Tyr Thr Leu His Tyr Lys Thr Asp Ala Pro
                325                 330                 335

Leu Asn Ile Arg Ser Ile Phe Tyr Val Pro Asp Met Lys Pro Ser Met
            340                 345                 350

Phe Asp Val Ser Arg Glu Leu Gly Ser Ser Val Ala Leu Tyr Ser Arg
        355                 360                 365

Lys Val Leu Ile Gln Thr Lys Ala Thr Asp Ile Leu Pro Lys Trp Leu
    370                 375                 380

Arg Phe Ile Arg Gly Val Val Asp Ser Glu Asp Ile Pro Leu Asn Leu
385                 390                 395                 400

Ser Arg Glu Leu Leu Gln Glu Ser Ala Leu Ile Arg Lys Leu Arg Asp
                405                 410                 415

Val Leu Gln Gln Arg Leu Ile Lys Phe Phe Ile Asp Gln Ser Lys Lys
            420                 425                 430

Asp Ala Glu Lys Tyr Ala Lys Phe Phe Glu Asp Tyr Gly Leu Phe Met
        435                 440                 445

Arg Glu Gly Ile Val Thr Ala Thr Glu Gln Glu Val Lys Glu Asp Ile
    450                 455                 460

Ala Lys Leu Leu Arg Tyr Glu Ser Ser Ala Leu Pro Ser Gly Gln Leu
465                 470                 475                 480

Thr Ser Leu Ser Glu Tyr Ala Ser Arg Met Arg Ala Gly Thr Arg Asn
                485                 490                 495

Ile Tyr Tyr Leu Cys Ala Pro Asn Arg His Leu Ala Glu His Ser Pro
            500                 505                 510

Tyr Tyr Glu Ala Met Lys Lys Lys Asp Thr Glu Val Leu Phe Cys Phe
        515                 520                 525

Glu Gln Phe Asp Glu Leu Thr Leu Leu His Leu Arg Glu Phe Asp Lys
    530                 535                 540

Lys Lys Leu Ile Ser Val Glu Thr Asp Ile Val Val Asp His Tyr Lys
545                 550                 555                 560

Glu Glu Lys Phe Glu Asp Arg Ser Pro Ala Ala Glu Cys Leu Ser Glu
                565                 570                 575

Lys Glu Thr Glu Glu Leu Met Ala Trp Met Arg Asn Val Leu Gly Ser
            580                 585                 590

Arg Val Thr Asn Val Lys Val Thr Leu Arg Leu Asp Thr His Pro Ala
        595                 600                 605

Met Val Thr Val Leu Glu Met Gly Ala Ala Arg His Phe Leu Arg Met
    610                 615                 620

Gln Gln Leu Ala Lys Thr Gln Glu Glu Arg Ala Gln Leu Leu Gln Pro
625                 630                 635                 640

Thr Leu Glu Ile Asn Pro Arg His Ala Leu Ile Lys Lys Leu Asn Gln
                645                 650                 655

Leu Arg Ala Ser Glu Pro Gly Leu Ala Gln Leu Leu Val Asp Gln Ile
            660                 665                 670

Tyr Glu Asn Ala Met Ile Ala Ala Gly Leu Val Asp Asp Pro Arg Ala
        675                 680                 685
```

Met Val Gly Arg Leu Asn Glu Leu Leu Val Lys Ala Leu Glu Arg His
690                 695                 700

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
ggggtcaacg ttgagggggg                                          20

UNITED STATES PATENT AND TRADEMARK OFFICE
CERTIFICATE OF CORRECTION

PATENT NO. : 10,421,758 B2
APPLICATION NO. : 14/912082
DATED : September 24, 2019
INVENTOR(S) : Chiosis et al.

Page 1 of 4

It is certified that error appears in the above-identified patent and that said Letters Patent is hereby corrected as shown below:

In the Claims

In Claim 2, Column 370, at Line 46, please delete:
"$Z^2$ is;"
And insert:
-- $Z^2$ is –N–; --

In Claim 3, Column 373, at Line 10, please insert:

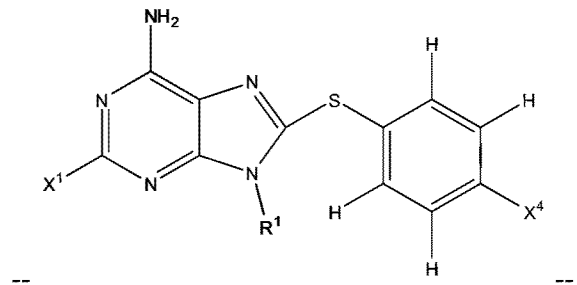

--                                --

In Claim 7, Column 381, beginning at Line 34 and ending at Line 49, please delete:

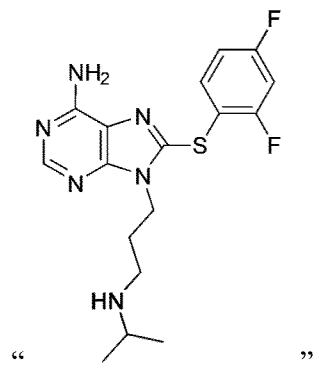

"                    "

Signed and Sealed this
Fourth Day of February, 2020

Andrei Iancu
*Director of the United States Patent and Trademark Office*

And insert:
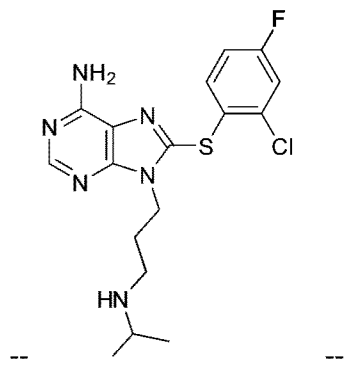
--                    --
In Claim 7, Column 383, at Line 15, please insert:
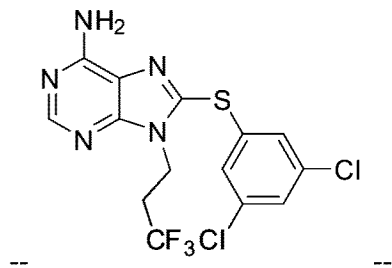
--                    --
In Claim 7, Column 388, at Line 50, please insert:
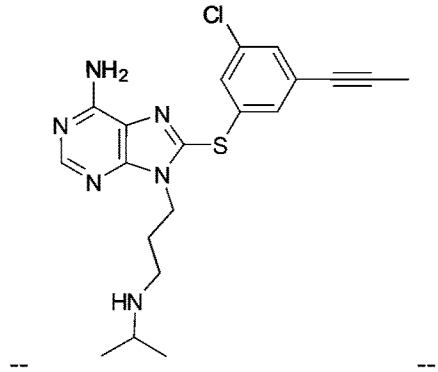
--                    --
In Claim 7, Column 393, at Line 35, please insert:
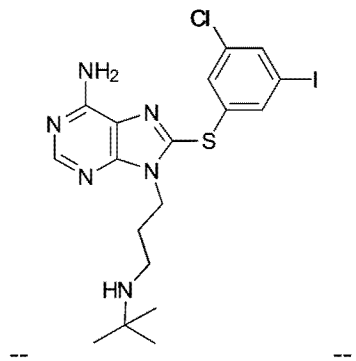
--                    --

CERTIFICATE OF CORRECTION (continued)
U.S. Pat. No. 10,421,758 B2

In Claim 7, Column 393, beginning at Line 51 and ending at Line 67, please delete:

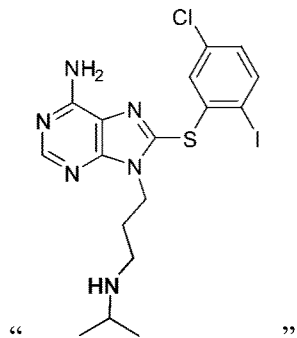

" "

And insert:

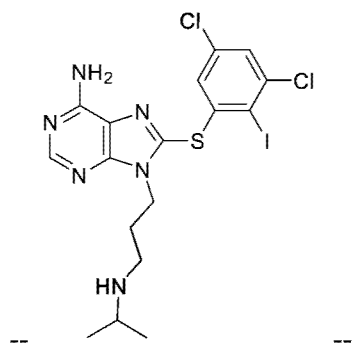

-- --

In Claim 7, Column 394, at Line 1, please insert:

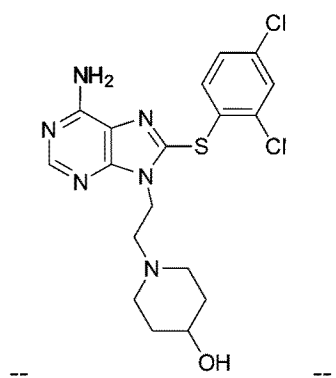

-- --

In Claim 15, Column 395, beginning at Line 55 and ending at Line 65, please delete:

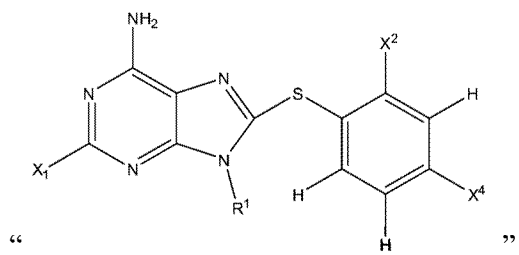

" "

And insert:
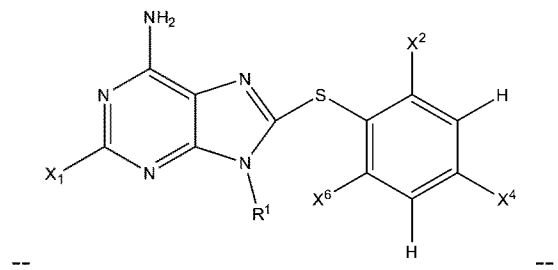
-- --